United States Patent
Charton et al.

(10) Patent No.: US 9,932,309 B2
(45) Date of Patent: Apr. 3, 2018

(54) 2-OXO-3,4-DIHYDROPYRIDINE-5-CARBOXYLATES AND THEIR USE

(71) Applicants: UNIVERSITE DE LILLE 2 DROIT ET SANTE, Lille (FR); INSTITUT PASTEUR DE LILLE, Lille (FR); INSERM (INSTITUT NATIONAL DE LA SANTE ET DE LA RECHERCHE MEDICALE), Paris (FR)

(72) Inventors: Julie Charton, Haubourdin (FR); Benoit Deprez, Lille (FR); Florence Leroux, Templemars (FR); Bart Staels, Petit-Enghien (BE); Anne Muhr-Tailleux, Marcq en Baroeul (FR); Nathalie Hennuyer, Corbehem (FR); Sophie Lestavel, Villeneuve d'ascq (FR); Sylvain Picon, Beziers (FR); Karen Aknin, Taverny (FR); Rajaa Boulahjar, Lille (FR); Barbara Dubanchet, Blotzheim (FR)

(73) Assignees: Universite de Lille 2 Droit et Sante, Lille (FR); Institut Pasteur de Lille, Lille (FR); INSERM, Paris (FR)

( * ) Notice: Subject to any disclaimer, the term of this patent is extended or adjusted under 35 U.S.C. 154(b) by 0 days.

(21) Appl. No.: 15/326,848

(22) PCT Filed: Jul. 28, 2015

(86) PCT No.: PCT/EP2015/067264
§ 371 (c)(1),
(2) Date: Jan. 17, 2017

(87) PCT Pub. No.: WO2016/016238
PCT Pub. Date: Feb. 4, 2016

(65) Prior Publication Data
US 2017/0210710 A1      Jul. 27, 2017

(30) Foreign Application Priority Data
Jul. 29, 2014  (EP) .................................... 14306214

(51) Int. Cl.
| C07D 211/90 | (2006.01) |
|---|---|
| C07D 413/06 | (2006.01) |
| C07D 417/14 | (2006.01) |
| C07D 401/04 | (2006.01) |
| C07D 405/14 | (2006.01) |
| C07D 401/06 | (2006.01) |
| C07D 405/06 | (2006.01) |

(52) U.S. Cl.
CPC .......... *C07D 211/90* (2013.01); *C07D 401/04* (2013.01); *C07D 401/06* (2013.01); *C07D 405/06* (2013.01); *C07D 405/14* (2013.01); *C07D 413/06* (2013.01); *C07D 417/14* (2013.01)

(58) Field of Classification Search
CPC .. C07D 211/90; C07D 401/04; C07D 401/06; C07D 405/06; C07D 405/14; C07D 413/06; C07D 417/14
USPC ........................................................ 514/210
See application file for complete search history.

(56) References Cited

U.S. PATENT DOCUMENTS

| 6,727,264 B1 | 4/2004 | Marzabadi et al. |
| 2008/0261953 A1* | 10/2008 | Lindquist ............. A61K 31/522 514/215 |

FOREIGN PATENT DOCUMENTS

| WO | 00/25782 A1 | 5/2000 |
| WO | 2004/020410 A2 | 3/2004 |
| WO | 2011071565 A1 | 6/2011 |

OTHER PUBLICATIONS

Hoffmann-Emery et al., J. Org. Chem., vol. 71, No. 5, 2006, 2000-2008.*
The International Search Report and Written Opinion, dated Sep. 14, 2015, in the corresponding PCT Appl. No. PCT/EP2015/067264.
Nantermet et al., "Selective alphala adrenergic receptor antagonists based on 4-aryl-3,4-dihydropyridine-2-ones", Bioorganic & Medicinal Chemistry Letters, Pergamon, Amsterdam, NL, vol. 10, No. 15, Aug. 7, 2000, pp. 1625-1628.
Vellalath et al: "Direct Catalytic Asymmetric Synthesis of N-Heterocycles from Commodity Acid Chlorides by Employing [alpha],[beta]-Unsaturated Acylammonium Salts", Angewandte Chemie International Edition, vol. 52, No. 51, Oct. 31, 2013(Oct. 31, 2013), pp. 13688-13693.

* cited by examiner

*Primary Examiner* — Kristin Vajda

(57) ABSTRACT

The present invention is directed to novel compounds of Formula (I), pharmaceutically acceptable salts or solvates thereof, and their use.

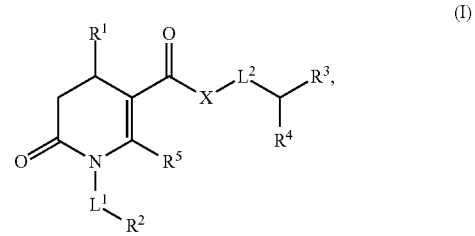

39 Claims, No Drawings

2-OXO-3,4-DIHYDROPYRIDINE-5-CARBOXYLATES AND THEIR USE

CROSS-REFERENCE TO RELATED APPLICATIONS

This application is a National Stage Application of PCT/EP2015/067264 filed Jul. 28, 2015, which claims priority from European Patent Application No. 14306214.9 filed Jul. 29, 2014. Each of the prior mentioned applications is hereby incorporated by reference herein in its entirety.

The present invention relates to novel compounds including their pharmaceutically acceptable salts and solvates, which are agonists of TGR5 (G protein-coupled bile acid receptor 1, also named Gpbar1 or M-BAR) and are useful as therapeutic compounds, particularly in the treatment and/or prevention of TGR5 related diseases, such as Type 2 diabetes (T2D) also known as diabetes mellitus and conditions that are often associated with this disease including, lipid disorders such as dyslipidemia, hypertension, obesity, atherosclerosis and its sequelae.

BACKGROUND OF THE INVENTION

Type 2 diabetes (T2D) also known as diabetes mellitus is a growing health problem. Recent estimates indicate there were 171 million people in the world with diabetes in the year 2000 and this is projected to increase to 366 million by 2030 (Wild S, Roglic G, Green A, Sicree R, King H. Global Prevalence of Diabetes: Estimates for the year 2000 and projections for 2030. Diabetes Care. 2004, 27, 1047-1053). The classical treatment for type 2 diabetes developed over the past 20 years has been based on 2 types of oral anti-hyperglycemic drugs; sulfonylureas that stimulate insulin secretion and the biguanides that have a broad spectrum of effects, but act primarily on hepatic insulin resistance. Then, alpha glucosidase inhibitors (i.e. acarbose) have been developed which decrease the intestinal absorption of glucose. A new category of molecules has appeared called thiazolidinediones (TZD). They act through binding and activation of the nuclear receptor peroxisome proliferator-activated receptor gamma (PPARγ). More recently, the recognition that hormones secreted by the gut play a role in maintaining blood glucose homeostasis has led to emergence of several novel class of medications acting as analogs of the incretin glucagon-like peptide (GLP-1) or as inhibitors of its degradating enzyme dipeptidyl peptidase IV (DPP-IV inhibitors) stabilizing its half-life. GLP-1 is an incretin hormone causing enhanced post-prandial insulin secretion, but also known to have a range of additional effects including reduced gastric motility and appetite suppression, which indirectly impact on glucose metabolism in vivo (Drucker, D. J.; Sherman, S. I.; Bergenstal, R. M.; Buse, J. B., The safety of incretin-based therapies—review of the scientific evidence. J Clin Endocrinol Metab 2011, 96, 2027-2031. Baggio, L. L.; Drucker, D. J., Biology of Incretins: GLP-1 and GIP. Gastroenterology 2007, 132, 2131-2157). These new incretin-based medications offer the advantage of highly successful efficacy associated with an exceedingly favorable side effect profile and neutral effects on weight (Cefalu, W. T., Evolving treatment strategies for the management of type 2 diabetes. Am J Med Sci 2012, 343, 21-6. Gallwitz, B., Glucagon-like peptide-1 analogues for Type 2 diabetes mellitus: current and emerging agents. Drugs 2011, 71, 1675-88).

Despite the use of various hypoglycemic agents, current treatments often fail to achieve sufficient lowering of serum glucose and/or are often associated with deficiencies including hypoglycemic episodes, gastrointestinal problems, weight gain, and loss of effectiveness over time (El-Kaissi, S.; Sherbeeni, S., Pharmacological management of type 2 diabetes mellitus: an update. Curr Diabetes Rev 2011, 7, 392-405).

In this context, the bile acid receptor TGR5 appears as an emerging and promising therapeutic target (Chen X Fau-Lou, G.; Lou G Fau-Meng, Z.; Meng Z Fau-Huang, W.; Huang, W., TGR5: A Novel Target for Weight Maintenance and Glucose Metabolism. Exp Diabetes Res. 2011, 2011: 853501. Pols Tw Fau-Noriega, L. G.; Noriega Lg Fau-Nomura, M.; Nomura M Fau-Auwerx, J.; Auwerx J Fau-Schoonjans, K.; Schoonjans, K., The bile acid membrane receptor TGR5: a valuable metabolic target. Dig. Dis. 2011, 29, 37-44. Porez, G.; Prawitt, J.; Gross, B.; Staels, B. J. Lipid Res. 2012, 53, 1723-1737). TGR5 (also named Gpbar1 or M-BAR) (Maruyama, T.; Miyamoto, Y.; Nakamura, T.; Tamai, Y.; Okada, H.; Sugiyama, E.; Nakamura, T.; Itadani, H.; Tanaka, K., Identification of membrane-type receptor for bile acids (M-BAR). Biochem. Biophys. Res. Commun 2002, 298, 714-719. Kawamata, Y.; Fujii, R.; Hosoya, M.; Harada, M.; Yoshida, H.; Miwa, M.; Fukusumi, S.; Habata, Y.; Itoh, T.; Shintani, Y.; Hinuma, S.; Fujisawa, Y.; Fujino, M., A G Protein-coupled Receptor Responsive to Bile Acids. J. Biol. Chem. 2003, 278, 9435-9440) is a member of the G-protein coupled receptor (GPCR) family. TGR5 is broadly expressed in human tissues, including those that are not usually known as targets of bile acids. In particular, TGR5 is highly expressed in adipose tissue, muscle and enteroendocrine cells. A body of evidence supports a role for TGR5 in energy homeostasis. Indeed, administration of bile acids to mice increased energy expenditure in the brown adipose tissue and prevented diet-induced obesity and insulin-resistance. This effect was ascribed to a cAMP dependant intracellular induction of the type 2 iodothyronine deiodase (D2) enzyme, which converts inactive thyroxine (T4) into active 3,5,5'-tri-iodothyronine (T3). By this pathway, bile acids increase energy expenditure in part through activation of mitochondrial function in brown adipose tissue and skeletal muscle, hence preventing obesity and resistance to insulin (Watanabe, M.; Houten, S. M.; Mataki, C.; Christoffolete, M. A.; Kim, B. W.; Sato, H.; Messaddeq, N.; Harney, J. W.; Ezaki, O.; Kodama, T.; Schoonjans, K.; Bianco, A. C.; Auwerx, J., Bile acids induce energy expenditure by promoting intracellular thyroid hormone activation. Nature 2006, 439, (7075), 484-489). Consistent for a role of TGR5 in energy homeostasis, female TGR5 deficient mice although not obese under chow fed conditions, showed significant fat accumulation with body weight gain compared to wild-type mice when fed a high fat diet (Maruyama, T.; Tanaka, K.; Suzuki, J.; Miyoshi, H.; Harada, N.; Nakamura, T.; Miyamoto, Y.; Kanatani, A.; Tamai, Y., Targeted disruption of G protein-coupled bile acid receptor 1 (Gpbar1/M-Bar) in mice. Journal of Endocrinology 2006, 191, 197-205). Moreover, it was shown that oleanolic acid, a component of olive oil that binds to and activates TGR5, lowers glucose and insulin levels in mice fed with a high fat diet and enhances glucose tolerance (Sato, H.; Genet, C.; Strehle, A.; Thomas, C.; Lobstein, A.; Wagner, A.; Mioskowski, C.; Auwerx, J.; Saladin, R., Anti-hyperglycemic activity of a TGR5 agonist isolated from *Olea europaea*. Biochem. Biophys. Res. Commun 2007, 362, 793-798). Very interestingly, bile acids and compounds that affect TGR5 activity have been shown to increase GLP-1 secretion from enteroendocrine intestinal cells (Katsuma, S.; Hirasawa, A.; Tsujimoto, G. Bile acids promote glucagon-like peptide-1 secretion through TGR5 in a murine enteroendocrine cell line STC-1 Biochem. Biophys. Res. Commun. 2005, 329, 386-390). More recently, using a combination of pharmacological and genetic gain- and loss-of-function studies in vivo, Thomas et al. (Thomas, C.; Gioiello, A.; Noriega, L.; Strehle, A.; Oury, J.; Rizzo, G.; Macchiarulo, A.; Yamamoto, H.; Mataki, C.; Pruzanski, M.; Pellicciari, R.; Auwerx, J.; Schoonjans, K., TGR5-mediated bile acid sensing controls glucose homeostasis. Cell Metab 2009, 10, 167-177) showed that TGR5 signaling induced GLP-1 release also in vivo, leading to improved liver and pancreatic function and enhanced glucose tolerance in obese mice. Therefore, pharmacological targeting of TGR5 may constitute a promising incretin-based strategy for the treatment of diabesity and associated metabolic disorders. Interestingly, in addition to its expression in enteroendocrine L cells and its incretin secretagogue activity, TGR5 has also been shown to be expressed in inflammatory cells and its activation leads to anti-inflammatory effects and to anti-atherosclerotic effects in mouse. (Kawamata, Y.; Fujii, R.; Hosoya, M.; Harada, M.; Yoshida, H.; Miwa, M.; Fukusumi, S.; Habata, Y.; Itoh, T.; Shintani, Y.; Hinuma, S.; Fujisawa, Y.; Fujino, M., A G Protein-coupled Receptor Responsive to Bile Acids. J. Biol. Chem. 2003, 278, 9435-9440. Keitel, V.; Donner, M.; Winandy, S.; Kubitz, R.; Haussinger, D., Expression and function of the bile acid receptor TGR5 in Kupffer cells. Biochem Biophys Res Commun 2008, 372, 78-84. Pols, T. W. H.; Nomura, M.; Harach, T.; LoÂ Sasso, G.; Oosterveer, M. H.; Thomas, C.; Rizzo, G.; Gioiello, A.; Adorini, L.; Pellicciari, R.; Auwerx, J.; Schoonjans, K., TGR5 Activation Inhibits Atherosclerosis by Reducing Macrophage Inflammation and Lipid Loading. Cell Metabolism 2007, 14, (6), 747-757).

TGR5 agonists including natural or semi-synthetic bile acids (Pellicciari, R.; Gioiello, A.; Macchiarulo, A.; Thomas, C.; Rosatelli, E.; Natalini, B.; Sardella, R.; Pruzanski, M.; Roda, A.; Pastorini, E.; Schoonjans, K.; Auwerx, J., Discovery of 6-Ethyl-23(S)-methylcholic Acid (S-EMCA, INT-777) as a Potent and Selective Agonist for the TGR5 Receptor, a Novel Target for Diabesity J. Med. Chem. 2009, 52, 7958.7961), bile alcohols, triterpenoid compounds such as oleanolic acid, betulinic acids (Genet, C. d.; Strehle, A.; Schmidt, C. I.; Boudjelal, G.; Lobstein, A.; Schoonjans, K.; Souchet, M.; Auwerx, J.; Saladin, R. g.; Wagner, A. Structure-Activity Relationship Study of Betulinic Acid, A Novel and Selective TGR5 Agonist, and Its Synthetic Derivatives: Potential Impact in Diabetes J. Med. Chem. 2010, 53, 178-190), nomilin (Ono, E.; Inoue, J.; Hashidume, T.; Shimizu, M.; Sato, R. Anti-obesity and anti-hyperglycemic effects of the dietary citrus limonoid nomilin in mice fed a high-fat diet. Biochem. Biophys. Res. Commun. 2011, 410, 677-681) or avicholic acid and synthetic nonsteroidal small molecules (Gioiello, A.; Rosatelli, E.; Nuti, R.; Macchiarulo, A.; Pellicciari, R., Patented TGR5 modulators: a review (2006-present). Expert Opin Ther Pat 2012, 22, (12), 1399-1414) have been described recently.

However, safety concerns for some systemic TGR5 agonists were recently mentioned. Hyperplasia of the gall bladder which becomes enlarged due to delayed emptying, increased filling, or a combination of these effects was reported by investigators working with systemic TGR5 agonists in mouse models. Li, T.; Holmstrom, S. R.; Kir, S.; Umetani, M.; Schmidt, D. R.; Kliewer, S. A.; angelsdorf, D. J. The G protein-coupled bile acid receptor, TGR5, stimulates gallbladder filling. Mol. Endocrinol. 2011, 25, 1066-1071, Duan, H.; Ning, M.; Chen, X.; Zou, Q.; Zhang, L.; Feng, Y.; Zhang, L.; Leng, Y.; Shen, J., Design, Synthesis, and Antidiabetic Activity of 4-Phenoxynicotinamide and 4-Phenoxypyrimidine-5-carboxamide Derivatives as Potent and Orally Efficacious TGR5 Agonists. Journal of Medicinal Chemistry 2012, 55, (23), 10475.

More recently, it was reported that TGR5 stimulation in skin by systemic agonists triggers intense pruritus, comparable to the effect of the naturally occurring bile acids during cholestasis (Alemi, F.; Kwon, E.; Poole, D. P.; Lieu, T.; Lyo, V.; Cattaruzza, F.; Cevikbas, F.; Steinhoff, M.; Nassini, R.; Materazzi, S.; Guerrero-Alba, R.; Valdez-Morales, E.; Cottrell, G. S.; Schoonjans, K.; Geppetti, P.; Vanner, S. J.; Bunnett, N. W.; Corvera, C. U., The TGR5 receptor mediates bile acid-induced itch and analgesia. The Journal of Clinical Investigation 2013, 123, (4), 1513). Consequently, a much lower systemic exposure or even a non systemic exposure may be necessary for the development of a non-toxic TGR5 agonist.

International patent application WO 2011/071565 describes imidazole and triazole based TGR5 agonists having a quaternary ammonium moiety.

On this basis, there is still a need for new compounds that may be of therapeutic value in the treatment of TGR5 related diseases, such as T2D and conditions that are associated with this disease including, lipid disorders such as dyslipidemia, hypertension, obesity, atherosclerosis and its sequelae.

SUMMARY OF THE INVENTION

The invention thus encompasses compounds of general Formula I, their pharmaceutically acceptable salts and solvates as well as methods of use of such compounds or compositions comprising such compounds as agonists of TGR5 activity.

In a general aspect, the invention provides compounds of general Formula I:

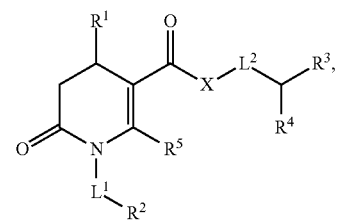

or pharmaceutically acceptable salts or solvates thereof,
wherein
$R^1$ is C1-C6-alkyl, aryl or heteroaryl, wherein said aryl moiety is independently substituted by one or more groups selected from the group consisting of halo, cyano, C1-C2-alkyl, C1-C2-alkoxy, C1-C2-haloalkyl, and 5- or 6-membered aryl, and said heteroaryl moiety is optionally independently substituted by one or more groups selected from the group consisting of halo, cyano, C1-C2-alkyl, C1-C2-alkoxy, C1-C2-haloalkyl, and 5- or 6-membered aryl;
$L^1$ is a single bond or $(CH_2)_n$, wherein n is 1, 2 or 3;
$R^2$ is H, C1-C4 alkyl, alkenyl, alkinyl, alkoxy, hydroxy, hydroxycarbonyl, alkoxycarbonyl, carbamoyl, aminoalkyl, alkylaminoalkyl, dialkylaminoalkyl, alkoxycarbonylamino, cyano, alkylsulfonyl, aralkyl, cycloalkyl, heterocyclyl, heteroaryl, wherein said heterocyclyl moiety is optionally substituted by one or more substituents independently selected from the group consisting of alkyl and alkoxycarbonyl, and said heteroaryl moiety is optionally substituted by one or more C1-C2 alkyl;

$L^2$ is a single bond or $(CH_2)_n$, wherein n is 1 or 2;

$R^3$ is aryl, heteroaryl, cycloalkyl or arylcarbonyl wherein each of said moieties is optionally substituted by one or more substituents independently selected from the group consisting of halo, alkyl, haloalkyl, aryl, cyano, alkoxy, haloalkoxy, alkoxycarbonyl, aminoalkoxy, alkylaminoalkoxy, dialkylaminoalkoxy, $HO_3S$-alkoxy,

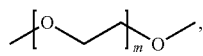

wherein m is 1 to 500, $[N(R^8)_3\text{-alkoxy}]^+$ $Q^-$, wherein $R^8$ is linear C1-C4-alkyl and $Q^-$ is a counter anion, and a cyclic moiety selected from the group consisting of

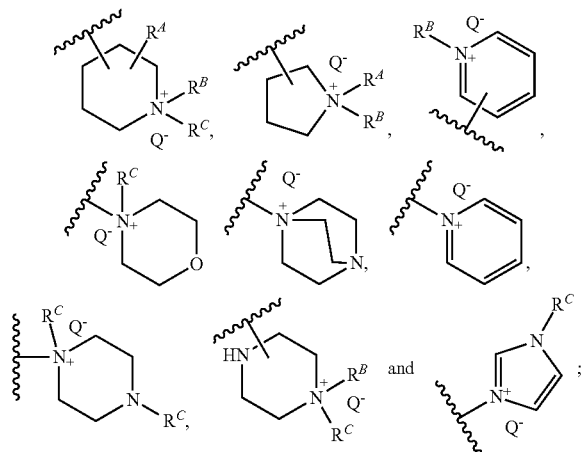

wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion;

or wherein said cycloalkyl moiety is fused to a an aryl, preferably phenyl, moiety;

$R^4$ is H, C1-C2-alkyl or 5- or 6-membered aryl;

$R^5$ is H, C1-C4-alkyl, 5- or 6-membered aryl, alkoxyalkyl; and

X is O or NR', wherein R' is H, C1-C2-alkyl or R' taken together with $L^2$ and $R^3$ form a 5- or 6-membered heterocyclyl moiety which is optionally fused to an aryl moiety.

Suitable, generally pharmaceutically acceptable, counter anions $Q^-$ are well known to those skilled in the art. Non-limiting examples of suitable counter anions $Q^-$ include acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, halides such as fluoride, chloride, bromide and iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate. Preferred counter anions $Q^-$ are halides such as fluoride, chloride, bromide and iodide, especially iodide. Unless otherwise specified, the above definition of $Q^-$ applies at all occurrences of Q throughout the application.

In another aspect, the present invention provides a pharmaceutical composition comprising at least one compound according to the invention or a pharmaceutically acceptable salt or solvate thereof.

The invention also relates to the use of the above compounds or their pharmaceutically acceptable salts and solvates as modulators of TGR5, preferably as agonists of TGR5 and more preferably as agonists of TGR5 exerting their action locally in the intestine with low or even without systemic exposure. In view of the drawbacks reported for systemic TGR5 agonists, the preferred agonists of the invention have the advantage of enhancing safety and the therapeutic index for potential chronic administration. The invention further provides the use of a compound according to the invention or a pharmaceutically acceptable salt or solvate thereof as a medicament. Preferably, the medicament is used for the treatment and/or prevention of TGR5 related diseases, such as metabolic and/or gastrointestinal diseases.

Metabolic diseases within the meaning of the present invention include, but are not limited to, type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

In a preferred embodiment, the metabolic disease is type II diabetes, a lipid disorder such as dyslipidemia, hypertension, obesity, or atherosclerosis and its sequelae, preferably the disease is type II diabetes.

Gastrointestinal diseases within the meaning of the present invention include, but are not limited to, Inflammatory Bowel Diseases (IBD) including but not limited to colitis, Ulcerative colitis (UC) and Crohn's Disease (CD), and Irritable Bowel Syndrome (IBS), intestinal injury disorders such as short-bowel syndrome, diseases involving intestinal barrier dysfunction such as proctitis and pouchitis, and gastrointestinal disorders characterized by hypermotilenemia or gastrointestinal hypermotility, including but not limited to any type of diarrhea.

In a preferred embodiment the gastrointestinal disease is Inflammatory Bowel Diseases (IBD) including but not limited to colitis, Ulcerative colitis (UC) and Crohn's Disease (CD).

DETAILED DESCRIPTION OF THE INVENTION

As noted above, the invention relates to compounds of Formula I, as well as their pharmaceutically acceptable salts and solvates.

Preferred compounds of Formula I and pharmaceutically acceptable salts and solvates thereof are those wherein one or more of $R^1$, $R^2$, $R^3$, $R^4$, $R^5$, $L^1$, $L^2$ and X are defined as follows:

$R^1$ is C1-C4 alkyl, 5- or 6-membered aryl or 5- to 9-membered heteroaryl, wherein said aryl moiety is independently substituted by one or more groups selected from the group consisting of halo, C1-C2-alkyl, C1-C2-alkoxy, C1-C2-haloalkyl, and 5- or 6-membered aryl, and said heteroaryl moiety is optionally independently substituted by one or more groups selected from the group consisting of halo, C1-C2-alkyl, C1-C2-alkoxy, C1-C2-haloalkyl, and 5- or 6-membered aryl, preferably $R^1$ is C2-C4-alkyl, phenyl, pyridinyl or benzothiadiazolyl, wherein said phenyl or pyridinyl moiety is independently substituted by one or more substituents selected from the group consisting of halo, C1-C2-alkyl, C1-C2-alkoxy, C1-C2-haloalkyl, and 5- or 6-membered aryl, more preferably $R^1$ is n-propyl, phenyl or pyridinyl, independently substituted by one or more substituents selected from the group consisting of halo, C1-C2-alkyl, C1-C2-haloalkyl, still more preferably $R^1$ is phenyl or pyridinyl, independently substituted by one or more substituents selected from the group consisting of chloro, cyano, and trifluoromethyl, even more preferably $R^1$ is phenyl substituted by one chloro;

$L^1$ is $(CH_2)_n$, wherein n is 1, 2 or 3, preferably $L^1$ is $CH_2$;

$R^2$ is alkoxy, hydroxy, alkoxycarbonyl, cycloalkyl, heterocyclyl, or heteroaryl, said heteroaryl moiety being optionally substituted by one or more C1-C2 alkyl preferably methyl groups; preferably $R^2$ is C1-C2-alkoxy, hydroxyl, C1-C2-alkoxycarbonyl, C3-C5-cycloalkyl, C5-C6-heterocyclyl comprising 1 or 2 oxygen atoms, C5-C6-heteroaryl comprising 1 oxygen atom and 0, 1 or 2 nitrogen atoms, said C5-C6-heteroaryl moiety being optionally substituted by one methyl group, more preferably $R^2$ is methoxy, hydroxyl, methoxycarbonyl, cyclopropyl, cyclobutyl, furanyl, 3-methyl-1,2,4-oxadiazol-5-yl, tetrahydrofuranyl or 1,3-dioxolanyl, even more preferably $R^2$ is tetrahydrofuranyl;

$L^2$ is a single bond;

$R^3$ is phenyl, substituted by one or more substituents independently selected from the group consisting of halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C8-alkoxy,

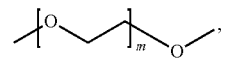

wherein m is 1 to 500, preferably 1 to 50, and $[N(R^8)_3$—C2-C6-alkoxy$]^+$ $Q^-$, wherein $R^8$ is C1-C2-alkyl and $Q^-$ is a counter anion, preferably $R^3$ is phenyl, substituted by one or more substituents independently selected from the group consisting of halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C6-alkoxy,

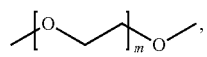

wherein m is 1 to 500, preferably 1 to 50, and $[N(R^8)_3$—C2-C6-alkoxy$]^+$ $Q^-$, wherein $R^8$ is C1-C2-alkyl and $Q^-$ is a counter anion, more preferably $R^3$ is phenyl, substituted by one or more substituents independently selected from the group consisting of halo, methyl, trifluoromethyl, phenyl, cyano, methoxy, trifluoromethoxy, methoxycarbonyl, di-methylaminoalkoxy, $HO_3S$—$CH_2CH_2O$—

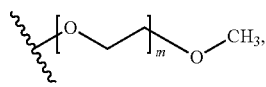

wherein m is 1 to 500, preferably 1 to 50, and $[N(R^8)_3$—C2-C6-alkoxy$]^+$ $Q^-$, wherein $R^8$ is methyl and $Q^-$ is a counter anion, still more preferably $R^3$ is phenyl, substituted by one or more substituents independently selected from the group consisting of chloro, fluoro, methyl, trifluoromethyl, phenyl, cyano, methoxy, trifluoromethoxy, methoxycarbonyl, di-methylaminoalkoxy,

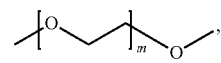

wherein m is 1 to 500, preferably 1 to 50, and $[N(R^8)_3$—C2-C6-alkoxy$]^+$ $Q^-$, wherein $R^8$ is methyl and $Q^-$ is a counter anion;

$R^4$ is H;

$R^5$ is methyl;

X is O.

Particularly preferred compounds of Formula I and pharmaceutically acceptable salts and solvates thereof are those wherein $R^3$ is aryl, heteroaryl, cycloalkyl or arylcarbonyl, preferably aryl or heterorayl, more preferably phenyl or pyridinyl, even more preferably phenyl, wherein each of said moieties is substituted by one or more substituents independently selected from $HO_3S$-alkoxy, preferably $HO_3S$—C2-C8-alkoxy, more preferably $HO_3S$—C2-C6-alkoxy, even more preferably $HO_3S$—$CH_2CH_2O$—, in particular in form of one of its salts, such as ammonium salts, preferably its $NH_4^+$ salt,

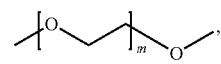

wherein m is 1 to 500, preferably 1 to 50, and $[N(R^8)_3$-alkoxy$]^+$ $Q^-$, wherein $R^8$ is linear C1-C4-alkyl and $Q^-$ is a counter anion, preferably $[N(R^8)_3$—C2-C6-alkoxy$]^+$ $Q^-$, wherein $R^8$ is C1-C2-alkyl and $Q^-$ is a counter anion, more preferably $[N(R^8)_3$—C2-C6-alkoxy$]^+$ $Q^-$, wherein $R^8$ is methyl and $Q^-$ is a counter anion. Indeed, without wanting to be bound to any theory, the present inventors believe that the $HO_3S$-alkoxy, polyethyleneglycol, and $[N(R^8)_3$-alkoxy$]^+$ $Q^-$, moieties on the $R^3$ substituent as defined herein (in the case of the $HO_3S$-alkoxy moiety especially its pharmaceutically acceptable salts) particularly limit the absorption of the compounds of the invention in the intestine and thus decrease their systemic action.

Further preferred compounds of Formula I and pharmaceutically acceptable salts and solvates thereof are those wherein $L^1$ and $R^2$ are taken together to form a moiety selected from the group consisting of cycloalkylmethyl, heterocyclylmethyl, heteroarylmethyl, 2-alkoxyeth-1-yl, 3-alkoxyprop-1-yl, alkoxycarbonylmethyl, said heteroarylmethyl moiety being optionally substituted by one or more C1-C2 alkyl groups on its heteroaryl part, preferably $L^1$ and $R^2$ are taken together to form a moiety selected from the group consisting of C3-C5-cycloalkylmethyl, C5-C6-heterocyclylmethyl, C5-C6-heteroarylmethyl, 2-C1-C2-alkoxyeth-1-yl, 3-C1-C2-alkoxyprop-1-yl, C1-C2-alkoxycarbonylmethyl, said C5-C6-heteroarylmethyl moiety being optionally substituted by one or more methyl groups on its heteroaryl part more preferably $L^1$ and $R^2$ are taken together to form a moiety selected from the group consisting of C3-C4-cycloalkylmethyl, C5-heterocyclylmethyl, C5-heteroarylmethyl, 2-methoxyeth-1-yl, 3-methoxyprop-1-yl, methoxycarbonylmethyl, said C5-heteroarylmethyl moiety being optionally substituted by one methyl group on its heteroaryl part, even more preferably $L^1$ and $R^2$ are taken together to form a moiety selected from the group consisting of C3-C4-cycloalkylmethyl, furanylmethyl, 3-methyl-1,2,4-oxadiazol-5-ylmethyl, tetrahydrofuranylmethyl or 1,3-dioxolanylmethyl, 2-methoxyeth-1-yl, 3-methoxyprop-1-yl, methoxycarbonylmethyl, still more preferably $L^1$ and $R^2$ are taken together to form 2-methoxyeth-1-yl or tetrahydrofuranylmethyl, and still more preferably $L^1$ and $R^2$ are taken together to form tetrahydrofuranylmethyl.

In one embodiment of the invention, the compounds of Formula I are those of Formula II

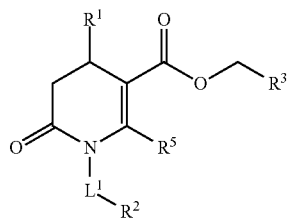

II and pharmaceutically acceptable salts and solvates thereof, wherein
$R^1$, $R^2$, $R^3$, $R^5$, and $L^1$ are as defined above with respect to Formula I.

Preferred compounds of Formula II and pharmaceutically acceptable salts and solvates thereof are those wherein $L^1$ and $R^2$ are taken together to form a moiety selected from the group consisting of cycloalkylmethyl, heterocyclylmethyl, heteroarylmethyl, 2-alkoxyeth-1-yl, 3-alkoxyprop-1-yl, alkoxycarbonylmethyl, said heteroarylmethyl moiety being optionally substituted by one or more C1-C2 alkyl groups on its heteroaryl part, preferably $L^1$ and $R^2$ are taken together to form a moiety selected from the group consisting of C3-C5-cycloalkylmethyl, C5-C6-heterocyclylmethyl, C5-C6-heteroarylmethyl, 2-C1-C2-alkoxyeth-1-yl, 3-C1-C2-alkoxyprop-1-yl, C1-C2-alkoxycarbonylmethyl, said C5-C6-heteroarylmethyl moiety being optionally substituted by one or more methyl groups on its heteroaryl part, more preferably $L^1$ and $R^2$ are taken together to form a moiety selected from the group consisting of C3-C4-cycloalkylmethyl, C5-heterocyclylmethyl, C5-heteroarylmethyl, 2-methoxyeth-1-yl, 3-methoxyprop-1-yl, methoxycarbonylmethyl, said C-5-heteroarylmethyl moiety being optionally substituted by one methyl group on its heteroaryl part, even more preferably $L^1$ and $R^2$ are taken together to form a moiety selected from the group consisting of C3-C4-cycloalkylmethyl, furanylmethyl, 3-methyl-1,2,4-oxadizol-5-ylmethyl, tetrahydrofuranylmethyl or 1,3-dioxolanylmethyl, 2-methoxyeth-1-yl, 3-methoxyprop-1-yl, methoxycarbonylmethyl, still more preferably $L^1$ and $R^2$ are taken together to form 2-methoxyeth-1-yl or tetrahydrofuranylmethyl, and still more preferably $L^1$ and $R^2$ are taken together to form tetrahydrofuranylmethyl.

In one embodiment, preferred compounds of Formula II are those of Formula IIa

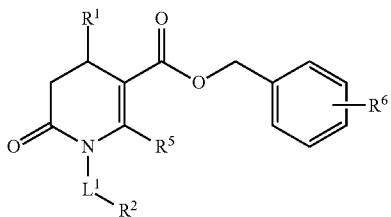

IIa and pharmaceutically acceptable salts and solvates thereof, wherein
$R^1$, $R^2$, $R^5$ and $L^1$ are as defined above with respect to Formula II, and
$R^6$ is halo, alkyl, haloalkyl, aryl, cyano, alkoxy, haloalkoxy, alkoxycarbonyl, aminoalkoxy, alkylaminoalkoxy, dialkylaminoalkoxy, HO$_3$S-alkoxy,

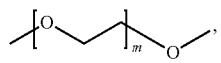

wherein m is 1 to 500, preferably 1 to 50,
$[N(R^8)_3\text{-alkoxy}]^+$ $Q^-$, wherein $R^8$ is linear C1-C4-alkyl and $Q^-$ is a counter anion, or
a cyclic moiety selected from the group consisting of

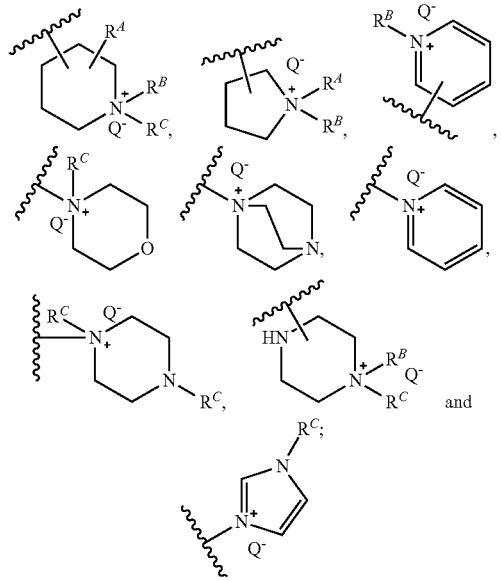

and wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion;
preferably $R^G$ is halo, C1-C2-alkyl, C1-C2-haloalkyl, phenyl, cyano C-1-C2-alkoxy, C1-C2-haloalkoxy, C1-C2-alkoxycarbonyl, aminoalkoxy, C1-C2-alkylaminoalkoxy, di-C1-C2-alkylaminoalkoxy, HO$_3$S—C2-C8-alkoxy,

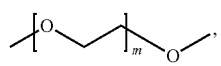

wherein m is 1 to 500, preferably 1 to 50, or
$[N(R^8)_3\text{—C2-C6-alkoxy}]^+$ $Q^-$, wherein $R^8$ is C1-C2-alkyl and $Q^-$ is a counter anion,
more preferably $R^6$ is halo, C1-C2-alkyl, C1-C2-haloalkyl, phenyl, cyano, C1-C2-alkoxy, C1-C2-haloalkoxy, C1-C2- alkoxycarbonyl, aminoalkoxy, C1-C2-alkylaminoalkoxy, di-C1-C2-alkylaminoalkoxy, HO₃S—C2-C6-alkoxy,

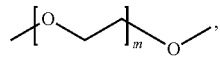

wherein m is 1 to 500, preferably 1 to 50, or [N(R⁸)₃—C2-C6-alkoxy]⁺ Q⁻, wherein R⁸ is C1-C2-alkyl and Q⁻ is a counter anion,
still more preferably R⁶ is halo, methyl, trifluoromethyl, phenyl, cyano, methoxy, trifluoromethoxy, methoxycarbonyl, di-methylaminoalkoxy, HO₃S—CH₂CH₂O—, or

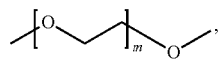

wherein m is 1 to 500, preferably 1 to 50, or [N(R⁸)₃—C2-C6-alkoxy]⁺ Q⁻, wherein R⁸ is methyl and Q⁻ is a counter anion,
even more preferably R⁶ is chloro, fluoro, methyl, trifluoromethyl, phenyl, cyano, methoxy, trifluoromethoxy, methoxycarbonyl, di-methylaminoalkoxy, HO₃S—CH₂CH₂O—,

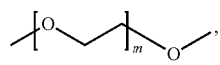

wherein m is 1 to 500, preferably 1 to 50, or [N(R⁸)₃—C2-C6-alkoxy]⁺ Q⁻, wherein R⁸ is methyl and Q⁻ is a counter anion.

Particularly interesting compounds of Formula IIa and pharmaceutically acceptable salts and solvates thereof are those, wherein R⁶ is HO₃S-alkoxy, preferably HO₃S—C2-C8-alkoxy, more preferably HO₃S—C2-C6-alkoxy, still more preferably HO₃S—CH₂CH₂O—, in particular in form of one of its salts, such as ammonium salts,

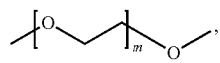

wherein m is 1 to 500 preferably 1 to 50, or [N(R⁸)₃-alkoxy]⁺ Q⁻, wherein R⁸ is linear C1-C4-alkyl and Q⁻ is a counter anion, preferably [N(R⁸)₃—C2-C6-alkoxy]⁺ Q⁻, wherein R⁸ is C1-C2-alkyl and Q⁻ is a counter anion, more preferably [N(R⁸)₃—C2-C6-alkoxy]⁺ Q⁻, wherein R⁸ is methyl and Q⁻ is a counter anion.

In one embodiment, the compounds of Formula IIa are selected from the group consisting of Formulae IIa-1, IIIa-2, and IIa-3:

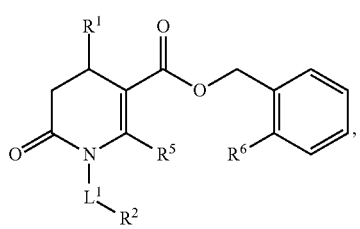

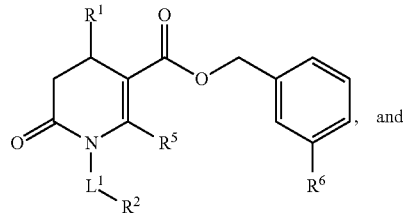

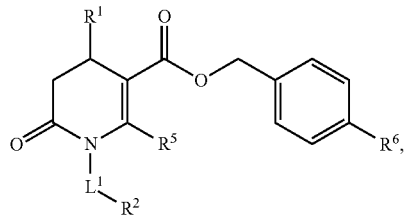

and pharmaceutically acceptable salts and solvates thereof, wherein R¹, R², R⁵, L¹, and R⁶ are as defined above with respect to Formula IIa.

Particularly preferred compounds of Formulae II, IIa, IIa-1, IIa-2, IIa-3 and IIb and pharmaceutically acceptable salts and solvates thereof are those wherein R⁵ is methyl.

In another embodiment, preferred compounds of Formula I are those of Formula III

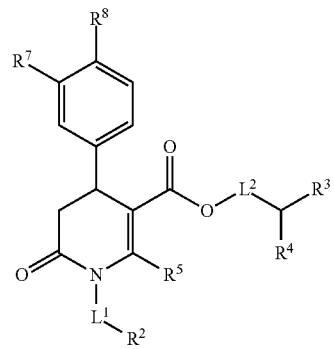

and pharmaceutically acceptable salts and solvates thereof, wherein
R², R³, R⁴, R⁵, L¹ and L² are as defined above with respect to Formula I; and
R⁷ and R⁸ are independently selected from the group consisting of H, halo, haloalkyl, and cyano, with the proviso that at least one of R⁷ and R⁸ is not H; preferably R⁷ and R⁸ are independently selected from the group consisting of H, chloro, trifluoromethyl, and cyano, with the proviso that at least one of R⁷ and R⁸ is not H.

Preferred compounds of Formula III and pharmaceutically acceptable salts and solvates thereof are those wherein L¹ and R² are taken together to form a moiety selected from the group consisting of cycloalkylmethyl, heterocyclylmethyl, heteroarylmethyl, 2-alkoxyeth-1-yl, 3-alkoxyprop-1-yl, alkoxycarbonylmethyl, said heteroarylmethyl moiety being optionally substituted by one or more C1-C2 alkyl groups on its heteroaryl part, preferably L¹ and R² are taken together to form a moiety selected from the group consisting of C3-C5-cycloalkylmethyl, C5-C6-heterocyclylmethyl, C5-C6-heteroarylmethyl, 2-C1-C2-alkoxyeth-1-yl, 3-C1-

C2-alkoxyprop-1-yl, C1-C2-alkoxycarbonylmethyl, said C5-C6-heteroarylmethyl moiety being optionally substituted by one or more methyl groups on its heteroaryl part, more preferably $L^1$ and $R^2$ are taken together to form a moiety selected from the group consisting of C3-C4-cycloalkylmethyl, C5-heterocyclylmethyl, C5-heteroarylmethyl, 2-methoxyeth-1-yl, 3-methoxyprop-1-yl, methoxycarbonylmethyl, said C5-heteroarylmethyl moiety being optionally substituted by one methyl group on its heteroaryl part, even more preferably $L^1$ and $R^2$ are taken together to form a moiety selected from the group consisting of C3-C4-cycloalkylmethyl, furanylmethyl, 3-methyl-1,2,4-oxadiazol-5-ylmethyl, tetrahydrofuranylmethyl or 1,3-dioxolanylmethyl, 2-methoxyeth-1-yl, 3-methoxyprop-1-yl, methoxycarbonylmethyl, still more preferably $L^1$ and $R^2$ are taken together to form 2-methoxyeth-1-yl or tetrahydrofuranylmethyl, and still more preferably $L^1$ and $R^2$ are taken together to form tetrahydrofuranylmethyl.

In one embodiment, preferred compounds of Formula III are those of Formula IIIa

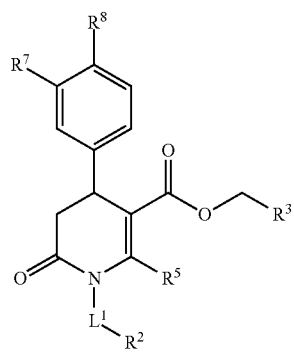

IIIa and pharmaceutically acceptable salts and solvates thereof, wherein
$R^2$, $R^3$, $R^4$, $R^6$, $R^7$, $R^8$, and $L^1$ are as defined above with respect to Formula III.

Particularly preferred compounds of Formula IIa are those of Formula IIIb

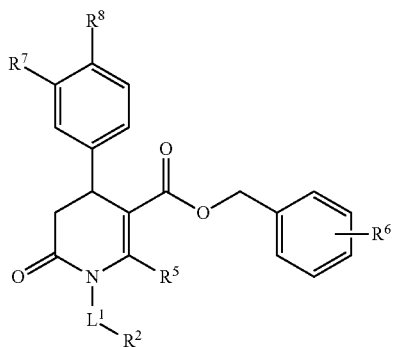

IIIb and pharmaceutically acceptable salts and solvates thereof, wherein
$R^2$, $R^3$, $R^4$, $R^5$, $R^7$, $R^8$, and $L^1$ are as defined above with respect to Formula IIIa; and
$R^6$ is halo, alkyl, haloalkyl, aryl, cyano, alkoxy, haloalkoxy, alkoxycarbonyl, aminoalkoxy, alkylaminoalkoxy, dialkylaminoalkoxy, $HO_3S$-alkoxy,

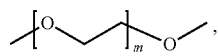

wherein m is 1 to 500, preferably 1 to 50,
$[N(R^8)_3\text{-alkoxy}]^+$ $Q^-$, wherein $R^8$ is linear C1-C4-alkyl and $Q^-$ is a counter anion, or
a cyclic moiety selected from the group consisting of

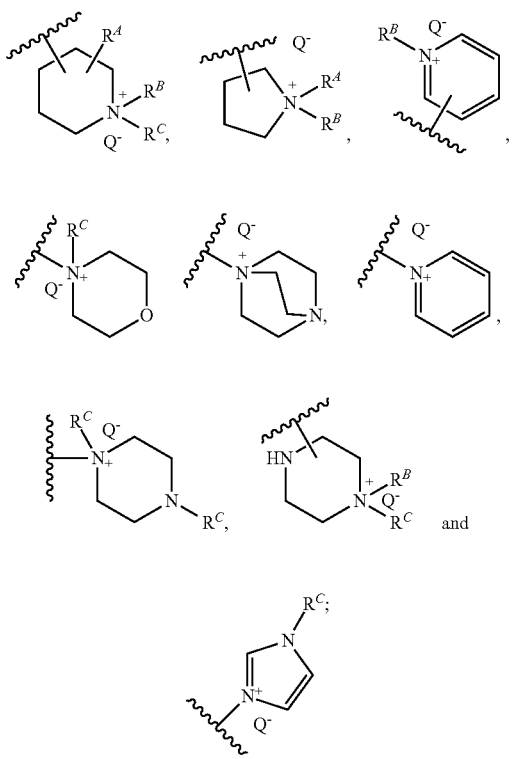

and wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion;
preferably $R^6$ is halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C8-alkoxy,

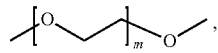

wherein m is 1 to 500, preferably 1 to 50, or
$[N(R^6)_3$—C2-C6-alkoxy$]^+$ $Q^-$, wherein $R^8$ is C1-C2-alkyl and $Q^-$ is a counter anion,
more preferably $R^6$ is halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C6-alkoxy,

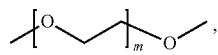

wherein m is 1 to 500, preferably 1 to 50, or
$[N(R^8)_3$—C2-C6-alkoxy$]^+$ $Q^-$, wherein $R^8$ is C1-C2-alkyl and $Q^-$ is a counter anion, still more preferably $R^6$ is halo, methyl, trifluoromethyl, phenyl, cyano, methoxy, trifluoromethoxy, methoxycarbonyl, di-methylaminoalkoxy, $HO_3S$—$CH_2CH_2O$—,

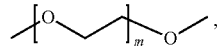

wherein m is 1 to 500, preferably 1 to 50, or
[$N(R^8)_3$—C2-C6-alkoxy]$^+$ Q$^-$, wherein $R^8$ is methyl and Q$^-$ is a counter anion, even more preferably $R^6$ is chloro, fluoro, methyl, trifluoromethyl, phenyl, cyano, methoxy, trifluoromethoxy, methoxycarbonyl, di-methylaminoalkoxy, $HO_3S$—$CH_2CH_2O$—,

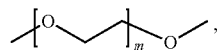

wherein m is 1 to 500, preferably 1 to 50, or
[$N(R^8)_3$—C2-C6-alkoxy]$^+$ Q$^-$, wherein $R^8$ is methyl and Q$^-$ is a counter anion.

Particularly interesting compounds of Formula IIIb and pharmaceutically acceptable salts and solvates thereof are those, wherein $R^6$ is $HO_3S$-alkoxy, preferably $HO_3S$—C2-C8-alkoxy, more preferably $HO_3S$—C2-C6-alkoxy, still more preferably $HO_3S$—$CH_2CH_2O$—, in particular in form of one of its salts, such as ammonium salts, or

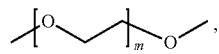

wherein m is 1 to 500 preferably 1 to 50, or [$N(R^8)_3$-alkoxy]$^+$ Q$^-$, wherein $R^8$ is linear C1-C4-alkyl and Q$^-$ is a counter anion, preferably [$N(R^8)_3$—C2-C6-alkoxy]$^+$ Q$^-$, wherein $R^8$ is C1-C2-alkyl and Q$^-$ is a counter anion, more preferably [$N(R^8)_3$—C2-C6-alkoxy]$^+$ Q$^-$, wherein $R^8$ is methyl and Q$^-$ is a counter anion.

In one embodiment, the compounds of Formula IIIb are selected from the group consisting of Formulae IIIb-1, IIIb-2, and IIIb-3:

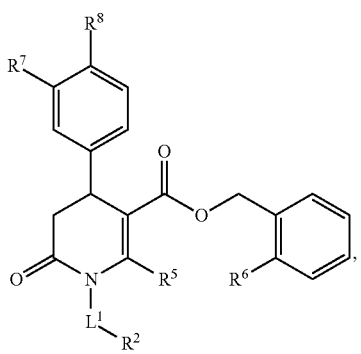

IIIb-1

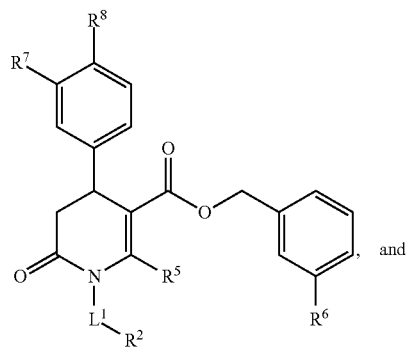

IIIb-2

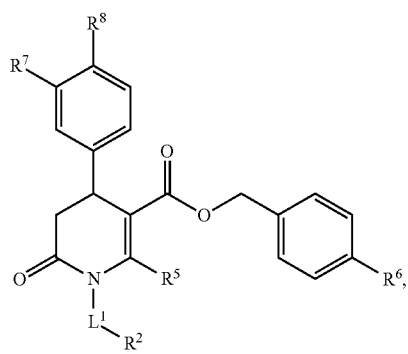

IIIb-3 and pharmaceutically acceptable salts and solvates thereof, wherein $R^2$, $R^3$, $R^4$, $R^5$, $R^7$, $R^8$, $L^1$, and $R^6$ are as defined above with respect to Formula IIIb.

Particularly preferred compounds of Formulae III, IIIa, IIIb, IIIb-1, IIIb-2 and IIIb-3 and pharmaceutically acceptable salts and solvates thereof are those wherein $R^5$ is methyl.

In another embodiment, preferred compounds of Formula I are those of Formula IV

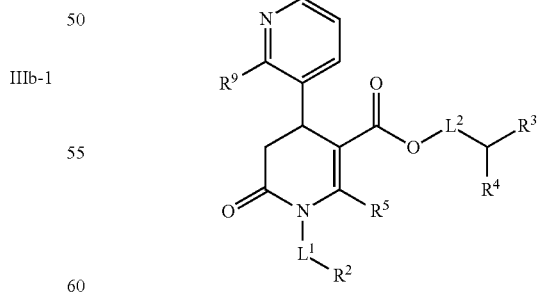

IV and pharmaceutically acceptable salts and solvates thereof, wherein
$R^2$, $R^3$, $R^4$, $R^5$, $L^1$ and $L^2$ are as defined above with respect to Formula I; and
$R^9$ and $R^{10}$ are independently selected from the group consisting of H, halo, haloalkyl, and cyano, with the proviso that at least one of $R^9$ and $R^{10}$ is not H, preferably $R^9$ and $R^{10}$ are independently selected from the group consisting of H, chloro, trifluoromethyl, and cyano, with the proviso that at least one of $R^9$ and $R^{10}$ is not H, more preferably $R^9$ and $R^{10}$ are independently selected from the group consisting of H, chloro, and trifluoromethyl, with the proviso that at least one of $R^9$ and $R^{10}$ is not H.

Preferred compounds of Formula IV and pharmaceutically acceptable salts and solvates thereof are those wherein $L^1$ and $R^2$ are taken together to form a moiety selected from the group consisting of cycloalkylmethyl, heterocyclylmethyl, heteroarylmethyl, 2-alkoxyeth-1-yl, 3-alkoxyprop-1-yl, alkoxycarbonylmethyl, said heteroarylmethyl moiety being optionally substituted by one or more C1-C2 alkyl groups on its heteroaryl part, preferably $L^1$ and $R^2$ are taken together to form a moiety selected from the group consisting of C3-C5-cycloalkylmethyl, C5-C6-heterocyclylmethyl, C5-C6-heteroarylmethyl, 2-C1-C2-alkoxyeth-1-yl, 3-C1-C2-alkoxyprop-1-yl, C1-C2-alkoxycarbonylmethyl, said C5-C6-heteroarylmethyl moiety being optionally substituted by one or more methyl groups on its heteroaryl part, more preferably $L^1$ and $R^2$ are taken together to form a moiety selected from the group consisting of C3-C4-cycloalkylmethyl, C5-heterocyclylmethyl, C5-heteroarylmethyl, 2-methoxyeth-1-yl, 3-methoxyprop-1-yl, methoxycarbonylmethyl, said C5-heteroarylmethyl moiety being optionally substituted by one methyl group on its heteroaryl part, even more preferably $L^1$ and $R^2$ are taken together to form a moiety selected from the group consisting of C3-C4-cycloalkylmethyl, furanylmethyl, 3-methyl-1,2,4-oxadiazol-5-ylmethyl, tetrahydrofuranylmethyl or 1,3-dioxolanylmethyl, 2-methoxyeth-1-yl, 3-methoxyprop-1-yl, methoxycarbonylmethyl, still more preferably $L^1$ and $R^2$ are taken together to form 2-methoxyeth-1-yl or tetrahydrofuranylmethyl, and still more preferably $L^1$ and $R^2$ are taken together to form tetrahydrofuranylmethyl.

In one embodiment, preferred compounds of Formula IV are those of Formula IVa

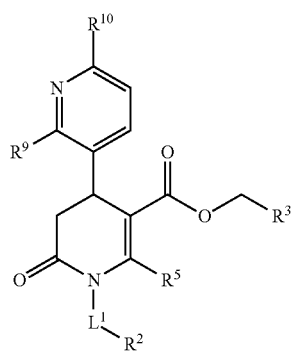

IVa and pharmaceutically acceptable salts and solvates thereof, wherein
$R^2, R^3, R^5, R^9, R^{10}$, and $L^1$ are as defined above with respect to Formula IV.

Particularly preferred compounds of Formula IVa and pharmaceutically acceptable salts and solvates thereof are those of Formula IVb

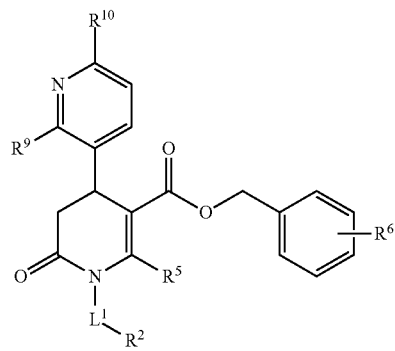

IVb and pharmaceutically acceptable salts, and solvates thereof, wherein
$R^2, R^5, R^9, R^{10}$, and $L^1$ are as defined above with respect to Formula IVa; and
$R^6$ is halo, alkyl, haloalkyl, aryl, cyano, alkoxy, haloalkoxy, alkoxycarbonyl, aminoalkoxy, alkylaminoalkoxy, dialkylaminoalkoxy, $HO_3S$-alkoxy, or

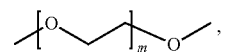

wherein m is 1 to 500, preferably 1 to 50,
$[N(R^8)_3\text{-alkoxy}]^+ Q^-$, wherein $R^8$ is linear C1-C4-alkyl and $Q^-$ is a counter anion, or
a cyclic moiety selected from the group consisting of

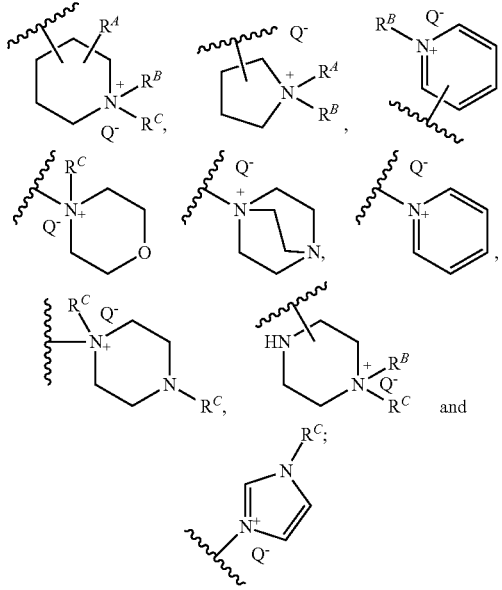

and wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion;
preferably $R^6$ is halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C8-alkoxy,

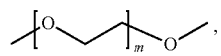

wherein m is 1 to 500, preferably 1 to 50, or
[N(R$^8$)$_3$—C2-C6-alkoxy]$^+$ Q$^-$, wherein R$^8$ is C1-C2-alkyl and Q$^-$ is a counter anion,
more preferably R$^6$ is halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, HO$_3$S—C2-C6-alkoxy,

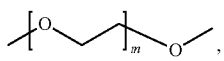

wherein m is 1 to 500, preferably 1 to 50, or
[N(R$^8$)$_3$—C2-C6-alkoxy]$^+$ Q$^-$, wherein R$^8$ is C1-C2-alkyl and Q$^-$ is a counter anion,
still more preferably R$^6$ is halo, methyl, trifluoromethyl, phenyl, cyano, methoxy, trifluoromethoxy, methoxycarbonyl, di-methylaminoalkoxy, HO$_3$S—CH$_2$CH$_2$O—, or

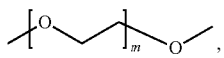

wherein m is 1 to 500, preferably 1 to 50, or
[N(R$^8$)$_3$—C2-C6-alkoxy]' a, wherein R$^8$ is methyl and Q$^-$ is a counter anion,
even more preferably R$^6$ is chloro, fluoro, methyl, trifluoromethyl, phenyl, cyano, methoxy, trifluoromethoxy, methoxycarbonyl, di-methylaminoalkoxy, HO$_3$S—CH$_2$CH$_2$O—,

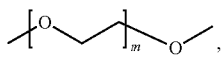

wherein m is 1 to 500, preferably 1 to 50, or
[N(R$^8$)$_3$—C2-C6-alkoxy]$^+$ Q$^-$, wherein R$^8$ is methyl and Q$^-$ is a counter anion.

Particularly interesting compounds of Formula IVb and pharmaceutically acceptable salts and solvates thereof are those, wherein R$^6$ is HO$_3$S-alkoxy, preferably HO$_3$S—C2-C8-alkoxy, more preferably HO$_3$S—C2-C6-alkoxy, still more preferably HO$_3$S—CH$_2$CH$_2$O—, in particular in form of one of its salts, such as ammonium salts, or

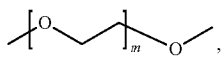

wherein m is 1 to 500 preferably 1 to 50, or [N(R$^8$)$_3$-alkoxy]$^+$ Q$^-$, wherein R$^8$ is linear C1-C4-alkyl and Q$^-$ is a counter anion, preferably [N(R$^8$)$_3$—C2-C6-alkoxy]$^+$ Q$^-$, wherein R$^8$ is C1-C2-alkyl and Q$^-$ is a counter anion, more preferably [N(R$^8$)$_3$—C2-C6-alkoxy]$^+$ Q$^-$, wherein R$^8$ is methyl and Q$^-$ is a counter anion.

In one embodiment, the compounds of Formula IVb are selected from the group consisting of Formulae IVb-1, IVb-2, and IVb-3:

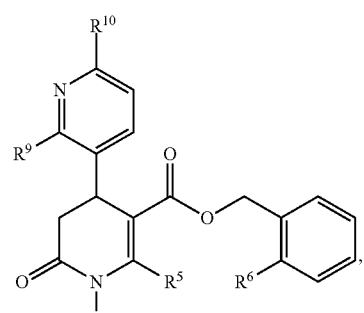

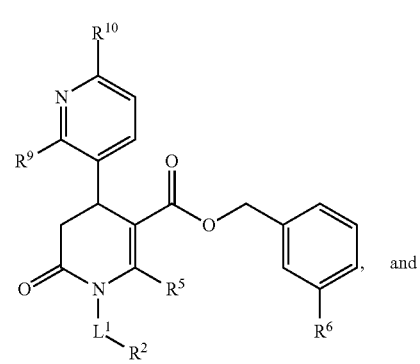

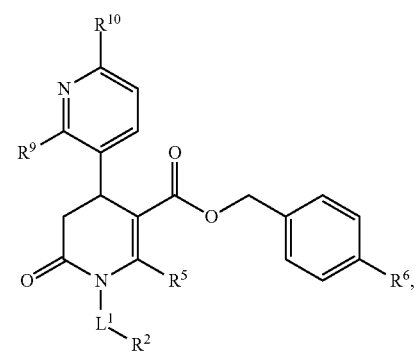

and pharmaceutically acceptable salts and solvates thereof, wherein R$^2$, R$^5$, R$^9$, R$^{10}$, L$^1$, and R$^6$ are as defined above with respect to Formula IVb.

Particularly preferred compounds of Formulae IV, IVa, IVb, IVb-1, IVb-2, and IVb-3, and pharmaceutically acceptable salts and solvates thereof are those wherein R$^5$ is methyl.

In another embodiment, preferred compounds of Formula I are those of Formula V

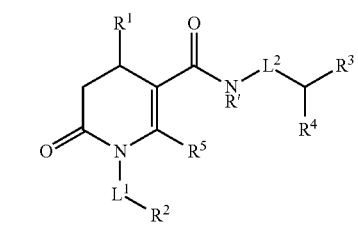

and pharmaceutically acceptable salts, and solvates thereof, wherein $R^1$, $R^2$, $R^3$, $R^4$, $R^5$, R', $L^1$, and $L^2$ are as defined above with respect to Formula I.

Preferred compounds of Formula V and pharmaceutically acceptable salts and solvates thereof are those wherein R' is H, methyl or R' taken together with $L^2$ and $R^3$ form a 5- or 6-membered heterocyclyl moiety which is optionally fused to an aryl moiety, preferably R' is H, methyl or R' taken together with $L^2$ and $R^3$ form a 6-membered heterocyclyl moiety which is optionally fused to a phenyl moiety, more preferably R' is H, methyl or R' taken together with $L^2$ and $R^3$ form a piperazinyl moiety which is optionally fused to a phenyl moiety, even more preferably R' is H, methyl or R' taken together with $L^2$ and $R^3$ form a piperazinyl moiety which is fused to a phenyl moiety; and/or $L^1$ and $R^2$ are taken together to form a moiety selected from the group consisting of cycloalkylmethyl, heterocyclylmethyl, heteroarylmethyl, 2-alkoxyeth-1-yl, 3-alkoxyprop-1-yl, alkoxycarbonylmethyl, said heteroarylmethyl moiety being optionally substituted by one or more C1-C2 alkyl groups on its heteroaryl part, preferably $L^1$ and $R^2$ are taken together to form a moiety selected from the group consisting of C3-C5-cycloalkylmethyl, C5-C6-heterocyclylmethyl, C5-C6-heteroarylmethyl, 2-C1-C2-alkoxyeth-1-yl, 3-C1-C2-alkoxyprop-1-yl, C1-C2-alkoxycarbonylmethyl, said C5-C6-heteroarylmethyl moiety being optionally substituted by one or more methyl groups on its heteroaryl part, more preferably $L^1$ and $R^2$ are taken together to form a moiety selected from the group consisting of C3-C4-cycloalkylmethyl, C5-heterocyclylmethyl, C5-heteroarylmethyl, 2-methoxyeth-1-yl, 3-methoxyprop-1-yl, methoxycarbonylmethyl, said C5-heteroarylmethyl moiety being optionally substituted by one methyl group on its heteroaryl part, even more preferably $L^1$ and $R^2$ are taken together to form a moiety selected from the group consisting of C3-C4-cycloalkylmethyl, furanylmethyl, 3-methyl-1,2,4-oxadiazol-5-ylmethyl, tetrahydrofuranylmethyl or 1,3-dioxolanylmethyl, 2-methoxyeth-1-yl, 3-methoxyprop-1-yl, methoxycarbonylmethyl, still more preferably $L^1$ and $R^2$ are taken together to form 2-methoxyeth-1-yl or tetrahydrofuranylmethyl, and still more preferably $L^1$ and $R^2$ are taken together to form tetrahydrofuranylmethyl.

Preferred compounds of Formula V are those of Formula Va

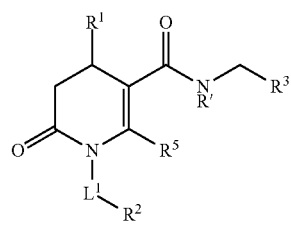

and pharmaceutically acceptable salts and solvates thereof, wherein
$R^1$, $R^2$, $R^3$, $R^5$, R' and $L^1$ are as defined above with respect to Formula V.

In one embodiment, preferred compounds of Formula Va are those of Formula Vb

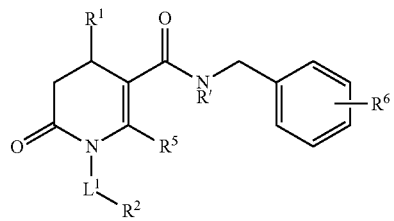

and pharmaceutically acceptable salts and solvates thereof, wherein
$R^1$, $R^2$, $R^5$, R', and $L^1$ are as defined above with respect to Formula Va; and $R^6$ is halo, alkyl, haloalkyl, aryl, cyano, alkoxy, haloalkoxy, alkoxycarbonyl, aminoalkoxy, alkylaminoalkoxy, dialkylaminoalkoxy, $HO_3S$-alkoxy,

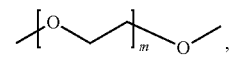

wherein m is 1 to 500, preferably 1 to 50,
$[N(R^8)_3\text{-alkoxy}]^+$ $Q^-$, wherein $R^8$ is linear C1-C4-alkyl and $Q^-$ is a counter anion, or
a cyclic moiety selected from the group consisting of

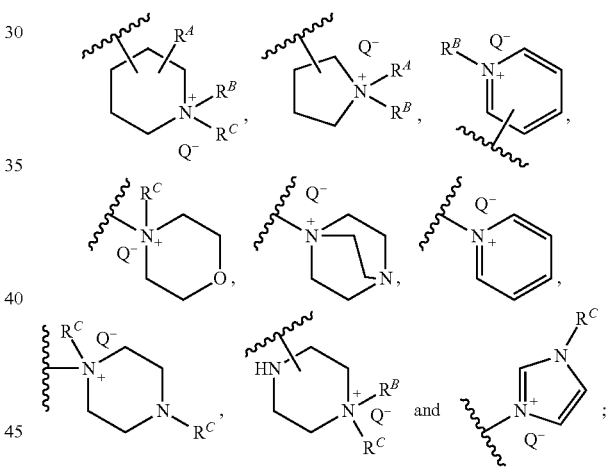

wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion,
preferably $R^6$ is halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C8-alkoxy,

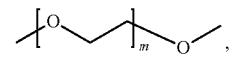

wherein m is 1 to 500, preferably 1 to 50, or
$[N(R^8)_3\text{—C2-C6alkoxy}]^+$ $Q^-$, wherein $R^8$ is C1-C2-alkyl and $Q^-$ is a counter anion,
more preferably $R^6$ is halo, C1-C2-alkyl, C1-C2-haloalkyl, phenyl, cyano, C1-C2-alkoxy, C1-C2-haloalkoxy, C1-C2-alkoxycarbonyl, aminoalkoxy, C1-C2-alkylaminoalkoxy, di-C1-C2-alkylaminoalkoxy, $HO_3S$—C2-C6-alkoxy,

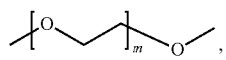

wherein m is 1 to 500, preferably 1 to 50, or
[N(R⁸)₃—C2-C6alkoxy]⁺ Q⁻, wherein R⁸ is C1-C2-alkyl and Q⁻ is a counter anion,
still more preferably R⁶ is halo, methyl, trifluoromethyl, phenyl, cyano, methoxy, trifluoromethoxy, methoxycarbonyl, di-methylaminoalkoxy, HO₃S—CH₂CH₂O—,

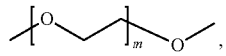

wherein m is 1 to 500, preferably 1 to 50, or
[N(R⁸)₃—C2-C6-alkoxy]⁺ Q⁻, wherein R⁸ is methyl and Q⁻ is a counter anion,
even more preferably R⁶ is chloro, fluoro, methyl, trifluoromethyl, phenyl, cyano, methoxy, trifluoromethoxy, methoxycarbonyl, di-methylaminoalkoxy, HO₃S—CH₂CH₂O—, or

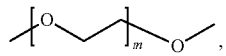

wherein m is 1 to 500, preferably 1 to 50,
[N(R⁸)₃—C2-C6-alkoxy]⁺ Q⁻, wherein R⁸ is methyl and Q⁻ is a counter anion.

Particularly interesting compounds of Formula Vb and pharmaceutically acceptable salts and solvates thereof are those, wherein R⁶ is HO₃S-alkoxy, preferably HO₃S—C2-C8-alkoxy, more preferably HO₃S—C2-C6-alkoxy, still more preferably HO₃S—CH₂CH₂O—, in particular in form of one of its salts, such as ammonium salts, or

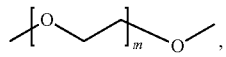

wherein m is 1 to 500 preferably 1 to 50, or [N(R⁸)₃-alkoxy]⁺ Q⁻, wherein R⁸ is linear C1-C4-alkyl and Q⁻ is a counter anion, preferably [N(R⁸)₃—C2-C6-alkoxy]⁺ Q⁻, wherein R⁸ is C1-C2-alkyl and Q⁻ is a counter anion, more preferably [N(R⁸)₃—C2-C6-alkoxy]⁺ Q⁻, wherein R⁸ is methyl and Q⁻ is a counter anion.

In one embodiment, the compounds of Formula Vb are selected from the group consisting of Formulae Vb-1, Vb-2, and Vb-3:

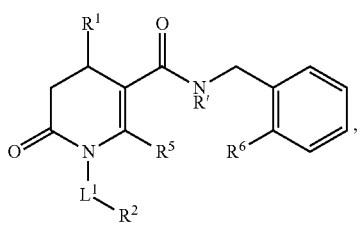

Vb-1

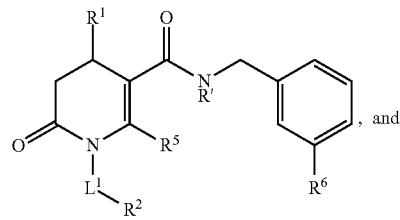

Vb-2

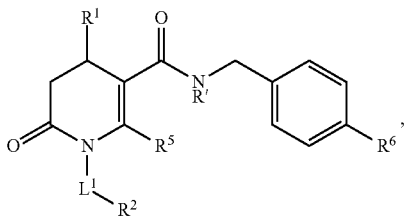

Vb-3 and pharmaceutically acceptable salts and solvates thereof, wherein R¹, R², R⁵, R', L¹, and R⁶ are as defined above with respect to Formula Vb.

In one embodiment, preferred compounds of Formula Vb are those of Formula Vc

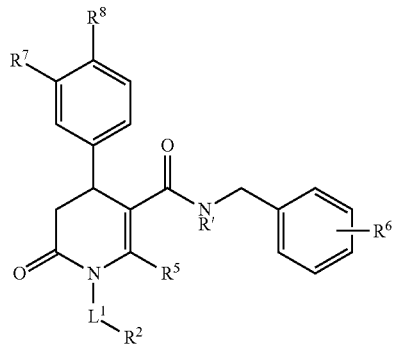

Vc and pharmaceutically acceptable salts, and solvates thereof, wherein R², R⁵, R⁶, R' and L¹ are as defined above with respect to Formula Vb; and
R⁷ and R⁸ are independently selected from the group consisting of H, halo, haloalkyl, and cyano, with the proviso that at least one of R⁷ and R⁸ is not H; preferably R⁷ and R⁸ are independently selected from the group consisting of H, chloro, trifluoromethyl, and cyano, with the proviso that at least one of R⁷ and R⁸ is not H, more preferably R⁷ is H and R⁸ is chloro.

In one embodiment, the compounds of Formula Vc are selected from the group consisting of Formulae Vc-1, Vc-2, and Vc-3:

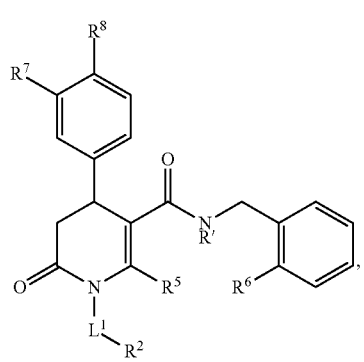

Vc-1

-continued

Vc-2

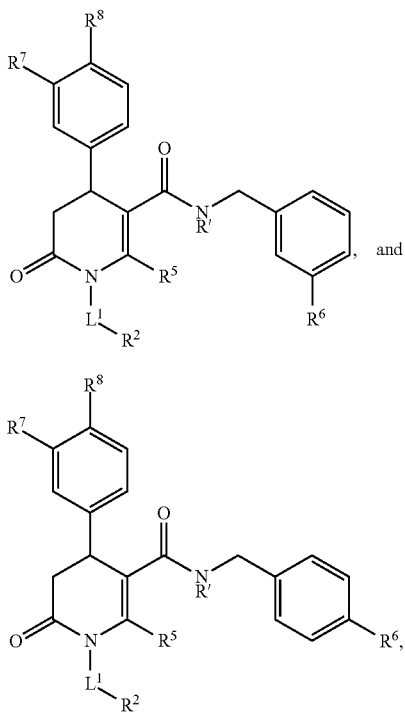

Vc-3 and pharmaceutically acceptable salts and solvates thereof, wherein $R^2$, $R^5$, $R^6$, $R^7$, $R^8$, R', and $L^1$ are as defined above with respect to Formula Vc.

Particularly preferred compounds of Formulae V, Va, Vb, Vb-1, Vb-2, Vb-3, Vc, Vc-1, Vc-2, Vc-3 and pharmaceutically acceptable salts and solvates thereof are those wherein $R^5$ is methyl.

In a particularly preferred embodiment, the compounds of Formula I, any of its subformulae, and their pharmaceutically acceptable salts and solvates as described herein are those wherein $R^2$ is tetrahydrofuranyl, preferably $L^1$ is $CH_2$ and $R^2$ is tetrahydrofuranyl, more preferably they have Formula VI

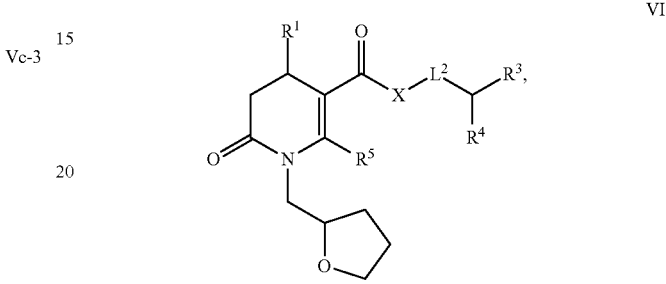

VI wherein $R^1$, $R^3$, $R^4$, $R^5$, X, and $L^2$ are as defined above with respect to Formula I or any of its subformulae and corresponding embodiments.

Particularly preferred compounds of the invention are those listed in Table 1 hereafter:

TABLE 1

| Compound | Structure |
|---|---|
| 1 | ![structure] |
| 2 | ![structure] |
| 3 | ![structure] |

TABLE 1-continued
| Compound | Structure |
|---|---|
| 4 | 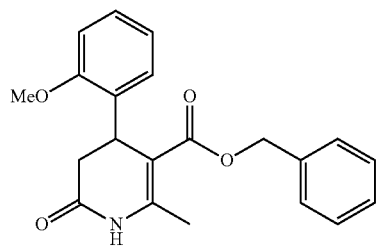 [SMILES: COc1ccccc1C1CC(=O)NC(C)=C1C(=O)OCc1ccccc1] |
| 5 | 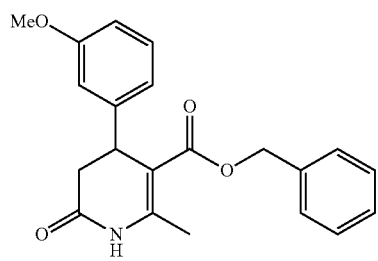 |
| 6 | 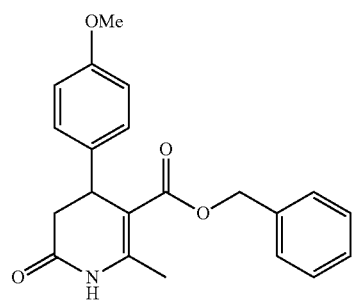 [SMILES: COc1ccc(C2CC(=O)NC(C)=C2C(=O)OCc2ccccc2)cc1] |
| 7 | 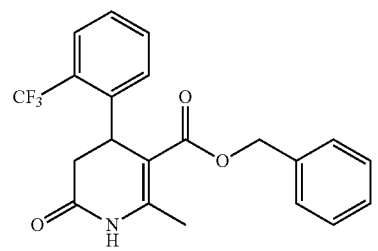 [SMILES: CC1=C(C(=O)OCc2ccccc2)C(c2ccccc2C(F)(F)F)CC(=O)N1] |
| 8 | 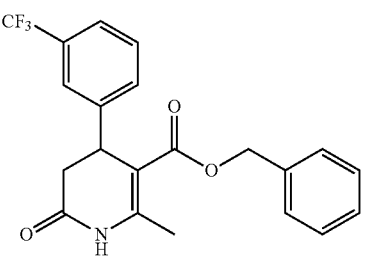 [SMILES: CC1=C(C(=O)OCc2ccccc2)C(c2cccc(C(F)(F)F)c2)CC(=O)N1] |

TABLE 1-continued

| Compound | Structure |
|---|---|
| 9 | *4-(4-trifluoromethylphenyl)-6-oxo-2-methyl-1,4,5,6-tetrahydropyridine-3-carboxylic acid benzyl ester* |
| 10 | *4-(2-chlorophenyl)-6-oxo-2-methyl-1,4,5,6-tetrahydropyridine-3-carboxylic acid benzyl ester* |
| 11 | *4-(3-chlorophenyl)-6-oxo-2-methyl-1,4,5,6-tetrahydropyridine-3-carboxylic acid benzyl ester* |
| 12 | *4-(4-chlorophenyl)-6-oxo-2-methyl-1,4,5,6-tetrahydropyridine-3-carboxylic acid benzyl ester* |
| 13 | *4-(4-fluorophenyl)-6-oxo-2-methyl-1,4,5,6-tetrahydropyridine-3-carboxylic acid benzyl ester* |

TABLE 1-continued

| Compound | Structure |
|---|---|
| 14 | benzyl 2-methyl-6-oxo-4-phenyl-1,4,5,6-tetrahydropyridine-3-carboxylate |
| 15 | benzyl 4-(4-chloro-2-fluorophenyl)-2-methyl-6-oxo-1,4,5,6-tetrahydropyridine-3-carboxylate |
| 16 | benzyl 4-(4-bromophenyl)-2-methyl-6-oxo-1,4,5,6-tetrahydropyridine-3-carboxylate |
| 17 | benzyl 4-(4-chlorophenyl)-1,2-dimethyl-6-oxo-1,4,5,6-tetrahydropyridine-3-carboxylate |
| 18 | benzyl 4-(4-chlorophenyl)-2-ethyl-1-methyl-6-oxo-1,4,5,6-tetrahydropyridine-3-carboxylate |

TABLE 1-continued
| Compound | Structure |
|---|---|
| 19 | 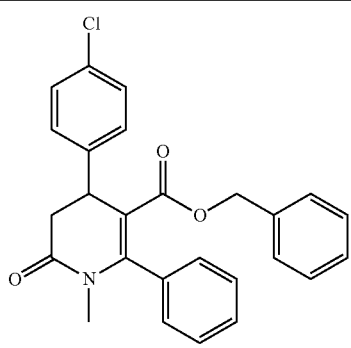 |
| 22 | 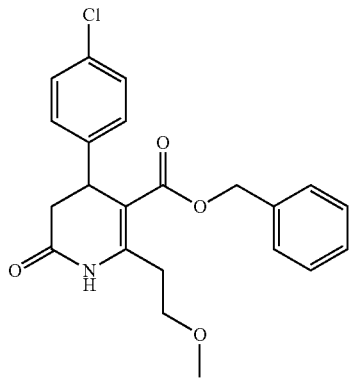 [SMILES: COCCC1=C(C(=O)OCc2ccccc2)C(c2ccc(Cl)cc2)CC(=O)N1] |
| 23 | 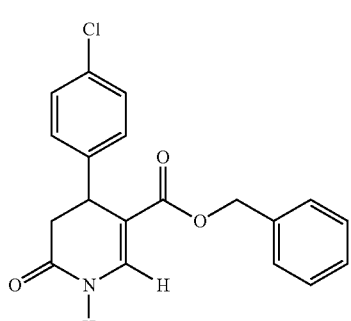 |
| 24 | 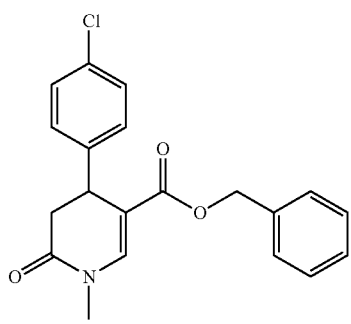 [SMILES: CN1C=C(C(=O)OCc2ccccc2)C(c2ccc(Cl)cc2)CC1=O] |

TABLE 1-continued
| Compound | Structure |
|---|---|
| 25 | 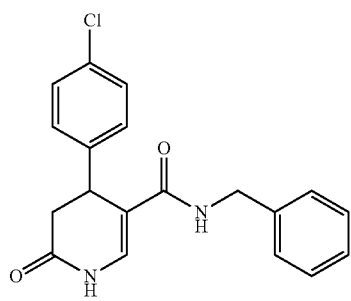 [SMILES: O=C1CC(c2ccc(Cl)cc2)C(C(=O)NCc2ccccc2)=CN1] |
| 26 | 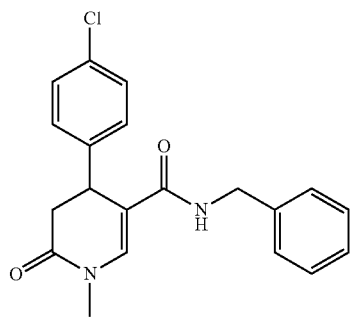 |
| 27 | 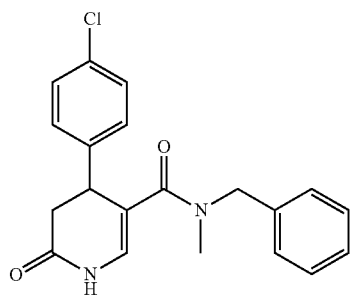 [SMILES: CN(Cc1ccccc1)C(=O)C1=CNC(=O)CC1c1ccc(Cl)cc1] |
| 29 | 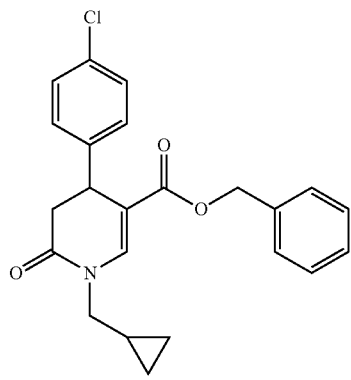 [SMILES: O=C(OCc1ccccc1)C1=CN(CC2CC2)C(=O)CC1c1ccc(Cl)cc1] |

TABLE 1-continued
| Compound | Structure |
|---|---|
| 30 | 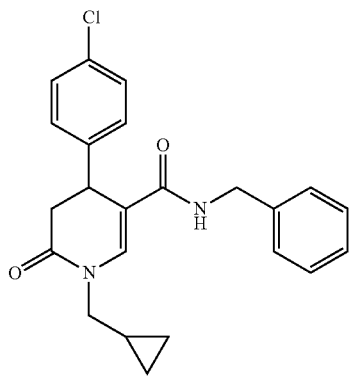 [SMILES: O=C(NCc1ccccc1)C1=CN(CC2CC2)C(=O)CC1c1ccc(Cl)cc1] |
| 32 | 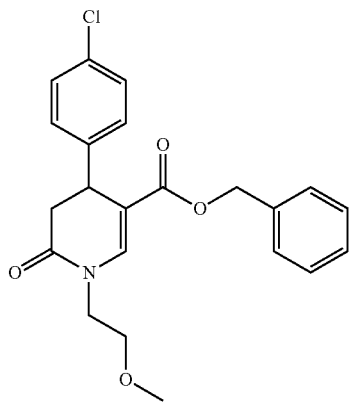 [SMILES: COCCN1C=C(C(=O)OCc2ccccc2)C(c2ccc(Cl)cc2)CC1=O] |
| 33 | 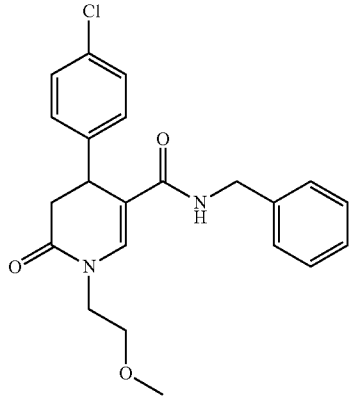 [SMILES: COCCN1C=C(C(=O)NCc2ccccc2)C(c2ccc(Cl)cc2)CC1=O] |
| 33a | 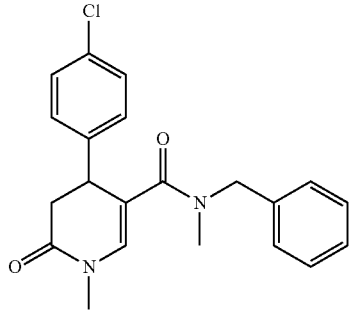 [SMILES: CN1C=C(C(=O)N(C)Cc2ccccc2)C(c2ccc(Cl)cc2)CC1=O] |

TABLE 1-continued

| Compound | Structure |
|---|---|
| 34 | *4-(4-chlorophenyl)-1-ethyl-2-methyl-6-oxo-1,4,5,6-tetrahydropyridine-3-carboxylic acid benzyl ester* |
| 35 | *4-(4-chlorophenyl)-2-methyl-6-oxo-1-propyl-1,4,5,6-tetrahydropyridine-3-carboxylic acid benzyl ester* |
| 36 | *1-butyl-4-(4-chlorophenyl)-2-methyl-6-oxo-1,4,5,6-tetrahydropyridine-3-carboxylic acid benzyl ester* |
| 37 | *4-(4-chlorophenyl)-1-(2-methoxyethyl)-2-methyl-6-oxo-1,4,5,6-tetrahydropyridine-3-carboxylic acid benzyl ester* |

TABLE 1-continued
| Compound | Structure |
|---|---|
| 38 | 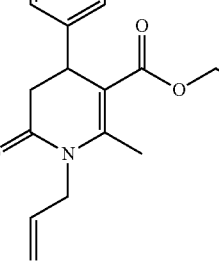 |
| 39 | 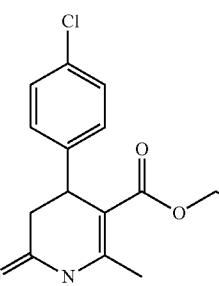 |
| 40 | 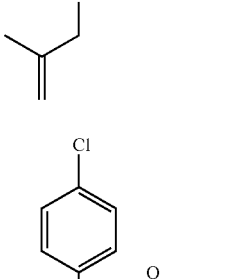 |
| 41 | 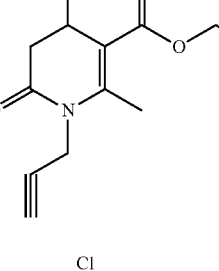 |

TABLE 1-continued

| Compound | Structure |
|---|---|
| 42 | 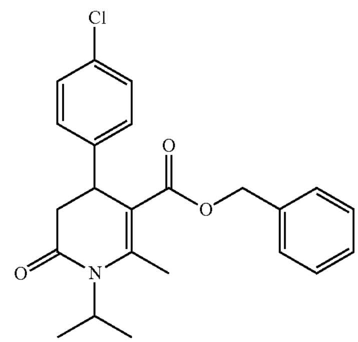 [SMILES: CC1=C(C(=O)OCc2ccccc2)C(c2ccc(Cl)cc2)CC(=O)N1C(C)C] |
| 43 | 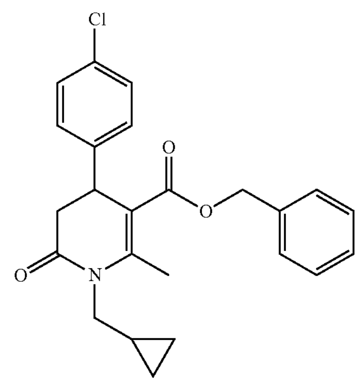 [SMILES: CC1=C(C(=O)OCc2ccccc2)C(c2ccc(Cl)cc2)CC(=O)N1CC1CC1] |
| 44 | 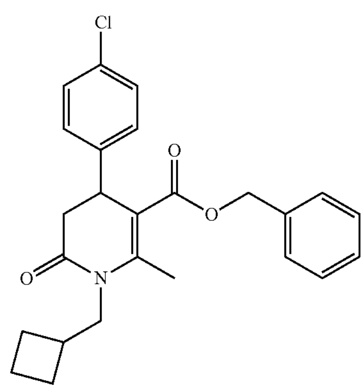 [SMILES: CC1=C(C(=O)OCc2ccccc2)C(c2ccc(Cl)cc2)CC(=O)N1CC1CCC1] |
| 45 | 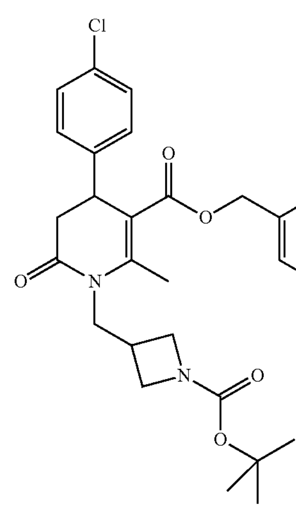 |

TABLE 1-continued

| Compound | Structure |
|---|---|
| 46 | 4-(4-chlorophenyl)-2-methyl-6-oxo-1-(azetidin-3-ylmethyl)-1,4,5,6-tetrahydropyridine-3-carboxylic acid benzyl ester |
| 47 | 4-(4-chlorophenyl)-2-methyl-6-oxo-1-((1-methylazetidin-3-yl)methyl)-1,4,5,6-tetrahydropyridine-3-carboxylic acid benzyl ester |
| 48 | 4-(4-chlorophenyl)-2-methyl-6-oxo-1-((1,1-dimethylazetidin-1-ium-3-yl)methyl)-1,4,5,6-tetrahydropyridine-3-carboxylic acid benzyl ester iodide |
| 49 | 4-(4-chlorophenyl)-2-methyl-6-oxo-1-isobutyl-1,4,5,6-tetrahydropyridine-3-carboxylic acid benzyl ester |

TABLE 1-continued

| Compound | Structure |
| --- | --- |
| 50 | 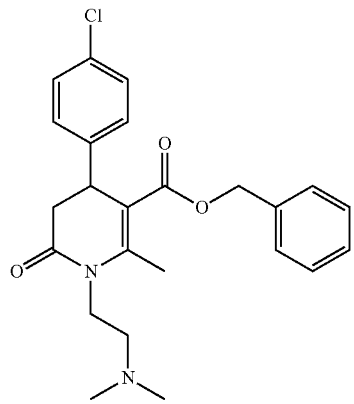 [SMILES: CC1=C(C(=O)OCc2ccccc2)C(c2ccc(Cl)cc2)CC(=O)N1CCN(C)C] |
| 51 | 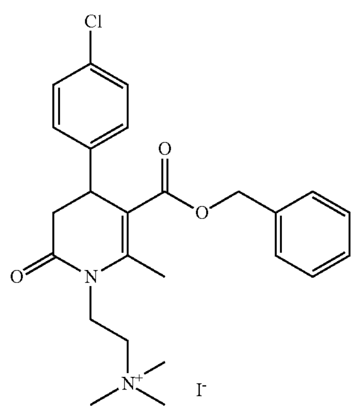 [SMILES: CC1=C(C(=O)OCc2ccccc2)C(c2ccc(Cl)cc2)CC(=O)N1CC[N+](C)(C)C ; [I-]] |
| 52 | 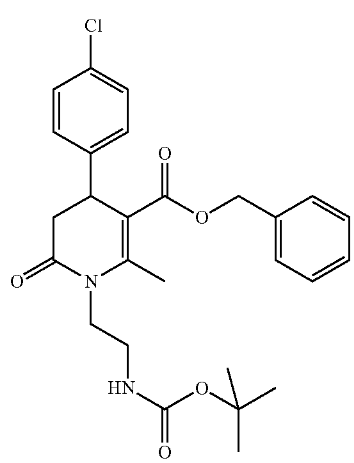 [SMILES: CC1=C(C(=O)OCc2ccccc2)C(c2ccc(Cl)cc2)CC(=O)N1CCNC(=O)OC(C)(C)C] |

TABLE 1-continued
| Compound | Structure |
| --- | --- |
| 53 | 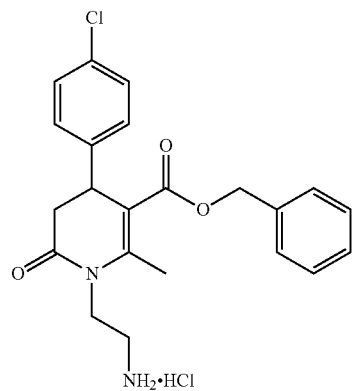 |
| 54 | 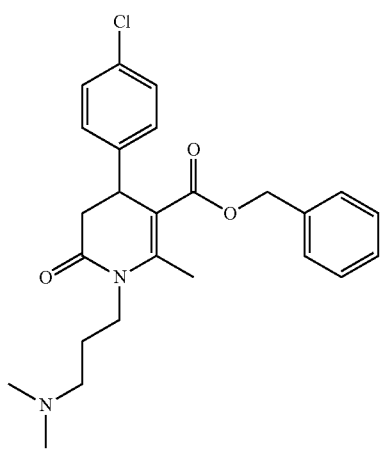 [SMILES: CC1=C(C(=O)OCc2ccccc2)C(c2ccc(Cl)cc2)CC(=O)N1CCCN(C)C] |
| 55 | 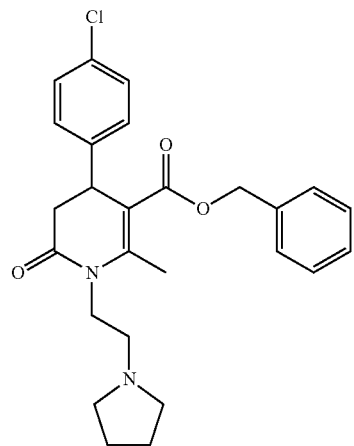 [SMILES: CC1=C(C(=O)OCc2ccccc2)C(c2ccc(Cl)cc2)CC(=O)N1CCN1CCCC1] |

TABLE 1-continued
| Compound | Structure |
|---|---|
| 56 | 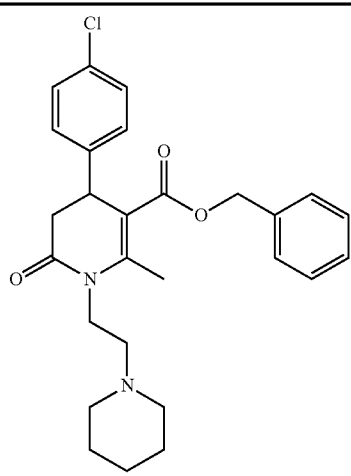 |
| 57 | 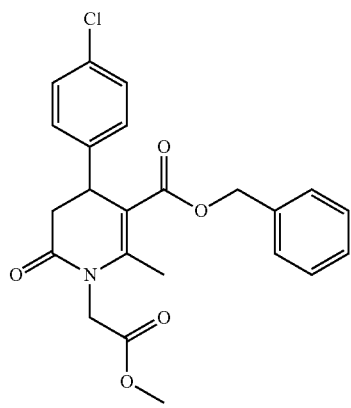 [SMILES: COC(=O)CN1C(=O)CC(c2ccc(Cl)cc2)C(C(=O)OCc2ccccc2)=C1C] |
| 58 | 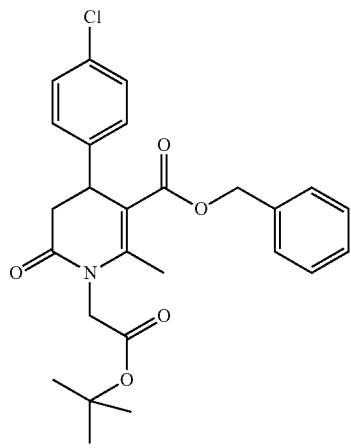 [SMILES: CC1=C(C(=O)OCc2ccccc2)C(c2ccc(Cl)cc2)CC(=O)N1CC(=O)OC(C)(C)C] |

TABLE 1-continued

| Compound | Structure |
|---|---|
| 59 | 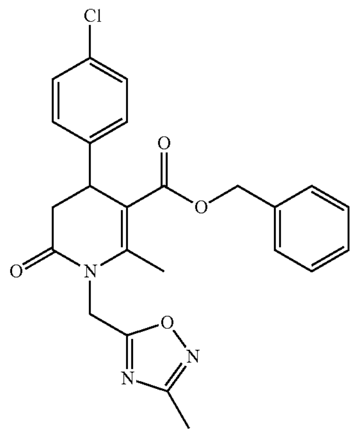 [SMILES: CC1=C(C(=O)OCc2ccccc2)C(c2ccc(Cl)cc2)CC(=O)N1Cc1nc(C)no1] |
| 60 | 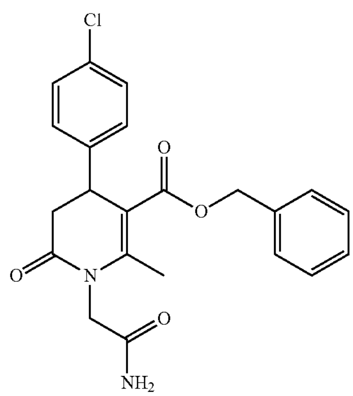 [SMILES: CC1=C(C(=O)OCc2ccccc2)C(c2ccc(Cl)cc2)CC(=O)N1CC(N)=O] |
| 61 | 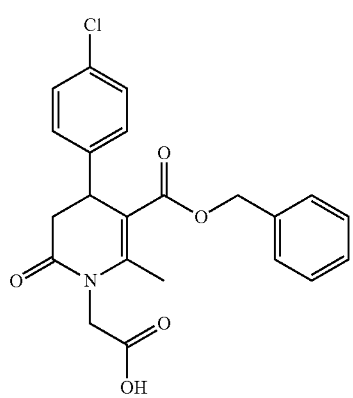 [SMILES: CC1=C(C(=O)OCc2ccccc2)C(c2ccc(Cl)cc2)CC(=O)N1CC(=O)O] |

TABLE 1-continued

| Compound | Structure |
|---|---|
| 62 | (4-chlorophenyl dihydropyridinone with benzyl ester, 2-methyl, N-(2-(methylsulfonyl)ethyl)) |
| 63 | (4-chlorophenyl dihydropyridinone with benzyl ester, 2-methyl, N-cyanomethyl) |
| 64 | (4-chlorophenyl dihydropyridinone with 2-methoxybenzyl ester, 2-methyl, N-(2-methoxyethyl)) |
| 65 | (4-chlorophenyl dihydropyridinone with 2-methoxybenzyl ester, 2-methyl, N-(2-hydroxyethyl)) |

TABLE 1-continued
| Compound | Structure |
|---|---|
| 66 | 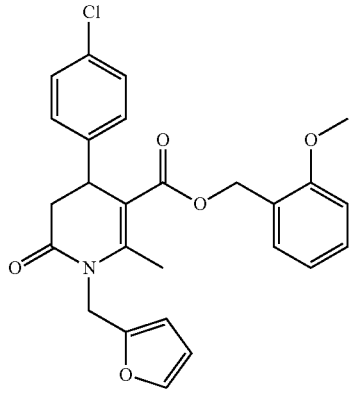 [SMILES: COc1ccccc1COC(=O)C1=C(C)N(Cc2ccco2)C(=O)CC1c1ccc(Cl)cc1] |
| 67 | 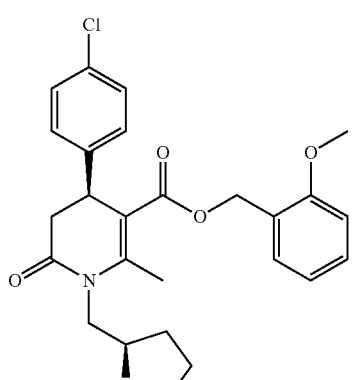 |
| 68 | 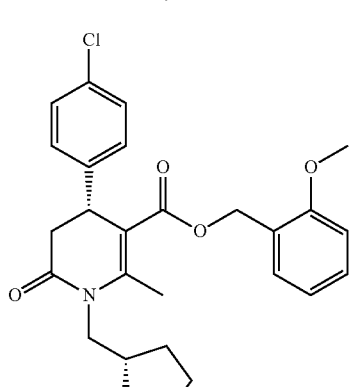 |

TABLE 1-continued
| Compound | Structure |
|---|---|
| | 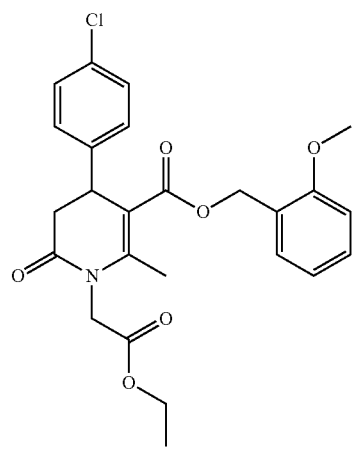 [SMILES: CCOC(=O)CN1C(=O)CC(c2ccc(Cl)cc2)C(C(=O)OCc2ccccc2OC)=C1C] |
| 69 | 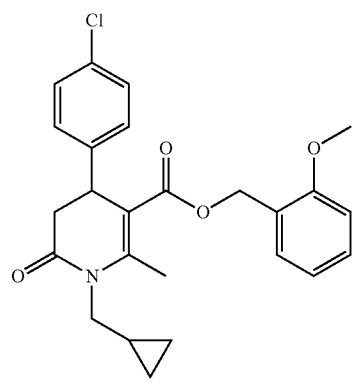 |
| 70 | 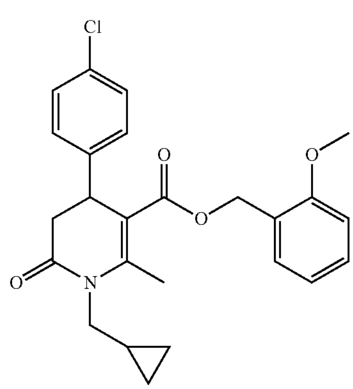 [SMILES: COc1ccccc1COC(=O)C1=C(C)N(CC2CC2)C(=O)CC1c1ccc(Cl)cc1] |

TABLE 1-continued
| Compound | Structure |
|---|---|
| 71 | 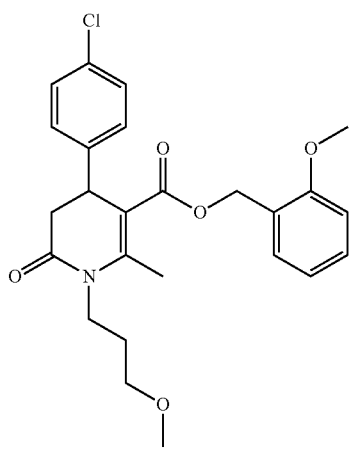 [SMILES: COCCCN1C(=O)CC(c2ccc(Cl)cc2)C(C(=O)OCc2ccccc2OC)=C1C] |
| 72 | 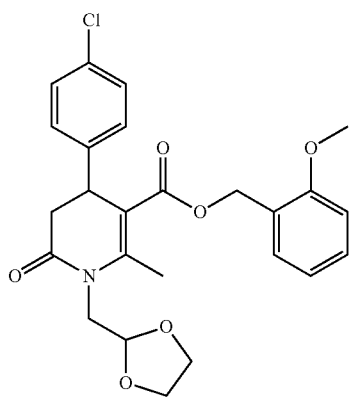 [SMILES: COc1ccccc1COC(=O)C1=C(C)N(CC2OCCO2)C(=O)CC1c1ccc(Cl)cc1] |
| 73 | 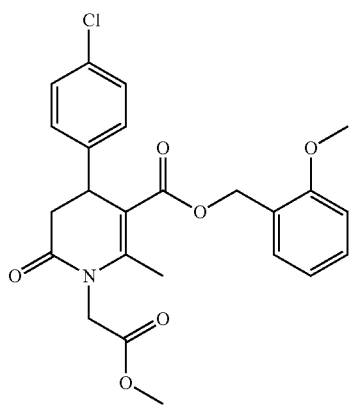 [SMILES: COC(=O)CN1C(=O)CC(c2ccc(Cl)cc2)C(C(=O)OCc2ccccc2OC)=C1C] |

TABLE 1-continued
| Compound | Structure |
|---|---|
| 75 | 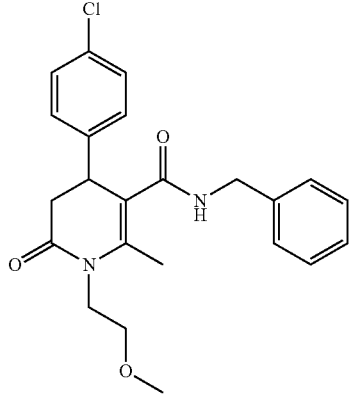 [SMILES: COCCN1C(=O)CC(c2ccc(Cl)cc2)C(C(=O)NCc2ccccc2)=C1C] |
| 76 | 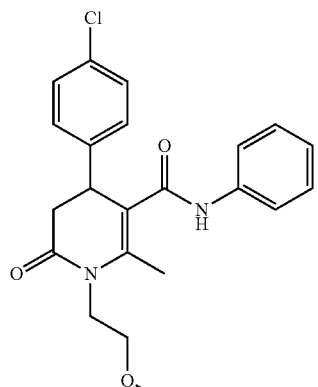 |
| 77 | 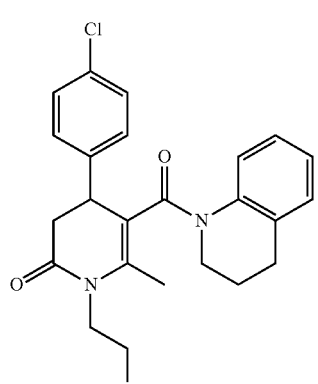 |
| 79 | 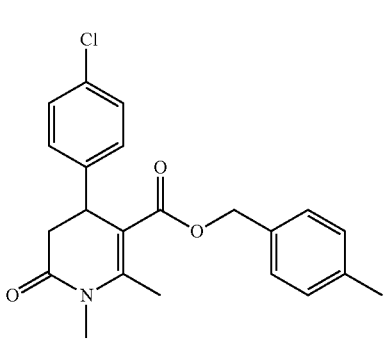 [SMILES: CC1=C(C(=O)OCc2ccc(C)cc2)C(c2ccc(Cl)cc2)CC(=O)N1C] |

TABLE 1-continued
| Compound | Structure |
|---|---|
| 80 | 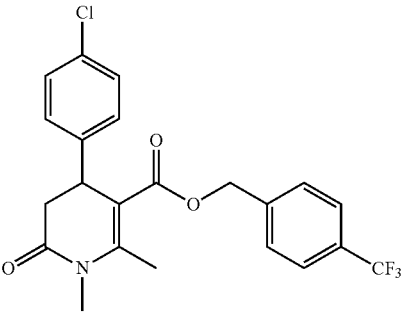 [SMILES: CC1=C(C(=O)OCc2ccc(C(F)(F)F)cc2)C(c2ccc(Cl)cc2)CC(=O)N1C] |
| 81 | 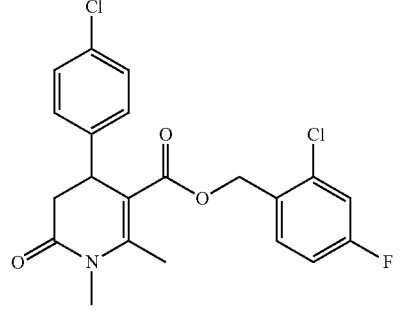 [SMILES: CC1=C(C(=O)OCc2ccc(F)cc2Cl)C(c2ccc(Cl)cc2)CC(=O)N1C] |
| 82 | 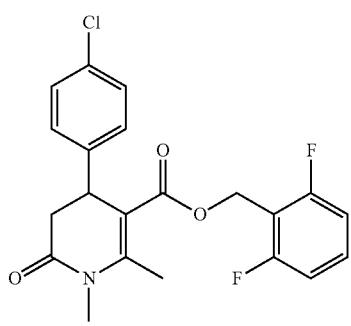 [SMILES: CC1=C(C(=O)OCc2c(F)cccc2F)C(c2ccc(Cl)cc2)CC(=O)N1C] |
| 83 | 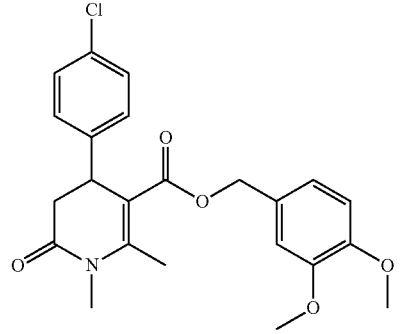 [SMILES: COc1ccc(COC(=O)C2=C(C)N(C)C(=O)CC2c2ccc(Cl)cc2)cc1OC] |

TABLE 1-continued
| Compound | Structure |
|---|---|
| 84 | 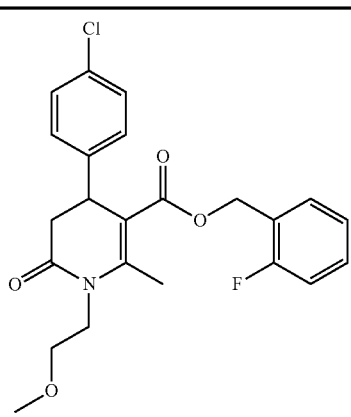 |
| 85 | 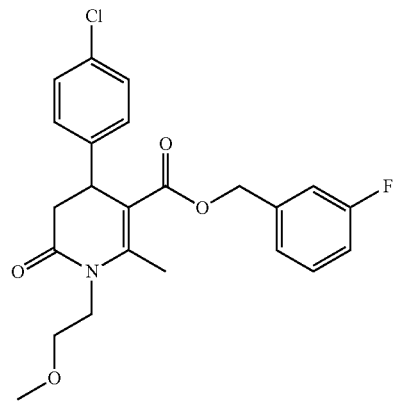 [SMILES: COCCN1C(=O)CC(c2ccc(Cl)cc2)C(C(=O)OCc2cccc(F)c2)=C1C] |
| 86 | 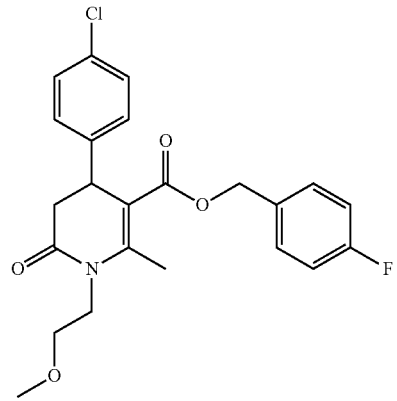 [SMILES: COCCN1C(=O)CC(c2ccc(Cl)cc2)C(C(=O)OCc2ccc(F)cc2)=C1C] |
| 87 | 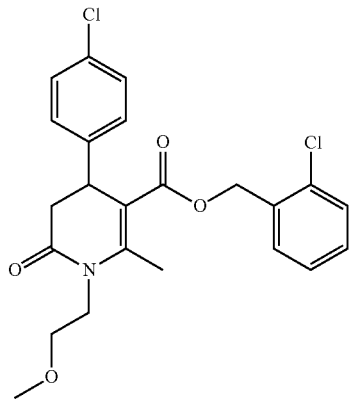 [SMILES: COCCN1C(=O)CC(c2ccc(Cl)cc2)C(C(=O)OCc2ccccc2Cl)=C1C] |

TABLE 1-continued
| Compound | Structure |
|---|---|
| 88 | 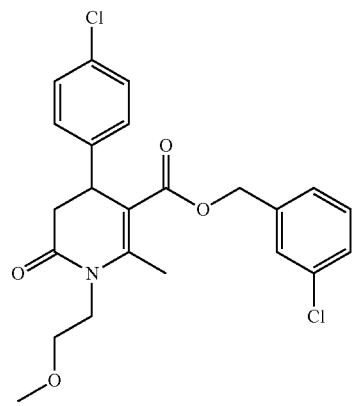 [SMILES: COCCN1C(=O)CC(c2ccc(Cl)cc2)C(C(=O)OCc2cccc(Cl)c2)=C1C] |
| 89 | 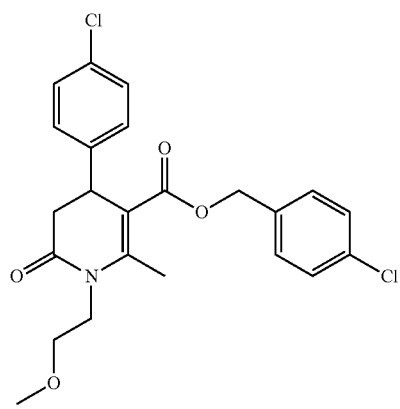 [SMILES: COCCN1C(=O)CC(c2ccc(Cl)cc2)C(C(=O)OCc2ccc(Cl)cc2)=C1C] |
| 90 | 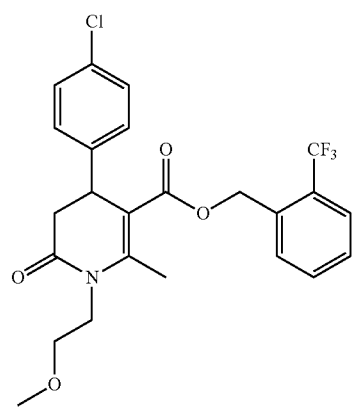 |

TABLE 1-continued
| Compound | Structure |
|---|---|
| 91 | 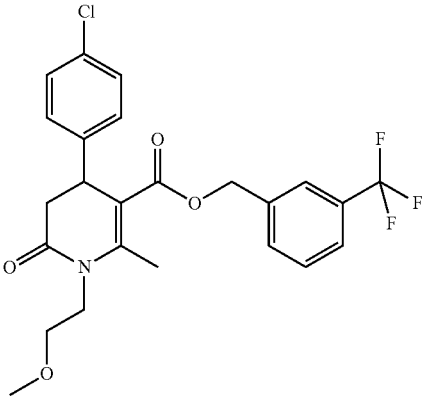 [SMILES: COCCN1C(=O)CC(c2ccc(Cl)cc2)C(C(=O)OCc2cccc(C(F)(F)F)c2)=C1C] |
| 92 | 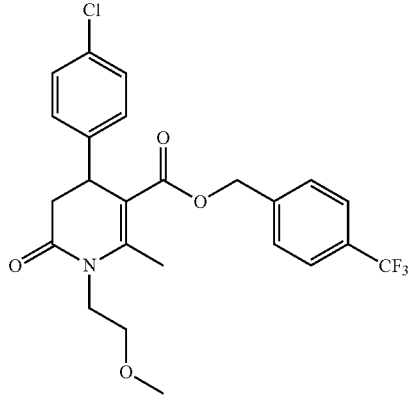 [SMILES: COCCN1C(=O)CC(c2ccc(Cl)cc2)C(C(=O)OCc2ccc(C(F)(F)F)cc2)=C1C] |
| 93 | 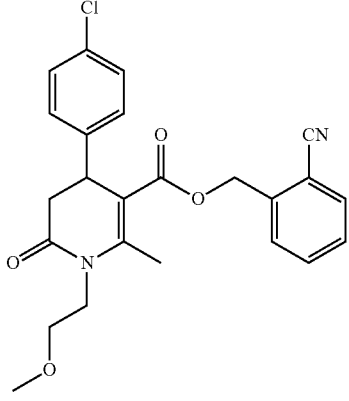 [SMILES: COCCN1C(=O)CC(c2ccc(Cl)cc2)C(C(=O)OCc2ccccc2C#N)=C1C] |
| 94 | 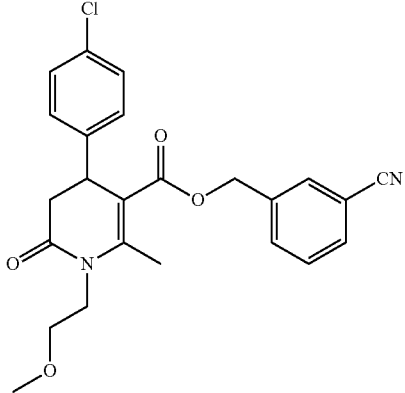 [SMILES: COCCN1C(=O)CC(c2ccc(Cl)cc2)C(C(=O)OCc2cccc(C#N)c2)=C1C] |

TABLE 1-continued
| Compound | Structure |
|---|---|
| 95 | 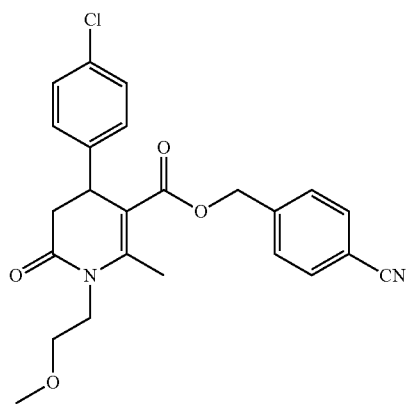 [SMILES: COCCN1C(=O)CC(c2ccc(Cl)cc2)C(C(=O)OCc2ccc(C#N)cc2)=C1C] |
| 96 | 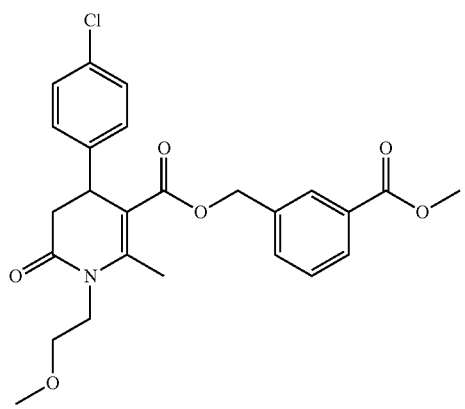 [SMILES: COCCN1C(=O)CC(c2ccc(Cl)cc2)C(C(=O)OCc2cccc(C(=O)OC)c2)=C1C] |
| 97 | 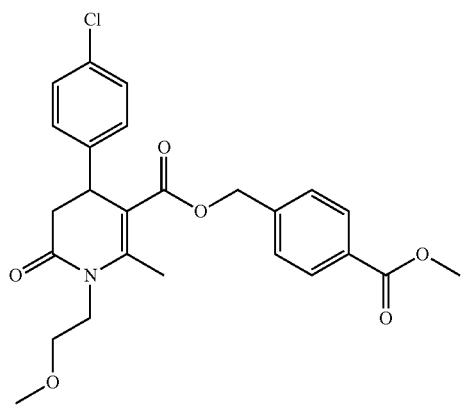 [SMILES: COCCN1C(=O)CC(c2ccc(Cl)cc2)C(C(=O)OCc2ccc(C(=O)OC)cc2)=C1C] |

TABLE 1-continued

| Compound | Structure |
|---|---|
| 98 | (4-chlorophenyl at C4; 2-methylbenzyl ester; N-(2-methoxyethyl); 2-methyl-6-oxo-1,4,5,6-tetrahydropyridine-3-carboxylate) |
| 99 | (4-chlorophenyl at C4; 3-methylbenzyl ester; N-(2-methoxyethyl); 2-methyl-6-oxo-1,4,5,6-tetrahydropyridine-3-carboxylate) |
| 100 | (4-chlorophenyl at C4; 4-methylbenzyl ester; N-(2-methoxyethyl); 2-methyl-6-oxo-1,4,5,6-tetrahydropyridine-3-carboxylate) |
| 101 | (4-chlorophenyl at C4; 2,4,6-trimethylbenzyl ester; N-(2-methoxyethyl); 2-methyl-6-oxo-1,4,5,6-tetrahydropyridine-3-carboxylate) |

TABLE 1-continued
| Compound | Structure |
| --- | --- |
| 103 | 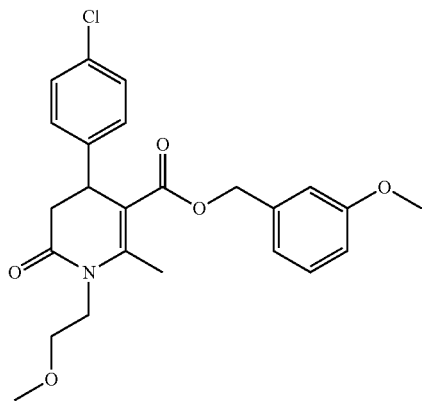 [SMILES: COCCN1C(=O)CC(c2ccc(Cl)cc2)C(C(=O)OCc2cccc(OC)c2)=C1C] |
| 104 | 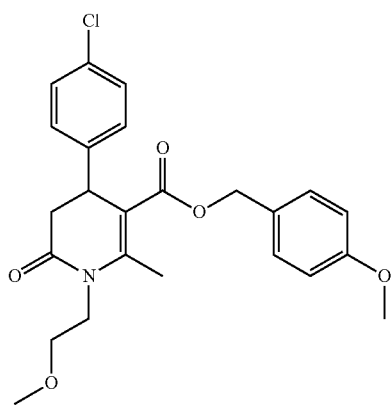 |
| 105 | 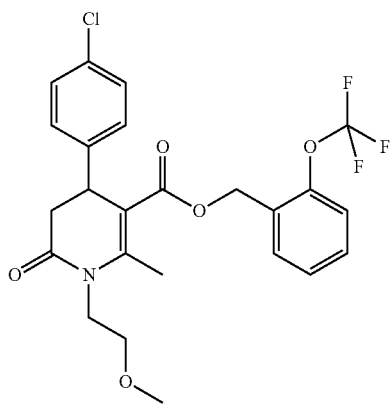 [SMILES: COCCN1C(=O)CC(c2ccc(Cl)cc2)C(C(=O)OCc2ccccc2OC(F)(F)F)=C1C] |

TABLE 1-continued

| Compound | Structure |
|---|---|
| 106 | 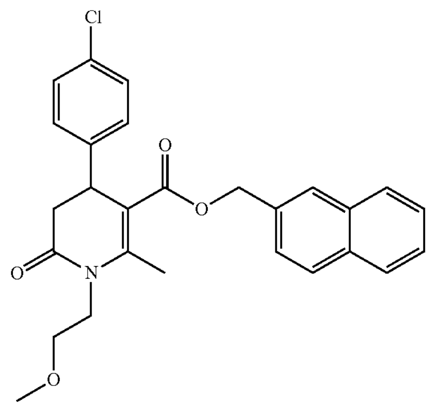 [SMILES: COCCN1C(=O)CC(c2ccc(Cl)cc2)C(C(=O)OCc2ccc3ccccc3c2)=C1C] |
| 107 | 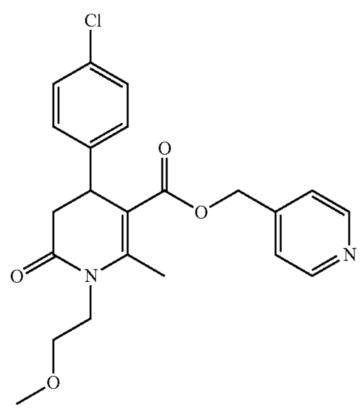 [SMILES: COCCN1C(=O)CC(c2ccc(Cl)cc2)C(C(=O)OCc2ccncc2)=C1C] |
| 108 | 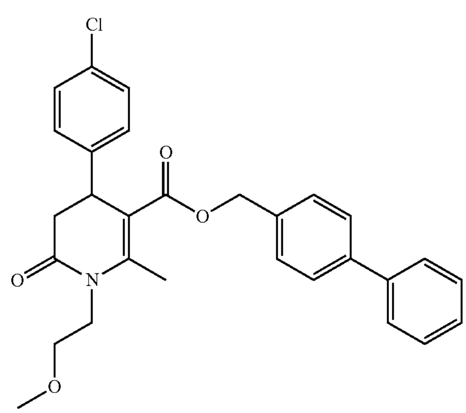 [SMILES: COCCN1C(=O)CC(c2ccc(Cl)cc2)C(C(=O)OCc2ccc(-c3ccccc3)cc2)=C1C] |
| 109 | 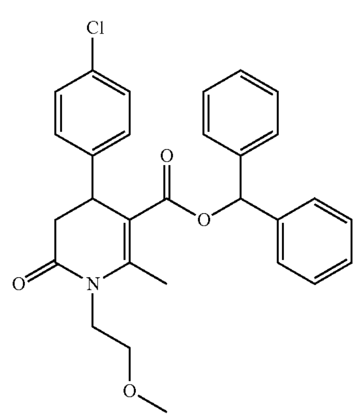 [SMILES: COCCN1C(=O)CC(c2ccc(Cl)cc2)C(C(=O)OC(c2ccccc2)c2ccccc2)=C1C] |

US 9,932,309 B2
TABLE 1-continued
| Compound | Structure |
|---|---|
| 110 | 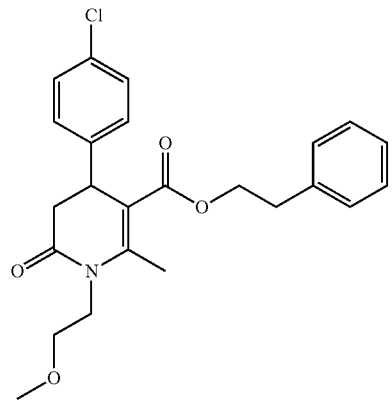 [SMILES: COCCN1C(=O)CC(c2ccc(Cl)cc2)C(C(=O)OCCc2ccccc2)=C1C] |
| 111 | 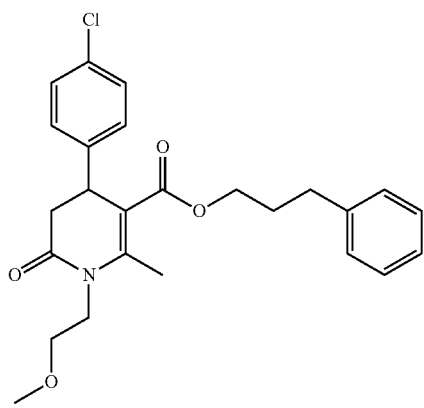 |
| 112 | 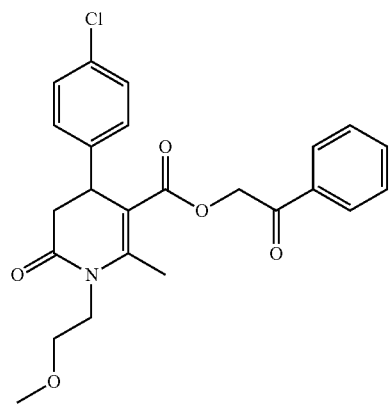 [SMILES: COCCN1C(=O)CC(c2ccc(Cl)cc2)C(C(=O)OCC(=O)c2ccccc2)=C1C] |

TABLE 1-continued
| Compound | Structure |
|---|---|
| 113 | 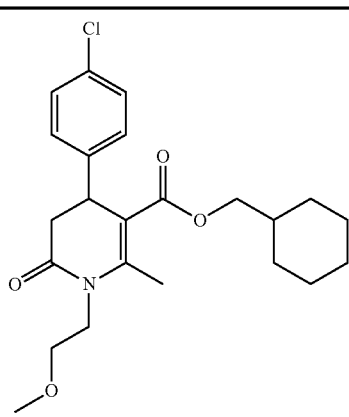 |
| 116 | 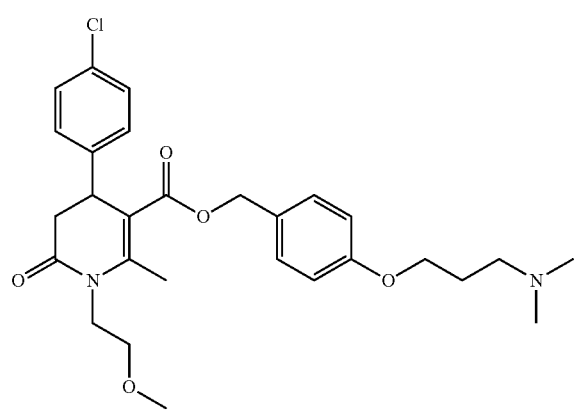 [SMILES: COCCN1C(=O)CC(c2ccc(Cl)cc2)C(C(=O)OCc2ccc(OCCCN(C)C)cc2)=C1C] |
| 117 | 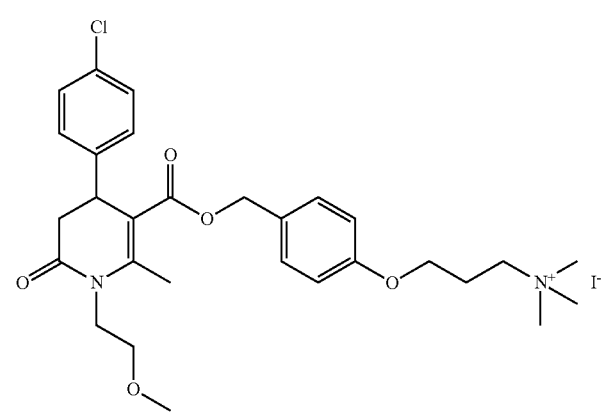 [SMILES: COCCN1C(=O)CC(c2ccc(Cl)cc2)C(C(=O)OCc2ccc(OCCC[N+](C)(C)C)cc2)=C1C ; [I-]] |
| 119 | 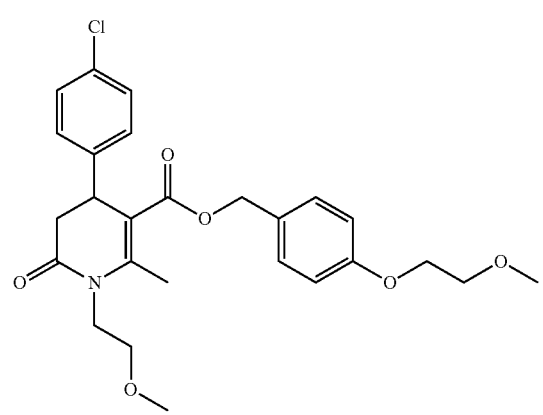 [SMILES: COCCOc1ccc(COC(=O)C2=C(C)N(CCOC)C(=O)CC2c2ccc(Cl)cc2)cc1] |

TABLE 1-continued
| Compound | Structure |
|---|---|
| 121 | 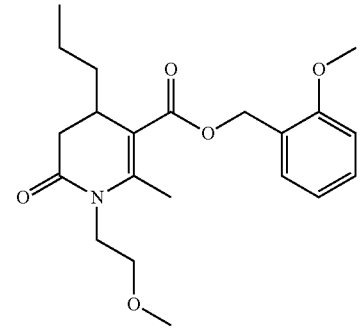 [SMILES: CCCC1CC(=O)N(CCOC)C(C)=C1C(=O)OCc1ccccc1OC] |
| 122 | 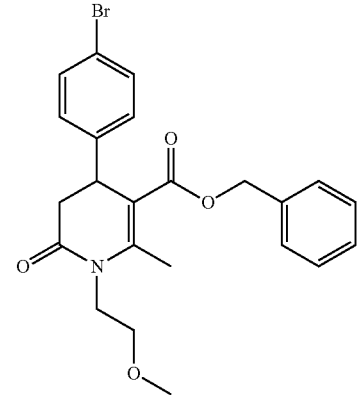 [SMILES: COCCN1C(=O)CC(c2ccc(Br)cc2)C(C(=O)OCc2ccccc2)=C1C] |
| 123 | 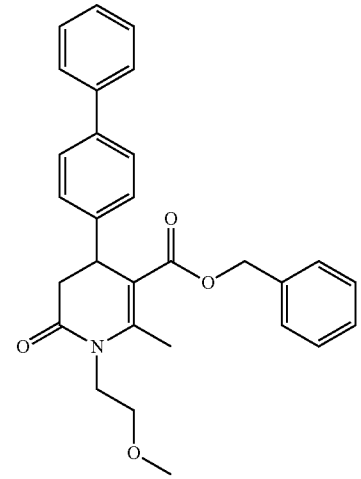 [SMILES: COCCN1C(=O)CC(c2ccc(-c3ccccc3)cc2)C(C(=O)OCc2ccccc2)=C1C] |
| 124 | 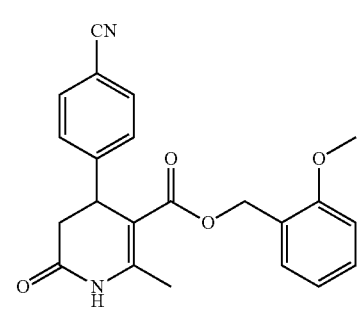 [SMILES: COc1ccccc1COC(=O)C1=C(C)NC(=O)CC1c1ccc(C#N)cc1] |

TABLE 1-continued
| Compound | Structure |
|---|---|
| 125 | 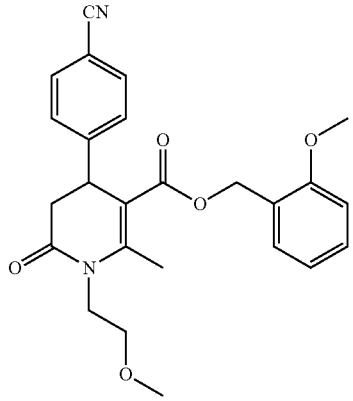 [SMILES: COCCN1C(=O)CC(c2ccc(C#N)cc2)C(C(=O)OCc2ccccc2OC)=C1C] |
| 126 | 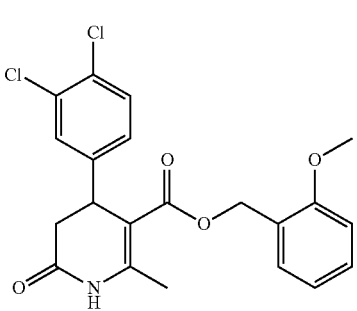 [SMILES: COc1ccccc1COC(=O)C1=C(C)NC(=O)CC1c1ccc(Cl)c(Cl)c1] |
| 127 | 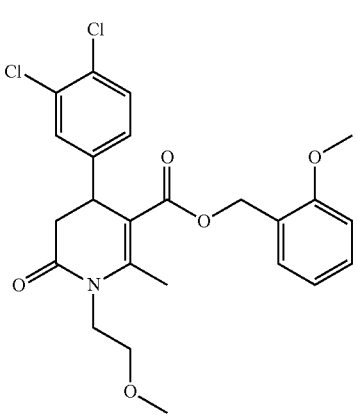 [SMILES: COCCN1C(=O)CC(c2ccc(Cl)c(Cl)c2)C(C(=O)OCc2ccccc2OC)=C1C] |
| 128 | 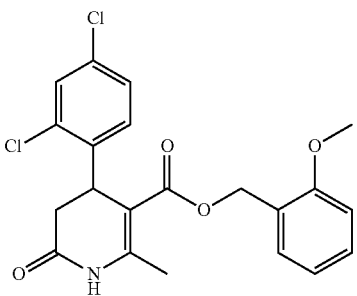 [SMILES: COc1ccccc1COC(=O)C1=C(C)NC(=O)CC1c1ccc(Cl)cc1Cl] |

TABLE 1-continued
| Compound | Structure |
|---|---|
| 129 | 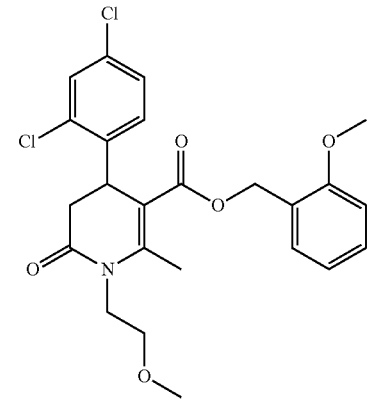 [SMILES: COCCN1C(=O)CC(c2ccc(Cl)cc2Cl)C(C(=O)OCc2ccccc2OC)=C1C] |
| 130 | 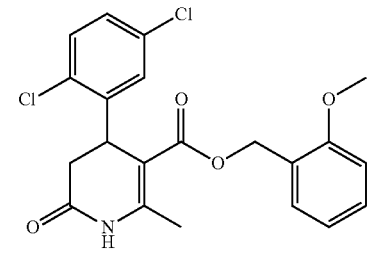 [SMILES: COc1ccccc1COC(=O)C1=C(C)NC(=O)CC1c1cc(Cl)ccc1Cl] |
| 131 | 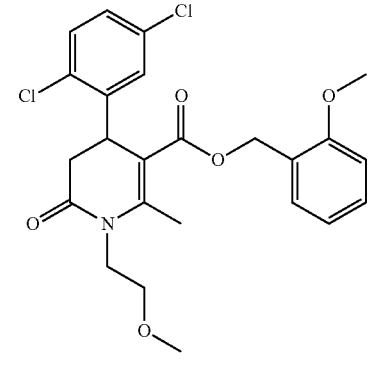 [SMILES: COCCN1C(=O)CC(c2cc(Cl)ccc2Cl)C(C(=O)OCc2ccccc2OC)=C1C] |
| 132 | 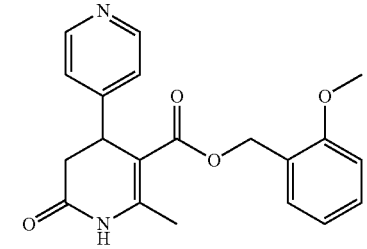 [SMILES: COc1ccccc1COC(=O)C1=C(C)NC(=O)CC1c1ccncc1] |

TABLE 1-continued

| Compound | Structure |
|---|---|
| 133 | 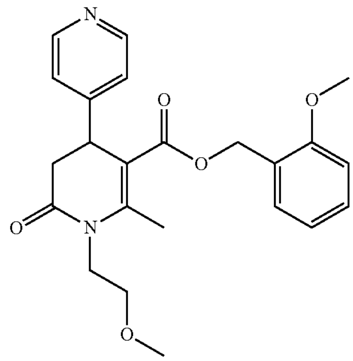 [SMILES: COCCN1C(=O)CC(c2ccncc2)C(C(=O)OCc2ccccc2OC)=C1C] |
| 136 | 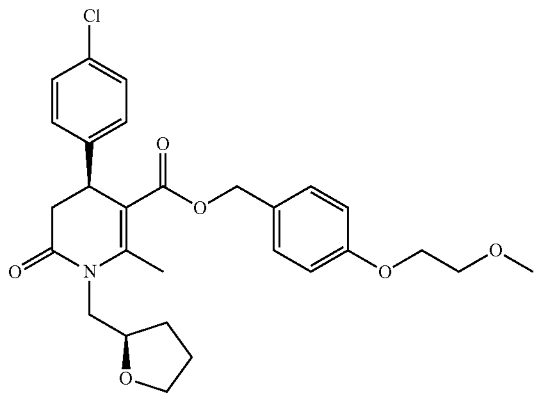 [SMILES: COCCOc1ccc(COC(=O)C2=C(C)N(C[C@H]3CCCO3)C(=O)C[C@H]2c2ccc(Cl)cc2)cc1] |
| | |
| 137 | 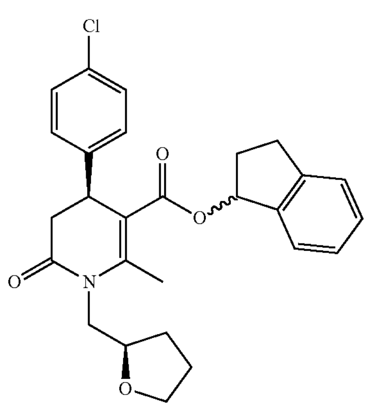 [SMILES: CC1=C(C(=O)OC2CCc3ccccc32)[C@H](c2ccc(Cl)cc2)CC(=O)N1C[C@H]1CCCO1] |

TABLE 1-continued
| Compound | Structure |
|---|---|
|  | 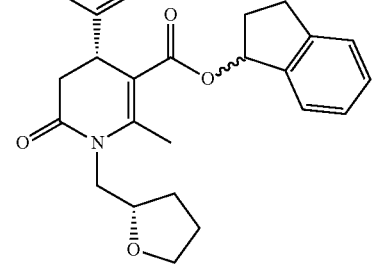 |
| 138 | 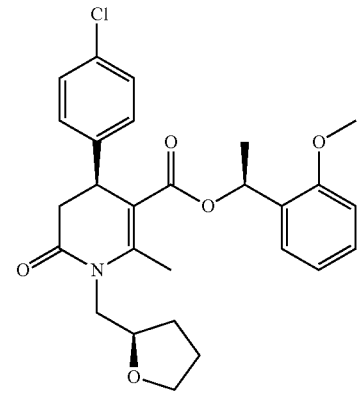 [SMILES: COc1ccccc1[C@H](C)OC(=O)C1=C(C)N(C[C@H]2CCCO2)C(=O)C[C@H]1c1ccc(Cl)cc1] |
|  | 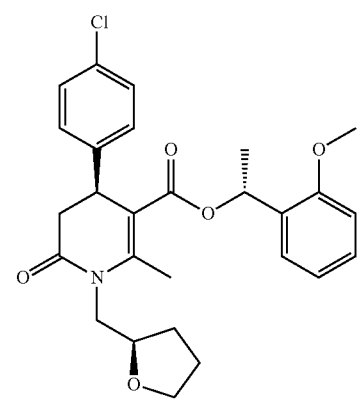 [SMILES: COc1ccccc1[C@@H](C)OC(=O)C1=C(C)N(C[C@H]2CCCO2)C(=O)C[C@H]1c1ccc(Cl)cc1] |
|  | 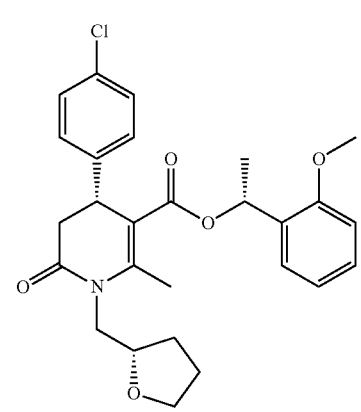 [SMILES: COc1ccccc1[C@@H](C)OC(=O)C1=C(C)N(C[C@@H]2CCCO2)C(=O)C[C@@H]1c1ccc(Cl)cc1] |

TABLE 1-continued
| Compound | Structure |
|---|---|
| | 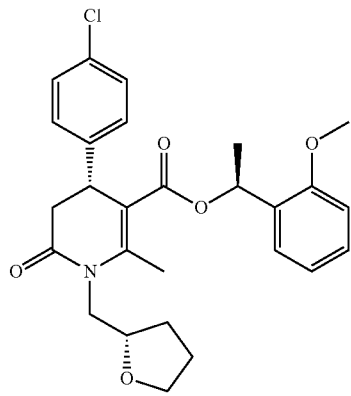 [SMILES: COc1ccccc1[C@H](C)OC(=O)C1=C(C)N(C[C@@H]2CCCO2)C(=O)C[C@@H]1c1ccc(Cl)cc1] |
| 141 | 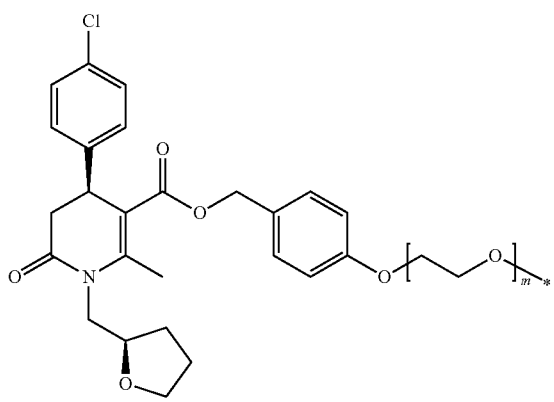
m = 8-13 |
| | 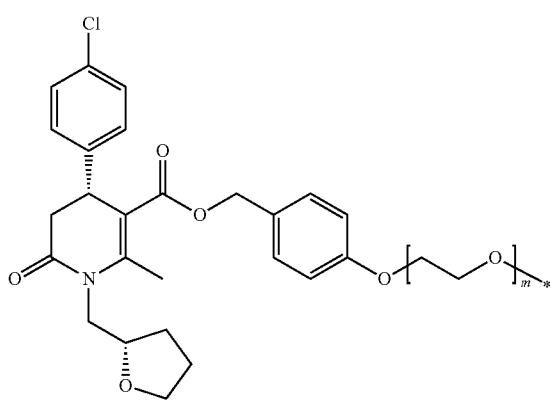
m = 8-13 |

TABLE 1-continued
| Compound | Structure |
|----------|-----------|
| 144 | 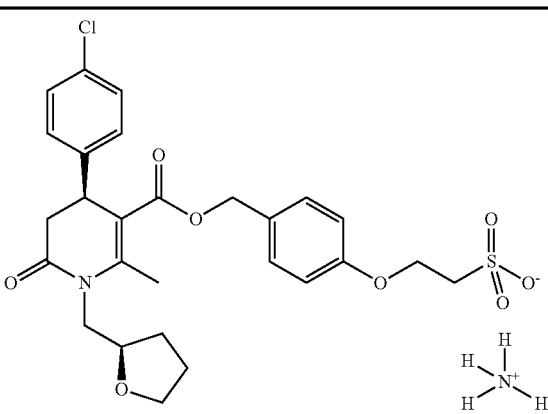 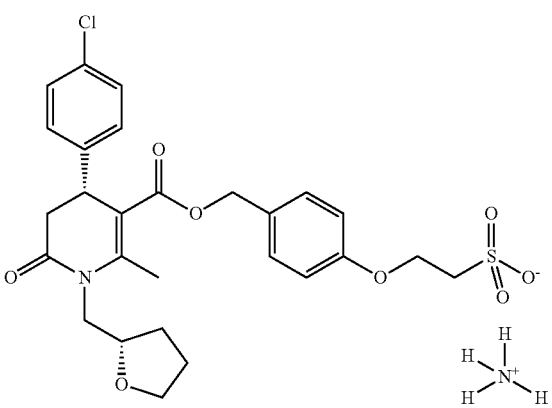 [SMILES: CC1=C(C(=O)OCc2ccc(OCCS(=O)(=O)[O-])cc2)[C@@H](c2ccc(Cl)cc2)CC(=O)N1C[C@@H]1CCCO1 ; [NH4+]] |
| 145 | 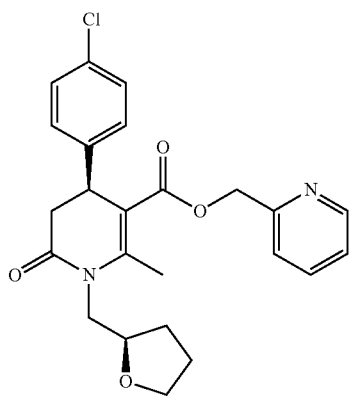 [SMILES: CC1=C(C(=O)OCc2ccccn2)[C@H](c2ccc(Cl)cc2)CC(=O)N1C[C@H]1CCCO1] 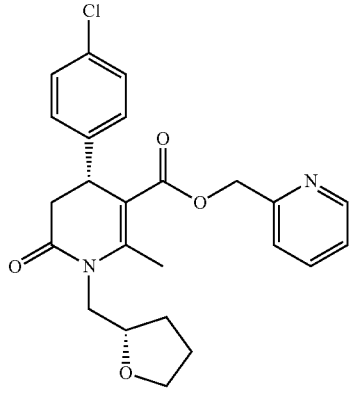 [SMILES: CC1=C(C(=O)OCc2ccccn2)[C@@H](c2ccc(Cl)cc2)CC(=O)N1C[C@@H]1CCCO1] |

TABLE 1-continued

| Compound | Structure |
|---|---|
| 146 | (two stereoisomeric structures: 4-(4-chlorophenyl)-2-methyl-6-oxo-1-((tetrahydrofuran-2-yl)methyl)-1,4,5,6-tetrahydropyridine-3-carboxylic acid pyridin-3-ylmethyl ester) |
| 147 | (two stereoisomeric structures: 4-(4-chlorophenyl)-2-methyl-6-oxo-1-((tetrahydrofuran-2-yl)methyl)-1,4,5,6-tetrahydropyridine-3-carboxylic acid 4-(2-methoxyethoxy)benzyl ester) |

TABLE 1-continued
| Compound | Structure |
|---|---|
| 148 | 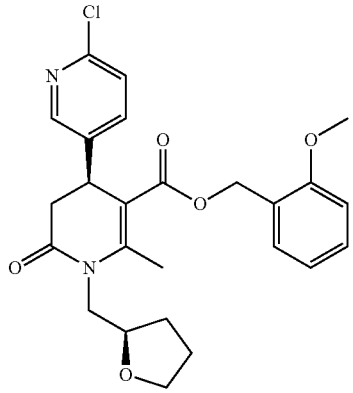 [SMILES: COc1ccccc1COC(=O)C1=C(C)N(C[C@H]2CCCO2)C(=O)C[C@H]1c1ccc(Cl)nc1] 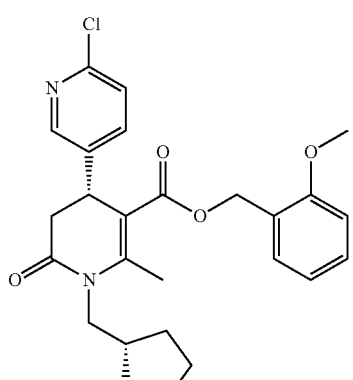 |
| 149 | 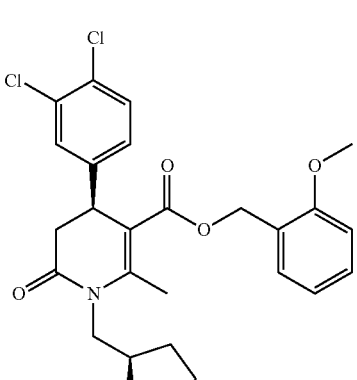 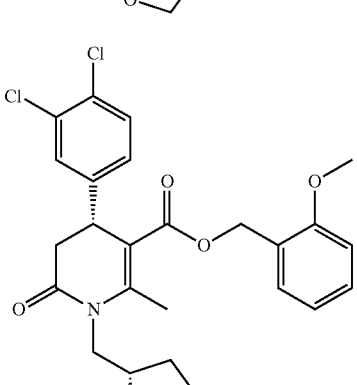 |

TABLE 1-continued
| Compound | Structure |
|---|---|
| 150 | 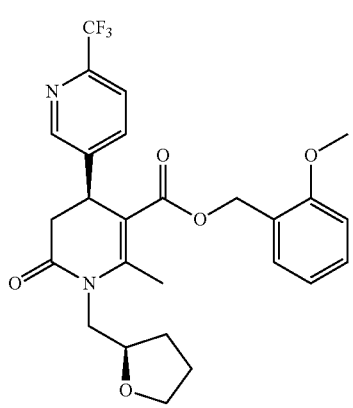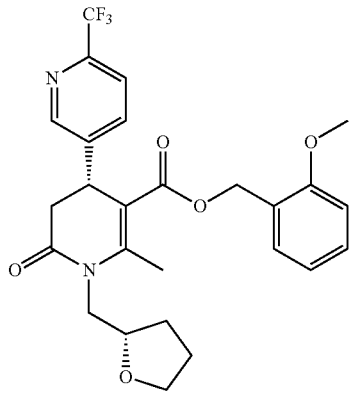 [SMILES: COc1ccccc1COC(=O)C1=C(C)N(C[C@@H]2CCCO2)C(=O)C[C@@H]1c1ccc(Cl)nc1] |
| 151 | 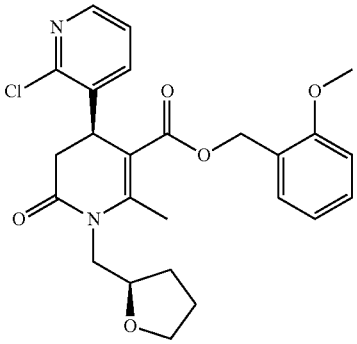 [SMILES: COc1ccccc1COC(=O)C1=C(C)N(C[C@H]2CCCO2)C(=O)C[C@H]1c1cccnc1Cl]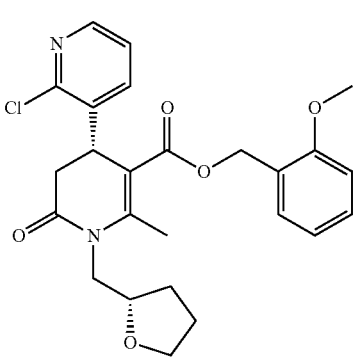 [SMILES: COc1ccccc1COC(=O)C1=C(C)N(C[C@@H]2CCCO2)C(=O)C[C@@H]1c1cccnc1Cl] |

TABLE 1-continued
| Compound | Structure |
|---|---|
| 152 | 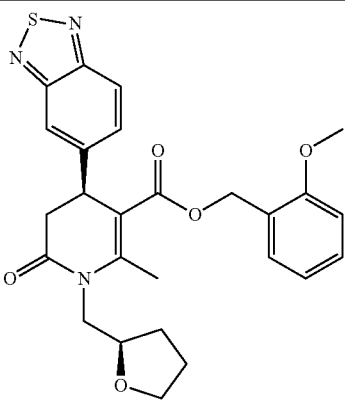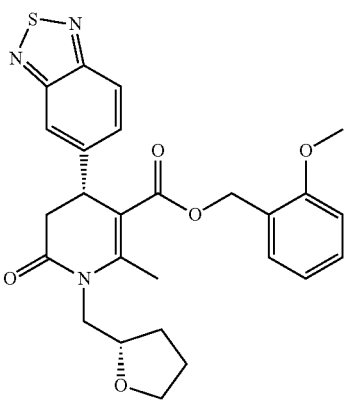 [SMILES: COc1ccccc1COC(=O)C1=C(C)N(C[C@@H]2CCCO2)C(=O)C[C@@H]1c1ccc2nsnc2c1] |
| 153 | 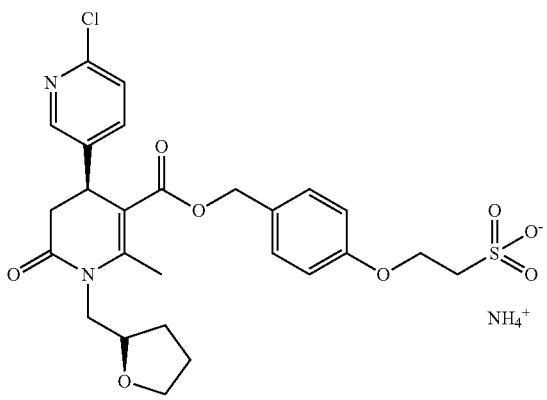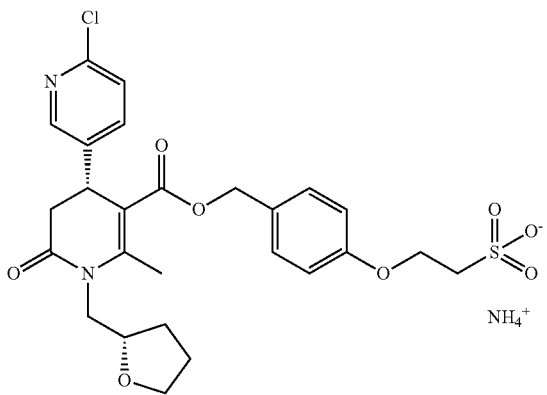 [SMILES: CC1=C(C(=O)OCc2ccc(OCCS(=O)(=O)[O-])cc2)[C@@H](c2ccc(Cl)nc2)CC(=O)N1C[C@@H]1CCCO1 ; [NH4+]] |

TABLE 1-continued
| Compound | Structure |
|---|---|
| 154 | 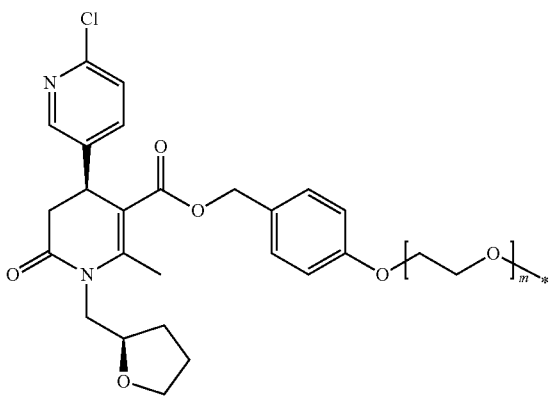<br>m = 7-10 |
| | 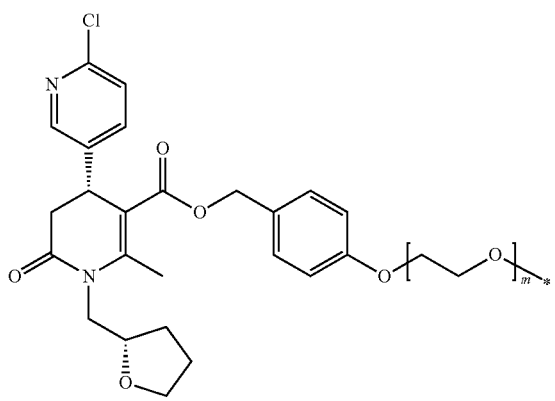<br>m = 7-10 |
| 155 | 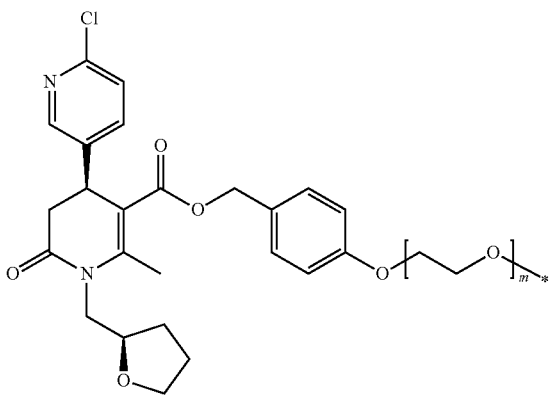<br>m = 18-23 |

TABLE 1-continued
| Compound | Structure |
|---|---|
| | 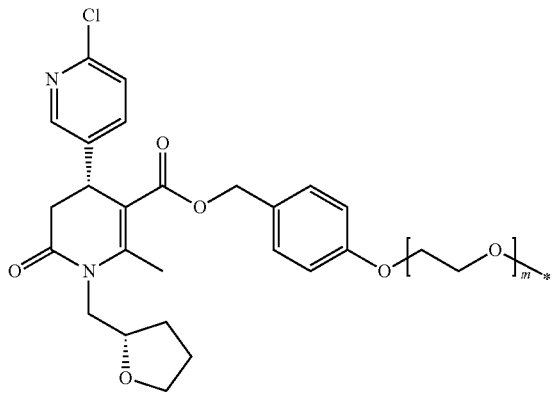
m = 18-23 |
| 156 | 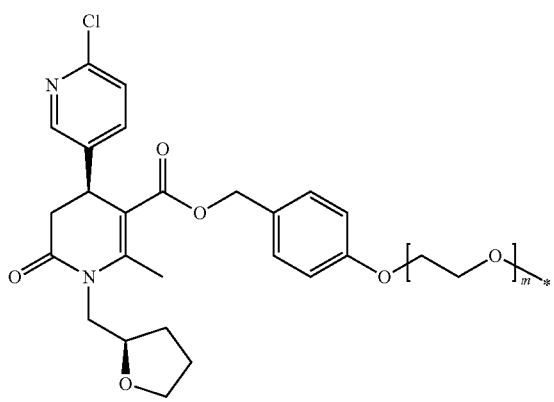
m = 35-44 |
| | 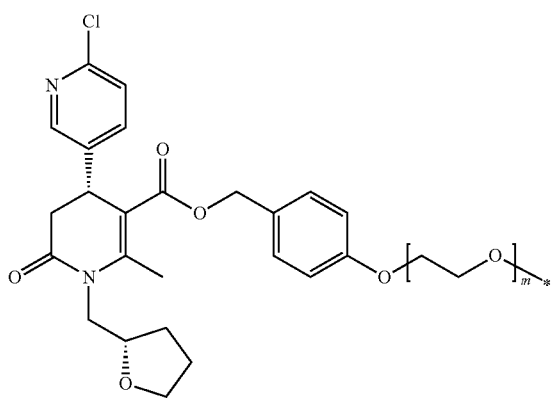
m = 35-44 |

TABLE 1-continued
| Compound | Structure |
|---|---|
| 157 | 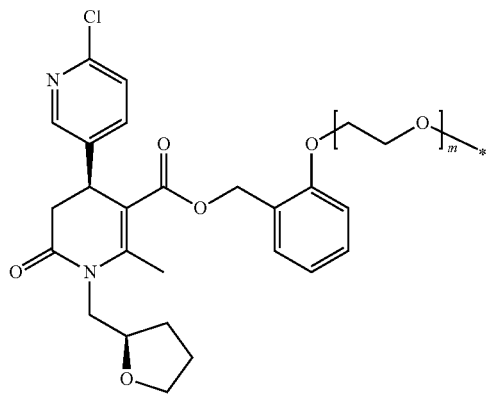<br>m = 10-14<br><br>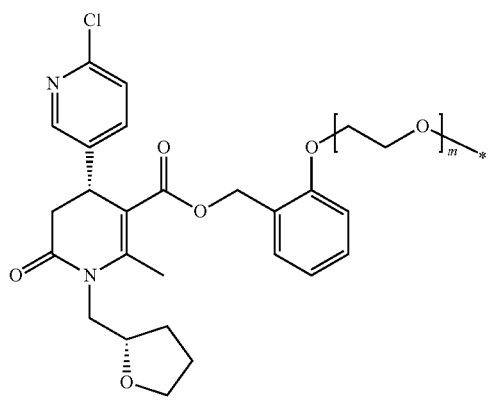<br>m = 10-14 |
| 158 | 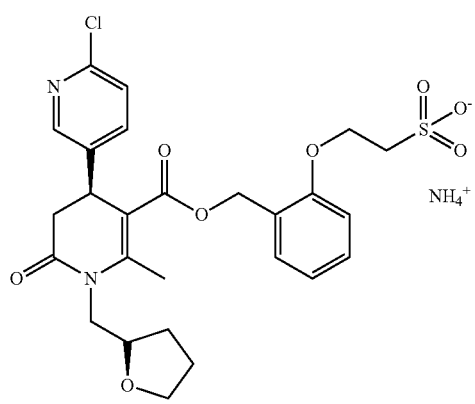 |

TABLE 1-continued
| Compound | Structure |
|---|---|
|  | 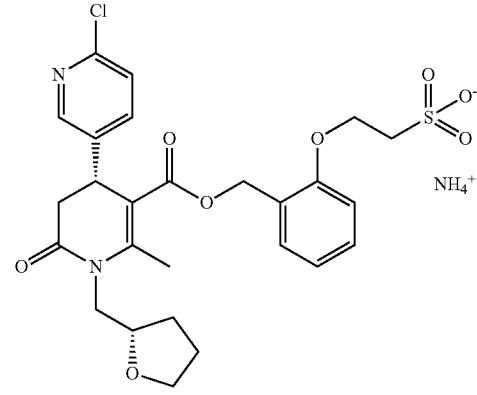 [SMILES: CC1=C(C(=O)OCc2ccccc2OCCS(=O)(=O)[O-])[C@@H](c2ccc(Cl)nc2)CC(=O)N1C[C@@H]1CCCO1 ; [NH4+]] |
| 159 | 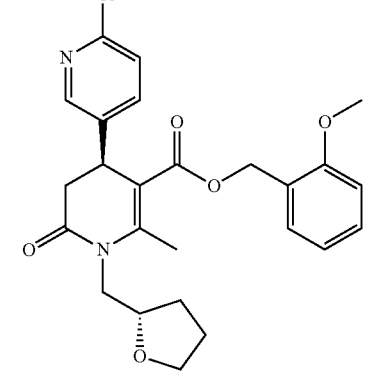 |
|  | 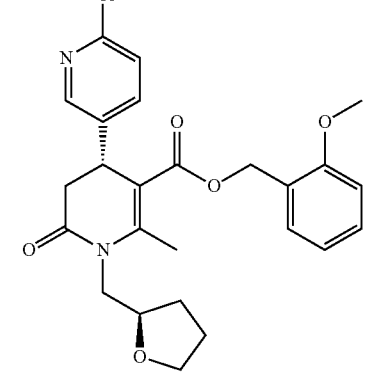 |
| 160 | 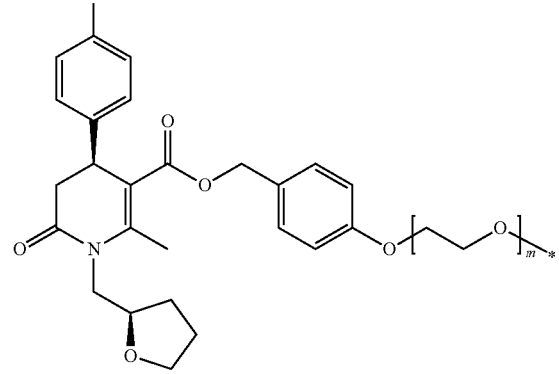<br>m = 11-18 |

TABLE 1-continued
| Compound | Structure |
|---|---|
| | 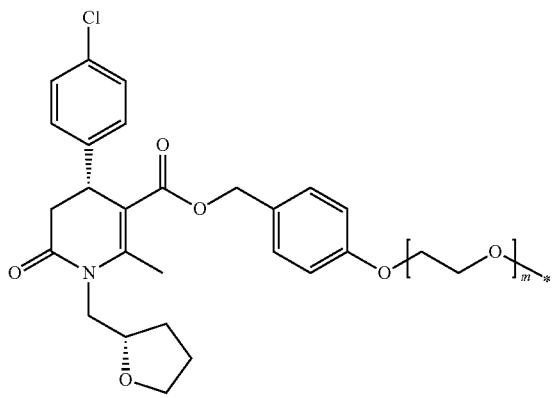
m = 11-18 |
| 161 | 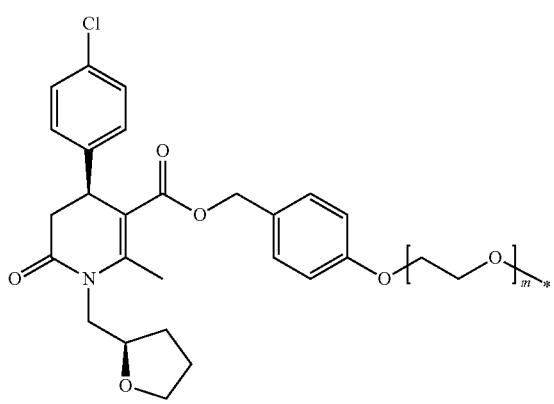
m = 38-48 |
| | 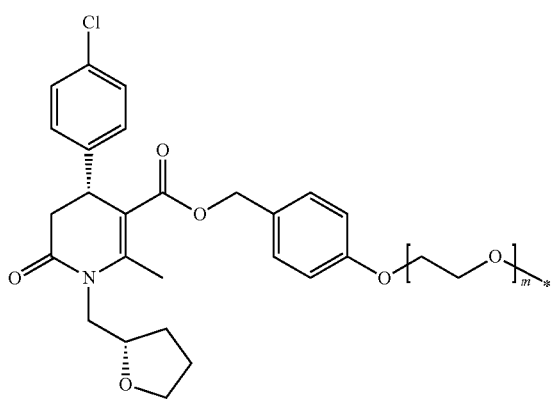
m = 38-48 |

TABLE 1-continued

| Compound | Structure |
|---|---|
| 162 | *(chemical structure)* |
| 163 | *(chemical structure)* |
| 164 | *(chemical structure)* |
| 165 | *(chemical structure)* |

TABLE 1-continued
| Compound | Structure |
|---|---|
| 166 | 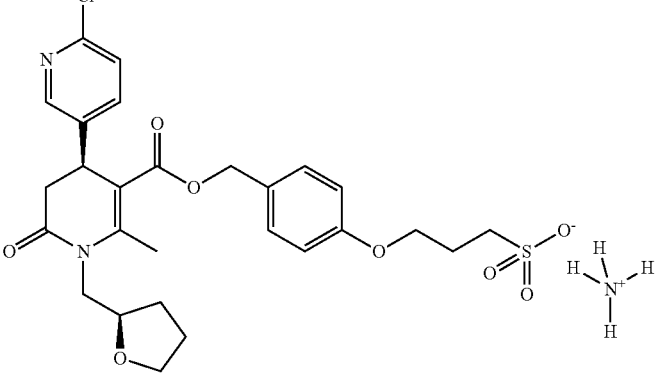 |
| 167 | 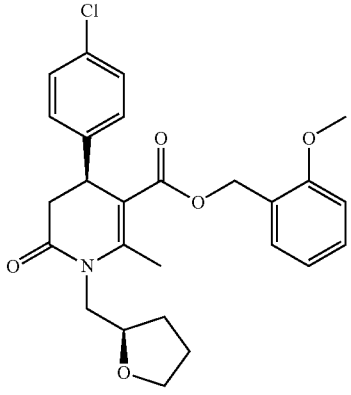 [SMILES: COc1ccccc1COC(=O)C1=C(C)N(C[C@H]2CCCO2)C(=O)C[C@H]1c1ccc(Cl)cc1] |
| 168 | 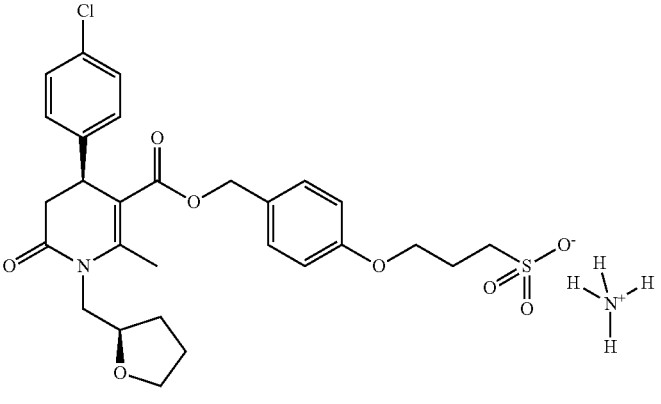 [SMILES: CC1=C(C(=O)OCc2ccc(OCCCS(=O)(=O)[O-])cc2)[C@H](c2ccc(Cl)cc2)CC(=O)N1C[C@H]1CCCO1 ; [NH4+]] |
| 169 | 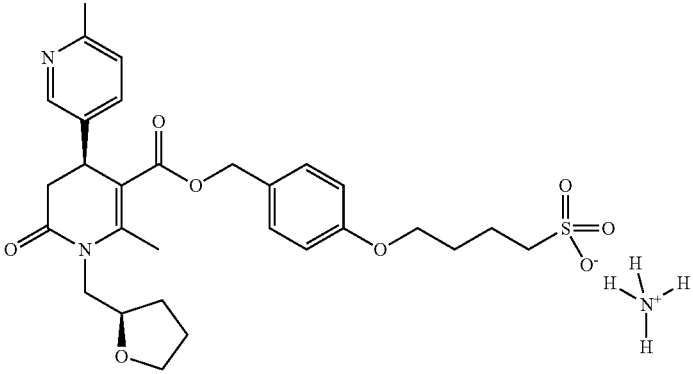 |

The compounds of the invention and their pharmaceutically acceptable salts and solvates can be prepared by different ways with reactions known by the person skilled in the art. Reaction schemes as described in the example section illustrate by way of example different possible approaches.

The invention further provides the use of the compounds of the invention or pharmaceutically acceptable salts, and/or solvates thereof as agonists of TGR5, in particular agonists of TGR5 having low or no systemic activity.

Accordingly, in a particularly preferred embodiment, the invention relates to the use of compounds of Formula I and subformulae in particular those of Table 1 above, or pharmaceutically acceptable salts and solvates thereof, as TGR5 agonists, in particular agonists of TGR5 having low or no systemic activity.

[Applications]

The compounds of the invention are therefore useful in the prevention and/or the treatment of TGR5 related diseases, such as metabolic and/or gastrointestinal diseases.

The invention thus also relates to the use of a compound of the invention or a pharmaceutically acceptable salt and/or solvate thereof for use in treating and/or preventing a TGR5 related disease, in particular a metabolic and/or a gastrointestinal disease. Or in other terms, the invention also relates to a method of treating and/or preventing a TGR5 related disease, in particular a metabolic and/or a gastrointestinal disease comprising the administration of a therapeutically effective amount of a compound or pharmaceutically acceptable salt or solvate of the invention, to a patient in need thereof. Preferably the patient is a warm-blooded animal, more preferably a human.

Metabolic diseases within the meaning of the present invention include, but are not limited to, type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

In a preferred embodiment, the metabolic disease is type II diabetes, a lipid disorder such as dyslipidemia, hypertension, obesity, or atherosclerosis and its sequelae.

In a particularly preferred embodiment the diseases are type II diabetes and a lipid disorder such as dyslipidemia, preferably type II diabetes.

Gastrointestinal diseases within the meaning of the present invention include, but are not limited to, Inflammatory Bowel Diseases (IBD) including but not limited to colitis, Ulcerative colitis (UC) and Crohn's Disease (CD), and Irritable Bowel Syndrome (IBS), intestinal injury disorders such as short-bowel syndrome, diseases involving intestinal barrier dysfunction such as proctitis and pouchitis, and gastrointestinal disorders characterized by hypermotilenemia or gastrointestinal hypermotility, including but not limited to any type of diarrhea.

In a preferred embodiment, the gastrointestinal disease is Inflammatory Bowel Diseases (IBD) including but not limited to colitis, Ulcerative colitis (UC) and Crohn's Disease (CD).

The invention also provides for a compound of the invention or a pharmaceutically acceptable salt and/or solvate thereof for use in delaying the onset of a TGR5 related disease, such as a metabolic and/or a gastrointestinal disease. Or in other terms, the invention also provides for a method for delaying in patient the onset of a TGR5 related diseases, such as a metabolic and/or a gastrointestinal disease comprising the administration of a therapeutically effective amount of a compound or pharmaceutically acceptable salt or solvate of the invention, to a patient in need thereof. Preferably the patient is a warm-blooded animal, more preferably a human. The metabolic and/or gastrointestinal diseases are preferably those defined above.

The invention further provides the use of a compound of the invention or a pharmaceutically acceptable salt and/or solvates thereof for the manufacture of a medicament for use in treating and/or preventing TGR5 related diseases, in particular metabolic and/or gastrointestinal diseases. Preferably, the metabolic and/or gastrointestinal diseases are those defined above.

According to a further feature of the present invention, there is provided the use of a compound of the invention or a pharmaceutically acceptable salt and/or solvate for modulating TGR5 receptor activity, in a patient, in need of such treatment, comprising administering to said patient an effective amount of a compound of the present invention, or a pharmaceutically acceptable salt and/or solvate thereof. In other terms, the invention also provides a method for modulating TGR5 receptor activity, in a patient, in need of such treatment, which comprises administering to said patient an effective amount of a compound of the present invention, or a pharmaceutically acceptable salt and/or solvate thereof. Preferably, the patient is a warm blooded animal, and even more preferably a human.

According to one embodiment, the compounds of the invention, their pharmaceutical acceptable salts and/or solvates may be administered as part of a combination therapy. Thus, are included within the scope of the present invention embodiments comprising coadministration of, and compositions and medicaments which contain, in addition to a compound of the present invention, a pharmaceutically acceptable salt and/or solvate thereof as active ingredient, additional therapeutic agents and/or active ingredients. Such multiple drug regimens, often referred to as combination therapy, may be used in the treatment and/or prevention of any of the diseases or conditions related to with TGR5 receptor modulation, particularly type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH). The use of such combinations of therapeutic agents is especially pertinent with respect to the treatment of the above-mentioned list of diseases within a patient in need of treatment or one at risk of becoming such a patient.

In addition to the requirement of therapeutic efficacy, which may necessitate the use of active agents in addition to the TGR5 agonist compounds of the invention or their pharmaceutical acceptable salts and/or solvates thereof, there may be additional rationales which compel or highly recommend the use of combinations of drugs involving active ingredients which represent adjunct therapy, i.e., which complement and supplement the function performed by the TGR5 receptor agonist compounds of the present invention. Suitable supplementary therapeutic agents used for the purpose of auxiliary treatment include drugs which, instead of directly treating or preventing a disease or condition related to TGR5 receptor modulation, treat diseases or conditions which directly result from or indirectly accompany the basic or underlying TGR5 receptor related disease or condition.

Thus, the methods of treatment and pharmaceutical compositions of the present invention may employ the compounds of the invention or their pharmaceutical acceptable salts and/or solvates thereof in the form of monotherapy, but said methods and compositions may also be used in the form of multiple therapy in which one or more compounds of the invention or their pharmaceutically acceptable salts and/or solvates are coadministered in combination with one or more other therapeutic agents.

The invention also provides pharmaceutical compositions comprising a compound of the invention or a pharmaceutically acceptable salt and/or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt and/or solvate thereof as active ingredient, additional therapeutic agents and/or active ingredients.

Another object of this invention is a medicament comprising at least one compound of the invention, or a pharmaceutically acceptable salt and/or solvate thereof, as active ingredient.

Generally, for pharmaceutical use, the compounds of the invention or a pharmaceutically acceptable salt and/or solvate thereof may be formulated as a pharmaceutical preparation comprising at least one compound of the invention or a pharmaceutically acceptable salt and/or solvate thereof and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

[Definitions]

The definitions and explanations below are for the terms as used throughout the entire application, including both the specification and the claims.

Unless otherwise stated any reference to compounds of the invention herein, means the compounds as such as well as there pharmaceutically acceptable salts and/or solvates.

When describing the compounds of the invention, the terms used are to be construed in accordance with the following definitions, unless indicated otherwise.

The term "halo" or "halogen" means fluoro, chloro, bromo, or iodo. Preferred halo groups are fluoro and chloro, fluoro being particularly preferred.

The term "alkyl" by itself or as part of another substituent refers to a hydrocarbyl radical of Formula $C_nH_{2n+1}$ wherein n is a number greater than or equal to 1. Suitable alkyl groups include methyl, ethyl, n-propyl, i-propyl, n-butyl, i-butyl, s-butyl and t-butyl.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. A preferred haloalkyl radical is trifluoromethyl.

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The term "aryl" as used herein refers to a polyunsaturated, aromatic hydrocarbyl group having a single ring (i.e. phenyl) or multiple aromatic rings fused together (e.g. naphtyl), typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Non-limiting examples of aryl comprise phenyl, biphenylyl, biphenylenyl, 5- or 6-tetralinyl, naphthalen-1- or -2-yl, 4-, 5-, 6 or 7-indenyl, 1-2-, 3-, 4- or 5-acenaphtylenyl, 3-, 4- or 5-acenaphtenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "heteroaryl" as used herein by itself or as part of another group refers but is not limited to 5 to 12 carbon-atom aromatic rings or ring systems containing 1 to 2 rings which are fused together, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl.

The compounds of Formula I and subformulae thereof may contain at least one asymmetric center and thus may exist as different stereoisomeric forms. Accordingly, the present invention includes all possible stereoisomers and includes not only racemic compounds but the individual enantiomers and their non racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be carried out by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry.

The bonds from an asymmetric carbon in compounds of the present invention may be depicted herein using a solid line (———), a zigzag line (∿∿∿), a solid wedge (═══), or a dotted wedge (⋯⋯). The use of a solid line to depict bonds from an asymmetric carbon atom is meant to indicate that all possible stereoisomers are meant to be included, unless it is clear from the context that a specific stereoisomer is intended. The use of either a solid or dotted wedge to depict bonds from an asymmetric carbon atom is meant to indicate that only the stereoisomer shown is meant to be included.

The compounds of the invention may also contain more than one asymmetric carbon atom. In those compounds, the use of a solid line to depict bonds from asymmetric carbon atoms is meant to indicate that all possible stereoisomers are meant to be included, unless it is clear from the context that a specific stereoisomer is intended.

The compounds of the invention containing a basic functional group and/or an acidic functional group may be in the form of pharmaceutically acceptable salts. Pharmaceutically acceptable salts of the compounds of the invention containing one or more basic functional group include in particular the acid addition salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Compounds containing one or more acidic functional groups may be capable of forming pharmaceutically acceptable salts with a pharmaceutically acceptable base, for example and without limitation, inorganic bases based on alkaline metals or alkaline earth metals or organic bases such as ammonia ($NH_3$) and primary amine compounds, secondary amine compounds, tertiary amine compounds, cyclic amines or basic ion exchange resins. Compounds containing one or more basic functional groups may be capable of forming pharmaceutically acceptable salts, e.g. amine groups may be transformed into ammonium groups by reacting the amine group with an inorganic or organic base or an alkylating agent such as e.g. an alkylhalide (e.g. methyliodide). When the compounds of the invention contain an acidic group as well as a basic group the compounds of the invention may also form internal salts, and such compounds are within the scope of the invention.

Generally, pharmaceutically acceptable salts of compounds of Formula I may for example be prepared as follows:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

All references to compounds of Formula I include references to salts and solvates thereof.

The compounds of the invention include compounds of Formula I as hereinbefore defined, including all polymorphs and crystal habits thereof, prodrugs and isomers thereof (including optical, geometric and tautomeric isomers) and isotopically-labeled compounds of Formula I.

In addition, although generally, with respect to the salts of the compounds of the invention, pharmaceutically acceptable salts are preferred, it should be noted that the invention in its broadest sense also includes non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The term "patient" refers to a warm-blooded animal, more preferably a human, who/which is awaiting or receiving medical care or is or will be the object of a medical procedure.

The term "human" refers to subjects of both genders and at any stage of development (i.e. neonate, infant, juvenile, adolescent, adult). In one embodiment, the human is an adolescent or adult, preferably an adult.

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e. g. TGR5 agonist) which is sufficient to achieve the desired therapeutic or prophylactic effect in the individual to which it is administered.

The term "administration", or a variant thereof (e.g., "administering"), means providing the active agent or active ingredient (e. g. a TGR5 agonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "agonist" as used herein means a ligand that activates an intracellular response when it binds to a receptor.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The term "lipid disorder" as used herein means any plasma lipid disorder including but not limited to dyslipidemia such as mixed or diabetic dyslipidemia, hypercholesterolemia, low HDL cholesterol, high LDL cholesterol, hyperlipidemia and hypertriglyceridemia.

The present invention will be better understood with reference to the following examples. These examples are intended to representative of specific embodiments of the invention, and are not intended as limiting the scope of the invention.

CHEMISTRY EXAMPLES

All reagents, solvents and starting materials were purchased from commercial suppliers and used without further purification. $^1$H NMR spectra were recorded on a Brucker Avance 300 MHz spectrometer with methanol-d6, CDCl$_3$ or DMSO-d6 as the solvent. $^{13}$C NMR spectra are recorded at 100 MHz. All coupling constants are measured in hertz (Hz) and the chemical shifts (δ) are quoted in parts per million (ppm). Liquid chromatography mass spectroscopy analyses (LC-MS) were performed using LCMS-MS triple-quadrupole system (Waters) with a C18 TSK-GEL Super ODS (2 μm particle size column, 50*4.6 mm). LCMS gradient starting from 98% H$_2$O/0.1% formic acid and reaching 2% H2O/98% MeOH within 5 min (method A) at a flow rate of 2 mL/min or starting from 100% H$_2$O/0.1% formic acid and reaching 5% H$_2$O/95% MeOH within 10 min (method B) at a flow rate of 1 mL/min was used. Purity (%) was determined by Reversed Phase HPLC, using UV detection (215 nM). High resolution mass spectroscopy (HRMS) were carried out on an Waters LCT Premier XE (TOF), ESI ionization mode, with a Waters XBridge C18 (150*4.6 mm, 3.5 μm particle size). LCMS gradient starting from 98% ammonium formate buffer 5 mM (pH 9.2) and reaching 95% CH3CN/5% ammonium formate buffer 5 mM (pH 9.2) within 15 min at a flow rate of 1 mL/min was used.

Solvents, reagents and starting materials were purchased from well known chemical suppliers such as for example Sigma Aldrich, Acros Organics, Fluorochem, Eurisotop, VWR International, Sopachem and Polymer labs.

Solvents, reagents and starting materials were purchased from well known chemical suppliers such as for example Sigma Aldrich, Acros Organics, Fluorochem, Eurisotop, VWR International, and the following abbreviations are used:
ACN: Acetonitrile,
DCM: Dichloromethane,
DMF: N,N-dimethylformamide,
EtOAc: Ethyl acetate,
EtOH: Ethanol,
MeOH: Methanol,
RT: Room temperature,
DIEA: N,N-diisopropylethylamine,
Y: Yield,
g: Grams,
mg: Milligrams,
L: Liters,
mL: Milliliters,
μL: Microliters,
mol: Moles,
mmol: Millimoles,
h: Hours,
min: Minutes,
TLC: Thin layer chromatography,
MW: Molecular weight,
eq: Equivalent,
μW: Microwave,
THF: Tetrahydrofuran,
TFA: Trifluoroacetic acid,
Ac: Acetyl,
tBu: tert-Butyl,
Bn: Benzyl,
Rt: Retention time,
Mn: Number average molecular mass.

As illustrated in the Examples hereafter, the compounds of the invention bearing a polyethylenoxy side chain (OCH$_2$CH$_2$)$_m$ may be prepared from poly(ethylene glycol) starting materials which are in the form of a polydisperse mixture of polymers having different degrees of polymerization (i.e. the chain lengths) (m). These starting materials are thus characterized by a degree of polymerization given in the form of range and/or by a Mn.

Therefore, the exemplified compounds of the invention bearing a polyethylenoxy side chain (OCH$_2$CH$_2$)$_m$ may be obtained as mixtures of compounds having different degrees of polymerization (m) given as a range.

Therefore, within the meaning of the invention, a compound of the invention having a moiety of the following Formula

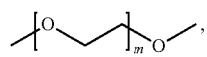

wherein the degree of polymerization m is identified as range, i.e. as m is x to y or as m=x-y, x and y being integers different from one another, are comprised all compounds bearing said moiety with a polymerization degree superior or equal to x and inferior or equal to y as well as mixtures thereof.

For instance, in the compound depicted by the following formula

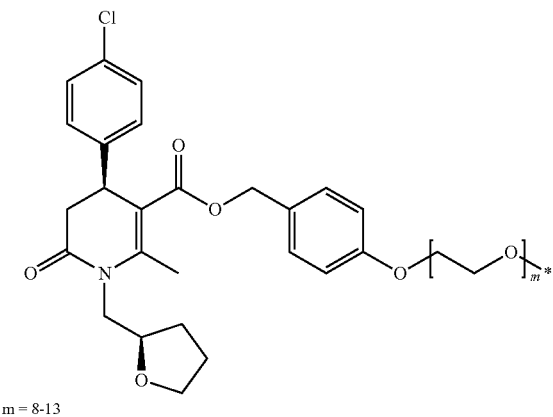

m = 8-13 the indication m=8-13 means that all compounds with m superior or equal to 8 and inferior or equal to 13 as well as mixtures thereof are comprised within this formula.
General Procedure A.

Appropriate aldehyde (1 equiv), meldrum acid (1 equiv), acetoacetate (1 equiv) and ammonium acetate (1.5 equiv) were dissolved in acetic acid (1N). The reaction mixture was stirred overnight under reflux. The solvent was removed. The crude was precipitated in EtOH and filtered to give the desired compound.

TABLE 2

| Example | R″ |
|---|---|
| 1 | o-Me |
| 2 | m-Me |
| 3 | p-Me |
| 4 | o-OMe |
| 5 | m-OMe |
| 6 | p-OMe |
| 7 | o-CF$_3$ |
| 8 | m-CF$_3$ |
| 9 | p-CF$_3$ |
| 10 | o-Cl |
| 11 | m-Cl |
| 12 | p-Cl |
| 13 | p-F |
| 14 | Ø |
| 15 | 2-F, 4-Cl |
| 16 | p-Br |

Example 1: 2-Methyl-6-oxo-4-o-tolyl-1,4, 5,6-tetrahydro-pyridine-3-carboxylic acid benzyl ester 2-Methyl-6-oxo-4-o-tolyl-1,4,5,6-tetrahydro-pyridine-3-carboxylic acid benzyl ester was prepared according to general protocol A, starting from 2-methylbenzaldehyde (0.27 mL), benzoyl acetylacetate (384 mg) and obtained as a white powder (137 mg, 20%) after purification by preparative LC-MS, $^1$H NMR (CDCl$_3$) δ7.61 (s, 1H); 7.30-6.95 (m, 9H); 5.14 (d, J=12.6 Hz, 1H); 5.08 (d, J=12.6 Hz, 1H); 4.26 (d, J=7.4 Hz, 1H); 2.93 (dd, J=16.5 Hz and 8.6 Hz, 1H); 2.70 (dd, J=16.5 Hz and 1.2 Hz, 1H); 2.43 (s, 3H); 2.29 (s, 3H); MS [M+H]$^+$=336; HRMS: calcd for C$_{21}$H$_{22}$NO$_3$, (MH$^+$) 336.1600, found 336.1588.

Example 2: 2-M ethyl-6-oxo-4-m-tolyl-1,4,5,6-tetrahydro-pyridine-3-carboxylic acid benzyl ester 2-Methyl-6-oxo-4-m-tolyl-1,4,5,6-tetrahydro-pyridine-3-carboxylic acid benzyl ester was prepared according to general protocol A, starting from 3-methylbenzaldehyde (0.27 mL), benzoyl acetylacetate (384 mg) and obtained as a white powder (78 mg, 11%) after precipitation in ethanol. $^1$H NMR (CDCl$_3$) δ 7.41 (s, 1H); 7.30-6.95 (m, 9H); 5.14 (d, J=12.6 Hz, 1H); 5.08 (d, J=12.6 Hz, 1H), 4.26 (d, J=7.4 Hz, 1H); 2.93 (dd, J=16.5 Hz and 8.1 Hz, 1H); 2.70 (dd, J=16.5 Hz and 1.1 Hz, 1H); 2.43 (s, 3H); 2.29 (s, 3H); MS[M+H]$^+$=336; HRMS: calcd for C$_{21}$H$_{22}$NO$_3$, (MH$^+$) 336.1600, found 336.1596.

Example 3: 2-Methyl-6-oxo-4-p-tolyl-1,4, 5,6-tetrahydro-pyridine-3-carboxylic acid benzyl ester 2-Methyl-6-oxo-4-p-tolyl-1,4,5,6-tetrahydro-pyridine-3-carboxylic acid benzyl ester was prepared according to general protocol A, starting from 4-methylbenzaldehyde (0.27 mL), benzoyl acetylacetate (384 mg) and obtained as a white powder (137 mg, 20%) after precipitation in ethanol. $^1$H NMR (CDCl$_3$) δ 7.58 (s, 1H); 7.30-7.04 (m, 9H); 5.12 (s, 2H); 4.27 (d, J=7.5 Hz, 1H); 2.93 (dd, J=16.5 Hz and 8 Hz, 1H); 2.68 (dd, J=16.5 Hz and 1.2 Hz, 1H); 2.42 (s, 3H); 2.32 (s, 3H); MS[M+H]$^+$=336; HRMS: calcd for C$_{21}$H$_{22}$NO$_3$, (MH$^+$) 336.1600, found 336.1591.

Example 4: 4-(2-Methoxy-phenyl)-2-methyl-6-oxo-1,4,5,6-tetrahydro-pyridine-3-carboxylic acid benzyl ester 4-(2-Methoxy-phenyl)-2-methyl-6-oxo-1,4,5,6-tetrahydro-pyridine-3-carboxylic acid benzyl ester was prepared according to general protocol A, starting from 2-methoxybenzaldehyde (150 mg), benzoyl acetylacetate (210 mg) and obtained as a white powder (63 mg) after precipitation in ethanol (16%). $^1$H NMR (CDCl$_3$) δ 7.51 (s, 1H); 7.25-6.81 (m, 9H); 5.07 (d, J=12.7.0 Hz, 1H); 5.03 (d, J=12.7.0 Hz, 1H); 4.67 (d, J=8.2 Hz, 1H); 3.79 (s, 3H); 2.86 (dd, J=16.6 Hz and 7.9 Hz, 1H); 2.70 (d, J=16.7 Hz, 1H); 2.46 (s, 3H); MS [M+H]$^+$ 352; HRMS: calcd for C$_{21}$H$_{22}$NO$_4$, (MH$^+$) 352.1549, found 352.1548.

Example 5: 4-(3-M ethoxy-phenyl)-2-methyl-6-oxo-1,4,5,6-tetrahydro-pyridine-3-carboxylic acid benzyl ester 4-(3-Methoxy-phenyl)-2-methyl-6-oxo-1,4,5,6-tetrahydro-pyridine-3-carboxylic acid benzyl ester was prepared according to general protocol A, starting from 3-methoxylbenzaldehyde (0.3 mL), benzoyl acetylacetate (384 mg) and obtained as a white powder (36 mg, 5%) after precipitation in ethanol. $^1$H NMR (CDCl$_3$) δ7.52 (s, 1H); 7.30-6.70 (m, 9H); 5.14 (d, J=12.7 Hz, 1H); 5.09 (d, J=12.7 Hz, 1H); 4.27

(d, J=7.2 Hz, 1H); 3.74 (s, 3H); 2.93 (dd, J=16.5 Hz and 8.1 Hz, 1H); 2.70 (dd, J=16.5 Hz and 1.1 Hz, 1H); 2.43 (s, 3$H_3$); MS[M+H]$^+$=352; HRMS: calcd for $C_{21}H_{22}NO_4$, (MH$^+$) 352.1549, found 352.1546.

Example 6: 4-(4-Methoxy-phenyl)-2-methyl-6-oxo-1,4,5,6-tetrahydro-pyridine-3-carboxylic acid benzyl ester 4-(4-Methoxy-phenyl)-2-methyl-6-oxo-1,4,5,6-tetrahydro-pyridine-3-carboxylic acid benzyl ester was prepared according to general protocol A, starting from 4-methoxylbenzaldehyde (0.3 mL), benzoyl acetylacetate (384 mg) and obtained as a yellow powder (27 mg, 5%) after purification by preparative LC-MS.; $^1$H NMR (CDC$_3$) δ7.59 (s, 1H); 7.31-6.79 (m, 9H); 5.14 (d, J=12.5 Hz, 1H); 5.09 (d, J=12.5 Hz, 1H); 4.25 (d, J=7.3 Hz, 1H); 3.79 (s, 3H); 2.91 (dd, J=16.4 Hz and 8.0 Hz, 1H); 2.68 (d, J=15.4 Hz, 1H); 2.42 (s, 3H); MS [M+H]$^+$=352; HRMS: calcd for $C_{21}H_{22}NO_4$, (M H+) 352.1549, found 352.1542.

Example 7: 2-Methyl-6-oxo-4-(2-trifluoromethyl-phenyl)-1,4,5,6-tetrahydro-pyridine-3-carboxylic acid benzyl ester 2-M ethyl-6-oxo-4-(2-trifluoromethyl-phenyl)-1,4,5,6-tetrahydro-pyridine-3-carboxylic acid benzyl ester was prepared according to general protocol A, starting from 2-trifluoromethylbenzaldehyde (0.27 mL), benzoyl acetylacetate (384 mg) and obtained as a white powder (138 mg, 18%) after precipitation in ethanol. $^1$H NMR (CDCl$_3$) δ 7.66 (s, 1H); 7.64-6.96 (m, 9H); 5.04 (d, J=12.3 Hz, 1H); 4.98 (d, J=12.3 Hz, 1H); 4.70 (d, J=8.7 Hz, 1H); 3.00 (dd, J=16.8 Hz and 9 Hz, 1H); 2.65 (d, J=17.3 Hz, 1H); 2.48 (s, 3H); MS[M+H]$^+$=390; HRMS: calcd for $C_{21}H_{19}NO_3F_3$, (MH$^+$) 390.1317, found 390.1306.

Example 8: 2-Methyl-6-oxo-4-(3-trifluoromethyl-phenyl)-1,4,5,6-tetrahydro-pyridine-3-carboxylic acid benzyl ester 2-Methyl-6-oxo-4-(3-trifluoromethyl-phenyl)-1,4,5,6-tetrahydro-pyridine-3-carboxylic acid benzyl ester was prepared according to general protocol A, starting from 3-trifluoromethylbenzaldehyde (0.45 mL), benzoyl acetylacetate (384 mg) and obtained as a white powder (141 mg, 18%) after precipitation in ethanol. $^1$H NMR (CDCl$_3$) δ 7.71 (s, 1H); 7.51-7.11 (m, 9H); 5.14 (d, J=12.6 Hz, 1H); 5.07 (d, J=12.6 Hz, 1H); 4.35 (d, J=7.9 Hz, 1H); 2.99 (dd, J=16.6 Hz and 8.3 Hz, 1H); 2.69 (d, J=16.5 Hz, 1H); 2.46 (s, 3H); MS [M+H]$^+$=390; HRMS: calcd for $C_{21}H_{19}NO_3F_3$, (MH$^+$) 390.1317, found 390.1319.

Example 9: 2-Methyl-6-oxo-4-(4-trifluoromethyl-phenyl)-1,4,5,6-tetrahydro-pyridine-3-carboxylic acid benzyl ester 2-Methyl-6-oxo-4-(4-trifluoromethyl-phenyl)-1,4,5,6-tetrahydro-pyridine-3-carboxylic acid benzyl ester was prepared according to general protocol A, starting from 4-trifluoromethylbenzaldehyde (0.44 mL), benzoyl acetylacetate (384 mg) and obtained as a white powder (96 mg, 13%) after precipitation in ethanol. $^1$H NMR (CDCl$_3$) δ7.59 (s, 1H); 7.54-7.09 (m, 9H); 5.15 (d, J=12.5 Hz, 1H); 5.06 (d, J=12.5 Hz, 1H); 4.34 (d, J=7.7 Hz, 1H); 2.99 (dd, J=16.6 Hz and 8.2 Hz, 1H); 2.69 (d, J=16.7 Hz, 1H); 2.45 (s, 3H); MS [M+H]$^+$=390; HRMS: calcd for $C_{21}H_{19}NO_3F_3$, (MH$^+$) 390.1317, found 390.1311.

Example 10: 4-(2-Chloro-phenyl)-2-methyl-6-oxo-1,4,5,6-tetrahydro-pyridine-3-carboxylic acid benzyl ester 4-(2-Chloro-phenyl)-2-methyl-6-oxo-1,4,5,6-tetrahydro-pyridine-3-carboxylic acid benzyl ester was prepared according to general protocol A, starting from 2-chlorobenzaldehyde (0.19 mL), benzoyl acetylacetate (205 mg). 26 mg of white powder were obtained after precipitation in ethanol. $^1$H NMR (CDCl$_3$) δ: 7.65 (s, 1H, NH); 7.41-7.05 (m, 9H, ArH); 5.08 (d, J=12.7 Hz, 1H, CH$_2$); 5.04 (d, J=12.7 Hz, 1H, CH$_2$); 4.79 (d, J=8.25 Hz, 1H, CH); 2.94 (dd, J=16.7 Hz and 8.5 Hz, 1H, CH$_2$); 2.73 (d, J=16.7 Hz, 1H, CH$_2$); 2.50 (s, 3H, CH$_3$); MS [M+H]$^+$ 356; HRMS: calcd for $C_{20}H_{19}NO_3Cl$, (MH$^+$) 356.1053, found 356.1048.

Example 11: 4-(3-Chloro-phenyl)-2-methyl-6-oxo-1,4,5,6-tetrahydro-pyridine-3-carboxylic acid benzyl ester 4-(3-Chloro-phenyl)-2-methyl-6-oxo-1,4,5,6-tetrahydro-pyridine-3-carboxylic acid benzyl ester was prepared according to general protocol A, starting from 3-chlorobenzaldehyde (0.35 mL), benzoyl acetylacetate (384 mg) and obtained as a white powder (185 mg, 26%) after precipitation in ethanol $^1$H NMR (CDCl$_3$) δ 7.54 (s, 1H); 7.32-7.03 (m, 9H); 5.14 (d, J=12.4 Hz, 1H); 5.07 (d, J=12.4 Hz, 1H); 4.27 (d, J=7.7 Hz, 1H); 2.95 (dd, J=16.6 Hz and 8.2 Hz, 1H); 2.68 (dd, J=16.6 Hz and 0.9 Hz, 1H); 2.45 (s, 3H); MS [M+H]$^+$=356; HRMS: calcd for $C_{20}H_{19}NO_3Cl$, (MH$^+$) 390.1053, found 390.1058.

Example 12: Benzyl 4-(4-chlorophenyl)-6-methyl-2-oxo-3,4-dihydro-1H-pyridine-5-carboxylate Benzyl 4-(4-chlorophenyl)-6-methyl-2-oxo-3,4-dihydro-1H-pyridine-5-carboxylate was prepared according to general protocol A, starting from p-chlorobenzaldehyde (15 mmol, 2.108 g), benzoyl acetylacetate (15 mmol, 2.58 mL) and obtained as a pale yellow powder (1.54 g, 29%) after precipitation in ethanol. $^1$H NMR (300 MHz, CDCl$_3$) δ 2.44 (s, 3H), 2.66 (dd, J=16.6 Hz and 1.5 Hz, 1H), 2.95 (dd, J=16.6 hz and 8.2 Hz, 1H), 4.27 (d, J=8.2 Hz, 1H), 5.08 (d, J=12.6 Hz, 1H), 5.15 (d, J=12.6 Hz, 1H), 7.10 (d, J=8.5 Hz, 2H), 7.13-7.18 (m, 2H), 7.25 (d, J=8.5 Hz, 2H), 7.29-7.33 (m, 3H), 8.40 (s, 1H). MS [M+H]$^+$ 356

Example 13: 4-(4-Fluoro-phenyl)-2-methyl-6-oxo-1,4,5,6-tetrahydro-pyridine-3-carboxylic acid benzyl ester 4-(4-Fluoro-phenyl)-2-methyl-6-oxo-1,4,5,6-tetrahydro-pyridine-3-carboxylic acid benzyl ester was prepared according to general protocol A, starting from 4-fluorobenzaldehyde (0.22 mL), benzoyl acetylacetate (384 mg) and obtained as a white powder (122 mg) after precipitation in ethanol (18%). $^1$H NMR (CDCl$_3$) δ 7.76 (s, 1H); 7.30-6.92 (m, 9H); 5.14 (d, J=12.5 Hz, 1H); 5.08 (d, J=12.5 Hz, 1H); 4.27 (d, J=7.74 Hz, 1H); 2.94 (dd, J=16.5 Hz and 8.1 Hz, 1H); 2.66 (dd, J=16.5 Hz and 0.9 Hz, 1H); 2.43 (3H, s, 3H), MS [M+H]$^+$ 340

Example 14: 2-Methyl-6-oxo-4-phenyl-1,4,5,6-tetrahydro-pyridine-3-carboxylic acid benzyl ester 2-Methyl-6-oxo-4-phenyl-1,4,5,6-tetrahydro-pyridine-3-carboxylic acid benzyl ester was prepared according to general protocol A, starting from benzaldehyde (0.22 mL), benzoyl acetylacetate (384 mg) and obtained as a white powder (171 mg, 26%) after precipitation in ethanol. $^1$H NMR (CDCl$_3$) δ 7.79 (s, 1H); 7.29-7.12 (m, 10H); 5.13 (d, J=12.6 Hz, 1H); 5.08 (d, J=12.6 Hz, 1H); 4.30 (d, J=7.8 Hz, 1H); 2.95 (dd, J=16.5 Hz and 8.1 Hz, 1H); 2.70 (d, J=16.5 Hz, 1H); 2.43 (s, 3H); MS[M+H]$^+$=322; HRMS: calcd for $C_{20}H_{20}NO_3$, (MH$^+$) 322.1443, found 322.1436.

Example 15: benzyl 4-(4-chloro-2-fluoro-phenyl)-6-methyl-2-oxo-3,4-dihydro-1H-pyridine-5-carboxylate benzyl 4-(4-chloro-2-fluoro-phenyl)-6-methyl-2-oxo-3,4-dihydro-1H-pyridine-5-carboxylate was prepared according to general protocol A, starting from 4-Chloro-2-fluorobenzaldehyde (800 mg), benzoyl acetylacetate (860 μL) and obtained as a white powder (730 mg, 39%) after precipitation in ethanol. $^1$H NMR (CDCl$_3$) δ 8.17 (s, 1H); 7.29 (m, 3H); 7.12-6.91 (m, 5H), 5.11 (d, J=12.6 Hz, 1H), 5.05 (d, J=12.6 Hz, 1H), 4.57 (d, J=8.1 Hz, 1H); 2.96 (dd, J=16.5 Hz and 8.4 Hz, 1H); 2.64 (d, J=15.6 Hz, 1H); 2.46 (s, 3H); MS [M+H]$^+$=373

Example 16: benzyl 4-(4-bromophenyl)-6-methyl-2-oxo-3,4-dihydro-1H-pyridine-5-carboxylate p-bromobenzaldehyde (15.0 mmol, 2.77 g), meldrum acid (15.0 mmol, 2.16 g), benzyl acetoacetate (15.0 mmol, 2.58 mL) and ammonium acetate (22.5 mmol, 1.73 g) were dissolved in acetic acid (15 mL). The reaction mixture was stirred at 110° C. for 18 h. The solvent was removed. The crude was precipitated in EtOH, cooled to 0° C. and filtered to give the desired benzyl 4-(4-bromophenyl)-6-methyl-2-oxo-3,4-dihydro-1H-pyridine-5-carboxylate as a white powder (2.35 g, 39%). $^1$H NMR (300 MHz, CDCl$_3$) δ 2.42 (s, 3H), 2.64 (dd, J=16.6, 1.5 Hz, 1H), 2.93 (dd, J=16.6, 8.2 Hz, 1H), 4.23 (d, J=8.2 Hz, 1H), 5.05 (d, J=12.5 Hz, 1H), 5.13 (d, J=12.5 Hz, 1H), 7.01 (d, J=8.4 Hz, 2H), 7.09-7.16 (m, 2H), 7.26-7.32 (m, 3H), 7.38 (dt, J=8.4, 2.0 Hz, 2H), 7.93 (brs, 1H). MS [M+H]$^+$ 400. HRMS: calcd for C$_{20}$H$_{19}$NO$_3$Br, [M+H]$^+$ 400.0548, found 400.0567.

TABLE 3

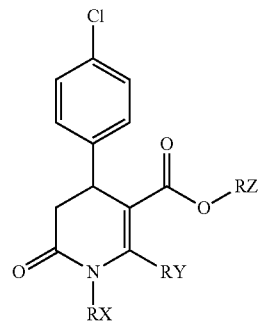

| Example | RX | RY | RZ |
|---|---|---|---|
| 17 | CH$_3$ | —CH$_3$ | benzyl |
| 18 | CH$_3$ | isopropyl | benzyl |
| 19 | CH$_3$ | phenyl | benzyl |
| 20 | CH$_3$ | phenyl | isopropyl |
| 21 | CH$_3$ | isopropyl | isopropyl |
| 22 | H | methoxyethyl | benzyl |

Example 17: 4-(4-Chloro-phenyl)-1,2-dimethyl-6-oxo-1,4,5,6-tetrahydro-pyridine-3-carboxylic acid benzyl ester Benzyl 4-(4-chlorophenyl)-6-methyl-2-oxo-3,4-dihydro-1H-pyridine-5-carboxylate (300 mg, 0.84 mmol) was dissolved in DMF (4 mL). NaH (33 mg) and iodomethan (52 μL) were added. After completion, water was added and reaction mixture was extracted with Et$_2$O. The organic layer was dried over MgSO$_4$ and evaporated under reduced pression. The product was purified by flash chromatography (Cyclohexane/EtOAc 4:1) to give 4-(4-Chloro-phenyl)-1,2-dimethyl-6-oxo-1,4,5,6-tetrahydro-pyridine-3-carboxylic acid benzyl ester as a white powder (31 mg, 10%). MS (ESI)=370[M+H]$^+$; $^1$H NMR (CDCl$_3$) δ 7.31-7.00 (m, 9H); 5.14 (d, J=12.5 Hz, 1H), 5.09 (d, J=12.5 Hz, 1H), 4.21 (d, J=5.79 Hz, 1H, CH); 3.21 (s, 3H); 2.90 (dd, J=16.0 Hz and 7.4 Hz, 1H); 2.75 (dd, J=16.0 Hz and 2.4 Hz, 1H); 2.58 (s, 3H); HRMS: calcd for C21H21NO3Cl, (MH+) 370.1210, found 370.1205.

Example 18: Benzyl 4-(4-chlorophenyl)-6-ethyl-1-methyl-2-oxo-3,4-dihydropyridine-5-carboxylate Step 1.

p-chlorobenzaldehyde (15 mmol, 2.108 g), meldrum acid (15 mmol, 2.16 g), ethyl propionylacetate (15 mmol, 2.13 mL) and ammonium acetate (22.5 mmol, 1.73 g) were dissolved in acetic acid (15 mL). The reaction mixture was stirred overnight under reflux. The solvent was removed. The crude was dissolved in EtOAc and washed by an aqueous solution of HCl 1N and a saturated solution of NaHCO$_3$. The organic layer was dried on MgSO$_4$, the solvent was removed under reduced pressure. The crude product was purified by flash chromatography using a mixture of Cyclohexane/EtOAc (8/2) as eluent to give the desired compound as yellow oil (470 mg, 11%).

$^1$H NMR (300 MHz, CDCl$_3$) δ 1.20 (t, J=7.2 Hz, 3H), 1.26 (t, J=7.2 Hz, 3H), 2.60-3.00 (m, 4H), 4.07-4.18 (m, 2H), 4.24 (dd, J=8.0, 2.0 Hz, 1H), 7.12 (d, J=8.6 Hz, 2H), 7.25 (d, J=8.6 Hz, 2H). MS [M+H]$^+$ 308.

Step 2.

The dihydropyridone intermediate obtained in step 1 (180 mg, 0.58 mmol) was dissolved in anhydrous DMF (2 mL). Cesium carbonate (377 mg, 1.16 mmol) and iodomethane (72 µL, 1.16 mmol) were added. The reaction mixture was stirred at 60° C. for 3 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/DCM (1/1) as eluent to give the desired compound as a colorless oil (143 mg, 76%).

$^1$H NMR (300 MHz, CDCl$_3$) δ 1.16-1.28 (m, 6H), 2.75 (dd, J=15.9, 2.8 Hz, 1H), 2.82-2.97 (m, 2H), 3.03-3.19 (m, 1H), 3.21 (s, 3H), 4.03-4.22 (m, 3H), 7.07 (d, J=8.6 Hz, 2H), 7.22 (d, J=8.6 Hz, 2H). MS [M+H]$^+$ 322. HRMS: calcd for C$_{17}$H$_{21}$NO$_3$Cl, [M+H]$^+$ 322.1210, found 322.1217.

Step 3.

The dihydropyridone intermediate obtained in step 2 (83 mg, 0.26 mmol) was dissolved in MeOH (1 mL) and a solution of aqueous NaOH 1 N (1 mL, 4.0 equiv.) was added. The reaction mixture was stirred at 60° C. for 18 h. The reaction mixture was cooled to RT and extracted once with diethyl ether. The aqueous phase was then acidified until pH=1 with an aqueous solution of hydrochloric acid. The aqueous phase was extracted by EtOAc. The organic layer was then washed with brine and dried with MgSO$_4$. The solvent was removed under reduced pressure to give the desired acid (56 mg, 0.19 mmol). The crude product was then used without further purification in the next step. The acid was dissolved in anhydrous DMF (2 mL) then Cs$_2$CO$_3$ (123 mg, 0.38 mmol) and benzyl bromide (45 µL, 0.38 mmol) were added. The reaction mixture was stirred for 1 h at RT. Water was then added and the aqueous phase was extracted with diethyl ether. The organic layer was then washed with brine and dried with MgSO$_4$. The solvent was removed under reduced pressure. The crude product was purified by flash chromatography using a mixture of cyclohexane/dichloromethane 3/1 to give the desired benzyl 4-(4-chlorophenyl)-6-ethyl-1-methyl-2-oxo-3,4-dihydropyridine-5-carboxylate (28 mg, 28%). $^1$H NMR (300 MHz, CDCl$_3$) δ 1.24 (dd, J=7.7 Hz, 3H), 2.76 (t, J=16.2, 2.8 Hz, 1H), 2.83-2.89 (m, 2H), 3.07-3.20 (m, 2H), 3.24 (s, 3H), 4.18 (dd, J=7.3, 2.8 Hz, 1H), 5.13 (s, 2H), 7.02 (d, J=8.4 Hz, 2H), 7.12-7.19 (m, 2H), 7.23 (d, J=8.4 Hz, 2H), 7.28-7.34 (m, 3H). MS [M+H]$^+$ 384; HRMS: calcd for C$_{22}$H$_{23}$NO$_3$Cl, [M+H]$^+$ 384.1366, found 384.1375.

Example 19: Benzyl 4-(4-chlorophenyl)-1-methyl-2-oxo-6-phenyl-3,4-dihydropyridine-5-carboxylate Step 1.

p-chlorobenzaldehyde (15 mmol, 2.108 g), meldrum acid (15 mmol, 2.16 g), ethyl benzoylacetate (15 mmol, 2.6 mL) and ammonium acetate (22.5 mmol, 1.73 g) were dissolved in acetic acid (15 mL). The reaction mixture was stirred overnight under reflux. The solvent was removed. The crude was precipitated in EtOH and filtered to give the desired compound as a white powder (1.1 g, 21%). $^1$H NMR (300 MHz, CDCl$_3$) δ 0.85 (t, J=7.1 Hz, 3H), 2.78 (dd, J=16.5, 2.4 Hz, 1H), 3.08 (dd, J=16.5, 8.0 Hz, 1H), 3.89 (q, J=6.9 Hz, 2H), 4.33 (dd, J=8.0, 2.4 Hz, 1H), 7.17 (brs, 1H), 7.27-7.60 (m, 9H). MS [M+H]$^+$ 356

Step 2.

The dihydropyridone intermediate obtained in step 1 (213 mg, 0.6 mmol) was dissolved in anhydrous DMF (2 mL). Cesium carbonate (292 mg, 0.9 mmol) and iodomethane (56 µL, 0.9 mmol) were added. The reaction mixture was stirred at 60° C. for 1 h. The DMF was removed under reduced pressure. The residue was diluted in water and extracted by EtOAc. The organic layers were assembled, washed by brine and dried on MgSO$_4$. The solvent was removed under reduced pressure to give the desired compound as a white powder (224 mg, 100%). $^1$H NMR (300 MHz, CDCl$_3$) δ 0.80 (t, J=7.1 Hz, 3H), 2.78 (s, 3H), 2.91 (dd, J=16.2, 2.8 Hz, 1H), 3.10 (dd, J=16.2, 7.2 Hz, 1H), 3.83 (q, J=7.1 Hz, 2H), 4.23 (dd, J=7.2, 2.8 Hz, 1H), 7.20-7.35 (m, 6H), 7.41-7.49 (m, 3H). MS [M+H]$^+$=370. HRMS: calcd for C$_{21}$H$_{21}$NO$_3$Cl, [M+H]$^+$ 370.1210, found 370.1219.

Step 3.

The dihydropyridone intermediate obtained in step 2 (184 mg, 0.50 mmol) was dissolved in MeOH (2 mL) and a solution of aqueous NaOH 1 N (2 mL, 4.0 equiv.) was added. The reaction mixture was stirred at 60° C. for 18 h. The reaction mixture was cooled to RT and extracted once with diethyl ether.

The aqueous phase was then acidified until pH=1 with an aqueous solution of hydrochloric acid. The aqueous phase was extracted by EtOAc. The organic layer was then washed with brine and dried with MgSO$_4$. The solvent was removed under reduced pressure to give the desired acid (116 mg, 0.34 mmol). The crude product was then used without further purification in the next step. The acid was dissolved in anhydrous DMF (3 mL) then Cs$_2$CO$_3$ (221 mg, 0.68 mmol) and benzyl bromide (81 µL, 0.68 mmol) were added. The reaction mixture was stirred for 1 h at RT. Water was then added and the aqueous phase was extracted with diethyl ether. The organic layer was then washed with brine and dried with MgSO$_4$. The solvent was removed under reduced pressure. The crude product was purified by flash chromatography using a mixture of cyclohexane/dichloromethane 7/3 to give the benzyl 4-(4-chlorophenyl)-1-methyl-2-oxo-6-phenyl-3,4-dihydropyridine-5-carboxylate as a white powder (21 mg, 10%). $^1$H NMR (300 MHz, CDCl$_3$) δ 2.77 (s, 3H), 2.91 (dd, J=16.3, 2.9 Hz), 3.10 (dd, J=16.3, 7.2 Hz, 1H), 4.23 (dd, J=7.2, 2.9 Hz, 1H), 4.81 (d, J=12.3 Hz, 1H), 4.87 (d, J=12.3 Hz, 1H), 6.91 (dd, J=7.3, 2.1 Hz, 2H), 7.19-7.33 (m, 9H), 7.36-7.44 (m, 3H). MS [M+H]$^+$ 433. HRMS: calcd for C$_{26}$H$_{23}$NO$_3$Cl, [M+H]$^+$ 432.1366, found 432.1360.

Example 20: Ethyl 4-(4-chlorophenyl)-1-methyl-2-oxo-6-phenyl-3,4-dihydropyridine-5-carboxylate (Intermediate Product)

Step 1.

p-chlorobenzaldehyde (15 mmol, 2.108 g), meldrum acid (15 mmol, 2.16 g), ethyl benzoylacetate (15 mmol, 2.6 mL) and ammonium acetate (22.5 mmol, 1.73 g) were dissolved in acetic acid (15 mL). The reaction mixture was stirred overnight under reflux. The solvent was removed. The crude was precipitated in EtOH and filtered to give the desired compound as a white powder (1.1 g, 21%). $^1$H NMR (300 MHz, CDCl$_3$) δ 0.85 (t, J=7.1 Hz, 3H), 2.78 (dd, J=16.5, 2.4 Hz, 1H), 3.08 (dd, J=16.5, 8.0 Hz, 1H), 3.89 (q, J=6.9 Hz, 2H), 4.33 (dd, J=8.0, 2.4 Hz, 1H), 7.17 (brs, 1H), 7.27-7.60 (m, 9H). MS [M+H]$^+$ 356.

Step 2.

The intermediate obtained in step 1 (213 mg, 0.6 mmol) was dissolved in anhydrous DMF (2 mL). Cesium carbonate (292 mg, 0.9 mmol) and iodomethane (56 µL, 0.9 mmol) were added. The reaction mixture was stirred at 60° C. for 1 h. The DMF was removed under reduced pressure. The residue was diluted in water and extracted by EtOAc. The organic layers were assembled, washed by brine and dried on MgSO$_4$. The solvent was removed under reduced pressure to give the desired compound as a white powder (224 mg, 100%). $^1$H NMR (300 MHz, CDCl$_3$) δ 0.80 (t, J=7.1 Hz, 3H), 2.78 (s, 3H), 2.91 (dd, J=16.2, 2.8 Hz, 1H), 3.10 (dd, J=16.2, 7.2 Hz, 1H), 3.83 (q, J=7.1 Hz, 2H), 4.23 (dd, J=7.2, 2.8 Hz, 1H), 7.20-7.35 (m, 6H), 7.41-7.49 (m, 3H). MS [M+H]$^+$ 370. HRMS: calcd for C$_{21}$H$_{21}$NO$_3$Cl, [M+H]$^+$ 370.1210, found 370.1219.

Example 21: Ethyl 4-(4-chlorophenyl)-6-ethyl-1-methyl-2-oxo-3,4-dihydropyridine-5-carboxylate (Intermediate Product)

Step 1.

p-chlorobenzaldehyde (15 mmol, 2.108 g), meldrum acid (15 mmol, 2.16 g), ethyl propionylacetate (15 mmol, 2.13 mL) and ammonium acetate (22.5 mmol, 1.73 g) were dissolved in acetic acid (15 mL). The reaction mixture was stirred overnight under reflux. The solvent was removed. The crude was dissolved in EtOAc and washed by an aqueous solution of HCl 1N and a saturated solution of NaHCO$_3$. The organic layer was dried on MgSO$_4$, the solvent was removed under reduced pressure. The crude product was purified by flash chromatography using a mixture of Cyclohexane/EtOAc (8/2) as eluent to give the desired compound as yellow oil (470 mg, 11%). $^1$H NMR (300 MHz, CDCl$_3$) δ 1.20 (t, J=7.2 Hz, 3H), 1.26 (t, J=7.2 Hz, 3H), 2.60-3.00 (m, 4H), 4.07-4.18 (m, 2H), 4.24 (dd, J=8.0, 2.0 Hz, 1H), 7.12 (d, J=8.6 Hz, 2H), 7.25 (d, J=8.6 Hz, 2H). MS [M+H]$^+$ 308.

Step 2.

The intermediate obtained in step 1 (180 mg, 0.58 mmol) was dissolved in anhydrous DMF (2 mL). Cesium carbonate (377 mg, 1.16 mmol) and iodomethane (72 µL, 1.16 mmol) were added. The reaction mixture was stirred at 60° C. for 3 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/DCM (1/1) as eluent to give the desired compound as a colorless oil (143 mg, 76%). $^1$H NMR (300 MHz, CDCl$_3$) δ 1.16-1.28 (m, 6H), 2.75 (dd, J=15.9, 2.8 Hz, 1H), 2.82-2.97 (m, 2H), 3.03-3.19 (m, 1H), 3.21 (s, 3H), 4.03-4.22 (m, 3H), 7.07 (d, J=8.6 Hz, 2H), 7.22 (d, J=8.6 Hz, 2H). MS [M+H]$^+$ 322. HRMS: calcd for C$_{17}$H$_{21}$NO$_3$Cl, [M+H]$^+$ 322.1210, found 322.1217.

Example 22: benzyl 4-(4-chlorophenyl)-6-(2-methoxyethyl)-2-oxo-3,4-dihydro-1H-pyridine-5-carboxylate Step 1.

p-chlorobenzaldehyde (12 mmol, 1.68 g), meldrum acid (12 mmol, 1.73 g), Methyl 5-methoxy-3-oxovalerate (12 mmol, 1.5 mL) and ammonium acetate (18 mmol, 1.39 g) were dissolved in acetic acid (12 mL). The reaction mixture was stirred overnight under reflux. The solvent was removed. The crude was dissolved in EtOAc and washed by an aqueous solution of HCl 1N and a saturated solution of NaHCO$_3$. The organic layer was dried on MgSO$_4$, the solvent was removed under reduced pressure. The crude product was purified by flash chromatography using a mixture of Cyclohexane/EtOAc (8/2) as eluent to give the desired compound as yellow oil (344 mg, 10%).

Step 2.

The dihydropyridone intermediate obtained (300 mg, 0.93 mmol) was dissolved in MeOH (4 mL) and a solution of aqueous NaOH 1 N (3.3 mL) was added. The reaction mixture was stirred at 60° C. for 8 h. The reaction mixture was cooled to RT. The aqueous phase was acidified until pH=1 with an aqueous solution of hydrochloric acid. The aqueous phase was extracted by EtOAc. The organic layer was then washed with brine and dried with MgSO$_4$.

The solvent was removed under reduced pressure to give the desired acid as an oil (260 mg, 0.91 mmol, 97%).

Step 3.

A fraction of this crude (80 mg, 0.26 mmol) was then used without further purification in the next step. The acid was dissolved in anhydrous DMF (3 mL) then DIEA (54 µL, 0.31 mmol) and benzyl bromide (31 µL, 0.26 mmol) were added. The reaction mixture was stirred for 18 h at RT. The reaction was controlled by LCMS and showed an incomplete conversion of the starting material. DIEA (54 µL, 0.31 mmol) and benzyl bromide (31 µL, 0.26 mmol) were added. The reaction mixture was stirred for 18 h at r.t. and then 3 h at 40° C. The reaction mixture was cooled to RT. Water was then added and the aqueous phase was extracted with EtOAc. The organic layer was then washed with brine and dried with MgSO$_4$. The solvent was removed under reduced pressure. The crude product was purified by flash chromatography using a mixture of cyclohexane/EtOAc 9/1 to give the desired compound (44 mg, 43%). $^1$H NMR (300 MHz, CDCl$_3$) δ 2.62 (d, J=16.3 Hz, 1H), 2.86-3.02 (m, 2H), 3.95 (s, 3H), 3.48 (ddd, J=15.5, 6.3, 3.5 Hz, 1H), 3.59-3.75 (m, 2H), 4.25 (d, J=8.5 Hz, 1H), 5.04 (d, J=12.0 Hz, 1H), 5.11 (d, J=12.0 Hz, 1H), 7.04-7.16 (m, 4H), 7.23 (dt, J=8.5, 2.2 Hz, 2H), 7.28-7.33 (m, 3H), 8.11 (s, 1H). MS [M+H]$^+$ 400. HRMS: calcd for C$_{22}$H$_{23}$NO$_4$Cl, [M+H]$^+$ 400.1316, found 400.1306.

TABLE 4

[Structure: 4-(4-chlorophenyl)-substituted dihydropyridinone scaffold with N-R11 and C(=O)-X-CH2-phenyl group]

| Example | R11 | X |
|---------|-----|---|
| 23 | H | O |
| 24 | CH$_3$ | O |
| 25 | H | NH |
| 26 | CH$_3$ | NH |
| 27 | H | NCH$_3$ |
| 29 | cyclopropylmethyl | O |
| 30 | cyclopropylmethyl | NH |
| 32 | 2-methoxyethyl | O |
| 33 | 2-methoxyethyl | NH |
| 33a | CH$_3$ | NCH$_3$ |

Example 23: benzyl 4-(4-chlorophenyl)-2-oxo-3,4-dihydro-1H-pyridine-5-carboxylate The methyl 4-(4-chlorophenyl)-2-oxo-3,4-dihydro-1H-pyridine-5-carboxylate (265 mg, 1.0 mmol) was dissolved in anhydrous methanol (2 mL) and water (2 mL). LiOH.H$_2$O (72 mg, 3.0 mmol) was added. The reaction mixture was stirred for 4 h at 60° C. Water was added, the aqueous phase was washed with Et$_2$O and then extracted by EtOAc. The organic phase was washed with brine and dried over MgSO$_4$. The solvent was removed under reduced pressure to give the desired 4-(4-chlorophenyl)-2-oxo-3,4-dihydro-1H-pyridine-5-carboxylic acid as a white powder (160 mg, 64%). The 4-(4-chlorophenyl)-2-oxo-3,4-dihydro-1H-pyridine-5-carboxylic acid (89 mg, 0.35 mmol) was dissolved in anhydrous DMF (1 mL) then DIEA (122 µL, 0.71 mmol) and benzyl bromide (63 µL, 0.53 mmol) were added. The reaction mixture was stirred for 1 h at RT. The solvent was removed under reduced pressure to give the desired benzyl 4-(4-chlorophenyl)-2-oxo-3,4-dihydro-1H-pyridine-5-carboxylate as a white powder (90 mg, 74%). $^1$H NMR (300 MHz, CDCl$_3$) δ 2.72 (d, J=16.5 Hz, 1H), 3.01 (dd, J=16.5, 8.4 Hz, 1H), 4.20 (dd, J=8.4, 1.3 Hz, 1H), 5.09 (d, J=12.2 Hz, 1H), 5.20 (d, J=12.2 Hz, 1H), 7.15 (d, J=8.6 Hz, 2H), 7.22-7.27 (m, 4H), 7.31-7.37 (m, 3H), 7.53 (d, J=5.7 Hz, 1H). MS [M+H]$^-$ 340.

Example 24: Benzyl 4-(4-chlorophenyl)-1-methyl-2-oxo-3,4-dihydropyridine-5-carboxylate The benzyl 4-(4-chlorophenyl)-2-oxo-3,4-dihydro-1H-pyridine-5-carboxylate (70 mg, 0.20 mmol) was dissolved in anhydrous DMF (1 mL). Cesium carbonate (133 mg, 0.41 mmol) and iodomethane (26 µL, 0.41 mmol) were added. The reaction mixture was stirred at 60° C. for 3 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (95/5) as eluent to give the desired benzyl 4-(4-chlorophenyl)-1-methyl-2-oxo-3,4-dihydropyridine-5-carboxylate as a yellow oil (48 mg, 68%). $^1$H NMR (300 MHz, CDCl$_3$) δ 2.72 (d, J=16.5 Hz, 1H), 3.01 (dd, J=16.5, 8.4 Hz, 1H), 4.20 (dd, J=8.4, 1.3 Hz, 1H), 5.09 (d, J=12.2 Hz, 1H), 5.20 (d, J=12.2 Hz, 1H), 7.15 (d, J=8.6 Hz, 2H), 7.22-7.27 (m, 4H), 7.31-7.37 (m, 3H), 7.53 (d, J=5.7 Hz, 1H). MS [M+H]$^-$ 340. HRMS: calcd for C$_{22}$H$_{22}$N$_2$O$_3$Cl, [M+CH$_3$CN+H]$^+$ 397.1319, found 397.1350.

Example 25: N-benzyl-4-(4-chlorophenyl)-2-oxo-3,4-dihydro-1H-pyridine-5-carboxamide The methyl 4-(4-chlorophenyl)-2-oxo-3,4-dihydro-1H-pyridine-5-carboxylate (265 mg, 1.0 mmol) was dissolved in anhydrous methanol (2 mL) and water (2 mL). LiOH.H$_2$O (72 mg, 3.0 mmol) was added. The reaction mixture was stirred for 4 h at 60° C. Water was added, the aqueous phase was washed with Et$_2$O and then extracted by EtOAc. The organic phase was washed with brine and dried over MgSO$_4$. The solvent was removed under reduced pressure to give the desired 4-(4-chlorophenyl)-2-oxo-3,4-dihydro-1H-pyridine-5-carboxylic acid as a white powder (160 mg, 64%).

The 4-(4-chlorophenyl)-2-oxo-3,4-dihydro-1H-pyridine-5-carboxylic acid S was used without further purification in the next step. The acid (77 mg, 0.31 mmol) was dissolved in anh. EtOAc (3 mL). Benzylamine (51 µL, 0.46 mmol), DIEA (158 µL, 0.93 mmol) and a 50% solution of T3P in EtOAc (365 µL, 0.62 mmol) were added. The same amount of all the reactants (except substrate) were added again 3 times more. The reaction mixture was stirred at RT. for 48 h overall. The solvent was removed under reduced pressure. The crude was purified by flash chromatography on silica using a mixture DCM/EA/acetone 2/1/1 to afford the desired N-benzyl-4-(4-chlorophenyl)-2-oxo-3,4-dihydro-1H-pyridine-5-carboxamide as a white powder (12 mg, 11%). $^1$H NMR (300 MHz, DMSO d6) δ 2.40 (d, J=16.2 Hz, 1H), 2.45-2.55 (s, 3H), 2.96 (dd, J=16.2, 8.2 Hz, 1H), 4.14-4.38 (m, 3H), 7.10-7.32 (m, 8H), 7.36 (d, J=8.5 Hz, 1H), 8.31 (t, J=5.7 Hz, 1H), 9.76 (d, J=5.4 Hz, 1H). MS [M+H]$^+$ 351. HRMS: calcd for C$_{19}$H$_{18}$N$_2$O$_2$Cl, [M+H]$^+$ 341.1057, found 341.1056.

Example 26: N-benzyl-4-(4-chlorophenyl)-1-methyl-2-oxo-3,4-dihydropyridine-5-carboxamide The methyl 4-(4-chlorophenyl)-2-oxo-3,4-dihydro-1H-pyridine-5-carboxylate (131 mg, 0.50 mmol) was dissolved in anhydrous DMF (2 mL). Cesium carbonate (325 mg, 1.0 mmol) and iodomethane (62 μL, 1.0 mmol) were added. The reaction mixture was stirred at 30° C. for 1 h. The DMF was removed under reduced pressure. The residue was diluted in water and extracted by EtOAc. The organic layers were assembled, washed by brine and dried on MgSO$_4$. The solvent was removed under reduced pressure. The crude 4-(4-chlorophenyl)-1-methyl-2-oxo-3,4-dihydropyridine-5-carboxylate (143 mg) was used in the next step without further purification. The crude methyl 4-(4-chlorophenyl)-1-methyl-2-oxo-3,4-dihydropyridine-5-carboxylate was dissolved in methanol (0.75 mL) and water (1.5 ml). Lithium hydroxide (36 mg, 1.5 mmol) was added. The reaction mixture was stirred at 50° C. for 3 h. The reaction mixture was washed with diethyl ether. The aqueous phase was then acidified to pH=1 and extracted by EtOAc. The organic phases were assembled, washed with brine and dried over MgSO$_4$. The solvents were removed under reduced pressure to afford the crude 4-(4-chlorophenyl)-1-methyl-2-oxo-3,4-dihydropyridine-5-carboxylic acid as a whitish powder (100 mg). The crude 4-(4-chlorophenyl)-1-methyl-2-oxo-3,4-dihydropyridine-5-carboxylic acid (100 mg) was dissolved in anhydrous EtOAc (2 mL). Benzylamine (66 μL, 0.60 mmol), DIEA (215 μL, 1.25 mmol) and a 50% solution of T3P in EtOAc (454 μL, 0.75 mmol) were added. The reaction mixture was stirred 4 h at RT. The solvent was removed under reduced pressure. The reaction mixture was washed with water and extracted with EtOAc. The organic phases were assembled, washed with brine and dried over MgSO$_4$. The solvent was removed under reduced pressure. The crude was purified by flash chromatography on silica using a mixture cyclohexane/EA (7/3 to 3/7) to afford the desired N-benzyl-4-(4-chlorophenyl)-1-methyl-2-oxo-3,4-dihydropyridine-5-carboxamide as a white powder (68 mg, 38% over the 3 steps). $^1$H NMR (300 MHz, DMSO d6) δ 2.50-2.56 (m, 1H), 3.01 (dd, J=16.0, 7.7 Hz, 1H), 3.06 (s, 3H), 4.15-4.41 (m, 3H), 7.10-7.30 (m, 7H), 7.35 (d, J=8.3 Hz, 2H), 7.47, s, 1H), 7.53 (t, J=6.0 Hz, 1H). MS [M+H]$^+$ 355. HRMS: calcd for C$_{20}$H$_{20}$N$_2$O$_2$Cl, [M+H]$^+$ 355.1213, found 355.1212.

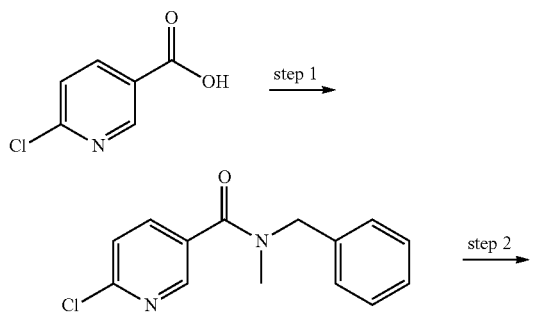

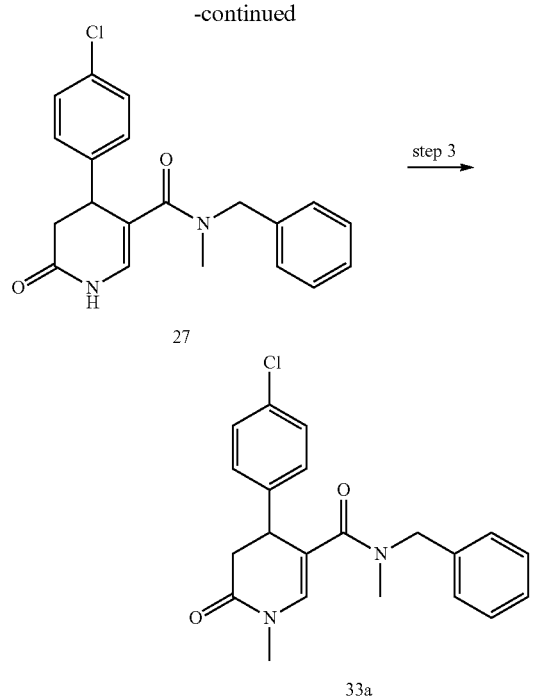

Example 27: N-benzyl-4-(4-chlorophenyl)-N-methyl-2-oxo-3,4-dihydro-1H-pyridine-5-carboxamide Step 1.

Nicotinic acid (472 mg, 3.0 mmol) was dissolved in ethyl acetate (30 mL). DIEA (1.29 mL, 7.5 mmol), N-methylbenzylamine (460 μL, 3.6 mmol) and a solution of propylphosphonic anhydride 50% in ethyl acetate (2.64 mL, 4.5 mmol) were added. The reaction mixture was stirred 18 h at RT. A 5% aqueous solution of NaHCO$_3$ was added and the aqueous phase extracted with ethyl acetate. The organic phases were assembled, washed with brine and dried over MgSO$_4$. The solvent was removed under reduced pressure. The crude was purified by flash chromatography using a mixture of Cy/EA (8/2) as eluent to give the desired N-benzyl-6-chloro-N-methylnicotinamide as a yellow oil (421 mg, 54%).

Step 2.

The N-benzyl-6-chloro-N-methylnicotinamide (390 mg, 1.5 mmol) was dissolved in anh. THF (1.5 mL). The solution was cooled to 0° C. A solution 1.0 M of 4-chlorophenylmagnesium chloride in Et$_2$O (3.0 mL, 3.0 mmol) was added slowly over a period of 30 min. The reaction mixture was allowed to warm to r.t. and stirred for 18 h at RT. The reaction was stopped by addition of AcOH (1.0 mL). The reaction mixture was stirred for 10 min then a saturated solution of ammonium chloride was added and the reaction mixture extracted with ethyl acetate. The organic phases were assembled and dried over MgSO$_4$, the solvents were removed under reduced pressure. The crude was purified by flash chromatography using a mixture of DCM/MeOH (9/1) as eluent to give the desired N-benzyl-4-(4-chlorophenyl)-N-methyl-2-oxo-3,4-dihydro-1H-pyridine-5-carboxamide as a white powder (151 mg, 28%). $^1$H NMR (300 MHz, CDCl$_3$) δ 2.71 (dd, J=16.7, 6.1 Hz, 1H), 2.83 (s, 3H), 2.98 (dd, J=16.7, 8.0 Hz, 1H), 4.22 (dd, J=8.0, 6.1 Hz, 1H), 4.51 (s, 2H), 6.50 (d, J=5.0 Hz, 2H), 6.93 (m, 2H), 7.16 (d, J=8.5 Hz, 2H), 7.23-7.30 (m, 4H), 7.82 (brs, 1H). MS [M+H]$^+$ 355. HRMS: calcd for C$_{20}$H$_{20}$N$_2$O$_2$Cl, [M+H]$^+$ 355.1213, found 355.1212.

Preparation of Benzyl 4-(4-chlorophenyl)-1-(cyclopropylmethyl)-2-oxo-3,4-dihydropyridine-5-carboxylate (Example 29) and N-benzyl-4-(4-chlorophenyl)-1-(cyclopropylmethyl)-2-oxo-3,4-dihydropyridine-5-carboxamide (Example 30)
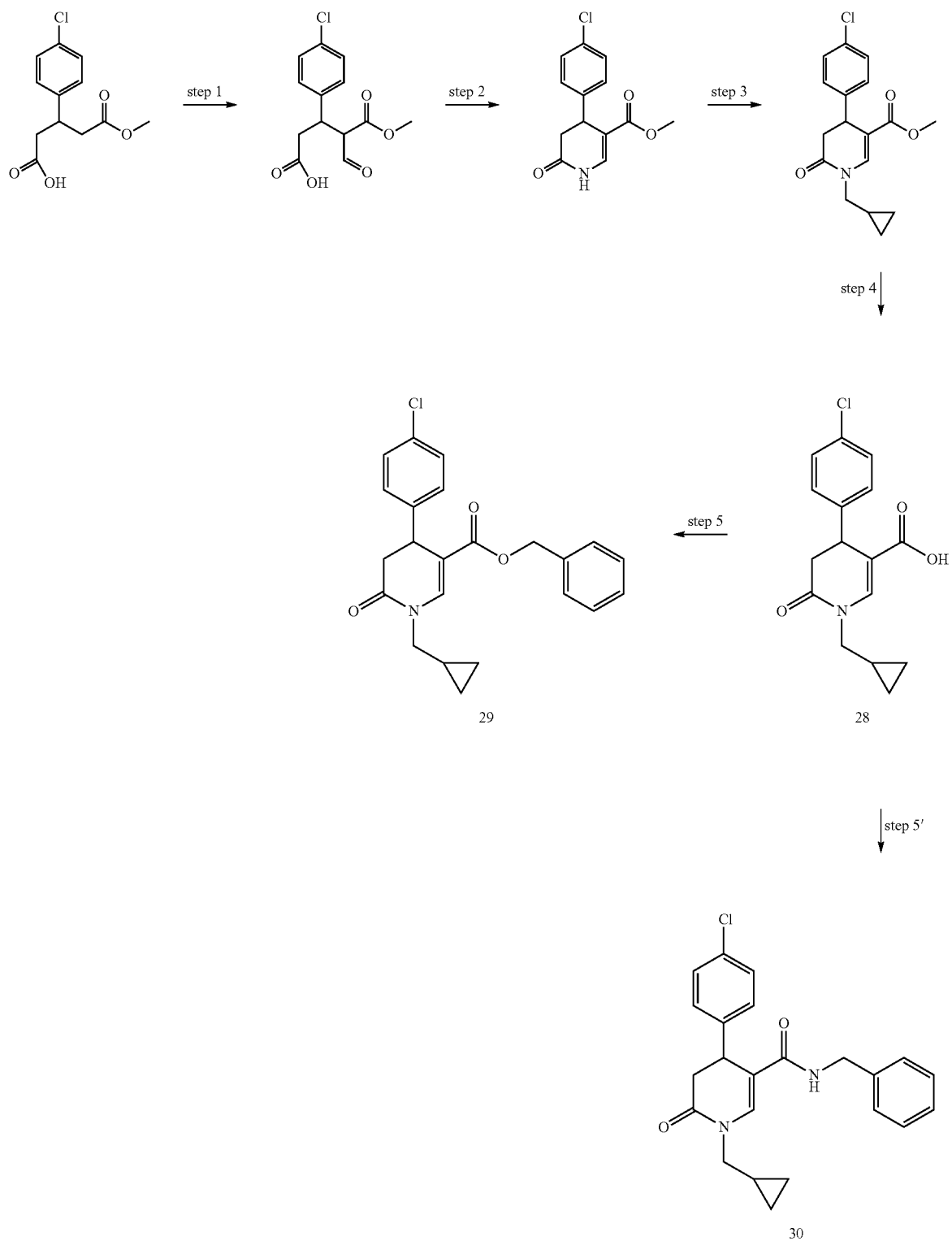

Step 1.

To a solution of diisopropylamine (1.52 mL, 10.8 mmol) in anh. THF (6 mL) at 0° C. was added slowly a 2.5 M solution of n-BuLi in hexane (4.32 mL, 10.8 mmol). The reaction mixture was stirred 20 min at r.t. and then cooled at −55° C. To this LDA solution, a solution of 3-(4-chlorophenyl)-5-methoxy-5-oxo-pentanoic acid (1.38 g, 5.4 mmol) in anh. THF (6 mL) was added over 20 min. After 40 min at −45° C., methyl formate (826 µL, 13.5 mmol) was added. The mixture was slowly warmed to −20° C. and then stirred at −20° C. for 1 h. The mixture was slowly quenched with conc. HCl until pH=1 and the aqueous phase was extracted with EtOAc. The organic layer was separated, washed with brine and dried over MgSO$_4$. The solvents were removed under reduced pressure to give 3-(4-chlorophenyl)-4-formyl-5-methoxy-5-oxo-pentanoic acid as a thick oil.

Step 2.

This thick oil was then dissolved into acetic acid (18 mL) and ammonium acetate was added (1.25 g, 16.2 mmol). The reaction mixture was stirred at 80° C. for 18 h. The solvent was removed under reduced pressure. Precipitation of the crude in EtOH afforded the desired methyl 4-(4-chlorophenyl)-2-oxo-3,4-dihydropyridine-5-carboxylate as a white powder (487 mg, 34%). $^1$H NMR (300 MHz, CDCl$_3$) δ 2.70 (d, J=16.8 Hz, 1H), 3.00 (dd, J=16.8, 8.5 Hz, 1H), 3.71 (s, 3H), 4.18 (d, J=8.5 Hz, 1H), 7.16 (d, J=8.4 Hz, 2H), 7.27 (d, J=8.4 Hz, 2H), 7.48 (d, J=5.4 Hz, 1H), 7.83 (brs, 1H). MS [M−H]$^-$ 264.

Step 3.

methyl 4-(4-chlorophenyl)-)-2-oxo-3,4-dihydropyridine-5-carboxylate (240 mg, 0.9 mmol) was dissolved in anhydrous DMF (3 mL). Cesium carbonate (585 mg, 1.8 mmol) and (bromomethyl)cyclopropane (172 µL, 1.8 mmol) were added. The reaction mixture was stirred at 60° C. for 4 h. The DMF was removed under reduced pressure. The residue was diluted in water. The aqueous phase was extracted by EtOAc and the combined organic layers were washed with brine and dried over MgSO$_4$. Removal of the solvent was removed under reduced pressure gave the desired (methyl 4-(4-chlorophenyl)-1-(cyclopropylmethyl)-2-oxo-3,4-dihydropyridine-5-carboxylate as a colorless oil (287 mg, 100%).

Step 4.

The (methyl 4-(4-chlorophenyl)-1-(cyclopropylmethyl)-2-oxo-3,4-dihydropyridine-5-carboxylate (287 mg, 0.90 mmol) was dissolved an aqueous solution of NaOH 1 N (20 mL, 20.0 mmol). The reaction mixture was stirred at 60° C. for 18 h. The reaction mixture was cooled to r.t. and extracted once with diethyl ether. The aqueous phase was then acidified until pH=1 with an aqueous solution of hydrochloric acid. The aqueous phase was extracted by EtOAc. The organic layer was then washed with brine and dried over MgSO$_4$. The solvent was removed under reduced pressure to give the desired 4-(4-chlorophenyl)-1-(cyclopropylmethyl)-2-oxo-3,4-dihydropyridine-5-carboxylic acid (example 28) (210 mg, 78%).

Example 29: Benzyl 4-(4-chlorophenyl)-1-(cyclopropylmethyl)-2-oxo-3,4-dihydropyridine-5-carboxylate Step 5.

4-(4-chlorophenyl)-1-(cyclopropylmethyl)-2-oxo-3,4-dihydropyridine-5-carboxylic acid (example 28, 70 mg, 0.23 mmol) was dissolved in anhydrous DMF (1 mL) then cesium carbonate (160 mg, 0.45 mmol) and benzyl bromide (38 µL, 0.36 mmol) were added. The reaction mixture was stirred at RT for 18 h. The solvent was removed under reduced pressure. The residue was dissolved in EtOAc and water. The aqueous phase was extracted with EtOAc. The combined organic layers were washed with brine and dried over MgSO$_4$. The solvent was removed under reduced pressure to give the desired benzyl 4-(4-chlorophenyl)-1-(cyclopropylmethyl)-2-oxo-3,4-dihydropyridine-5-carboxylate as a colorless oil (76 mg, 83%). $^1$H NMR (300 MHz, CDCl$_3$) δ 0.28-0.36 (m, 2H), 0.54-0.63 (m, 2H), 1.04-1.18 (m, 1H), 2.75 (dd, J=16.2, 1.6 Hz, 1H), 3.00 (dd, J=16.2, 8.2 Hz, 1H), 3.25 (dd, J=14.1, 7.1 Hz, 1H), 3.72 (dd, J=14.1, 7.2 Hz, 1H), 5.10 (d, J=12.6 Hz, 1H), 5.22 (d, J=12.6 Hz, 1H), 7.15 (d, J=8.5 Hz, 2H), 7.22-7.28 (m, 4H), 7.30-7.42 (m, 3H), 7.61 (s, 1H). MS [M+H]$^+$ 396. HRMS: calcd for C$_{23}$H$_{23}$NO$_3$Cl, [M+H]$^+$ 396.1366, found 396.1371.

Example 30: N-benzyl-4-(4-chlorophenyl)-1-(cyclopropylmethyl)-2-oxo-3,4-dihydropyridine-5-carboxamide Step 5'.

4-(4-chlorophenyl)-1-(cyclopropylmethyl)-2-oxo-3,4-dihydropyridine-5-carboxylic acid (example 28, 90 mg, 0.30 mmol) was dissolved in anhydrous EtOAc (2 mL) then benzylamine (52 µL, 0.48 mmol), DIEA (172 µL, 1.0 mmol) and a 50% solution of T3P in EtOAc (353 µL, 0.6 mmol) were added. The reaction mixture was stirred at RT for 24 h. The same amount of reactants was added again twice every 24 h. After 72 h at RT overall, water was added and the aqueous phase was extracted with EtOAc. The organic phases were combined, washed with brine and dried over MgSO$_4$. The solvent was removed under reduced pressure. Purification of the crude by flash chromatography using a mixture of Cyclohexane/EtOAc (8/2) as eluent gave the desired N-benzyl-4-(4-chlorophenyl)-1-(cyclopropylmethyl)-2-oxo-3,4-dihydropyridine-5-carboxamide as a yellow oil (67 mg, 55%). $^1$H NMR (300 MHz, CDCl$_3$) δ 0.27-0.38 (m, 2H), 0.53-0.62 (m, 2H), 1.04-1.14 (m, 1H), 2.69 (dd, J=16.1, 2.5 Hz, 1H), 3.02 (dd, J=16.1, 8.1 Hz, 1H), 3.24 (dd, J=13.9, 7.0 Hz, 1H), 3.91 (dd, J=13.9, 7.2 Hz, 1H), 4.41 (t, J=6.3 Hz, 1H), 5.66 (t, J=5.5 Hz, 1H), 7.03-7.09 (m, 2H), 7.16 (d, J=8.5 Hz, 2H), 7.23-7.32 (m, 5H), 7.54 (s, 1H). MS [M+H]$^+$ 395. HRMS: calcd for C$_{23}$H$_{24}$N$_2$O$_2$Cl, [M+H]$^+$ 395.1526, found 395.1530.

Preparation of Benzyl 4-(4-chlorophenyl)-1-(2-methoxyethyl)-2-oxo-3,4-dihydropyridine-5-carboxylate (Example 32) and N-benzyl-4-(4-chlorophenyl)-1-(2-methoxyethyl)-2-oxo-3,4-dihydropyridine-5-carboxamide (Example 33)

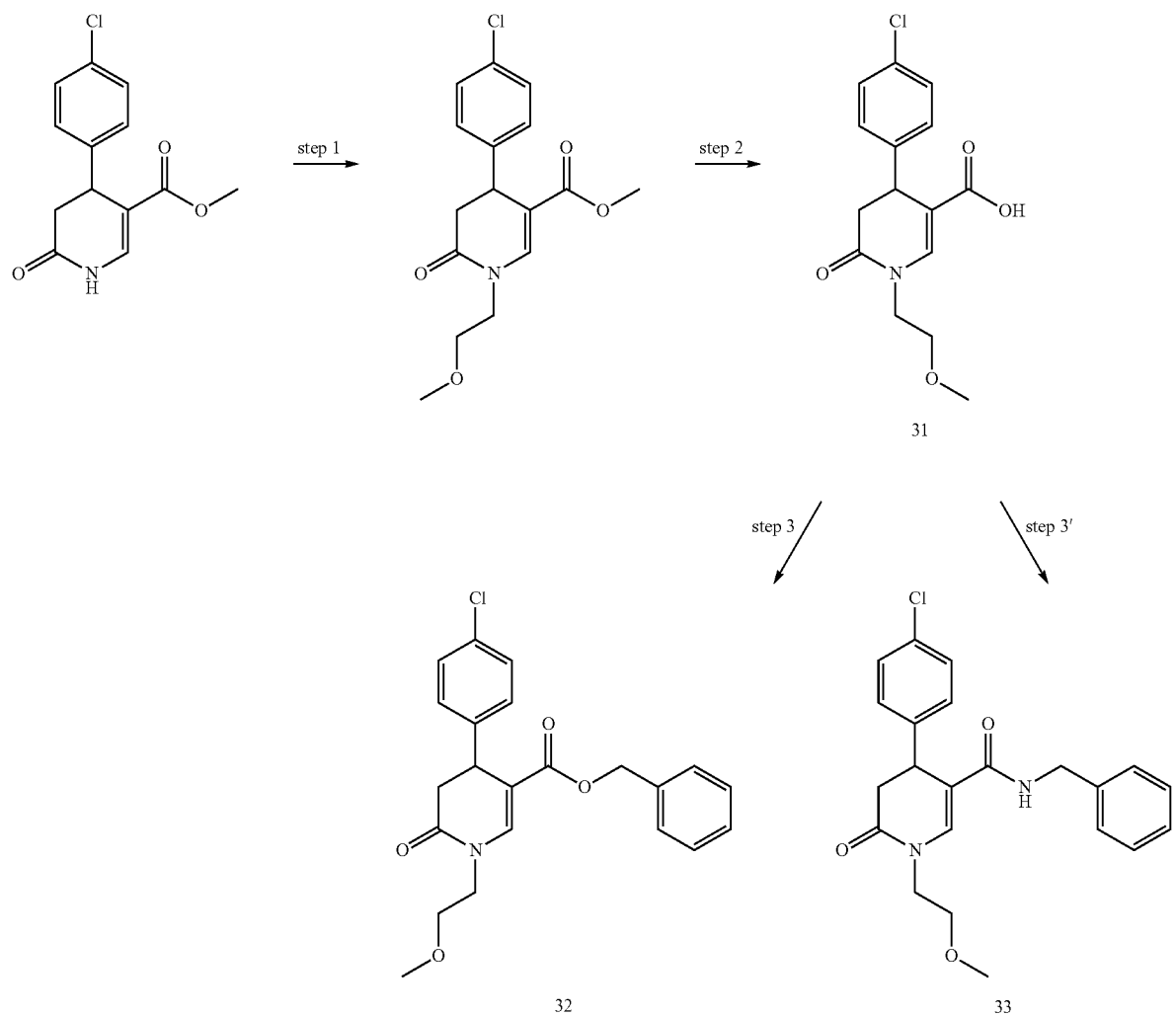

Step 1.

Methyl 4-(4-chlorophenyl)-2-oxo-3,4-dihydropyridine-5-carboxylate (227 mg, 0.86 mmol) was dissolved in anhydrous DMF (3 mL). Cesium carbonate (556 mg, 1.71 mmol) and 2-bromoethyl methyl ether (161 µL, 1.71 mmol) were added. The reaction mixture was stirred at 60° C. for 18 h. The DMF was removed under reduced pressure. The residue was diluted in water. The aqueous phase was extracted by EtOAc and the combined organic layers were washed with brine and dried over MgSO$_4$. Removal of the solvents under reduced pressure gave the desired methyl 4-(4-chlorophenyl)-1-(2-methoxyethyl)-2-oxo-3,4-dihydropyridine-5-carboxylate as a colorless oil (254 mg, 91%). MS [M+H]$^+$ 324.

Step 2.

The methyl 4-(4-chlorophenyl)-1-(2-methoxyethyl)-2-oxo-3,4-dihydropyridine-5-carboxylate (254 mg, 0.78 mmol) was dissolved in methanol (5 mL) and an aqueous solution of NaOH 1 N (20 mL, 20.0 mmol). The reaction mixture was stirred at 60° C. for 4 h. The reaction mixture was cooled to RT and extracted once with diethyl ether. The aqueous phase was then acidified until pH=1 with an aqueous solution of hydrochloric acid. The aqueous phase was extracted by EtOAc. The organic layer was then washed with brine and dried over MgSO$_4$. Removal of the solvent under reduced pressure gave the desired 4-(4-chlorophenyl)-1-(2-methoxyethyl)-2-oxo-3,4-dihydropyridine-5-carboxylic acid (example 31) (214 mg, 89%). MS [M−H]308.

Example 32: Benzyl 4-(4-chlorophenyl)-1-(2-methoxyethyl)-2-oxo-3,4-dihydropyridine-5-carboxylate 4-(4-chlorophenyl)-1-(2-methoxyethyl)-2-oxo-3,4-dihydropyridine-5-carboxylic acid (97 mg, 0.31 mmol) was dissolved in anhydrous DMF (1 mL) then cesium carbonate (305 mg, 0.86 mmol) and benzyl bromide (69 µL, 0.65 mmol) were added. The reaction mixture was stirred at RT for 24 h. The solvent was removed under reduced pressure. The residue was dissolved in EtOAc and water. The aqueous phase was extracted with EtOAc. The combined organic layers were washed with brine and dried over MgSO$_4$. The solvent was removed under reduced pressure. Purification of the crude by flash chromatography using a mixture of Cyclohexane/EtOAc (8/2) as eluent gave the desired benzyl 4-(4-chlorophenyl)-1-(2-methoxyethyl)-2-oxo-3,4-dihydropyridine-5-carboxylate as a yellow oil (59 mg, 47%). $^1$H NMR (300 MHz, CDCl$_3$) δ 2.72 (dd, J=16.4, 1.8 Hz, 1H), 3.00 (dd, J=16.4, 8.2 Hz, 1H), 3.37 (s, 3H), 3.46-3.57 (m, 3H), 3.96-4.07 (m, 1H), 4.13 (dd, J=8.2, 1.8 Hz, 1H), 5.09 (d, J=12.6 Hz, 1H), 5.22 (d, J=12.6 Hz, 1H), 7.16 (d, J=8.7 Hz, 2H), 7.22-7.28 (m, 4H), 7.30-7.38 (m, 3H), 7.59 (s, 1H). MS [M+H]$^+$ 400. HRMS: calcd for C$_{22}$H$_{23}$NO$_4$Cl, [M+H]$^+$ 400.1316, found 400.1317.

Example 33 N-benzyl-4-(4-chlorophenyl)-1-(2-methoxyethyl)-2-oxo-3,4-dihydropyridine-5-carboxamide 4-(4-chlorophenyl)-1-(2-methoxyethyl)-2-oxo-3,4-dihydropyridine-5-carboxylic acid (116 mg, 0.38 mmol) was dissolved in anhydrous EtOAc (2 mL) then benzylamine (168 μL, 1.55 mmol), DIEA (555 μL, 1.0 mmol) and a 50% solution of T3P in EtOAc (1.14 mL, 0.6 mmol) were added. The reaction mixture was stirred atRT for 18 h. Water was added and the aqueous phase was extracted with EtOAc. The organic phases were combined, washed with brine and dried over MgSO$_4$. The solvent was removed under reduced pressure. Purification of the crude by flash chromatography using a mixture of Cyclohexane/EtOAc (1/1) as eluent gave the desired N-benzyl-4-(4-chlorophenyl)-1-(2-methoxyethyl)-2-oxo-3,4-dihydropyridine-5-carboxamide as a yellow powder (67 mg, 55%). $^1$H NMR (300 MHz, CDCl$_3$) δ 2.67 (dd, J=16.2, 2.2 Hz, 1H), 3.00 (dd, J=16.2, 8.3 Hz, 1H), 3.36 (s, 3H), 3.43-3.55 (m, 3H), 3.92-4.02 (m, 2H), 4.40 (t, J=5.5 Hz, 2H), 5.77 (t, J=5.5 Hz, 1H), 7.07 (dd, J=7.0, 1.7 Hz, 2H), 7.16 (d, J=8.4 Hz, 2H), 7.23-7.30 (m, 5H), 7.42 (s, 1H). MS [M+H]$^+$ 399. HRMS: calcd for C$_{22}$H$_{24}$N$_2$O$_3$Cl, [M+H]$^+$ 399.1475, found 399.1479.

Example 33a N-benzyl-4-(4-chlorophenyl)-N,1-dimethyl-2-oxo-3,4-dihydropyridine-5-carboxamide N-benzyl-4-(4-chlorophenyl)-N-methyl-2-oxo-3, 4-dihydro-1H-pyridine-5-carboxamide (example 27, 120 mg, 0.34 mmol) was dissolved in anhydrous DMF (1 mL). Cesium carbonate (220 mg, 0.68 mmol) and iodomethane (42 μL, 0.68 mmol) were added. The reaction mixture was stirred at 60° C. for 1 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of DCM/ EtOAc (8/2) as eluent to give the desired N-benzyl-4-(4-chlorophenyl)-N,1-dimethyl-2-oxo-3,4-dihydropyridine-5-carboxamide as a colorless oil (72 mg, 58%). $^1$H NMR (300 MHz, CDCl$_3$) ☐ 2.74 (dd, J=16.4, 7.2 Hz, 1H), 2.84 (s, 3H), 2.95 (dd, J=16.4, 7.6 Hz, 1H), 3.09 (s, 3H), 4.16 (t, J=7.4 Hz, 1H), 4.46 (d, J=15.4 Hz, 1H), 4.52 (d, J=15.4 Hz, 1H), 6.47 (d, J=1.2 Hz, 1H), 6.93 (dd, J=6.5, 1.8 Hz, 2H), 7.13 (d, J=8.5 Hz, 2H), 7.23-7.31 (m, 6H). [M+H]$^+$=369 g/mol, HRMS: calcd for C$_{21}$H$_{22}$N$_2$O$_2$Cl, [M+H]$^+$ 369.1370, found 369.1378.

TABLE 5

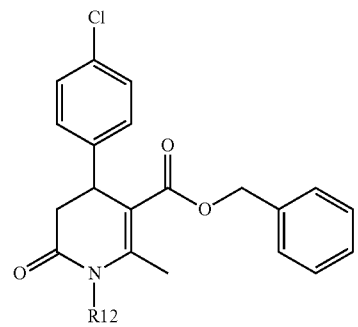

| Example | R12 |
|---------|-----|
| 34 | |
| 35 | |
| 36 | |
| 37 | |
| 38 | |
| 39 | |
| 40 | |
| 41 | |
| 42 | |
| 43 | |

TABLE 5-continued

[Structure: benzyl 4-(4-chlorophenyl)-6-methyl-2-oxo-3,4-dihydro-1H-pyridine-5-carboxylate with R12 on N]

| Example | R12 |
|---------|-----|
| 44 | cyclobutylmethyl |
| 45 | (1-boc-azetidin-3-yl)methyl |
| 46 | (azetidin-3-yl)methyl |
| 47 | (1-methylazetidin-3-yl)methyl |
| 48 | (1,1-dimethylazetidinium-3-yl)methyl I⁻ |
| 49 | isobutyl |
| 50 | 2-(dimethylamino)ethyl |
| 51 | 2-(trimethylammonio)ethyl I⁻ |
| 52 | 2-(Boc-amino)ethyl |
| 53 | aminoethyl·HCl |
| 54 | 3-(dimethylamino)propyl |
| 55 | 2-(pyrrolidin-1-yl)ethyl |
| 56 | 2-(piperidin-1-yl)ethyl |
| 57 | methoxycarbonylmethyl |
| 58 | tert-butoxycarbonylmethyl |
| 59 | (3-methyl-1,2,4-oxadiazol-5-yl)methyl |
| 60 | carbamoylmethyl |
| 61 | carboxymethyl |
| 62 | 2-(methylsulfonyl)ethyl |
| 63 | cyanomethyl |

General Procedure B.

The benzyl 4-(4-chlorophenyl)-6-methyl-2-oxo-3,4-dihydro-1H-pyridine-5-carboxylate (1 equiv.) was dissolved in anhydrous DMF (0.1-0.3 M). Cesium carbonate (1.5 equiv.) and R12-X (1-3 equiv.) were added. The reaction mixture was stirred at 60° C. until completion. The DMF was removed under reduced pressure. The residue was diluted in water and extracted by EtOAc. The organic layers were assembled, washed by brine, dried on MgSO$_4$ and evaporated under reduced pressure.

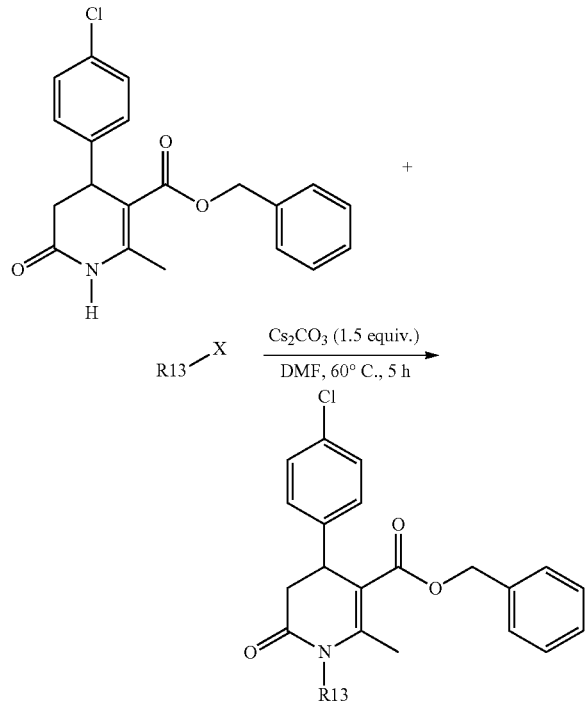

Example 34: Benzyl 4-(4-chlorophenyl)-1-ethyl-6-methyl-2-oxo-3,4-dihydropyridine-5-carboxylate Benzyl 4-(4-chlorophenyl)-1-ethyl-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (100 mg, 62%) after flash chromatography purification (cyclohexane/EtOAc). $^1$H NMR (300 MHz, CDCl$_3$) δ 1.14 (t, J=7.2 Hz, 3H), 2.60 (s, 3H), 2.74 (dd, J=2.4 and 15.6 Hz, 1H), 2.91 (dd, J=7.5 and 15.6 Hz, 1H), 3.67 (m, 1H), 3.97 (m, 1H), 4.21 (d, J=5.7 Hz, 1H), 5.09 (d, J=12.6 Hz, 1H), 5.15 (d, J=12.6 Hz, 1H), 7.03 (d, J=8.4 Hz, 2H), 7.12-7.16 (m, 2H), 7.22 (d, J=8.4 Hz, 2H), 7.28-7.32 (m, 3H). MS [M+H]$^+$ 384.

Example 35: Benzyl 4-(4-chlorophenyl)-6-methyl-2-oxo-1-propyl-3,4-dihydropyridine-5-carboxylate Benzyl 4-(4-chlorophenyl)-6-methyl-2-oxo-1-propyl-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (108 mg, 65%) after flash chromatography purification (cyclohexane/EtOAc). $^1$H NMR (300 MHz, CDCl$_3$) δ 0.88 (t, J=7.5 Hz, 3H), 1.51 (m, 2H), 2.59 (s, 3H), 2.76 (dd, J=2.4 and 15.9 Hz, 1H), 2.91 (dd, J=7.5 and 15.9 Hz, 1H), 3.48 (m, 1H), 3.91 (m, 1H), 4.22 (d, J=5.7 Hz, 2H), 5.09 (d, J=12.6 Hz, 1H), 5.15 (d, J=12.6 Hz, 1H), 7.04 (d, J=8.4 Hz, 2H), 7.13-7.16 (m, 2H), 7.22 (d, J=8.4 Hz, 2H), 7.29-7.31 (m, 3H). MS [M+H]$^+$ 398.

Example 36: Benzyl 1-butyl-4-(4-chlorophenyl)-6-methyl-2-oxo-3,4-dihydropyridine-5-carboxylate Benzyl 1-butyl-4-(4-chlorophenyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (111 mg, 64%) after flash chromatography purification (cyclohexane/EtOAc). $^1$H NMR (300 MHz, CDCl$_3$) δ 0.90 (t, J=7.2 Hz, 3H), 1.27 (m, 2H), 1.44 (m, 2H), 2.58 (s, 3H), 2.75 (dd, J=2.4 and 15.6 Hz, 1H), 2.89 (dd, J=7.2 and 15.6 Hz, 1H), 3.51 (m, 1H), 3.95 (m, 1H), 4.21 (d, J=5.7 Hz, 2H), 5.08 (d, J=12.6 Hz, 1H), 5.14 (d, J=12.6 Hz, 1H), 7.03 (d, J=8.4 Hz, 2H), 7.12-7.15 (m, 2H), 7.21 (d, J=8.4 Hz, 2H), 7.28-7.30 (m, 3H). MS [M+H]$^+$ 412.

Example 37: Benzyl 4-(4-chlorophenyl)-1-(2-methoxyethyl)-6-methyl-2-oxo-3,4-dihydropyridine-5-carboxylate Benzyl 4-(4-chlorophenyl)-1-(2-methoxyethyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a yellow oil (142 mg, 81%). $^1$H NMR (300 MHz, CDCl$_3$) δ 2.63 (s, 3H), 2.72 (dd, J=15.8, 2.1 Hz, 1H), 2.93 (dd, J=15.8, 7.4 Hz, 1H), 3.33 (s, 3H), 3.36-3.52 (m, 4H), 3.76 (ddd, J=14.5, 8.6, 3.8 Hz, 1H), 4.13-4.26 (m, 2H), 5.08 (d, J=11.9 Hz, 1H), 5.14 (d, J=11.9 Hz, 1H), 7.07-7.15 (m, 4H), 7.22 (d, J=8.3 Hz, 2H), 7.25-7.33 (m, 3H). MS [M+H]$^+$ 414. HRMS: calcd for C$_{23}$H$_{25}$NO$_4$Cl, [M+H]$^+$ 414.1472, found 414.1459.

Example 38: Benzyl 1-allyl-4-(4-chlorophenyl)-6-methyl-2-oxo-3,4-dihydropyridine-5-carboxylate Benzyl 1-allyl-4-(4-chlorophenyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.50 mmol) and obtained as a colorless oil (152 mg, 77%). $^1$H NMR (300 MHz, CDCl$_3$) δ 2.58 (s, 3H), 2.79 (dd, J=2.4 and 15.6 Hz, 1H), 2.94 (dd, J=7.2 and 15.6 Hz, 1H), 4.33-4.23 (m, 2H), 4.52-4.45 (m, 1H), 5.19-5.05 (m, 1H), 5.08 (d, J=12.6 Hz, 1H), 5.14 (d, J=12.6 Hz, 1H), 5.82-5.69 (m, 1H), 7.04 (d, J=8.4 Hz, 2H), 7.12-7.15 (m, 2H), 7.22 (d, J=8.4 Hz, 2H), 7.28-7.30 (m, 3H). MS [M+H]$^-$ 396.

Example 39: Benzyl 4-(4-chlorophenyl)-6-methyl-1-(2-methylallyl)-2-oxo-3,4-dihydropyridine-5-carboxylate Benzyl 4-(4-chlorophenyl)-6-methyl-1-(2-methylallyl)-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (125 mg, 72%). $^1$H NMR (300 MHz, CDCl$_3$) δ 1.66 (s, 3H), 2.53 (s, 3H), 2.86 (dd, J=3.0 and 15.9 Hz, 1H), 2.96 (dd, J=7.2 and 15.9 Hz, 1H), 4.25 (m, 1H), 4.28 (m, 2H), 4.54 (m, 1H), 4.82 (m, 1H), 5.09 (d, J=12.6 Hz, 1H), 5.15 (d, J=12.6 Hz, 1H), 7.07 (d, J=8.4 Hz, 2H), 7.14-7.17 (m, 2H), 7.21 (d, J=8.4 Hz, 2H), 7.29-7.31 (m, 3H). MS [M+H]+ 410.

Example 40: Benzyl 4-(4-chlorophenyl)-6-methyl-2-oxo-1-prop-2-ynyl-3,4-dihydropyridine-5-carboxylate Benzyl 4-(4-chlorophenyl)-6-methyl-2-oxo-1-prop-2-ynyl-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (85 mg, 51%)%) after flash chromatography purification (cyclohexane/EtOAc). $^1$H NMR (300 MHz, CDCl$_3$) δ 2.29 (m, 1H), 2.71 (s, 3H), 2.76 (dd, J=2.1 and 15.9 Hz, 1H), 2.93 (dd, J=7.5 and 15.9 Hz, 1H), 4.21 (d, J=6.3 Hz, 1H), 4.33 (dd, J=2.1 and 18.0 Hz, 1H), 4.83 (dd, J=2.1 and 17.7 Hz, 1H), 5.09 (d, J=12.6 Hz, 1H), 5.14 (d, J=12.6 Hz, 1H), 7.07 (d, J=8.4 Hz, 2H), 7.12-7.15 (m, 2H), 7.21 (d, J=8.4 Hz, 2H), 7.29-7.31 (m, 3H). MS [M+H]+ 394.

Example 41: Benzyl 1-benzyl-4-(4-chlorophenyl)-6-methyl-2-oxo-3,4-dihydropyridine-5-carboxylate Benzyl 1-benzyl-4-(4-chlorophenyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (70 mg, 37%) after flash chromatography purification (cyclohexane/EtOAc). $^1$H NMR (300 MHz, CDCl$_3$) δ 2.55 (s, 3H), 2.93 (dd, J=2.7 and 15.9 Hz, 1H), 3.03 (dd, J=6.9 and 15.9 Hz, 1H), 4.28 (d, J=4.8 Hz, 1H), 4.72 (d, J=15.9 Hz, 1H), 5.07 (d, J=12.6 Hz, 1H), 5.13 (d, J=12.6 Hz, 1H), 5.33 (d, J=15.9 Hz, 1H), 7.02 (d, J=8.4 Hz, 2H), 7.05-7.00 (m, 2H), 7.11-7.14 (m, 2H), 7.21 (d, J=8.4 Hz, 2H), 7.25-7.31 (m, 6H). MS [M+H]+ 446.

Example 42: Benzyl 4-(4-chlorophenyl)-1-isopropyl-6-methyl-2-oxo-3,4-dihydropyridine-5-carboxylate Benzyl 4-(4-chlorophenyl)-1-isopropyl-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (23 mg, 14%) after flash chromatography purification (cyclohexane/Et$_2$O). $^1$H NMR (300 MHz, CDCl$_3$) δ 1.34 (d, J=6.8 Hz, 1H), 1.46 (d, J=6.8 Hz, 1H), 2.53 (s, 3H), 2.69 (dd, J=16.1, 2.4 Hz, 1H), 2.87 (dd, J=16.1, 7.1 Hz, 1H), 4.12 (s$^p$, J=6.8 Hz, 1H), 5.11 (d, J=12.5 Hz, 1H), 5.18 (d, J=12.5 Hz, 1H), 7.07 (d, J=8.4 Hz, 2H), 7.15-7.21 (m, 2H), 7.23 (d, J=8.4 Hz, 1H), 7.28-7.33 (m, 3H). $^{13}$C NMR (75 MHz, CDC$_3$) δ 17.9, 20.2, 20.6, 35.9, 39.6, 49.3, 66.2, 111.8, 127.9, 128.1, 128.3, 128.5, 128.7, 132.6, 136.0, 139.2, 151.3, 166.9, 169.5. MS [M+H]+ 398. HRMS: calcd for C$_{23}$H$_{25}$NO$_3$Cl, [M+H]+ 398.1523, found 398.1505.

Example 43: Benzyl 4-(4-chlorophenyl)-1-(cyclopropylmethyl)-6-methyl-2-oxo-3,4-dihydropyridine-5-carboxylate Benzyl 4-(4-chlorophenyl)-1-(cyclopropylmethyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (140 mg, 81%) after flash chromatography purification (cyclohexane/EtOAc). $^1$H NMR (300 MHz, CDCl$_3$) δ 0.24-0.58 (m, 4H), 0.88-1.04 (m, 1H), 2.63 (s, 3H), 2.74 (dd, J=15.7, 2.1 Hz, 1H), 2.91 (dd, J=15.7, 7.3 Hz, 1H), 3.52 (dd, J=14.7, 6.1 Hz, 1H), 3.91 (dd, J=14.7, 8.2 Hz, 1H), 4.23 (dd, J=7.3, 2.1 Hz, 1H), 5.09 (d, J=12.8 Hz, 1H), 5.15 (d, J=12.8 Hz, 1H), 7.09-7.18 (m, 4H), 7.22 (dt, J=8.6, 2.2 Hz, 2H), 7.26-7.32 (m, 3H). MS [M+H]+ 410. HRMS: calcd for C$_{24}$H$_{25}$NO$_3$Cl, [M+H]+ 410.1523, found 410.1510.

Example 44: Benzyl 4-(4-chlorophenyl)-1-(cyclobutylmethyl)-6-methyl-2-oxo-3,4-dihydropyridine-5-carboxylate Benzyl 4-(4-chlorophenyl)-1-(cyclobutylmethyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.70 mmol) and obtained as a colorless oil (163 mg, 55%) after flash chromatography purification (cyclohexane/EtOAc). $^1$H NMR (300 MHz, CDCl$_3$) δ 2.44 (m, 1H), 1.97-1.64 (m, 6H), 2.55 (s, 3H), 2.77 (dd, J=2.7 and 15.9 Hz, 1H), 2.89 (dd, J=6.9 and 15.9 Hz, 1H), 3.44 (dd, J=6.0 and 14.4 Hz, 1H), 4.25-4.18 (m, 1H+1H), 5.09 (d, J=12.6 Hz, 1H), 5.15 (d, J=12.6 Hz, 1H), 7.04 (d, J=8.4 Hz, 2H), 7.13-7.16 (m, 2H), 7.21 (d, J=8.4 Hz, 2H), 7.28-7.30 (m, 3H). MS [M+H]+ 324

Example 45: Benzyl 1-[(1-tert-butoxycarbonylazetidin-3-yl)methyl]-4-(4-chlorophenyl)-6-methyl-2-oxo-3,4-dihydropyridine-5-carboxylate Benzyl 1-[(1-tert-butoxycarbonylazetidin-3-yl)methyl]-4-(4-chlorophenyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.62 mmol) and obtained as a colorless oil (228 mg, 70%) after flash chromatography purification (cyclohexane/EtOAc). $^1$H NMR (300 MHz, CDCl$_3$) δ 1.44 (s, 9H), 2.55 (s, 3H), 2.61 (brs, 1H), 2.80-2.87 (m, 2H), 3.44-3.89 (m, 5H), 4.22 (dd, J=5.7, 3.3 Hz, 1H), 4.27-4.46 (brs, 1H), 5.10 (d, J=12.5 Hz, 1H), 5.17 (d, J=12.5 Hz, 1H), 6.99 (d, J=8.3 Hz, 2H), 7.12-7.19 (m, 2H), 7.22, (d, J=8.3 Hz, 2H), 7.26-7.33 (m, 3H). MS [M+H]+ 469. HRMS: calcd for C$_{29}$H$_{34}$N$_2$O$_5$Cl, [M+H]+ 525.2156, found 525.2155.

Example 46: Benzyl 1-(azetidin-3-ylmethyl)-4-(4-chlorophenyl)-6-methyl-2-oxo-3,4-dihydropyridine-5-carboxylate Benzyl 1-[(1-tert-butoxycarbonylazetidin-3-yl)methyl]-4-(4-chlorophenyl)-6-methyl-2-oxo-3,4-dihydropyridine-5-carboxylate (180 mg, 0.34 mmol) was dissolved in DCM (255 µL). TFA (255 µL) was added and the reaction mixture was stirred at RT for 2 h. An aqueous saturated solution of ammonium chloride was added and the aqueous phase was extracted by DCM. The organic phase was dried under MgSO$_4$. The solvent was removed under reduced pressure. The crude was purified by flash chromatography on silica using a mixture of DCM/MeOH (98/2 to 9/1) to give the desired benzyl 1-(azetidin-3-ylmethyl)-4-(4-chlorophenyl)-6-methyl-2-oxo-3,4-dihydropyridine-5-carboxylate as a white powder (105 mg, 72%). $^1$H NMR (300 MHz, CDCl$_3$) δ 2.55 (s, 3H), 2.74 (dd, J=15.7, 2.6 Hz, 1H), 2.84 (dd, J=15.7, 6.6 Hz, 1H), 2.98 (qt, J=7.6 Hz, 1H), 3.68-3.89 (m, 5H), 4.12-4.26 (m, 2H), 5.09 (d, J=17.4 Hz, 1H), 5.15 (d, J=17.4 Hz, 1H), 6.95 (d, J=8.4 Hz, 2H), 7.12-7.17 (m, 2H), 7.22 (d, J=8.4 Hz, 2H), 7.25-7.31 (m, 3H), 9.10-10.0 (brs, 1H). MS [M+H]$^+$ 425. HRMS: calcd for $C_{22}H_{26}N_2O_3Cl$, [M+H]$^+$ 425.1632, found 425.1638.

Example 47: Benzyl 4-(4-chlorophenyl)-6-methyl-1-[(1-methylazetidin-3-yl)methyl]-2-oxo-3,4-dihydropyridine-5-carboxylate Benzyl 1-(azetidin-3-ylmethyl)-4-(4-chlorophenyl)-6-methyl-2-oxo-3,4-dihydropyridine-5-carboxylate (180 mg, 0.42 mmol), sodium methoxide (34 mg, 0.63 mmol) and paraformaldehyde (19 mg, 0.63 mmol) were dissolved in methanol (4 mL). The reaction mixture was stirred at RT for 2 h. Sodium borohydride (16 mg, 0.42 mmol) was then added. The reaction mixture was stirred at RT for 2 h. An aqueous solution of sodium hydroxide 1N was added. The aqueous phase was extracted by EtOAc. The organic phases were assembled, washed with brine and dried over $MgSO_4$. The solvents were removed under reduced pressure. Purification of the crude by Flash chromatography on silica using a mixture of DCM/methanol (95/5) as eluent afforded the desired benzyl 4-(4-chlorophenyl)-6-methyl-1-[(1-methylazetidin-3-yl)methyl]-2-oxo-3,4-dihydropyridine-5-carboxylate (23 mg, 12%) as a colorless oil. $^1$H NMR (300 MHz, $CDC_3$) δ 2.27 (s, 3H), 2.57 (s, 3H), 2.78 (dd, J=16.1, 2.8 Hz, 1H), 2.81-2.94 (m, 4H), 3.17 (t, J=7.1 Hz, 1H), 3.30 (t, J=7.1 Hz, 1H), 3.65 (dd, J=14.5, 6.4 Hz, 1H), 4.22 (dd, J=7.1, 2.0 Hz, 1H), 4.27 (dd, J=14.5, 6.4 Hz, 1H), 5.09 (d, J=13.5 Hz, 1H), 5.15 (d, J=13.5 Hz, 1H), 7.00 (d, J=8.5 Hz, 2H), 7.11-7.17 (m, 1H), 7.22 (d, J=8.5 Hz, 2H), 7.26-7.32 (m, 3H). MS [M+H]$^+$ 439; HRMS: calcd for $C_{25}H_{28}N_2O_3Cl$, [M+H]$^+$ 439.1788, found 439.1796.

Example 48: Benzyl 4-(4-chlorophenyl)-1-[(1,1-dimethylazetidin-1-ium-3-yl)methyl]-6-methyl-2-oxo-3,4-dihydropyridine-5-carboxylate iodide Benzyl 4-(4-chlorophenyl)-6-methyl-1-[(1-methylazetidin-3-yl)methyl]-2-oxo-3,4-dihydropyridine-5-carboxylate (14 mg, 0.032 mmol) was dissolved in anh. DMF (0.1 mL). Iodomethane (3 μL, 0.048 mmol) was added. The reaction mixture was stirred at RT for 1 h. Removal of the solvent under reduced pressure gave the desired benzyl 4-(4-chlorophenyl)-1-[(1,1-dimethylazetidin-1-ium-3-yl)methyl]-6-methyl-2-oxo-3,4-dihydropyridine-5-carboxylate iodide as a colorless oil (18 mg, 100%). $^1$H NMR (300 MHz, DMSO d6) δ 2.50 (s, 3H), 2.40-2.60 (m, 1H), 2.93-3.19 (m, 1H), 3.09 (s, 3H), 3.14 (s, 3H), 3.30-3.50 (m, 1H), 3.70-3.89 (m, 2H), 3.94-4.12 (m, 2H), 4.15-4.29 (m, 3H), 5.04 (d, J=13.0 Hz, 1H), 5.12 (d, J=13.0 Hz, 1H), 7.06-7.18 (m, 4H), 7.22-7.30 (m, 3H), 7.36 (d, J=8.6 Hz, 2H). $^{13}$C NMR (75 MHz, DMSO d6) 16.9, 27.7, 36.6, 43.3, 51.7, 53.3, 65.8, 68.7, 69.2, 110.4, 127.8, 128.3, 128.7, 129.1, 131.9, 136.7, 140.5, 150.5, 166.7, 170.0. MS [M+H]$^+$ 453 HRMS: calcd for $C_{26}H_{30}N_2O_3Cl$, [M+H]$^+$ 453.1945, found 453.1923.

Example 49: Benzyl 4-(4-chlorophenyl)-1-isobutyl-6-methyl-2-oxo-3,4-dihydropyridine-5-carboxylate Benzyl 4-(4-chlorophenyl)-1-isobutyl-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.56 mmol) and obtained as a colorless oil (171 mg, 74%) after flash chromatography purification (cyclohexane/EtOAc). $^1$H NMR (300 MHz, $CDCl_3$) δ 0.70 (d, J=6.6 Hz, 3H), 0.84 (d, J=6.6 Hz, 3H), 1.74 (m, 1H), 2.55 (s, 3H), 2.94-2.86 (m, 2H), 3.25 (dd, J=6.3 and 14.4 Hz, 1H), 3.91 (dd, J=8.1 and 14.1 Hz, 1H), 4.2 (m, 1H), 5.10 (d, J=12.6 Hz, 1H), 5.16 (d, J=12.6 Hz, 1H), 7.08 (d, J=8.4 Hz, 2H), 7.14-7.17 (m, 2H), 7.21 (d, J=8.4 Hz, 2H), 7.28-7.30 (m, 3H). MS [M+H]$^+$ 412.

Example 50: Benzyl 4-(4-chlorophenyl)-1-[2-(dimethylamino)ethyl]-6-methyl-2-oxo-3,4-dihydropyridine-5-carboxylate Benzyl 4-(4-chlorophenyl)-1-[2-(dimethylamino)ethyl]-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.42 mmol) and obtained as a colorless oil (177 mg, 98%). $^1$H NMR (300 MHz, $CDC_3$) δ 2.26 (s, 6H), 2.26-2.43 (m, 2H), 2.60 (m, 3H), 2.73 (dd, J=15.7, 2.2 Hz, 2H), 2.90 (dd, J=15.7, 7.1 Hz, 2H), 3.58-3.67 (m, 1H), 4.02-4.12 (m, 1H), 4.22 (d, J=7.0 Hz, 1H), 5.06 (d, J=12.7 Hz, 1H), 5.13 (d, J=12.7 Hz, 1H), 7.07 (d, J=8.4 Hz, 2H), 7.09-7.14 (m, 2H), 7.21 (d, J=8.4 Hz, 2H), 7.25-7.31 (m, 3H). MS [M+H]$^+$ 427. HRMS: calcd for $C_{24}H_{28}N_2O_3Cl$, [M+H]$^+$ 427.1788, found 427.1775.

Example 51: 2-[5-benzyloxycarbonyl-4-(4-chlorophenyl)-6-methyl-2-oxo-3,4-dihydropyridin-1-yl]ethyl-trimethyl-ammonium iodide The benzyl 4-(4-chlorophenyl)-1-[2-(dimethylamino)ethyl]-6-methyl-2-oxo-3,4-dihydropyridine-5-carboxylate (65 mg, 0.15 mmol) was dissolved in anh. DMF (1 mL). Iodomethane (14 μL, 0.23 mmol) was added. The reaction mixture was stirred at RT for 2 h. The solvent was removed under reduced pressure to afford the desired 2-[5-benzyloxycarbonyl-4-(4-chlorophenyl)-6-methyl-2-oxo-3,4-dihydropyridin-1-yl]ethyl-trimethyl-ammonium iodide as a yellow powder (79 mg, 93%). $^1$H NMR (300 MHz, DMSO d6) δ 2.61 (s, 3H), 2.61-2.68 (dd, J=15.5, 2.3 Hz, 1H), 3.02-3.12 (1H, J=15.5, 7.0 Hz, 1H), 3.12 (s, 3H), 3.12-3.24 (m, 1H), 3.32 (s, 3H), 3.32-3.52 (m, 1H), 3.90, -4.20 (m, 2H), 4.25 (d, J=6.0 Hz, 1H), 5.07 (d, J=12.9 Hz, 1H), 5.14 (d, J=12.9 HZ, 1H), 7.09-7.16 (m, 2H), 7.18 (d, J=8.3 Hz, 2H), 7.24-7.30 (m, 3H), 7.34 (d, J=8.3 Hz, 2H). MS [M]$^+$441. HRMS: calcd for $C_{25}H_{30}N_2O_3Cl$, [M+H]$^+$ 441.1945, found 441.1943.

Example 52: Benzyl 1-[2-(tert-butoxycarbonylamino)ethyl]-4-(4-chlorophenyl)-6-methyl-2-oxo-3,4-dihydropyridine-5-carboxylate Benzyl 1-[2-(tert-butoxycarbonylamino)ethyl]-4-(4-chlorophenyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.60 mmol) and obtained as a colorless oil (157 mg, 52%) after flash chromatography purification (cyclohexane/EtOAc). $^1$H NMR (300 MHz, $CDCl_3$) δ 1.44 (s, 9H), 2.59 (s, 3H), 2.80 (dd, J=16.0, 2.7 Hz, 1H), 2.91 (dd, J=16.0, 7.1 Hz, 1H), 3.15 (q, J=6.2 Hz, 1H), 3.69-3.81 (m, 1H), 3.89-4.01 (m, 1H), 4.24 (dd, J=7.1, 2.7 Hz, 1H), 4.50 (t, J=5.5 Hz, 1H), 5.10 (d, J=12.6 Hz, 1H), 5.16 (d, J=12.6 Hz, 1H), 7.05 (d, J=8.4 Hz, 2H), 7.13-7.20 (m, 2H), 7.24 (d, J=8.4 Hz, 2H), 7.26-7.33 (m, 3H). MS [M+H]$^+$ 499; HRMS: calcd for $C_{27}H_{32}N_2O_5Cl$, [M+H]$^+$ 499.2000, found 499.2008.

Example 53: Hydrochloride salt of benzyl 1-(2-aminoethyl)-4-(4-chlorophenyl)-6-methyl-2-oxo-3,4-dihydropyridine-5-carboxylate Benzyl 1-[2-(tert-butoxycarbonylamino)ethyl]-4-(4-chlorophenyl)-6-methyl-2-oxo-3,4-dihydropyridine-5-carboxylate (38 mg, 0.076 mmol) was dissolved in a 4M solution of hydrochloric acid in dioxane (1 mL). The reaction mixture was stirred 1 h at RT. The solvents were removed under reduced pressure to give the desired hydrochloride salt of benzyl 1-(2-aminoethyl)-4-(4-chlorophenyl)-6-methyl-2-oxo-3,4-dihydropyridine-5-carboxylate as a colorless oil (32 mg, 97%). $^1$H NMR (300 MHz, DMSO d6) δ 2.57 (s, 3H), 2.67-2.81 (m, 1H), 2.81-2.95 (m, 1H), 3.02 (dd, J=15.9, 7.5 Hz, 1H), 3.62-3.75 (m, 1H), 3.80-4.04 (m, 2H), 4.20 (d, J=6.0 Hz, 1H), 5.04 (d, J=13.5 Hz, 1H), 5.10 (d, J=13.5 Hz, 1H), 7.07-7.13 (m, 1H), 7.16 (d, J=7.9 Hz, 2H), 7.21-7.28 (m, 4H), 7.31 (d, J=7.9 Hz, 2H), 8.21 (brs, 3H). MS [M+H]$^+$ 399; HRMS: calcd for $C_{22}H_{24}N_2O_3Cl$, [M+H]$^+$ 399.1475, found 399.1486.

Example 54: Benzyl 4-(4-chlorophenyl)-1-[3-(dimethylamino)propyl]-6-methyl-2-oxo-3,4-dihydropyridine-5-carboxylate Benzyl 4-(4-chlorophenyl)-1-[3-(dimethylamino)propyl]-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.28 mmol) and obtained as a colorless oil (66 mg, 53%) after flash chromatography purification (cyclohexane/EtOAc). $^1$H NMR (300 MHz, CDCl$_3$) δ 1.37-1.62 (m, 2H), 2.06 (s, 6H), 2.08 (t, J=7.2 Hz, 2H), 2.56 (s, 3H), 2.57-2.62 (m, 1H), 2.97 (dd, J=15.7, 7.2 Hz, 1H), 3.51 (ddd, J=14.6, 9.1, 3.7 Hz, 1H), 3.82 (ddd, J=14.6, 9.1, 5.4 Hz, 1H), 4.18 (d, J=6.4 Hz, 1H), 5.05 (d, J=13.2 Hz, 1H), 5.12 (d, J=13.2 Hz, 1H), 7.12-7.16 (m, 4H), 7.26 (m, 3H), 7.32 (d, J=8.1 Hz, 2H). MS [M+H]$^+$ 441. HRMS: calcd for $C_{25}H_{30}N_2O_3Cl$, [M+H]$^+$ 441.1945, found 441.1950.

Example 55: Benzyl 4-(4-chlorophenyl)-6-methyl-2-oxo-1-(2-pyrrolidin-1-ylethyl)-3,4-dihydropyridine-5-carboxylate The benzyl 4-(4-chlorophenyl)-6-methyl-2-oxo-3,4-dihydro-1H-pyridine-5-carboxylate (71 mg, 0.20 mmol) was dissolved in anhydrous DMF (1 mL). Sodium hydride (14 mg, 0.60 mmol) was added. The reaction mixture was stirred at r.t. for 15 min. N-(-2-chloroethyl)pyrrolidine hydrochloride (55 mg, 0.30 mmol) were added. The reaction mixture was stirred at 60° C. for 4 h. LCMS analysis showed the reaction was incomplete. Sodium hydride (7 mg, 0.30 mmol) andN-(-2-chloroethyl)pyrrolidine hydrochloride (18 mg, 0.10 mmol) were added The reaction mixture was stirred for an additional hour at 60° C. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of DCM/Acetone (8/2) as eluent to give the desired compound as a white powder (55 mg, 61%). $^1$H NMR (300 MHz, CDCl$_3$) δ 1.72-1.86 (m, 4H), 2.45-2.66 (m, 6H), 2.62 (s, 3H), 2.74 (dd, J=15.9, 2.3 Hz, 1H), 2.92 (dd, J=15.9, 7.5 Hz, 1H), 3.69 (ddd, J=14.5, 8.8, 5.9 Hz, 1H), 4.14 (ddd, J=14.5, 8.8, 5.9 Hz, 1H), 4.22 (dd, J=7.5, 2.3 Hz, 1H), 5.09 (d, J=12.6 Hz, 1H), 5.15 (d, J=12.6 Hz, 1H), 7.07 (dt, J=8.6, 2.2 Hz, 2H), 7.11-7.18 (m, 2H), 7.22 (dt, J=8.6, 2.2 Hz, 2H), 7.26-7.34 (m, 3H). MS [M+H]$^+$ 453. HRMS: calcd for $C_{26}H_{30}N_2O_3Cl$, [M+H]$^+$ 453.1945, found 453.1920.

Example 56: Benzyl 4-(4-chlorophenyl)-6-methyl-2-oxo-1-[2-(1-piperidyl)ethyl]-3,4-dihydropyridine-5-carboxylate The benzyl 4-(4-chlorophenyl)-6-methyl-2-oxo-3,4-dihydro-1H-pyridine-5-carboxylate (71 mg, 0.20 mmol) was dissolved in anhydrous DMF (1 mL).

Sodium hydride (14 mg, 0.60 mmol) was added. The reaction mixture was stirred at RT for 15 min. N-(-2-chloroethyl)piperidine hydrochloride (55 mg, 0.30 mmol) were added. The reaction mixture was stirred at 60° C. for 4 h. LCMS analysis showed the reaction was incomplete. Sodium hydride (7 mg, 0.30 mmol) and N-(-2-chloroethyl) piperidine hydrochloride (18 mg, 0.10 mmol) were added The reaction mixture was stirred for an additional hour at 60° C. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of DCM/Acetone (8/2) as eluent to give the desired compound as a white powder (48 mg, 52%). $^1$H NMR (300 MHz, CDCl$_3$) δ 1.40-1.50 (m, 2H), 1.53-1.66 (m, 4H), 2.29-2.53 (m, 6H), 2.61 (s, 3H), 2.74 (dd, J=15.8, 2.3 Hz, 1H), 2.92 (dd, J=15.8, 7.5 Hz, 1H), 3.67 (dt, J=14.0, 7.5 Hz, 1H), 4.07 (ddd, J=14.0, 7.5, 5.5 Hz, 1H), 4.22 (dd, J=7.5, 2.3 Hz, 1H), 5.10 (d, J=12.8 Hz, 1H), 5.15 (d, J=12.8 Hz, 1H), 7.08 (dt, J=8.5, 2.3 Hz, 2H), 7.11-7.17 (m, 2H), 7.22 (dt, J=8.5, 2.3 Hz, 2H), 7.26-7.33 (m, 3H). MS [M+H]$^+$ 467. HRMS: calcd for $C_{27}H_{32}N_2O_3Cl$, [M+H]$^+$ 467.2101, found 467.2120.

Example 57: Benzyl 4-(4-chlorophenyl)-1-(2-methoxy-2-oxo-ethyl)-6-methyl-2-oxo-3,4-dihydropyridine-5-carboxylate The benzyl 4-(4-chlorophenyl)-6-methyl-2-oxo-3,4-dihydro-1H-pyridine-5-carboxylate (75 mg, 0.21 mmol) was dissolved in anhydrous DMF (1 mL). Sodium hydride (10 mg, 0.42 mmol) and methylbromoacetate (45 µL, 0.42 mmol) were added. The reaction mixture was stirred at RT for 5 h. The DMF was removed under reduced pressure. The residue was diluted in water and extracted by EtOAc. The organic layers were assembled, washed by brine and dried on MgSO$_4$. The solvent was removed under reduced pressure to give the desired compound as a yellow oil (90 mg, 100%). $^1$H NMR (300 MHz, CDCl$_3$) δ 2.50 (s, 3H), 2.78 (dd, J=16.0, 2.0 Hz, 1H), 2.99 (dd, J=16.0, 7.9 Hz, 1H), 3.76 (s, 3H), 4.25 (d, J=7.9 Hz, 1H), 4.43 (d, J=18.0 Hz, 1H), 4.65 (d, J=18.0 Hz, 1H), 5.07 (d, J=12.6 Hz, 1H), 5.14 (d, J=12.6 Hz, 1H), 7.07-7.14 (m, 2H), 7.16 (d, J=8.6 Hz, 2H), 7.23 (d, J=8.6 Hz, 2H), 7.26-7.33 (m, 3H). MS [M+H]$^+$ 428. HRMS: calcd for $C_{23}H_{23}NO_5Cl$, [M+H]$^+$ 428.1265, found 428.1251.

Example 58: Benzyl 1-(2-tert-butoxy-2-oxo-ethyl)-4-(4-chlorophenyl)-6-methyl-2-oxo-3,4-dihydropyridine-5-carboxylate The benzyl 4-(4-chlorophenyl)-6-methyl-2-oxo-3,4-dihydro-1H-pyridine-5-carboxylate (106 mg, 0.30 mmol) was dissolved in anhydrous DMF (2 mL). Sodium hydride (9 mg, 0.36 mmol) was added. The reaction mixture was stirred at RT for 30 min. tert-butylbromoacetate (73 µL, 0.45 mmol) were added. The reaction mixture was stirred at r.t. for 4 h. LCMS analysis showed the reaction was incomplete. Sodium hydride (4 mg, 0.15 mmol) and tert-butylbromoacetate (24 µL, 0.15 mmol) were added. The reaction mixture was stirred for 1 h at RT The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (9/1) as eluent to give the desired benzyl 1-(2-tert-butoxy-2-oxo-ethyl)-4-(4-chlorophenyl)-6-methyl-2-oxo-3,4-dihydropyridine-5-carboxylate as a white powder (112 mg, 79%). $^1$H NMR (300 MHz, CDC$_3$) δ 1.49 (s, 9H), 2.50 (s, 3H), 2.76 (dd, J=16.1, 2.4 Hz, 1H), 2.99 (dd, J=16.1, 7.9 Hz, 1H), 4.24 (d, J=7.9 Hz, 1H), 4.38 (d, J=17.8 Hz, 1H), 4.52 (d, J=17.8 Hz, 1H), 5.06 (d, J=12.5 Hz, 1H), 5.13 (d, J=12.5 Hz, 1H), 7.08-7.14 (m, 2H), 7.17 (d, J=8.7 Hz, 2H), 7.23 (d, J=8.7 Hz, 2H), 7.28-7.32 (m, 3H). MS [M+H]$^+$ 470. HRMS: calcd for C$_{26}$H$_{32}$N$_2$O$_5$Cl, [M+NH$_4$]$^+$ 487.2000, found 487.1992.

Example 59: Benzyl 4-(4-chlorophenyl)-6-methyl-1-[(3-methyl-1,2,4-oxadiazol-5-yl)methyl]-2-oxo-3,4-dihydropyridine-5-carboxylate

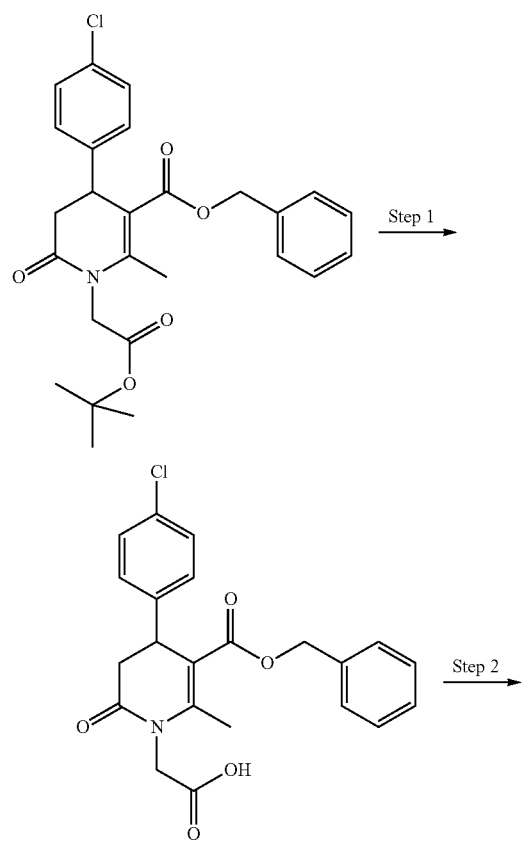

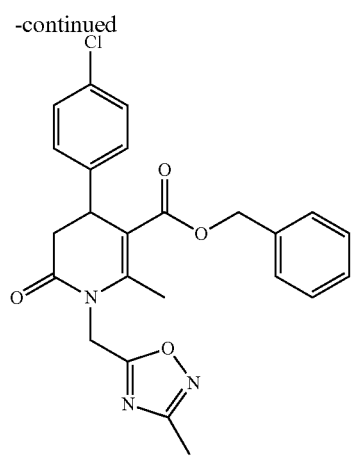

Step 1. 2-[5-benzyloxycarbonyl-4-(4-chlorophenyl)-6-methyl-2-oxo-3,4-dihydropyridin-1-yl]acetic acid Benzyl 1-(2-tert-butoxy-2-oxo-ethyl)-4-(4-chlorophenyl)-6-methyl-2-oxo-3,4-dihydropyridine-5-carboxylate (100 mg, 0.21 mmol) was dissolved in DCM (160 µL). Trifluoroacetic acid (160 µL, 2.3 mmol) was added. The reaction mixture was stirred at RT for 1 h. Water was added. The acid was extracted by EtOAc. The organic layers were assembled, washed by brine and dried on MgSO$_4$. The solvent was removed under reduced pressure. The crude product was purified by flash chromatography using a mixture of Cyclohexane/Acetone/EtOAc (3/1/1) as eluent to give a mixture of the desired compound and unidentified byproducts (80 mg). This mixture was diluted in diethyl ether and washed with an aqueous solution of NaHCO$_3$ 1 M. The aqueous solution was acidified by hydrochloric acid until pH=1 and extracted by EtOAc. The organic layers were assembled, washed by brine and dried on MgSO$_4$. The solvent was removed under reduced pressure to give the desired 2-[5-benzyloxycarbonyl-4-(4-chlorophenyl)-6-methyl-2-oxo-3,4-dihydropyridin-1-yl]acetic acid as a white powder (44 mg, 50%) $^1$H NMR (300 MHz, CDCl$_3$) δ 2.48 (s, 3H), 2.75 (d, J=16.0 Hz, 1H), 2.97 (dd, J=16.0, 7.5 Hz, 1H), 4.38-4.67 (m, 4H), 5.05 (d, J=12.6 Hz, 1H), 5.12 (d, J=12.6 Hz, 1H), 6.34 (brs, 1H), 7.05-7.15 (m, 4H), 7.18 (d, J=8.4 Hz, 2H), 7.24-7.31 (m, 3H). MS [M+H]$^+$ 414. HRMS: calcd for C$_{22}$H$_{21}$NO$_5$Cl, [M+H]$^+$ 414.1108, found 414.1121.

Step 2. Benzyl 4-(4-chlorophenyl)-6-methyl-1-[(3-methyl-1,2,4-oxadiazol-5-yl)methyl]-2-oxo-3,4-dihydropyridine-5-carboxylate The 2-[5-benzyloxycarbonyl-4-(4-chlorophenyl)-6-methyl-2-oxo-3,4-dihydropyridin-1-yl]acetic acid (207 mg, 0.5 mmol) of step 1 was dissolved in anh. DMF (2 mL). DIEA (430 µL, 2.5 mmol) and HBTU (228 mg, 0.6 mmol) were added. The reaction mixture was stirred at RT for 10 min. The amidoxime (41 mg, 0.55 mmol) was then added.

The reaction mixture was stirred at RT for 1 h. Water was added. The aqueous phase was extracted with EtOAc. The organic phases were assembled, washed with brine and dried over MgSO$_4$. The solvents were removed under reduced pressure. The crude was dissolved in anh. DMF (2 mL). The reaction mixture was stirred at 110° C. for 3 h. The solvent was removed under reduced pressure. Water was added. The aqueous phase was extracted with EtOAc. The organic phases were assembled, washed with brine and dried over MgSO$_4$. The solvents were removed under reduced pressure. Purification of the crude by Flash chromatography using a mixture Cyclohexane/EtOAc (8/2) gave the desired benzyl 4-(4-chlorophenyl)-6-methyl-1-[(3-methyl-1,2,4-oxadiazol-5-yl)methyl]-2-oxo-3,4-dihydropyridine-5-carboxylate as a white powder (124 mg, 55%). $^1$H NMR (300 MHz, CDCl$_3$) δ 2.38 (s, 3H), 2.56 (s, 3H), 2.81 (dd, J=16.0, 2.3 Hz, 1H), 3.01 (dd, J=16.0, 7.6 Hz, 1H), 4.28 (d, J=7.6 Hz, 1H), 5.03 (d, J=17.5 Hz, 1H), 5.07 (d, J=12.4 Hz, 1H), 5.14 (d, J=12.4 Hz, 1H), 5.28 (d, J=17.5 Hz, 1H), 7.08-7.17 (m, 4H), 7.21 (d, J=8.2 Hz, 2H), 7.24-7.32 (m, 3H). $^{13}$C NMR (75 MHz, CDCl$_3$) δ 11.6, 16.8, 36.9, 37.9, 38.1, 66.5, 111.5, 127.9, 128.2, 128.5, 128.9, 132.9, 135.7, 139.3, 148.2, 166.5, 167.5, 168.9, 174.6. MS [M+H]$^+$ 452. HRMS: calcd for C$_{24}$H$_{23}$N$_3$O$_4$Cl, [M+H]$^+$ 452.1377, found 452.1355.

Example 60: Benzyl 1-(2-amino-2-oxo-ethyl)-4-(4-chlorophenyl)-6-methyl-2-oxo-3,4-dihydropyridine-5-carboxylate The benzyl 4-(4-chlorophenyl)-6-methyl-2-oxo-3,4-dihydro-1H-pyridine-5-carboxylate (106 mg, 0.30 mmol) was dissolved in anhydrous DMF (2 mL). Sodium hydride (9 mg, 0.36 mmol) was added. The reaction mixture was stirred at RT for 30 min. 2-bromoacetamide (62 mg, 0.45 mmol) were added. The reaction mixture was stirred at RT for 4 h. LCMS analysis showed the reaction was incomplete. Sodium hydride (4 mg, 0.15 mmol) and 2-bromoacetamide (21 mg, 0.15 mmol) were added. The reaction mixture was stirred for 1 h at RT The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (9/1) as eluent to give the desired compound as a white powder (100 mg, 81%). $^1$H NMR (300 MHz, CDCl$_3$) δ 2.58 (s, 3H), 2.83 (dd, J=16.0, 2.4 Hz, 1H), 3.00 (dd, J=16.0, 7.3 Hz, 1H), 4.27 (dd, J=7.3, 2.4 Hz, 1H), 4.31 (d, J=16.2 Hz, 1H), 4.51 (d, J=16.2 Hz, 1H), 5.09 (d, J=12.5 Hz, 1H), 5.16 (d, J=12.5 Hz, 1H), 5.46 (brs, 1H), 5.68 (brs, 1H), 7.10-7.18 (m, 4H), 7.24 (dt, J=8.6, 2.2 Hz, 2H), 7.28-7.34 (m, 3H). MS [M−H]$^−$ 411. HRMS: calcd for C$_{22}$H$_{22}$N$_2$O$_4$Cl, [M+H]$^+$ 413.1268, found 413.1250.

Example 61: 2-[5-benzyloxycarbonyl-4-(4-chlorophenyl)-6-methyl-2-oxo-3,4-dihydropyridin-1-yl]acetic acid The benzyl 1-(2-tert-butoxy-2-oxo-ethyl)-4-(4-chlorophenyl)-6-methyl-2-oxo-3,4-dihydropyridine-5-carboxylate (100 mg, 0.21 mmol) was dissolved in DCM (160 μL). Trifluoroacetic acid (160 μL, 2.3 mmol) was added. The reaction mixture was stirred at RT for 1 h. Water was added. The acid was extracted by EtOAc. The organic layers were assembled, washed by brine and dried on MgSO$_4$. The solvent was removed under reduced pressure. The crude product was purified by flash chromatography using a mixture of Cyclohexane/Acetone/EtOAc (3/1/1) as eluent to give a mixture of the desired compound and unidentified byproducts (80 mg). This mixture was diluted in diethyl ether and washed with an aqueous solution of NaHCO$_3$ 1 M. The aqueous solution was acidified by hydrochloric acid until pH=1 and extracted by EtOAc. The organic layers were assembled, washed by brine and dried on MgSO$_4$. The solvent was removed under reduced pressure to give the desired 2-[5-benzyloxycarbonyl-4-(4-chlorophenyl)-6-methyl-2-oxo-3,4-dihydropyridin-1-yl]acetic acid as a white powder (44 mg, 50%) $^1$H NMR (300 MHz, CDCl$_3$) δ 2.48 (s, 3H), 2.75 (d, J=16.0 Hz, 1H), 2.97 (dd, J=16.0, 7.5 Hz, 1H), 4.38-4.67 (m, 4H), 5.05 (d, J=12.6 Hz, 1H), 5.12 (d, J=12.6 Hz, 1H), 6.34 (brs, 1H), 7.05-7.15 (m, 4H), 7.18 (d, J=8.4 Hz, 2H), 7.24-7.31 (m, 3H). MS [M+H]$^+$ 414. HRMS: calcd for C$_{22}$H$_{21}$NO$_5$Cl, [M+H]$^+$ 414.1108, found 414.1121.

Example 62: Benzyl 4-(4-chlorophenyl)-6-methyl-1-(2-methylsulfonylethyl)-2-oxo-3,4-dihydropyridine-5-carboxylate Benzyl 4-(4-chlorophenyl)-6-methyl-1-(2-methylsulfonylethyl)-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.50 mmol) and obtained as a white powder (51 mg, 22%) after flash chromatography purification (cyclohexane/EtOAc). $^1$H NMR (300 MHz, CDC$_3$) δ 2.61 (s, 3H), 2.79 (dd, J=16.0, 2.7 Hz, 1H), 2.87-2.97 (m, 1H), 2.94 (s, 3H), 3.17 (t, J=7.3 Hz, 2H), 3.98-4.28 (m, 2H), 4.26 (d, J=7.6 Hz, 1H), 5.10 (d, J=12.4 Hz, 1H), 5.16 (d, J=7.4 Hz, 2H), 7.03 (d, J=8.3 Hz, 2H), 7.12-7.18 (m, 2H), 7.24 (d, J=8.3 Hz, 2H), 7.27-7.33 (m, 3H). $^{13}$C NMR (75 MHz, CDC$_3$) δ 16.8, 36.3, 36.5, 38.2, 41.1, 52.8, 66.5, 111.8, 127.9, 128.1, 128.2, 128.5, 129.0, 133.0, 135.7, 138.9, 148.3, 166.5, 169.4. MS [M+H]$^+$ 462. HRMS: calcd for C$_{26}$H$_{21}$NO$_5$Cl, [M+H]$^+$ 462.1108, found 462.1138.

Example 63: Benzyl 4-(4-chlorophenyl)-1-(cyanomethyl)-6-methyl-2-oxo-3,4-dihydropyridine-5-carboxylate Benzyl 4-(4-chlorophenyl)-1-(cyanomethyl)-6-methyl-2-oxo-3,4-dihydropyridine-5-carboxylate was obtained according general procedure B starting from benzyl 4-(4-chlorophenyl)-6-methyl-2-oxo-3,4-dihydro-1H-pyridine-5-carboxylate (0.50 mmol) and obtained as a colorless oil (162 mg, 88%) after flash chromatography purification (dichloromethane). $^1$H NMR (300 MHz, CDCl$_3$) δ 2.68 (s, 3H), 2.82 (dd, J=16.1, 2.5 Hz, 1H), 2.96 (dd, J=16.1, 7.3 Hz, 1H), 4.27 (dd, J=7.3, 2.5 Hz, 1H), 4.53 (d, J=17.7 Hz, 1H), 4.81 (d, J=17.7 Hz, 1H), 5.10 (d, J=12.4 Hz, 1H), 5.15 (d, J=12.4 Hz, 1H), 7.01 (d, J=8.5 Hz, 2H), 7.12-7.18 (m, 2H), 7.24 (d, J=8.5 Hz, 2H), 7.28-7.35 (m, 3H). $^{13}$C NMR (75 MHz, CDCl$_3$) δ 16.7, 29.5, 36.7, 38.1, 66.6, 112.8, 114.7, 127.9, 128.0, 128.3, 128.5, 129.1, 133.2, 135.5, 138.4, 146.8, 166.1, 168.3. MS [M+H]$^+$ 395; HRMS: calcd for C$_{22}$H$_{20}$N$_2$O$_3$Cl, [M+H]$^+$ 395.1162, found 395.1167.

TABLE 6
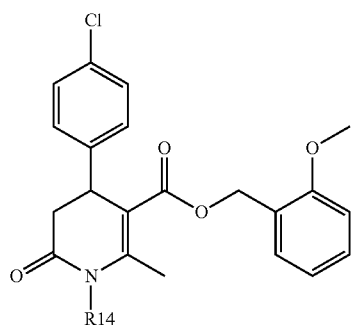
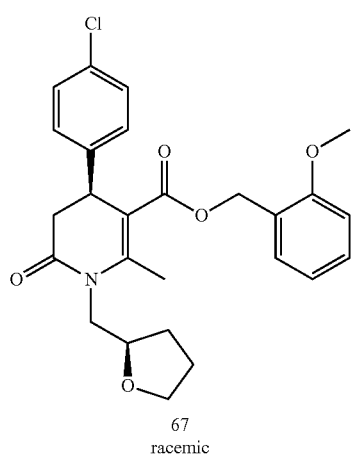 [SMILES: COc1ccccc1COC(=O)C1=C(C)N(C[C@H]2CCCO2)C(=O)C[C@H]1c1ccc(Cl)cc1]
67
racemic
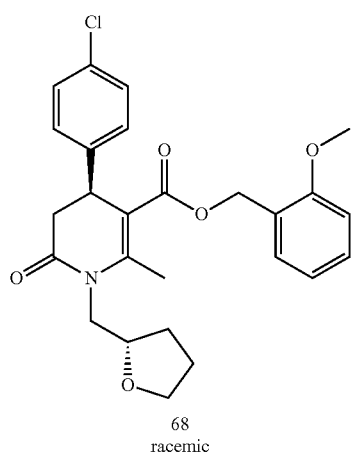 [SMILES: COc1ccccc1COC(=O)C1=C(C)N(C[C@@H]2CCCO2)C(=O)C[C@H]1c1ccc(Cl)cc1]
68
racemic
| Examples | R14 |
|---|---|
| 64 | 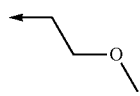 |
| 65 | 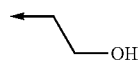 |
| 66 | 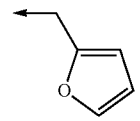 |
TABLE 6-continued
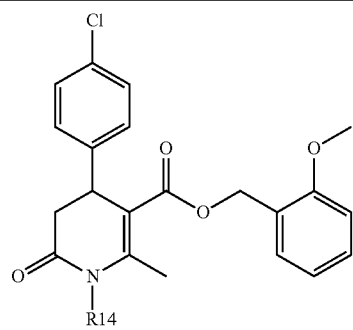
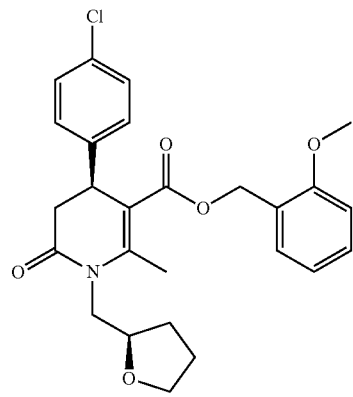
67
racemic
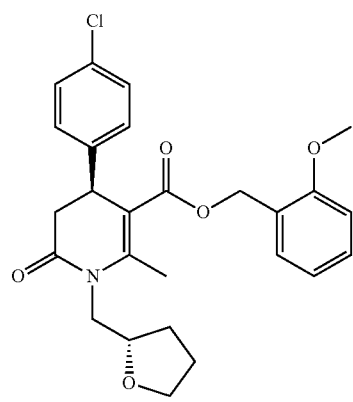
68
racemic
| Examples | R14 |
|---|---|
| 67 |  |
| 68 |  |
| 69 | 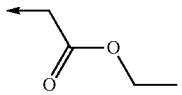 |

TABLE 6-continued (Structures for examples 67 racemic and 68 racemic, with R14 variable, shown in both columns)

| Examples | R14 |
|---|---|
| 70 | cyclopropylmethyl |
| 71 | 3-methoxypropyl |
| 72 | (1,3-dioxolan-2-yl)methyl |
| 73 | methoxycarbonylmethyl (methyl acetate group) |

Example 64: (2-methoxyphenyl)methyl 4-(4-chlorophenyl)-1-(2-methoxyethyl)-6-methyl-2-oxo-3,4-dihydropyridine-5-carboxylate 2-methoxybenzyl alcohol (268 µL, 2.0 mmol) and triethylamine (335 µL, 2.4 mmol) were dissolved in anh. DCM (7 mL). Thionyl chloride (218 µL, 3.0 mmol) was added slowly. The reaction mixture was stirred at RT for 1 h. The reaction mixture was washed with an aqueous solution of HCl 1N. The organic phase was dried over MgSO$_4$. The solvent was removed under reduced pressure to give the desired 2-methoxybenzyl chloride (300 mg, 96%) as a yellowish oil. 4-(4-chlorophenyl)-1-(2-methoxyethyl)-6-methyl-2-oxo-3,4-dihydropyridine-5-carboxylic acid (example 74, 85 mg, 0.26 mmol) was dissolved in anhydrous DMF (1 mL) then cesium carbonate (169 mg, 0.52 mmol) and 2-methoxybenzyl chloride (81 mg, 0.52 mmol) were added. The reaction mixture was stirred at RT for 18 h. The solvent was removed under reduced pressure. The residue was dissolved in EtOAc and water. The aqueous phase was extracted with EtOAc. The combined organic layers were washed with brine and dried over MgSO$_4$. The solvent was removed under reduced pressure. Purification of the crude by flash chromatography using a mixture of Cyclohexane/EtOAc (8/2) as eluent gave the desired (2-methoxyphenyl) methyl 4-(4-chlorophenyl)-1-(2-methoxyethyl)-6-methyl-2-oxo-3,4-dihydropyridine-5-carboxylate as a yellowish oil (36 mg, 31%). $^1$H NMR (300 MHz, CDCl$_3$) δ 2.60 (s, 3H), 2.71 (dd, J=15.9, 2.4 Hz, 1H), 2.91 (dd, J=15.9, 7.6 Hz, 1H), 3.31 (s, 3H), 3.36 (ddd, J=9.8, 8.3, 3.7 Hz, 1H), 3.46 (dt, J=9.8, 4.2 Hz, 1H), 3.74 (s, 3H), 3.69-3.78 (m, 1H), 4.13-4.21 (m, 2H), 5.10 (d, J=12.9 Hz, 1H), 5.19 (d, J=12.9 Hz, 1H), 6.80-6.85 (m, 2H), 6.98 (dd, J=7.8, 1.6 Hz, 1H), 7.09 (d, J=8.4 Hz, 2H), 7.19 (d, J=8.4 Hz, 2H), 7.26 (t, J=7.8 Hz, 1H). $^{13}$C NMR (75 MHz, CDCl$_3$) δ 17.0, 36.8, 38.6, 41.8, 55.1, 58.8, 61.8, 71.0, 110.1, 110.3, 120.2, 124.2, 128.4, 128.6, 129.1, 129.2, 132.4, 139.8, 150.6, 157.2, 167.1, 169.0. MS [M+H]$^+$ 444. HRMS: calcd for C$_{24}$H$_{27}$NO$_5$Cl, [M+H]$^+$ 444.1578, found 444.1585.

Example 65a o-methoxybenzyl 4-(4-chlorophenyl)-6-methyl-2-oxo-3,4-dihydro-1H-pyridine-5-carboxylate (Intermediate)

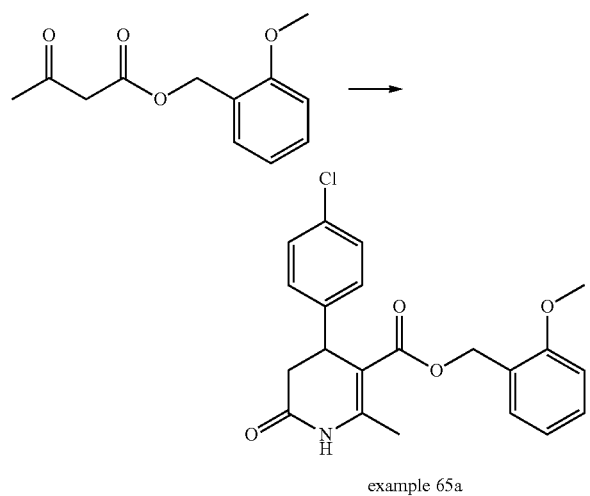

example 65a

The (2-methoxyphenyl)methyl 3-oxobutanoate (1334 mg, 6.0 mmol) was dissolved in acetic acid (6 mL). p-chlorobenzaldehyde (843 mg, 6.0 mmol), meldrum acid (865 mg, 6.0 mmol) and ammonium acetate (676 mg, 9.0 mmol) were added and the reaction mixture was stirred at 110° C. for 18 h. The reaction mixture was cooled to RT. The solvent was removed under reduced pressure. The crude was precipitated in EtOH, cooled to 0° C. and filtered to give the desired o-methoxybenzyl 4-(4-chlorophenyl)-6-methyl-2-oxo-3,4-dihydro-1H-pyridine-5-carboxylate as a white powder (1.041 g, 45%). $^1$H NMR (300 MHz, CDCl$_3$) ☐ 2.42 (s, 3H), 2.64 (d, J=16.5 Hz, 1H), 2.94 (dd, J=16.5, 8.1 Hz, 1H), 3.75 (s, 3H), 4.26 (d, J=8.1 Hz, 1H), 5.10 (d, J=12.7 Hz, 1H), 5.21 (d, J=12.7 Hz, 1H), 6.80-6.90 (m, 2H), 7.03 (d, J=7.5 Hz, 1H), 7.08 (d, J=8.5 Hz, 2H), 7.22 (d, J=8.5 Hz, 2H), 7.28 (td, J=8.1, 2.1 Hz, 1H), 8.47 (s, 1H). $^{13}$C NMR (75 MHz, CDCl$_3$) ☐☐☐☐☐☐☐☐☐☐☐☐☐☐☐☐☐☐☐☐☐☐☐☐☐☐☐☐☐☐☐☐☐. 106.8, 110.2, 120.3, 124.2, 128.2, 128.8, 129.4, 129.4, 132.6, 140.7, 146.7, 157.4, 166.5, 170.9

Example 65: (2-methoxyphenyl)methyl 4-(4-chlorophenyl)-1-(2-hydroxyethyl)-6-methyl-2-oxo-3,4-dihydropyridine-5-carboxylate o-methoxybenzyl 4-(4-chlorophenyl)-6-methyl-2-oxo-3,4-dihydro-1H-pyridine-5-carboxylate (example 65a, 96 mg, 0.25 mmol) was dissolved in anhydrous DMF (1 mL). Cesium carbonate (162 mg, 0.50 mmol) and 2-bromoethanol (35 μL, 0.50 mmol) were added. The reaction mixture was stirred at 60° C. for 24 h. The reaction was uncomplete. Cesium carbonate (324 mg, 1.00 mmol) and 2-bromoethanol (70 μL, 1.00 mmol) were added 4 times more every 24 h. The DMF was removed under reduced pressure. The residue was diluted in water.

The aqueous phase was extracted by EtOAc and the combined organic layers were washed with brine and dried over MgSO$_4$. The solvent was removed under reduced pressure. Purification of the crude by flash chromatography using a mixture of Cyclohexane/EtOAc (4/6) as eluent gave the desired (2-methoxyphenyl) methyl 4-(4-chlorophenyl)-1-(2-hydroxyethyl)-6-methyl-2-oxo-3,4-dihydropyridine-5-carboxylate as a colorless oil (9 mg, 8%). $^1$H NMR (300 MHz, CDCl$_3$) δ 1.88 (brs, 1H), 2.58 (s, 3H), 2.78 (dd, J=16.0, 2.4 Hz, 1H), 2.95 (dd, J=16.0, 7.5 Hz, 1H), 3.74 (s, 3H), 3.74-3.85 (m, 3H), 4.02-4.13 (m, 1H), 4.24 (d, J=7.0 Hz, 1H), 5.12 (d, J=12.8 Hz, 1H), 5.23 (d, J=12.8 Hz, 1H), 6.84-6.90 (m, 2H), 6.99-7.07 (m, 1H), 7.10 (d, J=8.3 Hz, 2H), 7.21 (d, J=8.3 Hz, 2H), 7.25-7.32 (m, 1H). MS [M+H]$^+$ 430. HRMS: calcd for C$_{23}$H$_{25}$NO$_5$Cl, [M+H]$^+$ 430.1421, found 430.1425.

Example 66: 2-benzyl 4-(4-chlorophenyl)-1-(2-furylmethyl)-6-methyl-2-oxo-3,4-dihydropyridine-5-carboxylate o-methoxybenzyl 4-(4-chlorophenyl)-6-methyl-2-oxo-3,4-dihydro-1H-pyridine-5-carboxylate (example 65a, 96 mg, 0.25 mmol) was dissolved in anhydrous DMF (1 mL). Cesium carbonate (162 mg, 0.50 mmol) and 2-chloromethylfuran (145 mg, 0.50 mmol) were added. The reaction mixture was stirred at 60° C. for 18 h. The DMF was removed under reduced pressure. The residue was diluted in water. The aqueous phase was extracted by EtOAc and the combined organic layers were washed with brine and dried over MgSO$_4$. The solvent was removed under reduced pressure. Purification of the crude by flash chromatography using a mixture of Cyclohexane/EtOAc (9/1) as eluent gave the desired 2-benzyl 4-(4-chlorophenyl)-1-(2-furylmethyl)-6-methyl-2-oxo-3,4-dihydropyridine-5-carboxylate=as a yellow oil (43 mg, 50%). $^1$H NMR (300 MHz, CDCl$_3$) δ 2.70 (s, 3H), 2.74 (dd, J=16.1, 2.1 Hz, 1H), 2.94 (dd, J=16.1, 7.3 Hz, 1H), 3.73 (s, 3H), 4.18 (d, J=7.3 Hz, 1H), 4.66 (d, J=15.8 Hz, 1H), 5.11 (d, J=12.8 Hz, 1H), 5.20 (d, J=12.8 Hz, 1H), 5.28 (d, J=15.8 Hz, 1H), 6.20 (d, J=3.2 Hz, 1H), 6.34 (dd, J=3.2, 1.8 Hz, 1H), 6.80-6.88 (m, 2H), 7.00 (dd, J=7.4, 1.3 Hz, 1H), 7.09 (d, J=8.5 Hz, 2H), 7.24-7.32 (m, 1H), 7.33-7.36 (m, 1H). $^{13}$C NMR (75 MHz, CDCl$_3$) δ 16.9, 36.8, 37.9, 38.4, 55.2, 61.9, 108.9, 110.2, 110.5, 111.5, 120.2, 124.1, 128.3, 128.6, 129.3, 129.4, 132.4, 139.5, 142.0, 149.2, 150.3, 157.3, 166.9, 168.7. MS [M+H]$^+$ 466. HRMS: calcd for C$_{26}$H$_{25}$NO$_5$Cl, [M+H]$^+$ 466.1421, found 466.1433.

Example 67: (4S)-4-(4-chlorophenyl)-6-methyl-2-oxo-1-[[(2R)-tetrahydrofuran-2-yl]methyl]-3,4-dihydropyridine-5-carboxylate (racemic)

The o-methoxybenzyl 4-(4-chlorophenyl)-6-methyl-2-oxo-3,4-dihydro-1H-pyridine-5-carboxylate (example 65a, 96 mg, 0.25 mmol) was dissolved in anhydrous DMF (1 mL). Cesium carbonate (162 mg, 0.50 mmol) and tetrahydrofurfuryl bromide (57 μL, 0.50 mmol) were added. The reaction mixture was stirred at 60° C. for 18 h. Cesium carbonate (162 mg, 0.50 mmol) and tetrahydrofurfuryl bromide (57 μL, 0.50 mmol) were added 3 times more every 12 h. Overall, the reaction mixture was stirred at 60° C. for 66 h. The DMF was removed under reduced pressure. The residue was diluted in water. The aqueous phase was extracted with EtOAc and the combined organic layers were washed with brine and dried over MgSO$_4$. The solvent was removed under reduced pressure. Purification of the crude by flash chromatography using a mixture of Cyclohexane/EtOAc (9/1) as eluent gave the desired (2-methoxyphenyl) methyl (4S)-4-(4-chlorophenyl)-6-methyl-2-oxo-1-[[(2R)-tetrahydrofuran-2-yl]methyl]-3,4-dihydropyridine-5-carboxylate as a colorless oil (25 mg, 21%) $^1$H NMR (300 MHz, CDCl$_3$) δ 1.41-1.53 (m, 1H), 1.78-1.99 (m, 3H), 2.63 (s, 3H), 2.92 (dd, J=15.7, 2.4 Hz, 1H), 2.92 (dd, J=15.7, 7.3 Hz, 1H), 3.41 (dd, J=14.4, 8.6 Hz, 1H), 3.73 (s, 3H), 3.63-3.95 (m, 3H), 4.21 (d, J=7.3 Hz, 1H), 4.26 (dd, J=14.4, 3.7 Hz, 1H), 5.10 (d, J=13.2 Hz, 1H), 5.20 (d, J=13.2 Hz, 1H), 6.79-6.87 (m, 2H), 6.97 (dd, J=7.7, 1.7 Hz, 1H), 7.15-7.30 (m, 5H). $^{13}$C NMR (75 MHz, CDCl$_3$) δ 17.1, 25.5, 29.2, 37.0, 39.0, 45.6, 55.2, 61.8, 68.1, 77.9, 110.2, 110.5, 120.2, 124.4, 128.6, 128.7, 129.0, 129.2, 132.5, 139.6, 150.9, 157.2, 167.1, 169.0. MS [M+H]$^-$ 470 HRMS: calcd for C$_{26}$H$_{29}$NO$_5$Cl, [M+H]$^+$ 470.1734, found 470.1714.

Example 68: (4S)-4-(4-chlorophenyl)-6-methyl-2-oxo-1-[[(2S)-tetrahydrofuran-2-yl]methyl]-3,4-dihydropyridine-5-carboxylate (racemic)

The o-methoxybenzyl 4-(4-chlorophenyl)-6-methyl-2-oxo-3,4-dihydro-1H-pyridine-5-carboxylate (example 65a, 96 mg, 0.25 mmol) was dissolved in anhydrous DMF (1 mL). Cesium carbonate (162 mg, 0.50 mmol) and tetrahydrofurfuryl bromide (57 μL, 0.50 mmol) were added. The reaction mixture was stirred at 60° C. for 18 h. Cesium carbonate (162 mg, 0.50 mmol) and tetrahydrofurfuryl bromide (57 μL, 0.50 mmol) were added 3 times more every 12 h. Overall, the reaction mixture was stirred at 60° C. for 66 h. The DMF was removed under reduced pressure. The residue was diluted in water. The aqueous phase was extracted by EtOAc and the combined organic layers were washed with brine and dried over MgSO$_4$. The solvent was removed under reduced pressure. Purification of the crude by flash chromatography using a mixture of Cyclohexane/EtOAc (9/1) as eluent gave the (4S)-4-(4-chlorophenyl)-6-methyl-2-oxo-1-[[(2S)-tetrahydrofuran-2-yl]methyl]-3,4-dihydropyridine-5-carboxylate as a colorless oil (21 mg, 18%). $^1$H NMR (300 MHz, CDCl$_3$) δ 1.25-1.37 (m, 1H), 1.74-1.94 (m, 3H), 2.62 (s, 3H), 2.79 (dd, J=15.9, 2.4 Hz, 1H), 2.94 (dd, J=15.9, 7.4 Hz, 1H), 3.75 (s, 3H), 3.65-3.84 (m, 3H), 3.89-4.06 (m, 2H), 4.23 (dd, J=7.4, 2.4 Hz, 1H), 5.11 (d, J=12.6 Hz, 1H), 5.23 (d, J=12.6 Hz, 1H), 6.82-6.89 (m, 2H), 7.05 (dd, J=7.6, 1.5 Hz, 1H), 7.10 (d, J=8.6 Hz, 2H), 7.19 (d, J=8.6 Hz, 2H), 7.24-7.32 (m, 1H). $^{13}$C NMR (75 MHz, CDC$_3$) δ 17.4, 25.3, 28.9, 36.3, 38.2, 45.1, 55.2, 61.8, 67.7, 77.5, 110.2, 110.7, 120.2, 124.2, 128.5, 129.3, 132.4, 139.8, 150.3, 157.3, 167.1, 169.5. MS [M+H]$^+$ 470; HRMS: calcd for C$_{26}$H$_{29}$NO$_5$Cl, [M+H]$^+$ 470.1734, found 470.1746.

Example 69: (2-methoxyphenyl)methyl 4-(4-chlorophenyl)-1-(2-ethoxy-2-oxo-ethyl)-6-methyl-2-oxo-3,4-dihydropyridine-5-carboxylate o-methoxybenzyl 4-(4-chlorophenyl)-6-methyl-2-oxo-3,4-dihydro-1H-pyridine-5-carboxylate (example 65a, 75 mg, 0.19 mmol) was dissolved in anhydrous DMF (0.3M). Cesium carbonate (114 mg, 0.35 mmol) and Methylbromoacetate (33 μL, 0.35 mmol) were added. The reaction mixture was stirred at RT for 2 hours. The DMF was removed under reduced pressure. The residue was diluted in water. The aqueous phase was extracted by EtOAc and the combined organic layers were washed with brine and dried over Na$_2$SO$_4$. The solvent was removed under reduced pressure. EtOH was added and was removed under reduced pressure (transesterification). Purification of the crude by flash chromatography using a DCM as eluent gave the desired compound as a colorless oil. $^1$H NMR (300 MHz, CDCl$_3$) δ 1.29 (t, J=7.1 Hz, 3H), 2.49 (s, 3H), 2.77 (dd, J=15.9, 2.1 Hz, 1H), 3.00 (dd, J=15.9, 7.9 Hz, 1H), 3.74 (s, 3H), 4.22 (q, J=7.1 Hz, 2H), 4.22-4.28 (m, 1H), 4.43 (d, J=17.9 Hz, 1H), 4.61 (d, J=17.9 Hz, 1H), 5.10 (d, J=12.8 Hz, 1H), 5.21 (d, J=12.8 Hz, 1H), 6.81-6.89 (m, 2H), 7.02 (dd, J=7.2, 1.4 Hz, 1H), 7.16 (d, J=8.8 Hz, 2H), 7.21 (d, J=8.8 Hz, 2H), 7.28 (td, J=8.1, 2.1 Hz, 1H). MS [M−H]$^-$ 472; HRMS: calcd for C$_{31}$H$_{22}$NO$_4$, [M+H]$^+$ 472.1549, found 472.1545.

Example 70: o-methoxybenzyl 4-(4-chlorophenyl)-1-(cyclopropylmethyl)-6-methyl-2-oxo-3,4-dihydropyridine-5-carboxylate The o-methoxybenzyl 4-(4-chlorophenyl)-6-methyl-2-oxo-3,4-dihydro-1H-pyridine-5-carboxylate (example 65a, 96 mg, 0.25 mmol) was dissolved in anhydrous DMF (1 mL). Cesium carbonate (162 mg, 0.50 mmol) and (bromomethyl)cyclopropane (48 μL, 0.50 mmol) were added. The reaction mixture was stirred at 60° C. for 18 h. The DMF was removed under reduced pressure. The residue was diluted in water. The aqueous phase was extracted by EtOAc and the combined organic layers were washed with brine and dried over MgSO$_4$. The solvent was removed under reduced pressure. Purification of the crude by flash chromatography using a mixture of Cyclohexane/EtOAc (9/1) as eluent gave the desired o-methoxybenzyl 4-(4-chlorophenyl)-1-(cyclopropyl methyl)-6-methyl-2-oxo-3,4-dihydropyridine-5-carboxylate as a yellow oil (77 mg, 71%). $^1$H NMR (300 MHz, CDC$_3$) δ 0.22-0.36 (m, 2H), 0.36-0.46 (m, 1H), 0.46-0.56 (m, 1H), 0.86-1.04 (m, 1H), 2.61 (s, 3H), 2.73 (dd, J=15.8, 2.4 Hz, 1H), 2.91 (dd, J=15.8, 7.3 Hz, 1H), 3.50 (dd, J=14.6, 5.8 Hz, 1H), 3.74 (s, 3H), 3.90 (dd, J=14.6, 7.9 Hz, 1H), 4.22 (d, J=7.3 Hz, 1H), 5.12 (d, J=12.8 Hz, 1H), 5.23 (d, J=12.8 Hz, 1H), 6.82-6.89 (m, 2H), 7.04 (dd, J=7.4, 1.1 Hz, 1H), 7.12 (d, J=7.6 Hz, 2H), 7.20 (d, J=7.6 Hz, 2H), 7.28 (td, J=7.7, 1.8 Hz, 1H). $^{13}$C NMR (75 MHz, CDCl$_3$) δ 4.0, 4.1, 11.0, 16.9, 36.6, 38.5, 45.5, 55.14, 61.8, 110.2, 111.4, 120.2, 124.2, 128.4, 128.5, 129.2, 129.3, 132.4 139.7, 132.4, 139.7, 149.5, 157.3, 166.9, 169.0. MS [M+H]⁺ 440. HRMS: calcd for $C_{25}H_{27}NO_4Cl$, [M+H]⁺ 440.1629, found 440.1618.

Example 71: (2-methoxyphenyl)methyl 4-(4-chlorophenyl)-1-(3-methoxypropyl)-6-methyl-2-oxo-3,4-dihydropyridine-5-carboxylate The (2-methoxyphenyl)methyl 4-(4-chlorophenyl)-6-methyl-2-oxo-3,4-dihydro-1H-pyridine-5-carboxylate (115 mg, 0.30 mmol) was dissolved in anhydrous DMF (1 mL). Cesium carbonate (195 mg, 0.60 mmol) and 1-bromo-3-methoxypropane (68 μL, 0.60 mmol) were added. The reaction mixture was stirred at 60° C. for 18 h. The DMF was removed under reduced pressure. The residue was diluted in water and extracted by EtOAc. The organic layers were assembled, washed by brine and dried on MgSO₄. The solvent was removed under reduced pressure. The crude product was purified by flash chromatography using a mixture of Cyclohexane/EtOAc (9/1) as eluent to give the desired (2-methoxyphenyl)methyl 4-(4-chlorophenyl)-1-(3-methoxypropyl)-6-methyl-2-oxo-3,4-ihydropyridine-5-carboxylate as a colorless oil (96 mg, 70%). ¹H NMR (300 MHz, CDCl₃) δ 1.62-1.84 (m, 2H), 2.57 (s, 3H), 2.76 (dd, J=15.9, 2.4 Hz, 1H), 2.89 (dd, J=15.9, 7.5 Hz, 1H), 3.18-3.35 (m, 2H), 3.28 (s, 3H), 3.64 (ddd, J=14.6, 8.9, 6.0 Hz, 1H), 3.74 (s, 3H), 3.99 (ddd, J=14.6, 8.7, 6.5 Hz, 1H), 4.22 (td, J=7.5, 2.4 Hz, 1H), 5.12 (d, J=12.7 Hz, 1H), 5.23 (d, J=12.7 Hz, 1H), 6.82-6.89 (m, 2H), 7.02-7.08 (m, 3H), 7.20 (d, J=8.5 Hz, 2H), 7.28 (td, J=7.8, 1.7 Hz, 1H). ¹³C NMR (75 MHz, CDCl₃) δ 16.6, 29.3, 36.3, 38.2, 39.5, 55.2, 58.6, 61.9, 69.8, 110.2, 111.0, 120.2, 124.1, 128.2, 128.6, 129.3, 129.4, 132.5, 139.6, 149.5, 157.3, 167.0, 169.0. MS [M+H]⁺ 458; HRMS: calcd for $C_{25}H_{29}NO_5Cl$, [M+H]⁺ 458.1734, found 458.1744.

Example 72: (2-methoxyphenyl)methyl 4-(4-chlorophenyl)-1-(1,3-dioxolan-2-ylmethyl)-6-methyl-2-oxo-3,4-dihydropyridine-5-carboxylate The (2-methoxyphenyl)methyl 4-(4-chlorophenyl)-6-methyl-2-oxo-3,4-dihydro-1H-pyridine-5-carboxylate (115 mg, 0.30 mmol) was dissolved in anhydrous DMF (1 mL). Cesium carbonate (195 mg, 0.60 mmol) and 2-Bromomethyl-1,3-dioxolane (62 μL, 0.60 mmol) were added. The reaction mixture was stirred at 60° C. for 18 h. The DMF was removed under reduced pressure. The residue was diluted in water and extracted by EtOAc. The organic layers were assembled, washed by brine and dried on MgSO₄. The solvent was removed under reduced pressure. The crude product was purified by flash chromatography using a mixture of Cyclohexane/EtOAc (8/2) as eluent to give the desired (2-methoxyphenyl)methyl 4-(4-chlorophenyl)-1-(1,3-dioxolan-2-ylmethyl)-6-methyl-2-oxo-3,4-dihydropyridine-5-carboxylate as a colorless oil (73 mg, 52%). ¹H NMR (300 MHz, CDCl₃) δ 2.61 (s, 3H), 2.76 (dd, J=15.9, 2.2 Hz, 1H), 2.93 (dd, J=15.9, 7.4 Hz, 1H), 3.64 (dd, J=14.6, 5.4 Hz, 1H), 3.83 (s, 3H), 3.78-3.94 (m, 4H), 4.23 (dd, J=7.4, 2.2 Hz, 1H), 4.34 (dd, J=14.6, 3.1 Hz, 1H), 4.86 (dd, J=5.4, 3.1 Hz, 1H), 5.11 (d, J=12.9 Hz, 1H), 5.23 (d, J=12.9 Hz, 1H), 6.81-6.87 (m, 2H), 7.01 (dd, J=7.4, 1.5 Hz, 1H), 7.13 (d, J=8.6 Hz, 2H), 7.19 (d, J=8.6 Hz, 2H), 7.27 (td, J=7.9, 1.9 Hz, 1H). ¹³C NMR (75 MHz, CDCl₃) δ 17.1, 36.6, 38.4, 43.6, 55.1, 61.8, 64.9, 101.3, 110.1, 110.8, 120.2, 124.2, 128.5, 128.5, 129.1, 129.3, 132.4, 139.5, 150.0, 157.5, 167.0, 169.2. MS [M+H]⁺ 472. HRMS: calcd for $C_{25}H_{27}NO_6Cl$, [M+H]⁺ 472.1527, found 472.1533.

Example 73: (2-methoxyphenyl)methyl 4-(4-chlorophenyl)-1-(2-methoxy-2-oxo-ethyl)-6-methyl-2-oxo-3,4-d ihydropyridine-5-carboxylate (2-methoxyphenyl)methyl 4-(4-chlorophenyl)-6-methyl-2-oxo-3,4-dihydro-1H-pyridine-5-carboxylate (116 mg, 0.30 mmol) was dissolved in anh. DMF (1 mL). 2-bromomethylacetate (41 μL, 0.45 mmol) and Cs₂CO₃ were added. The reaction mixture was stirred at RT for 18 h. 2-bromomethylacetate (28 μL, 0.30 mmol) was added again and the reaction mixture was stirred at 50° C. during 6 h. The solvent was removed under reduced pressure. Water was added and the aqueous phase was extracted by Et₂O, washed with brine and dried over Na₂SO₄. Removal of the solvent afforded the desired (2-methoxyphenyl)methyl 4-(4-chlorophenyl)-1-(2-methoxy-2-oxo-ethyl)-6-methyl-2-oxo-3,4-dihydropyridine-5-carboxylate as a colorless oil (120 mg, 87%). ¹H NMR (300 MHz, CDCl₃) δ 2.48 (s, 3H), 2.78 (dd, J=16.0, 2.3 Hz, 1H), 3.00 (dd, J=16.0, 7.8 Hz, 1H), 3.74-3.74 (s, 3H), 3.76 (s, 3H), 4.25 (d, J=7.8 Hz, 1H), 4.45 (d, J=17.8 Hz, 1H), 4.62 (d, J=17.8 Hz, 1H), 5.10 (d, J=12.5 Hz, 1H), 5.20 (d, J=12.5 Hz, 1H), 6.86 (m, 2H), 7.02 (dd, J=7.5, 1.5 Hz, 1H), 7.15 (d, J=8.8 Hz, 2H), 7.21 (d, J=8.8 Hz, 2H), 7.25-7.30 (m, 2H). ¹³C NMR (75 MHz, CDCl₃) δ 16.7, 36.8, 38.0, 43.4, 52.5, 55.2, 62.0, 110.2, 110.9, 120.3, 124.1, 128.7, 129.5, 129.5, 132.6, 139.8, 148.2, 166.8, 169.1, 169.2. MS [M+H]⁺ 458, HRMS: calcd for C24H25NO6Cl, [M+H]⁺ 458.1370, found 458.1378.

TABLE 7

| Example | R15 |
|---|---|
| 75 | benzylamide (–C(=O)NH-CH₂-Ph) |
| 76 | phenylamide (–C(=O)NH-Ph) |
| 77 | 1,2,3,4-tetrahydroquinolin-1-yl carbonyl |

Example 74: 4-(4-chlorophenyl)-1-(2-methoxyethyl)-6-methyl-2-oxo-3,4-dihydropyridine-5-carboxylic acid (Intermediate Product)

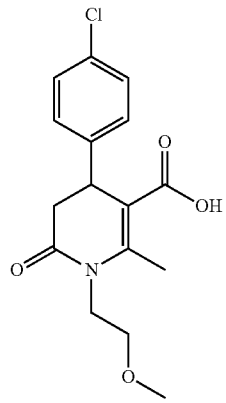 [SMILES: COCCN1C(=O)CC(c2ccc(Cl)cc2)C(C(=O)O)=C1C]

The methyl 4-(4-chlorophenyl)-1-(2-methoxyethyl)-6-methyl-2-oxo-3,4-dihydropyridine-5-carboxylate (4.55 g, 13.5 mmol) was dissolved in methanol (47 mL). An aqueous solution of NaOH 1M (47 mL) was added. The reaction mixture was stirred at 50° C. for 18 h. The reaction mixture was washed with diethyl ether. The aqueous phase was acidified to pH=1 with a concentrated solution of hydrochloric acid and then extracted with EtOAc. The organic phases were assembled, washed with brine and dried over MgSO$_4$. The solvent was removed under reduced pressure. Precipitation of the crude in diethyl ether gave the desired 4-(4-chlorophenyl)-1-(2-methoxyethyl)-6-methyl-2-oxo-3,4-dihydropyridine-5-carboxylic acid as a white powder (2.82 g, 65%). $^1$H NMR (300 MHz, CDCl$_3$) δ 2.62 (s, 3H), 2.75 (dd, J=15.7, 2.1 Hz, 1H), 2.91 (dd, J=15.7, 7.1 Hz, 1H), 3.09 (s, 3H), 3.30-3.38 (m, 1H), 3.46 (dt, J=9.9, 4.0 Hz, 1H), 3.76 (ddd, J=14.7, 8.9, 3.8 Hz, 1H), 4.13-4.23 (m, 2H), 7.13 (d, J=8.5 Hz, 2H), 7.23 (d, J=8.5 Hz, 2H). $^{13}$C NMR (300 MHz, CDCl$_3$) δ 17.4, 36.5, 38.7, 42.0, 58.8, 71.0, 109.1, 128.3, 128.8, 132.7, 139.3, 153.6, 169.1, 172.7. MS [M−H]$^−$ 322.

Example 75: N-benzyl-4-(4-chlorophenyl)-1-(2-methoxyethyl)-6-methyl-2-oxo-3,4-dihydropyridine-5-carboxamide 4-(4-chlorophenyl)-1-(2-methoxyethyl)-6-methyl-2-oxo-3,4-dihydropyridine-5-carboxylic acid (example 74, 323 mg, 1.0 mmol), benzylamine (262 µL, 2.4 mmol), DIEA (860 µL, 5.0 mmol) and a 50% solution of T3P in ethyl acetate (883 µL, 3.0 mmol) were dissolved in anhydrous EtOAc (3 mL). After stirring the reaction mixture at RT for 24 h, the reaction was uncomplete. Benzylamine (131 µL, 1.2 mmol), DIEA (430 µL, 2.5 mmol) and a 50% solution of T3P in ethyl acetate (441 µL, 1.5 mmol) were added. The reaction mixture was stirred at r.t. for 6 h. 1 M hydrochloric acid aqueous solution (20 mL) was added and the aqueous phase was extracted by EtOAc. The organic phases were combined, washed with brine and dried over MgSO$_4$. The solvent was removed under reduced pressure. Purification of the crude by flash chromatography on silica using a mixture of DCM/MeOH 9/1 gave the desired (2-methoxyphenyl) methyl 1-(2-methoxyethyl)-6-methyl-2-oxo-4-propyl-3,4-dihydropyridine-5-carboxylate as a white powder (267 mg, 65%). $^1$H NMR (300 MHz, CDCl$_3$) δ 2.34 (s, 3H), 2.67 (dd, J=15.8, 2.6 Hz, 1H), 3.01 (dd, J=15.8, 7.6 Hz, 1H), 3.35 (s, 3H), 3.43-3.52 (m, 2H), 3.66 (ddd, J=14.5, 7.9, 4.7 Hz, 1H), 3.87 (dd, J=7.6, 2.6 Hz, 1H), 4.14 (dt, J=14.5, 4.7 Hz, 1H), 4.33 (dd, J=14.9, 5.4 Hz, 1H), 4.49 (dd, J=14.9, 5.4 Hz, 1H), 5.55 (t, J=5.4 Hz, 1H), 7.05-7.13 (m, 2H), 7.17 (d, J=8.4 Hz, 1H), 7.25 (d, J=8.4 Hz, 1H), 7.27-7.35 (m, 3H). MS [M+H]$^+$ 413. HRMS: calcd for C$_{23}$H$_{26}$N$_2$O$_3$Cl, [M+H]$^+$ 413.1632, found 413.1641.

Example 76: 4-(4-chlorophenyl)-1-(2-methoxyethyl)-6-methyl-2-oxo-N-phenyl-3,4-dihydropyridine-5-carboxamide 4-(4-chlorophenyl)-1-(2-methoxyethyl)-6-methyl-2-oxo-3,4-dihydropyridine-5-carboxylic acid (example 74, 97 mg, 0.30 mmol), aniline (31 µL, 0.33 mmol), EDCI (69 mg, 0.36 mmol) and DMAP (36 mg, 0.30 mmol) were dissolved in anh. DCM (2 mL). The reaction mixture was stirred for 18 h at RT. An aqueous solution of hydrochloric acid 1 M was added. The aqueous phase was extracted with DCM. The organic phases were assembled and dried over MgSO$_4$. The solvent was removed under reduced pressure. Purification of the crude by flash chromatography on silica using a mixture of Cyclohexane/EtOAc 7/3 gave the desired 4-(4-chlorophenyl)-1-(2-methoxyethyl)-6-methyl-2-oxo-N-phenyl-3,4-dihydropyridine-5-carboxamide as a white powder (62 mg, 52%). $^1$H NMR (300 MHz, CDCl$_3$) δ 2.42 (s, 3H), 2.69 (dd, J=15.8, 2.3 Hz, 1H), 3.03 (dd, J=15.8, 7.6 Hz, 1H), 3.38 (s, 3H), 3.45-3.55 (m, 2H), 3.70 (ddd, J=14.5, 8.2, 4.5 Hz, 1H), 3.93 (dd, J=7.6, 2.3 Hz, 1H), 4.19 (dt, J=14.6, 3.5 Hz, 1H), 6.99-7.15 (m, 2H), 7.20-7.38 (m, 7H). $^{13}$C NMR (75 MHz, CDCl$_3$) δ 16.8, 38.6, 39.2, 41.7, 58.9, 71.2, 114.2, 119.8, 124.4, 128.6, 128.9, 129.5, 133.6, 137.5, 138.7, 143.1, 167.1, 168.2. MS [M+H]$^+$ 399. HRMS: calcd for C$_{22}$H$_{24}$N$_2$O$_3$Cl, [M+H]$^+$ 399.1475, found 399.1498.

Example 77: 4-(4-chlorophenyl)-5-(3,4-dihydro-2H-quinoline-1-carbonyl)-1-(2-methoxyethyl)-6-methyl-3,4-dihydropyridin-2-one 4-(4-chlorophenyl)-1-(2-methoxyethyl)-6-methyl-2-oxo-3,4-dihydropyridine-5-carboxylic acid (example 74, 97 mg, 0.30 mmol), tetrahydroquinoline (44 µL, 0.33 mmol), EDCI (69 mg, 0.36 mmol) and DMAP (36 mg, 0.30 mmol) were dissolved in anh. DCM (2 mL). The reaction mixture was stirred for 72 h at RT.

The reaction was uncomplete; tetrahydroquinoline (44 µL, 0.33 mmol) and EDCI (69 mg, 0.36 mmol) were added. The reaction mixture was stirred for 24 h at RT. An aqueous solution of hydrochloric acid 1 M was added. The aqueous phase was extracted with DCM. The organic phases were assembled and dried over MgSO$_4$. The solvent was removed under reduced pressure. Purification of the crude by flash chromatography on silica using a mixture of Cyclohexane/EtOAc 6/4 gave the desired 4-(4-chlorophenyl)-5-(3,4-dihydro-2H-quinoline-1-carbonyl)-1-(2-methoxyethyl)-6-methyl-3,4-dihydropyridin-2-one as a colorless oil (62 mg, 52%). MS [M+H]$^+$ 439. HRMS: calcd for C$_{25}$H$_{28}$N$_2$O$_3$Cl, [M+H]$^+$ 439.1788, found 439.1767.

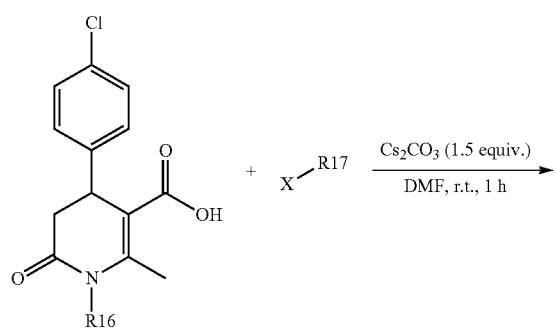

TABLE 8

| Example | R16 | R17 |
|---|---|---|
| 79 | CH₃ | 4-Me-Bn |
| 80 | CH₃ | 4-CF₃-Bn |
| 81 | CH₃ | 2-Cl,4-F-Bn |
| 82 | CH₃ | 2,6-diF-Bn |
| 83 | CH₃ | 3,4-diOMe-Bn |
| 84 | -CH₂CH₂OCH₃ | 2-F-Bn |
| 85 | -CH₂CH₂OCH₃ | 3-F-Bn |
| 86 | -CH₂CH₂OCH₃ | 4-F-Bn |
| 87 | -CH₂CH₂OCH₃ | 2-Cl-Bn |

TABLE 8-continued

| Example | R16 | R17 |
|---|---|---|
| 88 | -CH₂CH₂OCH₃ | 3-Cl-Bn |
| 89 | -CH₂CH₂OCH₃ | 4-Cl-Bn |
| 90 | -CH₂CH₂OCH₃ | 2-CF₃-Bn |
| 91 | -CH₂CH₂OCH₃ | 3-CF₃-Bn |
| 92 | -CH₂CH₂OCH₃ | 4-CF₃-Bn |
| 93 | -CH₂CH₂OCH₃ | 2-CN-Bn |
| 94 | -CH₂CH₂OCH₃ | 3-CN-Bn |
| 95 | -CH₂CH₂OCH₃ | 4-CN-Bn |
| 96 | -CH₂CH₂OCH₃ | 3-COOMe-Bn |
| 97 | -CH₂CH₂OCH₃ | 4-COOMe-Bn |
| 98 | -CH₂CH₂OCH₃ | 2-Me-Bn |
| 99 | -CH₂CH₂OCH₃ | 3-Me-Bn |

TABLE 8-continued

[Structure: 4-(4-chlorophenyl)-2-oxo-6-methyl-1,2,3,4-tetrahydropyridine-5-carboxylate with R16 on N and OR17 ester]

| Example | R16 | R17 |
|---|---|---|
| 100 | -CH2CH2-O-Me | 4-Me-Bn |
| 101 | -CH2CH2-O-Me | 2,4,6-triMe-Bn |
| 103 | -CH2CH2-O-Me | 3-OMe-Bn |
| 104 | -CH2CH2-O-Me | 4-OMe-Bn |
| 105 | -CH2CH2-O-Me | 2-OCF3 |
| 106 | -CH2CH2-O-Me | 2-naphthylmethyl |
| 107 | -CH2CH2-O-Me | 4-pyridylmethyl |
| 108 | -CH2CH2-O-Me | 4-biphenylmethyl |
| 109 | -CH2CH2-O-Me | diphenylmethyl |
| 110 | -CH2CH2-O-Me | phenethyl |
| 111 | -CH2CH2-O-Me | 3-phenylpropyl |
| 112 | -CH2CH2-O-Me | phenacyl (PhC(O)CH2-) |
| 113 | -CH2CH2-O-Me | cyclohexylmethyl |
| 116 | -CH2CH2-O-Me | 4-(3-dimethylaminopropoxy)benzyl |
| 117 | -CH2CH2-O-Me | 4-(3-trimethylammoniopropoxy)benzyl I− |
| 119 | -CH2CH2-O-Me | 4-(2-methoxyethoxy)benzyl |

Example 78: 4-(4-chlorophenyl)-1,6-dimethyl-2-oxo-3,4-dihydropyridine-5-carboxylic acid (Intermediate Product)

[Reaction scheme: methyl 4-(4-chlorophenyl)-6-methyl-2-oxo-1,2,3,4-tetrahydropyridine-5-carboxylate + MeI (1.5 equiv.), Cs2CO3 (1.5 equiv.), DMF, 60° C., 1 h →]

181

-continued

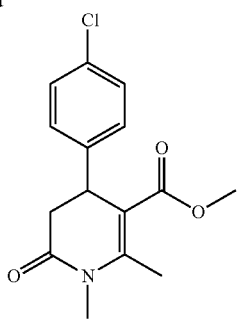

Step 1.

The dihydropyridone intermediate obtained following general procedure A (1.05 g, 3.75 mmol) was dissolved in anhydrous DMF (12.5 mL). Cesium carbonate (1.83 g, 5.63 mmol) and iodomethane (350 μL, 5.63 mmol) were added. The reaction mixture was stirred at 60° C. for 1 h. The DMF was removed under reduced pressure. The residue was diluted in water and extracted by EtOAc. The organic layers were assembled, washed by brine and dried on $MgSO_4$. Removal of the solvents under reduced pressure gave the desired compound as a yellow oil (1.10 g, quantitative). MS $[M+H]^+$ 294.

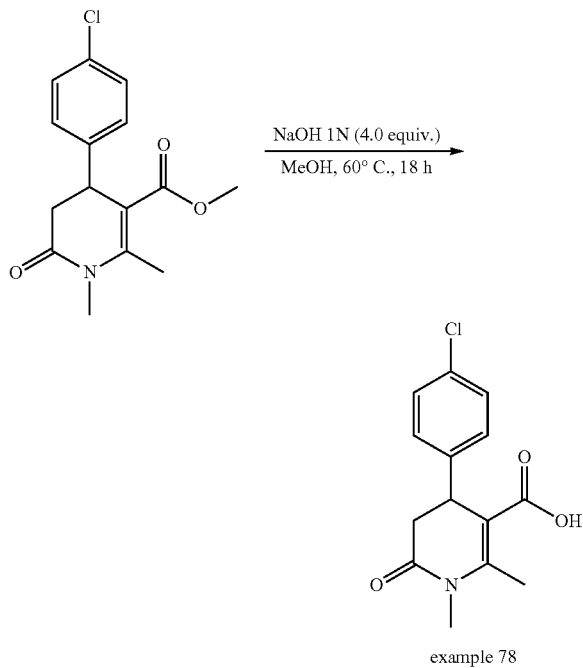

example 78

Step 2.

The intermediate obtained in step 1 (1.10 mg, 3.75 mmol) was dissolved in MeOH (15 mL) and an aqueous solution of NaOH 1 N (13 mL, 13.1 mmol) was added. The reaction mixture was stirred at 60° C. for 18 h. The reaction mixture was cooled to r.t. and extracted once with diethyl ether. The aqueous phase was then acidified until pH=1 with an aqueous solution of hydrochloric acid. The aqueous phase was extracted by EtOAc. The organic layer was then washed with brine and dried with $MgSO_4$. The solvent was removed under reduced pressure to give the 4-(4-chlorophenyl)-1,6-dimethyl-2-oxo-3,4-dihydropyridine-5-carboxylic acid (680 mg, 62%).

Example 79: p-tolylmethyl 4-(4-chlorophenyl)-1,6-dimethyl-2-oxo-3,4-dihydropyridine-5-carboxylate 4-(4-chlorophenyl)-1,6-dimethyl-2-oxo-3,4-dihydropyridine-5-carboxylic acid (example 78, 0.36 mmol) was dissolved in anhydrous DMF (1.2 mL) then $Cs_2CO3$ (349 mg, 1.07 mmol) and alpha bromo-p-xylene (66 mg, 0.36 mmol) were added. The reaction mixture was stirred for 1 h at RT. Water was then added and the aqueous phase was extracted with EtOAc. The organic layer was then washed with brine and dried with $MgSO_4$. The solvent was removed under reduced pressure to give the desired compound as a white solid (87 mg, 63%). $^1H$ NMR (300 MHz, $CDCl_3$) δ 2.35 (s, 3H), 2.56 (s, 3H), 2.75 (dd, J=2.7 and 15.9 Hz, 1H), 2.89 (dd, J=7.2 and 15.9 Hz, 1H), 3.20 (s, 3H) 5.20 (d, J=5.4 Hz, 1H), 5.07 (s, 2H), 7.00 (d, J=8.4 Hz, 2H), 7.05 (d, J=8.1 Hz, 2H), 7.11 (d, J=8.1 Hz, 2H), 7.20 (d, J=8.4 Hz, 2H), MS $[M+H]^+$ 384.

Example 80: [4-(trifluoromethyl)phenyl]methyl 4-(4-chlorophenyl)-1,6-dimethyl-2-oxo-3,4-dihydropyridine-5-carboxylate 4-(4-chlorophenyl)-1,6-dimethyl-2-oxo-3,4-dihydropyridine-5-carboxylic acid (example 78, 0.36 mmol) was dissolved in anhydrous DMF (1.2 mL) then $Cs_2CO3$ (349 mg, 1.07 mmol) and 4-(trifluoromethyl)benzyl bromide (85 mg, 0.36 mmol) were added. The reaction mixture was stirred for 1 h at RT. Water was then added and the aqueous phase was extracted with EtOAc. The organic layer was then washed with brine and dried with $MgSO_4$. The solvent was removed under reduced pressure to give the desired compound as a white solid (117 mg, 75%). $^1H$ NMR (300 MHz, $CDCl_3$) δ 2.59 (s, 3H), 2.76 (dd, J=2.4 and 15.9 Hz, 1H), 2.92 (dd, J=7.5 and 15.9 Hz, 1H), 3.23 (s, 3H), 4.21 (d, J=6.3 Hz, 1H), 5.11 (d, J=13.0 Hz, 1H), 5.19 (d, J=13.1 Hz, 1H), 7.02 (d, J=8.4 Hz, 2H), 7.21 (d, J=6.2 Hz, 2H), 7.23 (d, J=8.4 Hz, 2H), 7.53 (d, J=6.0 Hz, 2H), MS $[M+H]^+$ 438.

Example 81: (2-chloro-4-fluoro-phenyl)methyl 4-(4-chlorophenyl)-1,6-dimethyl-2-oxo-3,4-dihydropyridine-5-carboxylate 4-(4-chlorophenyl)-1,6-dimethyl-2-oxo-3,4-dihydropyridine-5-carboxylic acid (example 78, 0.36 mmol) was dissolved in anhydrous DMF (1.2 mL) then $Cs_2CO_3$ (349 mg, 1.07 mmol) and 2-Chloro-4-fluorobenzyl bromide (85 mg, 0.36 mmol) were added. The reaction mixture was stirred at RT. Water was then added and the aqueous phase was extracted with EtOAc. The organic layer was then washed with brine and dried with $MgSO_4$. The solvent was removed under reduced pressure to give the desired compound as a colorless oil (38 mg, 26%). $^1H$ NMR (300 MHz, $CDCl_3$) δ 2.59 (s, 3H), 2.76 (dd, J=2.4 and 15.9 Hz, 1H), 2.92 (dd, J=7.5 and 15.9 Hz, 1H), 3.22 (s, 3H), 4.19 (d, J=5.7 Hz, 1H), 5.12 (d, J=13.2 Hz, 1H), 5.21 (d, J=12.9 Hz, 1H), 6.86 (dt, J=2.4 and 8.1 Hz, 1H), 7.00 (d, J=8.4 Hz, 2H), 7.12-7.04 (m, 2H) 7.20 (d, J=8.4 Hz, 2H), MS $[M+H]^+$ 422.

Example 82: (2,6-difluorophenyl)methyl 4-(4-chlorophenyl)-1,6-dimethyl-2-oxo-3,4-dihydropyridine-5-carboxylate 4-(4-chlorophenyl)-1,6-dimethyl-2-oxo-3,4-dihydropyridine-5-carboxylic acid (example 78, 75 mg, 0.27 mmol) was dissolved in anhydrous DMF (1 mL) then Cs$_2$CO$_3$ (131 mg, 0.68 mmol) and 2,6-difluorobenzyl bromide (83 mg, 0.40 mmol) were added. The reaction mixture was stirred for 1 h at RT. Water was then added and the aqueous phase was extracted with EtOAc. The organic layer was then washed with brine and dried with MgSO$_4$. The solvent was removed under reduced pressure. The crude product was purified by flash chromatography using a mixture of cyclohexane/EtOAc 9/1 to give the desired compound as a colorless oil (73 mg, 66%). $^1$H NMR (300 MHz, CDCl$_3$) δ 2.53 (s, 3H), 2.72 (dd, J=16.0, 2.4 Hz, 1H), 2.87 (dd, J=16.0, 7.5 Hz, 1H), 3.19 (s, 3H), 4.12 (dd, J=7.5, 2.4 Hz, 1H), 5.18 (d, J=12.6 Hz, 1H), 5.23 (d, J=12.6 Hz, 1H), 6.82-6.92 (m, 2H), 6.96 (d, J=8.4 Hz, 2H), 7.14 (d, J=8.4 Hz, 2H), 7.23-7.36 (m, 3H). MS [M+H]$^+$ 406. HRMS: calcd for C$_{23}$H$_{22}$N$_2$O$_3$Cl, [M+CH$_3$CN+H]$^+$ 447.1287, found 447.1310.

Example 83: (3,4-dimethoxyphenyl)methyl 4-(4-chlorophenyl)-1,6-dimethyl-2-oxo-3,4-dihydropyridine-5-carboxylate The appropriate acid intermediate (75 mg, 0.27 mmol) was dissolved in anhydrous DMF (1 mL) then Cs$_2$CO$_3$ (104 mg, 0.32 mmol) and 3,4-dimethoxybenzyl chloride (60 mg, 0.32 mmol) were added. The reaction mixture was stirred for 1 h at RT. The solvents were removed under reduced pressure. The residue was dissolved in EtOAc and water. The aqueous phase was extracted 3 times with EtOAc. The organic layer was then washed with brine and dried with MgSO$_4$. The solvent was removed under reduced pressure. The crude product was purified by flash chromatography using a mixture of cyclohexane/EtOAc 95/5 to give the desired compound as a colorless oil (115 mg, 100%). $^1$H NMR (300 MHz, CDCl$_3$) δ 2.58 (d, J=0.7 Hz, 3H), 2.76 (dd, J=16.1, 2.5 Hz, 1H), 2.91 (dd, J=16.1, 7.5 Hz, 1H), 3.21 (s, 3H), 3.77 (s, 3H), 3.89 (s, 3H), 4.21 (d, J=7.5 Hz, 1H), 5.02 (d, J=12.3 Hz, 1H), 5.09 (d, J=12.3 Hz, 1H), 6.68 (d, J=1.8 Hz, 1H), 6.73-6.82 (m, 2H), 7.02 (d, J=8.4 Hz, 2H), 7.22 (d, J=8.4 Hz, 2H). MS [M+H]$^+$ 430. HRMS: calcd for C$_{23}$H$_{25}$NO$_5$Cl$_2$, [M+H]$^+$ 430.1421, found 430.1421.

Example 84: (2-fluorophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 2-fluorobenzyl bromide (30 μL, 0.25 mmol) were added. The reaction mixture was stirred for 1 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (2-fluorophenyl)methyl 4-(4-chlorophenyl)-1-(2-m ethoxyethyl)-6-methyl-2-oxo-3,4-dihydropyridine-5-carboxylate as a colorless oil (94 mg, 95%). $^1$H NMR (300 MHz, CDCl$_3$) δ 2.53 (s, 3H), 2.64 (dd, J=15.7, 2.2 Hz, 1H), 2.84 (dd, J=15.7, 7.6 Hz, 1H), 3.24 (s, 3H), 3.31 (ddd, J=9.9, 8.6, 4.0 Hz, 1H), 3.39 (dt, J=9.9, 4.0 Hz, 1H), 3.68 (ddd, J=14.2, 8.6, 4.0 Hz, 1H), 4.04-4.13 (m, 2H), 5.06 (d, J=14.0 Hz, 1H), 5.11 (d, J=14.0 Hz, 1H), 6.91-6.98 (m, 3H), 7.01 (d, J=8.6 Hz, 2H), 7.12 (d, J=8.6 Hz, 2H), 7.16-7.24 (m, 1H). MS [M+H]$^+$ 432. HRMS: calcd for C$_{23}$H$_{24}$NO$_4$FCl, [M+H]$^+$ 432.1378, found 432.1378.

Example 85: (3-fluorophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 3-fluorobenzyl bromide (31 μL, 0.25 mmol) were added. The reaction mixture was stirred at RT. for 1 h. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (3-fluorophenyl)methyl 4-(4-chlorophenyl)-1-(2-methoxyethyl)-6-methyl-2-oxo-3,4-dihydropyridine-5-carboxylate as a white powder (95 mg, 95%). $^1$H NMR (300 MHz, CDCl$_3$) δ 2.63 (s, 3H), 2.72 (dd, J=15.7, 2.3 Hz, 1H), 2.93 (dd, J=15.7, 7.5 Hz, 1H), 3.32 (s, 3H), 3.38 (ddd, J=9.9, 8.6, 3.5 Hz, 1H), 3.47 (dt, J=9.9, 3.9 Hz, 1H), 3.76 (ddd, J=14.6, 8.6, 3.9 Hz, 1H), 4.14-4.21 (m, 2H), 5.04 (d, J=13.1 Hz, 1H), 5.12 (d, J=13.1 Hz, 1H), 6.76 (dt, J=9.6, 1.7 Hz, 1H), 6.86 (d, J=7.6 Hz, 1H), 6.95 (td, J=8.7, 2.4 Hz, 1H), 7.10 (d, J=8.4 Hz, 2H), 7.19-7.24 (m, 3H). MS [M+H]$^+$ 432. HRMS: calcd for C$_{23}$H$_{24}$NO$_4$ClF, [M+H]$^+$ 432.1378, found 432.1384.

Example 86: (4-fluorophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 45 mg, 0.14 mmol) was dissolved in anhydrous DMF (1 mL) then cesium carbonate (68 mg, 0.21 mmol) and 4-fluorobenzyl bromide (19 μL, 0.15 mmol) were added. The reaction mixture was stirred for 18 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (4-fluorophenyl)methyl 4-(4-chlorophenyl)-1-(2-methoxyethyl)-6-methyl-2-oxo-3,4-dihydropyridine-5-carboxylate as a colorless oil (48 mg, 80%). $^1$H NMR (300 MHz, CDCl$_3$) δ 2.53 (s, 3H), 2.63 (dd, J=15.7, 2.3 Hz, 1H), 2.84 (dd, J=15.7, 7.3 Hz, 1H), 3.24 (s, 3H), 3.30 (ddd, J=9.9, 8.6, 4.0 Hz, 1H), 3.39 (dt, J=9.9, 4.0 Hz, 1H), 3.68 (ddd, J=14.8, 8.6, 3.6 Hz, 1H), 4.06-4.13 (m, 2H), 4.94 (d, J=12.6 Hz, 1H), 5.00 (d, J=12.6 Hz, 1H), 6.88 (t, J=8.6 Hz, 2H), 6.97-7.03 (m, 4H), 7.14 (d, J=8.4 Hz, 2H). MS [M+H]$^+$ 432.

Example 87: (2-chlorophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 2-chlorobenzyl bromide (33 μL, 0.25 mmol) were added. The reaction mixture was stirred at RT. for 1 h. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (2-chlorophenyl)methyl 4-(4- chlorophenyl)-1-(2-methoxyethyl)-6-methyl-2-oxo-3,4-dihydropyridine-5-carboxylate as a white powder (99 mg, 96%). $^1$H NMR (300 MHz, CDCl$_3$) δ 2.55 (s, 3H), 2.65 (dd, J=15.8, 2.2 Hz, 1H), 2.86 (dd, J=15.8, 7.7 Hz, 1H), 3.25 (s, 3H), 3.31 (ddd, J=9.9, 8.6, 3.6 Hz, 1H), 3.40 (dt, J=9.9, 4.0 Hz, 1H), 3.69 (ddd, J=14.5, 8.6, 4.0 Hz, 1H), 4.04-4.16 (m, 2H), 5.09 (d, J=13.4 Hz, 1H), 5.16 (d, J=13.4 Hz, 1H), 6.93 (dd, J=7.5, 1.4 Hz, 1H), 7.01-7.07 (m, 3H), 7.11-7.17 (m, 3H), 7.26 (dd, J=8.0, 1.3 Hz, 1H). MS [M+H]$^+$ 448. HRMS: calcd for C$_{23}$H$_{24}$NO$_4$Cl$_2$, [M+H]$^+$ 448.1082, found 448.1083.

Example 88: (3-chlorophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 3-chlorobenzyl bromide (33 μL, 0.25 mmol) were added. The reaction mixture was stirred for 1 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (3-chlorophenyl)methyl 4-(4-chlorophenyl)-1-(2-m ethoxyethyl)-6-methyl-2-oxo-3,4-dihydropyridine-5-carboxylate as a colorless oil (100 mg, 97%). $^1$H NMR (300 MHz, CDC$_3$), δ 2.56 (s, 3H), 2.65 (dd, J=15.7, 2.1 Hz, 1H), 2.86 (dd, J=15.7, 7.3 Hz, 1H), 3.26 (s, 3H), 3.32 (ddd, J=9.6, 8.5, 3.7 Hz, 1H), 3.41 (dt, J=9.6, 3.7 Hz, 1H), 3.70 (ddd, J=14.5, 8.5, 3.7 Hz, 1H), 4.07-4.14 (m, 2H), 4.93 (d, J=12.9 Hz, 1H), 5.04 (d, J=12.9 Hz, 1H), 6.89 (d, J=7.3 Hz, 1H), 6.96 (s, 1H), 7.03 (d, J=8.4 Hz, 2H), 7.13 (d, J=7.3 Hz, 1H), 7.15-7.18 (m, 3H). MS [M+H]$^+$ 448. HRMS: calcd for C$_{23}$H$_{24}$NO$_4$Cl$_2$, [M+H]$^+$ 448.1082, found 448.1085.

Example 89: (4-chlorophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, mg, 0.23 mmol) was dissolved in anhydrous DMF (1 mL) then cesium carbonate (114 mg, 0.35 mmol) and 4-chlorobenzyl bromide (51 mg, 0.25 mmol) were added. The reaction mixture was stirred at RT. for 1 h. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (4-chlorophenyl)methyl 4-(4-chlorophenyl)-1-(2-methoxyethyl)-6-methyl-2-oxo-3,4-dihydropyridine-5-carboxylate as a white powder (68 mg, 66%). $^1$H NMR (300 MHz, CDCl$_3$) δ 2.54 (s, 3H), 2.64 (dd, J=15.8, 2.4 Hz, 1H), 2.84 (dd, J=15.8, 7.5 Hz, 1H), 3.25 (s, 3H), 3.30 (ddd, J=9.9, 8.7, 3.6 Hz, 1H), 3.39 (dt, J=9.9, 4.2 Hz, 1H), 3.68 (ddd, J=14.7, 8.7, 4.2 Hz, 1H), 4.06-4.13 (m, 2H), 4.93 (d, J=12.9 Hz, 1H), 5.01 (d, J=12.9 Hz, 1H), 6.94 (d, J=8.4 Hz, 2H), 7.01 (d, J=8.4 Hz, 2H), 7.10-7.21 (m, 4H). MS [M+H]$^+$ 448. HRMS: calcd for C$_{23}$H$_{24}$NO$_4$Cl$_2$, [M+H]$^+$ 448.1082, found 448.1085.

Example 90: [2-(trifluoromethyl)phenyl]methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 2-trifluoromethylbenzyl bromide (38 μL, 0.25 mmol) were added. The reaction mixture was stirred for 2 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired [2-(trifluoromethyl)phenyl]methyl 4-(4-chlorophenyl)-1-(2-methoxyethyl)-6-methyl-2-oxo-3,4-dihydropyridine-5-carboxylate as a colorless oil (100 mg, 90%). $^1$H NMR (300 MHz, CDCl$_3$) δ 2.63 (s, 3H), 2.72 (dd, J=15.7, 2.1 Hz, 1H), 2.94 (dd, J=15.7, 7.4 Hz, 1H), 3.33 (s, 3H), 3.35-3.42 (m, 1H), 3.48 (dt, J=10.0, 3.7 Hz, 1H), 3.77 (ddd, J=14.5, 8.5, 3.7 Hz, 1H), 4.14-4.22 (m, 2H), 5.24 (d, J=13.5 Hz, 1H), 5.34 (d, J=13.5 Hz, 1H), 7.03-7.06 (m, 1H), 7.10 (d, J=8.3 Hz, 2H), 7.21 (d, J=8.3 Hz, 2H), 7.32-7.42 (m, 2H), 7.61-7.64 (m, 1H). MS [M+H]$^+$ 482. HRMS: calcd for C$_{24}$H$_{24}$NO$_4$F$_3$Cl, [M+H]$^+$ 482.1346, found 482.1352.

Example 91: [3-(trifluoromethyl)phenyl]methyl 4-(4-chlorophenyl)-1-(2-methoxyethyl)-6-methyl-2-oxo-3,4-dihydropyridine-5-carboxylate The 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 3-trifluoromethylbenzyl bromide (38 μL, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired [3-(trifluoromethyl)phenyl]methyl 4-(4-chlorophenyl)-1-(2-methoxyethyl)-6-methyl-2-oxo-3,4-dihydropyridine-5-carboxylate as a colorless oil (108 mg, 98%). $^1$H NMR (300 MHz, CDCl$_3$) δ 2.64 (s, 3H), 2.72 (dd, J=15.7, 2.2 Hz, 1H), 2.93 (dd, J=15.7, 7.5 Hz, 1H), 3.33 (s, 3H), 3.35-3.42 (m, 1H), 3.48 (dt, J=9.8, 4.0 Hz, 1H), 3.77 (ddd, J=14.7, 8.9, 4.0 Hz, 1H), 4.09-4.22 (m, 2H), 5.09 (d, J=13.1 Hz, 1H), 5.17 (d, J=13.1 Hz, 1H), 7.10 (d, J=8.4 Hz, 2H), 7.22 (d, J=8.4 Hz, 2H), 7.20-7.26 (m, 1H), 7.35-7.40 (m, 2H), 7.53 (d, J=8.1 Hz, 1H). MS [M+H]$^+$ 482. HRMS: calcd for C$_{24}$H$_{24}$NO$_4$F$_3$Cl, [M+H]$^+$ 482.1346, found 482.1356.

Example 92: [4-(trifluoromethyl)phenyl]methyl 4-(4-chlorophenyl)-1-(2-methoxyethyl)-6-methyl-2-oxo-3,4-dihydropyridine-5-carboxylate The 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 4-trifluoromethylbenzyl bromide (60 mg, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired [4-(trifluoromethyl)phenyl]methyl 4-(4-chlorophenyl)-1-(2-methoxyethyl)-6-methyl-2-oxo-3,4-dihydropyridine-5-carboxylate as a white powder (103 mg, 93%). $^1$H NMR (300 MHz, CDCl$_3$) δ 2.63 (s, 3H), 2.73 (dd, J=15.7, 2.3 Hz, 1H), 2.93 (dd, J=15.7, 7.6 Hz, 1H), 3.33 (s, 3H), 3.34-3.50 (m, 2H), 3.72-3.81 (m, 1H), 4.13-4.21 (m, 2H), 5.09 (d, J=13.0 Hz, 1H), 5.18 (d, J=13.0 Hz, 1H), 7.10 (d, J=8.5 Hz, 2H), 7.17 (d, J=8.3 Hz), 7.23 (d, J=8.5 Hz), 7.51 (d, J=8.3 Hz, 2H). MS [M+H]$^+$ 482. HRMS: calcd for C$_{24}$H$_{24}$NO$_4$F$_3$Cl, [M+H]$^+$ 482.1346, found 482.1343.

Example 93: (2-cyanophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 2-cyanobenzyl bromide (49 mg, 0.25 mmol) were added. The reaction mixture was stirred for 18 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (2-cyanophenyl)methyl 4-(4-chlorophenyl)-1-(2-methoxyethyl)-6-methyl-2-oxo-3,4-dihydropyridine-5-carboxylate as a colorless oil (100 mg, 99%). $^1$H NMR (300 MHz, CDCl$_3$) δ 2.56 (s, 3H), 2.65 (dd, J=15.8, 2.3 Hz, 1H), 2.87 (dd, J=15.8, 7.6 Hz, 1H), 3.25 (s, 3H), 3.29-3.35 (m, 1H), 3.40 (dt, J=9.8, 3.9 Hz, 1H), 3.70 (ddd, J=14.6, 8.5, 3.6 Hz, 1H), 4.10 (dt, J=14.6, 3.9 Hz, 1H), 4.17 (d, J=7.6 Hz, 1H), 5.15 (d, J=13.3 Hz, 1H), 5.26 (d, J=13.3 Hz, 1H), 7.00-7.05 (m, 3H), 7.12 (d, J=8.5 Hz, 2H), 7.30 (td, J=7.5, 1.6 Hz, 1H), 7.38 (td, J=7.5, 1.6 Hz, 1H), 7.55 (dd, J=7.5, 1.7 Hz, 1H). MS [M+H]$^+$ 439. HRMS: calcd for C$_{24}$H$_{24}$N$_2$O$_4$Cl, [M+H]$^+$ 439.1425, found 439.1425.

Example 94: (3-cyanophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 3-cyanobenzyl bromide (49 mg, 0.25 mmol) were added. The reaction mixture was stirred for 18 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (3-cyanophenyl)methyl 4-(4-chlorophenyl)-1-(2-methoxyethyl)-6-methyl-2-oxo-3,4-dihydropyridine-5-carboxylate as a colorless oil (100 mg, 99%). $^1$H NMR (300 MHz, CDCl$_3$) δ 2.57 (s, 3H), 2.66 (dd, J=15.7, 2.2 Hz, 1H), 2.87 (dd, J=15.7, 7.6 Hz, 1H), 3.26 (s, 3H), 3.28-3.36 (m, 1H), 3.41 (dt, J=9.8, 3.9 Hz, 1H), 3.71 (ddd, J=14.5, 8.8, 3.9 Hz, 1H), 4.07-4.15 (m, 2H), 4.97 (d, J=13.4 Hz, 1H), 5.08 (d, J=13.4 Hz, 1H), 7.03 (d, J=8.4 Hz, 2H), 7.16-7.20 (m, 3H), 7.26-7.31 (m, 2H), 7.48 (d, J=7.4 Hz, 1H). MS [M+H]$^+$ 439. HRMS: calcd for C$_{24}$H$_{24}$N$_2$O$_4$Cl, [M+H]$^+$ 439.1425, found 439.1422.

Example 95: (4-cyanophenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 4-cyanobenzyl bromide (49 mg, 0.25 mmol) were added. The reaction mixture was stirred for 3 h at RT. The solvent was removed under reduced pressure. The residue was dissolved in EtOAc and water. The aqueous phase was extracted with EtOAc. The organic layers were assembled, washed with brine and dried over MgSO$_4$.

The solvent was removed under reduced pressure. The crude product was purified by flash chromatography using a mixture of Cyclohexane/EtOAc (9/1 to 8/2) as eluent to give the desired (4-cyanophenyl)methyl 4-(4-chlorophenyl)-1-(2-methoxyethyl)-6-methyl-2-oxo-3,4-dihydropyridine-5-carboxylate as a white powder (62 mg, 62%). $^1$H NMR (300 MHz, CDCl$_3$) δ 2.64 (s, 3H), 2.74 (dd, J=15.6, 2.1 Hz, 1H), 2.95 (dd, J=15.6, 7.6 Hz, 1H), 3.34 (s, 3H), 3.36-3.43 (m, 1H), 3.78 (ddd, J=14.5, 8.6, 3.9 Hz, 1H), 4.15-4.23 (m, 2H), 5.06 (d, J=13.7 Hz, 1H), 5.21 (d, J=13.7 Hz, 1H), 7.08-7.14 (m, 4H), 7.25 (d, J=8.4 Hz, 2H), 7.54 (d, J=8.4 Hz, 2H). MS [M+H]$^+$ 439. HRMS: calcd for C$_{24}$H$_{24}$N$_2$O$_4$Cl, [M+H]$^+$ 439.1425, found 439.1425.

Example 96: (3-methoxycarbonylphenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 3-(Bromomethyl)benzoic acid methyl ester (57 mg, 0.25 mmol) were added. The reaction mixture was stirred for 3 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure. The crude product was purified by flash chromatography using a mixture of Cyclohexane/EtOAc (9/1 to 8/2) as eluent to give the desired (3-methoxycarbonylphenyl)methyl 4-(4-chlorophenyl)-1-(2-methoxyethyl)-6-methyl-2-oxo-3,4-dihydropyridine-5-carboxylate as a yellowish oil (108 mg, 99%). $^1$H NMR (300 MHz, CDCl$_3$) δ 2.62 (s, 3H), 2.71 (dd, J=15.7, 2.2 Hz, 1H), 2.92 (dd, J=15.7, 7.4 Hz, 1H), 3.32 (s, 3H), 3.38 (ddd, J=9.9, 8.6, 3.7 Hz, 1H), 3.46 (dt, J=9.9, 4.2 Hz, 1H), 3.76 (ddd, J=14.5, 8.6, 3.8 Hz, 1H), 3.92 (s, 3H), 4.13-4.21 (m, 2H), 5.10 (d, J=12.9 Hz, 1H), 5.15 (d, J=12.9 Hz, 1H), 7.09 (d, J=8.5 Hz, 2H), 7.20 (d, J=8.5 Hz, 2H), 7.24-7.27 (m, 1H), 7.34 (t, J=7.7 Hz, 1H), 7.88 (s, 1H), 7.95 (d, J=7.7 Hz, 1H). MS [M+H]$^+$ 472. HRMS: calcd for C$_{25}$H$_{27}$NO$_6$Cl, [M+H]$^+$ 472.1527, found 472.1539.

Example 97: (4-methoxycarbonylphenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 4-(Bromomethyl)benzoic acid methyl ester (57 mg, 0.25 mmol) were added. The reaction mixture was stirred for 3 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired (4-methoxycarbonylphenyl)methyl 4-(4-chlorophenyl)-1-

(2-methoxyethyl)-6-methyl-2-oxo-3,4-dihydropyridine-5-carboxylate as a white powder (101 mg, 93%). $^1$H NMR (300 MHz, CDCl$_3$) δ 2.64 (s, 3H), 2.73 (dd, J=15.8, 2.1 Hz, 1H), 2.94 (dd, J=15.8, 7.4 Hz, 1H), 3.34 (s, 3H), 3.35-3.43 (m, 1H), 3.48 (dt, J=9.9, 4.8 Hz, 1H), 3.77 (ddd, J=14.5, 8.4, 3.8 Hz, 1H), 3.93 (s, 3H), 4.12-4.23 (m, 2H), 5.11 (d, J=13.4 Hz, 1H), 5.19 (d, J=13.4 Hz, 1H), 7.11 (d, J=8.4 Hz, 2H), 7.15 (d, J=8.1 Hz, 2H), 7.24 (d, J=8.4 Hz, 2H), 7.94 (d, J=8.1 Hz, 2H). MS [M+H]$^+$ 472. HRMS: calcd for C$_{25}$H$_{27}$NO$_6$Cl, [M+H]$^+$ 472.1527, found 472.1539.

Example 98: o-tolylmethyl 4-(4-chlorophenyl)-1-(2-methoxyethyl)-6-methyl-2-oxo-3,4-dihydropyridine-5-carboxylate The 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and o-methylbenzyl bromide (34 μL, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired o-tolylmethyl 4-(4-chlorophenyl)-1-(2-methoxyethyl)-6-methyl-2-oxo-3,4-dihydropyridine-5-carboxylate as a white powder (91 mg, 93%). $^1$H NMR (300 MHz, CDCl$_3$) δ 2.05 (s, 3H), 2.55 (s, 3H), 2.63 (dd, J=15.7, 2.1 Hz, 1H), 2.83 (dd, J=15.7, 7.4 Hz, 1H), 3.25 (s, 3H), 3.30 (ddd, J=12.3, 8.5, 3.7 Hz, 1H), 3.39 (dt, J=9.9, 4.1 Hz, 1H), 3.68 (ddd, J=14.6, 8.5, 4.1 Hz, 1H), 4.06-4.14 (m, 2H), 5.00 (d, J=13.4 Hz, 1H), 5.04 (d, J=13.4 Hz, 1H), 6.95-7.08 (m, 5H), 7.09-7.17 (m, 3H). MS [M+H]$^+$ 428. HRMS: calcd for C$_{24}$H$_{27}$NO$_4$Cl, [M+H]$^+$ 428.1629, found 428.1636.

Example 99: m-tolylmethyl 4-(4-chlorophenyl)-1-(2-methoxyethyl)-6-methyl-2-oxo-3,4-dihydropyridine-5-carboxylate The 4-(4-chlorophenyl)-1-(2-m ethoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and m-methylbenzyl bromide (34 μL, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired m-tolylmethyl 4-(4-chlorophenyl)-1-(2-methoxyethyl)-6-methyl-2-oxo-3,4-dihydropyridine-5-carboxylate as a colorless oil (91 mg, 93%). $^1$H NMR (300 MHz, CDCl$_3$) δ 2.27 (s, 3H), 2.62 (s, 3H), 2.71 (dd, J=15.6, 2.2 Hz, 1H), 2.93 (dd, J=15.6, 7.4 Hz, 1H), 3.33 (s, 3H), 3.35-3.51 (m, 2H), 3.71-3.81 (m, 1H), 4.14-4.23 (m, 2H), 5.03 (d, J=12.8 Hz, 1H), 5.12 (d, J=12.8 Hz, 1H), 6.85 (s, 1H), 6.91 (d, J=7.7 Hz, 1H), 7.05-7.19 (m, 4H), 7.22 (d, J=8.6 Hz, 2H). MS [M+H]$^+$ 428. HRMS: calcd for C$_{24}$H$_{27}$NO$_4$Cl, [M+H]$^+$ 428.1629, found 428.1627.

Example 100: p-tolylmethyl 4-(4-chlorophenyl)-1-(2-methoxyethyl)-6-methyl-2-oxo-3,4-dihydropyridine-5-carboxylate The 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and p-methylbenzyl bromide (34 μL, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired p-tolylmethyl 4-(4-chlorophenyl)-1-(2-m ethoxyethyl)-6-methyl-2-oxo-3, 4-dihydropyridine-5-carboxylate as a colorless oil (94 mg, 96%). $^1$H NMR (300 MHz, CDCl$_3$) δ 2.26 (s, 3H), 2.53 (s, 3H), 2.63 (dd, J=15.8, 2.2 Hz, 1H), 2.83 (dd, J=15.8, 7.6 Hz, 1H), 3.24 (s, 3H), 3.30 (ddd, J=9.8, 8.5, 3.9 Hz, 1H), 3.39 (dt, J=9.8, 3.9 Hz, 1H), 3.67 (ddd, J=14.4, 8.3, 4.0 Hz, 1H), 4.04-4.13 (m, 2H), 4.98 (s, 2H), 6.94 (d, J=8.4 Hz, 2H), 6.99-7.05 (m, 4H), 7.14 (d, J=8.4 Hz, 2H). MS [M+H]$^+$ 428. HRMS: calcd for C$_{24}$H$_{27}$NO$_4$Cl, [M+H]$^+$ 428.1629, found 428.1642.

Example 101: (2,4,6-trimethylphenyl)methyl 4-(4-chlorophenyl)-1-(2-methoxyethyl)-6-methyl-2-oxo-3,4-dihydropyridine-5-carboxylate Step 1.
2,4,6-trimethylbenzyl alcohol (150 mg, 1.0 mmol) was dissolved in anh. DCM (4 mL). Thionyl chloride (87 μL, 1.2 mmol) was added slowly at 0° C. The reaction mixture was stirred at RT. for 1 h. Removal of the solvent under reduced pressure gave the desired 2,4,6-trimethylbenzyl chloride (168 mg, 100%) as a white powder. $^1$H NMR (300 MHz, CDCl$_3$) δ 2.29 (s, 3H), 2.42 (s, 6H), 4.68 (s, 2H), 6.89 (s, 2H). MS [M+H]$^+$ 133.

Step 2.
4-(4-chlorophenyl)-1-(2-methoxyethyl)-6-methyl-2-oxo-3,4-dihydropyridine-5-carboxylic acid (example 74, 97 mg, 0.3 mmol) was dissolved in anhydrous DMF (1 mL) then cesium carbonate (97 mg, 0.3 mmol) and 2,4,6-trimethylbenzyl chloride (50 mg, 0.3 mmol) were added. The reaction mixture was stirred at RT. for 1 h. The solvent was removed under reduced pressure. The residue was dissolved in EtOAc and water. The aqueous phase was extracted with EtOAc. The combined organic layers were washed with brine and dried over MgSO$_4$. Removal of the solvent under reduced pressure gave the desired (2,4,6-trimethylphenyl)methyl 4-(4-chlorophenyl)-1-(2-methoxyethyl)-6-methyl-2-oxo-3,4-dihydropyridine-5-carboxylate as a yellowish oil (111 mg, 81%). $^1$H NMR (300 MHz, CDCl$_3$) δ 2.16 (s, 6H), 2.28 (s, 3H), 2.61 (s, 3H), 2.67 (dd, J=15.7, 2.3 Hz, 1H), 2.88 (dd, J=15.7, 7.7 Hz, 1H), 3.32 (s, 3H), 3.35-3.51 (m, 2H), 3.75 (ddd, J=14.7, 8.3, 4.0 Hz, 1H), 3.10 (dd, J=7.7, 2.3 Hz, 1H), 4.16 (dt, J=14.7, 4.2 Hz, 1H), 5.01 (d, J=12.1 Hz, 1H), 5.25 (d, J=12.1 Hz, 1H), 6.83 (s, 2H), 7.02 (d, J=8.6 Hz, 1H), 7.17 (d, J=8.6 Hz, 1H). $^{13}$C NMR (75 MHz, CDCl$_3$) δ 17.1, 19.3, 21.0, 36.8, 38.6, 41.9, 58.8, 60.9, 71.0, 110.1, 128.3, 128.6, 128.9, 129.0, 132.5, 138.1, 138.3, 139.7, 150.8, 167.2, 168.9. MS [M+H]$^+$ 456. HRMS: calcd for C$_{26}$H$_{31}$NO$_4$Cl, [M+H]$^+$ 456.1942, found 456.1938.

Example 103: (3-methoxyphenyl)methyl 4-(4-chlorophenyl)-1-(2-methoxyethyl)-6-methyl-2-oxo-3,4-dihydropyridine-5-carboxylate 3-methoxybenzyl alcohol (248 μL, 2.0 mmol) and triethylamine (335 μL, 2.4 mmol) were dissolved in anh. DCM (7 mL). Thionyl chloride (218 μL, 3.0 mmol) was added slowly. The reaction mixture was stirred at RT. for 1 h. The reaction mixture was washed with an aqueous solution of HCl 1N. The organic phase was dried over MgSO$_4$. The solvent was removed under reduced pressure to give the desired 2-methoxybenzyl chloride (313 mg, 100%) as a yellowish oil. 4-(4-chlorophenyl)-1-(2-methoxyethyl)-6-methyl-2-oxo-3,4-dihydropyridine-5-carboxylic acid (example 74, 85 mg, 0.26 mmol) was dissolved in anhydrous DMF (1 mL) then cesium carbonate (169 mg, 0.52 mmol) and 3-methoxybenzyl chloride (81 mg, 0.52 mmol) were added. The reaction mixture was stirred at r.t. for 18 h. The solvent was removed under reduced pressure. The residue was dissolved in EtOAc and water. The aqueous phase was extracted with EtOAc. The combined organic layers were washed with brine and dried over MgSO$_4$. The solvent was removed under reduced pressure. Purification of the crude by flash chromatography using a mixture of Cyclohexane/EtOAc (8/2) as eluent gave the desired (3-methoxyphenyl)methyl 4-(4-chlorophenyl)-1-(2-methoxyethyl)-6-methyl-2-oxo-3,4-dihydropyridine-5-carboxylate as a yellowish oil (11 mg, 9%). $^1$H NMR (300 MHz, CDCl$_3$) δ 2.62 (s, 3H), 2.71 (dd, J=15.8, 2.2 Hz, 1H), 2.92 (dd, J=15.8, 7.5 Hz, 1H), 3.31 (s, 3H), 3.37 (ddd, J=10.0, 8.5, 3.6 Hz, 1H), 3.46 (dt, J=10.0, 4.1 Hz, 1H), 3.70-3.79 (m, 4H), 4.13-4.23 (m, 2H), 5.04 (d, J=12.7 Hz, 1H), 5.11 (d, J=12.7 Hz, 1H), 6.64 (s, 1H), 6.70 (d, J=7.5, 1H), 6.81 (dd, J=8.2, 2.5 Hz, 1H), 7.10 (d, J=8.4 Hz, 2H), 7.16-7.23 (m, 3H). MS [M+H]$^+$ 444. HRMS: calcd for C$_{24}$H$_{27}$NO$_5$Cl, [M+H]$^+$ 444.1578, found 444.1579.

Example 104: (4-methoxyphenyl)methyl 4-(4-chlorophenyl)-1-(2-methoxyethyl)-6-methyl-2-oxo-3,4-dihydropyridine-5-carboxylate p-methoxybenzyl alcohol (54 mg, 0.39 mmol) was dissolved in anh. THF (1 mL). 4-(4-chlorophenyl)-1-(2-methoxyethyl)-6-methyl-2-oxo-3,4-dihydropyridine-5-carboxylic acid (example 74, 85 mg, 0.26 mmol) and triphenylphosphine (102 mg, 0.39 mmol) were added. A solution of DEAD (61 μL, 68 mg) in anh. THF (0.4 mL) was added slowly. The reaction mixture was stirred for 18 h at RT. The reaction was uncompleted. Triphenylphosphine (102 mg, 0.39 mmol), p-methoxybenzyl alcohol (54 mg, 0.39 mmol) and a solution of DEAD (61 μL, 68 mg) in anh. THF (0.4 mL) were added at 0° C. and the reaction mixture was stirred at 60° C. for 24 h. A saturated aqueous solution of NaHCO$_3$ was added. The aqueous phase was extracted with EtOAc. The combined organic layers were washed with brine and dried over MgSO$_4$. Purification of the crude by flash chromatography on silica using a mixture of Cy/EtOAc (8/2) gave the desired (4-methoxyphenyl)methyl 4-(4-chlorophenyl)-1-(2-methoxyethyl)-6-methyl-2-oxo-3,4-dihydropyridine-5-carboxylate as a colorless oil (74 mg, 64%). $^1$H NMR (300 MHz, CDC$_3$) δ 2.59 (s, 3H), 2.70 (dd, J=15.8, 2.3 Hz, 1H), 2.89 (dd, J=15.8, 7.5 Hz, 1H), 3.31 (s, 3H), 3.37 (ddd, J=9.9, 8.6, 3.9 Hz, 1H), 3.45 (dt, J=9.9, 3.9 Hz, 1H), 3.74 (ddd, J=14.3, 8.6, 3.9 Hz, 1H), 3.80 (s, 3H), 4.10-4.20 (m, 2H), 5.02 (s, 2H), 6.80 (d, J=8.7 Hz, 2H), 7.05-7.09 (m, 4H), 7.20 (d, J=8.7 Hz, 2H). MS [M+H]$^+$ 444. HRMS: calcd for C$_{24}$H$_{27}$NO$_5$Cl, [M+H]$^+$ 444.1578, found 444.1576.

Example 105: (2-trifluoromethoxyphenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 97 mg, 0.3 mmol) was dissolved in anhydrous DMF (1 mL) then cesium carbonate (146 mg, 0.45 mmol) and 2-trifluoromethoxybenzyl bromide (63 μL, 0.33 mmol) were added. The reaction mixture was stirred at RT. for 18 h. The solvent was removed under reduced pressure. The residue was dissolved in EtOAc and water. The aqueous phase was extracted with EtOAc. The combined organic layers were washed with brine and dried over MgSO$_4$. The solvents were removed under reduced pressure. Purification of the crude by flash chromatography on silica using a mixture of Cyclohexane/EtOAc 9/1 gave the desired (2-trifluoromethoxyphenyl)methyl 4-(4-chlorophenyl)-1-(2-methoxyethyl)-6-methyl-2-oxo-3,4-dihydropyridine-5-carboxylate as a colorless oil (121 mg, 81%). $^1$H NMR (300 MHz, CDCl$_3$) δ 2.63 (s, 3H), 2.72 (dd, J=15.7, 2.2 Hz, 1H), 2.94 (dd, J=15.7, 7.5 Hz, 1H), 3.33 (s, 3H), 3.34-3.52 (m, 2H), 4.18 (ddd, J=14.7, 8.6, 4.0 Hz, 1H), 4.13-4.23 (m, 2H), 5.16 (d, J=13.4 Hz, 1H), 5.22 (d, J=13.4 Hz, 1H), 7.04 (dd, J=7.7, 1.6 Hz, 1H), 7.10 (d, J=8.6 Hz, 2H), 7.15 (td, J=7.6, 1.2 Hz, 1H), 7.22 (d, J=8.6 Hz, 2H), 7.19-7.25 (m, 1H), 7.33 (td, J=7.9, 1.8 Hz, 1H). 13C NMR (75 MHz, CDCl$_3$) δ 17.2, 36.9, 38.8, 41.9, 58.9, 60.6, 71.1, 109.5, 120.4, 126.7, 128.4, 128.8, 129.4, 129.8, 132.6, 139.7, 151.7, 166.7, 168.9. MS [M+H]$^+$ 498. HRMS: calcd for C$_{33}$H$_{21}$NO$_2$Cl, [M+H]$^+$ 498.1261, found 498.1294.

Example 106: 2-naphthylmethyl 4-(4-chlorophenyl)-1-(2-methoxyethyl)-6-methyl-2-oxo-3,4-dihydropyridine-5-carboxylate The 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 4-(bromomethyl)pyridine hydrobromide (63 mg, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired product as a white powder (92 mg, 87%). $^1$H NMR (300 MHz, CDCl$_3$) δ 2.63 (s, 3H), 2.71 (dd, J=15.7, 2.0 Hz, 1H), 2.93 (dd, J=15.7, 7.5 Hz, 1H), 3.32 (s, 3H), 3.34-3.42 (m, 1H), 3.47 (dt, J=9.9, 4.2 Hz, 1H), 3.76 (ddd, J=14.7, 8.7, 4.2 Hz, 1H), 4.17 (dt, J=14.7, 3.9 Hz, 1H), 4.23 (d, J=7.5 Hz, 1H), 5.20 (d, J=12.9 Hz, 1H), 5.31 (d, J=12.9 Hz, 1H), 7.12 (d, J=8.6 Hz, 2H), 7.19 (dd, J=8.4, 1.6 Hz, 1H), 7.22 (d, J=8.4 Hz, 2H), 7.46-7.50 (m, 3H), 7.67-7.70 (m, 1H), 7.74 (d, J=8.4 Hz, 1H), 7.79-7.82 (m, 1H). MS [M+H]$^+$ 464. HRMS: calcd for C$_{27}$H$_{27}$NO$_4$Cl, [M+H]$^+$ 464.1629, found 464.1629.

Example 107: 4-pyridylmethyl 4-(4-chlorophenyl)-1-(2-methoxyethyl)-6-methyl-2-oxo-3,4-dihydropyridine-5-carboxylate The 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 4-(bromomethyl)pyridine hydrobromide (63 mg, 0.25 mmol) were added. The reaction mixture was stirred for 1 h at RT. The solvent was removed under reduced pressure. The residue was dissolved in EtOAc and water. The aqueous phase was extracted 3 times with EtOAc. The organic layers were assembled, washed with brine and dried over MgSO$_4$. The solvent was removed under reduced pressure to give the desired 4-pyridylmethyl 4-(4-chlorophenyl)-1-(2-methoxyethyl)-6-methyl-2-oxo-3,4-dihydropyridine-5-carboxylate as a white powder (95 mg, 99%). $^1$H NMR (300 MHz, CDCl$_3$) δ 2.58 (s, 3H), 2.67 (dd, J=15.7, 2.2 Hz, 1H), 2.88 (dd, J=15.7, 7.5 Hz, 1H), 3.26 (s, 3H), 3.29-3.36 (m, 1H), 3.41 (dt, J=9.9, 4.0 Hz, 1H), 3.71 (ddd, J=14.5, 8.7, 3.7 Hz, 1H), 4.08-4.17 (m, 2H), 4.96 (d, J=14.1 Hz, 1H), 5.11 (d, J=14.1 Hz, 1H), 6.87 (d, J=5.2 Hz, 2H), 7.06 (d, J=8.3 Hz, 2H), 7.18 (d, J=8.3 Hz, 2H), 8.41 (d, J=5.2 Hz, 2H). MS [M+H]$^+$ 415. HRMS: calcd for C$_{22}$H$_{24}$N$_2$O$_4$Cl, [M+H]$^+$ 415.1425, found 415.1424.

Example 108: (4-phenylphenyl)methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 4-phenylbenzyl chloride (65 mg, 0.33 mmol) were added. The reaction mixture was stirred for 18 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure. The crude product was purified by flash chromatography using a mixture of Cyclohexane/EtOAc (9/1 to 8/2) as eluent to give the desired (4-phenylphenyl)methyl 4-(4-chlorophenyl)-1-(2-methoxyethyl)-6-methyl-2-oxo-3,4-dihydropyridine-5-carboxylate as a colorless oil (67 mg, 60%). $^1$H NMR (300 MHz, CDCl$_3$) δ 2.56 (s, 3H), 2.65 (dd, J=15.8, 2.0 Hz, 1H), 2.86 (dd, J=15.8, 7.4 Hz, 1H), 3.25 (s, 3H), 3.27-3.34 (m, 1H), 3.40 (dt, J=10.0, 4.1 Hz, 1H), 3.69 (ddd, J=14.7, 8.7, 4.0 Hz, 1H), 4.10 (dt, J=14.7, 4.0 Hz, 1H), 4.16 (d, J=7.7 Hz, 1H), 5.04 (d, J=12.7 Hz, 1H), 5.09 (d, J=12.7 Hz, 1H), 7.04 (d, J=8.4 Hz, 2H), 7.10 (d, J=8.1 Hz, 2H), 7.15 (d, J=8.4 Hz, 2H), 7.28 (t, J=7.9 Hz, 1H), 7.37 (t, J=7.5 Hz, 2H), 7.43 (d, J=8.1 Hz, 2H), 7.50 (d, J=7.5 Hz, 2H). MS [M+H]$^+$ 490. HRMS: calcd for C$_{29}$H$_{29}$NO$_4$Cl, [M+H]$^+$ 490.1785, found 490.1767.

Example 109: Benzhydryl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 97 mg, 0.3 mmol) was dissolved in anhydrous DMF (1 mL) then cesium carbonate (146 mg, 0.45 mmol) and chlorodiphenylmethane (58 μL, 0.33 mmol) were added. The reaction mixture was stirred at RT for 18 h. The reaction wasn't complete. Chlorodiphenylmethane (58 μL, 0.33 mmol) was added again. The reaction mixture was stirred at 50° C. for 24 h. The solvent was removed under reduced pressure. The residue was dissolved in EtOAc and water. The aqueous phase was extracted with EtOAc. The combined organic layers were washed with brine and dried over MgSO$_4$. The solvents were removed under reduced pressure. Purification of the crude by flash chromatography on silica using a mixture of Cy/EtOAc 9/1 gave the desired benzhydryl 4-(4-chlorophenyl)-1-(2-methoxyethyl)-6-methyl-2-oxo-3,4-dihydropyridine-5-carboxylate as a white powder (107 mg, 73%). $^1$H NMR (300 MHz, CDCl$_3$) δ 2.63 (s, 3H), 2.75 (dd, J=15.7, 2.0 Hz, 1H), 2.96 (dd, J=15.7, 7.7 Hz, 1H), 3.33 (s, 3H), 3.36-3.52 (m, 2H), 3.77 (ddd, J=14.6, 8.6, 4.0 Hz, 1H), 4.18 (dt, J=14.6, 4.0 Hz, 1H), 4.29 (d, J=7.7 Hz, 1H), 6.81-6.87 (m, 3H), 7.08-7.19 (m, 5H), 7.24-7.37 (m, 7H). MS [M+H]$^+$ 490. HRMS: calcd for C$_{29}$H$_{29}$NO$_4$Cl, [M+H]$^+$ 490.1785, found 490.1806.

Example 110: 2-phenylethyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and (2-Bromoethyl)benzene (43 μL, 0.33 mmol) were added. The reaction mixture was stirred for 18 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure. The crude product was purified by flash chromatography using a mixture of Cyclohexane/EtOAc (9/1 to 8/2) as eluent to give the desired 2-phenylethyl 4-(4-chlorophenyl)-1-(2-methoxyethyl)-6-methyl-2-oxo-3,4-dihydropyridine-5-carboxylate as a colorless oil (64 mg, 65%). $^1$H NMR (300 MHz, CDC$_3$) δ 2.56 (s, 3H), 2.69 (dd, J=15.5, 2.1 Hz, 1H), 2.83-2.92 (m, 3H), 3.32 (s, 3H), 3.34-3.38 (m, 1H), 3.45 (dt, J=9.9, 4.0 Hz, 1H), 3.72 (ddd, J=14.6, 8.7, 4.0 Hz, 1H), 4.07 (d, J=7.3 Hz, 1H), 4.17 (dt, J=14.6, 4.0 Hz, 1H), 4.29 (t, J=6.6 Hz, 1H), 4.31 (d, J=6.6 Hz, 1H), 7.02-7.07 (m, 4H), 7.20-7.23 (m, 5H). MS [M+H]$^+$ 428. HRMS: calcd for C$_{24}$H$_{27}$NO$_4$Cl, [M+H]$^+$ 428.1629, found 428.1624.

Example 111: 3-phenylpropyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and (3-Bromopropyl)benzene (38 μL, 0.25 mmol) were added. The reaction mixture was stirred for 3 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure. The crude product was purified by flash chromatography using a mixture of Cyclohexane/EtOAc (9/1 to 8/2) as eluent to give the desired 3-phenylpropyl 4-(4-chlorophenyl)-1-(2-methoxyethyl)-6-methyl-2-oxo-3,4-dihydropyridine-5-carboxylate as a colorless oil (58 mg, 57%). $^1$H NMR (300 MHz, CDCl$_3$) δ 1.72-1.82 (m, 2H), 2.41 (t, J=7.7 Hz, 2H), 2.55 (s, 3H), 2.65 (dd, J=15.7, 2.1 Hz, 1H), 2.85 (dd, J=15.7, 7.4 Hz, 1H), 3.25 (s, 3H), 3.27-3.34 (m, 1H), 3.40 (dt, J=9.9, 3.9 Hz, 1H), 3.68 (ddd, J=14.6, 8.5, 3.9 Hz, 1H), 3.99 (t, J=6.2 Hz, 2H), 4.06-4.14 (m, 2H), 6.92 (d, J=7.6 Hz, 2H), 7.06 (d, J=8.7 Hz, 2H), 7.09-7.13 (m, 1H), 7.14-7.20 (m, 4H). MS [M+H]$^+$ 442. HRMS: calcd for C$_{25}$H$_{29}$NO$_4$Cl, [M+H]$^+$ 442.1785, found 442.1779.

Example 112: Phenacyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and 2-bromoacetophenone (65 mg, 0.33 mmol) were added. The reaction mixture was stirred for 18 h at RT. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure. The crude product was purified by flash chromatography using a mixture of Cyclohexane/EtOAc (9/1 to 8/2) as eluent to give the desired phenacyl 4-(4-chlorophenyl)-1-(2-methoxyethyl)-6-methyl-2-oxo-3,4-dihydropyridine-5-carboxylate as a colorless oil (99 mg, 98%). $^1$H NMR (300 MHz, CDCl$_3$) δ 2.64 (s, 3H), 2.77 (dd, J=15.7, 2.0 Hz, 1H), 3.00 (dd, J=15.7, 7.2 Hz, 1H), 3.31 (s, 3H), 3.33-3.39 (m, 1H), 3.46 (dt, J=9.9, 4.0 Hz, 1H), 3.75 (ddd, J=14.7, 8.8, 4.2 Hz, 1H), 4.19 (dt, J=14.7, 4.0 Hz, 1H), 4.33 (d, J=6.8 Hz, 1H), 5.21 (d, J=16.3 Hz, 1H), 5.42 (d, J=16.3 Hz, 1H), 7.17 (d, J=8.6 Hz, 2H), 7.23 (d, J=8.6 Hz, 2H), 7.45 (t, J=7.0 Hz, 2H), 7.59 (t, J=6.4 Hz, 1H), 7.87 (d, J=7.9 Hz, 2H). MS [M+H]$^+$ 442. HRMS: calcd for C$_{24}$H$_{25}$NO$_5$Cl, [M+H]$^+$ 442.1421, found 442.1422.

Example 113: [cyclohexylmethyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 75 mg, 0.23 mmol) was dissolved in anhydrous DMF (1 mL) then cesium carbonate (114 mg, 0.35 mmol) and cyclohexylmethylbromide (49 µL, 0.35 mmol) were added. The reaction mixture was stirred at 50° C. for 24 h. The solvent was removed under reduced pressure. The residue was dissolved in EtOAc and water. The aqueous phase was extracted with EtOAc. The organic layers were assembled, washed with brine and dried over MgSO$_4$. The solvent was removed under reduced pressure to give the desired [cyclohexylmethyl 4-(4-chlorophenyl)-1-(2-methoxyethyl)-6-methyl-2-oxo-3,4-dihydropyridine-5-carboxylate as a yellowish oil (95 mg, 99%). $^1$H NMR (300 MHz, CDCl$_3$) δ 0.71-1.18 (m, 5H), 1.46-1.63 (m, 6H), 2.61 (s, 3H), 2.71 (dd, J=15.7, 2.3 Hz, 1H), 2.92 (dd, J=15.7, 7.5 Hz, 1H), 3.32 (s, 3H), 3.38 (ddd, J=9.8, 8.5, 3.7 Hz, 1H), 3.47 (dt, J=9.8, 3.9 Hz, 1H), 3.75 (ddd, J=14.6, 8.5, 3.9 Hz, 1H), 3.81-3.91 (m, 2H), 4.13-4.21 (m, 2H), 7.11 (d, J=8.5 Hz, 2H), 7.22 (d, J=8.5 Hz, 2H). MS [M+H]$^+$ 420. HRMS: calcd for C$_{23}$H$_{31}$NO$_4$Cl, [M+H]$^+$ 420.1942, found 420.1937.

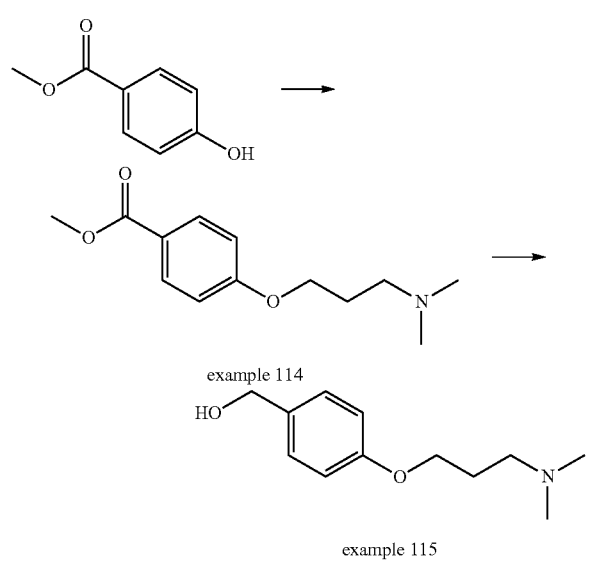

example 114 example 115

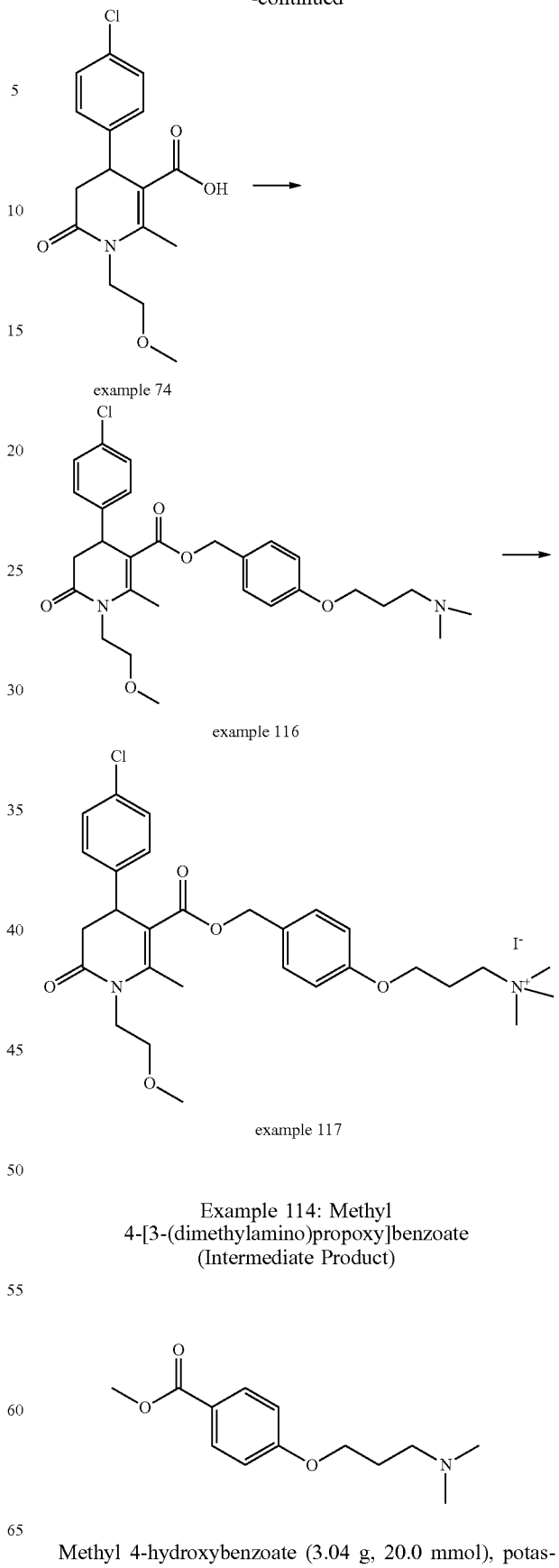

example 74 example 116 example 117

Example 114: Methyl 4-[3-(dimethylamino)propoxy]benzoate (Intermediate Product)

Methyl 4-hydroxybenzoate (3.04 g, 20.0 mmol), potassium carbonate (4.14 g, 30.0 mmol) and 3-dimethylaminopropyl chloride hydrochloride (4.74 g, 30.0 mmol) were dissolved in anh. DMF (30 mL). The reaction mixture was stirred at 60° C. for 18 h. The reaction was uncomplete; potassium carbonate (4.14 g, 30.0 mmol) and 3-dimethylaminopropyl chloride hydrochloride (4.74 g, 30.0 mmol) were added again. The reaction mixture was stirred for a further 24 h at 60° C. Removal of the solvent under reduced pressure afforded the desired methyl 4-[3-(dimethylamino)propoxy]benzoate (1.6 g, 34%) that was used in the next step without purification.

Example 115: [4-[3-(dimethylamino)propoxy]phenyl]methanol (Intermediate Product)

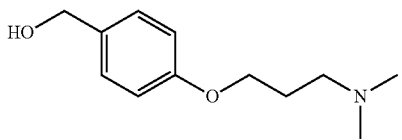

Methyl 4-[3-(dimethylamino)propoxy]benzoate (474 mg, 2.0 mmol) was dissolved in anh. THF (7 mL). The reaction mixture was cooled to 0° C. A 1 M solution of lithium aluminium hydride in diethyl ether (2.4 mL, 2.4 mmol) was added slowly. The reaction mixture was then stirred for 5 h at RT. Water was added and the aqueous phase was extracted with diethyl ether. The organic phases were assembled, washed with brine and dried over MgSO$_4$. Removal of the solvent under reduced pressure gave the desired [4-[3-(dimethylamino)propoxy]phenyl]methanol as a white oil (208 mg, 50%). $^1$H NMR (300 MHz, CDCl$_3$) δ 2.00 (q$^t$, J=6.8 Hz, 2H), 2.31 (s, 6H), 2.52 (t, J=7.2 Hz, 2H), 4.02 (t, J=7.2 Hz, 2H), 4.02 (t, J=6.2 Hz, 2H), 4.62 (s, 2H), 6.89 (d, J=8.8 Hz, 2H), 7.28 (d, J=8.8 Hz, 2H).

Example 116: [4-[3-(dimethylamino)propoxy]phenyl]methyl 4-(4-chlorophenyl)-1-(2-methoxyethyl)-6-methyl-2-oxo-3,4-dihydropyridine-5-carboxylate 4-(4-chlorophenyl)-1-(2-methoxyethyl)-6-methyl-2-oxo-3,4-dihydropyridine-5-carboxylic acid (example 74, 330 mg, 1.02 mmol), [4-[3-(dimethylamino)propoxy]phenyl]methanol (194 mg, 0.93 mmol), EDCI (213 mg, 1.12 mmol) and DMAP (113 mg, 0.93 mmol) were dissolved in anh. DCM (4 mL). The reaction mixture was stirred for 18 h at RT. An aqueous solution of NaHCO$_3$ 5% was added. The aqueous phase was extracted with DCM. The organic phases were assembled and dried over MgSO$_4$. The solvent was removed under reduced pressure. Purification of the crude by flash chromatography on silica using a mixture of DCM/MeOH 97/3 gave the desired [4-[3-(dimethylamino)propoxy]phenyl]methyl 4-(4-chlorophenyl)-1-(2-methoxyethyl)-6-methyl-2-oxo-3,4-dihydropyridine-5-carboxylate as a colorless oil (87 mg, 18%). $^1$H NMR (300 MHz, CDCl$_3$) δ 1.94 (qt, J=6.8 Hz, 2H), 2.24 (s, 6H), 2.43 (t, J=7.3 Hz, 2H), 2.58 (s, 3H), 2.69 (dd, J=15.9, 2.2 Hz, 1H), 2.89 (dd, J=15.9, 7.5 Hz, 1H), 3.30 (s, 3H), 3.31-3.48 (m, 2H), 3.72 (ddd, J=14.3, 8.2, 3.8 Hz, 1H), 3.99 (t, J=6.2 Hz, 2H), 4.10-4.20 (m, 2H), 5.01 (s, 2H), 6.79 (d, J=8.7 Hz, 2H), 7.04 (d, J=8.7 Hz, 2H), 7.07 (d, J=8.4 Hz, 2H), 7.20 (d, J=8.4 Hz, 2H). $^{13}$C NMR (75 MHz, CDCl$_3$) δ 17.0, 27.4, 36.7, 38.6, 41.7, 45.4, 56.2, 58.7, 65.8, 66.1, 70.9, 110.0, 114.2, 127.9, 128.3, 128.6, 129.4, 132.4, 139.7, 150.8, 158.8, 166.9, 168.8. MS [M+H]$^+$ 515. HRMS: calcd for C$_{28}$H$_{36}$N$_2$O$_5$Cl, [M+H]$^+$ 515.2313, found 515.2307.

Example 117: 3-[4-[[4-(4-chlorophenyl)-1-(2-methoxyethyl)-6-methyl-2-oxo-3,4-dihydropyridine-5-carbonyl]oxymethyl]phenoxy]propyl-trimethyl-ammonium; iodide

[4-[3-(dimethylamino)propoxy]phenyl]methyl 4-(4-chlorophenyl)-1-(2-methoxyethyl)-6-methyl-2-oxo-3,4-dihydropyridine-5-carboxylate (example 116) 27 mg, 0.05 mmol) was dissolved in anh. DMF (150 μL). Iodomethane (8 μL, 0.12 mmol) was added. The reaction mixture was stirred at RT for 24 h. The solvent was removed under reduced pressure to afford the desired 3-[4-[[4-(4-chlorophenyl)-1-(2-m ethoxyethyl)-6-methyl-2-oxo-3,4-dihydropyridine-5-carbonyl]oxymethyl]phenoxy]propyl-trimethylammonium iodide as a colorless oil (34 mg, 100%). $^1$H NMR (300 MHz, CDCl$_3$) δ 2.24-2.36 (m, 2H), 2.60 (s, 3H), 2.63 (dd, J=15.4, 2.0 Hz, 1H), 2.98 (dd, J=15.4, 7.5 Hz, 1H), 3.22 (s, 9H), 3.30-3.33 (m, 5H), 3.33-3.40 (m, 1H), 3.46 (dt, J=9.7, 4.1 Hz, 1H), 3.57-3.67 (m, 2H), 3.81 (ddd, J=14.8, 8.4, 3.8 Hz, 1H), 4.11 (t, J=5.9 Hz, 2H), 4.12-4.18 (m, 1H), 4.20 (d, J=7.5 Hz, 1H), 4.98 (d, J=12.1 Hz, 1H), 5.07 (d, J=12.1 Hz, 1H), 6.85 (d, J=8.8 Hz, 2H), 7.08 (d, J=8.8 Hz, 2H), 7.14 (d, J=8.5 Hz, 2H), 7.25 (d, J=8.5 Hz, 2H). MS [M+H]$^+$ 529. HRMS: calcd for C$_{29}$H$_{38}$N$_2$O$_5$Cl, [M+H]$^+$ 529.2469, found 529.2458.

Example 118: 1-(chloromethyl)-4-(2-methoxyethoxy)benzene (Intermediate Product)

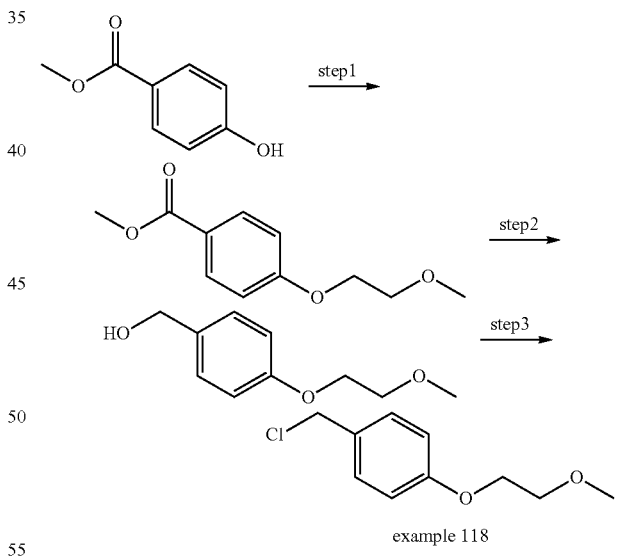

example 118

Step 1: [4-(2-methoxyethoxy)phenyl]methanol 4-hydroxybenzoic methyl ester (5.0 mmol, 760 mg) was dissolved in DMF (6 mL), potassium carbonate (7.5 mmol, 1.036 g) was added then bromoethylmethyl ether (7.5 mmol, 704 μL). The reaction mixture was stirred at 60° C. for 18 h. The solvents were removed under reduced pressure. Water was added to the residue. The aqueous phase was extracted with EtOAc. The organic phase were assembled, washed with brine and dried over Na$_2$SO$_4$. The solvents were removed under reduced pressure to afford the desired methyl 4-(2-methoxyethoxy)benzoate as a colorless oil (m=960 mg, 91%).

Step 2: 4-(2-methoxyethoxy)phenyl]methanol

Methyl 4-(2-methoxyethoxy)benzoate was dissolved in anhydrous DMF (15 mL). The reaction mixture was cooled to 0° C. and a solution of LiAlH$_4$ in THF (1 M, 4.6 mL) was added slowly. The reaction mixture was stirred at 0° C. for 3 h. The reaction was quenched by slow addition of an aqueous solution of HCl 1N. The organic phase was extracted with Et$_2$O, washed with brine and dried over Na$_2$SO$_4$. The solvents were removed under reduced pressure to afford the desired [4-(2-methoxyethoxy)phenyl]methanol as a colorless oil (m=554 mg, 67%) $^1$H NMR (300 MHz, CDCl$_3$) δ 3.46 (s, 3H), 3.74-3.78 (m, 2H), 4.11-4.16 (m, 2H), 4.63 (s, 2H), 6.93 (d, J=8.6 Hz, 2H), 7.29 (d, J=8.6 Hz, 2H).

Step 3: 1-(chloromethyl)-4-(2-methoxyethoxy)benzene

Thionyl chloride (109 μL, 1.5 mmol) was added to benzotriazole (179 mg, 1.5 mmol). The resulting yellow solution was dissolved in dry DCM (2 mL). After 5 min, this solution was added slowly to a solution of [4-(2-methoxyethoxy)phenyl]methanol (218 mg, 1.2 mmol) in DCM (8 mL). The benzotriazole salt started to precipitate. After 20 min of reaction, the salt was filtered. The organic phase was washed with water (10 mL) and NaOH solution (0.05 M, 10 mL). The organic phase was dried on Na$_2$SO$_4$ and the solvents were removed under reduced pressure to give the desired 1-(chloromethyl)-4-(2-methoxyethoxy)benzene as a yellow oil (190 mg, 79%).
$^1$H NMR (300 MHz, CDCl$_3$) δ 3.46 (s, 3H), 3.74-3.79 (m, 2H), 4.11-4.16 (m, 2H), 4.57 (s, 2H), 6.92 (d, J=8.7 Hz, 2H), 7.31 (d, J=8.7 Hz, 2H).

Example 119: [4-(2-methoxyethoxy)phenyl]methyl 4-(4-chlorophenyl)-1-(2-methoxyethyl)-6-methyl-2-oxo-3,4-dihydropyridine-5-carboxylate 1-(chloromethyl)-4-(2-methoxyethoxy)benzene (180 mg, 0.9 mmol) and 4-(4-chlorophenyl)-1-(2-methoxyethyl)-2-oxo-3,4-dihydropyridine-5-carboxylic acid (example 74, 194 mg, 0.6 mmol) were dissolved in anh. DMF (2 mL). Cesium carbonate (293 mg, 0.9 mmol) was added and the reaction mixture stirred at RT. for 4 h. The solvents were removed. Water was added and the aqueous phase was extracted with EtOAc. The organic layers were assembled, washed with brine and dried over Na$_2$SO$_4$. The solvents were removed under reduced pressure. Purification of the crude by flash chromatography using a mixture Cy/EA (95/5) as eluent gave the desired [4-(2-methoxyethoxy)phenyl]methyl 4-(4-chlorophenyl)-1-(2-methoxyethyl)-6-methyl-2-oxo-3,4-dihydropyridine-5-carboxylate as a white powder (123 mg, 42%). $^1$H NMR (300 MHz, CDCl$_3$) δ 2.59 (s, 3H), 2.70 (dd, J=15.7, 2.2 Hz, 1H), 2.91 (dd, J=15.7, 7.6 Hz, 1H), 3.31 (s, 3H), 3.30-3.54 (m, 2H), 3.46 (s, 3H), 3.68-3.80 (m, 3H), 4.08-4.22 (m, 4H), 5.02 (s, 2H), 6.83 (d, J=8.5 Hz, 2H), 7.02-7.12 (m, 4H), 7.21 (d, J=8.5 Hz, 2H). $^{13}$C NMR (75 MHz, CDCl$_3$) δ 17.1, 36.8, 38.7, 41.8, 58.8, 59.2, 65.9, 67.2, 71.0, 71.0, 110.0, 114.4, 128.3, 128.4, 128.7, 129.4, 132.5, 139.8, 150.9, 158.6, 167.0, 168.9. MS [M+H]$^+$ 488; HRMS: calcd for C$_{26}$H$_{31}$NO$_6$Cl, [M+H]$^+$ 488.1840, found 488.1820.

TABLE 9

| Examples | R18 | R19 |
|---|---|---|
| 121 | Pr | 2-OMe-Bn |
| 123 | 4-Ph-Ph | Bn |
| 125 | 4-CN-Ph | 2-OMe-Bn |
| 127 | 3,4-diCl-Ph | 2-OMe-Bn |
| 129 | 2,4-diCl-Ph | 2-OMe-Bn |
| 131 | 2,5-diCl-Ph | 2-OMe-Bn |
| 133 | 4-Pyridyl | 2-OMe-Bn |

Example 120: (2-methoxyphenyl)methyl 6-methyl-2-oxo-4-propyl-3,4-dihydro-1H-pyridine-5-carboxylate (Intermediate Product)

The (2-methoxyphenyl)methyl 3-oxobutanoate (444 mg, 2.0 mmol) was dissolved in acetic acid (2 mL). n-butanal (180 μL, 2.0 mmol), meldrum acid (288 mg, 2.0 mmol) and ammonium acetate (231 mg, 3.0 mmol) were added and the reaction mixture was stirred at 110° C. for 18 h. The reaction mixture was cooled to RT. The solvent was removed under reduced pressure. Purification of the crude by flash chromatography on silica using as eluent a mixture of Cyclohexane/EtOAc (85/15) gave the desired (2-methoxyphenyl)methyl 6-methyl-2-oxo-4-propyl-3,4-dihydro-1H-pyridine-5-carboxylate as a yellow oil (42 mg, 6%). $^1$H NMR (300 MHz, CDCl$_3$) δ 0.84 (t, J=6.7 Hz, 3H), 1.13-1.54 (m, 4H), 2.31 (s, 3H), 2.46 (dd, J=16.6, 1.8 Hz, 1H), 2.57 (dd, J=16.6, 6.8 Hz, 1H), 2.94-3.05 (m, 1H), 3.84 (s, 3H), 5.21 (d, J=12.7 Hz, 1H), 5.27 (d, J=12.7 Hz, 1H), 6.89 (d, J=8.2 Hz, 1H), 6.95 (td, J=7.1, 0.9 Hz, 1H), 7.26-7.36 (m, 2H), 8.43 (brs, 1H). $^{13}$C NMR (75 MHz, CDC$_3$) δ 13.9, 19.0, 19.7, 31.9, 34.9, 55.3, 61.6, 109.1, 110.3, 120.3, 124.6, 129.4, 129.6, 145.0, 157.6, 167.1, 172.3. MS [M+H]$^+$ 318. HRMS: calcd for C18H24NO4, [M+H]$^+$ 318.1705, found 318.1708.

Example 121: (2-methoxyphenyl)methyl 1-(2-methoxyethyl)-6-methyl-2-oxo-4-propyl-3,4-dihydropyridine-5-carboxylate (2-methoxyphenyl)methyl 6-methyl-2-oxo-4-propyl-3,4-dihydro-1H-pyridine-5-carboxylate (42 mg, 0.13 mmol) was dissolved in anhydrous DMF (1 mL). Cesium carbonate (85 mg, 0.26 mmol) and 2-bromoethyl methyl ether (25 μL, 0.26 mmol) were added. The reaction mixture was stirred at 60° C. for 4 days. The same amount of cesium carbonate (85 mg, 0.26 mmol) and 2-bromoethyl methyl ether (25 μL, 0.26 mmol) were added everyday. After 4 days at 60° C., the DMF was removed under reduced pressure. The residue was diluted in water. The aqueous phase was extracted by EtOAc and the combined organic layers were washed with brine and dried over MgSO$_4$. The solvent was removed under reduced pressure. Purification of the crude by flash chromatography using a mixture of Cyclohexane/EtOAc (8/2) as eluent gave the desired (2-methoxyphenyl)methyl 1-(2-methoxyethyl)-

6-methyl-2-oxo-4-propyl-3,4-dihydropyridine-5-carboxylate as a colorless oil (32 mg, 67%). $^1$H NMR (300 MHz, CDCl$_3$) δ 0.82 (t, J=7.0 Hz, 3H), 1.10-1.50 (m, 4H), 2.43 (s, 3H), 2.49 (dd, J=15.7, 2.4 Hz, 1H), 2.57 (dd, J=15.7, 5.9 Hz, 1H), 2.87-2.98 (m, 1H), 3.30 (s, 3H), 3.40-3.55 (m, 2H), 3.69 (ddd, J=14.4, 6.5, 5.1 Hz, 1H), 3.84 (s, 3H), 4.13 (dt, J=14.4, 5.6 Hz, 1H), 5.19 (d, J=12.8 Hz, 1H), 5.26 (d, J=12.8 Hz, 1H), 6.89 (d, J=8.2 Hz, 1H), 6.95 (td, J=7.5, 0.9 Hz, 1H), 7.27-7.37 (m, 2H). $^{13}$C NMR (75 MHz, CDC$_3$) δ 14.0, 16.9, 19.7, 31.3, 34.1, 35.8, 41.5, 55.2, 58.8, 61.7, 70.7, 110.3, 113.6, 120.3, 124.4, 129.4, 129.6, 147.7, 157.5, 167.7, 170.4. MS [M+H]$^+$ 376. HRMS: calcd for C$_{21}$H$_{30}$NO$_5$, [M+H]$^+$ 376.2124, found 376.2135.

Example 122: Benzyl 4-(4-bromophenyl)-1-(2-methoxyethyl)-6-methyl-2-oxo-3,4-dihydropyridine-5-carboxylate (Intermediate Product)

Benzyl 4-(4-bromophenyl)-6-methyl-2-oxo-3,4-dihydro-1H-pyridine-5-carboxylate (2.04 g, 5.1 mmol) was dissolved in anhydrous DMF (20 mL). Cesium carbonate (3.31 mg, 10.2 mmol) and (bromoethyl)methyl ether (960 µL, 10.2 mmol) were added. The reaction mixture was stirred at 60° C. for 24 h. The DMF was removed under reduced pressure. The residue was diluted in water and extracted by EtOAc. The organic layers were assembled, washed with brine and dried over MgSO$_4$. Removal of the solvent under reduced pressure gave the desired benzyl 4-(4-bromophenyl)-1-(2-methoxyethyl)-6-methyl-2-oxo-3,4-dihydropyridine-5-carboxylate as a colorless oil (2.08 g, 89%). $^1$H NMR (300 MHz, CDCl$_3$) δ 2.61 (s, 3H), 2.71 (dd, J=15.8, 2.3 Hz, 1H), 2.91 (dd, J=15.8, 7.7 Hz, 1H), 3.32 (s, 3H), 3.34-3.51 (m, 2H), 3.75 (ddd, J=14.8, 8.5, 2.0 Hz, 1H), 4.12-4.21 (m, 2H), 5.06 (d, J=12.7 Hz, 1H), 5.12 (d, J=12.7 Hz, 1H), 7.04 (d, J=8.4 Hz, 2H), 7.07-7.14 (m, 2H), 7.25-7.30 (m, 3H), 7.36 (d, J=8.4 Hz, 2H). MS [M+H]$^+$ 458. HRMS: calcd for C$_{23}$H$_{25}$NO$_4$Br, [M+H]$^+$ 458.0967, found 458.0970.

Example 123: Benzyl 1-(2-methoxyethyl)-6-methyl-2-oxo-4-(4-phenylphenyl)-3, 4-dihydropyridine-5-carboxylate Benzyl 4-(4-bromophenyl)-1-(2-methoxyethyl)-6-methyl-2-oxo-3,4-dihydropyridine-5-carboxylate (120 mg, 0.26 mmol), phenylboronic acid (63 mg, 0.52 mmol), sodium carbonate (41 mg, 0.39 mmol) and PdCl$_2$dppf (21 mg, 0.026 mmol) were dissolved in a mixture DME/water 1/1 (1 mL). The reaction mixture was warmed at 115° C. under microwaves for 30 min. The reaction mixture was cooled to r.t. then, filtered on celite and washed with Et$_2$O. The organic phase was washed with a saturated aqueous solution of NaHCO$_3$. The aqueous phase was extracted with EtOAc. The organic phases were combined, washed with brine and dried over MgSO$_4$. The solvents were removed under reduced pressure. Purification of the crude by flash chromatography using a mixture of Cyclohexane/EtOAc (85/15) as eluent gave the desired benzyl 1-(2-methoxyethyl)-6-methyl-2-oxo-4-(4-phenylphenyl)-3,4-dihydropyridine-5-carboxylate as a white powder (56 mg, 46%). $^1$H NMR (300 MHz, CDCl$_3$) δ 2.63 (s, 3H), 2.80 (dd, J=15.6, 2.2 Hz, 1H), 2.95 (dd, J=15.6, 7.4 Hz, 1H), 3.32 (s, 3H), 3.35-3.52 (m, 2H), 3.76 (ddd, J=14.7, 8.3, 4.0 Hz, 1H), 4.18 (dd, J=14.6, 6.1 Hz, 1H), 4.29 (dd, J=7.4, 2.2 Hz, 1H), 5.09 (d, J=12.7 Hz, 1H), 5.15 (d, J=12.7 Hz, 1H), 7.08-7.14 (m, 2H), 7.22-7.26 (m, 5H), 7.29-7.36 (m, 1H), 7.38-7.50 (m, 4H), 7.52-7.58 (m, 2H). $^{13}$C NMR (75 MHz, CDCl$_3$) δ 17.2, 37.0, 38.8, 41.9, 58.9, 65.9, 71.1, 110.2, 127.0, 127.1, 127.4, 127.5, 127.8, 128.3, 128.7, 136.1, 139.8, 140.2, 140.9, 150.9, 167.1, 169.2. MS [M+H]$^+$ 456 HRMS: calcd for C$_{29}$H$_{30}$NO$_4$, [M+H]$^+$ 456.2175, found 456.2177.

Example 124: (2-methoxyphenyl)methyl 4-(4-cyanophenyl)-6-methyl-2-oxo-3,4-dihydro-1H-pyridine-5-carboxylate (Intermediate Product)

The (2-methoxyphenyl)methyl 3-oxobutanoate (667 mg, 3.0 mmol) was dissolved in acetic acid (3 mL). 4-cyanobenzaldehyde (393 mg, 3.0 mmol), meldrum acid (432 mg, 3.0 mmol) and ammonium acetate (338 mg, 4.5 mmol) were added and the reaction mixture was stirred at 110° C. for 18 h. The reaction mixture was cooled to RT. The solvent was removed under reduced pressure. The crude was precipitated in EtOH, cooled to 0° C. and filtered to give the desired (2-methoxyphenyl)methyl 4-(4-cyanophenyl)-6-methyl-2-oxo-3,4-dihydro-1H-pyridine-5-carboxylate as a white powder (476 mg, 42%). $^1$H NMR (300 MHz, CDCl$_3$) δ 2.43 (s, 3H), 2.64 (d, J=16.7 Hz, 1H), 2.97 (dd, J=16.7 Hz, 1H), 3.74 (s, 3H), 4.31 (d, J=8.4 Hz, 1H), 5.09 (d, J=12.4 Hz, 1H), 5.21 (d, J=12.4 Hz, 1H), 6.81-6.89 (m, 2H), 7.04 (d, J=7.5 Hz, 1H), 7.26 (d, J=8.5 Hz, 2H), 7.30 (dd, J=8.0, 1.5 Hz, 1H), 7.53 (d, J=8.5 Hz, 2H). $^{13}$C NMR (75 MHz, CDCl$_3$) δ 18.9, 37.3, 38.0, 55.1, 61.7, 105.9, 110.2, 110.7, 118.6, 120.2, 123.9, 127.6, 129.5, 129.6, 132.5, 147.2, 147.7, 157.4. MS [M−H]$^-$ 375

Example 125: (2-methoxyphenyl)methyl 4-(4-cyanophenyl)-1-(2-methoxyethyl)-6-methyl-2-oxo-3,4-dihydropyridine-5-carboxylate o-methoxybenzyl 4-(4-cyanophenyl)-6-methyl-2-oxo-3,4-dihydro-1H-pyridine-5-carboxylate (113 mg, 0.30 mmol) was dissolved in anhydrous DMF (1 mL). Cesium carbonate (195 mg, 0.60 mmol) and 2-bromoethyl methyl ether (56 µL, 0.60 mmol) were added. The reaction mixture was stirred at 60° C. for 18 h. The reaction was incomplete and Cesium carbonate (39 mg, 0.12 mmol) and 2-bromoethyl methyl ether (11 µL, 0.12 mmol) were added. The reaction mixture was stirred at 60° C. for 18 h. The DMF was removed under reduced pressure.

The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (100/0 to 95/5) as eluent to give the desired (2-methoxyphenyl)methyl 4-(4-cyanophenyl)-1-(2-methoxyethyl)-6-methyl-2-oxo-3, 4-dihydropyridine-5-carboxylate as a colorless oil (102 mg, 78%). $^1$H NMR (300 MHz, CDC$_3$) δ 2.62 (s, 3H), 2.72 (dd, J=15.9, 2.2 Hz, 1H), 2.96 (dd, J=15.9, 7.7 Hz, 1H), 3.31 (s, 3H), 3.33-3.50 (m, 2H), 3.73 (s, 3H), 3.75 (ddd, J=14.6, 8.5, 3.8 Hz, 1H), 4.18 (dt, J=14.6, 3.8 Hz, 1H), 4.26 (d, J=7.7 Hz, 1H), 5.10 (d, J=13.1 Hz, 1H), 5.18 (d, J=13.1 Hz, 1H), 6.79-6.87 (m, 2H), 6.99 (dd, J=7.8, 1.9 Hz, 1H), 7.23-7.32 (m, 3H), 7.52 (d, J=8.3 Hz, 2H). $^{13}$C NMR (75 MHz, CDC$_3$) δ 17.0, 37.5, 38.2, 41.8, 55.1, 58.8, 61.9, 70.9, 109.4, 110.2, 110.6, 118.7, 120.2, 124.0, 127.9, 129.2, 129.4, 132.3, 147.0, 151.2, 157.3, 166.8, 168.5. MS [M+H]$^+$ 435; HRMS: calcd for C25H27N2O5Cl, [M+H]$^+$ 435.1920, found 435.1918.

Example 126: 4-(3,4-dichlorophenyl)-6-methyl-2-oxo-3,4-dihydro-1H-pyridine-5-carboxylate (Intermediate Product)

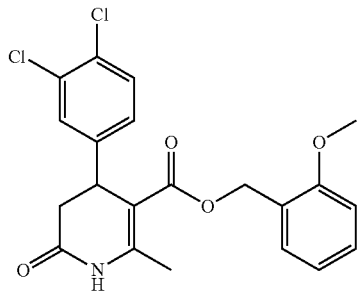 [SMILES: COc1ccccc1COC(=O)C1=C(C)NC(=O)CC1c1ccc(Cl)c(Cl)c1]

3,4-dichlorobenzaldehyde (3.0 mmol, 525 g), meldrum acid (3.0 mmol, 432 g), o-methoxybenzyl acetoacetate (3.0 mmol, 666 mg) and ammonium acetate (4.5 mmol, 338 mg) were dissolved in acetic acid (3 mL). The reaction mixture was stirred at 110° C. for 18 h. The solvent was removed. The crude didn't precipitate in EtOH. The crude has been purified by flash chromatography (Cy/EA (85/15) and precipitated in EtOH to give the desired (2-methoxyphenyl) methyl 4-(3,4-dichlorophenyl)-6-methyl-2-oxo-3,4-dihydro-1H-pyridine-5-carboxylate as a white powder (384 mg, 30%). $^1$H NMR (300 MHz, CDCl$_3$) δ 2.43 (s, 3H), 2.63 (dd, J=16.7, 1.3 Hz, 1H), 2.94 (dd, J=16.7, 8.1 Hz, 1H), 3.76 (s, 3H), 4.23 (d, J=7.7 Hz, 1H), 5.12 (d, J=12.6 Hz, 1H), 5.22 (d, J=12.6 Hz, 1H), 6.86 (d, J=8.3 Hz, 1H), 6.88 (td, J=7.4, 1.0 Hz, 1H), 6.99 (dd, J=8.5, 2.3 Hz, 1H), 7.08 (dd, J=7.4, 1.7 Hz, 1H), 7.22 (d, J=2.0 Hz, 1H), 7.26-7.33 (m, 2H), 8.34 (brs, 1H). $^{13}$C NMR (75 MHz, CDCl$_3$) δ 19.1, 37.3, 37.7, 55.2, 61.8, 106.3, 110.3, 120.3, 124.0, 126.2, 128.9, 129.6, 130.6, 130.9, 132.6, 142.5, 147.0, 157.4, 166.3, 170.3. MS [M−H]$^-$ 418.

Example 127: (2-methoxyphenyl)methyl 4-(3,4-dichlorophenyl)-1-(2-methoxyethyl)-6-methyl-2-oxo-3,4-dihydropyridine-5-carboxylate o-methoxybenzyl 4-(3, 4-dichlorophenyl)-6-methyl-2-oxo-3,4-dihydro-1H-pyridine-5-carboxylate (126 mg, 0.30 mmol) was dissolved in anhydrous DMF (1 mL). Cesium carbonate (195 mg, 0.60 mmol) and 2-bromoethyl methyl ether (56 μL, 0.60 mmol) were added. The reaction mixture was stirred at 60° C. for 18 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (100/0 to 85/15) as eluent to give the desired (2-methoxyphenyl)methyl 4-(3,4-dichlorophenyl)-1-(2-methoxyethyl)-6-methyl-2-oxo-3,4-dihydropyridine-5-carboxylate as a colorless oil (102 mg, 71%). $^1$H NMR (300 MHz, CDC$_3$) 2.63 (s, 3H), 2.71 (dd, J=15.7, 2.0 Hz, 1H), 2.93 (dd, J=15.7, 7.5 Hz, 1H), 3.33 (s, 3H), 3.37-3.51 (m, 2H), 3.74 (s, 3H), 3.70-3.81 (m, 1H), 4.15-4.26 (m, 2H), 5.11 (d, J=12.8 Hz, 1H), 5.20 (d, J=12.8 Hz, 1H), 6.81-6.90 (m, 2H), 6.98-7.06 (m, 2H), 7.21-7.32 (m, 3H). $^{13}$C NMR (75 MHz, CDCl$_3$) δ 17.1, 36.8, 38.4, 41.9, 55.2, 59.0, 61.9, 71.0, 109.6, 110.2, 120.2, 124.1, 126.5, 129.1, 129.3, 129.4, 130.4, 130.7, 132.4, 141.8, 151.1, 157.3, 166.9, 168.7. MS [M+H]$^+$ 478; HRMS: calcd for C$_{24}$H$_{26}$NO$_5$Cl$_2$, [M+H]$^+$ 478.1188, found 478.1190.

Example 128: (2-methoxyphenyl)methyl 4-(2,4-dichlorophenyl)-6-methyl-2-oxo-3,4-dihydro-1H-pyridine-5-carboxylate (Intermediate Product)

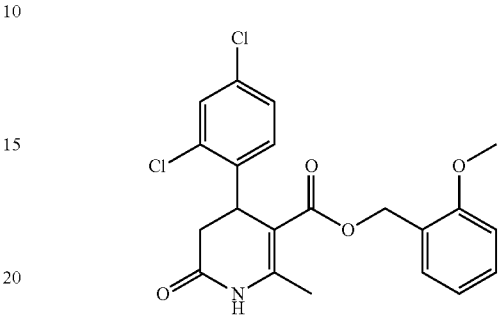

2,4-dichlorobenzaldehyde (3.0 mmol, 525 mg), meldrum acid (3.0 mmol, 432 mg), the o-methoxybenzyl acetoacetate (3.0 mmol, 666 mg) and ammonium acetate (4.5 mmol, 338 g) were dissolved in acetic acid (3 mL). The reaction mixture was stirred at 110° C. for 18 h. The solvent was removed. The crude was precipitated in EtOH, cooled to 0° C. and filtered to give the desired (2-methoxyphenyl)methyl 4-(2, 4-dichlorophenyl)-6-methyl-2-oxo-3,4-dihydro-1H-pyridine-5-carboxylate as a white powder (600 mg, 48%). $^1$H NMR (300 MHz, CDC$_3$) δ 2.48 (s, 3H), 2.67 (dd, J=16.9, 1.5 Hz, 1H), 2.92 (dd, J=16.9, 8.7 Hz, 1H), 3.73 (s, 3H), 4.70 (d, J=8.7 Hz, 1H), 5.06 (d, J=12.9 Hz, 1H), 5.70 (d, J=12.9 Hz, 1H), 6.78-6.87 (m, 2H), 6.94-7.01 (m, 2H), 7.13 (dd, J=8.5, 2.3 Hz, 1H), 725 (td, J=8.0, 1.6 Hz, 1H), 7.37 (d, J=2.0 Hz, 1H), 8.73 (brs, 1H). $^{13}$C NMR (75 MHz, CDC$_3$) δ 18.8, 34.7, 36.1, 55.1, 61.6, 105.6, 110.1, 120.1, 124.1, 127.3, 128.2, 128.8, 129.2, 129.8, 133.3, 134.0, 137.2, 148.0, 157.1, 166.0, 170.7. MS [M−H]$^-$ 418

Example 129: (2-methoxyphenyl)methyl 4-(2,4-dichlorophenyl)-1-(2-methoxyethyl)-6-methyl-2-oxo-3,4-dihydropyridine-5-carboxylate o-methoxybenzyl 4-(2,4-dichlorophenyl)-6-methyl-2-oxo-3,4-dihydro-1H-pyridine-5-carboxylate (126 mg, 0.30 mmol) was dissolved in anhydrous DMF (1 mL). Cesium carbonate (195 mg, 0.60 mmol) and 2-bromoethyl methyl ether (56 μL, 0.60 mmol) were added. The reaction mixture was stirred at 60° C. for 18 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (100/0 to 85/15) as eluent to give the desired (2-methoxyphenyl)methyl 4-(2,4-dichlorophenyl)-1-(2-methoxyethyl)-6-methyl-2-oxo-3,4-dihydropyridine-5-carboxylate as a colorless oil (111 mg, 77%). $^1$H NMR (300 MHz, CDCl$_3$) δ 2.67 (s, 3H), 2.78 (dd, J=15.9, 2.1 Hz, 1H), 2.89 (dd, J=15.9, 7.6 Hz, 1H), 3.38 (s, 3H), 3.43-3.53 (m, 2H), 3.73 (s, 3H), 3.74-3.85 (m, 1H), 4.20 (td, J=14.6, 3.6 Hz, 1H), 4.62 (d, J=7.6 Hz, 1H), 5.09 (d, J=12.9 Hz, 1H), 5.15 (d, J=12.9 Hz, 1H), 6.78-6.86 (m, 2H), 6.96 (d, J=7.4 Hz, 1H), 7.05-7.15 (m, 2H), 7.21-7.31 (m, 1H), 7.36 (d, J=1.8 Hz, 1H). $^{13}$C NMR (75 MHz, CDCl$_3$) δ 17.0, 26.9, 34.4, 36.5, 41.9, 55.1, 58.9, 61.7, 71.2, 109.1, 110.0, 120.1, 124.2, 127.1, 128.7, 128.9, 129.1, 129.6, 133.2, 134.3, 136.6, 152.1, 157.1, 166.7, 168.7. MS [M+H]$^+$ 478. HRMS: calcd for C$_{24}$H$_{26}$NO$_5$Cl$_2$, [M+H]$^+$ 478.1188, found 478.1173.

Example 130: o-methoxybenzyl 4-(2,4-dichlorophenyl)-6-methyl-2-oxo-3,4-dihydro-1H-pyridine-5-carboxylate (Intermediate Product)

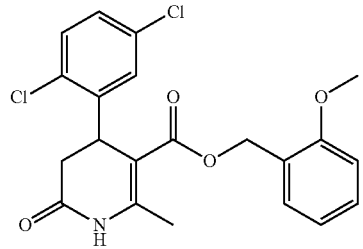 [SMILES: COc1ccccc1COC(=O)C1=C(C)NC(=O)CC1c1cc(Cl)ccc1Cl]

2-methoxybenzoyl acetoacetate (3.0 mmol, 666 mg) was dissolved in acetic acid (3 mL). Meldrum acid (3.0 mmol, 432 mg), 2,5-dichlorobenzaldehyde (3.0 mmol, 432 mg) and ammonium acetate (4.5 mmol, 338 mg) were added and the reaction mixture was stirred for 18 h at 110° C. The reaction mixture was cooled at RT. The solvent was removed under reduced pressure. The residue was dissolved in the minimum of ethanol. The mixture was sonicated with ultrasound and the product precipitated. The mixture was cooled and the precipitate was filtered, then washed with cold ethanol to give the desired o-methoxybenzyl 4-(2,4-dichlorophenyl)-6-methyl-2-oxo-3, 4-dihydro-1H-pyridine-5-carboxylate as a white powder (686 mg, 54%). $^1$H NMR (300 MHz, CDCl$_3$) δ 2.50 (s, 3H), 2.70 (d, J=16.8 Hz, 1H), 2.94 (dd, J=16.8, 8.7 Hz, 1H), 3.74 (s, 3H), 4.72 (d, J=8.7 Hz, 1H), 5.09 (d, J=12.9 Hz, 1H), 5.17 (d, J=12.9 Hz, 1H), 6.77-6.87 (m, 2H), 6.95-7.02 (m, 2H), 7.14 (dd, J=8.5, 2.3 Hz, 1H), 7.21-7.32 (m, 2H), 8.72 (brs, 1H). $^{13}$C NMR (75 MHz, CDCl$_3$) δ 18.9, 35.2, 36.0, 55.1, 61.6, 105.1, 110.0, 120.2, 124.1, 127.3, 128.4, 128.7, 129.1, 131.1, 133.0, 140.3, 166.0, 170.5. MS [M+H]$^+$ 422

Example 131: (2-methoxyphenyl)methyl 4-(2,5-dichlorophenyl)-1-(2-methoxyethyl)-6-methyl-2-oxo-3,4-dihydropyridine-5-carboxylate o-methoxybenzyl 4-(2,4-dichlorophenyl)-6-methyl-2-oxo-3,4-dihydro-1H-pyridine-5-carboxylate (126 mg, 0.30 mmol) was dissolved in anhydrous DMF (1 mL). Cesium carbonate (195 mg, 0.60 mmol) and 2-bromoethyl methyl ether (56 μL, 0.60 mmol) were added. The reaction mixture was stirred at 60° C. for 18 h. The DMF was removed under reduced pressure. The residue was diluted in water and extracted by EtOAc. The organic layers were assembled, washed by brine and dried on MgSO$_4$. The solvent was removed under reduced pressure. The crude product was purified by flash chromatography using a mixture of Cyclohexane/EtOAc (9/1) as eluent to give the desired (2-methoxyphenyl)methyl 4-(2, 5-dichlorophenyl)-1-(2-methoxyethyl)-6-methyl-2-oxo-3,4-dihydropyridine-5-carboxylate as a white powder (91 mg, 63%). $^1$H NMR (300 MHz, CDCl$_3$) δ 2.71 (s, 3H), 2.79 (dd, J=15.9, 2.1 Hz, 1H), 2.90 (dd, J=15.9, 7.8 Hz, 1H), 3.42 (s, 3H), 3.44-3.56 (m, 2H), 3.73 (s, 3H), 3.78 (ddd, J=14.2, 7.8, 3.2 Hz, 1H), 4.24 (dt, J=14.6, 4.0 Hz, 1H), 4.64 (d, J=7.8 Hz, 1H), 5.09 (d, J=13.2 Hz, 1H), 5.17 (d, J=13.2 Hz, 1H), 6.78-6.85 (m, 2H), 6.96 (dd, J=7.4, 1.2 Hz, 1H), 7.07-7.16 (m, 2H), 7.20-7.30 (m, 2H). $^{13}$C NMR (75 MHz, CDCl$_3$) δ 17.0, 34.9, 36.3, 41.9, 55.1, 59.4, 61.7, 71.2, 108.5, 110.0, 120.1, 124.2, 127.8, 128.4, 128.6, 129.0, 131.0, 131.8, 132.9, 139.9, 152.3, 157.0, 166.6, 168.7. MS [M+H]$^+$ 478. HRMS: calcd for C$_{24}$H$_{26}$NO$_5$Cl$_2$, [M+H]$^+$ 478.1188, found 478.1187.

Example 132: (2-methoxyphenyl)methyl 6-methyl-2-oxo-4-(4-pyridyl)-3,4-dihydro-1H-pyridine-5-carboxylate (Intermediate Product)

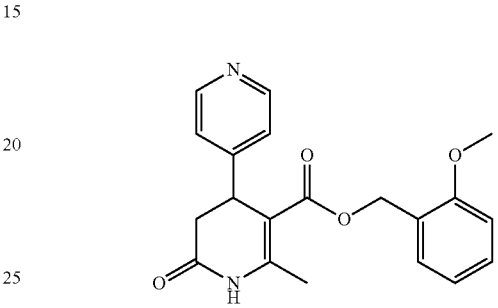

4-pyridylcarboxaldehyde (3.0 mmol, 280 μL), meldrum acid (3.0 mmol, 432 mg), o-methoxybenzyl acetoacetate (3.0 mmol, 666 mg) and ammonium acetate (3.0 mmol, 338 mg) were dissolved in acetic acid (3 mL). The reaction mixture was stirred at 110° C. for 18 h. The solvent was removed. The crude product was purified by flash chromatography using a mixture of DCM/MEOH (99/1 to 99/2) as eluent and then precipitated in EtOH and filtered to afford the desired (2-methoxyphenyl)methyl 6-methyl-2-oxo-4-(4-pyridyl)-3,4-dihydro-1H-pyridine-5-carboxylate as a white powder (164 mg, 16%). $^1$H NMR (300 MHz, CDCl$_3$) ) δ 2.43 (s, 3H), 2.67 (d, J=16.7 Hz, 1H), 2.95 (dd, J=16.7, 8.0 Hz, 1H), 3.73 (s, 3H), 4.25 (d, J=8.0 Hz, 1H), 5.11 (d, J=12.3 Hz, 1H), 5.21 (d, J=12.3 Hz, 1H), 6.80-6.90 (m, 2H), 7.02-7.12 (m, 3H), 7.28 (td, J=7.6, 1.7 Hz, 1H), 8.43-8.53 (m, 2H), 8.60 (brs, 1H). $^{13}$C NMR (75 MHz, CDCl$_3$) δ 19.0, 37.0, 37.3, 55.2, 61.9, 105.6, 110.3, 120.2, 122.1, 124.0, 129.6, 147.4, 150.0, 151.1, 157.4, 166.3, 170.3. MS [M–H]– 351

Example 133: (2-methoxyphenyl)methyl 1-(2-methoxyethyl)-6-methyl-2-oxo-4-(4-pyridyl)-3,4-dihydropyridine-5-carboxylate (2-methoxyphenyl)methyl 6-methyl-2-oxo-4-(4-pyridyl)-3,4-dihydropyridine-5-carboxylate (105 mg, 0.30 mmol) was dissolved in anhydrous DMF (1 mL). Cesium carbonate (195 mg, 0.6 mmol) and 2-bromoethyl methyl ether (56 μL, 0.6 mmol) were added. The reaction mixture was stirred at 60° C. for 18 h. Water (25 mL) was added. The product was extracted by EtOAc. The organic layers were assembled, washed with brine and dried on MgSO$_4$. The solvent was removed under reduced pressure. The crude product was purified by flash chromatography using a mixture of Cyclohexane/EtOAc (8/2-6/4 to 1/1) as eluent to give the desired (2-methoxyphenyl)methyl 1-(2-methoxyethyl)-6-methyl-2-oxo-4-(4-pyridyl)-3,4-dihydropyridine-5-carboxylate as a colorless oil (104 mg, 84%). $^1$H NMR (300 MHz, CDCl$_3$) δ 2.62 (s, 3H), 2.74 (dd, J=16.0, 2.2 Hz, 1H), 2.94 (dd, J=16.0 and 7.5 Hz, 1H), 3.28 (s, 3H), 3.28-3.38 (m, 1H), 3.44 (dt, J=9.8, 4.0 Hz, 1H), 3.70 (s, 3H), 3.74 (ddd, J=14.6, 8.2, 3.6 Hz, 1H), 4.13-4.23 (m, 2H), 5.10 (d, J=12.7 Hz, 1H), 5.20 (d, J=12.7 Hz, 1H), 6.79-6.87 (m, 2H), 7.04 (dd, J=7.3, 1.8 Hz, 1H), 7.08-7.13 (m, 2H), 7.26 (td, J=7.8, 1.7 Hz, 1H), 8.43-8.47 (m, 2H). $^{13}$C NMR (75 MHz, CDCl$_3$) δ 17.0, 36.7, 37.7, 41.8, 55.1, 58.7, 62.0, 70.9, 109.1, 110.2, 120.2, 122.3, 124.0, 129.3, 129.5, 149.8, 150.5, 151.4, 157.3, 166.8, 168.6. MS [M+H]$^+$ 412. HRMS: calcd for $C_{23}H_{27}N_2O_5$, [M+H]$^+$ 411.1920, found 411.1930.

TABLE 10

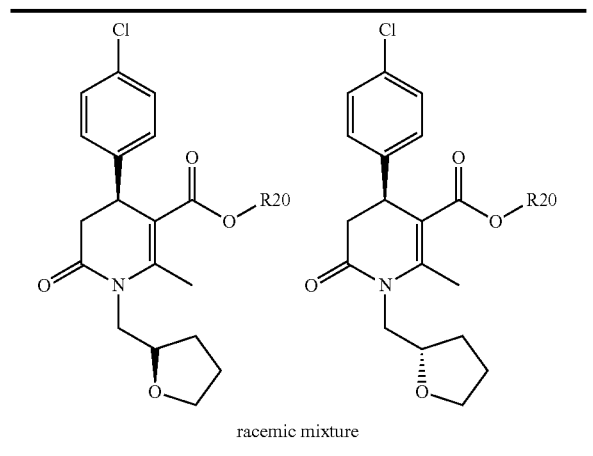

racemic mixture

| Example | R20 |
|---|---|
| 136 | 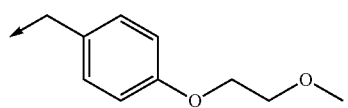 |
| 137 | 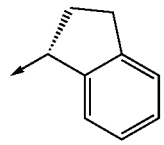 |
| 138 | 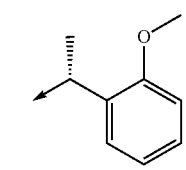 |
| 141 | 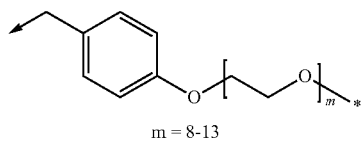 m = 8-13 |
| 144 | 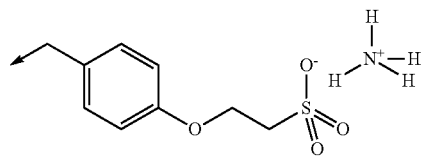 |
| 145 | 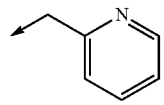 |

TABLE 10-continued

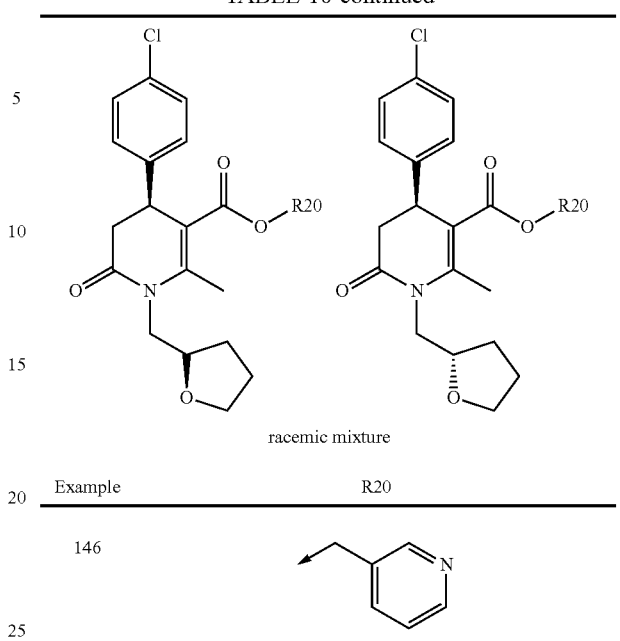

racemic mixture

| Example | R20 |
|---|---|
| 146 | 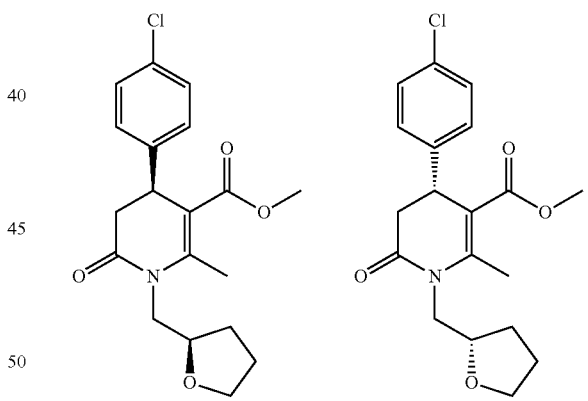 |

Example 134: Methyl (4S)-4-(4-chlorophenyl)-6-methyl-2-oxo-1-[[(2R)-tetrahydrofuran-2-yl]methyl]-3,4-dihydropyridine-5-carboxylate and Methyl (4R)-4-(4-chlorophenyl)-6-methyl-2-oxo-1-[[(2S)-tetrahydrofuran-2-yl]methyl]-3,4-dihydropyridine-5-carboxylate (Intermediate Product)

The methyl 4-(4-chlorophenyl)-6-methyl-2-oxo-3,4-dihydro-1H-pyridine-5-carboxylate (3.40 g, 12.15 mmol) was dissolved in anh. DMF (10 mL). Cesium carbonate (7.92 g, 24.31 mmol) and sodium iodide (91 mg, 0.61 mmol) were added followed by tetrahydrofurfuryl bromide (2.77 mL, 24.31 mmol). The reaction mixture was stirred at 50° C. for 18 h. The solvents were removed under reduced pressure. Water was added and the aqueous phase extracted by EtOAc. The organic phases were assembled, washed with brine and dried over MgSO$_4$. The crude was dissolved again in anh. DMF (10 mL). Cesium carbonate (7.92 g, 24.31 mmol) and sodium iodide (91 mg, 0.61 mmol) were added followed by tetrahydrofurfuryl bromide (2.77 mL, 24.31 mmol). The reaction mixture was stirred at 50° C. for 18 h.

The solvents were removed under reduced pressure. Water was added and the aqueous phase extracted by EtOAc. The organic phases were assembled, washed with brine and dried over MgSO$_4$. The solvent was removed under reduced pressure. The crude was purified by flash chromatography on silica using a mixture Cy/EA (95/5 to 88/12) as eluent to give methyl (4S)-4-(4-chlorophenyl)-6-methyl-2-oxo-1-[[(2R)-tetrahydrofuran-2-yl]methyl]-3,4-dihydropyridine-5-carboxylate and its enantiomer as a colorless oil (1.58 g, 36%)

$^1$H NMR (300 MHz, CDCl$_3$) δ 1.40-1.50 (m, 1H), 1.80-2.00 (m, 3H), 2.62 (s, 3H), 2.71 (dd, J=15.5, 2.2 Hz, 1H), 2.91 (dd, J=15.5, 7.0 Hz, 1H), 3.41 (dd, J=14.3, 8.8 Hz, 1H), 3.65 (s, 3H), 3.65-3.82 (m, 2H), 3.86-3.96 (m, 2H), 3.86-3.96 (m, 1H), 4.18 (dd, J=7.0, 2.2 Hz, 1H), 4.27 (dd, J=14.3, 3.2 Hz, 1H), 7.21 (s, 4H). MS [M+H]$^+$ 364.

Example 135: (4S)-4-(4-chlorophenyl)-6-methyl-2-oxo-1-[[(2R)-tetrahydrofuran-2-yl]methyl]-3,4-dihydropyridine-5-carboxylic acid and (4R)-4-(4-chlorophenyl)-6-methyl-2-oxo-1-[[(2S)-tetrahydrofuran-2-yl]methyl]-3,4-dihydropyridine-5-carboxylic acid
(Intermediate Product)

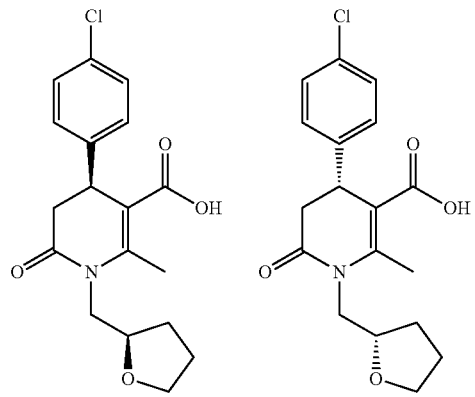 [SMILES: CC1=C(C(=O)O)[C@H](c2ccc(Cl)cc2)CC(=O)N1C[C@H]1CCCO1 ; CC1=C(C(=O)O)[C@@H](c2ccc(Cl)cc2)CC(=O)N1C[C@@H]1CCCO1]

An aqueous solution of NaOH 1N (15 mL) was added to a solution of methyl (4S)-4-(4-chlorophenyl)-6-methyl-2-oxo-1-[[(2R)-tetrahydrofuran-2-yl]methyl]-3,4-dihydropyridine-5-carboxylate and its enantiomer (example 134, 1.58 g, 4.35 mmol) in MeOH (15 mL). The reaction mixture was stirred overnight at 40° C. The solvent was removed under reduced pressure, the aqueous phase was washed with Et$_2$O, then acidified to pH=1 with HCl conc. The aqueous phase was extracted with DCM. The organic phases were assembled and dried over Na$_2$SO$_4$. The solvent was removed under reduced pressure to afford the desired (4S)-4-(4-chlorophenyl)-6-methyl-2-oxo-1-[[(2R)-tetrahydrofuran-2-yl]methyl]-3,4-dihydropyridine-5-carboxylic acid as a white powder (m=1.3 g, 88%). $^1$H NMR (300 MHz, DMSO d6) δ 1.34-1.48 (m, 1H), 1.74-1.88 (m, 3H), 2.49 (dd, J=15.5, 1.9 Hz, 1H), 2.53 (s, 3H), 2.95 (dd, J=15.5, 6.9 Hz, 1H), 3.42 (dd, J=14.2, 8.6 Hz, 1H), 3.60-3.72 (m, 2H), 3.78-3.88 (m, 1H), 4.05 (dd, J=14.8, 3.5 Hz, 1H), 4.11 (d, J=6.9 Hz, 1H), 7.25 (d, J=8.7 Hz, 2H), 7.29 (d, J=8.7 Hz, 2H), 12.24 (brs, 1H). $^{13}$C NMR (75 MHz, DMSO d6) δ 17.1, 25.4, 29.0, 37.0, 39.3, 45.3, 67.9, 78.1, 110.6, 128.7, 129.4, 131.6, 140.9, 150.5, 168.8, 169.0. MS [M+H]$^+$ 348. HRMS: calcd for C$_{18}$H$_{19}$NO$_4$C, [M−H]$^-$ 348.1003, found 348.1025.

Example 136: 4-(2-methoxyethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate and 4-(2-methoxyethoxy)phenyl]methyl (4R)-4-(4-chlorophenyl)-6-methyl-2-oxo-1-[[(2S)-tetrahydrofuran-2-yl]methyl]-3,4-dihydropyridine-5-carboxylate 1-(chloromethyl)-4-(2-methoxyethoxy) benzene (example 118, 125 mg, 0.60 mmol) and racemic mixture of (4S)-4-(4-chlorophenyl)-6-methyl-2-oxo-1-[[(2R)-tetrahydrofuran-2-yl]methyl]-3,4-dihydropyridine-5-carboxylic acid and its enantiomer (example 135, 192 mg, 0.55 mmol) were dissolved in anhydrous DMF (2 mL). Cesium carbonate (269 mg, 0.825 mmol) was added and the reaction mixture was stirred at r.t. for 18 h. The solvents were removed under reduced pressure. Water was added and the aqueous phase was extracted with diethyl ether, washed with brine and dried over Na$_2$SO$_4$. The solvents were removed under reduced pressure. Purification of the crude by flash chromatography using a mixture of Cy/EtOAc (9/1) as eluent gave the expected [4-(2-methoxyethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate as a colorless oil (m=105 mg, 37%) $^1$H NMR (300 MHz, CDCl$_3$) δ 1.23-1.30 (m, 1H), 1.78-1.98 (m, 3H), 2.61 (s, 3H), 2.70 (dd, J=15.5, 2.0 Hz, 1H), 2.90 (dd, J=15.5, 7.3 Hz, 1H), 3.41 (dd, J=14.5, 8.9 Hz, 1H), 3.46 (s, 3H), 3.64-3.94 (m, 5H), 4.11 (dd, J=4.8, 3.4 Hz, 2H), 4.17 (dd, J=7.3, 2.0 Hz, 1H), 4.25 (dd, J=14.5, 3.4 Hz, 1H), 5.02 (s, 2H), 6.82 (d, J=8.6 Hz, 2H), 7.04 (d, J=8.6 Hz, 2H), 7.16 (d, J=9.0 Hz, 2H), 7.20 (d, J=9.0 Hz, 2H). $^{13}$C NMR (75 MHz, CDCl$_3$) δ 17.0, 25.4, 29.1, 36.9, 38.9, 45.5, 59.1, 65.7, 67.1, 68.0, 70.9, 77.7, 110.1, 114.3, 128.3, 128.5, 128.6, 129.2, 132.3, 139.5, 151.0, 158.4, 166.9, 168.8. MS [M+H]$^+$ 514, HRMS: calcd for C$_{28}$H$_{33}$NO$_6$Cl, [M+H]$^+$ 514.1996, found 514.2004.

Example 137: Indan-1-yl (4S)-4-(4-chlorophenyl)-6-methyl-2-oxo-1-[[(2R)-tetrahydrofuran-2-yl]methyl]-3,4-dihydropyridine-5-carboxylate (racemic)

1-chloroindane (55 mg, 0.36 mmol) and (4S)-4-(4-chlorophenyl)-6-methyl-2-oxo-1-[[(2R)-tetrahydrofuran-2-yl]methyl]-3,4-dihydropyridine-5-carboxylic acid and its enantiomer (example 135, 115 mg, 0.33 mmol) were dissolved in anh. DMF (2 mL). Cesium carbonate (107 mg, 0.33 mmol) and sodium iodide (2.5 mg, 0.017 mmol) were added. The reaction mixture was stirred at r.t. for 24 h, at 60° C. for 2 h and at 80° C. for 1 h. The reaction mixture was cooled down to r.t. Water was added and the aqueous phase was extracted with EtOAc. The combined organic layers were washed with brine and dried over MgSO$_4$. The solvent was removed under reduced pressure. Purification of the crude by flash chromatography using a mixture of Cyclohexane/EtOAc (93/7) as eluent gave the desired indan-1-yl (4S)-4-(4-chlorophenyl)-6-methyl-2-oxo-1-[[(2R)-tetrahydrofuran-2-yl]methyl]-3,4-dihydropyridine-5-carboxylate as a single diastereomer and a yellow oil (30 mg, 17%). $^1$H NMR (300 MHz, CDCl$_3$) δ 1.38-1.52 (m, 1H), 1.71-1.82 (m, 1H), 1.82-1.98 (m, 3H), 2.26-2.40 (m, 1H), 2.63 (s, 3H), 2.65 (dd, J=15.9, 2.2 Hz, 1H), 2.72-2.96 (m, 3H), 3.42 (dd, J=14.3, 8.5 Hz, 1H), 3.69-3.96 (m, 3H), 4.08 (d, J=7.6 Hz, 1H), 4.25 (dd, J=14.3, 3.4 Hz, 1H), 6.19 (dd, J=6.9, 3.7 Hz, 1H), 7.14 (d, J=8.4 Hz, 2H), 7.19 (d, J=8.4 Hz, 2H), 7.21-7.34 (m, 3H), 7.43 (d, J=7.3 Hz, 1H). MS [M+H]$^+$ 466; HRMS: calcd for C$_{27}$H$_{29}$NO$_4$Cl, [M+H]$^+$ 466.1785, found 466.1798.

Example 138: 1-(2-methoxyphenyl)ethyl (4S)-4-(4-chlorophenyl)-6-methyl-2-oxo-1-[[(2R)-tetrahydrofuran-2-yl]methyl]-3,4-dihydropyridine-5-carboxylate (diastereoisomers mixture)

1-(1-chloroethyl)-2-methoxy-benzene (68 mg, 0.36 mmol) and racemic mixture of (4S)-4-(4-chlorophenyl)-6-methyl-2-oxo-1-[[(2R)-tetrahydrofuran-2-yl]methyl]-3,4-dihydropyridine-5-carboxylic acid and its enantiomer (example 135, 126 mg, 0.36 mmol) were dissolved in anh. DMF (2 mL). Cesium carbonate (117 mg, 0.36 mmol) was added and the reaction mixture was stirred at RT for 24 h, at 60° C. for 24 h and at 90° C. for 6 h. The reaction mixture was cooled down to r.t. Water was added and the aqueous phase was extracted with EtOAc. The combined organic layers were washed with brine and dried over MgSO$_4$. The solvent was removed under reduced pressure. Purification of the crude by flash chromatography using a mixture of Cyclohexane/EtOAc (93/7) as eluent gave the desired 1-(2-methoxyphenyl)ethyl (4S)-4-(4-chlorophenyl)-6-methyl-2-oxo-1-[[(2R)-tetrahydrofuran-2-yl]methyl]-3,4-dihydropyridine-5-carboxylate as a yellow oil and a mixture of diastereomers 1/1 (m=30 mg, 17%). $^1$H NMR (300 MHz, CDCl$_3$) δ 1.25-1.32 (d, J=6.5 Hz, 1.5H), 1.38-1.52 (m, 2.5H), 1.80-2.00 (m, 3H), 2.61 (s, 3H), 2.68-2.78 (m, 1H), 2.86-3.02 (m, 1H), 3.36-3.46 (m, 1H), 3.66-3.93 (m, 3H), 3.74 (s, 1.5H), 3.82 (s, 3H), 4.18-4.32 (m, 2H), 6.17-6.28 (m, 1H), 6.50 (dd, J=7.7, 1.7 Hz, 0.5H), 6.63 (t, J=7.6 Hz, 0.5H), 6.76 (d, J=8.5 Hz, 0.5H), 6.86 (d, J=8.0 Hz, 0.5H), 6.91 (t, J=7.0 Hz, 0.5H), 7.10-7.17 (m, 1H), 7.22-7.25 (m, 4.5H). MS [M+H]$^+$ 484; HRMS: calcd for C$_{26}$H$_{29}$NO$_5$Cl, [M+H]$^-$ 484.1904, found 484.1896.

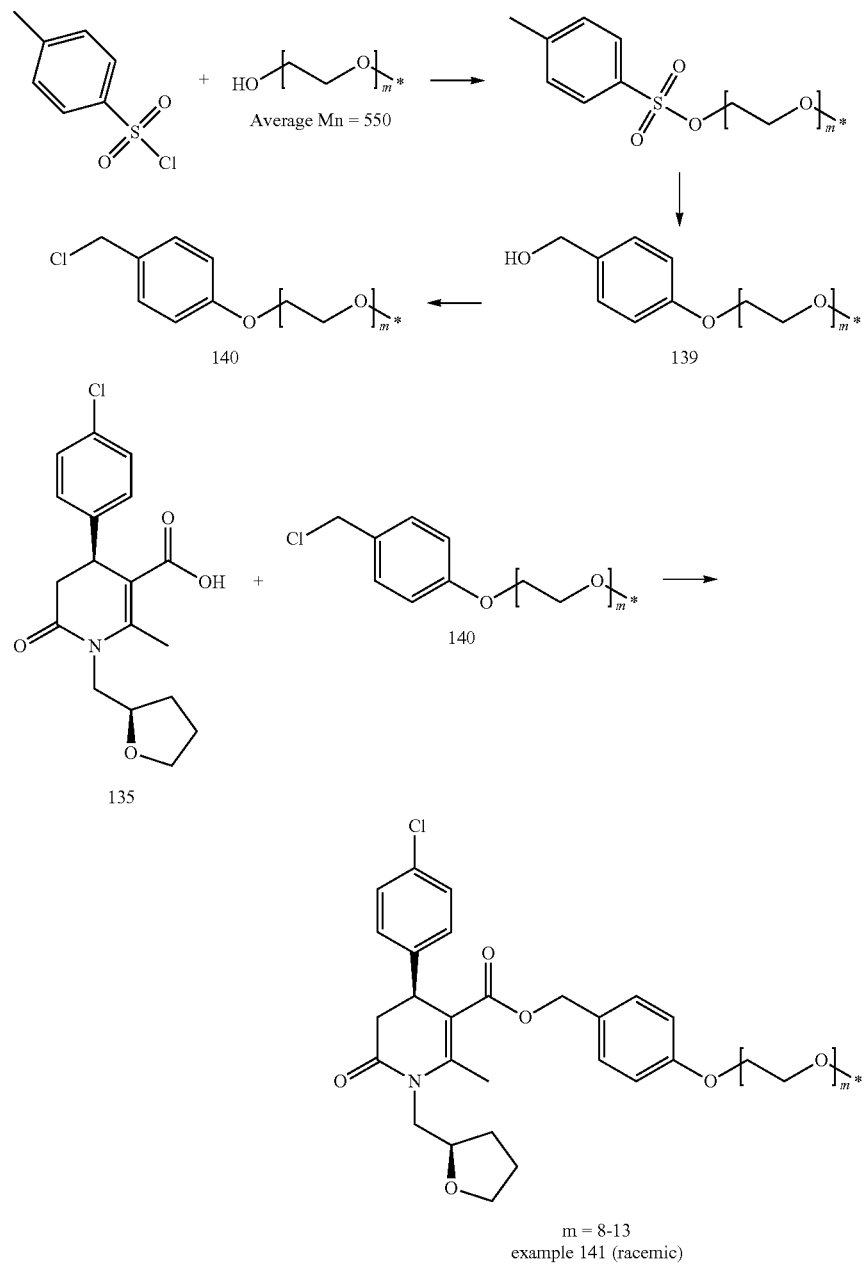

m = 8-13
example 141 (racemic)

Example 139: [4-(polyethyleneglycoxymethylether)phenyl]methanol (Intermediate Product)

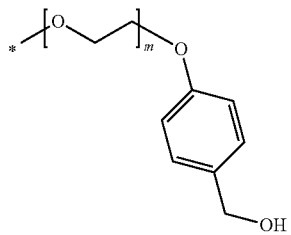

Poly(ethylene glycol) methyl ether (Sigma-Aldrich, ref 202487, average Mn 550, 1 mmol) was dissolved in THF (3 mL). The solution was cooled at 0° C. NaH (36 mg, 1.5 mmol) was added and the reaction mixture was stirred at 0° C. to 20° C. for 2 h. Then p-toluenesulfonyl chloride (381 mg, 2 mmol) was added at 0° C. and the reaction mixture was stirred at r.t. until completion. The solvent was removed under reduced pressure. Purification of the crude by flash chromatography using a mixture of DCM/MeOH 97/3 as eluent gave the desired poly(ethylene glycol) methyl ether tosylate (515 mg, 73%). Poly(ethylene glycol) methyl ether tosylate (0.73 mmol, 502 mg) was dissolved in MeCN (3 mL), the phenol (1.10 mmol, 136 mg) and $K_2CO_3$ (1.10 mmol, 151 mg) were added. The reaction mixture was stirred overnight under reflux. The reaction mixture became pink and, after being cooled down, it has been filtered. The filtrate has been concentrated under vacuum and purified by Flash Chromatography (DCM/MeOH 100/0 to 8/2) to give the expected [4-(polyethyleneglycoxy methylether)phenyl]methanol as a yellow oil (390 mg, 78%) 1H NMR (300 MHz, CDCl$_3$) δ 3.38 (s, 3H), 3.52-3.77 (m, 47H), 3.84-3.90 (m, 2H), 4.10-4.17 (m, 2H), 4.62 (s, 2H), 6.91 (d, J=8.7 Hz, 2H), 7.29 (d, J=8.7 Hz, 2H). MS [M+NH$^4$]$^+$ 684

Example 140: 1-chloromethyl-4-(polyethyleneglycoxy methylether)benzene (Intermediate Product)

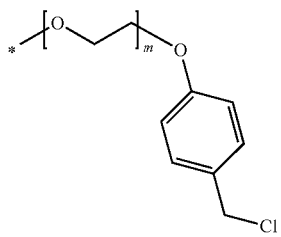

Thionyl chloride (0.71 mmol, 52 μL) was added to benzotriazole (0.71 mmol, 85 mg). The resulting yellow solution was dissolved in dry DCM (1 mL). After 5 min, this solution was added slowly to a solution of [4-(polyethyleneglycoxy methylether)phenyl]methanol in DCM (6 mL). After 1 h of reaction, the reaction mixture was quenched by addition of $MgSO_4.7H_2O$ and then filtered. The solvents were removed under reduced pressure to afford 1-chloromethyl-4-(polyethyleneglycoxy methylether)benzene as a yellow oil (m=400 mg, quantitative). $^1$H NMR (300 MHz, CDCl$_3$) δ 3.38 (s, 3H), 3.52-3.77 (m, 47H), 3.84-3.90 (m, 2H), 4.10-4.17 (m, 2H), 4.57 (s, 2H), 6.89 (d, J=8.7 Hz, 2H), 7.30 (d, J=8.7 Hz, 2H).

Example 141: [4-(polyethyleneglycoxy methylether)phenyl]methyl (4S)-4-(4-chlorophenyl)-6-methyl-2-oxo-1-[[(2R)-tetrahydrofuran-2-yl]methyl]-3,4-dihydropyridine-5-carboxylate (mixture m=8-13)

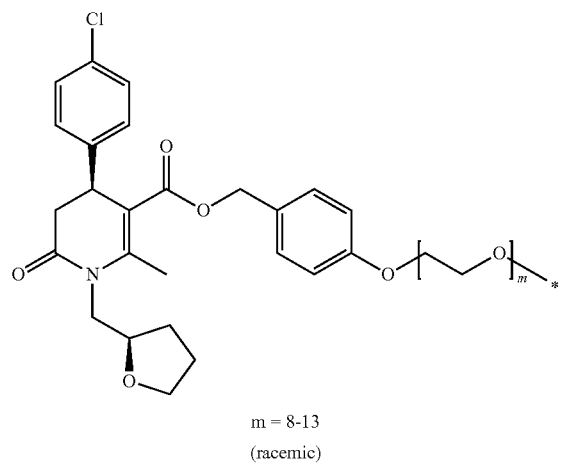

Example 141 m = 8-13

(racemic)

1-chloromethyl-4-(polyethyleneglycoxymethylether)benzene (example 140, 125 mg, 0.60 mmol) and (4S)-4-(4-chlorophenyl)-6-methyl-2-oxo-1-[[(2R)-tetrahydrofuran-2-yl]methyl]-3,4-dihydropyridine-5-carboxylic acid (example 135, 192 mg, 0.55 mmol) were dissolved in anh. DMF (2 mL). Cesium carbonate (269 mg, 0.82 mmol) was added and the reaction mixture stirred at RT for 24 h. An aqueous hydrochloric acid solution 1N and brine were added. The aqueous phase was extracted with ethyl acetate. The crude was purified by flash chromatography using a mixture DCM/MeOH (100/0 to 9/1) to give the desired product but not clean. A second purification by HPLC (acidic conditions) afforded the desired [4-(polyethyleneglycoxy methylether)phenyl]methyl(4S)-4-(4-chlorophenyl)-6-methyl-2-oxo-1-[[(2R)-tetrahydrofuran-2-yl]methyl]-3,4-dihydropyridine-5-carboxylate as a colorless oil (m=87 mg, 17%). $^1$H NMR (300 MHz, CDCl$_3$) δ 1.38-1.52 (m, 1H), 1.80-2.04 (m, 3H), 2.61 (s, 3H), 2.68 (dd, J=15.6, 2.2 Hz, 1H), 2.89 (dd, J=15.6, 7.2 Hz, 1H), 3.38 (s, 3H), 3.40 (dd, J=14.6, 8.8 Hz, 1H), 3.52-3.59 (m, 2H), 3.60-3.95 (m, 44H), 4.08-4.13 (m, 2H), 4.16 (dd, J=7.2, 2.2 Hz, 1H), 4.25 (dd, J=14.3, 3.1 Hz, 1H), 5.02 (s, 2H), 6.81 (d, J=8.5 Hz, 2H), 7.04 (d, J=8.5 Hz, 2H), 7.16 (d, J=8.9 Hz, 2H), 7.20 (d, J=8.9 Hz, 2H). $^{13}$C NMR (75 MHz, CDCl$_3$) δ 17.1, 25.5, 29.2, 37.0, 39.0, 45.6, 59.0, 65.8, 67.4, 68.1, 69.7, 70.5, 70.8, 71.9, 77.8, 110.2, 114.4, 128.3, 128.6, 129.4, 132.5, 139.5, 151.1, 158.6, 167.0, 169.0. MS [M+NH$_4$]1 884, 928, 972, 1016, 1060, HRMS: calcd for C$_{50}$H$_{80}$N$_2$O$_{17}$Cl, [M+NH$_4$]$^+$ 1015.5146, found 1015.5122.

Example 144: Ammonium 2-[4-[[(4S)-4-(4-chlorophenyl)-6-methyl-2-oxo-1-[[(2R)-tetrahydrofuran-2-yl]methyl]-3,4-dihydropyridine-5-carbonyl]oxymethyl]phenoxy]ethanesulfonate

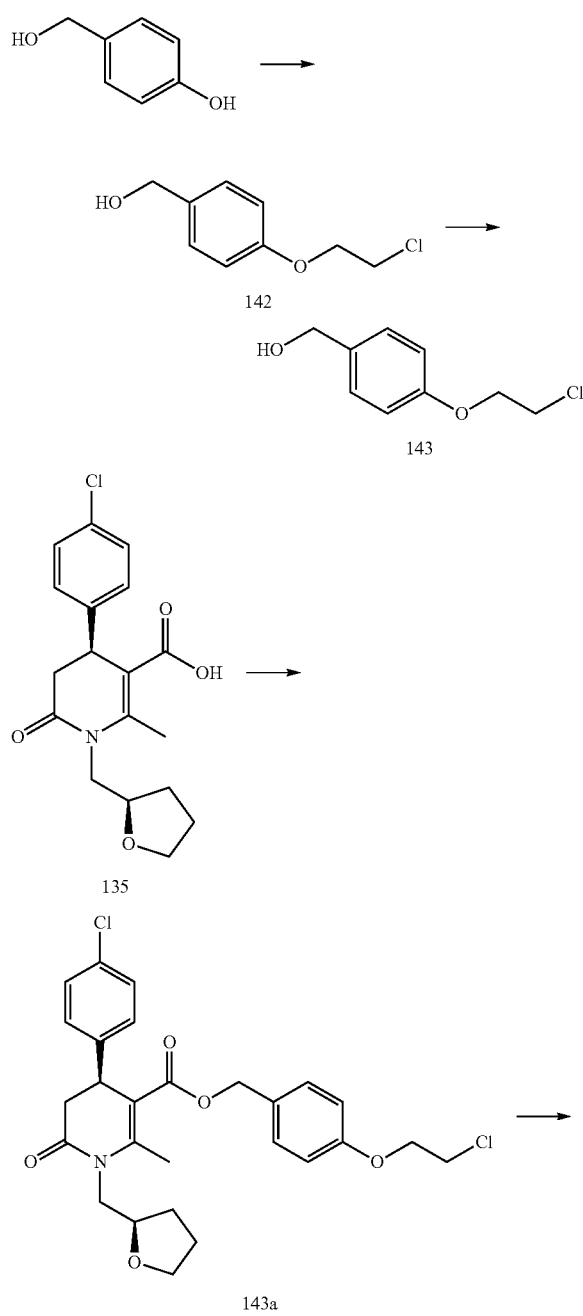

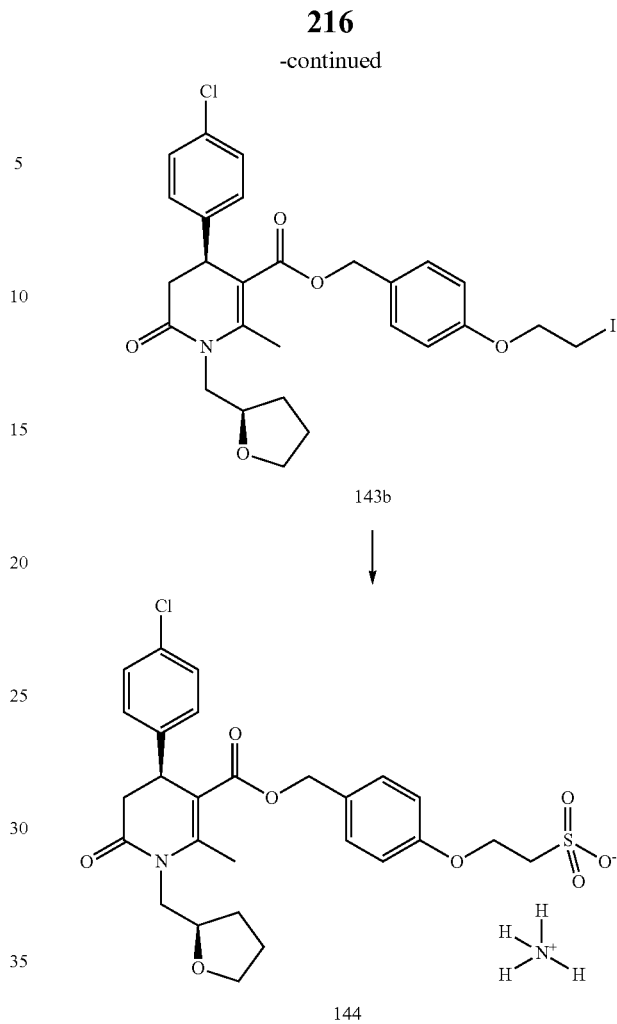

Example 142: [4-(2-chloroethoxy)phenyl]methanol (Intermediate Product)

1-bromo-2-chloroethane (30 mmol, 2.5 mL), 4-hydroxybenzyl alcohol (6 mmol, 745 mg) and potassium carbonate (30 mmol, 4.15 g) were added in acetonitrile (20 mL). The reaction mixture was stirred under reflux for 60 h. The solvent was removed under reduced pressure. The crude was dissolved in EtOAc and washed with water. The aqueous phase was extracted by EtOAc and washed with brine, dried under Na$_2$SO$_4$. The solvent was removed under reduced pressure to and the crude was purified by flash chromatography (Cy/EA 85/15) to afford the desired compound as a white powder (m=888 mg, 79%). $^1$H NMR (300 MHz, CDCl$_3$) δ 1.67 (brs, 1H), 3.82 (t, J=5.9 Hz, 2H), 4.24 (t, J=5.9 Hz, 2H), 4.63 (brs, 2H), 6.92 (d, J=8.7 Hz, 2H), 7.31 (d, J=8.7 Hz, 2H).

Example 143:
1-(2-chloroethoxy)-4-(chloromethyl)benzene (Intermediate Product)

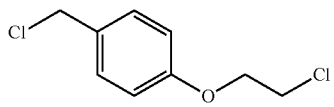 [SMILES: ClCCOc1ccc(CCl)cc1]

Thionyl chloride (45 μL, 0.63 mmol) was added to benzotriazole (75 mg, 0.63 mmol). The resulting yellow solution was dissolved in dry DCM (0.5 mL). After 5 min, this solution was added slowly to a solution of the alcohol 142 (93 mg, 0.50 mmol) in DCM (4 mL). After 20 min of reaction, the salt was filtered. The organic phase was washed with water (4 mL) and an aqueous solution of NaOH (0.05 M, 4 mL). The organic phase was dried on $Na_2SO_4$ and the solvent was removed under reduced pressure to give the desired chlorinated compound as a colorless oil (70 mg, 68%). $^1$H NMR (300 MHz, $CDCl_3$) δ 3.82 (t, J=6.1 Hz, 2H), 4.25 (t, J=6.1 Hz, 2H), 4.58 (s, 2H), 6.90 (d, J=8.8 Hz, 2H), 7.34 (d, J=8.8 Hz, 2H).

The (4S)-4-(4-chlorophenyl)-6-methyl-2-oxo-1-[[(2R)-tetrahydrofuran-2-yl]methyl]-3,4-dihydropyridine-5-carboxylic acid (example 135, 105 mg, 0.30 mmol) and cesium carbonate (108 mg, 0.33 mmol) were dissolved in anh. DMF (2 mL). 1-(2-chloroethoxy)-4-(chloromethyl)benzene 143 (67 mg, 0.33 mmol) was added. The reaction mixture was stirred at RT for 18 h. The solvents were removed under reduced pressure. The residue was dissolved in EtOAc and washed with water. The aqueous phase was extracted by EtOAc. The organic layers were assembled, washed with brine and dried with $Na_2SO_4$. The orange residue was purified by flash chromatography (Cy/DCM 1/1 to DCM) to afford the desired [4-(2-chloroethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate as a colorless oil (m=145 mg, 93%). $^1$H NMR (300 MHz, $CDC_3$) δ 1.40-1.50 (m, 1H), 1.80-2.00 (m, 3H), 2.62 (s, 3H), 2.69 (dd, J=15.8, 2.2 Hz, 1H), 2.89 (dd, J=15.8, 7.4 Hz, 1H), 3.41 (dd, J=14.3, 8.8, 1H), 3.68-3.96 (m, 3H), 3.82 (t, J=6.0 Hz, 2H), 4.17 (d, J=7.4 Hz, 1H), 4.22 (t, J=6.0 Hz, 2H), 4.22-4.29 (m, 1H), 5.03 (s, 2H), 6.81 (d, J=8.6 Hz, 2H), 7.05 (d, J=8.6 Hz, 2H), 7.17 (d, J=8.8 Hz, 2H), 7.21 (d, J=8.8 Hz, 2H). MS $[M+H]^+$ 518.

Example 143a: [4-(2-chloroethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate (racemic mixture) (Intermediate Product)

Example 143b: 4-(2-iodoethoxy)phenyl]methyl (4S)-4-(4-chlorophenyl)-6-methyl-2-oxo-1-[[(2R)-tetrahydrofuran-2-yl (Intermediate Product)

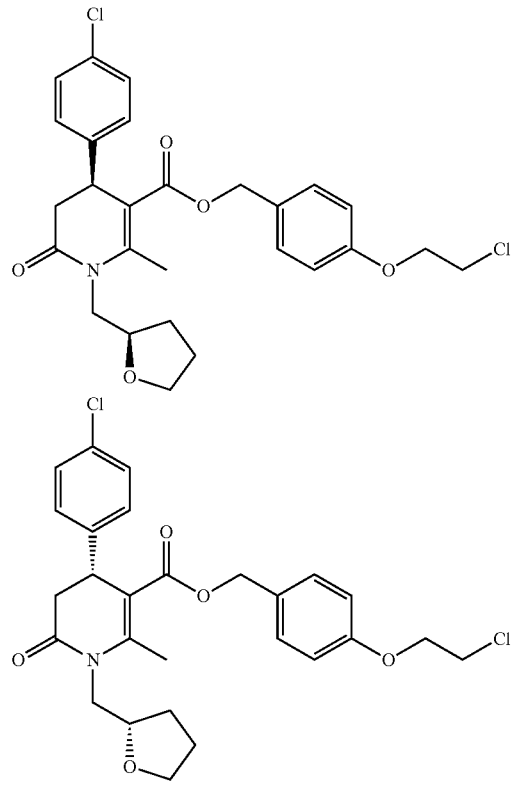

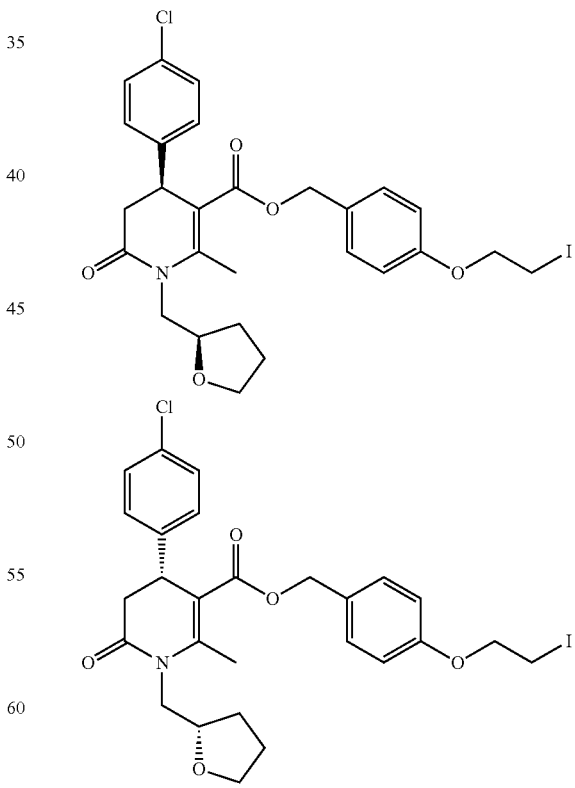

[4-(2-chloroethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate 143a (145 mg, 0.288 mmol) was dissolved in butanone (1 mL). Sodium iodide (168 mg, 1.12 mmol) was added and the reaction mixture was stirred at 80° C. for 32 h.

The solution was cooled to RT, filtered and washed by acetone. The solvents were removed under reduced pressure. Purification of the crude by flash chromatography using a mixture of Cy/DCM (1/1 to 0/1) gave the desired [4-(2-iodoethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate as a colorless oil (m=137 mg, 80%) $^1$H NMR (300 MHz, CDC$_3$) δ 1.39-1.51 (m, 1H), 1.81-2.00 (m, 3H), 2.62 (s, 3H), 2.69 (dd, J=15.6, 2.4 Hz, 1H), 2.90 (dd, J=15.6, 7.4 Hz, 1H), 3.36-3.46 (m, 3H), 3.68-3.96 (m, 3H), 4.17 (d, J=7.4 Hz, 1H), 4.20-4.30 (m, 3H), 5.03 (s, 2H), 6.81 (d, J=8.7 Hz, 2H), 7.05 (d, J=8.7 Hz, 2H), 7.16 (d, J=8.7 Hz, 2H), 7.21 (d, J=8.7 Hz, 2H). MS [M+H]$^+$ 610

Example 144: Ammonium 2-[4-[[[(4S)-4-(4-chlorophenyl)-6-methyl-2-oxo-1-[[(2R)-tetrahydrofuran-2-yl]methyl]-3,4-dihydropyridine-5-carbonyl]oxymethyl]phenoxy]ethanesulfonate The [4-(2-iodoethoxy)phenyl]methyl (4S)-4-(4-chlorophenyl)-6-methyl-2-oxo-1-[[(2R)-tetrahydrofuran-2-yl]methyl]-3,4-dihydropyridine-5-carboxylate 143b (145 mg, 0.24 mmol) was dissolved in a mixture iPrOH/water 1/1 (1 mL). Sodium sulfite (60 mg, 0.48 mmol) was added and the reaction mixture was stirred under reflux for 48 h. The solvents were removed under reduced pressure.

Purification of the crude by HPLC (basic conditions) gave the ammonium 2-[4-[[[(4S)-4-(4-chlorophenyl)-6-methyl-2-oxo-1-[[(2R)-tetrahydrofuran-2-yl]methyl]-3,4-dihydropyridine-5-carbonyl]oxymethyl]phenoxy]ethanesulfonate as a white powder (m=60 mg, 45%). $^1$H NMR (300 MHz, CDCl$_3$) δ 1.34-1.48 (m, 1H), 1.74-1.96 (m, 3H), 2.56 (s, 3H), 2.60 (d, J=15.9 Hz, 1H), 2.70-2.88 (m, 3H), 3.26 (t, J=6.1 Hz, 2H), 3.35 (dd, J=14.3-9.0 Hz, 1H), 3.62-3.90 (m, 3H), 4.09 (d, J=6.1 Hz, 1H), 4.14-4.28 (m, 3H), 4.82 (d, J=12.5 Hz, 1H), 4.94 (d, J=12.5 Hz, 1H), 6.73 (d, J=8.5 Hz, 2H), 6.89 (brs, 4H), 6.96 (d, J=8.5 Hz, 2H), 7.13 (s, 3H). $^{13}$C NMR (75 MHz, CDCl$_3$) δ 17.1, 25.5, 29.1, 36.9, 38.9, 45.6, 50.6, 63.5, 65.6, 68.1, 77.2, 77.8, 110.0, 114.6, 128.7, 129.1, 129.5, 132.4, 139.5, 151.1, 157.8, 167.0, 169.0. MS [M−H]$^−$=562; HRMS: calcd for C$_{27}$H$_{29}$NO$_8$SCl, [M+H]$^+$ 562.1302, found 562.1322.

Example 145: 2-pyridylmethyl (4S)-4-(4-chlorophenyl)-6-methyl-2-oxo-1-[[(2R)-tetrahydrofuran-2-yl]methyl]-3,4-dihydropyridine-5-carboxylate and 2-pyridylmethyl (4R)-4-(4-chlorophenyl)-6-methyl-2-oxo-1-[[(2S)-tetrahydrofuran-2-yl]methyl]-3,4-dihydropyridine-5-carboxylate Racemic mixture of (4S)-4-(4-chlorophenyl)-6-methyl-2-oxo-1-[[(2R)-tetrahydrofuran-2-yl]methyl]-3,4-dihydropyridine-5-carboxylic acid and its enantiomer (example 135, 105 mg, 0.30 mmol) was dissolved in anhydrous DMF (1 mL) then cesium carbonate (215 mg, 0.66 mmol) and 2-(Chloromethyl)pyridine hydrochloride (132 mg, 0.36 mmol) were added. The reaction mixture was stirred at RT for 18 h. Cesium carbonate (60 mg, 0.18 mmol) and 2-(Chloromethyl)pyridine hydrochloride (30 mg, 0.18 mmol) were added again. The reaction mixture was stirred at 60° C. for 12 h. The solvent was removed under reduced pressure. Water was added. The aqueous phase was extracted with Et$_2$O. The combined organic layers were washed with brine and dried over MgSO$_4$. The solvent was removed under reduced pressure.

Purification of the crude by flash chromatography on silica using a mixture of DCM/EtOAc (7/3) gave the desired (2-pyridylmethyl (4S)-4-(4-chlorophenyl)-6-methyl-2-oxo-1-[[(2R)-tetrahydrofuran-2-yl]methyl]-3, 4-dihydropyridine-5-carboxylate as a colorless oil (83 mg, 63%). $^1$H NMR (300 MHz, CDCl$_3$) δ 1.42-1.51 (m, 1H), 1.83-2.00 (m, 3H), 2.65 (s, 3H), 2.71 (dd, J=15.8, 2.2 Hz, 1H), 2.94 (dd, J=15.5, 7.4 Hz, 1H), 3.42 (dd, J=14.4, 8.8 Hz, 1H), 3.70-3.77 (m, 1H), 3.79-3.84 (m, 1H), 3.87-3.94 (m, 1H), 4.23-4.29 (m, 2H), 5.13 (d, J=14.0 Hz, 1H), 5.29 (d, J=14.0 Hz, 1H), 6.80 (d, J=8.1 Hz, 1H), 7.15 (dd, J=7.4, 5.0 Hz, 2H), 7.22 (s, 4H), 7.51 (td, J=7.7, 2.2 Hz, 1H), 8.51 (d, J=5.0 Hz, 1H). $^{13}$C NMR (75 MHz, CDCl$_3$) δ 17.3, 25.6, 29.2, 37.1, 39.2, 46.1, 66.3, 68.1, 77.9, 109.6, 121.2, 122.7, 128.7, 128.8, 132.6, 136.8, 139.5, 149.0, 152.1, 156.0, 166.7, 168.9. MS [M+H]$^+$ 441, HRMS: calcd for C$_{26}$H$_{28}$NO$_5$Cl$_2$, [M+H]$^+$ 441.1581, found 441.1584.

Example 146: 3-pyridylmethyl (4S)-4-(4-chlorophenyl)-6-methyl-2-oxo-1-[[(2R)-tetrahydrofuran-2-yl]methyl]-3,4-dihydropyridine-5-carboxylate and 3-pyridylmethyl (4R)-4-(4-chlorophenyl)-6-methyl-2-oxo-1-[[(2S)-tetrahydrofuran-2-yl]methyl]-3,4-dihydropyridine-5-carboxy late Racemic mixture of (4S)-4-(4-chlorophenyl)-6-methyl-2-oxo-1-[[(2R)-tetrahydrofuran-2-yl]methyl]-3,4-dihydropyridine-5-carboxylic acid and its enantiomer (example 135, 105 mg, 0.30 mmol) was dissolved in anhydrous DMF (1 mL) then cesium carbonate (215 mg, 0.66 mmol) and 3-(Chloromethyl)pyridine hydrochloride (132 mg, 0.36 mmol) were added. The reaction mixture was stirred at RT for 18 h. The solvent was removed under reduced pressure. Water was added. The aqueous phase was extracted with Et$_2$O. The combined organic layers were washed with brine and dried over MgSO$_4$. The solvent was removed under reduced pressure. Purification of the crude by flash chromatography on silica using a mixture of DCM/EtOAc (8/2) gave the desired (3-pyridylmethyl (4S)-4-(4-chlorophenyl)-6-methyl-2-oxo-1-[[(2R)-tetrahydrofuran-2-yl]methyl]-3,4-dihydropyridine-5-carboxylate (racemic) as a colorless oil (101 mg, 76%). $^1$H NMR (300 MHz, CDCl$_3$) δ 1.42-1.51 (m, 1H), 1.83-2.00 (m, 3H), 2.65 (s, 3H), 2.71 (dd, J=15.5, 2.2 Hz, 1H), 2.94 (dd, J=15.5, 7.4 Hz, 1H), 3.42 (dd, J=14.4, 8.8 Hz, 1H), 3.70-3.77 (m, 1H), 3.79-3.84 (m, 1H), 3.87-3.94 (m, 1H), 4.23-4.29 (m, 2H), 5.13 (d, J=14.0 Hz, 1H), 5.29 (d, J=14.0 Hz, 1H), 6.80 (d, J=8.1 Hz, 1H), 7.15 (dd, J=7.4, 5.0 Hz, 2H), 7.22 (s, 4H), 7.51 (td, J=7.7, 2.2 Hz, 1H), 8.51 (d, J=5.0 Hz, 1H). $^{13}$C NMR (75 MHz, CDCl$_3$) δ 17.2, 25.5, 29.2, 37.1, 39.1, 45.8, 63.4, 68.1, 77.8, 109.49, 123.4, 128.6, 128.7, 131.8, 132.6, 135.5, 139.4, 149.0, 149.3, 152.2, 166.7, 168.9. MS [M+H]$^+$ 441, HRMS: calcd for C$_{24}$H$_{26}$N$_2$O$_4$C0, [M+H]$^+$ 441.1581, found 441.1580.

TABLE 11

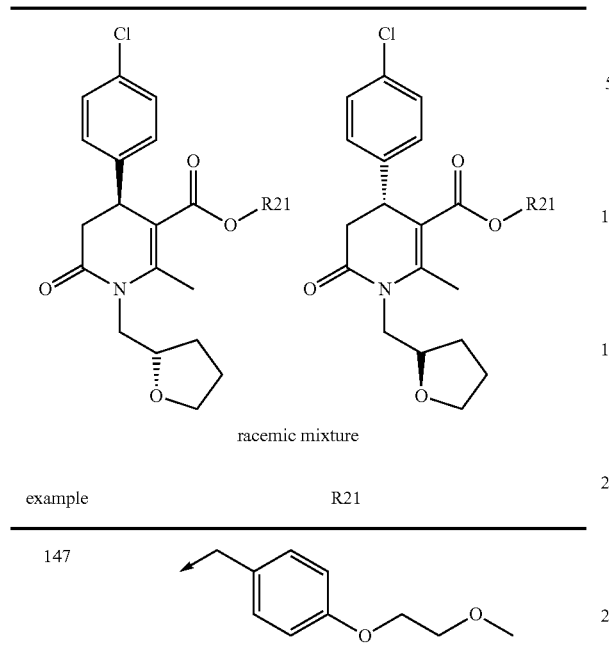

racemic mixture

| example | R21 |
| --- | --- |
| 147 | (4-methylbenzyl with para-OCH2CH2OCH3) |

Example 147: [4-(2-methoxyethoxy)phenyl]methyl (4S)-4-(4-chlorophenyl)-6-methyl-2-oxo-1-[[(2S)-tetrahydrofuran-2-yl]methyl]-3,4-dihydropyridine-5-carboxylate and [4-(2-methoxyethoxy)phenyl] methyl (4R)-4-(4-chlorophenyl)-6-methyl-2-oxo-1-[[(2R)-tetrahydrofuran-2-yl]methyl]-3,4-dihydropyridine-5-carboxylate 1-(chloromethyl)-4-(2-methoxyethoxy)benzene (example 118, 125 mg, 0.60 mmol) and (4S)-4-(4-chlorophenyl)-6-methyl-2-oxo-1-[[(2S)-tetrahydrofuran-2-yl]methyl]-3,4-dihydropyridine-5-carboxylic acid (192 mg, 0.55 mmol) were dissolved in anh. DMF (2 mL). Cesium carbonate (269 mg, 0.825 mmol) was added and the reaction mixture was stirred at RT for 18 h. The solvents were removed under reduced pressure. Water was added and the aqueous phase was extracted with diethyl ether, washed with brine and dried over $Na_2SO_4$. The solvents were removed under reduced pressure. Purification of the crude by flash chromatography using a mixture of Cy/DCM 1/1 to DCM gave the expected [4-(2-methoxyethoxy)phenyl]methyl (4S)-4-(4-chlorophenyl)-6-methyl-2-oxo-1-[[(2S)-tetrahydrofuran-2-yl] methyl]-3,4-dihydropyridine-5-carboxylate as a colorless oil (59 mg, 21%) $^1$H NMR (300 MHz, $CDCl_3$) δ 1.24-1.36 (m, 1H), 1.74-1.94 (m, 3H), 2.61 (s, 3H), 2.78 (dd, J=15.9, 2.7 Hz, 1H), 2.91 (dd, J=15.9, 7.3 Hz, 1H), 3.46 (s, 3H), 3.66-3.84 (m, 5H), 3.88-4.06 (m, 2 h), 4.09-4.14 (m, 2H), 4.18 (dd, J=7.3, 2.1 Hz, 1H), 5.01 (d, J=12.2 Hz, 1H), 5.07 (d, J=12.2 Hz, 1H), 6.85 (d, J=8.6 Hz, 2H), 7.06 (d, J=8.4 Hz, 2H), 7.08 (d, J=8.6 Hz, 2H), 7.19 (d, J=8.4 Hz, 2H). $^{13}$C NMR (75 MHz, $CDCl_3$) δ 17.4, 25.3, 28.9, 36.4, 38.3, 45.2, 59.2, 65.9, 67.2, 67.7, 71.0, 110.4, 114.4, 128.3, 128.4, 128.6, 129.6, 132.5, 139.8, 150.6, 158.6, 167.0, 169.4. MS [M+H]$^+$ 514, HRMS: calcd for $C_{28}H_{33}NO_6Cl$, [M+H]$^+$ 514.1996, found 514.2003.

TABLE 12

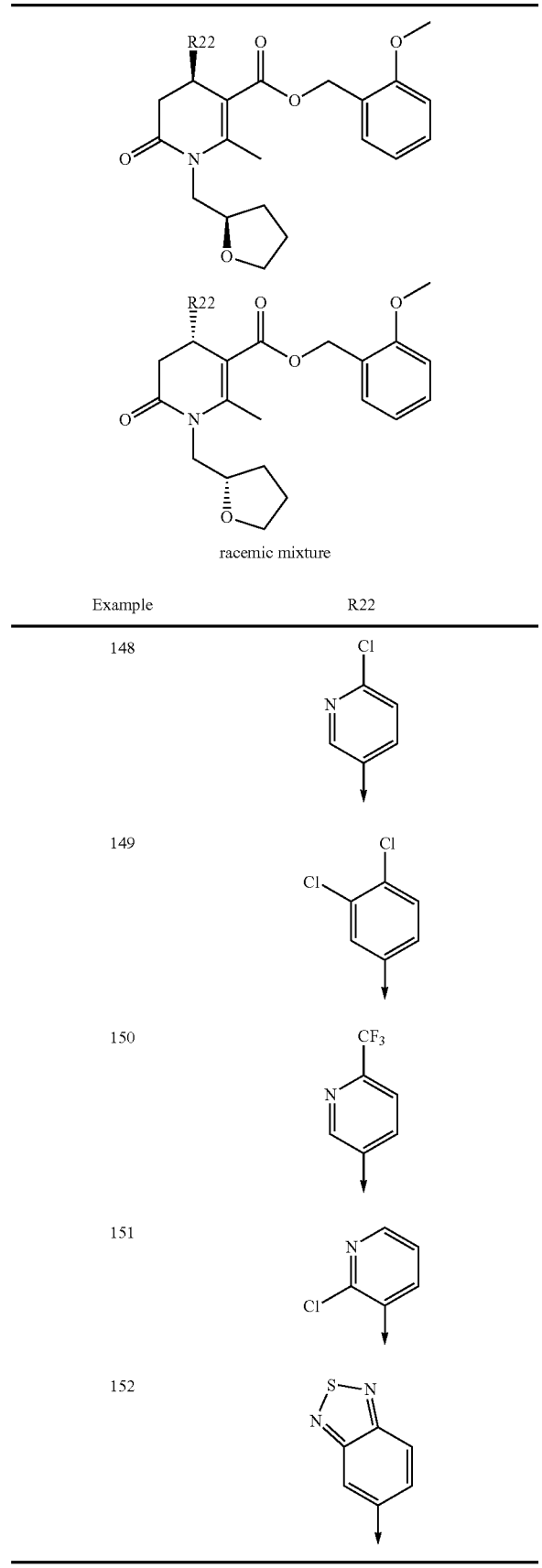

racemic mixture

| Example | R22 |
| --- | --- |
| 148 | 2-chloropyridin-5-yl |
| 149 | 3,4-dichlorophenyl |
| 150 | 2-(trifluoromethyl)pyridin-5-yl |
| 151 | 2-chloropyridin-3-yl |
| 152 | 2,1,3-benzothiadiazol-5-yl |

Example 148: (2-methoxyphenyl)methyl (4S)-4-(6-chloro-3-pyridyl)-6-methyl-2-oxo-1-[[(2R)-tetrahydrofuran-2-yl]methyl]-3,4-dihydropyridine-5-carboxylate and 2-methoxyphenyl)methyl (4R)-4-(6-chloro-3-pyridyl)-6-methyl-2-oxo-1-[[(2S)-tetrahydrofuran-2-yl]methyl]-3,4-dihydropyridine-5-carboxylate Step 1.

6-chloropyridine-3-carbaldehyde (3 mmol), meldrum acid (3 mmol), (2-methoxyphenyl)methyl-3-oxobutanoate (3 mmol) and ammonium acetate (4.5 equiv) were dissolved in acetic acid (1N). The reaction mixture was stirred overnight under reflux. The solvent was removed. The crude product was purified by flash chromatography and engaged in step 2.

Step 2.

The intermediate obtained in step 1 (1.3 g, 3.36 mmol) was dissolved in anh. DMF (12 mL). Tetrahydrofurfuryl bromide (573 µL, 5.04 mmol), $Cs_2CO_3$ (1.64 g, 5.04 mmol), sodium iodide (25 mg, 0.17 mmol) were added. The reaction mixture was stirred at 50° C. for 18 h. The DMF was removed under reduced pressure. The residue was diluted in water. The aqueous phase was extracted by EtOAc and the combined organic layers were washed with brine and dried over $MgSO_4$. The solvent was removed under reduced pressure. The crude was dissolved again in anh. DMF (1 mL). Tetrahydrofurfuryl bromide (573 µL, 5.04 mmol) and $Cs_2CO_3$ (1.64 g, 5.04 mmol) were added. The reaction mixture was stirred at 50° C. for 18 h. The DMF was removed under reduced pressure. The residue was diluted in water. The aqueous phase was extracted by EtOAc and the combined organic layers were washed with brine and dried over $MgSO_4$. The solvent was removed under reduced pressure. Purification of the crude by flash chromatography using a mixture of Cyclohexane/EtOAc (8/2) as eluent gave the desired (2-methoxyphenyl)methyl (4S)-4-(6-chloro-3-pyridyl)-6-methyl-2-oxo-1-[[(2R)-tetrahydrofuran-2-yl]methyl]-3,4-dihydropyridine-5-carboxylate and its enantiomer as a colorless oil (204 mg, 13%). $^1$H NMR (300 MHz, $CDCl_3$) δ 1.39-1.51 (m, 1H), 1.81-2.07 (m, 3H), 2.60 (s, 3H), 2.64 (dd, J=16.0, 2.0 Hz, 1H), 2.92 (dd, J=15.7, 7.5 Hz, 1H), 3.39 (dd, J=14.2, 9.3 Hz, 1H), 3.70 (s, 3H), 3.72-3.77 (m, 1H), 3.83-3.90 (m, 2H), 4.23 (dd, J=14.0, 2.8 Hz, 2H), 5.08 (d, J=12.5 Hz, 1H), 5.14 (d, J=12.5 Hz, 1H), 6.80-6.87 (m, 2H), 7.02 (dd, J=7.5, 1.7 Hz, 1H), 7.13 (d, J=8.3 Hz, 1H), 7.22-7.28 (td, J=7.8, 1.7 Hz, 1H), 7.57 (dd, J=8.3, 2.5 Hz, 1H), 8.21 (d, J=2.5 Hz, 1H). $^{13}$C NMR (75 MHz, $CDCl_3$) δ 17.08, 25.61, 29.18, 34.88, 38.62, 45.96, 55.21, 62.04, 68.16, 77.63, 109.31, 110.30, 120.25, 123.97, 124.02, 129.46, 129.58, 135.94, 137.88, 149.16, 149.79, 151.66, 157.42, 166.71, 168.4. MS [M+H]$^+$ 471 g/mol. HRMS: calcd for $C_{25}H_{28}N_2O_5Cl_2$, [M+H]$^+$ 471.1687, found 471.1695.

Example 149a: 4-(3,4-dichlorophenyl)-6-methyl-2-oxo-3,4-dihydro-1H-pyridine-5-carboxylate (Intermediate Product)

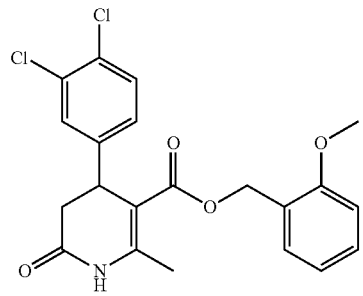 [SMILES: COc1ccccc1COC(=O)C1=C(C)NC(=O)CC1c1ccc(Cl)c(Cl)c1]

3,4-dichlorobenzaldehyde (3.0 mmol, 525 g), meldrum acid (3.0 mmol, 432 g), o-methoxybenzyl acetoacetate (3.0 mmol, 666 mg) and ammonium acetate (4.5 mmol, 338 mg) were dissolved in acetic acid (3 mL). The reaction mixture was stirred at 110° C. for 18 h. The solvent was removed. The crude didn't precipitate in EtOH. The crude has been purified by flash chromatography (Cy/EA (85/15) to and precipitated in EtOH. Then, a filtration yielded the desired (2-methoxyphenyl)methyl 4-(3,4-dichlorophenyl)-6-methyl-2-oxo-3,4-dihydro-1H-pyridine-5-carboxylate as a white powder (384 mg, 30%). $^1$H NMR (300 MHz, $CDCl_3$) δ 2.43 (s, 3H), 2.63 (dd, J=16.7, 1.3 Hz, 1H), 2.94 (dd, J=16.7, 8.1 Hz, 1H), 3.76 (s, 3H), 4.23 (d, J=7.7 Hz, 1H), 5.12 (d, J=12.6 Hz, 1H), 5.22 (d, J=12.6 Hz, 1H), 6.86 (d, J=8.3 Hz, 1H), 6.88 (td, J=7.4, 1.0 Hz, 1H), 6.99 (dd, J=8.5, 2.3 Hz, 1H), 7.08 (dd, J=7.4, 1.7 Hz, 1H), 7.22 (d, J=2.0 Hz, 1H), 7.26-7.33 (m, 2H), 8.34 (brs, 1H). $^{13}$C NMR (75 MHz, $CDC_3$) δ 19.1, 37.3, 37.7, 55.2, 61.8, 106.3, 110.3, 120.3, 124.0, 126.2, 128.9, 129.6, 130.6, 130.9, 132.6, 142.5, 147.0, 157.4, 166.3, 170.3. MS [M−H]$^-$ 418

Example 149: (2-methoxyphenyl)methyl (4S)-4-(3,4-dichlorophenyl)-6-methyl-2-oxo-1-[[(2R)-tetrahydrofuran-2-yl]methyl]-3,4-dihydropyridine-5-carboxylate and (2-methoxyphenyl)methyl (4R)-4-(3,4-dichlorophenyl)-6-methyl-2-oxo-1-[[(2S)-tetrahydrofuran-2-yl]methyl]-3,4-dihydropyridine-5-carboxylate 4-(3,4-dichlorophenyl)-6-methyl-2-oxo-3,4-dihydro-1H-pyridine-5-carboxylate (example 149a, 150 mg, 0.36 mmol) was dissolved in anh. DMF (1 mL). Tetrahydrofurfuryl bromide (81 µL, 0.72 mmol) and $Cs_2CO_3$ (232 mg, 0.72 mmol) were added. The reaction mixture was stirred at 50° C. for 18 h. The DMF was removed under reduced pressure. The residue was diluted in water.

The aqueous phase was extracted by EtOAc and the combined organic layers were washed with brine and dried over $MgSO_4$. The solvent was removed under reduced pressure. The crude was dissolved again in anh. DMF (1 mL). Tetrahydrofurfuryl bromide (81 µL, 0.72 mmol) and $Cs_2CO_3$ (232 mg, 0.72 mmol) were added. The reaction mixture was stirred at 50° C. for 18 h. The DMF was removed under reduced pressure. The residue was diluted in water. The aqueous phase was extracted by EtOAc and the combined organic layers were washed with brine and dried over MgSO₄. The solvent was removed under reduced pressure. Purification of the crude by flash chromatography using a mixture of Cyclohexane/EtOAc (8/2) as eluent gave the desired (2-methoxyphenyl)methyl (4S)-4-(3,4-dichlorophenyl)-6-methyl-2-oxo-1-[[(2R)-tetrahydrofuran-2-yl]methyl]-3,4-dihydropyridine-5-carboxylate as a colorless oil (52 mg, 29%) and its diastereomer as a colorless oil (33 mg, 18%). $^1$H NMR (300 MHz, CDCl₃) δ 1.46-1.52 (m, 1H), 1.87-2.00 (m, 3H), 2.64 (s, 3H), 2.69 (dd, J=15.6, 2.1 Hz, 1H), 2.91 (dd, J=15.6, 7.5 Hz, 1H), 3.41 (dd, J=14.3, 9.0 Hz, 1H), 3.73 (s, 3H), 3.76-3.95 (m, 3H), 4.17 (d, J=6.7 Hz, 1H), 4.29 (dd, J=14.3, 3.1 Hz, 1H), 5.10 (d, J=13.0 Hz, 1H), 5.20 (d, J=13.0 Hz, 1H), 6.84 (t, J=8.0 Hz, 2H), 7.00 (dd, J=7.3, 1.5 Hz, 1H), 7.08 (dd, J=8.4, 2.1 Hz, 1H), 7.27 (td, J=5.8, 1.8 Hz, 2H), 7.38 (d, J=2.1 Hz, 1H). $^{13}$C NMR (75 MHz, CDCl₃) δ 17.1, 25.6, 26.9, 29.3, 37.1, 38.9, 45.9, 55.2, 61.9, 68.2, 77.8, 109.8, 110.2, 120.2, 124.3, 127.0, 129.1, 129.2, 129.3, 130.4, 130.7, 132.5, 141.6, 151.5, 157.3, 166.9, 168.7. MS [M+H]⁺ 504, HRMS: calcd for C₂₈H₂₈NO₅Cl₂, [M+H]⁺ 504.1345, found 504.1351.

Example 150 (2-Methoxyphenyl)methyl (4S)-6-methyl-2-oxo-1-[[(2R)-tetrahydrofuran-2-yl]methyl]-4-[6-(trifluoromethyl)-3-pyridyl]-3,4-dihydropyridine-5-carboxylate and (2-methoxyphenyl)methyl (4R)-6-methyl-2-oxo-1-[[(2S)-tetrahydrofuran-2-yl]methyl]-4-[6-(trifluoromethyl)-3-pyridyl]-3,4-dihydropyridine-5-carboxylate

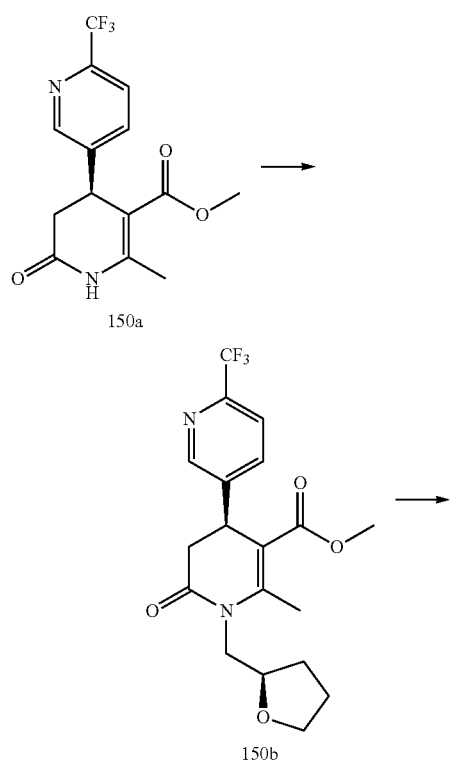

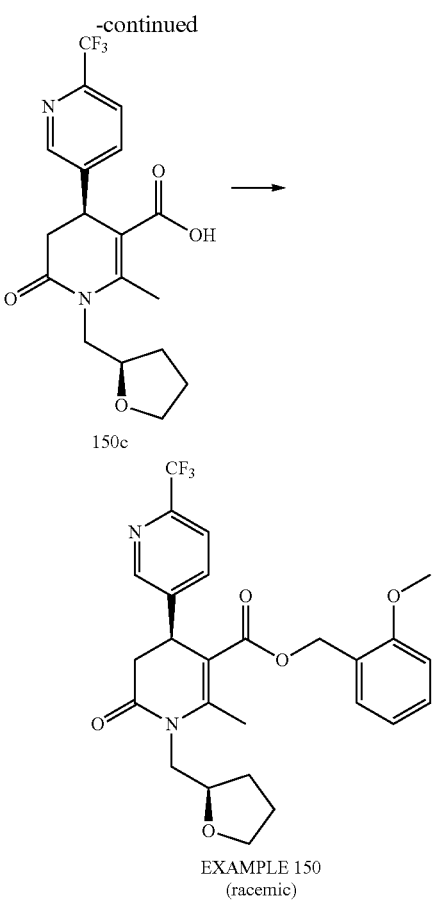

EXAMPLE 150
(racemic)

Example 150a. Methyl 6-methyl-2-oxo-4-[6-(trifluoromethyl)-3-pyridyl]-3,4-dihydro-1H-pyridine-5-carboxylate The methyl 3-oxobutanoate (0.37 mL, 3.43 mmol) was dissolved in acetic acid (9 mL). 6-(trifluoromethyl)pyridine-3-carbaldehyde (600 mg, 3.43 mmol), Meldrum's acid (494 mg, 3.43 mmol) and ammonium acetate (396 mg, 5.14 mmol) were added and the reaction mixture was stirred for 18 h at 110° C. The reaction mixture was cooled at r.t. Solvent was removed under reduced pressure and the residue was dissolved in the minimum of ethanol. The mixture was sonicated with ultrasound and the product precipitated. The mixture was cooled and the precipitate was filtered and washed with cold ethanol to give the desired product as a white powder (394 mg, 37%).

$^1$H NMR (300 MHz, CDCl₃) δ 2.39 (s, 3H), 2.64 (d, J=16.2 Hz, 1H), 2.99 (dd, J=16.7, 8.2 Hz, 1H), 3.63 (s, 3H), 4.33 (d, J=7.7 Hz, 1H), 7.59 (d, J=8.1 Hz, 1H), 7.65 (dd, J=8.1, 1.9 Hz, 1H), 8.57 (d, J=1.4 Hz, 1H), 9.20 (s, 1H). $^{13}$C NMR (75 MHz, CDCl₃) δ 19.0, 35.7, 37.4, 51.7, 105.4, 119.7, 120.7, 123.4, 135.7, 141.1, 148.1, 149.0, 166.8, 170.7. MS [M+H]⁺ 315 g/mol.

Example 150b. Methyl (4S)-6-methyl-2-oxo-1-[[(2R)-tetrahydrofuran-2-yl]methyl]-4-[6-(trifluoromethyl)-3-pyridyl]-3,4-dihydropyridine-5-carboxylate and methyl (4R)-6-methyl-2-oxo-1-[[(2S)-tetrahydrofuran-2-yl]methyl]-4-[6-(trifluoromethyl)-3-pyridyl]-3,4-dihydropyridine-5-carboxylate The methyl 6-methyl-2-oxo-4-[6-(trifluoromethyl)-3-pyridyl]-3,4-dihydro-1H-pyridine-5-carboxylate (150a, 328 mg, 1.04 mmol) and the 2-(bromomethyl)tetrahydrofuran (345 mg, 2.09 mmol) were dissolved in anhydrous DMF (3 mL), Cs$_2$CO$_3$ (681 mg, 2.09 mmol) and NaI (8 mg, 0.05 mmol) were added and the reaction mixture was stirred at 50° C. overnight. The solvent was removed under reduced pressure. Water was added and the mixture was extracted by ethyl acetate, the organic layers washed with brine, and dried over Na$_2$SO$_4$ and filtered. The solvent was removed and the crude product was purified by column chromatography on silica gel (CH$_2$Cl$_2$/Cy 70/30 to 100/0 and CH$_2$Cl$_2$/MeOH 100/0 to 96/4) to give the expected product as oil (100 mg, 24%).

$^1$H NMR (300 MHz, CDCl$_3$) δ 1.34-1.52 (m, 1H), 1.78-2.01 (m, 3H), 2.60 (s, 3H), 2.69 (dd, J=15.8, 2.0 Hz, 1H), 2.89-3.04 (m, 1H), 3.38 (dd, J=14.2, 9.4 Hz, 1H), 3.61 (s, 3H), 3.66-3.93 (m, 3H), 4.15-4.35 (m, 2H), 7.50 (d, J=8.1 Hz, 1H), 7.79-7.87 (m, 1H), 8.59 (d, J=1.9 Hz, 1H). $^{13}$C NMR (75 MHz, CDCl$_3$) δ 17.2, 25.7, 29.2, 35.3, 38.6, 46.0, 51.8, 68.2, 77.7, 108.8, 119.9, 120.4, 123.5, 136.1, 140.1, 149.8, 152.2, 167.3, 168.3. MS [M+H]$^+$ 399 g/mol.

Example 150c. (4S)-6-methyl-2-oxo-1-[[(2R)-tetra-hydrofuran-2-yl]methyl]-4-[6-(trifluoromethyl)-3-pyridyl]-3,4-dihydropyridine-5-carboxylic acid and (4R)-6-methyl-2-oxo-1-[[(2S)-tetrahydrofuran-2-yl]methyl]-4-[6-(trifluoromethyl)-3-pyridyl]-3,4-dihydropyridine-5-carboxylic acid 150b (95 mg, 0.24 mmol) was dissolved in MeOH (2 mL), NaOH 1N (1 mL) was added. The reaction mixture was stirred overnight at 40° C. The MeOH was evaporated under reduced pressure, the aqueous phase was extracted by Et$_2$O, then acidified to pH=1 with HCl (1N). The aqueous phase was extracted by EtOAc. The organic phases were assembled, dried under Na$_2$SO$_4$ and filtered. The solvents were removed under reduced pressure to afford a product as oil. (m=86 mg, 92%).

$^1$H NMR (300 MHz, CDCl$_3$) δ 1.37-1.50 (m, 1H), 1.80-1.99 (m, 3H), 2.61 (s, 3H), 2.73 (dd, J=15.8, 1.8 Hz, 1H), 2.98 (dd, J=15.8, 7.5 Hz, 1H), 3.40 (dd, J=14.2, 9.4 Hz, 1H), 3.65-3.90 (m, 3H), 4.22 (dd, J=14.3, 2.7 Hz, 1H), 4.31 (d, J=6.8 Hz, 1H), 7.51 (d, J=8.2 Hz, 1H), 7.83 (dd, J=8.1, 2.0 Hz, 1H), 8.62 (d, J=2.0 Hz, 1H), 10.40 (s, 1H). $^{13}$C NMR (75 MHz, CDCl$_3$) δ 17.5, 25.7, 29.2, 35.2, 38.4, 46.2, 68.3, 77.6, 108.2, 120.4, 123.5, 136.2, 140.1, 149.7, 154.5, 168.6, 172.0, 175.6. MS [M+H]$^+$ 385 g/mol.

Example 150 (2-Methoxyphenyl)methyl (4S)-6-methyl-2-oxo-1-[[(2R)-tetrahydrofuran-2-yl]methyl]-4-[6-(trifluoromethyl)-3-pyridyl]-3,4-dihydropyridine-5-carboxylate and (2-methoxyphenyl)methyl (4R)-6-methyl-2-oxo-1-[[(2S)-tetrahydrofuran-2-yl]methyl]-4-[6-(trifluoromethyl)-3-pyridyl]-3,4-dihydropyridine-5-carboxylate The 1-(chloromethyl)-2-methoxy-benzene (39 mg, 0.25 mmol) and the acid 150c (86 mg, 0.22 mmol) were dissolved in dry DMF (2 mL). Cesium carbonate (109 mg, 0.34 mmol) was added and the reaction mixture was stirred at RT overnight. The solvent was removed. Water was added and the aqueous phase was extracted by Et$_2$O, washed with brine and dried under Na$_2$SO$_4$. After filtration the solvent was removed and the crude product was purified by column chromatography on silica gel (Cy/EA 100 to 80/20) then by HPLC (acid conditions) to give the expected product as white solid (65 mg, 58%).

$^1$H NMR (300 MHz, CDCl$_3$) δ 1.50-1.67 (m, 1H), 1.79-2.12 (m, 3H), 2.58-2.80 (m, 4H), 2.99 (dd, J=15.4, 7.2 Hz, 1H), 3.42 (dd, J=14.1, 9.3 Hz, 1H), 3.59-3.80 (m, 4H), 3.81-3.99 (m, 2H), 4.17-4.38 (m, 2H), 5.12 (q, J=12.3 Hz, 2H), 6.82 (dd, J=11.2, 7.9 Hz, 2H), 7.01 (d, J=7.1 Hz, 1H), 7.25 (d, J=7.5 Hz, 1H), 7.49 (d, J=8.0 Hz, 1H), 7.81 (d, J=7.4 Hz, 1H), 8.55 (s, 1H). $^{13}$C NMR (75 MHz, CDCl$_3$) δ 17.2, 25.7, 29.3, 35.5, 38.5, 46.2, 55.3, 62.3, 68.3, 77.7, 109.1, 110.4, 120.3, 120.4, 123.6, 124.0, 129.7, 129.8, 136.1, 140.5, 146.7, 149.9, 152.1, 157.6, 166.8, 168.4. MS [M+H]$^+$ 505 g/mol.

Example 151: (2-Methoxyphenyl)methyl (4R)-4-(2-chloro-3-pyridyl)-6-methyl-2-oxo-1-[[(2R)-tetrahydrofuran-2-yl]methyl]-3,4-dihydropyridine-5-carboxylate and (2-methoxyphenyl)methyl (4S)-4-(2-chloro-3-pyridyl)-6-methyl-2-oxo-1-[[(2S)-tetrahydrofuran-2-yl]methyl]-3,4-dihydropyridine-5-carboxylate

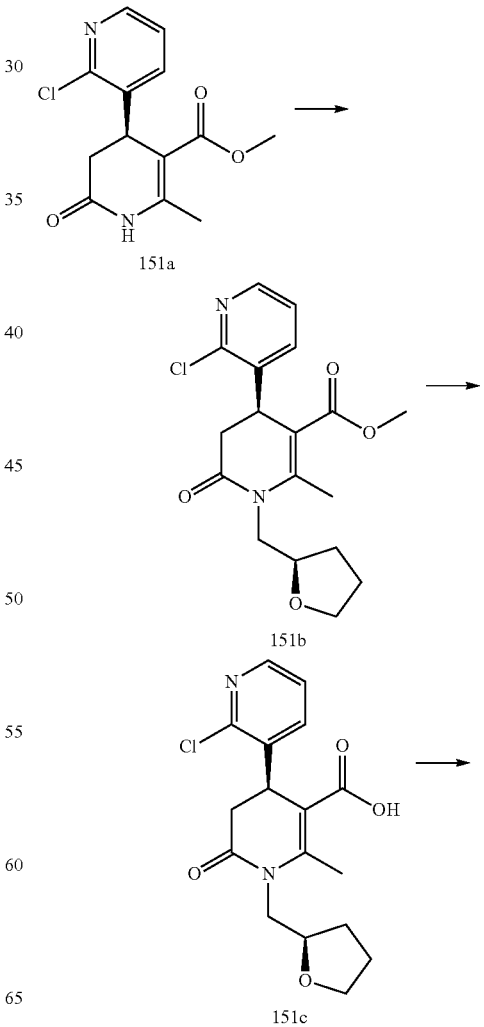

151a

151b

151c

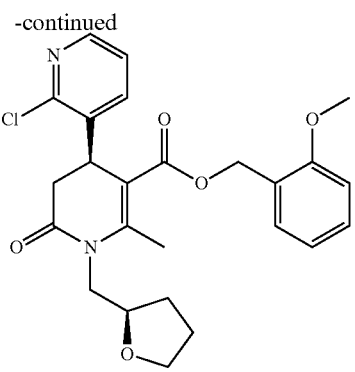

Example 151
(racemic)

Example 151a. Methyl 4-(2-chloro-3-pyridyl)-6-methyl-2-oxo-3,4-dihydro-1H-pyridine-5-carboxylate The methyl 3-oxobutanoate (0.68 mL, 6.30 mmol) was dissolved in acetic acid (7 mL). 2-chloropyridine-3-carbaldehyde (892 mg, 6.30 mmol), Meldrum's acid (908 mg, 6.30 mmol) and ammonium acetate (729 mg, 9.45 mmol) were added and the reaction mixture was stirred for 18 h at 110° C. The reaction mixture was cooled at RT. Solvent was removed under reduced pressure and the residue was purified by column chromatography on silica gel (CH$_2$Cl$_2$) to give the desired product as a white powder (850 mg, 48%).

$^1$H NMR (300 MHz, CDCl$_3$) δ 2.44 (s, 3H), 2.74 (dd, J=16.8, 1.1 Hz, 1H), 2.92 (dd, J=16.9, 8.3 Hz, 1H), 3.58 (s, 3H), 4.60 (d, J=7.8 Hz, 1H), 7.13 (dd, J=7.6, 4.7 Hz, 1H), 7.33 (dd, J=7.6, 1.8 Hz, 1H), 8.25 (dd, J=4.7, 1.9 Hz, 1H), 9.05 (s, 1H). $^{13}$C NMR (75 MHz, CDCl$_3$) δ 18.9, 35.0, 35.9, 51.7, 104.8, 123.0, 135.0, 136.3, 148.2, 148.7, 150.8, 166.7, 170.8. MS [M−H]$^−$ 279 g/mol.

Example 151b. Methyl (4R)-4-(2-chloro-3-pyridyl)-6-methyl-2-oxo-1-[[(2R)-tetrahydrofuran-2-yl]methyl]-3,4-dihydropyridine-5-carboxylate and methyl (4S)-4-(2-chloro-3-pyridyl)-6-methyl-2-oxo-1-[[(2S)-tetrahydrofuran-2-yl]methyl]-3,4-dihydropyridine-5-carboxylate The Methyl 4-(2-chloro-3-pyridyl)-6-methyl-2-oxo-3,4-dihydro-1H-pyridine-5-carboxylate (151a, 700 mg, 2.5 mmol) and the 2-(bromomethyl)tetrahydrofuran (0.57 mL, 5.0 mmol) were dissolved in dry DMF (6 mL), Cs$_2$CO$_3$ (1.63 g, 5.0 mmol) and NaI (19 mg, 0.13 mmol) were added and the reaction mixture was stirred at 50° C. overnight. The solvent was removed under reduced pressure. Water was added and the aqueous phase was extracted by ethyl acetate, the organic layers were washed with brine and dried over Na$_2$SO$_4$. The solvent was removed. The residue was dissolved again in 6 mL of DMF, 1.63 g of Cs$_2$CO$_3$, 19 mg of NaI and the alkyl bromide (0.57 mL) were added and the mixture was stirred at 50° C. for 18 h. Reaction finished. The solvent was removed under reduced pressure. Water was added and the aqueous phase was extracted by ethyl acetate, the organic layers were washed with brine, and dried over Na$_2$SO$_4$. The solvent was removed. The purification by columns chromatography on silica (CH$_2$Cl$_2$/Cy 50/50 to 100/0) give the desired product as white product (m=245 mg, 27%).

$^1$H NMR (300 MHz, CDCl$_3$) δ 1.42-1.56 (m, 1H), 1.81-2.07 (m, 3H), 2.63 (s, 3H), 2.82-2.91 (m, 2H), 3.31-3.44 (m, 1H), 3.61 (s, 3H), 3.68-3.86 (m, 2H), 3.87-3.98 (m, 1H), 4.24 (dd, J=14.3, 2.5 Hz, 1H), 4.53 (t, J=4.7 Hz, 1H), 7.07 (dd, J=7.7, 4.7 Hz, 1H), 7.76 (dd, J=7.7, 1.8 Hz, 1H), 8.22 (dd, J=4.7, 1.8 Hz, 1H). $^{13}$C NMR (75 MHz, CDCl$_3$) δ 17.2, 25.8, 29.2, 34.8, 36.4, 46.1, 51.9, 68.3, 78.0, 108.8, 122.9, 134.3, 137.8, 148.1, 151.0, 152.7, 167.5

Example 151c. (4R)-4-(2-chloro-3-pyridyl)-6-methyl-2-oxo-1-[[(2R)-tetrahydrofuran-2-yl]methyl]-3,4-dihydropyridine-5-carboxylic acid and (4S)-4-(2-chloro-3-pyridyl)-6-methyl-2-oxo-1-[[(2S)-tetrahydrofuran-2-yl]methyl]-3,4-dihydropyridine-5-carboxylic acid 151b (130 mg, 0.36 mmol) was dissolved in MeOH (3 mL), NaOH 1N (2 mL) was added. The reaction mixture was stirred overnight at 40° C. The MeOH was evaporated under reduced pressure and the aqueous phase was extracted by Et$_2$O, then acidified to pH=1 with HCl (1N). The aqueous phase was extracted by EtOAc and the organic layers were assembled and dried under Na$_2$SO$_4$. The solvent was removed under reduced pressure to afford a product as white solid (m=110 mg, 88%).

$^1$H NMR (300 MHz, CDCl$_3$) δ 1.40-1.55 (m, 1H), 1.78-2.07 (m, 3H), 2.63 (s, 3H), 2.88 (d, J=4.5 Hz, 2H), 3.38 (dd, J=14.1, 9.7 Hz, 1H), 3.70-3.85 (m, 2H), 3.90 (dd, J=14.5, 6.9 Hz, 1H), 4.23 (d, J=14.2 Hz, 1H), 4.55 (t, J=4.2 Hz, 1H), 7.07 (dd, J=7.5, 4.8 Hz, 1H), 7.74 (d, J=7.5 Hz, 1H), 8.23 (d, J=3.4 Hz, 1H), 9.84 (s, 1H). $^{13}$C NMR (75 MHz, CDCl$_3$) δ 17.6, 25.8, 29.2, 34.7, 36.2, 46.1, 68.3, 77.9, 108.1, 122.9, 134.2, 137.8, 148.0, 150.9, 155.0, 168.9, 172.1. MS [M+H]$^+$ 351 g/mol.

Example 151. (2-Methoxyphenyl)methyl (4R)-4-(2-chloro-3-pyridyl)-6-methyl-2-oxo-1-[[(2R)-tetrahydrofuran-2-yl]methyl]-3,4-dihydropyridine-5-carboxylate and (2-methoxyphenyl)methyl (4S)-4-(2-chloro-3-pyridyl)-6-methyl-2-oxo-1-[[(2S)-tetrahydrofuran-2-yl]methyl]-3,4-dihydropyridine-5-carboxylate The 1-(chloromethyl)-2-methoxy-benzene (44 mg, 0.28 mmol) and the acid 151c (90 mg, 0.26 mmol) were dissolved in dry DMF (2 mL). Cesium carbonate (125 mg, 0.38 mmol) was added and the reaction mixture was stirred at RT overnight.

The solvent was removed. Water was added and the aqueous phase was extracted by Et$_2$O, organic layer was washed with brine and dried under Na$_2$SO$_4$. The solvent was removed. The purification by column chromatography on silica gel (Cy/EtOAc 100/0 to 80/20) give the expected product as white powder (m=90 mg, 75%).

$^1$H NMR (300 MHz, CDCl$_3$) δ 1.39-1.56 (m, 1H), 1.77-2.06 (m, 3H), 2.65 (s, 3H), 2.86 (dd, J=5.8, 4.6 Hz, 2H), 3.39 (dd, J=14.2, 9.5 Hz, 1H), 3.69 (s, 3H), 3.70-3.87 (m, 2H), 3.87-3.97 (m, 1H), 4.23 (dd, J=14.3, 2.6 Hz, 1H), 4.59 (dd,

J=6.7, 2.6 Hz, 1H), 5.09 (s, 2H), 6.81 (ddd, J=8.2, 7.4, 3.5 Hz, 2H), 6.96-7.10 (m, 2H), 7.17-7.26 (m, 1H), 7.72-7.82 (m, 1H), 8.20 (dd, J=4.7, 1.9 Hz, 1H). $^{13}$C NMR (75 MHz, CDCl$_3$) δ 17.1, 25.8, 29.2, 34.9, 36.3, 46.0, 55.3, 62.0, 68.3, 77.9, 108.9, 110.2, 120.3, 122.8, 124.2, 129.0, 129.4, 134.5, 137.8, 148.0, 151.0, 152.6, 157.3, 166.7, 168.7. MS [M+H]$^+$ 471 g/mol.

Example 152 (2-Methoxyphenyl)methyl (4S)-4-(2,1,3-benzothiadiazol-5-yl)-6-methyl-2-oxo-1-[[(2R)-tetrahydrofuran-2-yl]methyl]-3,4-dihydropyridine-5-carboxylate and (2-methoxyphenyl)methyl (4R)-4-(2,1,3-benzothiadiazol-5-yl)-6-methyl-2-oxo-1-[[(2S)-tetrahydrofuran-2-yl]methyl]-3,4-dihydropyridine-5-carboxylate

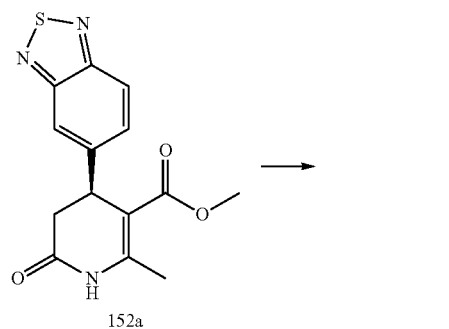

152a

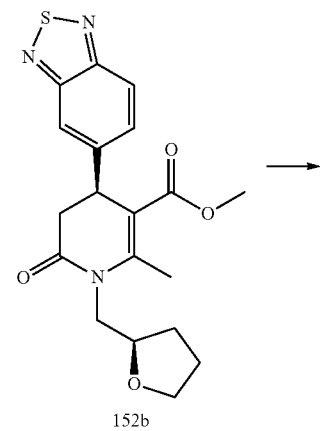

152b

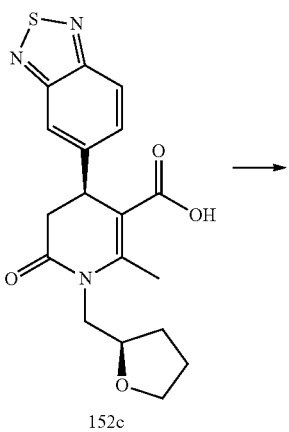

152c

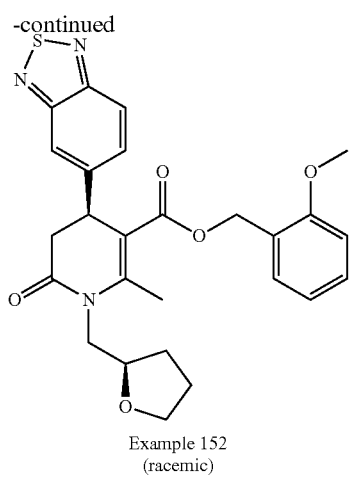

Example 152
(racemic)

Example 152a. Methyl 4-(2,1,3-benzothiadiazol-5-yl)-6-methyl-2-oxo-3,4-dihydro-1H-pyridine-5-carboxylate The methyl 3-oxobutanoate (0.4 mL, 3.65 mmol) was dissolved in acetic acid (9 mL). 2,1,3-benzothiadiazole-5-carbaldehyde (600 mg, 3.65 mmol), Meldrum's acid (527 mg, 3.65 mmol) and ammonium acetate (422 mg, 5.48 mmol) were added and the reaction mixture was stirred for 18 h at 110° C. The reaction mixture was cooled at RT. Solvent was removed under reduced pressure and the residue was dissolved in the minimum of ethanol. The mixture was sonicated with ultrasound and the product precipitated. The mixture was cooled and the precipitate was filtered and washed with cold ethanol to give the desired product as a beige powder (490 mg, 44%).
$^1$H NMR (300 MHz, CDC$_3$) δ 2.44 (s, 3H), 2.77 (d, J=16.6 Hz, 1H), 3.02 (dd, J=16.6, 8.2 Hz, 1H), 3.64 (s, 3H), 4.41 (d, J=7.8 Hz, 1H), 7.46 (dd, J=9.1, 1.7 Hz, 1H), 7.70 (s, 1H), 7.93 (d, J=9.1 Hz, 1H), 8.75 (s, 1H). $^{13}$C NMR (75 MHz, CDCl$_3$) δ 19.3, 37.7, 38.1, 51.7, 105.8, 118.1, 122.1, 130.2, 143.5, 147.8, 154.3, 155.2, 167.1, 170.7. MS [M+H]$^+$ 304 g/mol.

Example 152b. Methyl (4S)-4-(2,1,3-benzothiadiazol-5-yl)-6-methyl-2-oxo-1-[[(2S)-tetrahydrofuran-2-yl]methyl]-3,4-dihydropyridine-5-carboxylate and methyl (4R)-4-(2,1,3-benzothiadiazol-5-yl)-6-methyl-2-oxo-1-[[(2R)-tetrahydrofuran-2-yl]methyl]-3,4-dihydropyridine-5-carboxylate The methyl 4-(2,1,3-benzothiadiazol-5-yl)-6-methyl-2-oxo-3,4-dihydro-1H-pyridine-5-carboxylate (152a, 400 mg, 1.32 mmol) and the 2-(bromomethyl)tetrahydrofuran (435 mg, 2.64 mmol) were dissolved in anhydrous DMF (3 mL), Cs$_2$CO$_3$ (861 mg, 2.64 mmol) and NaI (10 mg, 0.07 mmol) were added and the reaction mixture was stirred at 50° C. overnight. The solvent was removed under reduced pressure. Water was added and the mixture was extracted by ethyl acetate, the organic layers washed with brine, and dried over Na$_2$SO$_4$ and filtered. The solvent was removed and the crude product was purified by column chromatography on silica gel (CH$_2$Cl$_2$/MeOH 100/0 to 96/4) to give the expected product as oil (m=120 mg, 24%). $^1$H NMR (300 MHz, CDCl$_3$) δ 1.25-1.28 (m, 1H), 1.57-1.88 (m, 3H), 2.68 (s, 3H), 2.89 (dd, J=16.0, 2.3 Hz, 1H), 3.03 (dd, J=15.9, 7.4 Hz, 1H), 3.59-3.73 (m, 4H), 3.74-3.92 (m, 2H), 3.92-4.07 (m, 2H), 4.36 (d, J=7.1 Hz, 1H), 7.47 (dd, J=9.1, 1.8 Hz, 1H), 7.60-7.72 (m, 1H), 7.91 (dd, J=9.1, 0.7 Hz, 1H). $^{13}$C NMR (75 MHz, CDCl$_3$) δ 17.6, 25.3, 29.2, 37.3, 38.3, 45.2, 51.8, 67.9, 77.5, 109.4, 118.6, 121.8, 130.4, 142.8, 151.7, 154.2, 155.2, 167.7, 169.2. MS [M+H]$^+$ 388 g/mol.

Example 152c. (4S)-4-(2,1,3-benzothiadiazol-5-yl)-6-methyl-2-oxo-1-[[(2R)-tetrahydrofuran-2-yl]methyl]-3,4-dihydropyridine-5-carboxylic acid and (4R)-4-(2,1,3-benzothiadiazol-5-yl)-6-methyl-2-oxo-1-[[(2S)-tetrahydrofuran-2-yl]methyl]-3,4-dihydropyridine-5-carboxylic acid Example 152b (88 mg, 0.23 mmol) was dissolved in MeOH (2 mL), NaOH 1N (1 mL) was added. The reaction mixture was stirred overnight at 40° C. The MeOH was evaporated under reduced pressure, the aqueous phase was extracted by Et$_2$O, then acidified to pH=1 with HCl (1N). The aqueous phase was extracted by EtOAc. The organic layers were assembled, dried under Na$_2$SO$_4$ and filtered. The solvents were removed under reduced pressure to afford a product as oil (m=70 mg, 82%).

$^1$H NMR (300 MHz, CDCl$_3$) δ 1.30-1.47 (m, 1H), 1.70-1.93 (m, 3H), 2.66 (s, 3H), 2.80 (dd, J=15.7, 2.0 Hz, 1H), 2.97 (dd, J=15.7, 7.3 Hz, 1H), 3.42 (dd, J=14.2, 8.9 Hz, 1H), 3.67-3.70 (m, 1H), 3.77-4.01 (m, 2H), 4.20-4.40 (m, 2H), 7.46 (dd, J=9.1, 1.8 Hz, 1H), 7.86 (dd, J=8.9, 0.8 Hz, 2H), 10.42 (s, 1H). $^{13}$C NMR (75 MHz, CDCl$_3$) δ 17.6, 25.4, 29.2, 37.6, 38.5, 45.8, 68.1, 78.0, 109.0, 118.9, 121.7, 130.5, 142.2, 154.3, 154.4, 155.3, 168.9, 172.4. MS [M+H]$^+$ 374 g/mol.

Example 152: (2-Methoxyphenyl)methyl (4S)-4-(2,1,3-benzothiadiazol-5-yl)-6-methyl-2-oxo-1-[[(2R)-tetrahydrofuran-2-yl]methyl]-3,4-dihydropyridine-5-carboxylate and (2-methoxyphenyl)methyl (4R)-4-(2,1,3-benzothiadiazol-5-yl)-6-methyl-2-oxo-1-[[(2S)-tetrahydrofuran-2-yl]methyl]-3,4-dihydropyridine-5-carboxylate The 1-(chloromethyl)-2-methoxy-benzene (32 mg, 0.21 mmol) and the acid 152c (70 mg, 0.19 mmol) were dissolved in dry DMF (2 mL). Cesium carbonate (92 mg, 0.28 mmol) was added and the reaction mixture was stirred at RT overnight.

The solvent was removed. Water was added and the aqueous phase was extracted by Et$_2$O, washed with brine and dried under Na$_2$SO$_4$. After filtration the solvent was removed and the crude product was purified by column chromatography on silica gel (Cy/EA 100 to 80/20) to give the expected product as oil (80 mg, 86%).

$^1$H NMR (300 MHz, CDCl$_3$) δ 1.35-1.51 (m, 1H), 1.75-1.97 (m, 3H), 2.69 (s, 3H), 2.79 (dd, J=15.7, 2.1 Hz, 1H), 3.01 (dd, J=15.7, 7.5 Hz, 1H), 3.45 (dd, J=14.2, 8.8 Hz, 1H), 3.64 (s, 3H), 3.71-3.83 (m, 1H), 3.82-3.40 (m, 2H), 4.29 (dd, J=14.2, 3.2 Hz, 1H), 4.38 (d, J=6.5 Hz, 1H), 5.13 (d, J=3.8 Hz, 2H), 6.65-6.75 (m, 2H), 6.99 (dd, J=7.4, 1.5 Hz, 1H), 7.18 (ddd, J=8.2, 7.5, 1.8 Hz, 1H), 7.47 (dd, J=9.1, 1.8 Hz, 1H), 7.89 (ddd, J=9.8, 5.4, 0.8 Hz, 2H). $^{13}$C NMR (75 MHz, CDCl$_3$) δ 17.3, 25.4, 29.3, 37.9, 38.6, 45.7, 55.2, 62.0, 68.1, 78.0, 110.0, 110.2, 119.1, 120.2, 121.5, 124.3, 129.2, 129.3, 130.6, 142.8, 151.8, 154.3, 155.4, 157.3, 167.0, 168.8. MS [M+H]$^+$ 494 g/mol.

TABLE 13

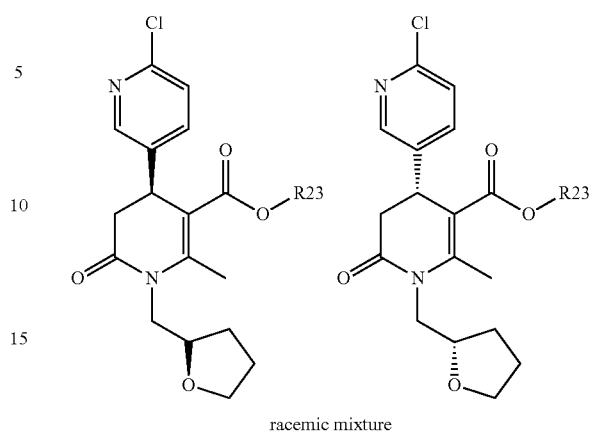

racemic mixture

| Examples | R23 |
|---|---|
| 153 | 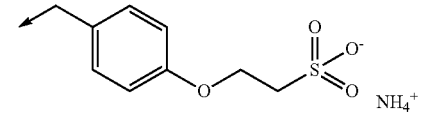 |
| 154 | 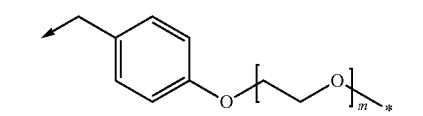 m = 7-10 |
| 155 | 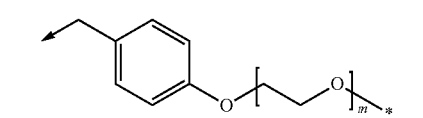 m = 18-23 |
| 156 | 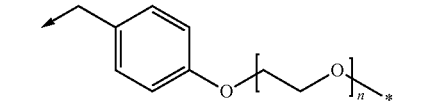 m = 35-44 |
| 157 | 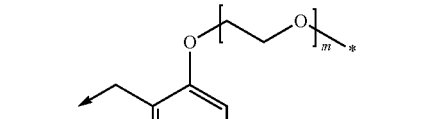 m = 10-14 |
| 158 | 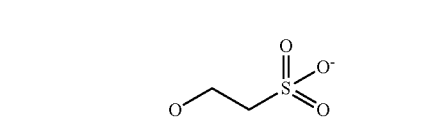 |

235
Example 153
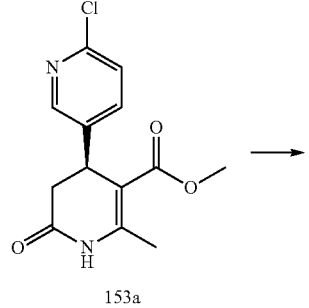
153a
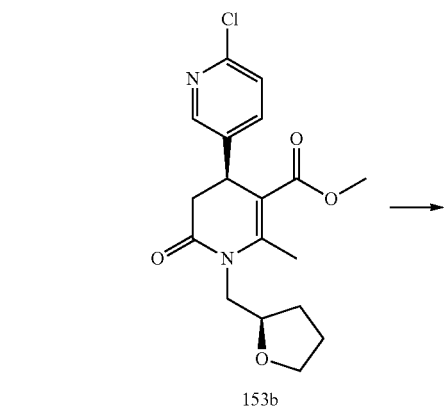
153b
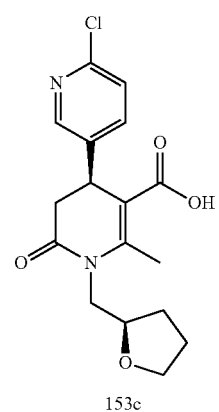
153c
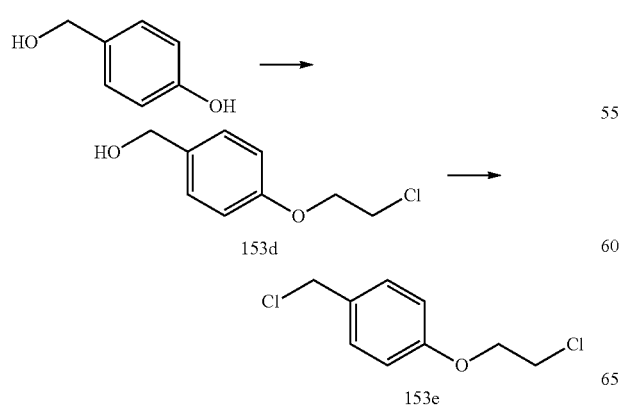
153d
153e
236
-continued
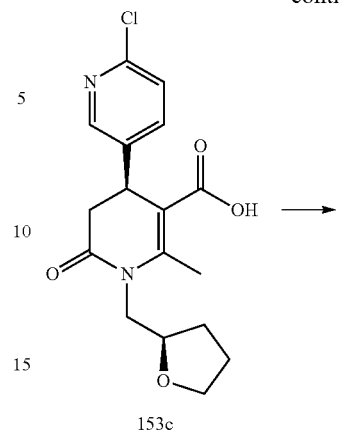
153c
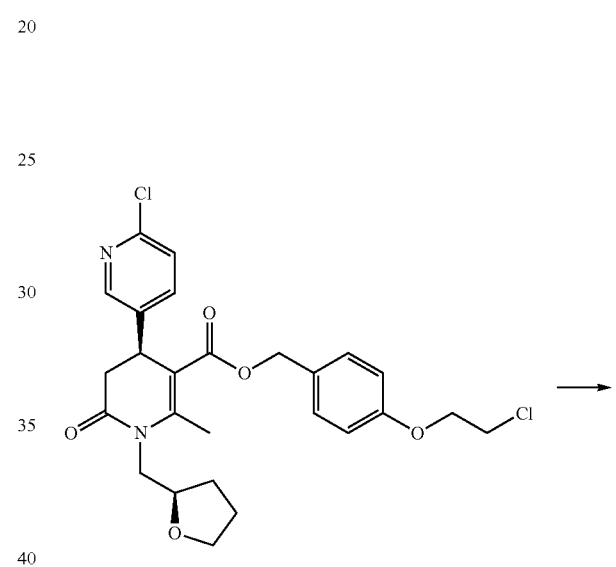
153f
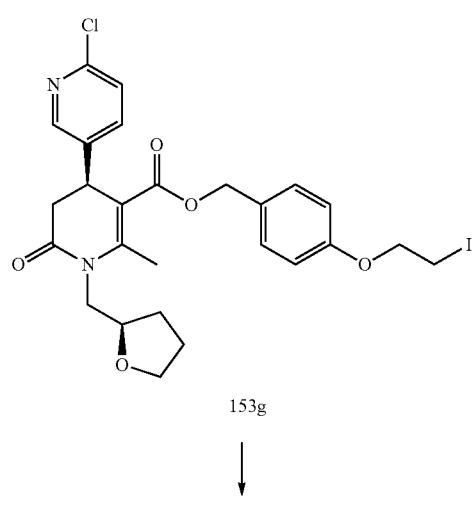
153g

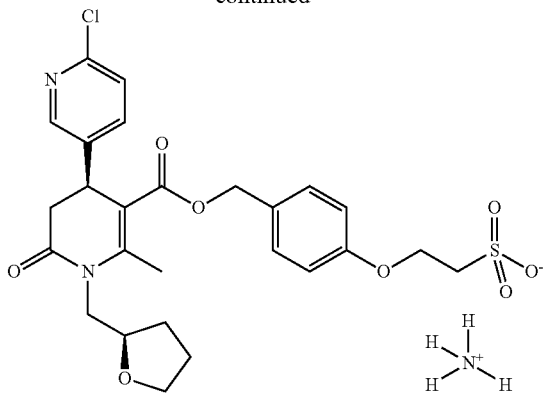

example 153 (racemic)

Example 153a. Methyl 4-(6-chloro-3-pyridyl)-6-methyl-2-oxo-3,4-dihydro-1H-pyridine-5-carboxylate The methyl 3-oxobutanoate (1.52 mL, 14.13 mmol) was dissolved in acetic acid (14 mL). 6-chloropyridine-3-carbaldehyde (2 g, 14.13 mmol), Meldrum's acid (2 g, 14.13 mmol) and ammonium acetate (1.63 g, 21.19 mmol) were added and the reaction mixture was stirred for 18 h at 110° C. The reaction mixture was cooled at RT. Solvent was removed under reduced pressure and the residue was dissolved in the minimum of ethanol. The mixture was sonicated with ultrasound and the product precipitated. The mixture was cooled and the precipitate was filtered and washed with cold ethanol to give the desired product as a beige powder (1.76 g, 44%).

$^1$H NMR (300 MHz, Acetone) δ 2.45 (s, 3H), 2.55 (dd, J=16.4, 1.9 Hz, 1H), 3.02 (dd, J=16.4, 7.8 Hz, 1H), 3.61 (s, 3H), 4.31 (d, J=7.5 Hz, 1H), 7.36 (d, J=8.3 Hz, 1H), 7.67 (dd, J=8.3, 2.6 Hz, 1H), 8.27 (d, J=2.6 Hz, 1H), 9.00 (s, 1H). $^{13}$C NMR (75 MHz, Acetone) δ 18.8, 36.1, 38.4, 51.5, 105.2, 125.0, 138.7, 149.5, 149.7, 149.8, 150.2, 167.5, 169.5. MS [M+H]$^+$ 281 g/mol.

Example 153b. Methyl (4S)-4-(6-chloro-3-pyridyl)-6-methyl-2-oxo-1-[[(2R)-tetrahydrofuran-2-yl]methyl]-3,4-dihydropyridine-5-carboxylate and methyl (4R)-4-(6-chloro-3-pyridyl)-6-methyl-2-oxo-1-[[(2S)-tetrahydrofuran-2-yl]methyl]-3,4-dihydropyridine-5-carboxylate The methyl 4-(6-chloro-3-pyridyl)-6-methyl-2-oxo-3,4-dihydro-1H-pyridine-5-carboxylate (600 mg, 2.14 mmol) and the 2-(bromomethyl)tetrahydrofuran (0.49 mL, 4.27 mmol) were dissolved in dry DMF (5 mL), Cs$_2$CO$_3$ (1,395 g, 4.28 mmol) and NaI (16.34 mg, 0.11 mmol) were added and the reaction mixture was stirred at 50° C. overnight. The solvent was removed under reduced pressure. Water was added and the aqueous phase was extracted by ethyl acetate, the organic layers were washed with brine and dried over Na$_2$SO$_4$. The solvent was removed. The residue was dissolved again in 5 mL of DMF, 1,395 g of Cs$_2$CO$_3$, 16 mg of NaI and the alkyl bromide (0.5 mL) were added and the mixture was stirred at 50° C. for 18 h. Reaction finished. The solvent was removed under reduced pressure. Water was added and the aqueous phase was extracted by ethyl acetate, the organic layers were washed with brine, and dried over Na$_2$SO$_4$. The solvent was removed. The purification by columns chromatography on silica gel (Cy/EtOAc 100/0 to 70/30 and CH$_2$Cl$_2$/Cy 70/30 to 100/0) give the desired product as white product (m=200 mg, 26%).

$^1$H NMR (300 MHz, CDCl$_3$) δ 1.40-1.51 (m, 1H), 1.76-2.03 (m, 3H), 2.58 (s, 3H), 2.65 (dd, J=15.7, 2.0 Hz, 1H), 2.92 (dd, J=15.7, 7.3 Hz, 1H), 3.36 (dd, J=14.2, 9.3 Hz, 1H), 3.61 (s, 3H), 3.67-3.92 (m, 3H), 4.13-4.30 (m, 2H), 7.16 (d, J=8.3 Hz, 1H), 7.60 (dd, J=8.3, 2.6 Hz, 1H), 8.25 (d, J=2.5 Hz, 1H). $^{13}$C NMR (75 MHz, CDC$_3$) δ 17.2, 25.7, 29.2, 34.8, 38.8, 46.0, 51.8, 68.2, 77.7, 109.1, 124.2, 135.6, 137.9, 149.2, 150.0, 151.9, 167.4, 168.4. MS [M+H]$^+$ 365 g/mol.

Example 153c. (4S)-4-(6-chloro-3-pyridyl)-6-methyl-2-oxo-1-[[(2R)-tetrahydrofuran-2-yl]methyl]-3,4-dihydropyridine-5-carboxylic acid and (4R)-4-(6-chloro-3-pyridyl)-6-methyl-2-oxo-1-[[(2S)-tetrahydrofuran-2-yl]methyl]-3,4-dihydropyridine-5-carboxylic acid The previous ester (200 mg, 0.55 mmol) was dissolved in MeOH (3 mL), NaOH 1N (2 mL) was added. The reaction mixture was stirred overnight at 40° C. The MeOH was evaporated under reduced pressure and the aqueous phase was extracted by Et$_2$O, then acidified to pH=1 with HCl (1N). The aqueous phase was extracted by EtOAc and the organic layers were assembled and dried under Na$_2$SO$_4$. The solvent was removed under reduced pressure to afford a product as white solid (m=175 mg, 91%).

$^1$H NMR (300 MHz, CDC$_3$) δ 1.35-1.50 (m, 1H), 1.74-1.95 (m, 3H), 2.56 (s, 3H), 2.65 (dd, J=15.8, 1.8 Hz, 1H), 2.90 (dd, J=15.8, 7.3 Hz, 1H), 3.35 (dd, J=14.2, 9.3 Hz, 1H), 3.61-3.72 (m, 1H), 3.73-3.87 (m, 2H), 4.18 (dd, J=14.0, 3.0 Hz, 2H), 7.13 (d, J=8.3 Hz, 1H), 7.59 (dd, J=8.3, 2.6 Hz, 1H), 8.25 (d, J=2.6 Hz, 1H), 10.00 (s, 1H). $^{13}$C NMR (75 MHz, CDC$_3$) δ 17.5, 25.7, 29.2, 34.7, 38.6, 46.1, 68.2, 77.7, 108.5, 124.2, 135.6, 138.1, 149.1, 149.9, 154.0, 168.7, 171.9. MS [M+H]$^+$ 351 g/mol.

Example 153d. [4-(2-Chloroethoxy)phenyl]methanol

The 1-bromo-2-chloroethane (2.5 mL, 30 mmol), the 4-hydroxybenzyl alcohol (1.24 g, 10 mmol) and the potassium carbonate (1.38 g, 10 mmol) were added in acetonitrile (33 mL) and the reaction mixture was stirred at 50° C. for 24 h. 4 equivalent of reactant and base were added and the reaction stirred under reflux over the week end. Reaction finished. The solvent was removed under reduced pressure. The crude was dissolved in EtOAc and washed by water. The aqueous phase was extracted by EtOAc and the organic layers were washed with brine, dried under Na$_2$SO$_4$. The solvent was removed under reduced pressure to afford the title compound. This crude was purified by flash chromatography (Cy/EA 100/0 to 70/30) to afford the desired compound as a white powder (m=1.2 g, 64%).

Example 153e. 1-(2-Chloroethoxy)-4-(chloromethyl)benzene

Thionyl chloride (0.10 mL, 1.34 mmol) was added to benzotriazole (192 mg, 1.61 mmol). The resulting mixture was dissolved in dry CH$_2$Cl$_2$ (1 mL). After 5 min, this solution was added slowly to a solution of the alcohol (200 mg, 1.07 mmol) in CH$_2$Cl$_2$ (8 mL). The benzotriazole salt started to precipitate. After 20 min of reaction, the salt was filtered. The organic phase was washed by water (8 mL) and NaOH solution (0.05 M, 8 mL) then, dried under Na$_2$SO$_4$, the solvent was removed under reduced pressure to give the desired chlorinated compound as colorless oil (m=120 mg, 55%).

$^1$H NMR (300 MHz, CDCl$_3$) δ 3.81 (t, J=5.9 Hz, 2H), 4.23 (t, J=5.9 Hz, 2H), 4.57 (s, 2H), 6.90 (d, J=8.7 Hz, 2H), 7.32 (d, J=8.7 Hz, 2H). 3C NMR (75 MHz, CDCl$_3$) δ 41.9, 46.2, 68.2, 115.1, 130.3, 130.6, 158.4.

Example 153f. [4-(2-Chloroethoxy)phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate and [4-(2-chloroethoxy)phenyl]methyl (4R)-4-(6-chloro-3-pyridyl)-6-methyl-2-oxo-1-[[(2S)-tetrahydrofuran-2-yl]methyl]-3,4-dihydropyridine-5-carboxylate The (4S)-4-(6-chloro-3-pyridyl)-6-methyl-2-oxo-1-[[(2R)-tetrahydrofuran-2-yl]methyl]-3,4-dihydropyridine-5-carboxylic acid and its enantiomer (162 mg, 0.46 mmol) and cesium carbonate (165 mg, 0.51 mmol) were dissolved in dry DMF (2 mL). The 1-(2-Chloroethoxy)-4-(chloromethyl) benzene (104 mg, 0.51 mmol) was added and the reaction mixture was stirred at r.t. for 18 h. The solvent was removed under reduced pressure. The residue was dissolved in EtOAc and washed with water. The aqueous phase was extracted by EtOAc and the organic layers were assembled, washed with brine and dried with Na$_2$SO$_4$. The purification by flash chromatography (Cy/CH$_2$Cl$_2$ 1/1 to CH$_2$Cl$_2$) afford the desired product as a colorless oil (m=170 mg, 71%).

$^1$H NMR (300 MHz, CDCl$_3$) δ 1.42-1.56 (m, 1H), 1.81-2.06 (m, 3H), 2.56-2.71 (m, 4H), 2.93 (dd, J=15.7, 7.4 Hz, 1H), 3.40 (dd, J=14.2, 9.3 Hz, 1H), 3.69-3.95 (m, 5H), 4.13-4.32 (m, 4H), 5.02 (d, J=4.4 Hz, 2H), 6.83 (d, J=8.8 Hz, 2H), 7.08 (d, J=8.8 Hz, 2H), 7.16 (d, J=8.6 Hz, 1H), 7.57 (dd, J=8.7, 2.6 Hz, 1H), 8.24 (d, J=2.5 Hz, 1H). $^{13}$C NMR (75 MHz, CDC$_3$) δ 17.5, 25.8, 29.3, 35.1, 38.8, 42.0, 46.3, 66.1, 68.2, 68.3, 77.8, 109.1, 114.8, 124.3, 129.9, 136.0, 138.1, 149.2, 150.1, 152.2, 158.3, 166.8, 168.5. MS [M]$^+$ 519 g/mol.

Example 153g. [4-(2-Iodoethoxy)phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate and [4-(2-iodoethoxy)phenyl]methyl (4R)-4-(6-chloro-3-pyridyl)-6-methyl-2-oxo-1-[[(2S)-tetrahydrofuran-2-yl]methyl]-3,4-dihydropyridine-5-carboxylate The previous compound (164 mg, 0.32 mmol) was dissolved in butanone (1.5 mL). NaI (189 mg, 1.26 mmol) was added and the reaction mixture stirred at 80° C. for 32 h. The solution was cooled to RT and then filtered. The solvent was removed under reduced pressure to afford yellowish oil. This residue was purified by flash chromatography (Cy/CH$_2$Cl$_2$ 1/1 to CH$_2$Cl$_2$) to give the desired product as white powder (m=130 mg, 67%).

$^1$H NMR (300 MHz, CDCl$_3$) δ 1.36-1.53 (m, 1H), 1.80-2.03 (m, 3H), 2.55-2.69 (m, 4H), 2.92 (dd, J=15.7, 7.5 Hz, 1H), 3.35-3.48 (m, 3H), 3.67-3.78 (m, 1H), 3.78-3.91 (m, 2H), 4.12-4.29 (m, 4H), 5.00 (d, J=4.2 Hz, 2H), 6.80 (d, J=8.7 Hz, 2H), 7.06 (d, J=8.7 Hz, 2H), 7.14 (d, J=8.3 Hz, 1H), 7.56 (dd, J=8.3, 2.6 Hz, 1H), 8.22 (d, J=2.3 Hz, 1H). $^{13}$C NMR (75 MHz, CDC$_3$) δ 1.2, 17.2, 25.7, 29.2, 35.0, 38.7, 46.1, 66.0, 68.2, 68.7, 77.7, 109.1, 114.8, 124.1, 128.8, 129.8, 135.9, 137.9, 149.2, 150.0, 152.1, 157.9, 166.7, 168.4. MS [M+H]$^+$ 611 g/mol.

Example 153 Ammonium,2-[4-[[[(4S)-4-(6-chloro-3-pyridyl)-6-methyl-2-oxo-1-[[(2R)-tetrahydrofuran-2-yl]methyl]-3,4-dihydropyridine-5-carbonyl]oxymethyl]phenoxy]ethanesulfonate and ammonium,2-[4-[[[(4R)-4-(6-chloro-3-pyridyl)-6-methyl-2-oxo-1-[[(2S)-tetrahydrofuran-2-yl]methyl]-3,4-dihydropyridine-5-carbonyl]oxymethyl]phenoxy] ethanesulfonate The [4-(2-iodoethoxy)phenyl]methyl(4S)-4-(6-chloro-3-pyridyl)-6-methyl-2-oxo-1-[[(2R)-tetrahydrofuran-2-yl] methyl]-3,4-dihydropyridine-5-carboxylate (130 mg, 0.213 mmol) was dissolved in a mixture of iPrOH/water 1/1 (1 mL). Sodium sulfite (54 mg, 0.426 mmol) was added and the reaction mixture was stirred under reflux for 48 h. The solvents were removed under reduced pressure. Purification of the crude by HPLC (basic conditions) gave the ammonium,2-[4-[[[(4S)-4-(6-chloro-3-pyridyl)-6-methyl-2-oxo-1-[[(2R)-tetrahydrofuran-2-yl]methyl]-3,4-dihydropyridine-5-carbonyl]oxymethyl]phenoxy]ethanesulfonate as a white powder (m=30 mg, 24%).

$^1$H NMR (300 MHz, CDCl$_3$) δ 1.35-1.55 (m, 1H), 1.77-2.04 (m, 3H), 2.50-2.65 (m, 4H), 2.83 (dd, J=15.6, 7.5 Hz, 2H), 3.25-3.45 (m, 3H), 3.70 (dd, J=14.5, 7.5 Hz, 1H), 3.77-3.91 (m, 2H), 4.04-4.36 (m, 4H), 4.83 (dd, J=26.9, 12.1 Hz, 2H), 6.73 (d, J=8.4 Hz, 2H), 6.90 (d, J=8.6 Hz, 2H), 7.09 (d, J=8.2 Hz, 4H), 7.56 (dd, J=8.3, 2.4 Hz, 1H), 8.12 (d, J=2.3 Hz, 1H). $^{13}$C NMR (75 MHz, CDCl$_3$) δ 17.2, 25.8, 29.3, 35.0, 38.6, 46.1, 58.1, 63.8, 66.0, 68.3, 77.7, 109.1, 114.9, 124.3, 128.5, 129.8, 136.4, 138.3, 149.2, 149.7, 152.2, 158.2, 166.6, 168.5. MS [M+H]$^+$ 565 g/mol.

Example 154

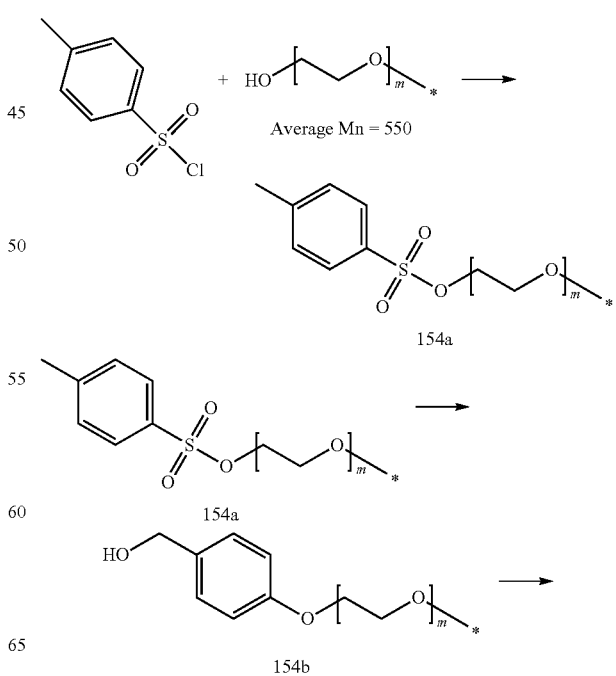

154a

154a

154b

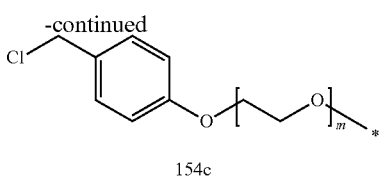

154c

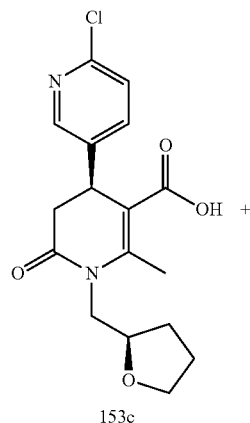

153c

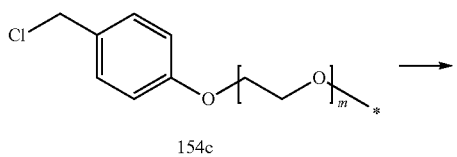

154c

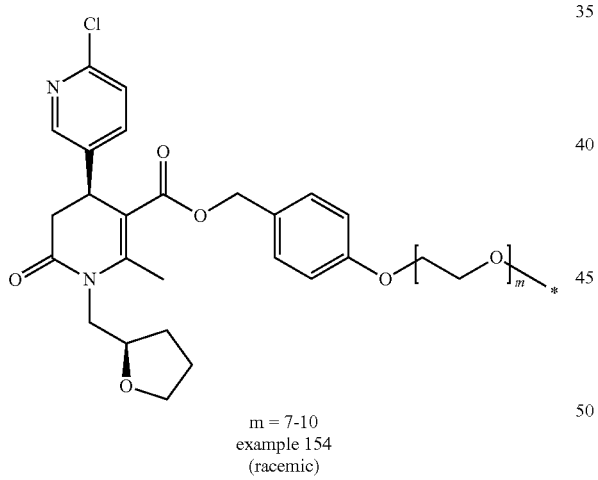

m = 7-10
example 154
(racemic)

Example 154a. Poly (Ethylene Glycol) Methyl Ether Tosylate

The Poly(ethylene glycol) methyl ether (Sigma-Aldrich, ref 202487, average Mn=550, (1.06 mmol) was dissolved in dry THF (3 mL). The solution was cooled at 0° C. NaH (56 mg, 60% in oil, 1.59 mmol) was added and the reaction mixture was stirred at 00° C. to 20° C. for 2 h. the 4-methylbenzenesulfonyl chloride (403 mg, 2.12 mmol) was added at 0° C. and the reaction mixture was stirred at RT. for 24 hours.

The solvent was evaporated and the residue was purified by flash chromatography ($CH_2Cl_2$ to $CH_2Cl_2$/MeOH 94/6) to give 497 mg of colorless oil corresponding to the expected product (m=497 mg, 75%).

$^1$H NMR (300 MHz, $CDCl_3$) δ 2.36 (s, 3H), 3.28 (s, 3H), 3.39-3.69 (m, 42H), 4.01-4.10 (m, 2H), 7.26 (d, J=7.9 Hz, 2H), 7.70 (d, J=8.5 Hz, 2H). $^{13}$C NMR (75 MHz, $CDCl_3$) δ 21.5, 58.9, 68.5, 69.2, 70.3, 70.4, 70.6, 71.8, 127.8, 129.7, 132.9, 144.6. MS $[M+NH_4]^+$ 688 g/mol.

Example 154b. 1-(Methanol)-4-[poly (ethylene glycol) methyl ether]benzene

The poly (ethylene glycol) methyl ether tosylate (0.48 mmol, 300 mg) was dissolved in dry MeCN (3 mL), the 4-(hydroxymethyl) phenol (0.72 mmol, 89 mg) and $K_2CO_3$ (0.72 mmol, 99 mg) were added. The reaction mixture was stirred overnight under reflux. After being cooled down, the mixture was filtered. The filtrate was concentrated under vacuum and purified by flash chromatography ($CH_2Cl_2$/ MeOH 97/3) to give the product as oil (m=122 mg, 44%).

$^1$H NMR (300 MHz, $CDCl_3$) δ 2.43 (s, 3H), 3.33 (s, 3H), 3.50 (dd, J=5.3, 3.3 Hz, 2H), 3.54-3.71 (m, 36H), 3.77-3.85 (m, 2H), 4.04-4.12 (m, 2H), 4.55 (s, 2H), 6.85 (d, J=8.7 Hz, 2H), 7.23 (d, J=8.7 Hz, 2H). $^{13}$C NMR (75 MHz, $CDCl_3$) δ 59.0, 64.7, 67.5, 69.7, 70.5, 70.5, 70.6, 70.6, 70.8, 71.9, 114.6, 128.5, 133.6, 158.3. MS $[M+NH_4]^+$ 596 g/mol.

Example 154c. 1-(Chloromethyl)-4-[poly (ethylene glycol) methyl ether]benzene

Thionyl chloride (0.26 mmol, 0.02 mL) was added to benzotriazole (0.26 mmol, 31 mg). The resulting mixture was dissolved in dry $CH_2Cl_2$ (1 mL). After 5 min, this solution was added slowly to a solution of the benzyl alcohol in $CH_2Cl_2$ (5 mL). The benzotriazole salt started to precipitate. After 1 h of reaction, the reaction mixture was quenched by addition of $MgSO_4.7H_2O$ and then filtered. The solvent was removed under reduced pressure to afford yellow oil (m=125 mg, 99%). $^1$H NMR (300 MHz, $CDC_3$) δ 3.30 (s, 3H), 3.42-3.68 (m, 36H), 3.73-3.81 (m, 2H), 4.00-4.09 (m, 2H), 4.48 (s, 2H), 6.81 (d, J=8.6 Hz, 2H), 7.21 (d, J=8.5 Hz, 2H).

Example 154 [4-([Poly (ethylene glycol) methyl ether])phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate and [4-([poly (ethylene glycol) methyl ether])phenyl] methyl (4R)-4-(6-chloro-3-pyridyl)-6-methyl-2-oxo-1-[[(2S)-tetrahydrofuran-2-yl]methyl]-3,4-dihydropyridine-5-carboxylate (mixture m=7-10)

The chlorinated compound 1-(Chloromethyl)-4-[poly (ethylene glycol) methyl ether] benzene (117 mg, 0.20 mmol) and the acid (69 mg, 0.20 mmol) were dissolved in dry DMF (2 mL). Cesium carbonate (64 mg, 0.20 mmol) and NaI (1.5 mg, 0.01 mmol) were added and the reaction mixture stirred at RT for 18 h.

Reaction stopped by addition of water. Solvent was removed under reduced pressure. The residue was extracted by EtOAc and the organics layers were washed by a solution of saturated NaCl, dried over $Na_2SO_4$ and the solvent was removed to give a crude product. Purification by flash chromatography ($CH_2Cl_2$/MeOH 100/0 to 80/20) then, by HPLC (basic conditions) give the expected product as white powder (m=63 mg, 35%).

243

$^1$H NMR (300 MHz, CDCl$_3$) δ 1.38-1.54 (m, 1H), 1.80-2.04 (m, 3H), 2.36 (s, 1H), 2.53-2.70 (m, 4H), 2.91 (dd, J=15.8, 7.5 Hz, 1H), 3.31-3.44 (m, 4H), 3.47-3.56 (m, 2H), 3.56-3.76 (m, 33H), 3.78-3.93 (m, 5H), 4.04-4.13 (m, 2H), 4.13-4.29 (m, 2H), 4.99 (q, J=12.2 Hz, 2H), 6.81 (d, J= 8.7 Hz, 2H), 7.05 (d, J=8.6 Hz, 2H), 7.13 (d, J=8.3 Hz, 1H), 7.54 (dd, J=8.3, 2.6 Hz, 1H), 8.22 (d, J=2.5 Hz, 1H). $^{13}$C NMR (75 MHz, CDC$_3$) δ 17.2, 25.7, 29.2, 35.0, 38.7, 46.1, 59.1, 66.2, 67.5, 68.2, 69.7, 70.6, 70.6, 70.7, 70.7, 70.9, 72.0, 77.7, 109.2, 114.6, 124.1, 128.2, 129.7, 135.9, 138.0, 149.2, 150.0, 152.0, 158.8, 166.7, 168.4. MS [M+NH$_4$]$^+$ 928 g/mol.

Example 155

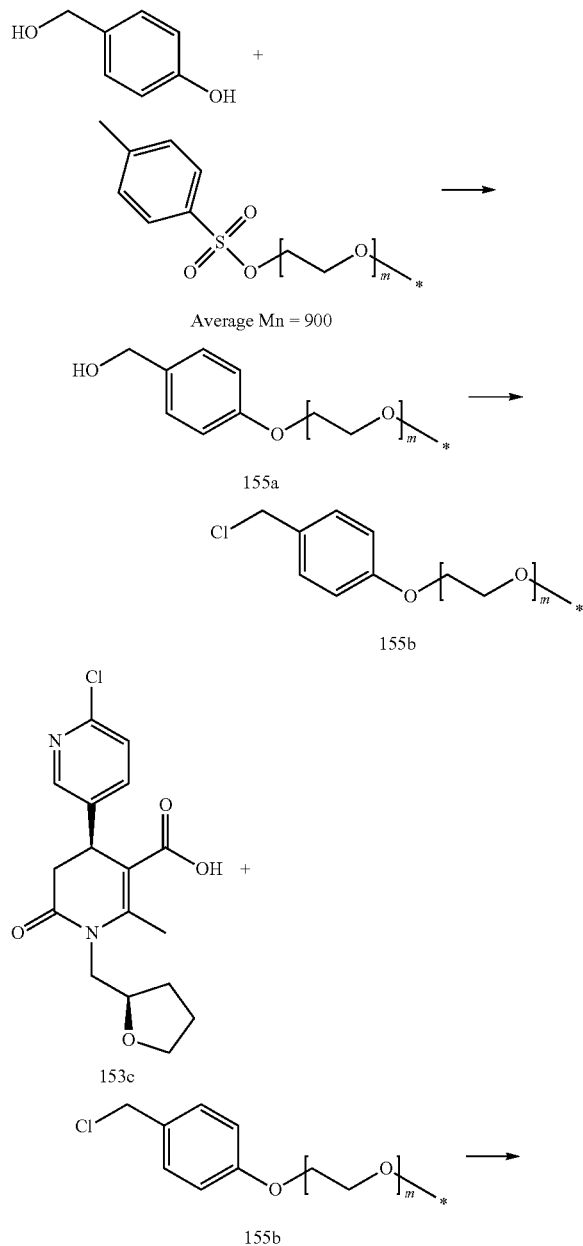

244

-continued

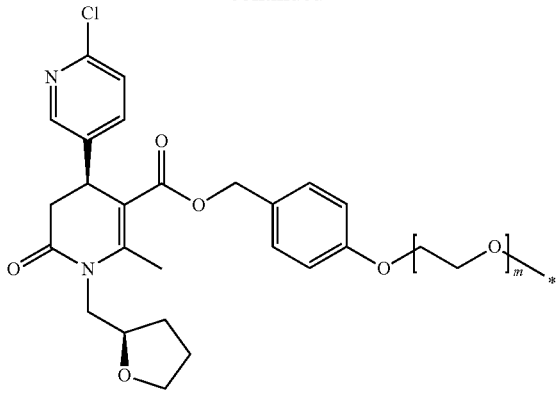

example 155
(racemic)
n = 18-23

Example 155a. 1-(Methanol)-4-[poly (ethylene glycol) methyl ether]benzene (mixture m=18-23)

The poly(ethylene glycol) methyl ether tosylate (Sigma-Aldrich, ref 729116, average Mn=900, 1.12 mmol) was dissolved in acetonitrile (4 mL), the 4-(hydroxymethyl) phenol (209 mg, 1.68 mmol) and K$_2$CO$_3$ (233 mg, 1.68 mmol) were added. The mixture was stirred overnight under reflux. The reaction became pink and after being cooled down, it has been filtered. The filtrate has been concentrated under vacuum and purified by flash chromatography (CH$_2$Cl$_2$/MeOH: 100/0 to 97/3) to give the expected product as oil (900 mg, 95%). $^1$H NMR (300 MHz, CDC$_3$) δ 3.31 (s, 3H), 3.44-3.70 (m, 100H), 3.75-3.85 (m, 3H), 4.01-4.11 (m, 2H), 4.52 (s, 2H), 6.83 (d, J=8.6 Hz, 2H), 7.21 (d, J=8.6 Hz, 2H).

Example 155b. 1-(Chloromethyl)-4-[poly (ethylene glycol) methyl ether]benzene (mixture m=18-23)

In dry CH$_2$Cl$_2$ (1 mL), thionyl chloride (0.01 mL, 0.19 mmol) and benzotriazole (22 mg, 0.19 mmol) were added. The resulting mixture was stirred 5 min, this solution was added slowly to a solution of the 1-(Methanol)-4-[poly (ethylene glycol) methyl ether] benzene in CH$_2$Cl$_2$ (9 mL). The benzotriazole salt started to precipitate. After 1 h of reaction, the reaction mixture was quenched by addition of MgSO$_4$.7H$_2$O and then filtered. The solvent was removed under reduced pressure to afford yellow oil (quantitative).

Example 155: [4-([Poly (ethylene glycol) methyl ether])phenyl]methyl (4S)-4-(6-chloro-3-pyridyl)-6-methyl-2-oxo-1-[[(2R)-tetrahydrofuran-2-yl] methyl]-3,4-dihydropyridine-5-carboxylate and [4-([poly (ethylene glycol) methyl ether])phenyl] methyl (4R)-4-(6-chloro-3-pyridyl)-6-methyl-2-oxo-1-[[(2S)-tetrahydrofuran-2-yl]methyl]-3,4-dihydropyridine-5-carboxylate (mixture m=18-23)

The chlorinated compound 155b (127 mg, 0.15 mmol) and the acid (67 mg, 0.19 mmol) were dissolved in dry DMF (2 mL). Cesium carbonate (63 mg, 0.19 mmol) and NaI (1.1 mg, 0.01 mmol) were added and the reaction mixture was stirred at room temperature for 18 h. Reaction stopped by addition of water. Solvent was removed under reduced pressure and the residue was extracted by EtOAc. The organics layers were washed by a solution of saturated NaCl, dried over $Na_2SO_4$, filtered and the solvent was removed to give the crude product. Purification by HPLC (acid conditions) gives the expected mixture of products (n=18-23) as oil (28 mg, 14%). $^1$H NMR (300 MHz, $CDCl_3$) δ 1.38-1.52 (m, 1H), 1.80-2.04 (m, 3H), 2.51-2.71 (m, 4H), 2.92 (dd, J=15.7, 7.4 Hz, 1H), 3.31-3.45 (m, 5H), 3.50-3.78 (m, 99H), 3.78-3.93 (m, 5H), 4.04-4.14 (m, 2H), 4.13-4.29 (m, 2H), 4.99 (q, J=12.1 Hz, 2H), 6.81 (d, J=8.8 Hz, 2H), 7.05 (d, J=8.8 Hz, 2H), 7.14 (d, J=8.3 Hz, 1H), 7.55 (dd, J=8.3, 2.6 Hz, 1H), 8.23 (d, J=2.6 Hz, 1H). $^{13}$C NMR (75 MHz, $CDCl_3$) δ 17.3, 25.7, 29.3, 35.0, 38.7, 46.1, 59.1, 66.2, 67.5, 68.3, 69.8, 70.6, 70.7, 70.9, 72.0, 77.4, 77.7, 109.2, 114.6, 124.2, 128.2, 129.7, 135.9, 138.0, 149.2, 150.0, 152.0, 158.8, 166.7, 168.5. MS $[M+NH_4]^+$ 1412 g/mol.

Example 156

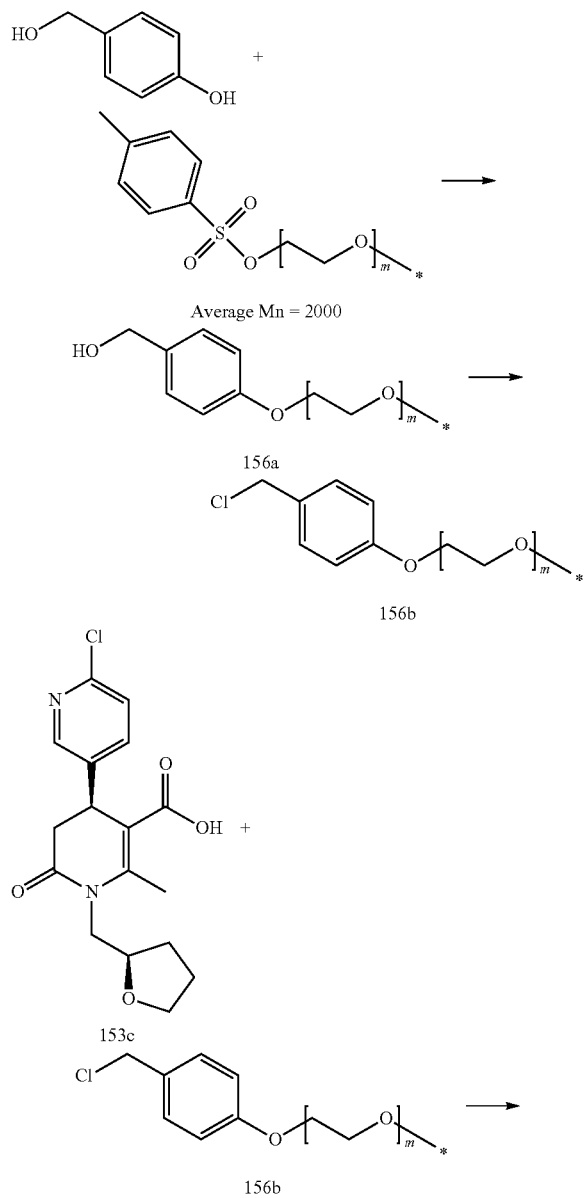

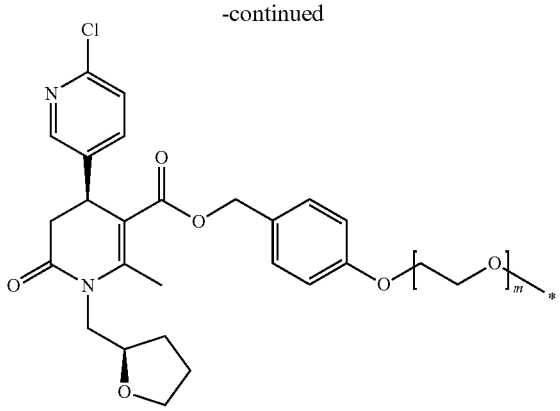

example 156
(racemic)
m = 35-44

Example 156a. 1-(Methanol)-4-[poly (ethylene glycol) methyl ether]benzene

The poly (ethylene glycol) methyl ether tosylate (sigma-Aldrich, ref 729124, average Mn=2000) (1 g, 0.48 mmol) was dissolved in MeCN (4 mL). The 4-(hydroxymethyl) phenol (89 mg, 0.72 mmol) and $K_2CO_3$ (100 mg, 0.72 mmol) were added. The reaction mixture was stirred overnight under reflux. After being cooled down, the mixture was filtered. The filtrate was concentrated under vacuum and purified by flash chromatography ($CH_2Cl_2$/MeOH 97/3) to give the expected product (m=778 mg, 80%).
$^1$H NMR (300 MHz, $CDCl_3$) δ 3.33-3.42 (m, 6H), 3.48-3.79 (m, 164H), 3.80-3.92 (m, 4H), 4.07-4.15 (m, 2H), 4.59 (s, 2H), 6.88 (d, J=8.7 Hz, 2H), 7.26 (d, J=8.6 Hz, 2H). $^{13}$C NMR (75 MHz, $CDCl_3$) δ 59.1, 67.6, 69.8, 70.6, 70.7, 70.9, 72.0, 114.8, 128.7.

Example 156b. 1-(Chloromethyl)-4-[poly (ethylene glycol) methyl ether]benzene Thionyl chloride (0.03 mL, 0.46 mmol) was added to benzotriazole (55 mg, 0.46 mmol). The resulting yellow solution was dissolved in dry $CH_2Cl_2$ (2 mL). After 5 min, this solution was added slowly to a solution of the 1-(Methanol)-4-[poly (ethylene glycol) methyl ether] benzene (750 mg, 0.37 mmol) in $CH_2Cl_2$ (10 mL). The benzotriazole salt started to precipitate. After 1 h of reaction, the mixture was quenched by addition of $MgSO_4.7H_2O$ and then filtered. The solvents were removed under reduced pressure to afford the desired compound as yellow oil (m=756 mg, 100%).
$^1$H NMR (300 MHz, $CDCl_3$) δ 3.17-3.28 (m, 6H), 3.33-3.66 (m, 163H), 3.66-3.76 (m, 4H), 3.92-4.02 (m, 2H), 4.40 (s, 2H), 6.73 (d, J=8.6 Hz, 2H), 7.13 (d, J=8.6 Hz, 2H).

Example 156: [4-([Poly (ethylene glycol) methyl ether])phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate and [4-([poly (ethylene glycol) methyl ether])phenyl]methyl (4R)-4-(6-chloro-3-pyridyl)-6-methyl-2-oxo-1-[[(2S)-tetrahydrofuran-2-yl]methyl]-3,4-dihydropyridine-5-carboxylate 1-(Methanol)-4-[poly (ethylene glycol) methyl ether] benzene (156b, 680 mg, 0.33 mmol) and the acid 153c (158 mg, 0.43 mmol) were dissolved in dry DMF (4 mL). Cesium carbonate (140 mg, 0.43 mmol) and NaI (2.5 mg, 0.02 mmol) were added and the reaction mixture stirred at RT for 18 h. Reaction stopped by addition of water. Solvent was removed under reduced pressure. The residue was extracted by EtOAc and the organics layers were washed by a solution of saturated NaCl, dried over $Na_2SO_4$ and the solvent was removed to give a crude product. Purification by HPLC (acid conditions) give the expected product as white powder (m=60 mg, 8%).

$^1$H NMR (300 MHz, $CDCl_3$) δ 1.35-1.52 (m, 1H), 1.78-2.00 (m, 3H), 2.53-2.72 (m, 5H), 2.90 (dd, J=15.7, 7.5 Hz, 1H), 3.28-3.44 (m, 5H), 3.44-3.92 (m, 159H), 4.01-4.11 (m, 2H), 4.12-4.29 (m, 2H), 4.87-5.06 (m, 2H), 6.79 (d, J=8.7 Hz, 2H), 7.03 (d, J=8.7 Hz, 2H), 7.12 (d, J=8.2 Hz, 1H), 7.53 (dd, J=8.3, 2.6 Hz, 1H), 8.21 (d, J=2.5 Hz, 1H). $^{13}$C NMR (75 MHz, $CDCl_3$) δ 17.2, 25.6, 29.2, 34.9, 38.7, 46.0, 59.1, 66.1, 67.5, 68.2, 69.7, 70.5, 70.6, 70.8, 72.0, 77.6, 109.1, 114.7, 124.1, 128.2, 129.6, 135.9, 137.9, 149.1, 149.9, 152.0, 158.8, 166.7, 168.4. MS $[M/2+NH_4]^+$ 1134 g/mol.

Example 157

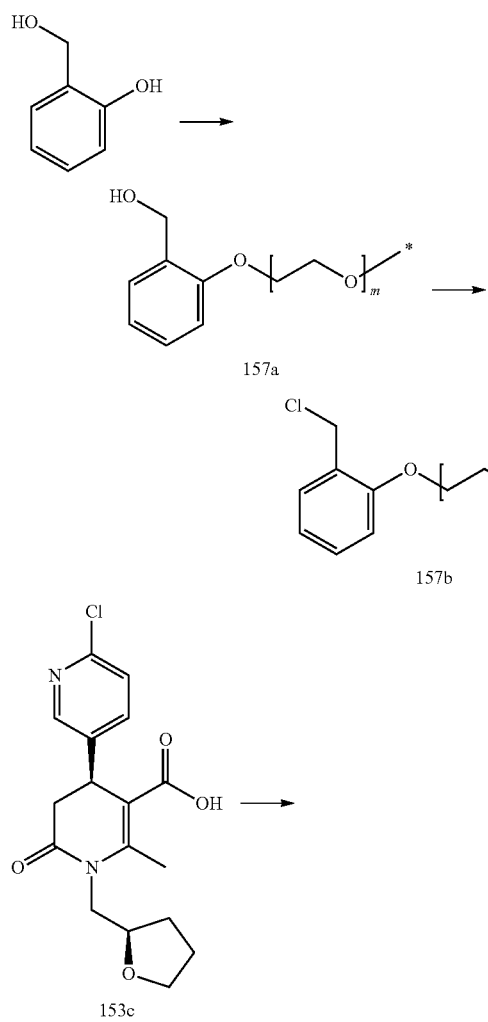

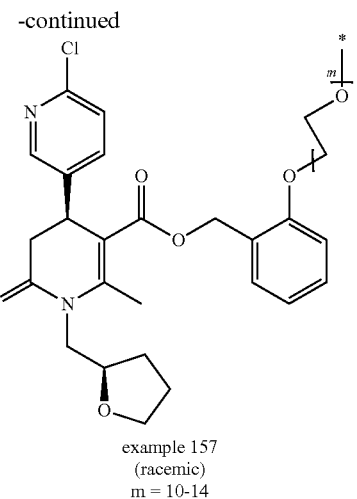

example 157
(racemic)
m = 10-14

Example 157a. 1-(Methanol)-2-[poly (ethylene glycol) methyl ether]benzene

The poly(ethylene glycol) methyl ether tosylate 154a (564 mg, 0.9 mmol) was dissolved in MeCN (3 mL), the 2-(hydroxymethyl)phenol (168 mg, 1.35 mmol) and $K_2CO_3$ (187 mg, 1.35 mmol) were added. The reaction mixture was stirred overnight under reflux. After being cooled down, it has been filtered. The filtrate has been concentrated under vacuum and purified by flash chromatography ($CH_2Cl_2$/MeOH: 100/0 to 97/3) to give the expected product as oil (460 mg, 77%). $^1$H NMR (300 MHz, $CDCl_3$) δ 3.29 (s, 3H), 3.40-3.65 (m, 45H), 3.76 (dd, J=5.4, 3.8 Hz, 2H), 4.10 (dd, J=5.4, 3.8 Hz, 2H), 4.58 (s, 2H), 6.79 (d, J=8.1 Hz, 1H), 6.85 (td, J=7.5, 0.9 Hz, 1H), 7.10-7.25 (m, 2H). MS $[M+NH_4]^+$ 684 g/mol.

Example 157b. 1-(Chloromethyl)-2-[poly (ethylene glycol) methyl ether]benzene

In dry $CH_2Cl_2$ (3 mL), thionyl chloride (0.02 mL, 0.34 mmol) and benzotriazole (40 mg, 0.34 mmol) were added. The resulting mixture was stirred 5 min, this solution was added slowly to a solution of the alcohol Example 157a. ($MM_{peg}$=550 g/mol) in $CH_2Cl_2$ (15 mL). The benzotriazole salt started to precipitate. After 1 h of reaction, the reaction mixture was quenched by addition of $MgSO_4.7H_2O$ and then filtered. The solvent was removed under reduced pressure to afford a yellow oil (quantitative).

Example 157: [2-([Poly (ethylene glycol) methyl ether])phenyl]methyl (4S)-4-(6-chloro-3-pyridyl)-6-methyl-2-oxo-1-[[(2R)-tetrahydrofuran-2-yl] methyl]-3,4-dihydropyridine-5-carboxylate and [2-([poly (ethylene glycol) methyl ether])phenyl] methyl (4R)-4-(6-chloro-3-pyridyl)-6-methyl-2-oxo-1-[[(2S)-tetrahydrofuran-2-yl]methyl]-3,4-dihydropyridine-5-carboxylate (mixture m=10-14)

Example 157b (152 mg, 0.25 mmol) and the acid 153c (98 mg, 0.28 mmol) were dissolved in dry DMF (3 mL). Cesium carbonate (108 mg, 0.33 mmol) and NaI (2 mg, 0.01 mmol) were added and the reaction mixture stirred at room temperature for 18 h. Reaction stopped by addition of water. DMF was removed under reduced pressure. The residue was extracted by EtOAc and the organics layers were washed by a solution of saturated NaCl, dried over Na$_2$SO$_4$, filtered and the solvent was removed. Purification by preparative HPLC gives the expected compound (mixture of products (m=10-14) as oil (45 mg, 17%). $^1$H NMR (300 MHz, CDCl$_3$) δ 1.36-1.55 (m, 1H), 1.80-2.04 (m, 3H), 2.54-2.72 (m, 4H), 2.93 (dd, J=15.7, 7.5 Hz, 1H), 3.32-3.46 (m, 4H), 3.48-3.57 (m, 2H), 3.57-3.70 (m, 46H), 3.70-3.80 (m, 3H), 3.80-3.92 (m, 2H), 3.97-4.13 (m, 2H), 4.18-4.31 (m, 2H), 5.13 (s, 2H), 6.80-6.90 (m, 2H), 6.99 (dd, J=7.5, 1.7 Hz, 1H), 7.12 (d, J=8.3 Hz, 1H), 7.18-7.25 (m, 1H), 7.56 (dd, J=8.3, 2.6 Hz, 1H), 8.21 (d, J=2.6 Hz, 1H). $^{13}$C NMR (75 MHz, CDCl$_3$) δ 17.2, 25.7, 29.3, 35.0, 38.7, 46.1, 59.1, 61.9, 67.8, 68.3, 69.7, 70.6, 70.7, 70.9, 72.0, 77.4, 77.7, 109.4, 111.6, 120.7, 124.1, 124.5, 129.2, 129.5, 136.0, 138.0, 149.2, 149.9, 151.8, 156.6, 166.7, 168.5. MS [M+H]$^+$ 1043 g/mol.

Example 158

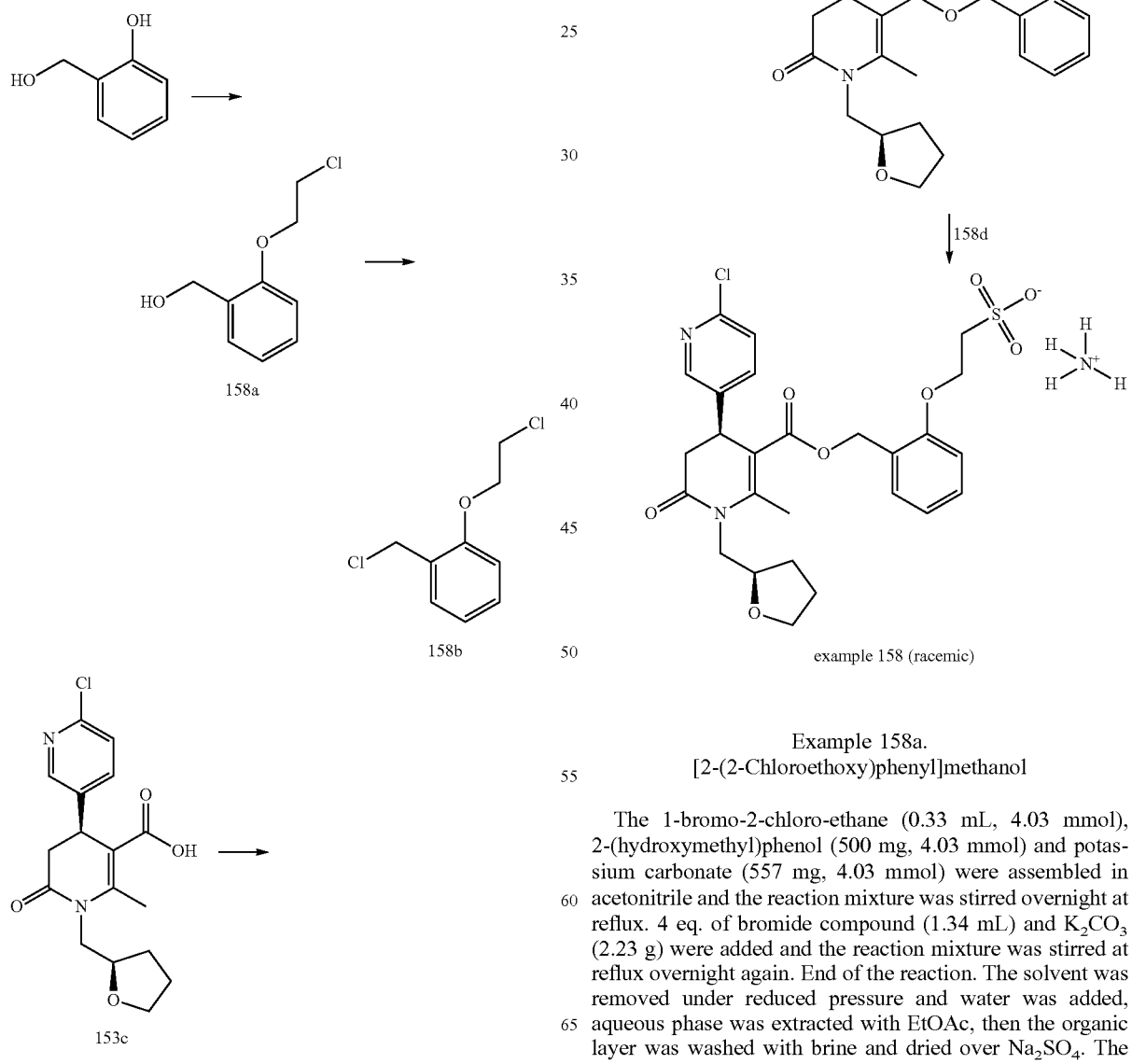

example 158 (racemic)

Example 158a.
[2-(2-Chloroethoxy)phenyl]methanol

The 1-bromo-2-chloro-ethane (0.33 mL, 4.03 mmol), 2-(hydroxymethyl)phenol (500 mg, 4.03 mmol) and potassium carbonate (557 mg, 4.03 mmol) were assembled in acetonitrile and the reaction mixture was stirred overnight at reflux. 4 eq. of bromide compound (1.34 mL) and K$_2$CO$_3$ (2.23 g) were added and the reaction mixture was stirred at reflux overnight again. End of the reaction. The solvent was removed under reduced pressure and water was added, aqueous phase was extracted with EtOAc, then the organic layer was washed with brine and dried over Na$_2$SO$_4$. The solvent was removed under reduced pressure. The crude was purified by flash chromatography on Silica gel using as eluant a mixture of Cy/EtOAc (100/0 to 70/30) to give the expected product as a yellow oil (m=500 mg, 66%). $^1$H NMR (300 MHz, CDC$_3$) δ 2.76 (s, 1H), 3.78-3.92 (m, 2H), 4.21-4.30 (m, 2H), 4.71 (s, 2H), 6.85 (d, J=8.2 Hz, 1H), 6.99 (td, J=7.5, 1.0 Hz, 1H), 7.23-7.35 (m, 2H).

Example 158b.
1-(2-Chloroethoxy)-2-(chloromethyl)benzene

In dry CH$_2$Cl$_2$ (5 mL), thionyl chloride (0.15 mL, 2.01 mmol) and benzotriazole (287 mg, 2.41 mmol) were added. The resulting mixture was stirred 5 min, this solution was added slowly to a solution of the alcohol 158a in CH$_2$Cl$_2$ (10 mL). The benzotriazole salt started to precipitate. After 20 min of reaction, the salt was filtered. The organic phase was washed with water (10 mL) and NaOH solution (0.05 M, 10 mL). The organic phase was dried on Na$_2$SO$_4$ and the solvent was removed under reduced pressure to give the desired chlorinated compound as colorless oil (300 mg, 91%). $^1$H NMR (300 MHz, CDCl$_3$) δ 3.86 (t, J=5.8 Hz, 2H), 4.30 (t, J=5.8 Hz, 2H), 4.70 (s, 2H), 6.88 (d, J=8.2 Hz, 1H), 7.00 (td, J=7.5, 1.0 Hz, 1H), 7.27-7.35 (m, 1H), 7.39 (dd, J=7.5, 1.6 Hz, 1H).

Example 158c. [2-(2-Chloroethoxy)phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate and [2-(2-chloroethoxy)phenyl]methyl (4R)-4-(6-chloro-3-pyridyl)-6-methyl-2-oxo-1-[[(2S)-tetrahydrofuran-2-yl]methyl]-3,4-dihydropyridine-5-carboxylate The acid 153c (93 mg, 0.27 mmol) and cesium carbonate (95 mg, 0.29 mmol) were dissolved in dry DMF (2 mL). Compound example 158b (60 mg, 0.29 mmol) was added. The reaction mixture was stirred at room temperature for 18 h. The solvent was removed under reduced pressure. The residue was dissolved in EtOAc and washed with water. The aqueous phase was extracted by EtOAc. The organic layers were assembled, washed with brine and dried with Na$_2$SO$_4$. The residue was purified by flash chromatography (Cy/CH$_2$Cl$_2$: 50/50 to 0/100) to afford the desired product as a colorless oil (m=112 mg, 81%). MS [M+H]$^+$ 519 g/mol.

Example 158d. [2-(2-Iodoethoxy)phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate and [2-(2-iodoethoxy)phenyl]methyl (4R)-4-(6-chloro-3-pyridyl)-6-methyl-2-oxo-1-[[(2S)-tetrahydrofuran-2-yl]methyl]-3,4-dihydropyridine-5-carboxylate Example 158c (200 mg, 0.39 mmol) was dissolved in butanone (3 mL). NaI (231 mg, 1.54 mmol) was added and the reaction mixture stirred at 80° C. overnight. The solution was cooled to room temperature, filtered and washed by acetone. The solvents were removed under reduced pressure to afford yellowish oil. This residue was purified by flash chromatography (Cy/CH$_2$Cl$_2$: 50/50 to 0/100) to give the desired product as oil (m=204 mg, 87%). $^1$H NMR (300 MHz, CDCl$_3$) δ 1.34-1.50 (m, 1H), 1.77-2.02 (m, 3H), 2.54-2.67 (m, 4H), 2.91 (dd, J=15.8, 7.5 Hz, 1H), 3.25-3.45 (m, 3H), 3.64-3.78 (m, 1H), 3.78-3.92 (m, 2H), 4.08-4.27 (m, 4H), 5.15 (q, J=12.6 Hz, 2H), 6.74 (d, J=7.7 Hz, 1H), 6.85 (td, J=7.5, 0.9 Hz, 1H), 7.02 (dd, J=7.5, 1.7 Hz, 1H), 7.10 (d, J=8.3 Hz, 1H), 7.17-7.25 (m, 1H), 7.55 (dd, J=8.3, 2.6 Hz, 1H), 8.19 (d, J=2.5 Hz, 1H). MS [M+H]$^+$ 611 g/mol.

Example 158: Ammonium, 2-[2-[[(4S)-4-(6-chloro-3-pyridyl)-6-methyl-2-oxo-1-[[(2R)-tetrahydrofuran-2-yl]methyl]-3,4-d ihydropyridine-5-carbonyl]oxymethyl]phenoxy]ethanesulfonate and ammonium,2-[2-[[(4R)-4-(6-chloro-3-pyridyl)-6-methyl-2-oxo-1-[[(2S)-tetrahydrofuran-2-yl]methyl]-3,4-dihydropyridine-5-carbonyl]oxymethyl]phenoxy]ethanesulfonate The compound 158d (200 mg, 0.33 mmol) was dissolved in a mixture of iPrOH/water 1/1 (2 mL). Sodium sulfite (83 mg, 0.65 mmol) was added and the reaction mixture was heated at 80° C. in sealed tube for 18 h. The solvents were removed under reduced pressure. Purification of the crude by HPLC (basic conditions) gave the expected product as a white powder (m=112 mg, 59%). $^1$H NMR (300 MHz, CDCl$_3$) δ 1.39-1.45 (m, 1H), 1.74-2.05 (m, 3H), 2.49-2.67 (m, 4H), 2.87 (dd, J=15.6, 7.3 Hz, 1H), 3.27 (t, J=6.8 Hz, 2H), 3.31-3.43 (m, 1H), 3.70 (dd, J=14.4, 7.5 Hz, 1H), 3.76-3.90 (m, 2H), 4.16 (d, J=10.7 Hz, 2H), 4.25 (t, J=6.8 Hz, 2H), 5.06 (s, 2H), 6.77 (dd, J=16.3, 8.1 Hz, 2H), 6.88-6.96 (m, 1H), 7.07-7.40 (m, 6H), 7.56 (dd, J=8.3, 2.5 Hz, 1H), 8.28 (d, J=2.5 Hz, 1H). $^{13}$C NMR (75 MHz, CDC$_3$) δ 17.2, 25.7, 29.3, 34.9, 38.6, 46.1, 50.8, 61.9, 63.9, 68.3, 77.7, 109.1, 111.9, 120.9, 124.4, 124.5, 129.2, 129.6, 136.6, 138.6, 149.0, 149.3, 152.3, 156.1, 167.0, 168.6. MS [M+H]$^+$ 565 g/mol.

Example 159

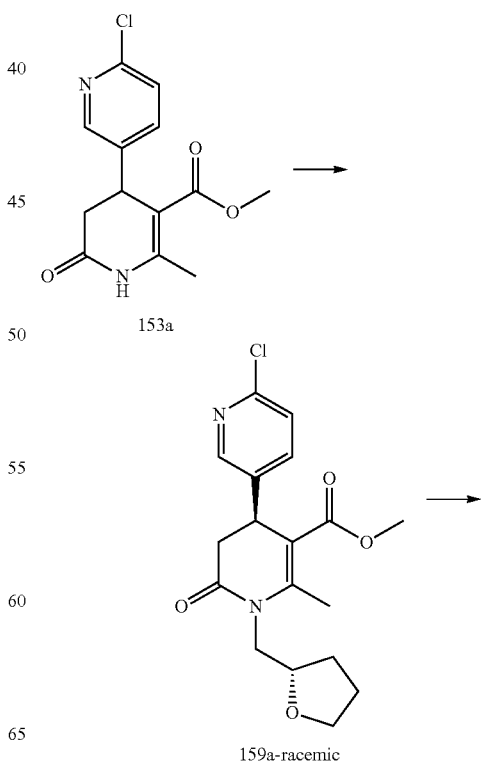

153a 159a-racemic

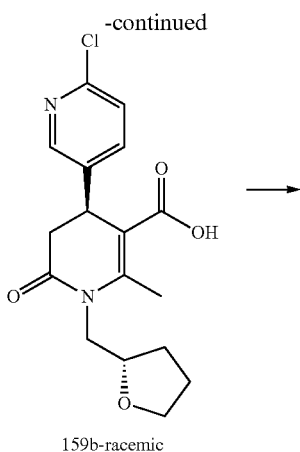

159b-racemic

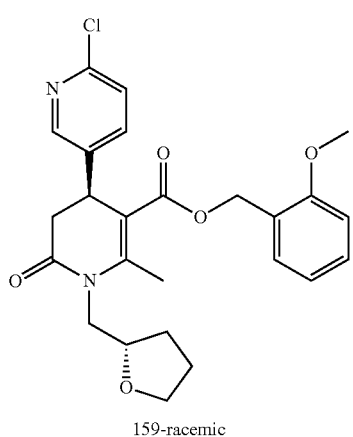

159-racemic

Example 159a. Methyl-(4S)-4-(6-chloro-3-pyridyl)-6-methyl-2-oxo-1-[[(2S)-tetrahydrofuran-2-yl]methyl]-3,4-dihydropyridine-5-carboxylate and methyl (4R)-4-(6-chloro-3-pyridyl)-6-methyl-2-oxo-1-[[(2R)-tetrahydrofuran-2-yl]methyl]-3,4-dihydropyridine-5-carboxylate The methyl 4-(6-chloro-3-pyridyl)-6-methyl-2-oxo-3,4-dihydro-1H-pyridine-5-carboxylate 153a (600 mg, 2.14 mmol) and the 2-(bromomethyl)tetrahydrofuran (0.5 mL, 4.27 mmol) were dissolved in dry DMF (5 mL), $Cs_2CO_3$ (1.4 g, 4.28 mmol) and NaI (16 mg, 0.11 mmol) were added and the reaction mixture was stirred at 50° C. overnight. The solvent was removed under reduced pressure. Water was added and the aqueous phase was extracted by ethyl acetate, the organic layers were washed with brine and dried over $Na_2SO_4$. The solvent was removed. The residue was dissolved again in 5 mL of DMF, 1.4 g of $Cs_2CO_3$, 16 mg of NaI and the alkyl bromide (0.5 mL) were added and the mixture was stirred at 50° C. for 18 h. Reaction finished. The solvent was removed under reduced pressure. Water was added and the aqueous phase was extracted by ethyl acetate, the organic layers were washed with brine, and dried over $MgSO_4$. The solvent was removed. The purification by columns chromatography on silica (Cy/EtOAc 100/0 to 70/30 and $CH_2Cl_2$/Cy 70/30 to 100/0) give the desired product as white product (m=300 mg, 39%). $^1H$ NMR (300 MHz, $CDC_3$) δ 1.19-1.35 (m, 1H), 1.77-1.97 (m, 3H), 2.61 (s, 3H), 2.76 (dd, J=16.0, 2.2 Hz, 1H), 2.95 (dd, J=16.0, 7.4 Hz, 1H), 3.66 (s, 3H), 3.67-3.86 (m, 3H), 3.93-4.09 (m, 2H), 4.19 (d, J=6.2 Hz, 1H), 7.19 (d, J=8.3 Hz, 1H), 7.51 (dd, J=8.3, 2.6 Hz, 1H), 8.19 (d, J=2.5 Hz, 1H). $^{13}C$ NMR (75 MHz, $CDCl_3$) δ 17.2, 25.7, 29.2, 34.8, 38.8, 46.0, 51.7, 68.2, 77.7, 109.1, 124.1, 135.6, 137.9, 149.2, 150.0, 151.9, 167.4, 168.4. MS $[M+H]^+$ 365 g/mol.

Example 159b. (4S)-4-(6-chloro-3-pyridyl)-6-methyl-2-oxo-1-[[(2S)-tetrahydrofuran-2-yl]methyl]-3,4-dihydropyridine-5-carboxylic acid and (4R)-4-(6-chloro-3-pyridyl)-6-methyl-2-oxo-1-[[(2R)-tetrahydrofuran-2-yl]methyl]-3,4-dihydropyridine-5-carboxylic acid The ester 159a (300 mg, 0.82 mmol) was dissolved in MeOH (5 mL), NaOH 1N (3 mL) was added. The reaction mixture was stirred overnight at 40° C. The MeOH was evaporated under reduced pressure and the aqueous phase was extracted by $Et_2O$, then acidified to pH=1 with HCl (1N). The aqueous phase was extracted by EtOAc and the organic layers were assembled and dried under $Na_2SO_4$. The solvent was removed under reduced pressure to afford a product as oil (m=200 mg, 69%). $^1H$ NMR (300 MHz, $CDC_3$) δ 1.20-1.34 (m, 1H), 1.72-1.92 (m, 3H), 2.60 (s, 3H), 2.76 (dd, J=16.1, 2.0 Hz, 1H), 2.93 (dd, J=16.1, 7.4 Hz, 1H), 3.58-3.84 (m, 3H), 3.89-4.02 (m, 2H), 4.19 (d, J=6.6 Hz, 1H), 7.17 (d, J=8.3 Hz, 1H), 7.51 (dd, J=8.3, 2.6 Hz, 1H), 8.21 (d, J=2.5 Hz, 1H), 10.53 (s, 1H). MS $[M+H]^+$ 351 g/mol.

Example 159. (2-Methoxyphenyl)methyl-(4S)-4-(6-chloro-3-pyridyl)-6-methyl-2-oxo-1-[[(2S)-tetrahydrofuran-2-yl]methyl]-3,4-dihydropyridine-5-carboxylate and (2-methoxyphenyl)methyl-(4R)-4-(6-chloro-3-pyridyl)-6-methyl-2-oxo-1-[[(2R)-tetrahydrofuran-2-yl]methyl]-3,4-dihydropyridine-5-carboxylate The 1-(chloromethyl)-2-methoxy-benzene (98 mg, 0.63 mmol) and the acid 159b (200 mg, 0.57 mmol) were dissolved in dry DMF (2 mL). Cesium carbonate (279 mg, 0.86 mmol) was added and the reaction mixture was stirred at r.t. overnight. The solvent was removed. Water was added and the aqueous phase was extracted by $Et_2O$, washed with brine and dried under $MgSO_4$. After filtration the solvent was removed and the crude product was purified by column chromatography on silica gel (Cy/AcOEt 100 to 80/20) to give the expected product as white solid (110 mg, 41%). $^1H$ NMR (300 MHz, $CDCl_3$) δ 1.15-1.40 (m, 1H), 1.73-1.96 (m, 3H), 2.61 (s, 3H), 2.73 (dd, J=16.0, 2.3 Hz, 1H), 2.95 (dd, J=16.0, 7.6 Hz, 1H), 3.62-3.89 (m, 6H), 3.92-4.07 (m, 2H), 4.20 (d, J=6.1 Hz, 1H), 5.14 (q, J=12.4 Hz, 2H), 6.80-6.92 (m, 2H), 7.08-7.20 (m, 2H), 7.23-7.32 (m, 1H), 7.47 (ddd, J=8.3, 2.6, 0.5 Hz, 1H), 8.16 (d, J=2.6 Hz, 1H). $^{13}C$ NMR (75 MHz, $CDC_3$) δ 17.4, 25.4, 29.2, 34.5, 38.1, 45.3, 55.3, 62.3, 67.9, 77.3, 109.9, 110.5, 120.4, 124.0, 124.0, 129.8, 129.9, 136.1, 137.8, 149.0, 149.9, 151.0, 157.7, 166.8, 169.0. MS $[M+H]^+$ 471 g/mol.

Example 160

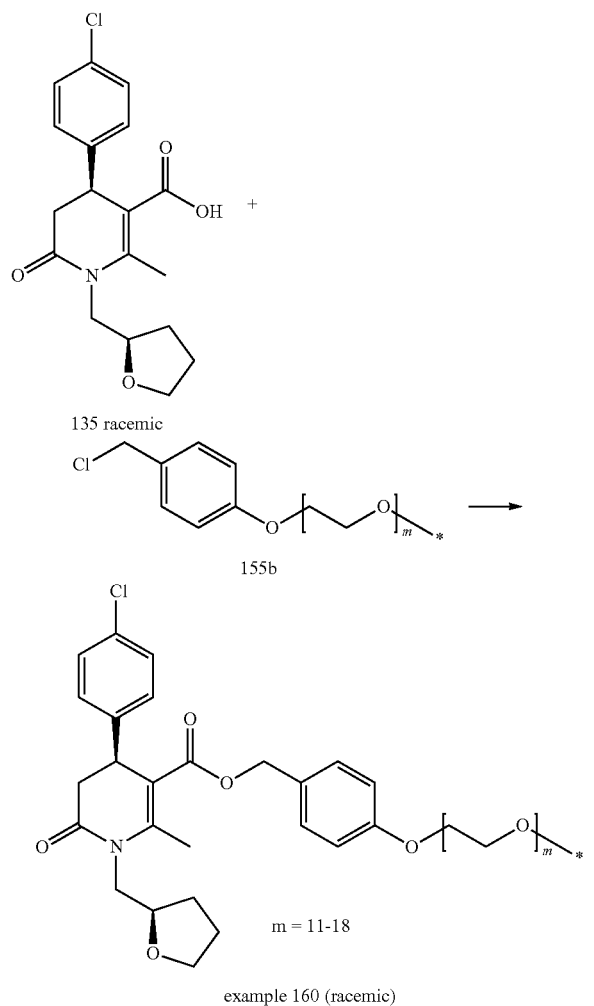

example 160 (racemic)

Example 160. [4-([Poly (ethylene glycol) methyl ether])phenyl]methyl (4S)-4-(4-chlorophenyl)-6-methyl-2-oxo-1-[[(2R)-tetrahydrofuran-2-yl]methyl]-3,4-dihydropyridine-5-carboxylate and [4-([poly (ethylene glycol) methyl ether])phenyl]methyl (4R)-4-(4-chlorophenyl)-6-methyl-2-oxo-1-[[(2S)-tetrahydrofuran-2-yl]methyl]-3,4-dihydropyridine-5-carboxylate. (m=11-18)

The 1-(Chloromethyl)-4-[poly (ethylene glycol) methyl ether] benzene. (MMpeg=900 g/mol) 155b (225 mg, 0.26 mmol) and the acid 135 (119 mg, 0.34 mmol) were dissolved in dry DMF (4 mL). Cesium carbonate (111 mg, 0.34 mmol) and NaI (2.0 mg, 0.01 mmol) were added and the reaction mixture was stirred at room temperature for 18 h. Reaction stopped by addition of water. Solvent was removed under reduced pressure. The residue was extracted by EtOAc and the organics layers were washed by a solution of saturated NaCl, dried over MgSO$_4$, filtered and the solvent was removed to give the crude product. Purification by HPLC (acid conditions) gives the expected product as oil (m=139 mg, 44%). $^1$H NMR (300 MHz, CDCl$_3$) δ 1.30-1.49 (m, 1H), 1.71-1.95 (m, 3H), 2.52-2.67 (m, 5H), 2.84 (dd, J=15.6, 7.4 Hz, 1H), 3.31-3.41 (m, 4H), 3.48-3.53 (m, 2H), 3.55-3.71 (m, 61H), 3.71-3.90 (m, 5H), 4.02-4.09 (m, 2H), 4.12 (d, J=5.8 Hz, 1H), 4.19 (dd, J=14.3, 3.2 Hz, 1H), 4.96 (s, 2H), 6.83 (d, J=8.8 Hz, 2H), 6.98 (d, J=8.7 Hz, 2H), 7.07-7.20 (m, 4H). $^{13}$C NMR (75 MHz, CDCl$_3$) δ 17.1, 25.5, 29.2, 37.0, 39.0, 45.6, 59.0, 65.8, 67.4, 68.1, 69.7, 70.5, 70.5, 70.6, 70.8, 71.9, 77.8, 110.2, 114.4, 128.3, 128.6, 128.7, 129.4, 132.4, 139.5, 151.1, 158.6, 167.0, 168.9. MS [M+NH$_4$]$^+$ 1059 g/mol. [n=11 (11%), n=12 (21%), n=13 (24%), n=14 (23%), n=15 (22%), n=16 (15%), n=17 (9%), n=18 (7%)].

Example 161

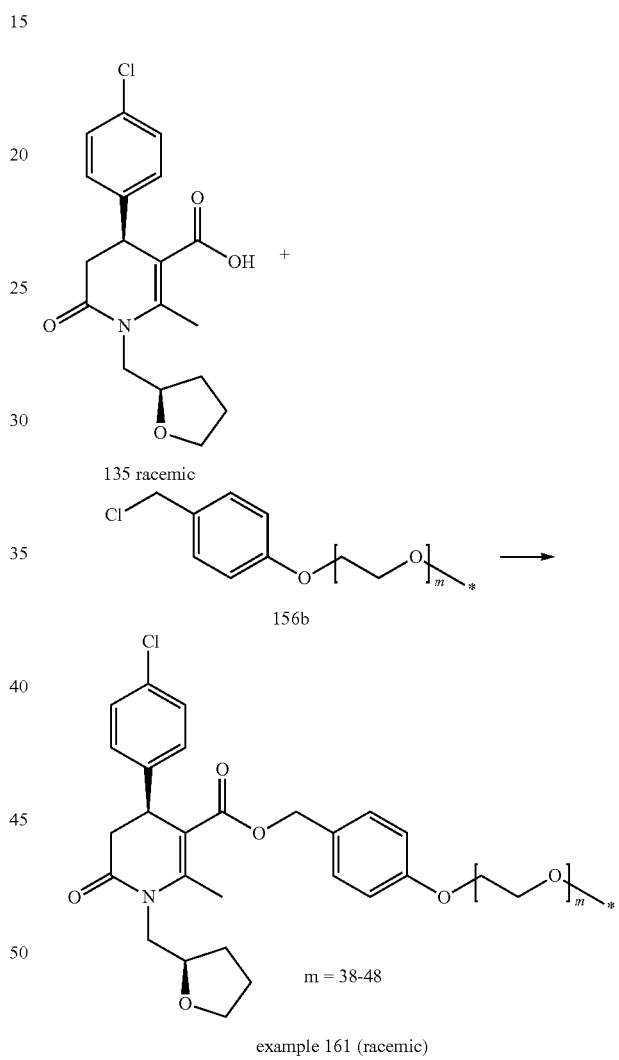

example 161 (racemic)

Example 161. [4-([Poly (ethylene glycol) methyl ether])phenyl]methyl (4S)-4-(4-chlorophenyl)-6-methyl-2-oxo-1-[[(2R)-tetrahydrofuran-2-yl]methyl]-3,4-dihydropyridine-5-carboxylate and [4-([poly (ethylene glycol) methyl ether])phenyl]methyl (4R)-4-(4-chlorophenyl)-6-methyl-2-oxo-1-[[(2S)-tetrahydrofuran-2-yl]methyl]-3,4-dihydropyridine-5-carboxylate. (m=38-48)

The 1-(Chloromethyl)-4-[poly (ethylene glycol) methyl ether] benzene (MMpeg=2000 g/mol) 156b (580 mg, 0.28 mmol) and the acid 135 (128 mg, 0.37 mmol) were dissolved in dry DMF (4 mL). Cesium carbonate (120 mg, 0.37 mmol) and NaI (2 mg, 0.05 mmol) were added and the reaction mixture stirred at r.t. for 18 h. Reaction stopped by addition of water. Solvent was removed under reduced pressure. The residue was extracted by EtOAc and the organics layers were washed by a solution of saturated NaCl, dried over MgSO$_4$ and the solvent was removed to give a crude product. Purification by HPLC (acid conditions) gives the expected product as oil (m=115 mg, 18%). $^1$H NMR (300 MHz, CDCl$_3$) δ 1.40-1.50 (m, 1H), 1.85-1.95 (m, 3H), 2.59 (s, 3H), 2.67 (dd, J=15.6, 2.3 Hz, 1H), 2.88 (dd, J=15.7, 7.3 Hz, 1H), 3.30-3.47 (m, 5H), 3.49-3.95 (m, 190H), 4.05-4.18 (m, 3H), 4.23 (dd, J=14.2, 3.3 Hz, 1H), 5.00 (s, 2H), 6.79 (d, J=8.7 Hz, 2H), 7.02 (d, J=8.7 Hz, 2H), 7.11-7.22 (m, 4H). $^{13}$C NMR (75 MHz, CDCl$_3$) δ 17.0, 25.4, 29.1, 36.9, 38.9, 45.5, 51.8, 63.4, 65.7, 67.3, 68.0, 68.9, 69.5, 70.4, 71.2, 71.8, 72.7, 73.6, 77.4, 81.9, 88.9, 110.1, 114.3, 128.2, 128.5, 128.6, 129.2, 132.3, 139.4, 151.0, 158.4, 166.9, 168.8. MS [M+2H$_3$O]$^2$+806 g/mol. Mixture of compounds containing PEG chains ranging from n=38 to n=48 (centered in: n=43).

Example 162

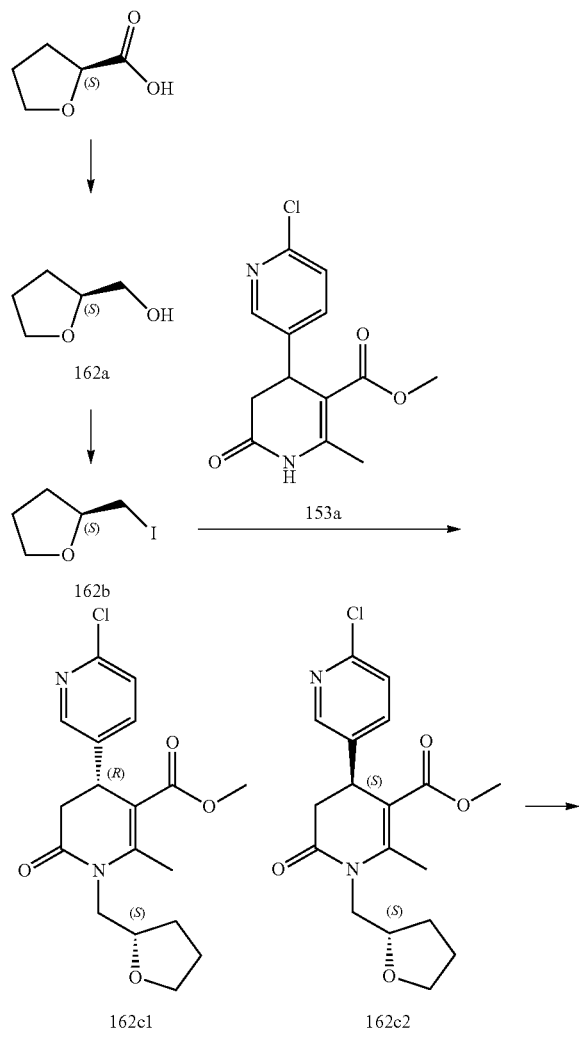

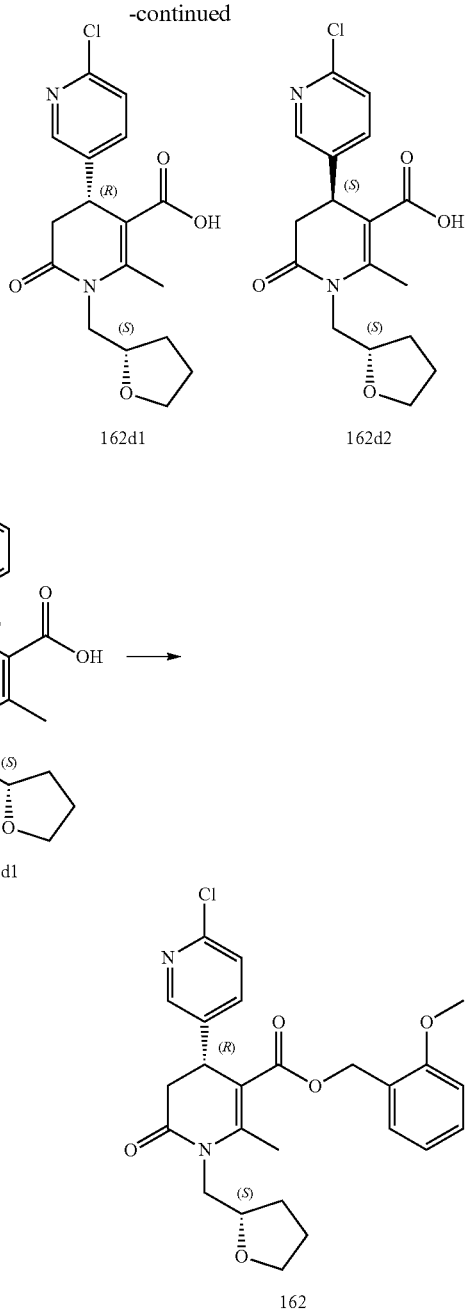

Example 162a. [(2S)-Tetrahydrofuran-2-yl)methanol (2S)-tetrahydrofuran-2-carboxylic acid (2 g, 17.22 mmol) was dissolved in 20 mL of THF under argon and the flask was cooled in an ice bath, BH$_3$.SMe$_2$ (2M solution in THF, 10 mL, 20.0 mmol) was added to the reaction solution over 10 minutes. The ice bath was removed and the solution was stirred for 1 h at room temperature. The solution was again cooled in an ice bath and methanol was slowly added until no gas evolution was observed then the solution was concentrated under vacuum to give the desired product as oil (m=1.7 g, 99%). $^1$H NMR (300 MHz, CDCl$_3$) δ 1.44-1.63 (m, 1H), 1.69-1.88 (m, 3H), 3.23-3.44 (m, 1H), 3.51 (dd, J=11.6, 3.5 Hz, 1H), 3.59-3.82 (m, 3H), 3.83-3.96 (m, 1H).

Example 162b. (2S)-2-(Iodomethyl)tetrahydrofuran

The mixture of triethylamine (1.65 mL, 11.75 mmol), TsCl (1.64 g, 8.62 mmol) and 48 mg of DMAP were combined in CH$_2$Cl$_2$ (25 mL). This solution was cooled in an ice bath and to it was added a solution of tetrahydrofurfuryl alcohol 162a (800 mg, 7.83 mmol) in 10 mL of CH$_2$Cl$_2$ over 20 min. The reaction stirred for 3 h and was then concentrated in vacuum, the residue was taken up in ethyl acetate and then washed 2 times with a saturated solution of NaHCO$_3$ and once with a saturated solution of NaCl. The organic layers were dried over MgSO$_4$, filtered and concentrated in vacuum. LiI (3.1 g, 23.41 mmol) was dried under vacuum for 30 min. then added to a solution of [(2S)-tetrahydrofuran-2-yl]methyl 4-methylbenzenesulfonate (2 g, 7.8 mmol) in 40 mL of acetone, the mixture was refluxed for 24 h and cooled to room temperature. The mixture was filtered and concentrated in vacuum to give brown oil. This oil was taken up in Et$_2$O and washed with water. The organic layer was dried over MgSO$_4$, filtered and concentrated in vacuum to give the product as brown oil (m=1.24 g, 75%). $^1$H NMR (300 MHz, CDCl$_3$) δ 1.52-1.70 (m, 1H), 1.78-1.99 (m, 2H), 2.00-2.13 (m, 1H), 3.05-3.28 (m, 2H), 3.70-3.80 (m, 1H), 3.85-3.95 (m, 2H).

Example 162c1. Methyl (4R)-4-(6-chloro-3-pyridyl)-6-methyl-2-oxo-1-[[(2S)-tetrahydrofuran-2-yl]methyl]-3,4-dihydropyridine-5-carboxylate and Example 162c2. Methyl (4S)-4-(6-chloro-3-pyridyl)-6-methyl-2-oxo-1-[[(2S)-tetrahydrofuran-2-yl]methyl]-3,4-dihydropyridine-5-carboxylate The methyl 4-(6-chloro-3-pyridyl)-6-methyl-2-oxo-3,4-dihydro-1H-pyridine-5-carboxylate 153a (200 mg, 0.71 mmol) and the (2S)-2-(iodomethyl)tetrahydrofuran 162b (302 mg, 1.42 mmol) were dissolved in dry DMF (3 mL), (464 mg, 1.42 mmol) of Cs$_2$CO$_3$ and (5 mg, 0.04 mmol) of NaI were added and the reaction mixture was stirred at 50° C. overnight. Little formation of product was observed by TLC and LCMS. The solvent was removed under reduced pressure. Water was added and the aqueous phase was extracted by ethyl acetate, the organic layers were washed with brine, and dried over MgSO$_4$, filtered and concentrated in vacuum. The crude was dissolved again in 3 mL of DMF, 464 mg of Cs$_2$CO$_3$, 5 mg of NaI and the alkyl iodide (300 mg) were added and the mixture was stirred at 50° C. for 18 h. Reaction finished. The solvent was removed under reduced pressure. Water was added and the aqueous phase was extracted by ethyl acetate, the organic layers were washed with brine, and dried over MgSO$_4$. The solvent was removed and the residue was purified by flash chromatography (CH$_2$Cl$_2$/CyHex: 100/0) and (MeOH/CH$_2$Cl$_2$: 0.5%) to give the desired products as oil (E1:m=58 mg, 22%) (E2: m=41 mg, 16%). MS [M+H]$^+$ 365 g/mol.

162c1: 1H NMR (300 MHz, CDCl$_3$) δ 1.40-1.50 (m, 1H), 1.80-2.01 (m, 3H), 2.58 (s, 3H), 2.65 (dd, J=15.7, 2.0 Hz, 1H), 2.92 (dd, J=15.7, 7.3 Hz, 1H), 3.37 (dd, J=14.2, 9.3 Hz, 1H), 3.62 (s, 3H), 3.67-3.94 (m, 3H), 4.09-4.32 (m, 2H), 7.16 (d, J=8.3 Hz, 1H), 7.60 (dd, J=8.3, 2.6 Hz, 1H), 8.26 (d, J=2.5 Hz, 1H).

162c2: 1H NMR (300 MHz, CDCl$_3$) δ 1.18-1.36 (m, 1H), 1.73-1.95 (m, 3H), 2.61 (s, 3H), 2.76 (dd, J=16.0, 2.2 Hz, 1H), 2.95 (dd, J=16.0, 7.4 Hz, 1H), 3.58-3.87 (m, 6H), 3.90-4.08 (m, 2H), 4.19 (d, J=6.1 Hz, 1H), 7.20 (d, J=8.3 Hz, 1H), 7.51 (ddd, J=8.3, 2.6, 0.5 Hz, 1H), 8.20 (d, J=2.6 Hz, 1H).

Example 162d1. (4R)-4-(6-Chloro-3-pyridyl)-6-methyl-2-oxo-1-[[(2S)-tetrahydrofuran-2-yl]methyl]-3,4-dihydropyridine-5-carboxylic acid The ester 162c1 (58 mg) was dissolved in MeOH (2 mL), a solution of NaOH 1N (2 mL) was added. The reaction mixture was stirred overnight at 40° C. LCMS showed completion of the reaction. The MeOH was evaporated under reduced pressure, the aqueous phase was extracted by Et$_2$O, then acidified to pH=1 with a solution of HCl (1N). The aqueous phase was extracted by EtOAC. The organics layers were assembled and dried over MgSO$_4$, the solvent was removed under reduced pressure to afford a product as oil (m=55 mg, 98%). $^1$H NMR (300 MHz, CDC$_3$) δ 1.36-1.51 (m, 1H), 1.80-2.00 (m, 3H), 2.56-2.74 (m, 4H), 2.93 (dd, J=15.8, 7.3 Hz, 1H), 3.38 (dd, J=14.2, 9.3 Hz, 1H), 3.65-3.90 (m, 3H), 4.15-4.30 (m, 2H), 7.17 (d, J=8.3 Hz, 1H), 7.61 (dd, J=8.3, 2.6 Hz, 1H), 8.28 (d, J=2.4 Hz, 1H), 9.64 (s, 1H). MS [M+H]$^+$ 351 g/mol.

Example 162. (2-M ethoxyphenyl)-methyl-(4R)-4-(6-chloro-3-pyridyl)-6-methyl-2-oxo-1-[[(2S)-tetrahydrofuran-2-yl]methyl]-3,4-dihydropyridine-5-carboxylate The 1-(chloromethyl)-2-methoxy-benzene (27 mg, 0.17 mmol) and the acid 162d1 (55 mg, 0.16 mmol) were dissolved in dry DMF (2 mL). Cesium carbonate (77 mg, 0.24 mmol) was added and the reaction mixture was stirred at room temperature overnight. The solvent was removed. Water was added and the aqueous phase was extracted by Et$_2$O, washed with brine and dried over MgSO$_4$. After filtration the solvent was removed and the crude product was purified by Column chromatography on silica gel (CH$_2$Cl$_2$/MeOH: 100/0 to 99/1) to give the expected product as oil (m=60 mg, 81%). $^1$H NMR (300 MHz, CDCl$_3$) δ 1.35-1.55 (m, 1H), 1.77-2.05 (m, 3H), 2.54-2.73 (m, 4H), 2.93 (dd, J=15.7, 7.5 Hz, 1H), 3.39 (dd, J=14.2, 9.2 Hz, 1H), 3.64-3.78 (m, 4H), 3.81-3.94 (m, 2H), 4.14-4.31 (m, 2H), 4.99-5.21 (m, 2H), 6.74-6.90 (m, 2H), 7.03 (dd, J=7.4, 1.6 Hz, 1H), 7.14 (d, J=8.3 Hz, 1H), 7.20-7.32 (m, 1H), 7.57 (dd, J=8.3, 2.6 Hz, 1H), 8.22 (d, J=2.5 Hz, 1H). $^{13}$C NMR (75 MHz, CDCl$_3$) δ 17.2, 25.7, 29.3, 35.0, 38.7, 46.1, 55.3, 62.2, 68.3, 77.7, 109.4, 110.4, 120.3, 124.1, 124.1, 129.6, 129.7, 136.0, 138.0, 149.2, 149.9, 151.8, 157.5, 166.8, 168.5. MS [M+H]$^+$ 471 g/mol.

Example 163

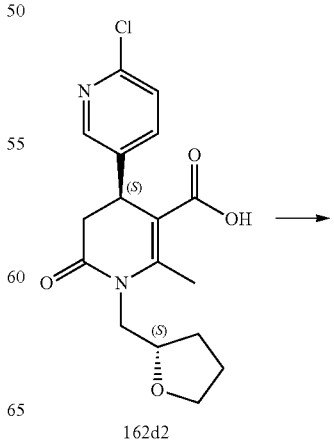

162d2

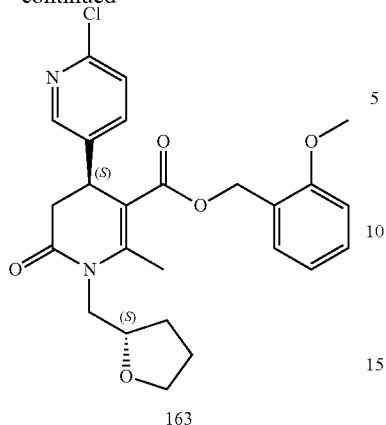

163

Example 162d2. (4S)-4-(6-Chloro-3-pyridyl)-6-methyl-2-oxo-1-[[(2S)-tetrahydrofuran-2-yl]methyl]-3,4-dihydropyridine-5-carboxylic acid The ester 162c2 (40 mg) was dissolved in MeOH (2 mL), a solution of NaOH 1N (2 mL) was added. The reaction mixture was stirred overnight at 40° C.

LCMS showed completion of the reaction. The MeOH was evaporated under reduced pressure, the aqueous phase was extracted by Et$_2$O, then acidified to pH=1 with a solution of HCl (1N). The aqueous phase was extracted by EtOAC. The organics phases were assembled and dried over MgSO$_4$, the solvents were removed under reduced pressure to afford a product as oil (quantitative). $^1$H NMR (300 MHz, CDCl$_3$) δ 1.20-1.34 (m, 1H), 1.76-1.95 (m, 3H), 2.64 (s, 3H), 2.79 (dd, J=16.1, 2.0 Hz, 1H), 2.96 (dd, J=16.0, 7.4 Hz, 1H), 3.64-3.84 (m, 3H), 3.93-4.06 (m, 2H), 4.22 (d, J=6.2 Hz, 1H), 7.20 (d, J=8.3 Hz, 1H), 7.46-7.57 (m, 1H), 8.23 (d, J=2.6 Hz, 1H), 9.55 (s, 1H). MS [M+H]$^+$ 351 g/mol.

Example 163. (2-Methoxyphenyl)methyl-(4S)-4-(6-chloro-3-pyridyl)-6-methyl-2-oxo-1-[[(2S)-tetrahydrofuran-2-yl]methyl]-3,4-dihydropyridine-5-carboxylate The 1-(chloromethyl)-2-methoxy-benzene (19 mg, 0.12 mmol) and the acid 162d2 (38 mg, 0.11 mmol) were dissolved in dry DMF (2 mL). Cesium carbonate (53 mg, 0.16 mmol) was added and the reaction mixture was stirred at r.t. overnight. The solvent was removed. Water was added and the aqueous layer was extracted by Et$_2$O, washed with brine and dried over MgSO$_4$. After filtration the solvent was removed and the crude product was purified by Column chromatography on silica gel (CH$_2$Cl$_2$/MeOH: 100/0 to 99/1) to give the expected product as oil (m=28 mg, 55%). $^1$H NMR (300 MHz, CDCl$_3$) δ 1.19-1.41 (m, 1H), 1.78-1.98 (m, 3H), 2.62 (s, 3H), 2.73 (dd, J=16.0, 2.3 Hz, 1H), 2.95 (dd, J=16.0, 7.6 Hz, 1H), 3.62-3.88 (m, 6H), 3.93-4.05 (m, 2H), 4.21 (d, J=6.2 Hz, 1H), 5.14 (q, J=12.4 Hz, 2H), 6.77-6.94 (m, 2H), 7.04-7.19 (m, 2H), 7.28 (dt, J=7.8, 1.4 Hz, 1H), 7.47 (dd, J=8.3, 2.6 Hz, 1H), 8.17 (d, J=2.6 Hz, 1H). $^{13}$C NMR (75 MHz, CDCl$_3$) δ 17.5, 25.4, 29.2, 34.5, 38.1, 45.3, 55.4, 62.3, 67.9, 77.3, 109.9, 110.5, 120.4, 124.0, 124.1, 129.9, 130.0, 136.1, 137.8, 149.0, 149.9, 151.0, 157.7, 166.8, 169.1. MS [M+H]$^+$ 471 g/mol.

Example 164

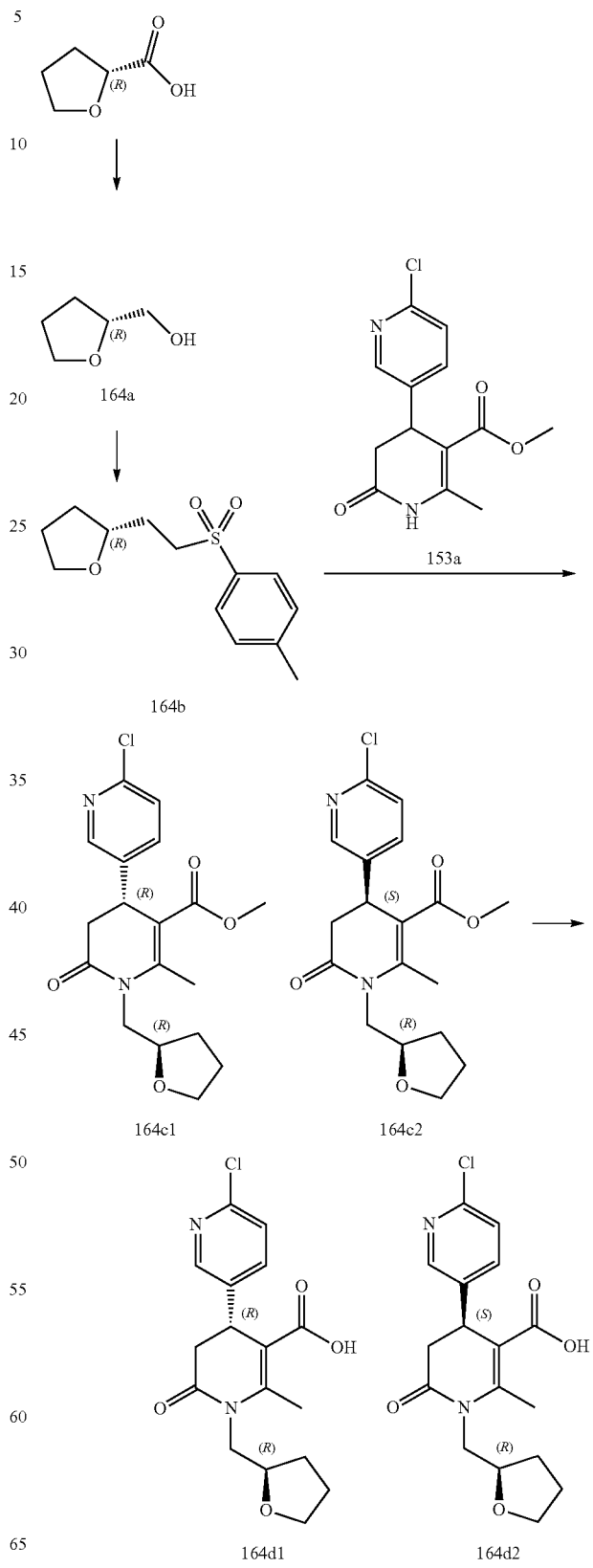

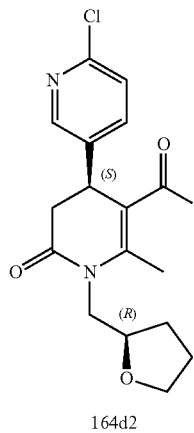

164d2

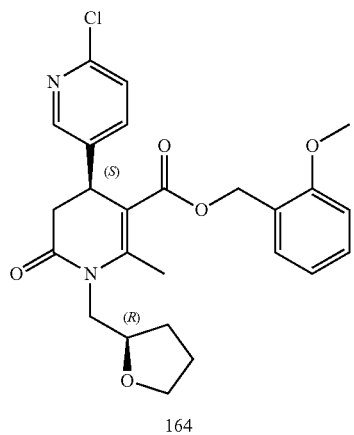

164

Example 164a.
[(2R)-Tetrahydrofuran-2-yl]methanol (2R)-tetrahydrofuran-2-carboxylic acid (2 g, 17.22 mmol) was dissolved in 20 mL of THF under argon and the flask was cooled in an ice bath, BH$_3$.SMe$_2$ (2M solution in THF, 10 mL, 20.0 mmol) was added to the reaction solution over 10 minutes. The ice bath was removed and the solution was stirred for 1 h at room temperature. The solution was again cooled in an ice bath and methanol slowly added until no gas evolution was observed. The solution was concentrated in vacuum to give the desired product as oil (m=1 g, 60%). $^1$H NMR (300 MHz, CDCl$_3$) δ 1.55-1.70 (m, 1H), 1.72-1.98 (m, 3H), 3.35-4.00 (m, 6H).

Example 164b. [(2R)-Tetrahydrofuran-2-yl]methyl 4-methylbenzenesulfonate

The mixture of triethylamine (6.4 mL, 45.53 mmol), TsCl (6.4 g, 33.39 mmol) and 185 mg of DMAP were combined in CH$_2$Cl$_2$ (70 mL). this solution was cooled in an ice bath and to it was added a solution of tetrahydrofurfuryl alcohol 164a (3.1 g, 30.35 mmol) in 30 mL of CH$_2$Cl$_2$ over 20 min. the reaction stirred overnight and was then concentrated in vacuum, the residue was taken up in ethyl acetate and then washed 2 times with a saturated solution of NaHCO$_3$ and once with a brine. The organic layers were dried over MgSO$_4$, filtered and concentrated in vacuum. The crude product was purified by Column chromatography on silica gel (CH$_2$Cl$_2$/CyHex: 50/50) to give the expected product as oil (m=5.6 g, 72%). $^1$H NMR (300 MHz, CDCl$_3$) δ 1.48-1.68 (m, 1H), 1.71-2.05 (m, 3H), 2.40 (s, 3H), 3.58-3.82 (m, 2H), 3.86-4.15 (m, 3H), 7.31 (d, J=8.0 Hz, 2H), 7.75 (d, J=8.2 Hz, 2H). MS [M+H]$^+$ 257 g/mol.

Example 164c1. Methyl-(4R)-4-(6-chloro-3-pyridyl)-6-methyl-2-oxo-1-[[(2R)-tetrahydrofuran-2-yl]methyl]-3,4-dihydropyridine-5-carboxylate and Example 164c2. Methyl-(4S)-4-(6-chloro-3-pyridyl)-6-methyl-2-oxo-1-[[(2R)-tetrahydrofuran-2-yl]methyl]-3,4-dihydropyridine-5-carboxylate The methyl 4-(6-chloro-3-pyridyl)-6-methyl-2-oxo-3,4-dihydro-1H-pyridine-5-carboxylate 153a (400 mg, 1.42 mmol) and the ((2R)-tetrahydrofuran-2-yl)methyl-4-methyl-benzenesulfonate 164b (470 mg, 2.85 mmol) were dissolved in dry DMF (6 mL), (929 mg, 2.85 mmol) of Cs$_2$CO$_3$ and (11 mg, 0.05 mmol) of NaI were added and the reaction mixture was stirred at 50° C. for 24 h. The solvent was removed under reduced pressure. Water was added and the aqueous phase was extracted by ethyl acetate, the organic layers were washed with brine, and dried over MgSO$_4$. The solvent was removed and the crude product was purified by column chromatography on silica gel (CH$_2$Cl$_2$/MeOH 100/0 to 95/5) to give the expected products as oil (e1: m=126 mg, 24%) (e2: m=109 mg, 21%). MS [M+H]$^+$ 365 g/mol. 164c1: H NMR (300 MHz, CDCl$_3$) δ 1.14-1.32 (m, 1H), 1.71-1.92 (m, 3H), 2.58 (s, 3H), 2.72 (dd, J=16.0, 2.2 Hz, 1H), 2.92 (dd, J=16.0, 7.4 Hz, 1H), 3.53-3.83 (m, 6H), 3.97 (dt, J=6.4, 4.4 Hz, 2H), 4.16 (d, J=5.9 Hz, 1H), 7.16 (d, J=8.2 Hz, 1H), 7.49 (dd, J=8.3, 2.6 Hz, 1H), 8.16 (d, J=2.6 Hz, 1H). 164c2: $^1$H NMR (300 MHz, CDCl$_3$) δ 1.35-1.45 (m, 1H), 1.76-2.01 (m, 3H), 2.57 (s, 3H), 2.63 (dd, J=15.7, 2.0 Hz, 1H), 2.91 (dd, J=15.7, 7.3 Hz, 1H), 3.35 (dd, J=14.2, 9.3 Hz, 1H), 3.61 (s, 3H), 3.66-3.91 (m, 3H), 4.10-4.29 (m, 2H), 7.09-7.20 (m, 1H), 7.59 (ddd, J=8.3, 2.6, 0.5 Hz, 1H), 8.24 (d, J=2.6 Hz, 1H).

Example 164d2. (4S)-4-(6-Chloro-3-pyridyl)-6-methyl-2-oxo-1-[[(2R)-tetrahydrofuran-2-yl]methyl]-3,4-dihydropyridine-5-carboxylic acid The ester 164c2 (126 mg) was dissolved in MeOH (2 mL), a solution of NaOH 1N (2 mL) was added. The reaction mixture was stirred overnight at 40° C. LCMS showed completion of the reaction. The MeOH was evaporated under reduced pressure, the aqueous phase was extracted by Et$_2$O, then acidified to pH=1 with HCl (1N). The aqueous phase was extracted by EtOAC. The organic phases were assembled and dried over MgSO$_4$. The solvents were removed under reduced pressure to afford a product as oil (m=66 mg, 55%).
$^1$H NMR (300 MHz, CDCl$_3$) δ 1.35-1.52 (m, 1H), 1.79-2.00 (m, 3H), 2.60 (s, 3H), 2.68 (dd, J=15.8, 1.9 Hz, 1H), 2.94 (dd, J=15.8, 7.4 Hz, 1H), 3.39 (dd, J=14.2, 9.4 Hz, 1H), 3.65-3.89 (m, 3H), 4.17-4.28 (m, 2H), 7.13-7.20 (m, 1H), 7.58-7.64 (m, 1H), 8.28 (d, J=2.6 Hz, 1H), 9.49 (s, 1H). MS [M+H]$^+$ 351 g/mol.

Example 164. (2-Methoxyphenyl)methyl-(4S)-4-(6-chloro-3-pyridyl)-6-methyl-2-oxo-1-[[(2R)-tetrahydrofuran-2-yl]methyl]-3,4-dihydropyridine-5-carboxylate The 1-(chloromethyl)-2-methoxy-benzene (33 mg, 0.21 mmol) and the acid 164d2 (66 mg, 0.19 mmol) were dissolved in dry DMF (3 mL). Cesium carbonate (92 mg, 0.28 mmol) was added and the reaction mixture was stirred at r.t. overnight. The solvent was removed. Water was added and the aqueous phase was extracted by Et$_2$O, washed with brine and dried over MgSO$_4$. After filtration the solvent was removed and the crude product was purified by Column chromatography on silica gel (CH$_2$Cl$_2$/MeOH: 100/0 to 99/1) to give the expected product as oil (m=48 mg, 54%). $^1$H NMR (300 MHz, CDCl$_3$) δ 1.40-1.55 (m, 1H), 1.82-2.06 (m, 3H), 2.56-2.71 (m, 4H), 2.94 (dd, J=15.8, 7.5 Hz, 1H), 3.40 (dd, J=14.2, 9.2 Hz, 1H), 3.67-3.79 (m, 4H), 3.80-3.94 (m, 2H), 4.16-4.29 (m, 2H), 5.03-5.20 (m, 2H), 6.79-6.90 (m, 2H), 7.04 (dd, J=7.4, 1.7 Hz, 1H), 7.14 (d, J=8.3 Hz, 1H), 7.22-7.31 (m, 1H), 7.58 (ddd, J=8.3, 2.6, 0.4 Hz, 1H), 8.22 (d, J=2.6 Hz, 1H). $^{13}$C NMR (75 MHz, CDCl$_3$) δ 17.2, 25.7, 29.3, 35.0, 38.7, 46.1, 55.3, 62.2, 68.3, 77.7, 109.4, 110.4, 120.4, 124.1, 124.1, 129.6, 129.7, 136.0, 138.0, 149.3, 149.9, 151.8, 157.6, 166.8, 168.5. MS [M+H]$^+$ 471 g/mol.

Example 165

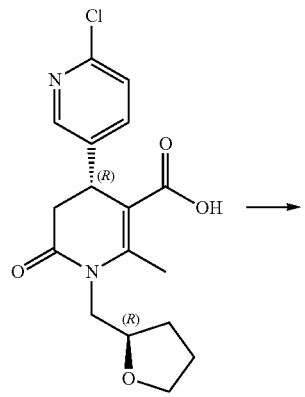

164d1

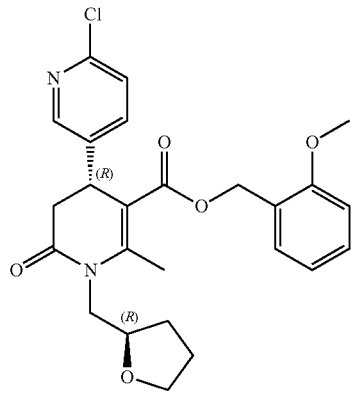

165

Example 164d1. (4R)-4-(6-Chloro-3-pyridyl)-6-methyl-2-oxo-1-[[(2R)-tetrahydrofuran-2-yl]methyl]-3,4-dihydropyridine-5-carboxylic acid The ester 164c1 (109 mg) was dissolved in MeOH (2 mL), a solution of NaOH 1N (2 mL) was added. The reaction mixture was stirred overnight at 40° C. LCMS showed completion of the reaction. The MeOH was evaporated under reduced pressure, the aqueous phase was extracted by Et$_2$O, then acidified to pH=1 with HCl (1N). The aqueous phase was extracted by EtOAC. The organic phases were assembled and dried over MgSO$_4$. The solvents were removed under reduced pressure to afford a product as oil (m=98 mg, 94%). $^1$H NMR (300 MHz, CDCl$_3$) δ 1.21-1.31 (m, 1H), 1.73-1.93 (m, 3H), 2.61 (s, 3H), 2.77 (dd, J=16.1, 2.0 Hz, 1H), 2.94 (dd, J=16.0, 7.4 Hz, 1H), 3.61-3.81 (m, 3H), 3.93-4.03 (m, 2H), 4.20 (d, J=6.2 Hz, 1H), 7.18 (d, J=8.3 Hz, 1H), 7.52 (dd, J=8.3, 2.6 Hz, 1H), 8.22 (d, J=2.5 Hz, 1H), 10.47 (s, 1H). MS [M+H]$^+$ 351 g/mol.

Example 165. (2-M ethoxyphenyl)methyl-(4R)-4-(6-chloro-3-pyridyl)-6-methyl-2-oxo-1-[[(2R)-tetrahydrofuran-2-yl]methyl]-3,4-dihydropyridine-5-carboxylate The 1-(chloromethyl)-2-methoxy-benzene (48 mg, 0.31 mmol) and the acid 164d1 (98 mg, 0.28 mmol) were dissolved in dry DMF (4 mL). Cesium carbonate (137 mg, 0.42 mmol) was added and the reaction mixture was stirred at r.t. overnight. The solvent was removed. Water was added and the aqueous phase was extracted by Et$_2$O, washed with brine and dried over MgSO$_4$. After filtration the solvent was removed and the crude product was purified by Column chromatography on silica gel (CH$_2$Cl$_2$/MeOH: 100/0 to 99/1) to give the expected product as oil (m=100 mg, 76%). $^1$H NMR (300 MHz, CDCl$_3$) δ 1.20-1.40 (m, 1H), 1.75-1.97 (m, 3H), 2.61 (s, 3H), 2.72 (dd, J=16.0, 2.2 Hz, 1H), 2.94 (dd, J=16.0, 7.6 Hz, 1H), 3.62-3.86 (m, 6H), 3.93-4.06 (m, 2H), 4.20 (d, J=6.1 Hz, 1H), 5.13 (q, J=12.4 Hz, 2H), 6.79-6.90 (m, 2H), 7.09 (dd, J=7.4, 1.7 Hz, 1H), 7.13 (d, J=8.3 Hz, 1H), 7.27 (td, J=8.1, 1.8 Hz, 1H), 7.47 (dd, J=8.3, 2.6 Hz, 1H), 8.16 (d, J=2.6 Hz, 1H). $^{13}$C NMR (75 MHz, CDCl$_3$) 17.4, 25.3, 29.1, 34.4, 38.0, 45.3, 55.3, 62.2, 67.9, 77.2, 109.8, 110.4, 120.3, 124.0, 124.0, 129.8, 129.9, 136.1, 137.8, 148.9, 149.9, 151.0, 157.6, 166.8, 169.0. MS [M+H]$^+$ 471 g/mol.

Example 166

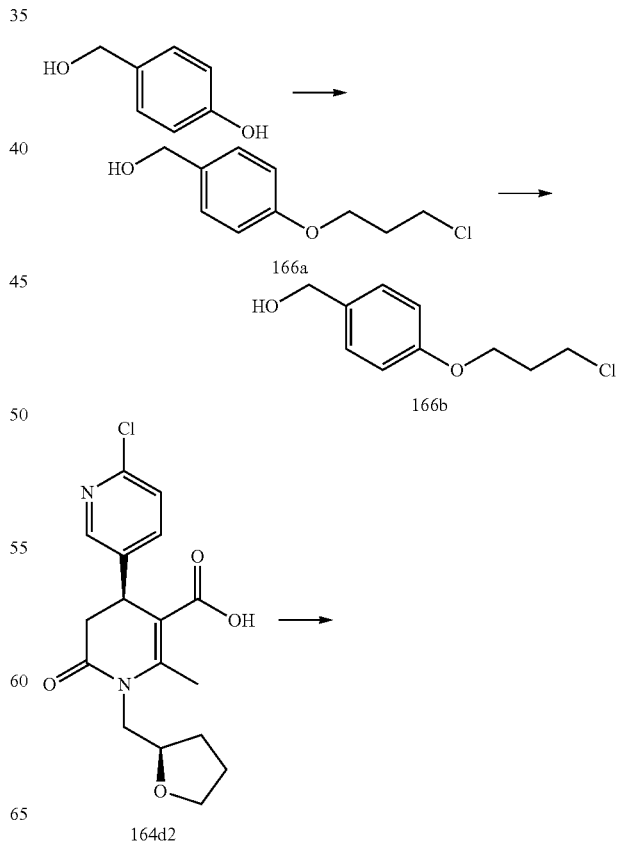

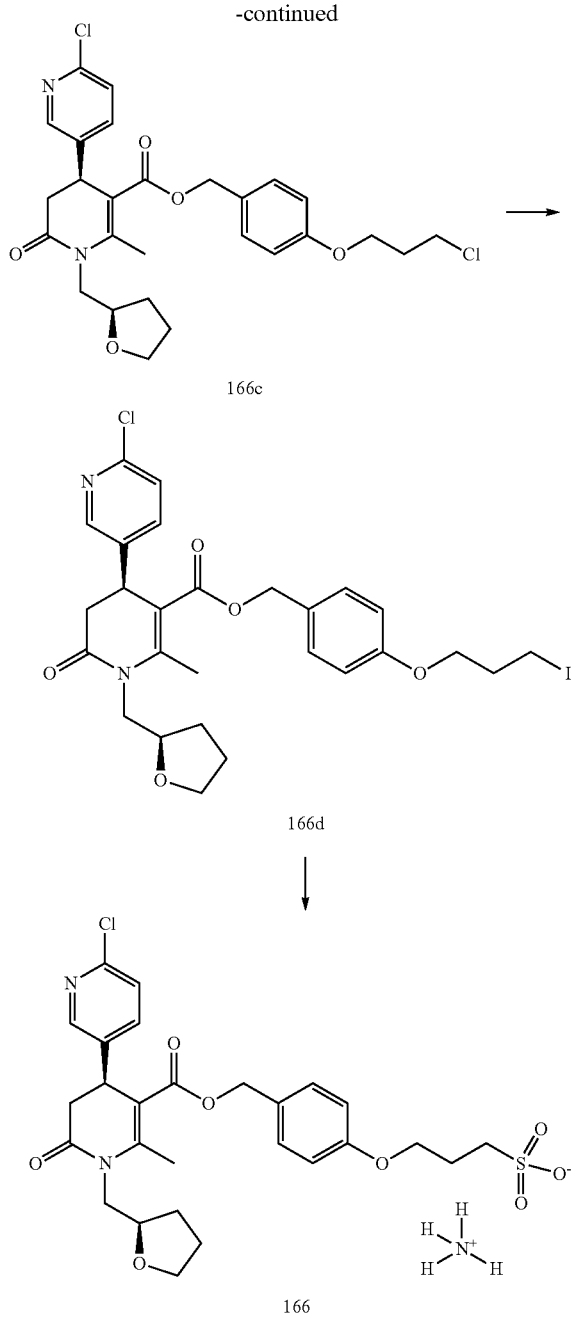

166c

166d

166

Example 166a.
[4-(3-Chloropropoxy)phenyl)methanol

A mixture of 1-bromo-3-chloro-propane (2.4 mL, 24 mmol), 4-hydroxybenzyl alcohol (1.0 g, 8 mmol) and potassium carbonate (1.11 g, 8 mmol) was added in acetonitrile (27 mL) and the reaction was stirred overnight at 50° C. Little formation of product was observed by TLC and LCMS. RM stirred at reflux for 8 h. little progress (20% conv. to 30% conv.). 3 equivalents of reactant and base were added. Reaction stirred under reflux overnight. Reaction finished. The solvent was removed under reduced pressure. The crude was dissolved in EtOAc and washed by water. The aqueous phase was extracted by EtOAc and the organic phase was washed with brine, dried under MgSO$_4$. The solvents were removed under reduced pressure to afford the title compound. This crude was purified by flash chromatography (Cy/EA 100/0 to 75/25) to afford the desired compound as an oil (m=1.34 g, 84%). $^1$H NMR (300 MHz, CDCl$_3$) δ 2.03 (s, 1H), 2.14-2.42 (m, 2H), 3.75 (t, J=6.3 Hz, 2H), 4.12 (t, J=5.8 Hz, 2H), 4.59 (s, 2H), 6.90 (d, J=8.4 Hz, 2H), 7.28 (d, J=8.2 Hz, 2H).

Example 166b.
1-(Chloromethyl)-4-(3-chloropropoxy)benzene

Thionyl chloride (90 µL, 1.25 mmol) was added to benzotriazole (178 mg, 1.50 mmol). The resulting mixture was dissolved in CH$_2$Cl$_2$ (3 mL). After 5 min, this solution was added slowly to the solution of the [4-(3-Chloropropoxy)phenyl)methanol 166a (200 mg, 1.0 mmol) in CH$_2$Cl$_2$ (7 mL).
The benzotriazole salt started to precipitate. After 20 min of reaction, the salt was filtered. The organic phase was washed by water and NaOH solution. The organic phase was dried under MgSO$_4$ and the solvent was removed under reduced pressure to give the desired chlorinated compound as yellow oil (m=184 mg, 84%). $^1$H NMR (300 MHz, CDCl$_3$) δ 2.17-2.33 (m, 2H), 3.75 (t, J=6.3 Hz, 2H), 4.12 (t, J=5.9 Hz, 2H), 4.58 (s, 2H), 6.90 (d, J=8.7 Hz, 2H), 7.32 (d, J=8.8 Hz, 2H).

Example 166c. [4-(3-Chloropropoxy)phenyl]methyl-(4S)-4-(6-chloro-3-pyridyl)-6-methyl-2-oxo-1-[[(2R)-tetrahydrofuran-2-yl]methyl]-3,4-dihydropyridine-5-carboxylate The acid 164d2 (80 mg, 0.23 mmol) and cesium carbonate (111 mg, 0.34 mmol) were dissolved in dry DMF (2 mL). The chlorinated compound 166b (75 mg, 0.34 mmol) was added. The reaction mixture was stirred at r.t. for 24 h. The solvent was removed under reduced pressure. The residue was dissolved in EtOAc and washed with water. The aqueous phase was extracted by EtOAc. The organic layers were assembled, washed with brine and dried over MgSO$_4$. The residue was purified by flash chromatography (Cy/CH$_2$Cl$_2$: 50/50 to 0/100) to afford the desired product as a colorless oil (m=97 mg, 80%). $^1$H NMR (300 MHz, CDCl$_3$) δ 1.37-1.54 (m, 1H), 1.80-2.08 (m, 3H), 2.17-2.31 (m, 2H), 2.54-2.73 (m, 4H), 2.92 (dd, J=15.7, 7.5 Hz, 1H), 3.39 (dd, J=14.2, 9.3 Hz, 1H), 3.67-3.78 (m, 3H), 3.79-3.94 (m, 2H), 4.09 (t, J=5.8 Hz, 2H), 4.14-4.28 (m, 2H), 5.00 (q, J=12.2 Hz, 2H), 6.81 (d, J=8.7 Hz, 2H), 7.07 (d, J=8.7 Hz, 2H), 7.15 (d, J=8.3 Hz, 1H), 7.56 (dd, J=8.3, 2.6 Hz, 1H), 8.23 (d, J=2.6 Hz, 1H). MS [M+H]$^+$ 533 g/mol.

Example 166d. [4-(3-Iodopropoxy)phenyl]methyl (4S)-4-(6-chloro-3-pyridyl)-6-methyl-2-oxo-1-[[(2R)-tetrahydrofuran-2-yl]methyl]-3,4-dihydropyridine-5-carboxylate The chlorinated compound 166c (96 mg, 0.18 mmol) was dissolved in butanone (4 mL). NaI (108 mg, 0.72 mmol) was added and the reaction mixture stirred at 80° C. overnight. The solution was cooled to r.t., filtered and the filtrate washed by acetone. The solvents were removed under reduced pressure to afford yellowish oil. This residue was purified by flash chromatography (CH$_2$Cl$_2$) to give the desired product as oil (m=103 mg, 92%). $^1$H NMR (300 MHz, CDCl$_3$) δ 1.40-1.52 (m, 1H), 1.82-2.03 (m, 3H), 2.19-2.30 (m, 2H), 2.54-2.70 (m, 4H), 2.91 (dd, J=15.8, 7.5 Hz, 1H), 3.27-3.47 (m, 3H), 3.65-3.78 (m, 1H), 3.78-3.93

(m, 2H), 4.01 (t, J=5.8 Hz, 2H), 4.11-4.29 (m, 2H), 5.00 (q, J=12.2 Hz, 2H), 6.80 (d, J=8.7 Hz, 2H), 7.06 (d, J=8.5 Hz, 2H), 7.14 (d, J=8.3 Hz, 1H), 7.56 (dd, J=8.3, 2.6 Hz, 1H), 8.23 (d, J=2.5 Hz, 1H). MS [M+H]+ 625 g/mol.

Example 166. Ammonium,3-[4-[[(4S)-4-(6-chloro-3-pyridyl)-6-methyl-2-oxo-1-[[(2R)-tetrahydrofuran-2-yl]methyl]-3,4-dihydropyridine-5-carbonyl]oxymethyl]phenoxy]propane-1-sulfonate The iodide compound 166d (100 mg, 0.16 mmol) was dissolved in a mixture of iPrOH/water (1/1, 2 mL). Sodium sulfite (40 mg, 0.32 mmol) was added and the reaction mixture was heated at 80° C. in sealed tube for 18 h. The solvents were removed under reduced pressure. Purification of the crude product by HPLC (acid conditions) gave the ammonium; 3-[4-[[(4S)-4-(6-chloro-3-pyridyl)-6-methyl-2-oxo-1-[[(2R)-tetrahydrofuran-2-yl]methyl]-3,4-dihydropyridine-5-carbonyl]oxymethyl]phenoxy]propane-1-sulfonate as a white powder (m=52 mg, 54%). 1H NMR (300 MHz, CDCl3) δ 1.35-1.50 (m, 1H), 1.80-2.00 (m, 3H), 2.17 (s, 2H), 2.50-2.65 (m, 4H), 2.85 (dd, J=15.8, 7.1 Hz, 1H), 3.04 (s, 2H), 3.36 (dd, J=14.0, 9.2 Hz, 1H), 3.70 (dd, J=14.2, 7.1 Hz, 1H), 3.80-3.95 (m, 4H), 4.10-4.25 (m, 2H), 4.87 (dd, J=29.3, 12.1 Hz, 2H), 6.69 (d, J=6.7 Hz, 2H), 6.85-7.40 (m, 3H+NH4+), 7.57 (d, J=7.9 Hz, 1H), 8.17 (s, 1H). 13C NMR (75 MHz, CDCl3) δ 17.3, 25.0, 25.8, 29.3, 34.9, 38.7, 46.1, 66.1, 66.6, 68.3, 77.7, 109.1, 114.7, 124.3, 128.2, 129.7, 136.3, 138.2, 149.7, 152.2, 158.7, 166.7, 168.5. MS [M]− 577 g/mol.

Example 167

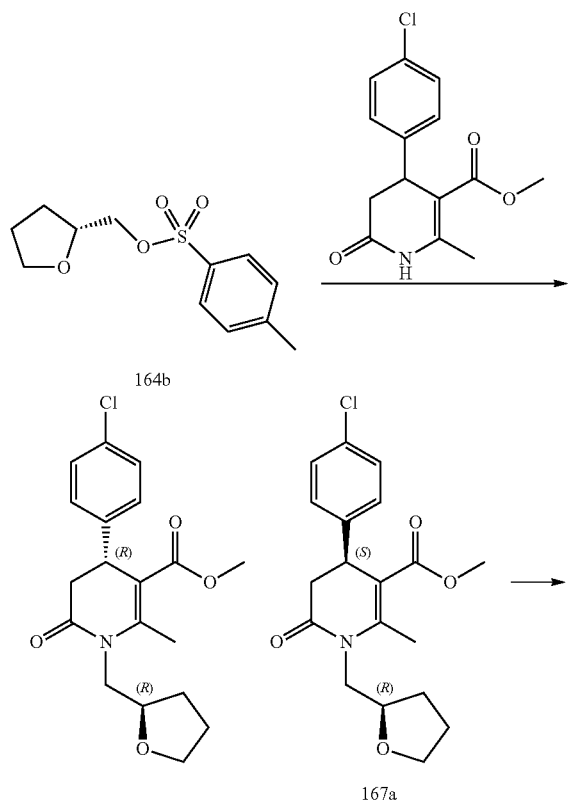

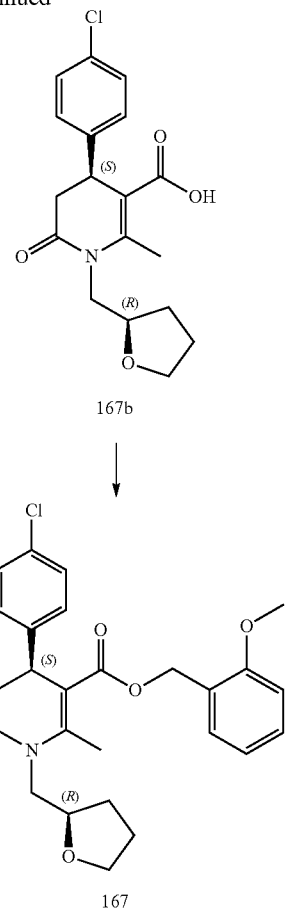

Example 167a. Methyl-(4S)-4-(4-chlorophenyl)-6-methyl-2-oxo-1-[[(2R)-tetrahydrofuran-2-yl]methyl]-3,4-dihydropyridine-5-carboxylate The dihydropyridone intermediate obtained following general procedure A (1.5 g, 5.36 mmol) and the [(2R)-tetrahydrofuran-2-yl]methyl 4-methylbenzenesulfonate 164b (2.75 g, 10.72 mmol) were dissolved in dry DMF (25 mL), Cs2CO3 (3.5 g, 10.72 mmol) and NaI (40 mg, 0.27 mmol) were added and the reaction mixture was stirred at 50° C. for 24 h. reaction finished. The solvent was removed under reduced pressure. Water was added and the aqueous phase was extracted by ethyl acetate, the organic layers were washed with brine, and dried over MgSO4. The solvent was removed and the crude was purified by flash chromatography (CH2Cl2/CyHex 30/70 to 100/0) to give the expected product as oil (m=500 mg, 26%). 1H NMR (300 MHz, CDCl3) δ 1.34-1.48 (m, 1H), 1.74-1.98 (m, 3H), 2.57 (d, J=0.5 Hz, 3H), 2.66 (dd, J=15.6, 2.2 Hz, 1H), 2.86 (dd, J=15.6, 7.2 Hz, 1H), 3.28-3.43 (m, 1H), 3.60 (s, 3H), 3.65-3.79 (m, 2H), 3.80-3.90 (m, 1H), 4.14 (dd, J=7.1, 1.5 Hz, 1H), 4.22 (dd, J=14.3, 3.3 Hz, 1H), 7.17 (s, 4H). MS [M+H]+ 364 g/mol.

Example 167b. (4S)-4-(4-Chlorophenyl)-6-methyl-2-oxo-1-[[(2R)-tetrahydrofuran-2-yl]methyl]-3,4-dihydropyridine-5-carboxylic acid The ester 167a (480 mg, 1.32 mmol) was dissolved in MeOH (8 mL), a solution of NaOH 1N (8 mL) was added.

The reaction mixture was stirred for 3 h at 40° C. LCMS showed completion of the reaction. The MeOH was evaporated under reduced pressure, the aqueous phase was extracted by Et$_2$O, then acidified to pH=1 with a solution of HCl (1N). The aqueous phase was extracted by EtOAC and the organic phases were assembled and dried under MgSO$_4$. The solvents were removed under reduced pressure to afford a product as white solid (m=459 mg, 99%). $^1$H NMR (300 MHz, CDCl$_3$) δ 1.32-1.52 (m, 1H), 1.76-1.99 (m, 3H), 2.61 (s, 3H), 2.71 (dd, J=15.6, 1.9 Hz, 1H), 2.89 (dd, J=15.6, 7.2 Hz, 1H), 3.39 (dd, J=14.2, 8.8 Hz, 1H), 3.68-3.80 (m, 2H), 3.88 (dt, J=13.0, 6.7 Hz, 1H), 4.13-4.33 (m, 2H), 7.19 (s, 4H), 11.47 (s, 1H). MS [M+H]$^+$ 350 g/mol.

Example 167. (2-Methoxyphenyl)methyl-(4S)-4-(4-chlorophenyl)-6-methyl-2-oxo-1-[[(2R)-tetrahydrofuran-2-yl]methyl]-3,4-dihydropyridine-5-carboxylate The 1-(chloromethyl)-2-methoxy-benzene (50 mg, 0.31 mmol) and the acid 167b (100 mg, 0.29 mmol) were dissolved in dry DMF (5 mL). Cesium carbonate (140 mg, 0.43 mmol) was added and the reaction mixture was stirred at r.t. overnight. The solvent was removed. Water was added and the aqueous phase was extracted by AcOEt, washed with brine and dried over MgSO$_4$. After filtration the solvent was removed and the crude product was purified by Column chromatography on silica gel (CH$_2$Cl$_2$/MeOH: 100/0 to 99/1) to give the expected product as oil (m=125 mg, 93%). $^1$H NMR (300 MHz, CDCl$_3$) δ 1.36-1.52 (m, 1H), 1.77-1.98 (m, 3H), 2.61 (d, J=0.5 Hz, 3H), 2.68 (dd, J=15.6, 2.2 Hz, 1H), 2.90 (dd, J=15.6, 7.4 Hz, 1H), 3.40 (dd, J=14.2, 8.6 Hz, 1H), 3.66-3.96 (m, 6H), 4.15-4.30 (m, 2H), 5.14 (dd, J=28.9, 13.0 Hz, 2H), 6.82 (ddd, J=8.5, 5.6, 1.1 Hz, 2H), 6.93-6.98 (m, 1H), 7.18 (s, 4H), 7.21-7.28 (m, 1H). $^{13}$C NMR (75 MHz, CDCl$_3$) δ 17.0, 25.6, 29.3, 37.0, 39.1, 45.6, 55.2, 61.8, 68.1, 77.9, 110.2, 110.4, 120.2, 124.4, 128.6, 128.7, 128.9, 129.2, 132.5, 139.7, 150.9, 157.3, 167.2, 169.0. MS [M+H]$^+$ 470 g/mol.

Example 168

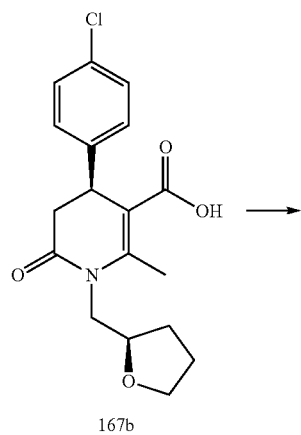

167b

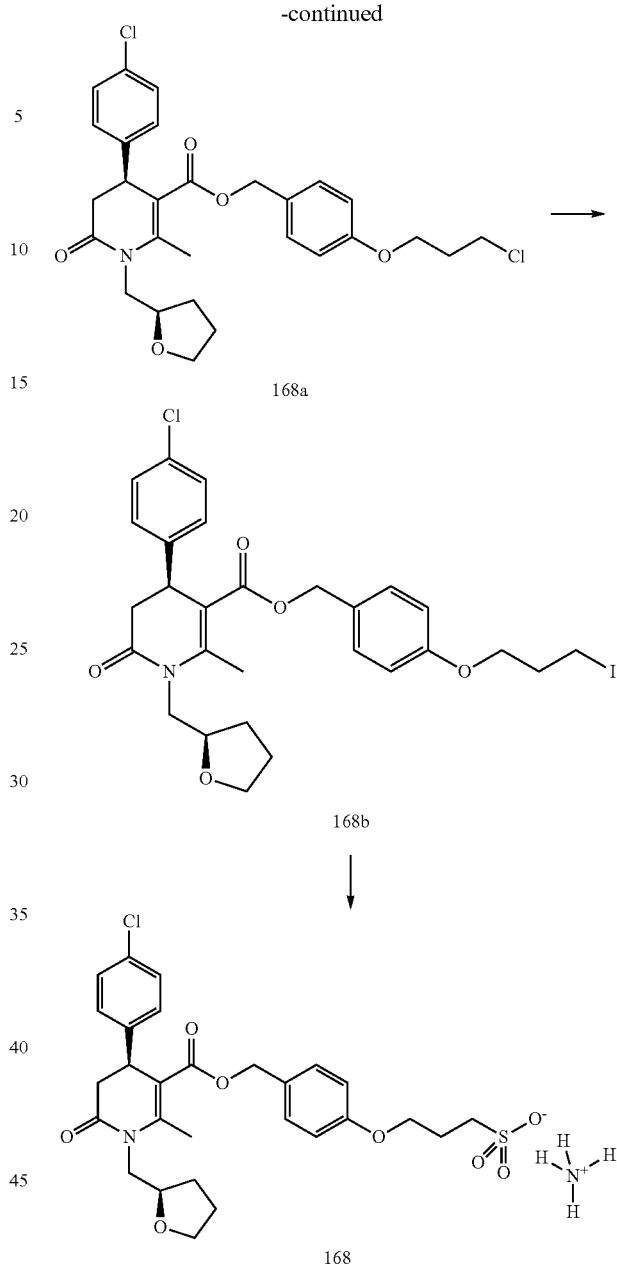

168a

168b

168

Example 168a. [4-(3-Chloropropoxy)phenyl] methyl-(4S)-4-(4-chlorophenyl)-6-methyl-2-oxo-1-[[(2R)-tetrahydrofuran-2-yl]methyl]-3,4-dihydropyridine-5-carboxylate The acid 167b (100 mg, 0.29 mmol) and cesium carbonate (140 mg, 0.43 mmol) were dissolved in dry DMF (3 mL), chlorinated compound 166b (94 mg, 0.43 mmol) was added and the reaction mixture was stirred at room temperature for 24 h. The solvent was removed under reduced pressure. The residue was dissolved in EtOAc and washed with water. The aqueous phase was extracted by EtOAc. The organic layers were assembled, washed with brine and dried over MgSO$_4$. The residue was purified by flash chromatography (Cy/ CH$_2$Cl$_2$: 50/50 to 0/100) to afford the desired product as a colorless oil (m=80 mg, 53%). $^1$H NMR (300 MHz, CDCl$_3$)

δ 1.34-1.54 (m, 1H), 1.79-2.01 (m, 3H), 2.18-2.32 (m, 2H), 2.61 (s, 3H), 2.67 (dd, J=15.6, 2.2 Hz, 1H), 2.88 (dd, J=15.6, 7.4 Hz, 1H), 3.40 (dd, J=14.3, 8.7 Hz, 1H), 3.63-3.84 (m, 4H), 3.84-3.96 (m, 1H), 4.09 (t, J=5.8 Hz, 2H), 4.16 (d, J=5.7 Hz, 1H), 4.24 (dd, J=14.3, 3.3 Hz, 1H), 5.01 (s, 2H), 6.79 (d, J=8.7 Hz, 2H), 7.04 (d, J=8.7 Hz, 2H), 7.12-7.24 (m, 4H). MS [M+H]+ 532 g/mol.

Example 168b. [4-(3-Iodopropoxy)phenyl]methyl-(4S)-4-(4-chlorophenyl)-6-methyl-2-oxo-1-[[(2R)-tetrahydrofuran-2-yl]methyl]-3,4-dihydropyridine-5-carboxylate The chlorinated compound 168a (80 mg, 0.15 mmol) was dissolved in butanone (4 mL), NaI (90 mg, 0.6 mmol) was added and the reaction mixture stirred at 80° C. overnight. The solution was cooled to room temperature, filtered and the filtrate washed by acetone. The solvents were removed under reduced pressure to afford yellowish oil. This residue was purified by flash chromatography (CH$_2$Cl$_2$) to give the desired product as oil (m=76 mg, 81%).

$^1$H NMR (300 MHz, CDC$_3$) δ 1.33-1.53 (m, 1H), 1.78-1.99 (m, 3H), 2.25 (qd, J=6.3, 4.7 Hz, 2H), 2.60 (d, J=0.6 Hz, 3H), 2.67 (dd, J=15.6, 2.2 Hz, 1H), 2.88 (dd, J=15.6, 7.4 Hz, 1H), 3.30-3.45 (m, 3H), 3.63-3.93 (m, 3H), 4.01 (t, J=5.8 Hz, 2H), 4.16 (d, J=5.7 Hz, 1H), 4.23 (dd, J=14.3, 3.3 Hz, 1H), 5.01 (s, 2H), 6.79 (d, J=8.8 Hz, 2H), 7.03 (d, J=8.8 Hz, 2H), 7.14-7.20 (m, 4H). MS [M+H]+ 624 g/mol.

Example 168. Ammonium,3-[4-[[(4S)-4-(4-chlorophenyl)-6-methyl-2-oxo-1-[[(2R)-tetrahydrofuran-2-yl]methyl]-3,4-dihydropyridine-5-carbonyl]oxymethyl]phenoxy]propane-1-sulfonate The iodide compound 168b (75 mg, 0.12 mmol) was dissolved in a mixture of iPrOH/water (1/1, 2 mL). Sodium sulfite (30 mg, 0.24 mmol) was added and the reaction mixture was heated at 80° C. in sealed tube for 18 h. The solvents were removed under reduced pressure. Purification of the crude by HPLC (acid conditions) gave the ammonium; 3-[4-[[(4S)-4-(6-chloro-3-pyridyl)-6-methyl-2-oxo-1-[[(2R)-tetrahydrofuran-2-yl]methyl]-3,4-dihydropyridine-5-carbonyl]oxymethyl]phenoxy]propane-1-sulfonate as a white powder (m=45 mg, 63%). $^1$H NMR (300 MHz, CDCl$_3$) δ 1.28-1.50 (m, 1H), 1.72-1.96 (m, 3H), 2.14 (s, 2H), 2.50-2.65 (m, 4H), 2.80 (dd, J=15.6, 7.2 Hz, 1H), 3.02 (s, 2H), 3.35 (dd, J=14.2, 8.7 Hz, 1H), 3.62-3.90 (m, 5H), 4.09 (d, J=6.6 Hz, 1H), 4.19 (dd, J=14.2, 2.7 Hz, 1H), 4.89 (dd, J=25.4, 12.5 Hz, 2H), 6.66 (d, J=8.3 Hz, 2H), 6.75-7.23 (m, 10H). $^{13}$C NMR (75 MHz, CDCl$_3$) δ 17.2, 25.0, 25.6, 29.3, 37.1, 39.1, 45.8, 48.4, 65.8, 66.4, 68.2, 77.9, 110.1, 114.5, 128.7, 128.8, 128.8, 129.5, 132.5, 139.7, 151.4, 158.4, 167.1, 169.2. MS [M]− 576 g/mol.

Example 169

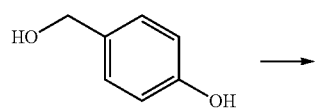

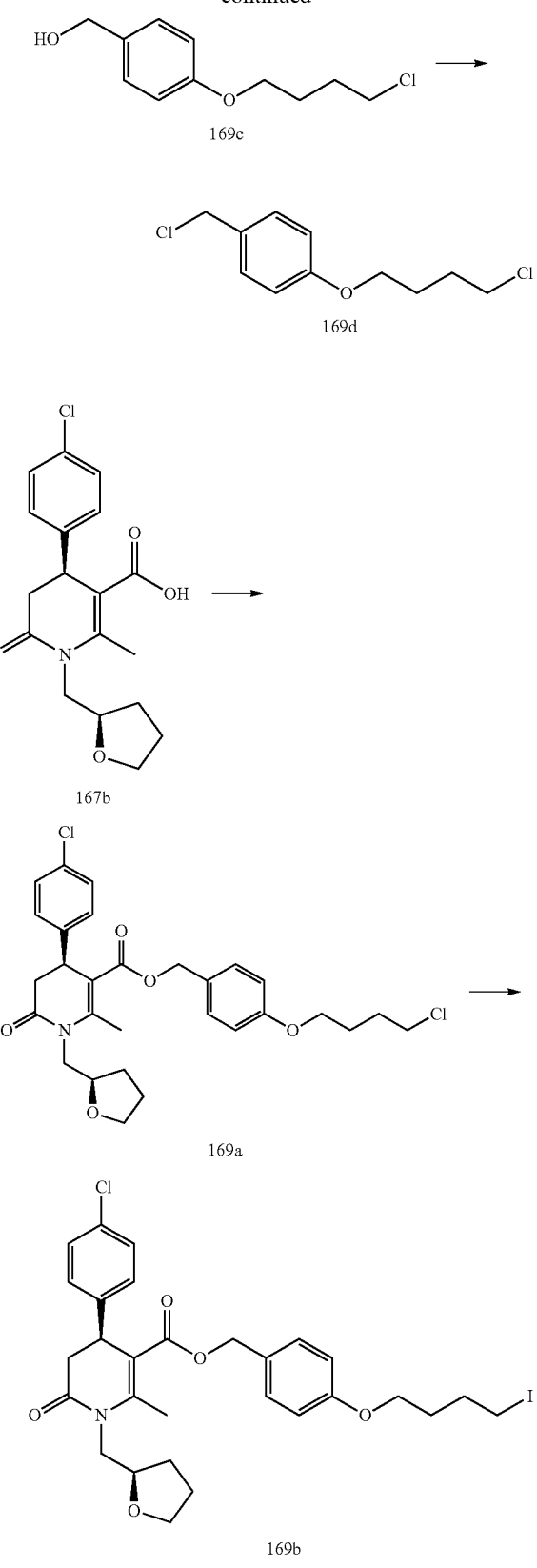

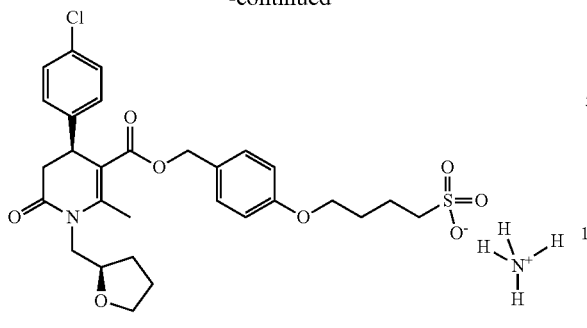

169

Example 169c.
[4-(4-Chlorobutoxy)phenyl]methanol

The mixture of 1-bromo-4-chloro-butane (1.67 mL, 14.5 mmol), 4-(hydroxymethyl)phenol (600 mg, 4.83 mmol) and potassium carbonate (668 mg, 4.83 mmol) were added in acetonitrile (16 mL) and the reaction was stirred overnight at 50° C. Little formation of product observed by TLC (CH$_2$Cl$_2$/MeOH: 98/2) and LCMS. 3 equivalents of reactant and base were added and the reaction stirred under reflux overnight. Reaction finished. The solvent was removed under reduced pressure. The crude was dissolved in EtOAc and washed by water. The aqueous phase was extracted by EtOAc and the organic phase washed with brine, dried over MgSO$_4$. The solvents were removed under reduced pressure and the crude product was purified by flash chromatography (Cy/EA 100/0 to 75/25) to afford the desired compound as an oil (m=1 g, 96%). $^1$H NMR (300 MHz, CDCl$_3$) δ 1.88 (s, 1H), 1.90-2.10 (m, 4H), 3.63 (t, J=6.3 Hz, 2H), 4.00 (t, J=5.8 Hz, 2H), 4.60 (s, 2H), 6.88 (d, J=8.7 Hz, 2H), 7.28 (d, J=8.7 Hz, 2H).

Example 169d.
1-(4-Chlorobutoxy)-4-(chloromethyl)benzene

The thionyl chloride (0.13 mL, 1.75 mmol) was added to benzotriazole (250 mg, 2.1 mmol). The resulting mixture was dissolved in CH$_2$Cl$_2$ (5 mL). After 5 min, this solution was added slowly to the solution of the alcohol 167a (300 mg, 1.4 mmol) in CH$_2$Cl$_2$ (10 mL). The benzotriazole salt started to precipitate. After 20 min of reaction, the salt was filtered. The organic phase was washed by water and NaOH solution (0.05 M). The organic phase was dried over MgSO$_4$ and the solvent was removed under reduced pressure to give the desired chlorinated compound as yellow oil (m=306 mg, 94%). $^1$H NMR (300 MHz, CDCl$_3$) δ 1.87-2.08 (m, 4H), 3.62 (t, J=6.2 Hz, 2H), 4.00 (t, J=5.7 Hz, 2H), 4.57 (s, 2H), 6.88 (d, J=8.7 Hz, 2H), 7.32 (d, J=8.7 Hz, 2H).

Example 169a. [4-(4-Chlorobutoxy)phenyl]methyl-(4S)-4-(4-chlorophenyl)-6-methyl-2-oxo-1-[[(2R)-tetrahydrofuran-2-yl]methyl]-3,4-dihydropyridine-5-carboxylate The acid 167b (60 mg, 0.17 mmol) and cesium carbonate (84 mg, 0.26 mmol) were dissolved in dry DMF (2 mL). The chlorinated compound 169d (60 mg, 0.26 mmol) was added.

The reaction mixture was stirred at r.t. for 24 h. The solvent was removed under reduced pressure. The residue was dissolved in EtOAc and washed with water. The aqueous phase was extracted by EtOAc. The organic layers were assembled, washed with brine and dried over MgSO$_4$. The residue was purified by flash chromatography (CH$_2$Cl$_2$) to afford the desired product as a colorless oil (m=54 mg, 58%). $^1$H NMR (300 MHz, CDCl$_3$) b 1.33-1.55 (m, 1H), 1.75-2.07 (m, 7H), 2.60 (s, 3H), 2.67 (dd, J=15.6, 2.2 Hz, 1H), 2.88 (dd, J=15.6, 7.4 Hz, 1H), 3.40 (dd, J=14.3, 8.7 Hz, 1H), 3.62 (t, J=6.2 Hz, 2H), 3.67-3.94 (m, 3H), 3.98 (t, J=5.7 Hz, 2H), 4.16 (d, J=5.8 Hz, 1H), 4.24 (dd, J=14.3, 3.3 Hz, 1H), 5.01 (s, 2H), 6.77 (d, J=8.7 Hz, 2H), 7.03 (d, J=8.7 Hz, 2H), 7.09-7.23 (m, 4H). MS [M+H]$^+$ 546 g/mol.

Example 169b. [4-(4-Iodobutoxy)phenyl]methyl-(4S)-4-(4-chlorophenyl)-6-methyl-2-oxo-1-[[(2R)-tetrahydrofuran-2-yl]methyl]-3,4-dihydropyridine-5-carboxylate The chlorinated compound 169a (54 mg, 0.1 mmol) was dissolved in butanone (3 mL). NaI (59 mg, 0.4 mmol) was added and the reaction mixture stirred at 80° C. overnight. The solution was cooled to r.t., filtered and the precipitate was washed by acetone. The solvents were removed under reduced pressure to afford yellowish oil. This residue was purified by flash chromatography (CH$_2$Cl$_2$) to give the desired product as oil (m=49 mg, 78%). $^1$H NMR (300 MHz, CDCl$_3$) δ 1.40-1.55 (m, 1H), 1.76-2.11 (m, 7H), 2.60 (s, 3H), 2.67 (dd, J=15.6, 2.2 Hz, 1H), 2.88 (dd, J=15.6, 7.4 Hz, 1H), 3.26 (t, J=6.8 Hz, 2H), 3.40 (dd, J=14.3, 8.7 Hz, 1H), 3.70-3.92 (m, 3H), 3.96 (t, J=6.0 Hz, 2H), 4.16 (d, J=5.8 Hz, 1H), 4.24 (dd, J=14.3, 3.3 Hz, 1H), 5.01 (s, 2H), 6.77 (d, J=8.6 Hz, 2H), 7.03 (d, J=8.6 Hz, 2H), 7.09-7.23 (m, 4H). MS [M+H]$^-$ 638 g/mol.

Example 169. Ammonium; 4-[4-[[(4S)-4-(4-chlorophenyl)-6-methyl-2-oxo-1-[[(2R)-tetrahydrofuran-2-yl]methyl]-3,4-dihydropyridine-5-carbonyl]oxymethyl]phenoxy]butane-1-sulfonate The iodide compound 169b (49 mg, 0.077 mmol) was dissolved in a mixture of iPrOH/water 1/1 (1 mL). Sodium sulfite (19 mg, 0.154 mmol) was added and the reaction mixture was heated at 80° C. in sealed tube for 18 h. The solvents were removed under reduced pressure. Purification of the crude by HPLC (basic conditions) gave the expected product as a yellow powder (m=40 mg, 85%). $^1$H NMR (300 MHz, CDCl$_3$) δ 1.30-1.52 (m, 1H), 1.65-1.99 (m, 7H), 2.48-2.69 (m, 4H), 2.73-3.02 (m, 3H), 3.36 (dd, J=14.2, 8.7 Hz, 1H), 3.61-3.91 (m, 5H), 4.04-4.27 (m, 2H), 4.92 (dd, J=23.7, 12.4 Hz, 2H), 6.48-7.64 (m, 12H). $^{13}$C NMR (75 MHz, CDCl$_3$) δ 17.2, 21.6, 25.6, 28.3, 29.3, 37.1, 39.1, 45.8, 51.2, 65.9, 67.4, 68.2, 77.9, 110.2, 114.4, 128.5, 128.8, 128.7, 129.6, 132.6, 139.7, 151.4, 158.7, 167.1, 169.1. MS [M]$^-$ 590 g/mol.

BIOLOGY EXAMPLES

TGR5/CRE Luciferase Assay

In the following Tables TGR5 activation by compounds of the invention and subsequent increase in intracellular cAMP were evaluated using a luciferase reporter gene assay. Human embryonic kidney (HEK) 293 cells were transiently co-transfected with pCMV tag4b-TGR5 h (to follow hTGR5 activation) or pCMV AC6-TGR5m (to follow mTGR5 activation) expression plasmids and the pCRE TA-Luciferase reporter plasmid using the JET PEI reagent (Polyplus transfection). Transfected cells were seeded in 96-well plates and incubated overnight with the test compounds at increasing concentrations tested in duplicate. Lithocolic acid (LCA) at 10 μM was used as a positive reference compound. The cAMP-dependent luciferase expression was followed using the BrightGlo reagent according to the manufacturer (Promega) instructions. Luminescence was read with a Mithras plate reader (Berthold) or a Victor3™ V1420 (Perkin Elmer). Data were expressed as percentage of the 10 μM LCA value and $EC_{50}$ values were calculated using XL fit 5 software or GraphPad Prism 5. Concentration-response curves were fitted by a nonlinear regression analysis to a 4 parameter logistic equation The results of the TGR5/CRE Luciferase assay are presented in Table 14 herafter.

TABLE 14

| Example | hTGR5 $EC_{50}$ (μM) | hTGR5 % trans | mTGR5 $EC_{50}$ (μM) | mTGR5 % trans |
|---|---|---|---|---|
| 3 | 7.4 | 65 | 10.4 | 45 |
| 4 | 10 | 17 | 8.5 | 18 |
| 5 | 10.6 | 31 | 11.1 | 34 |
| 6 | 12.8 | 19 | NC | 11 |
| 7 | 5.0 | 22 | NC | 14 |
| 9 | 1.5 | 48 | 1.4 | 37 |
| 11 | 4.5 | 17 | NC | 10 |
| 12 | 1.9 | 68 | 4.5 | 52 |
| 13 | 2.6 | 40 | 4.2 | 37 |
| 14 | 7.6 | 30 | 10.3 | 18 |
| 15 | 3.9 | 49 | — | — |
| 16 | 1.5 | 47 | 1.7 | 21 |
| 17 | 0.6 | 72 | 1.4 | 67 |
| 18 | 1.4 | 34 | 1.2 | 43 |
| 20 | 3.0 | 42 | 2.5 | 53 |
| 22 | 3.51 | 36 | 4.3 | 44 |
| 24 | 1.45 | 60 | 5.8 | 34 |
| 25 | 1.22 | 43 | 0.5 | 36 |
| 26 | 4.6 | 10 | 1.8 | 20 |
| 29 | 1.26 | 59 | 1.5 | 37 |
| 30 | 1.5 | 16 | 3.9 | 12 |
| 32 | 0.6 | 77 | 1.1 | 55 |
| 33 | 6.4 | 42 | 11 | 14 |
| 33a | 39 | 37 | 1.1 | 16 |
| 34 | 0.6 | 73 | 0.8 | 70 |
| 35 | 0.6 | 89 | 0.8 | 76 |
| 36 | 0.6 | 54 | 1.1 | 63 |
| 37 | 0.3 | 75 | 0.6 | 78 |
| 38 | 1.1 | 75 | 1.5 | 54 |
| 39 | 1.3 | 82 | 1.4 | 73 |
| 40 | 0.9 | 81 | 0.9 | 76 |
| 41 | 1.3 | 55 | 1.2 | 55 |
| 43 | 0.3 | 75 | 0.3 | 78 |
| 44 | 0.3 | 59 | 0.4 | 77 |
| 47 | 6.6 | 22 | NC | 0 |
| 48 | 12 | 13 | NC | 0 |
| 49 | 0.7 | 63 | 1.0 | 60 |
| 50 | 1.7 | 100 | 3.6 | 77 |
| 52 | 2.5 | 18 | NC | 0 |
| 53 | 4.3 | 16 | NC | 0 |
| 54 | 4.2 | 10 | NC | 0 |
| 55 | 4.5 | 47 | NC | 5 |
| 56 | 3.6 | 50 | NC | 3 |
| 57 | 0.1 | 95 | 0.2 | 95 |
| 58 | 1.34 | 50 | 0.42 | 70 |
| 59 | 1.1 | 21 | 12.4 | 18 |
| 60 | 13.5 | 42 | 14.4 | 32 |
| 62 | 2.3 | 69 | 5.9 | 42 |
| 63 | 2.2 | 50 | 2.0 | 57 |
| 64 | 0.1 | 82 | 0.2 | 100 |
| 65 | 0.1 | 91 | 0.3 | 107 |
| 66 | 0.2 | 62 | 0.1 | 78 |

TABLE 14-continued

| Example | hTGR5 $EC_{50}$ (μM) | hTGR5 % trans | mTGR5 $EC_{50}$ (μM) | mTGR5 % trans |
|---|---|---|---|---|
| 67 | 0.02 | 101 | 0.03 | 92 |
| 68 | 0.2 | 82 | 0.2 | 82 |
| 69 | 0.3 | 105 | 0.4 | 104 |
| 70 | 0.07 | 65 | 0.08 | 102 |
| 71 | 0.2 | 94 | 0.8 | 85 |
| 72 | 0.08 | 99 | 0.2 | 92 |
| 73 | 0.02 | 99 | 0.03 | 93 |
| 75 | 7.8 | 34 | 18.3 | 25 |
| 77 | 2.9 | 71 | 12.3 | 73 |
| 79 | 0.7 | 80 | 0.7 | 73 |
| 80 | 1.5 | 60 | 1.4 | 67 |
| 81 | 0.5 | 86 | 1.3 | 62 |
| 82 | 0.7 | 74 | 1.5 | 59 |
| 83 | 1.2 | 69 | 0.4 | 88 |
| 84 | 0.4 | 71 | 0.5 | 71 |
| 85 | 0.5 | 78 | 0.7 | 82 |
| 86 | 0.4 | 71 | 0.4 | 82 |
| 87 | 0.5 | 67 | 0.8 | 70 |
| 88 | 0.2 | 75 | 0.4 | 91 |
| 89 | 0.4 | 65 | 0.3 | 84 |
| 90 | 1.1 | 57 | 1.3 | 34 |
| 91 | 0.5 | 78 | 0.7 | 83 |
| 92 | 0.6 | 56 | 0.3 | 59 |
| 93 | 0.6 | 58 | 0.8 | 53 |
| 94 | 0.6 | 61 | 0.4 | 65 |
| 95 | 0.2 | 78 | 0.3 | 76 |
| 96 | 1.1 | 63 | 0.6 | 83 |
| 97 | 0.4 | 76 | 0.4 | 76 |
| 98 | 0.3 | 91 | 0.5 | 86 |
| 99 | 0.2 | 84 | 0.3 | 67 |
| 100 | 0.6 | 72 | 0.4 | 89 |
| 101 | 0.2 | 75 | 0.2 | 84 |
| 103 | 0.5 | 85 | 0.4 | 95 |
| 104 | 0.2 | 71 | 0.2 | 85 |
| 105 | 0.4 | 87 | 0.8 | 63 |
| 106 | 0.4 | 83 | 0.2 | 96 |
| 107 | 1.2 | 71 | 0.6 | 83 |
| 108 | 0.5 | 72 | 0.6 | 72 |
| 110 | 2.3 | 50 | 1.6 | 42 |
| 111 | 1.1 | 55 | 0.8 | 72 |
| 112 | 5.2 | 20 | 3.2 | 46 |
| 113 | 1.1 | 57 | 1.1 | 56 |
| 116 | 1.4 | 76 | 1.6 | 82 |
| 117 | 1.6 | 74 | 4.2 | 77 |
| 119 | 0.1 | 85 | 0.1 | 83 |
| 121 | 1.1 | 51 | 1.2 | 49 |
| 123 | 1.4 | 17 | 2.8 | 10 |
| 125 | 0.2 | 86 | 0.2 | 100 |
| 127 | 0.1 | 89 | 0.1 | 109 |
| 129 | 0.4 | 89 | 0.9 | 81 |
| 133 | 8.6 | 72 | 4.9 | 83 |
| 136 | 0.02 | 93 | 0.04 | 111 |
| 137 | 0.38 | 70 | 0.93 | 40 |
| 138 | 0.38 | 70 | 1.11 | 36 |
| 141 | 0.22 | 67 | 0.32 | 106 |
| 144 | 0.06 | 95 | 0.10 | 158 |
| 145 | 1.00 | 72 | 2.50 | 74 |
| 146 | 0.35 | 78 | 0.45 | 77 |
| 147 | 0.19 | 77 | 0.45 | 112 |
| 148 | 0.001 | 103 | 0.002 | 104 |
| 149 | 0.02 | 91 | 0.07 | 89 |
| 150 | 0.025 | 110 | 0.1 | 99 |
| 151 | 2.2 | 87 | 12.5 | 44 |
| 152 | 0.03 | 106 | 0.048 | 66 |
| 153 | 0.13 | 101 | 0.13 | 102 |
| 154 | 0.17 | 105 | 0.22 | 104 |
| 155 | 1.0 | 102 | 0.98 | 102 |
| 156 | 0.12 | 107 | 0.67 | 91 |
| 157 | 7.9 | 60 | 4.6 | 34 |
| 158 | 3.6 | 74 | 1.3 | 97 |
| 159 | 0.037 | 107 | 0.036 | 104 |
| 160 | 0.29 | 90 | 0.50 | 93 |
| 161 | 2.6 | 80 | 13 | 92 |
| 162 | 0.32 | 92 | 0.32 | 86 |
| 163 | 0.017 | 105 | 0.011 | 102 |
| 164 | 0.001 | 120 | 0.004 | 96 |

TABLE 14-continued

| Example | hTGR5 EC$_{50}$ (μM) | % trans | mTGR5 EC$_{50}$ (μM) | % trans |
|---|---|---|---|---|
| 165 | 0.13 | 99 | 0.40 | 71 |
| 166 | 0.16 | 103 | 0.10 | 113 |
| 167 | 0.008 | 103 | 0.018 | 92 |
| 168 | 0.065 | 106 | 0.026 | 120 |
| 169 | 0.03 | 103 | 0.009 | 103 |

NC: not calculated

The invention claimed is:

1. A compound of general Formula I:

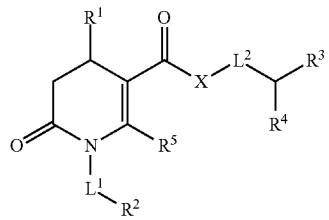

I or pharmaceutically acceptable salts or solvates thereof, wherein

R$^1$ is C1-C6-alkyl, aryl or heteroaryl, wherein said aryl moiety is independently substituted by one or more groups selected from the group consisting of halo, cyano, C1-C2-alkyl, C1-C2-alkoxy, C1-C2-haloalkyl, and 5- or 6-membered aryl, and said heteroaryl moiety is optionally independently substituted by one or more groups selected from the group consisting of halo, cyano, C1-C2-alkyl, C1-C2-alkoxy, C1-C2-haloalkyl, and 5- or 6-membered aryl;

L$^1$ is a single bond or (CH$_2$)$_n$, wherein n is 1, 2 or 3;

R$^2$ is C1-C4 alkyl, alkynyl, alkoxy, hydroxy, hydroxycarbonyl, alkoxycarbonyl, carbamoyl, aminoalkyl, alkylaminoalkyl, dialkylaminoalkyl, alkoxycarbonylamino, cyano, B alkylsulfonyl, aralkyl, cycloalkyl, heterocyclyl or heteroaryl, wherein said heterocyclyl moiety is optionally substituted by one or more substituents independently selected from the group consisting of alkyl and alkoxycarbonyl, and said heteroaryl moiety is optionally substituted by one or more C1-C2-alkyl;

L$^2$ is a single bond or (CH$_2$)$_n$, wherein n is 1 or 2;

R$^3$ is aryl, heteroaryl, cycloalkyl or arylcarbonyl wherein each of said moieties is optionally substituted by one or more substituents independently selected from the group consisting of halo, alkyl, haloalkyl, aryl, cyano, alkoxy, haloalkoxy, alkoxycarbonyl, aminoalkoxy, alkylaminoalkoxy, dialkylaminoalkoxy, HO$_3$S-alkoxy, wherein m is 1 to 500,

[N(R$^8$)$_3$-alkoxy]$^+$ Q$^-$, wherein R$^8$ is linear C1-C4-alkyl and Q$^-$ is a counter anion, and a cyclic moiety selected from the group consisting of wherein R$^A$ is H, OH, C0-C4-alkyl-COOH or C1-C6-alkyl, R$^B$ is C1-C6-alkyl optionally substituted with —COOH, R$^C$ is C1-C6-alkyl, and Q$^-$ is a counter anion;

or wherein said cycloalkyl moiety is fused to an aryl, preferably phenyl, moiety;

R$^4$ is H, C1-C2-alkyl or 5- or 6-membered aryl;

R$^5$ is H, C1-C4-alkyl, 5- or 6-membered aryl, or alkoxyalkyl; and

X is O or NR', wherein R' is H, C1-C2-alkyl or R' taken together with L$^2$ and R$^3$ form a 5- or 6-membered heterocyclyl moiety which is optionally fused to an aryl moiety.

2. The compound according to claim 1 having Formula II

II and pharmaceutically acceptable salts and solvates thereof.

3. The compound according to claim 2 having Formula IIa

IIa and pharmaceutically acceptable salts, and solvates thereof, wherein

R⁶ is halo, alkyl, haloalkyl, aryl, cyano, alkoxy, haloalkoxy, alkoxycarbonyl, aminoalkoxy, alkylaminoalkoxy, dialkylaminoalkoxy, HO₃S-alkoxy,

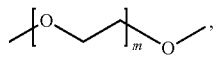

wherein m is 1 to 500,

[N(R⁸)₃-alkoxy]⁺ Q⁻, wherein R⁸ is linear C1-C4-alkyl and Q⁻ is a counter anion, or a cyclic moiety selected from the group consisting of

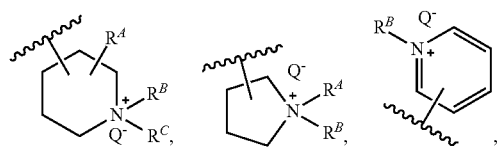

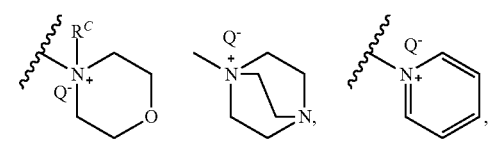

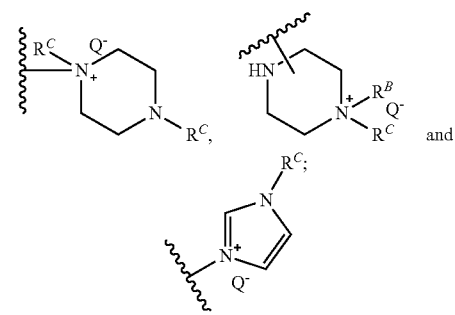

wherein R^A is H, OH, C0-C4-alkyl-COOH or C1-C6-alkyl, R^B is C1-C6-alkyl optionally substituted with —COOH, R^C is C1-C6-alkyl, and Q⁻ is a counter anion.

4. The compound according to claim 1 having Formula III

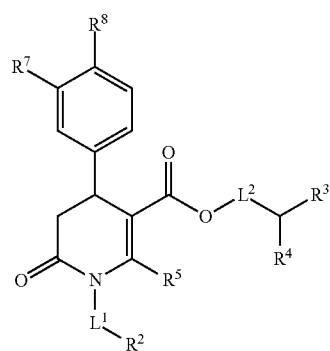

and pharmaceutically acceptable salts, and solvates thereof, wherein

R⁷ and R⁸ are independently selected from the group consisting of H, halo, haloalkyl, and cyano, with the proviso that at least one of R⁷ and R⁸ is not H.

5. The compound according to claim 1 having Formula IV

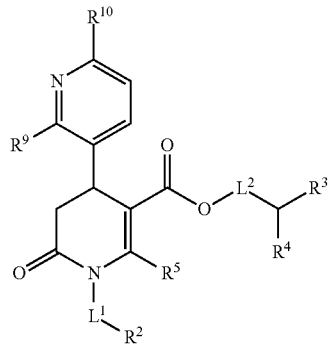

and pharmaceutically acceptable salts, and solvates thereof, wherein

R⁹ and R¹⁰ are independently selected from the group consisting of H, halo, haloalkyl, and cyano, with the proviso that at least one of R⁹ and R¹⁰ is not H.

6. The compound according to claim 1 having Formula V

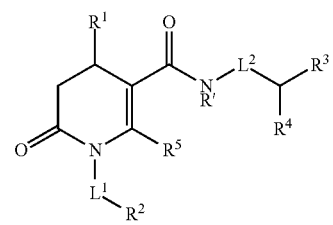

and pharmaceutically acceptable salts, and solvates thereof.

7. The compound according to claim 1 and pharmaceutically acceptable salts, and solvates thereof, wherein R⁵ is methyl.

8. The compound according to claim 1 and pharmaceutically acceptable salts, and solvates thereof, wherein L¹ and R² are taken together to form a moiety selected from the group consisting of cycloalkylmethyl, heterocyclylmethyl, heteroarylmethyl, 2-alkoxyeth-1-yl, 3-alkoxyprop-1-yl, and alkoxycarbonylmethyl, said heteroarylmethyl moiety being optionally substituted by one or more C1-C2 alkyl.

9. The compound according to claim 1 and pharmaceutically acceptable salts, and solvates thereof, wherein R² is tetrahydrofuranyl.

10. The compound according to claim 9 and pharmaceutically acceptable salts, and solvates thereof, wherein L¹ is CH₂.

11. The compound according to claim 1 selected from the group consisting of:

283
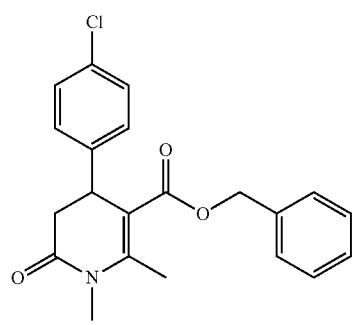
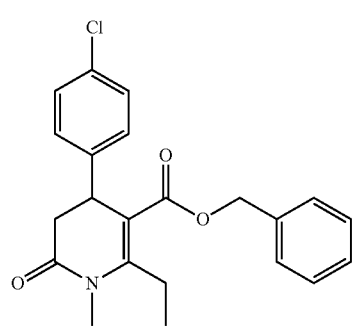
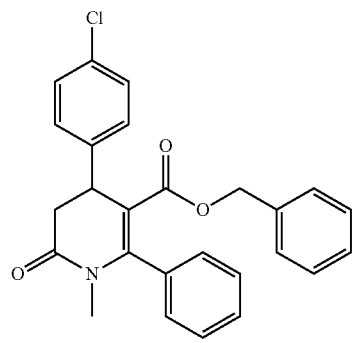
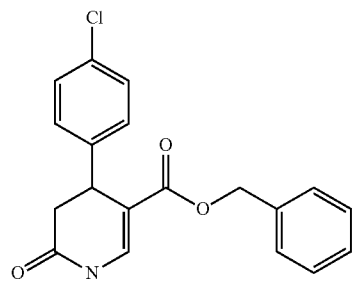
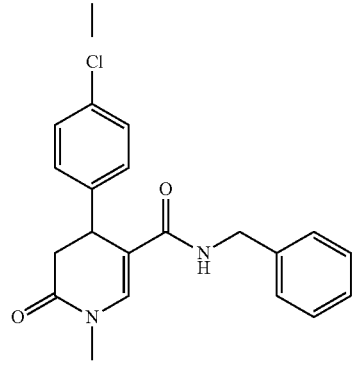
284
-continued
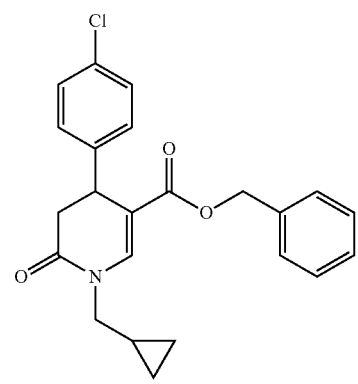
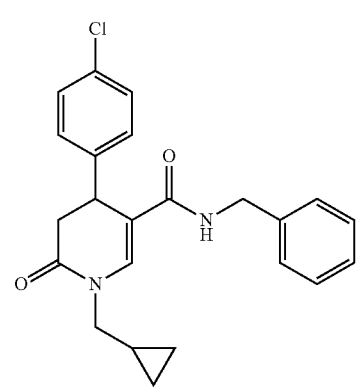
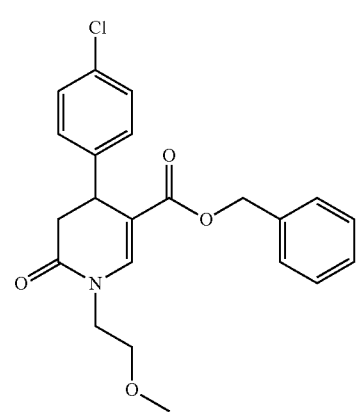
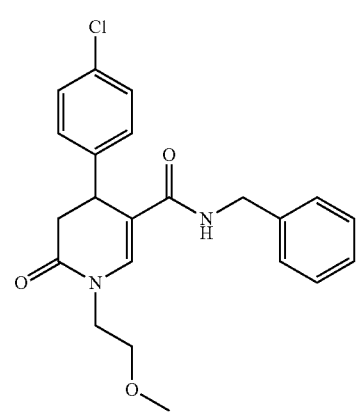

285
-continued
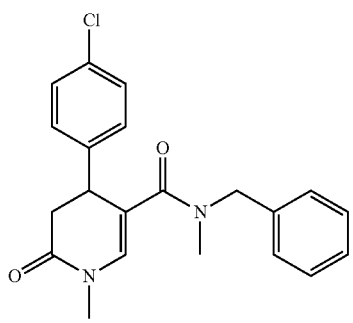
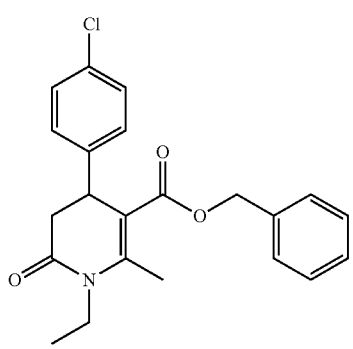
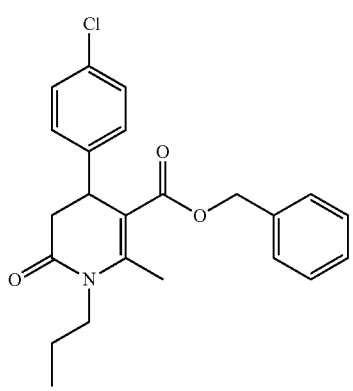
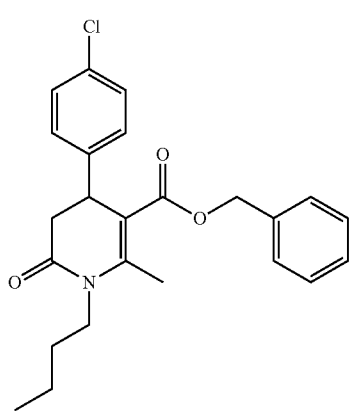
286
-continued
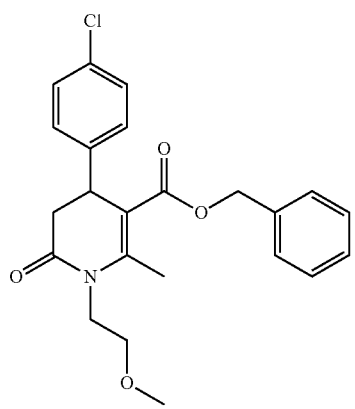
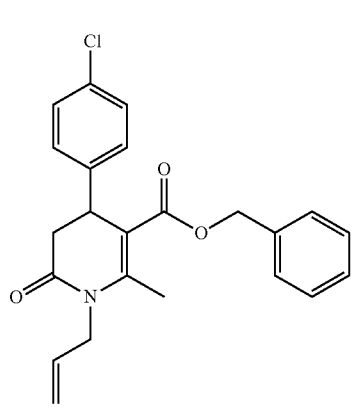
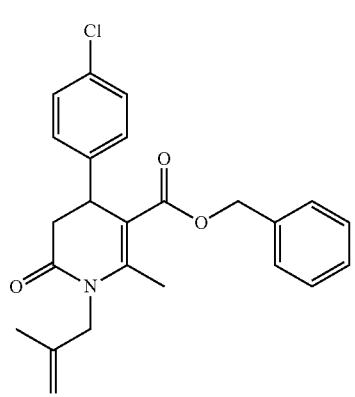
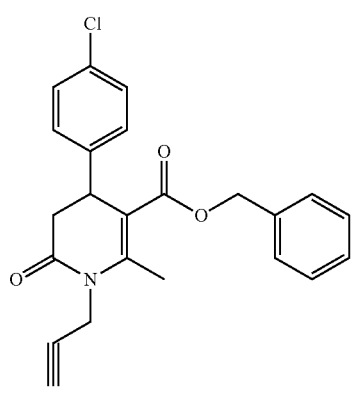

287
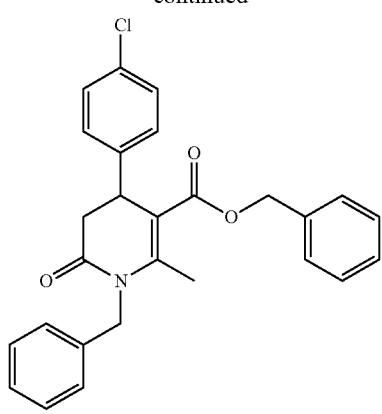
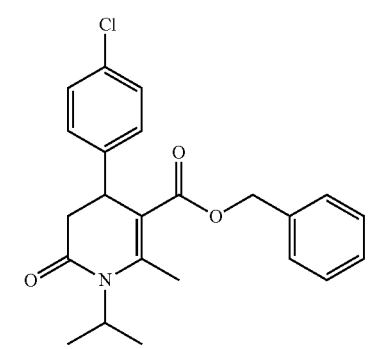
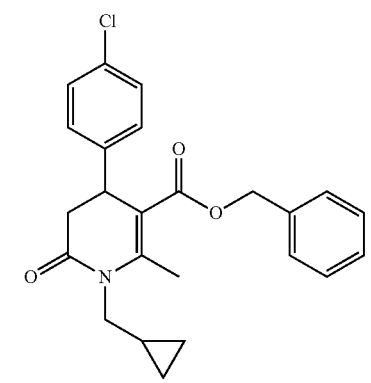
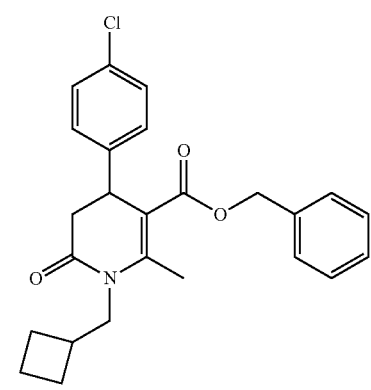
288
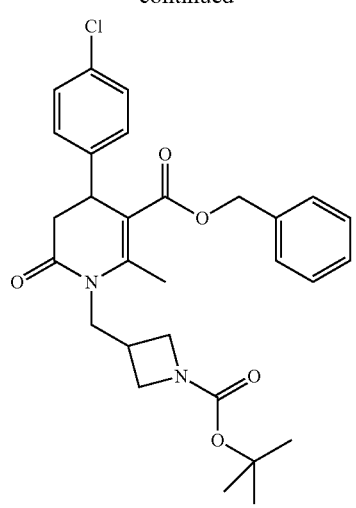
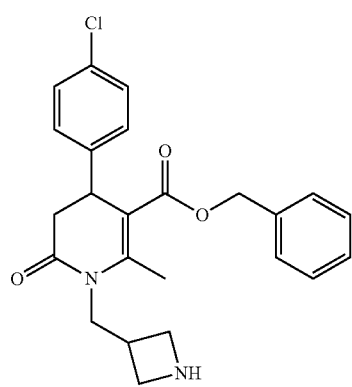
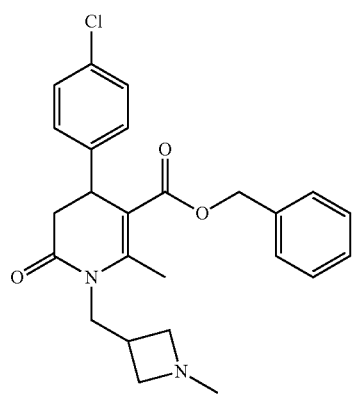
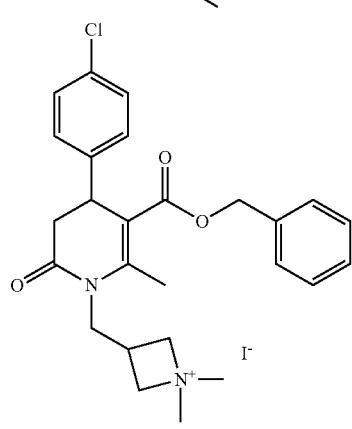

289
-continued
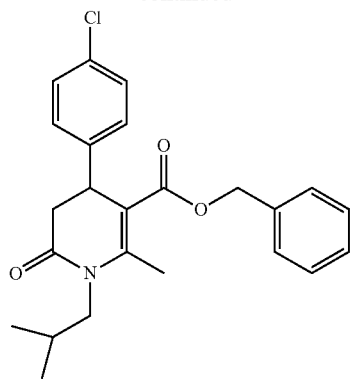
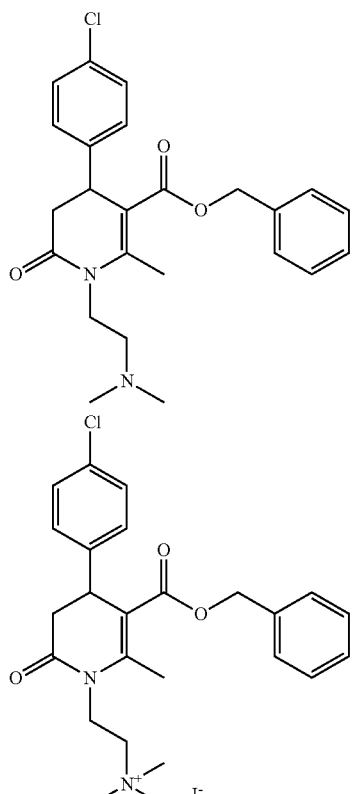
290
-continued
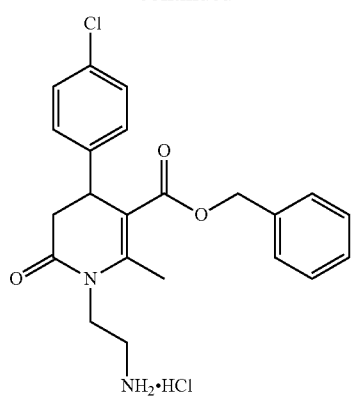
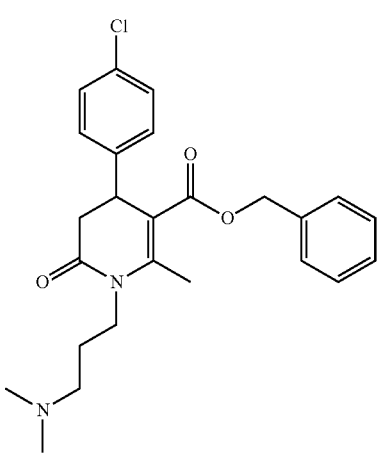
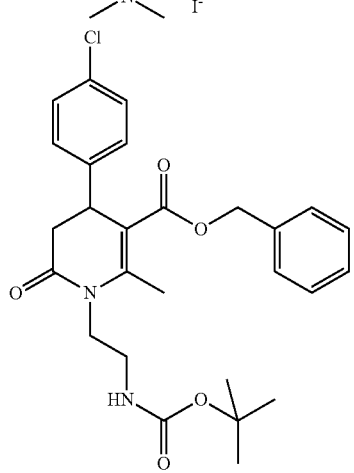
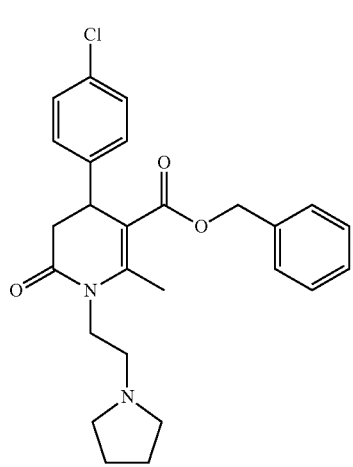

291
-continued
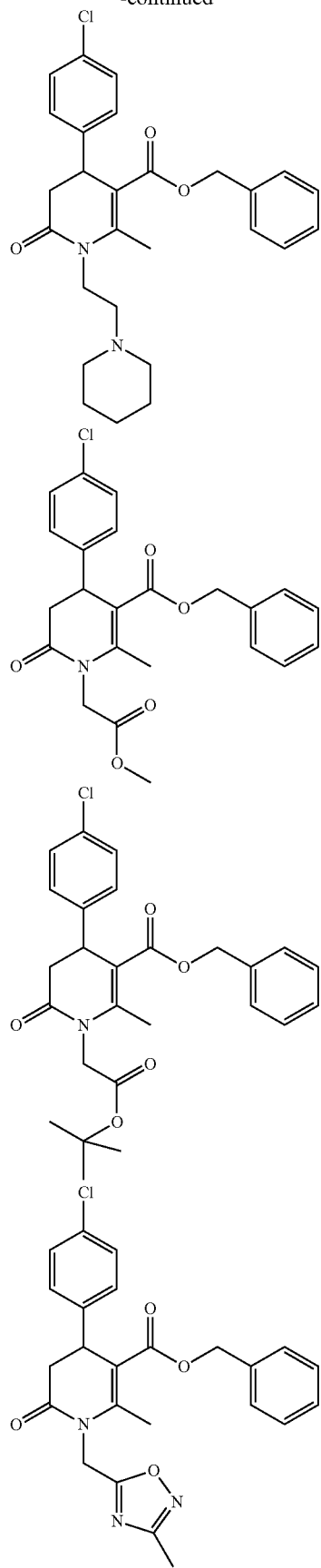
292
-continued
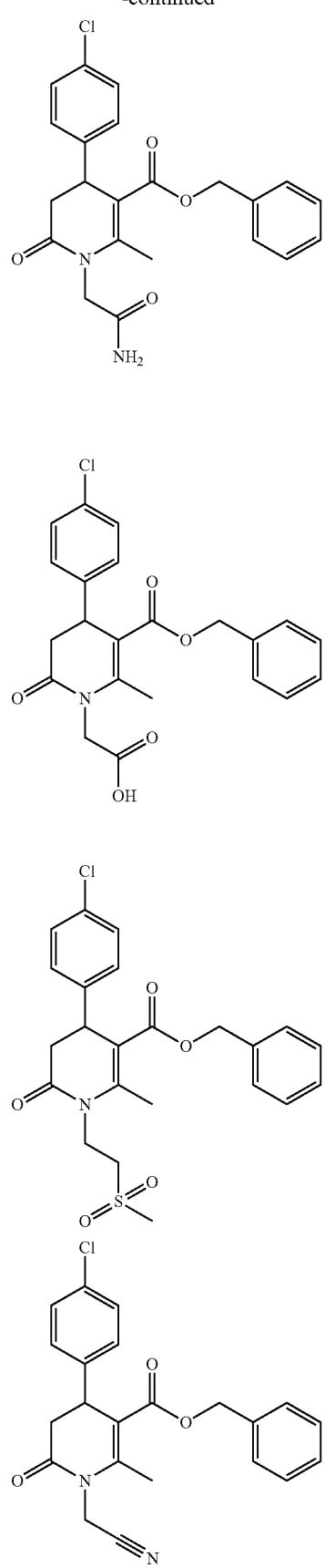

293
-continued
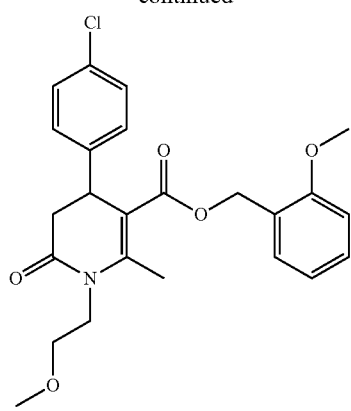
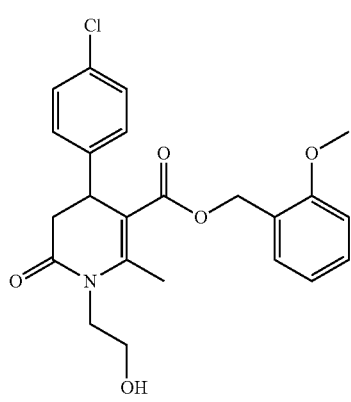
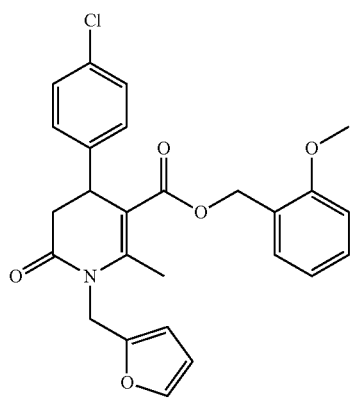
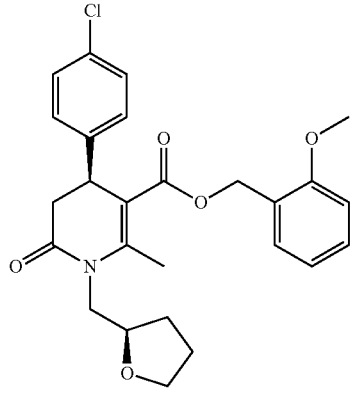
294
-continued
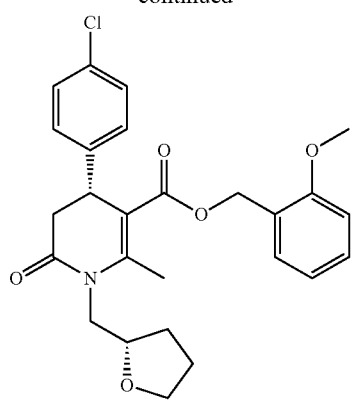
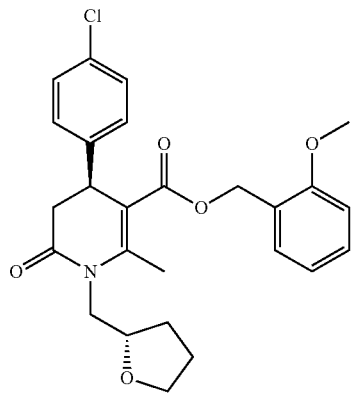
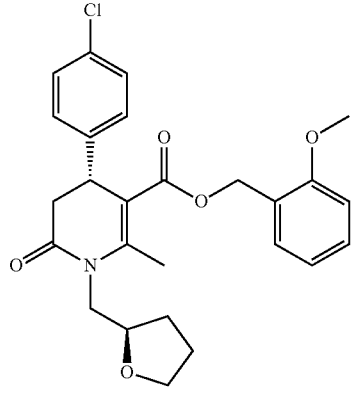
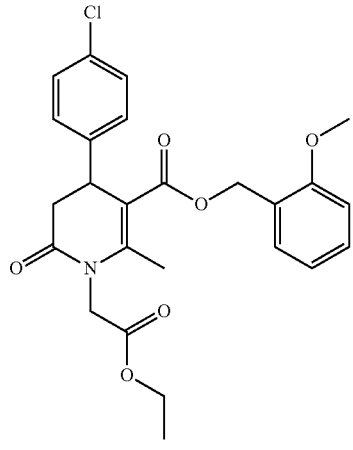

295
-continued
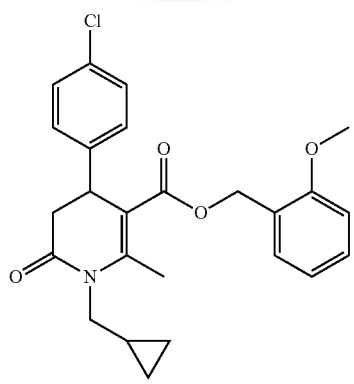
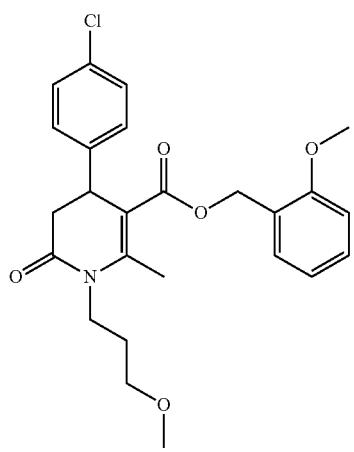
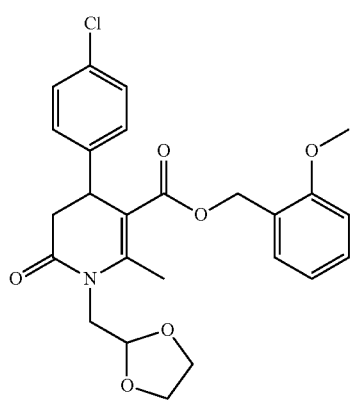
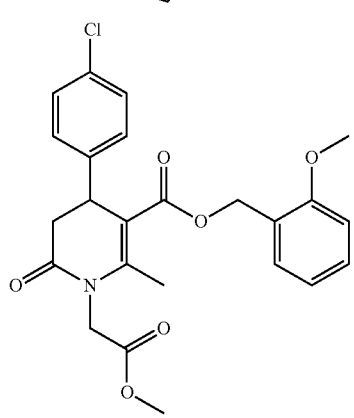
296
-continued
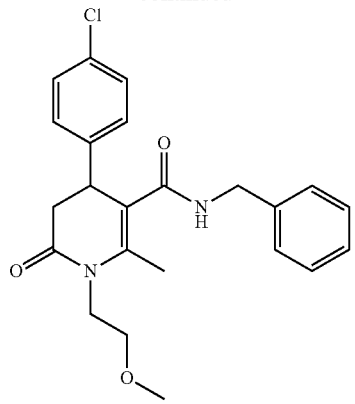
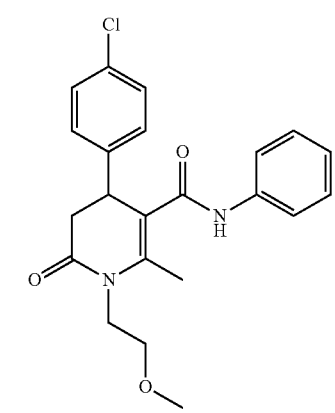
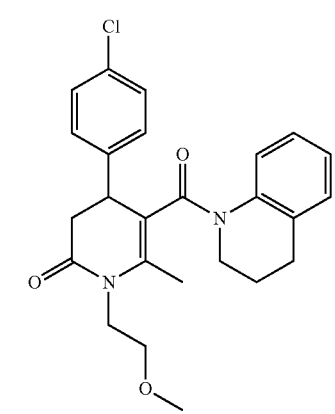
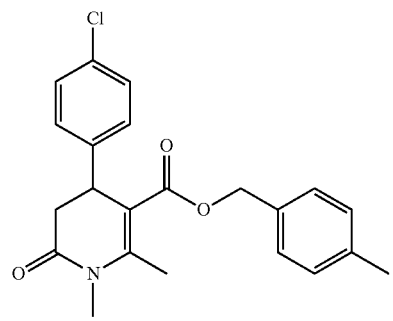

297
-continued
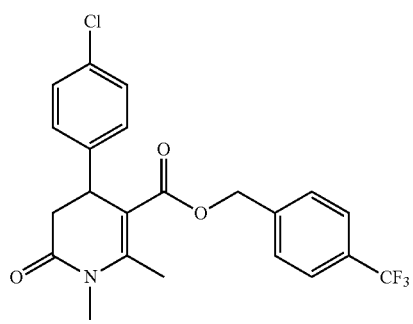
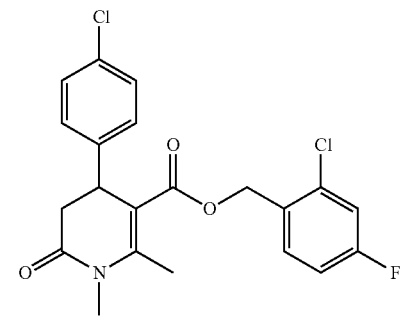
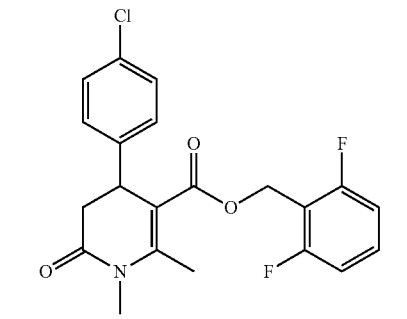
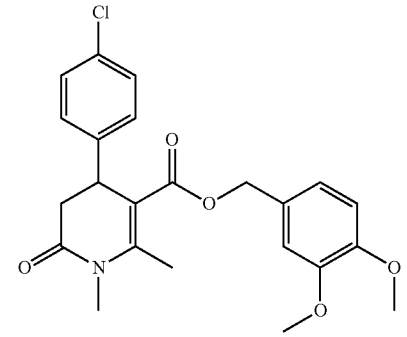
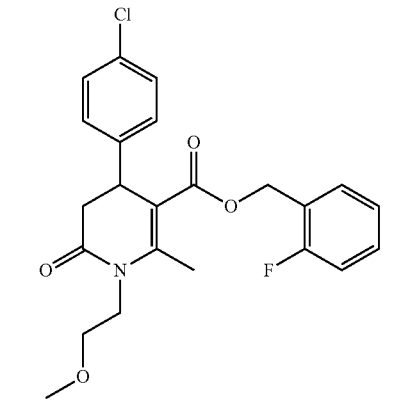
298
-continued
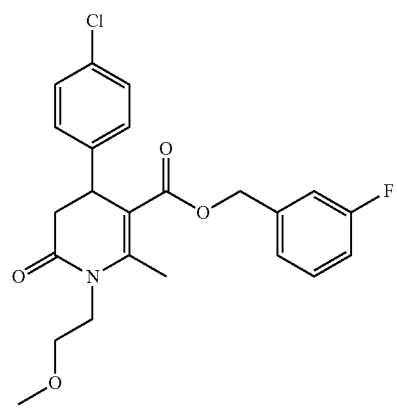
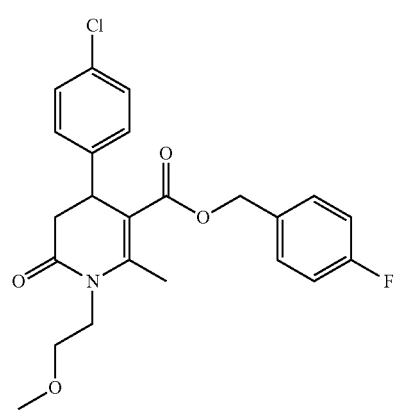
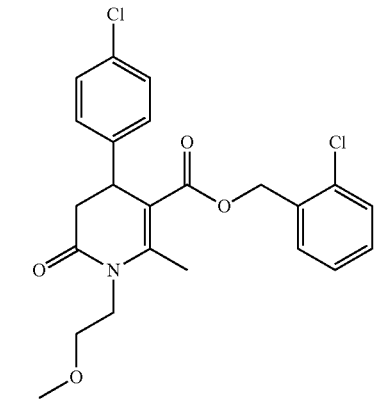
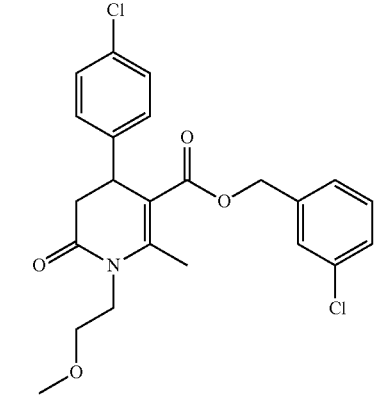

299
-continued
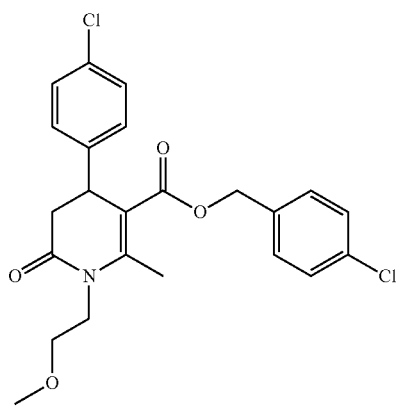
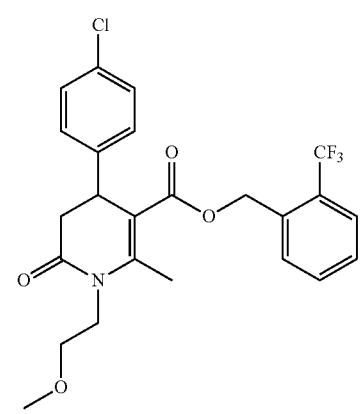
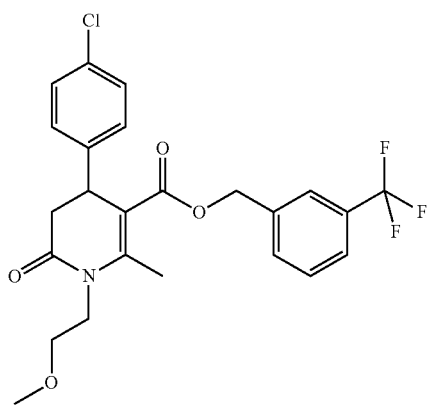
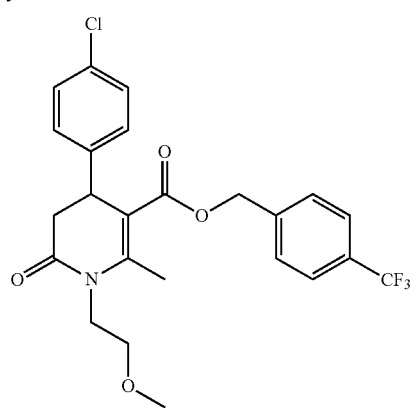
300
-continued
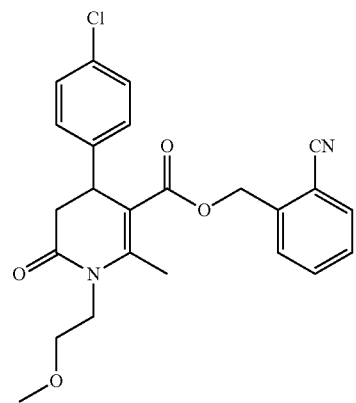
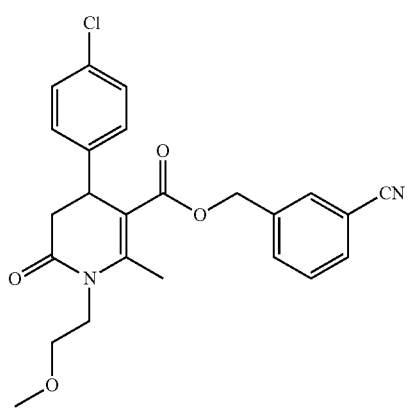
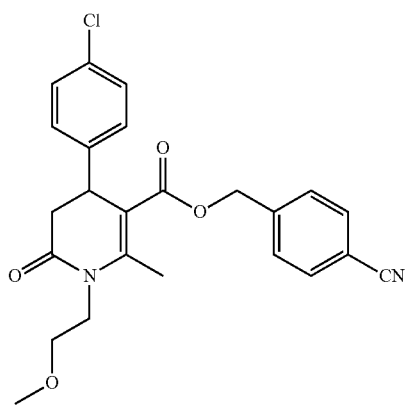
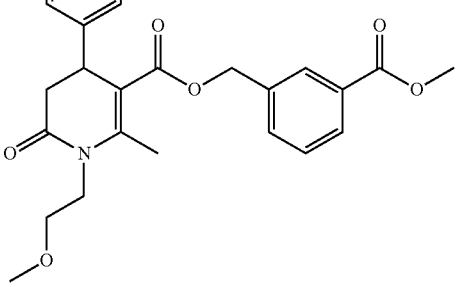

301
-continued
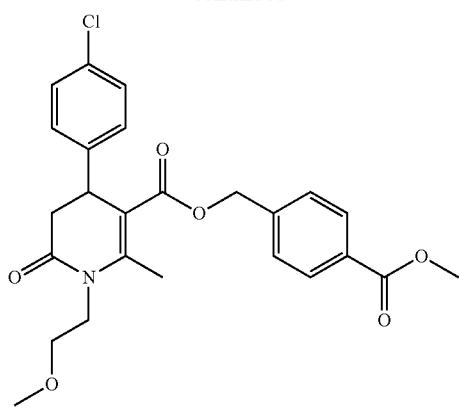
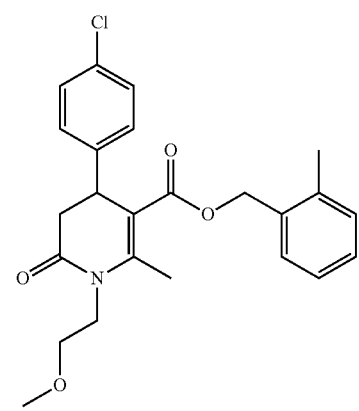
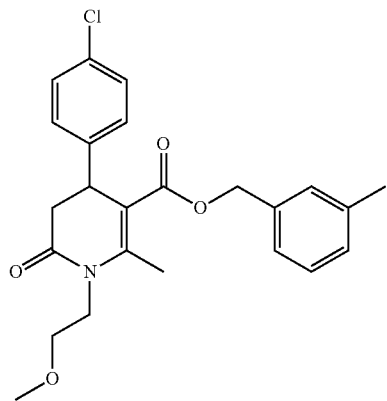
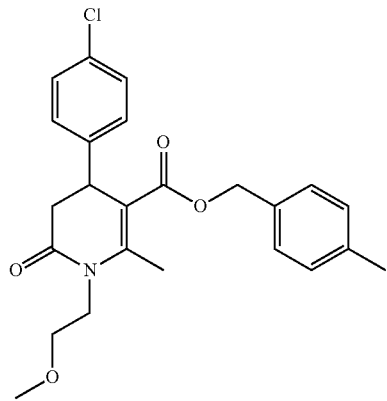
302
-continued
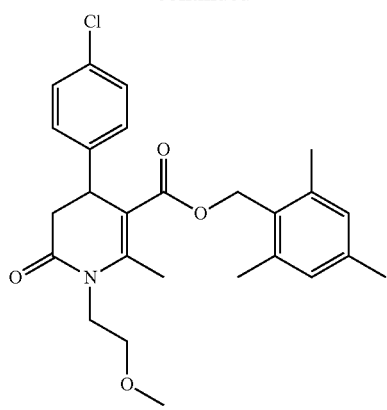
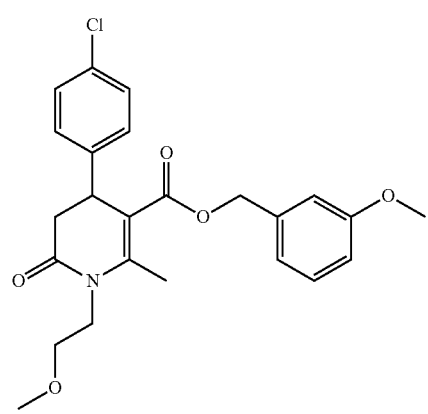
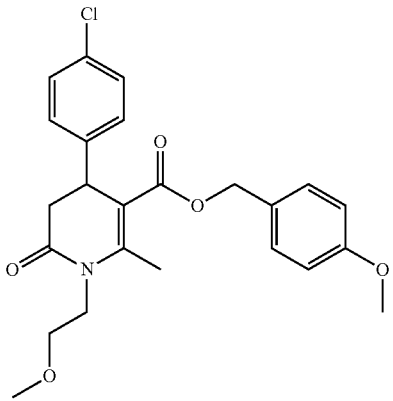
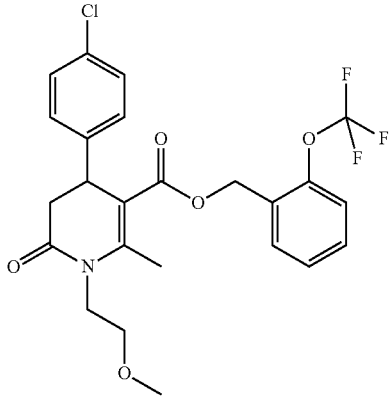

303
-continued
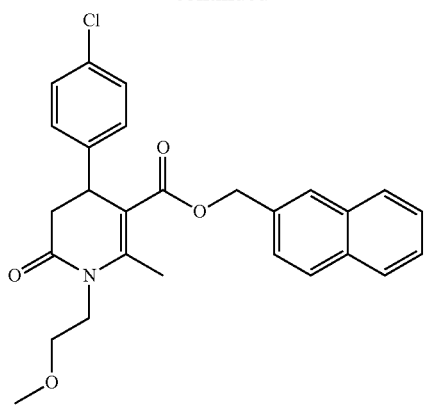
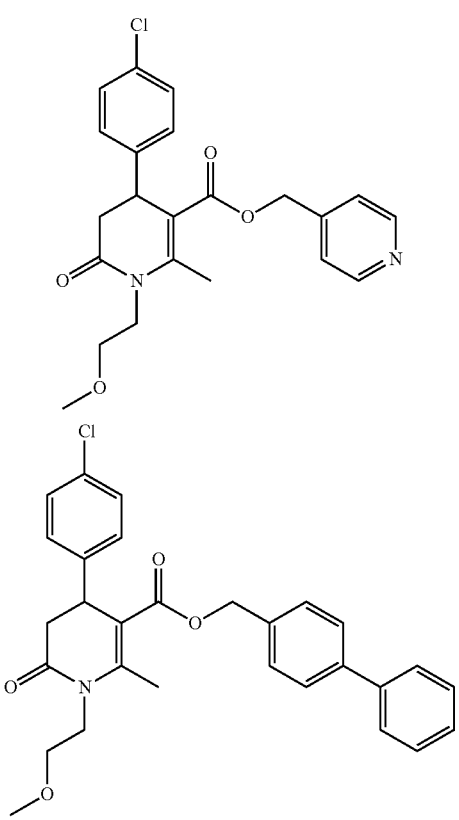
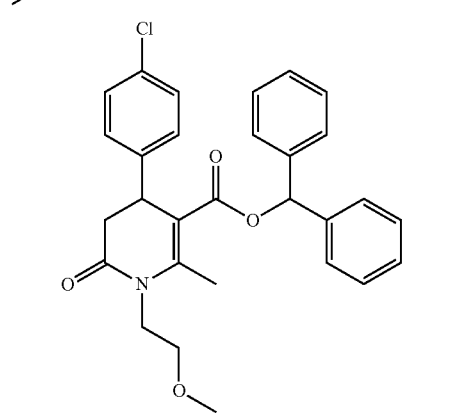
304
-continued
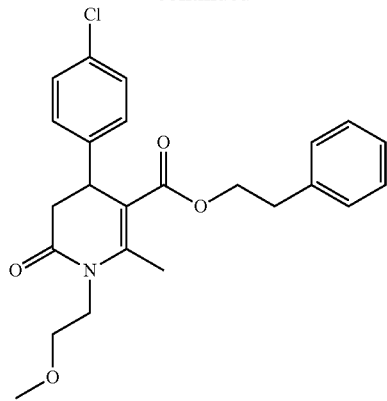
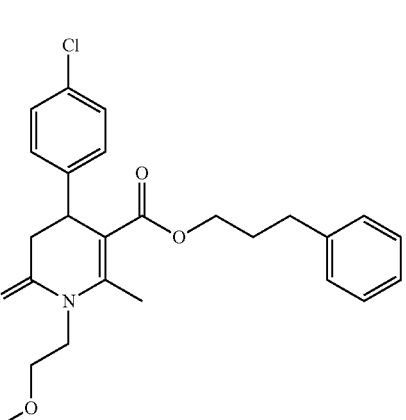
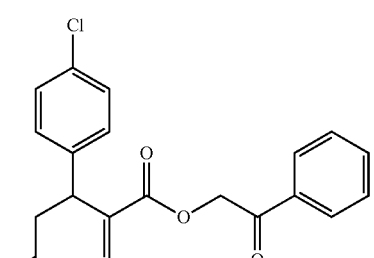
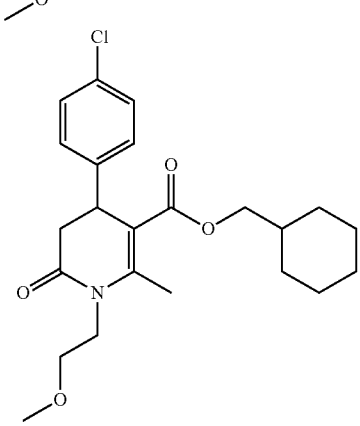

305
-continued
306
-continued
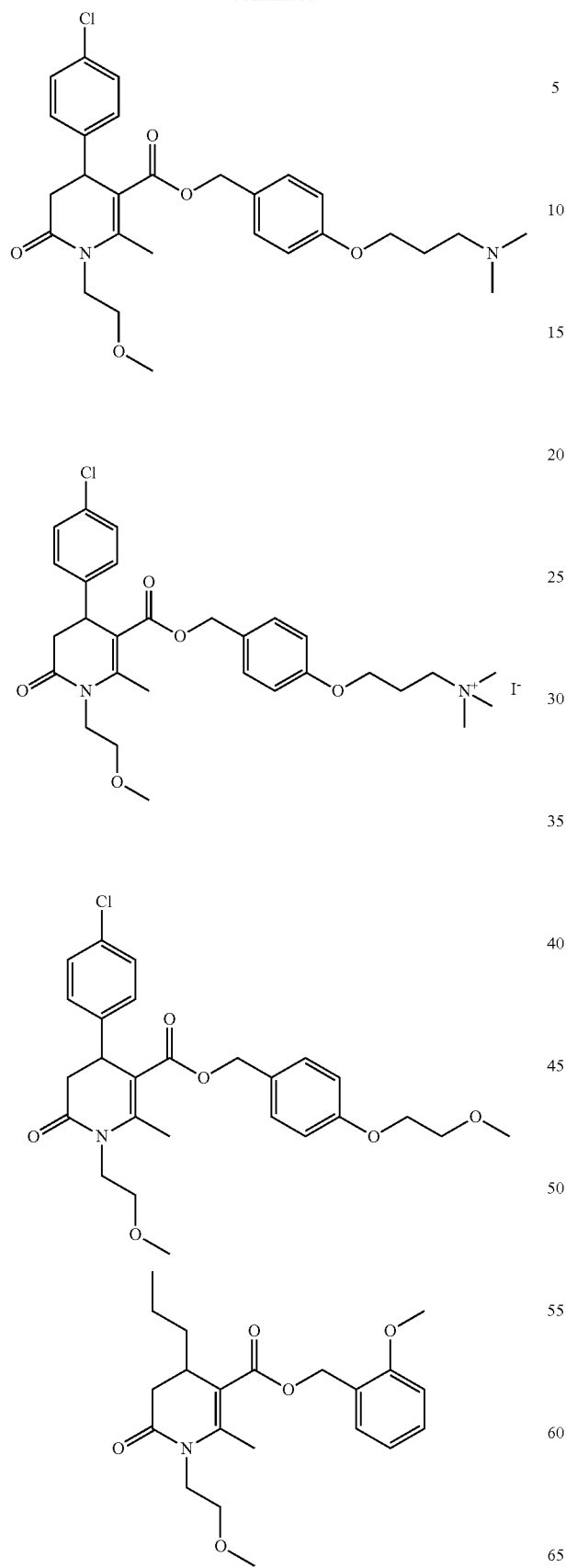
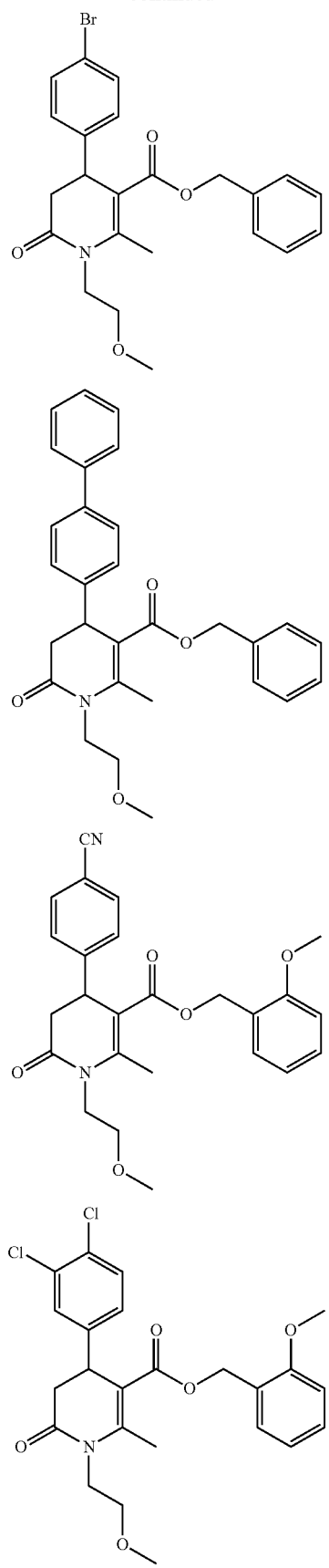

307
-continued
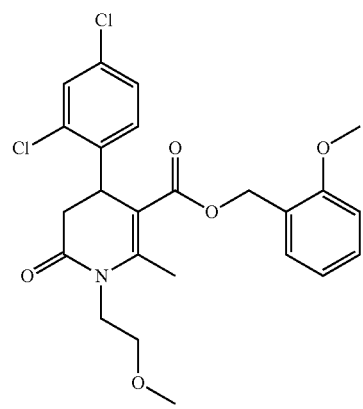
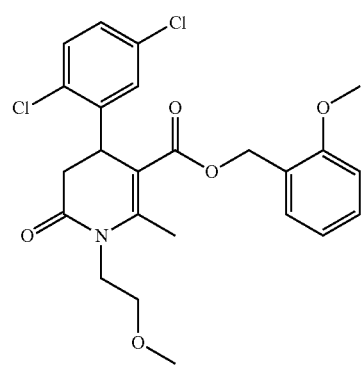
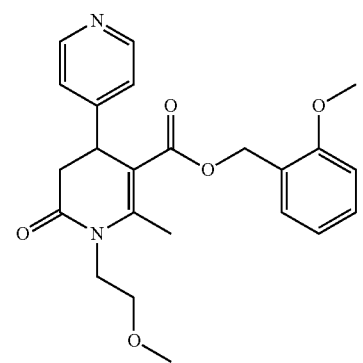
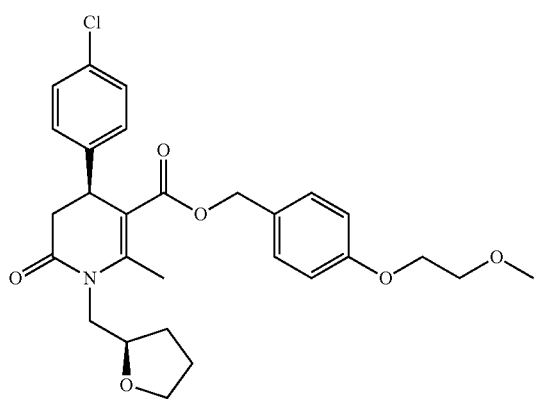
308
-continued
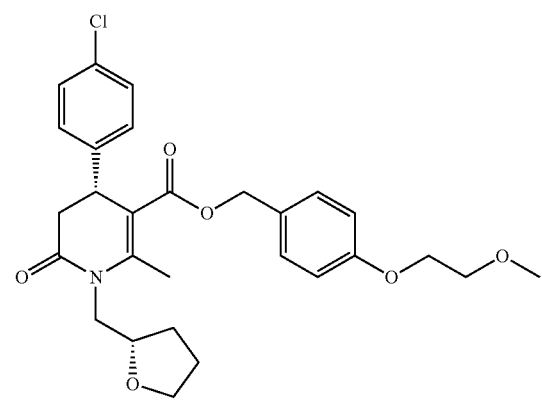
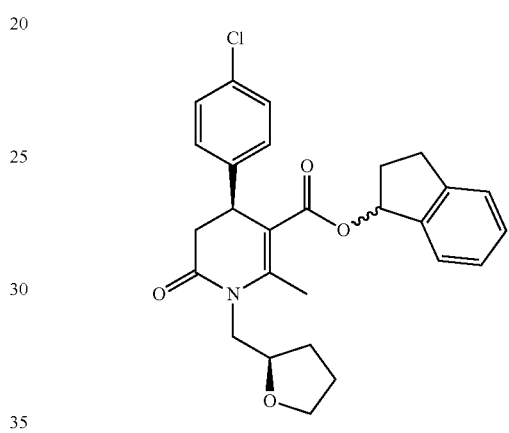
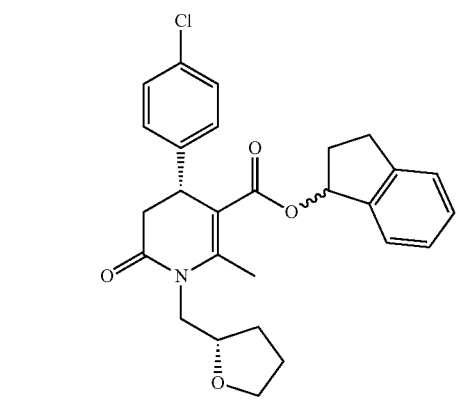
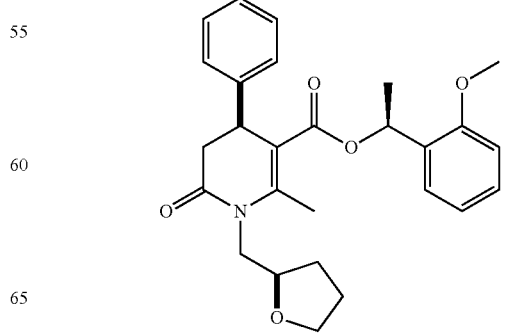

309
-continued
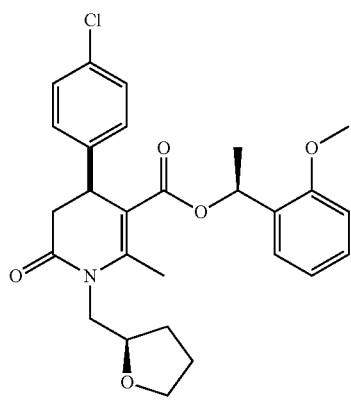
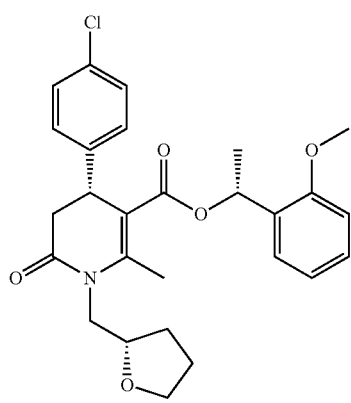
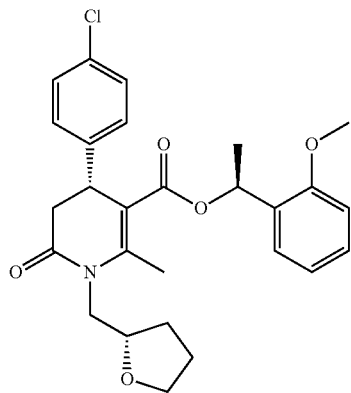
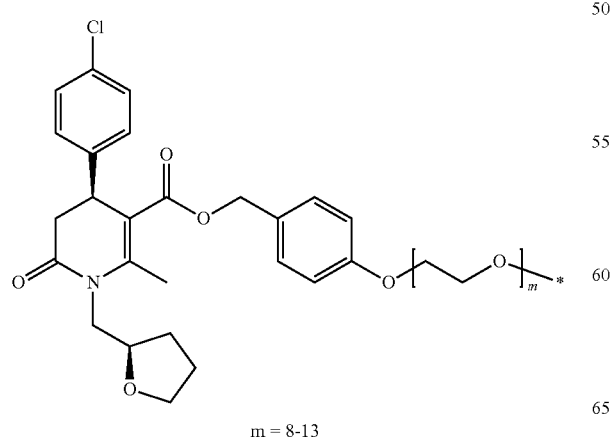
m = 8-13
310
-continued
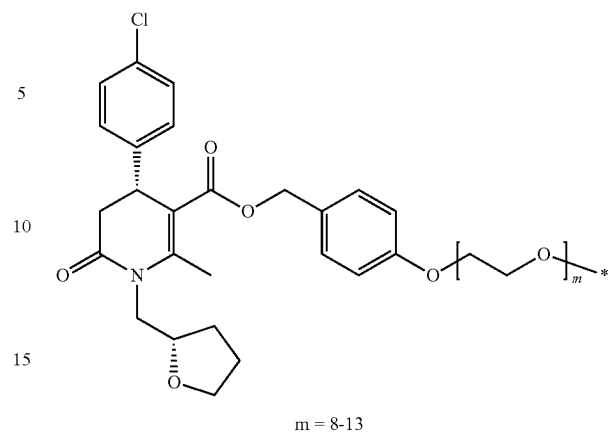
m = 8-13
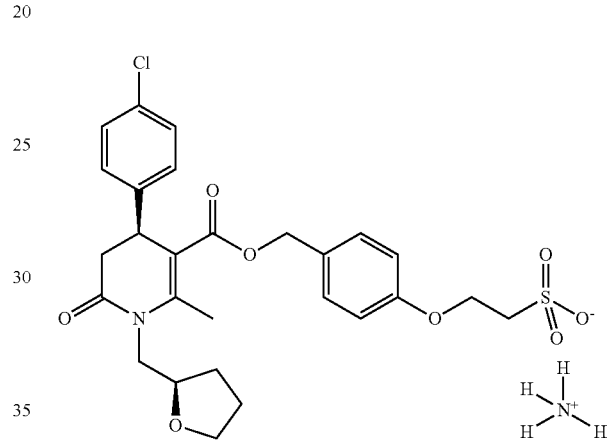
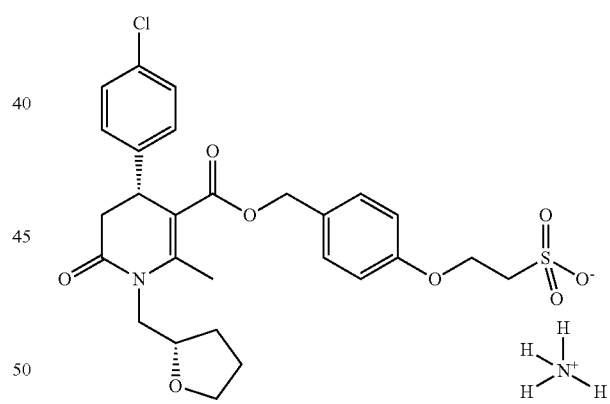
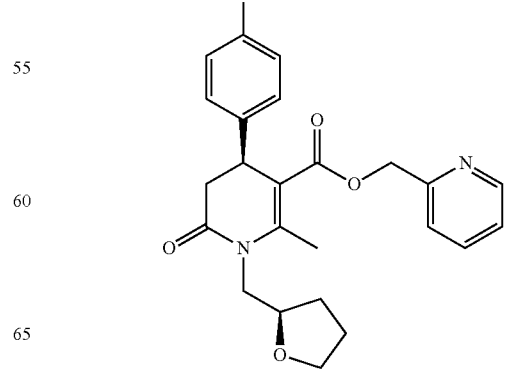

311
-continued
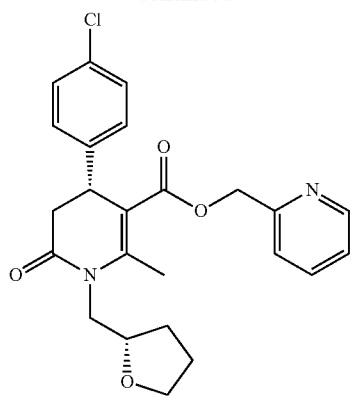
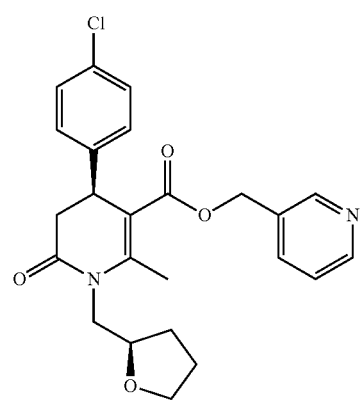
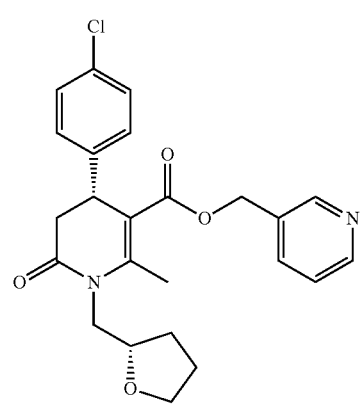
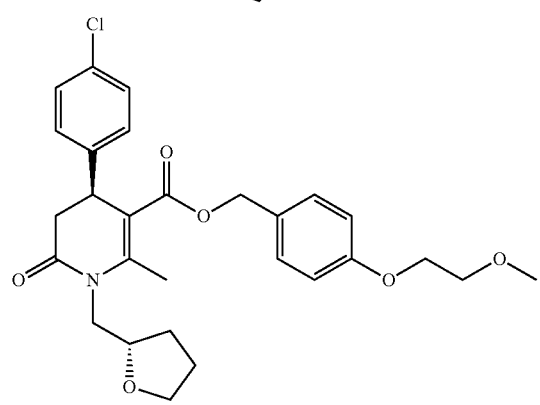
312
-continued
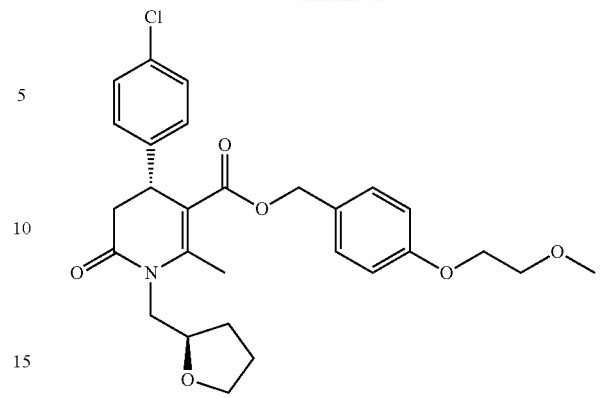
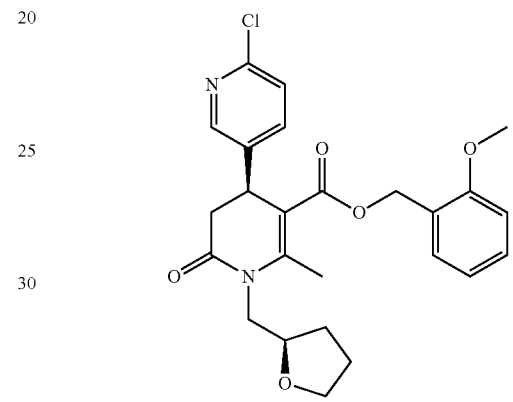
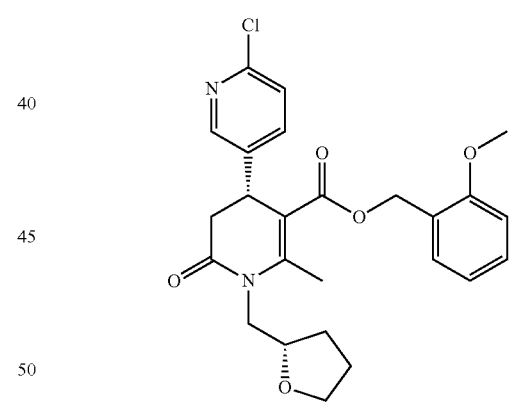
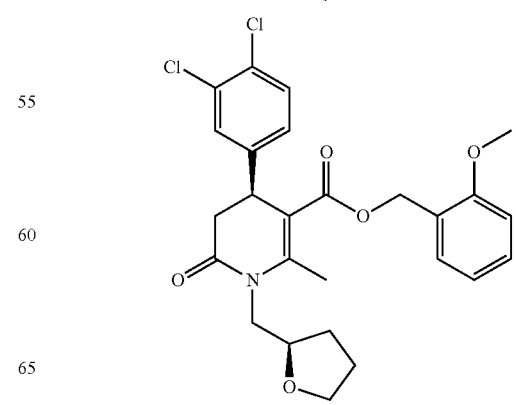

313
-continued
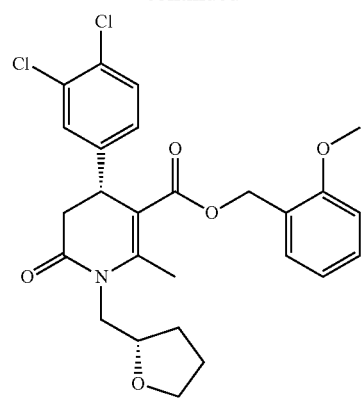
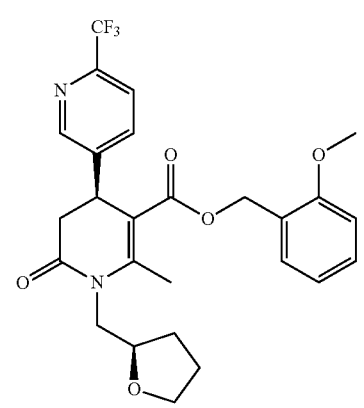
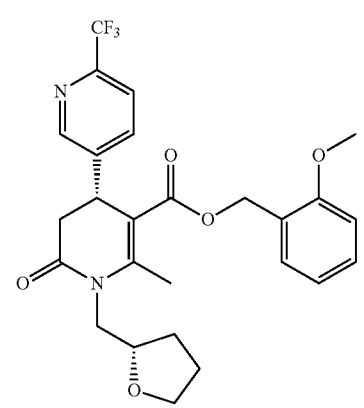
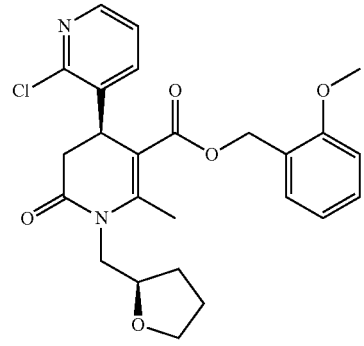
314
-continued
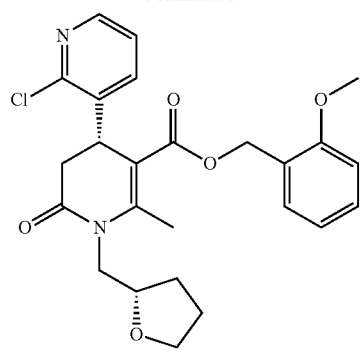
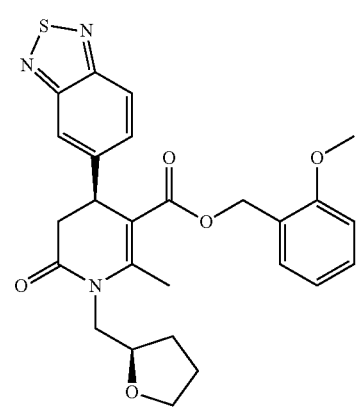
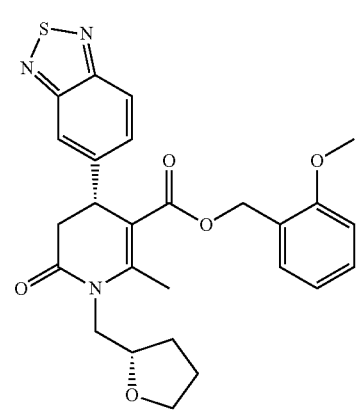
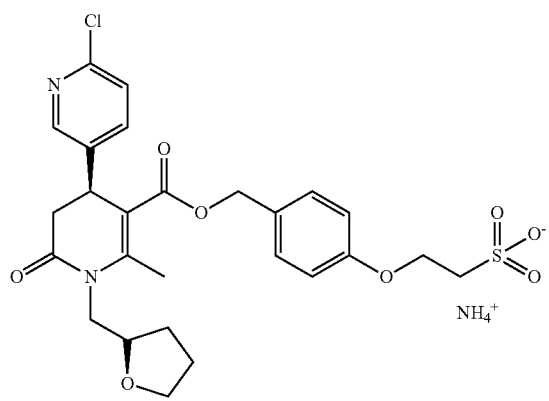

315
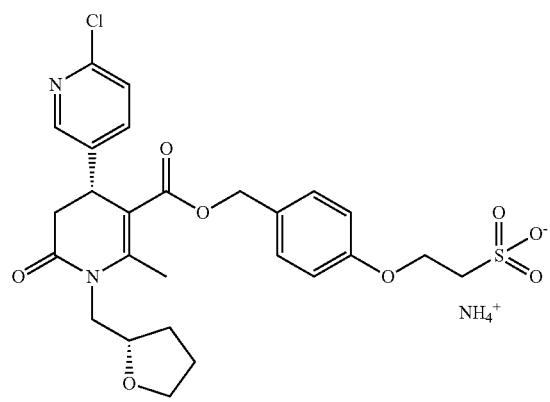
316
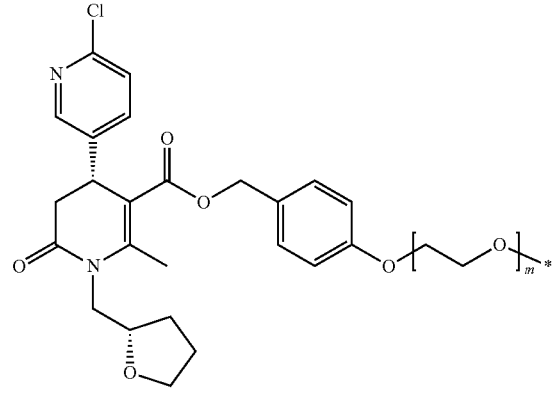
m = 18-23
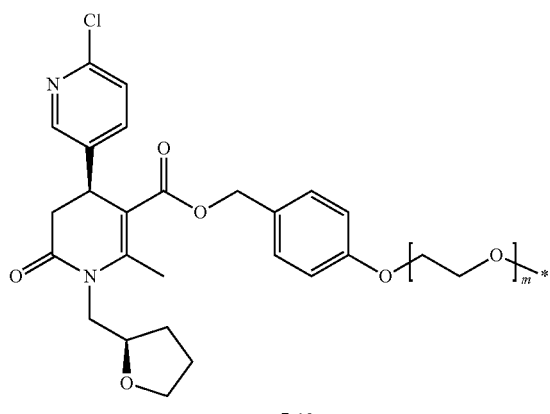
m = 7-10
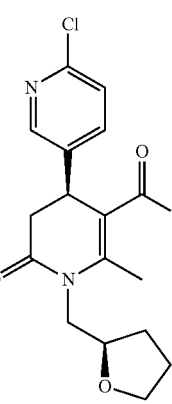
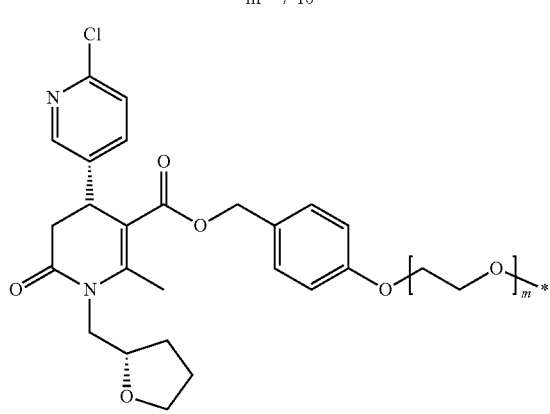
m = 7-10
m = 35-44
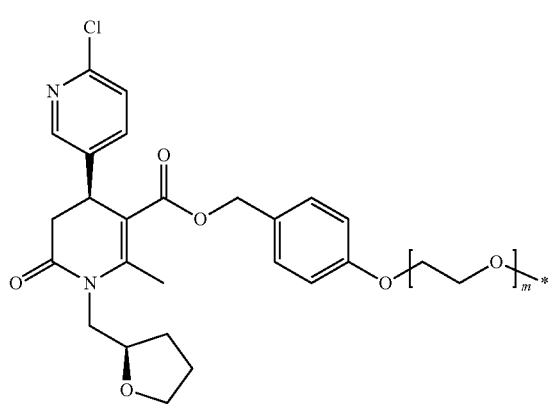
m = 18-23
m = 35-44

317
-continued
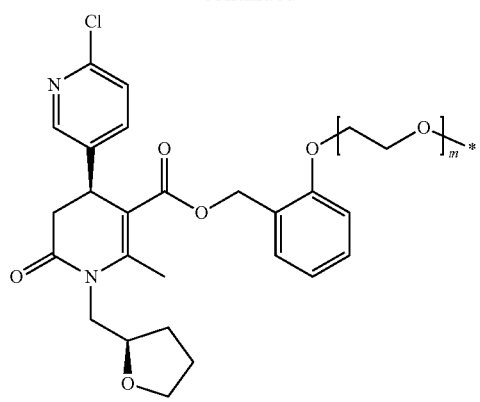
m = 10-14
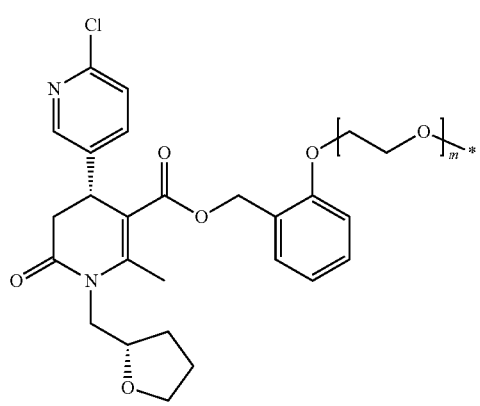
m = 10-14
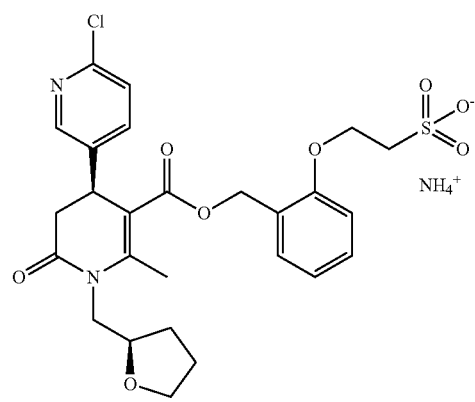
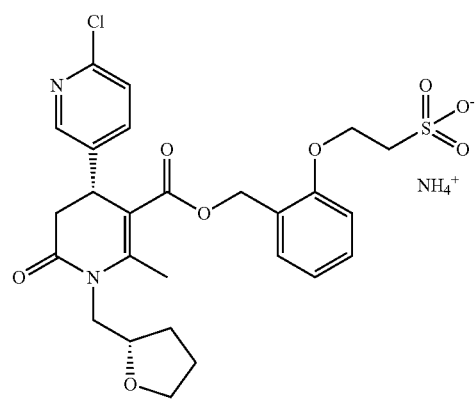
318
-continued
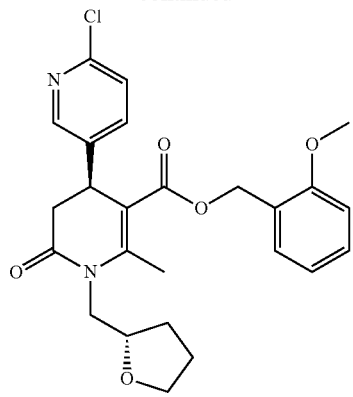
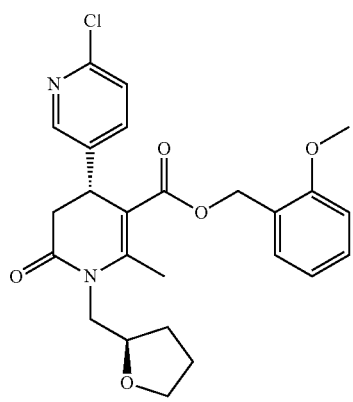
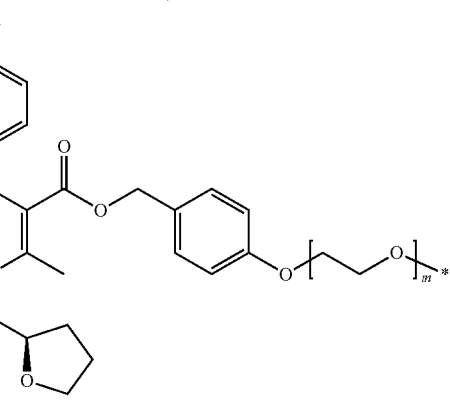
m = 11-18
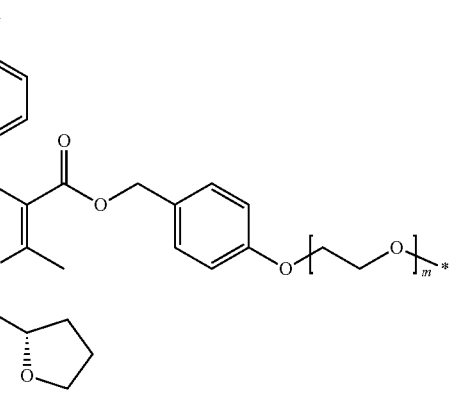
m = 11-18

319
-continued
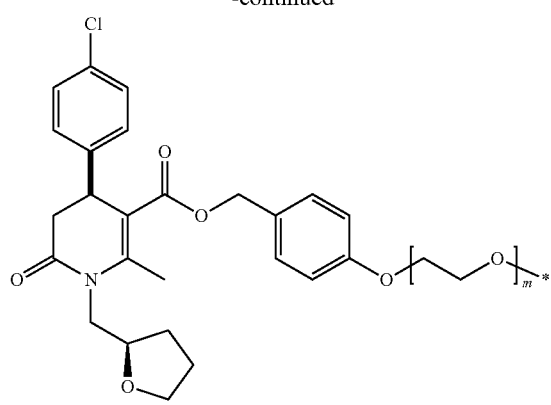
m = 38-48
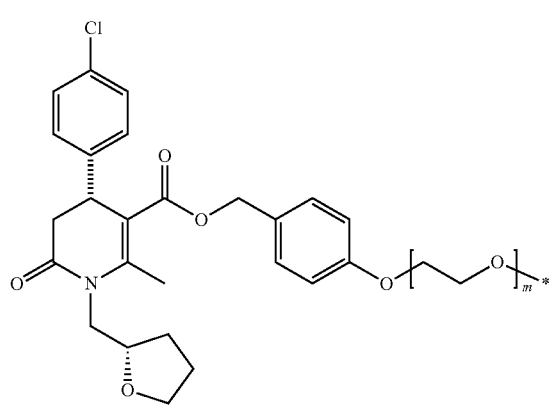
m = 38-48
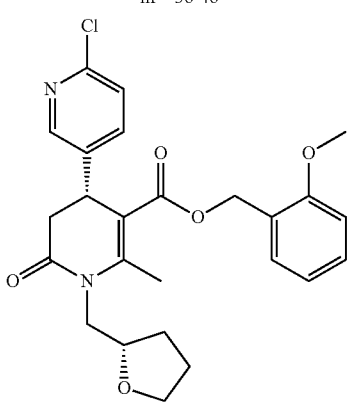
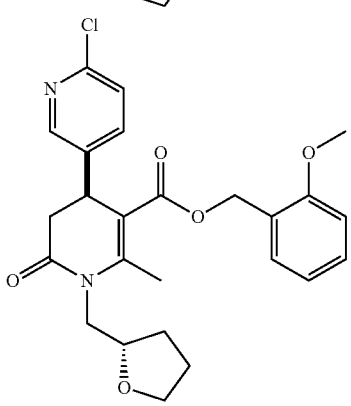
320
-continued
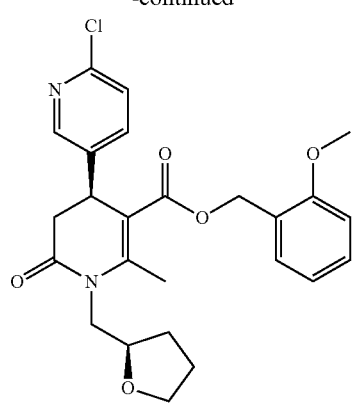
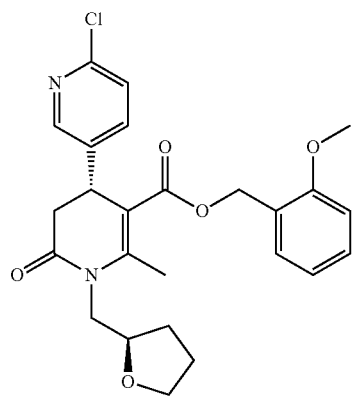
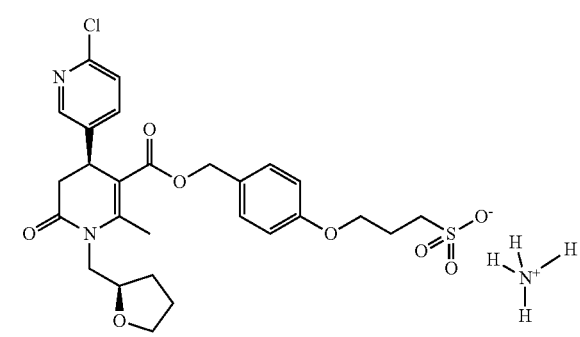
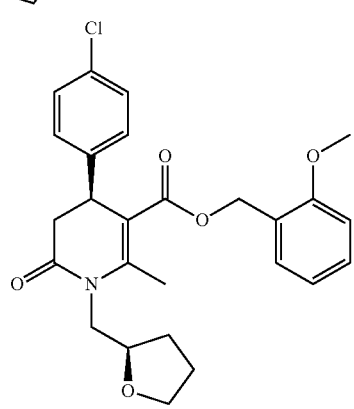

-continued

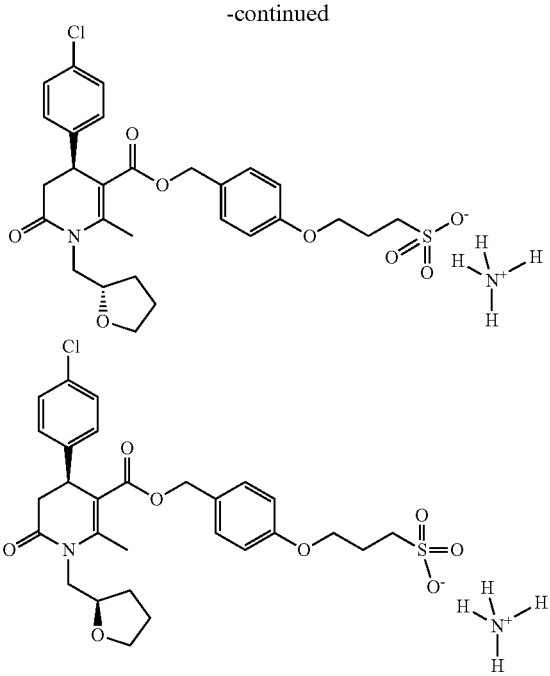

and pharmaceutically acceptable salts, and solvates thereof.

12. A pharmaceutical composition comprising a compound according to claim 1 or a pharmaceutically acceptable salt or solvate thereof and at least one pharmaceutically acceptable carrier, diluent, excipient and/or adjuvant.

13. A medicament comprising a compound according to claim 1.

14. A method for treating and/or preventing a TGR5 related disease comprising the administration of a therapeutically effective amount of a compound of Formula I

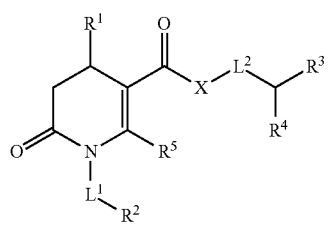

or pharmaceutically acceptable salts or solvates thereof, to a patient in need thereof,
wherein
$R^1$ is C1-C6-alkyl, aryl or heteroaryl, wherein said aryl moiety is independently substituted by one or more groups selected from the group consisting of halo, cyano, C1-C2-alkyl, C1-C2-alkoxy, C1-C2-haloalkyl, and 5- or 6-membered aryl, and said heteroaryl moiety is optionally independently substituted by one or more groups selected from the group consisting of halo, cyano, C1-C2-alkyl, C1-C2-alkoxy, C1-C2-haloalkyl, and 5- or 6-membered aryl;
$L^1$ is a single bond or $(CH_2)_n$, wherein n is 1, 2 or 3;
$R^2$ is H, C1-C4 alkyl, alkenyl, alkynyl, alkoxy, hydroxy, hydroxycarbonyl, alkoxycarbonyl, carbamoyl, aminoalkyl, alkylaminoalkyl, dialkylaminoalkyl, alkoxycarbonylamino, cyano, alkylsulfonyl, aralkyl, cycloalkyl, heterocyclyl or heteroaryl, wherein said heterocyclyl moiety is optionally substituted by one or more substituents independently selected from the group consisting of alkyl and alkoxycarbonyl, and said heteroaryl moiety is optionally substituted by one or more C1-C2-alkyl;
$L^2$ is a single bond or $(CH_2)_n$, wherein n is 1 or 2;
$R^3$ is aryl, heteroaryl, cycloalkyl or arylcarbonyl wherein each of said moieties is optionally substituted by one or more substituents independently selected from the group consisting of halo, alkyl, haloalkyl, aryl, cyano, alkoxy, haloalkoxy, alkoxycarbonyl, aminoalkoxy, alkylaminoalkoxy, dialkylaminoalkoxy, $HO_3S$-alkoxy,

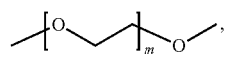

wherein m is 1 to 500,
$[N(R^8)_3\text{-alkoxy}]^+$ $Q^-$, wherein $R^8$ is linear C1-C4-alkyl and $Q^-$ is a counter anion, and
a cyclic moiety selected from the group consisting of

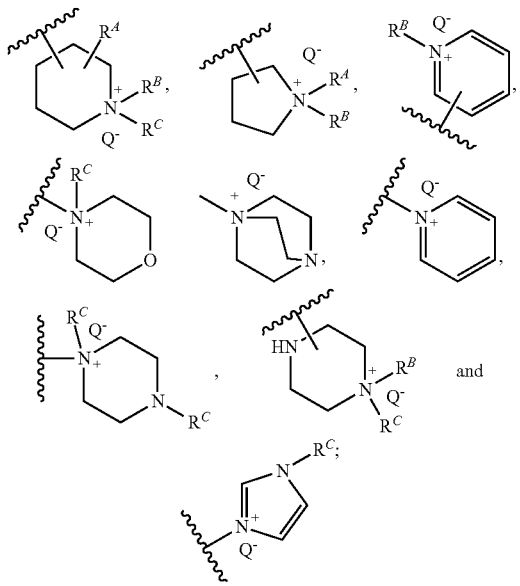

wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion;
or wherein said cycloalkyl moiety is fused to 4 an aryl, preferably phenyl, moiety;
$R^4$ is H, C1-C2-alkyl or 5- or 6-membered aryl;
$R^5$ is H, C1-C4-alkyl, 5- or 6-membered aryl, or alkoxyalkyl; and
X is O or NR', wherein R' is H, C1-C2-alkyl or R' taken together with $L^2$ and $R^3$ form a 5- or 6-membered heterocyclyl moiety which is optionally fused to an aryl moiety.

15. The method according to claim 14 wherein the compound has Formula II

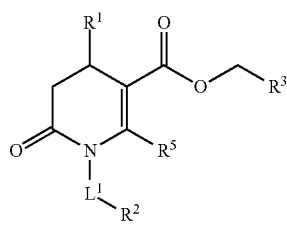

II and pharmaceutically acceptable salts and solvates thereof.

16. The method according to claim 14 wherein the compound has Formula IIa

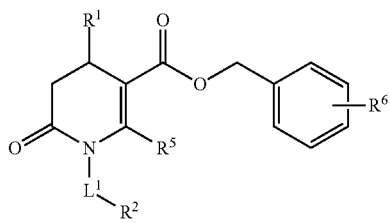

IIa and pharmaceutically acceptable salts, and solvates thereof, wherein

R$^6$ is halo, alkyl, haloalkyl, aryl, cyano, alkoxy, haloalkoxy, alkoxycarbonyl, aminoalkoxy, alkylaminoalkoxy, dialkylaminoalkoxy, HO$_3$S-alkoxy,

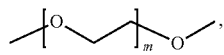

wherein m is 1 to 500,

[N(R$^8$)$_3$-alkoxy]$^+$ Q$^-$, wherein R$^8$ is linear C1-C4-alkyl and Q$^-$ is a counter anion, or a cyclic moiety selected from the group consisting of

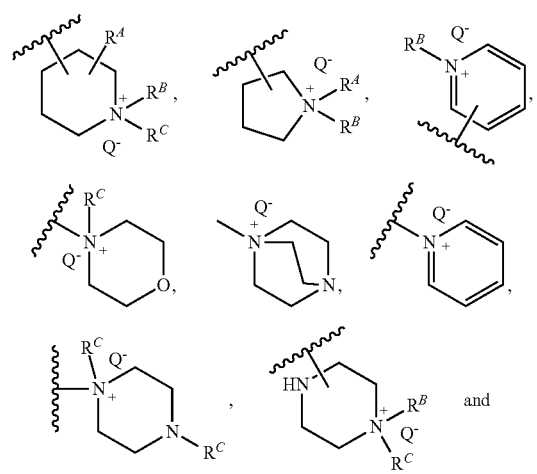

and

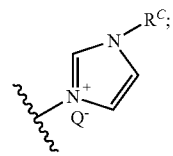

wherein R$^A$ is H, OH, C0-C4-alkyl-COOH or C1-C6-alkyl, R$^B$ is C1-C6-alkyl optionally substituted with —COOH, R$^C$ is C1-C6-alkyl, and Q$^-$ is a counter anion.

17. The method according to claim 14 wherein the compound has Formula III

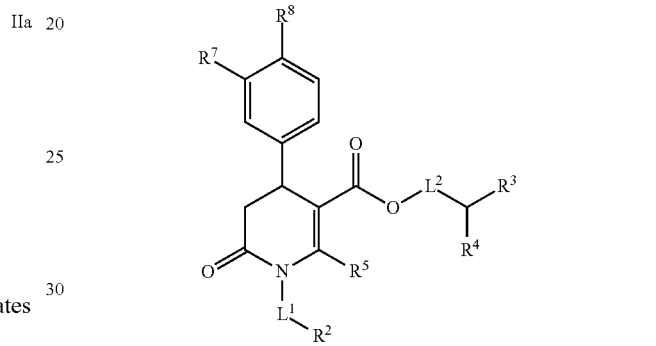

III and pharmaceutically acceptable salts, and solvates thereof, wherein

R$^7$ and R$^8$ are independently selected from the group consisting of H, halo, haloalkyl, and cyano, with the proviso that at least one of R$^7$ and R$^8$ is not H.

18. The method according to claim 14 wherein the compound has Formula IV

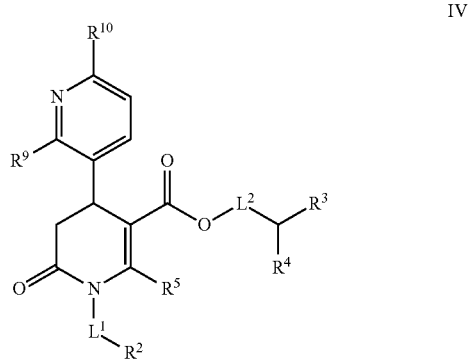

IV and pharmaceutically acceptable salts, and solvates thereof, wherein

R$^9$ and R$^{10}$ are independently selected from the group consisting of H, halo, haloalkyl, and cyano, with the proviso that at least one of R$^9$ and R$^{10}$ is not H.

19. The method according to claim 14 wherein the compound has Formula V

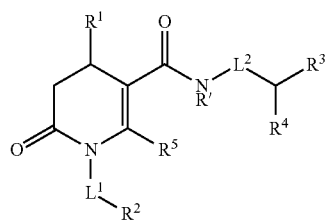

and pharmaceutically acceptable salts, and solvates thereof.

20. The method according to claim 14 wherein $R^5$ is methyl.

21. The method according to claim 14 wherein $L^1$ and $R^2$ are taken together to form a moiety selected from the group consisting of cycloalkylmethyl, heterocyclylmethyl, heteroarylmethyl, 2-alkoxyeth-1-yl, 3-alkoxyprop-1-yl, and alkoxycarbonylmethyl, said heteroarylmethyl moiety being optionally substituted by one or more C1-C2 alkyl.

22. The method according to claim 14 wherein $R^2$ is tetrahydrofuranyl.

23. The method according to claim 14 wherein $L^1$ is $CH_2$.

24. The method according to claim 14, wherein the compound is selected from the group consisting of:

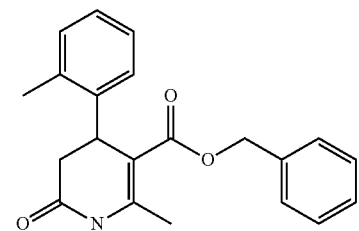

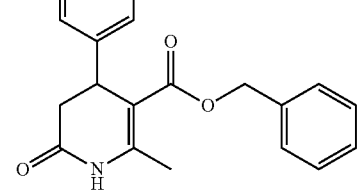

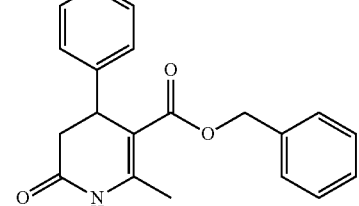

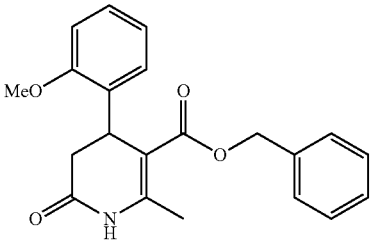

-continued

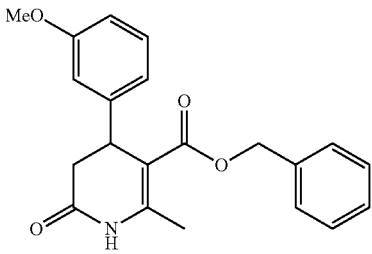

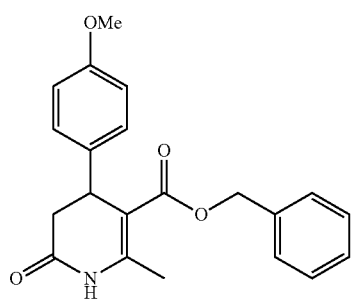

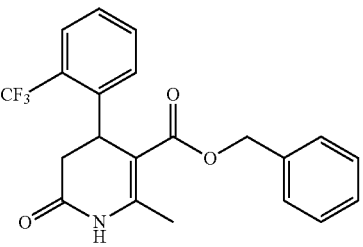

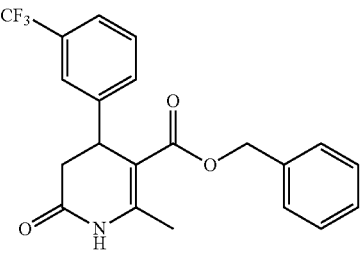

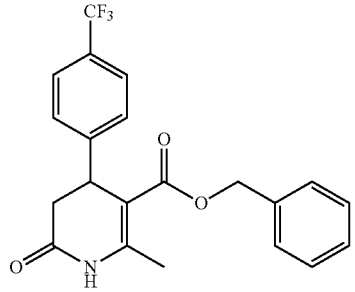

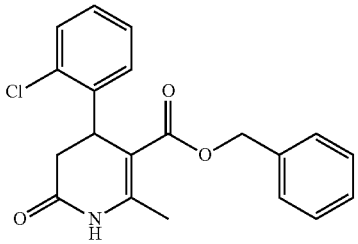

327
-continued
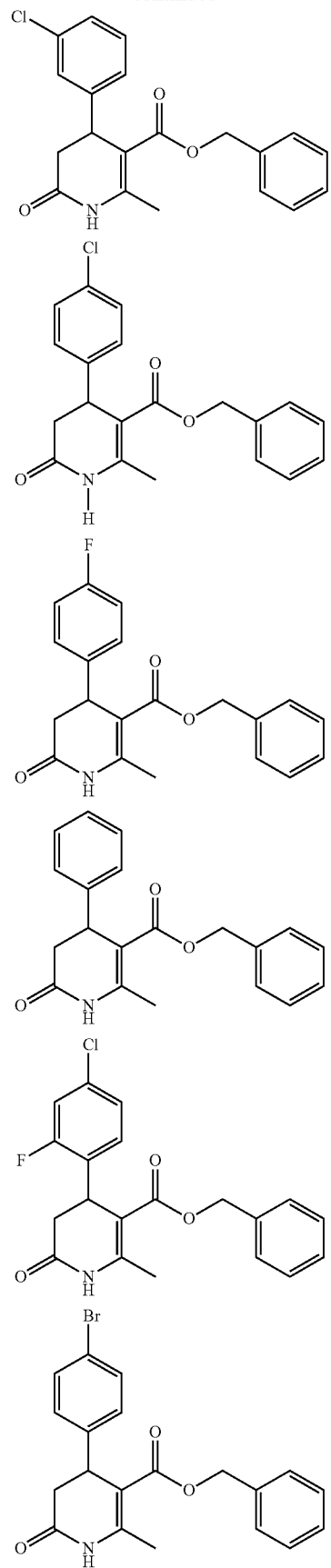
328
-continued
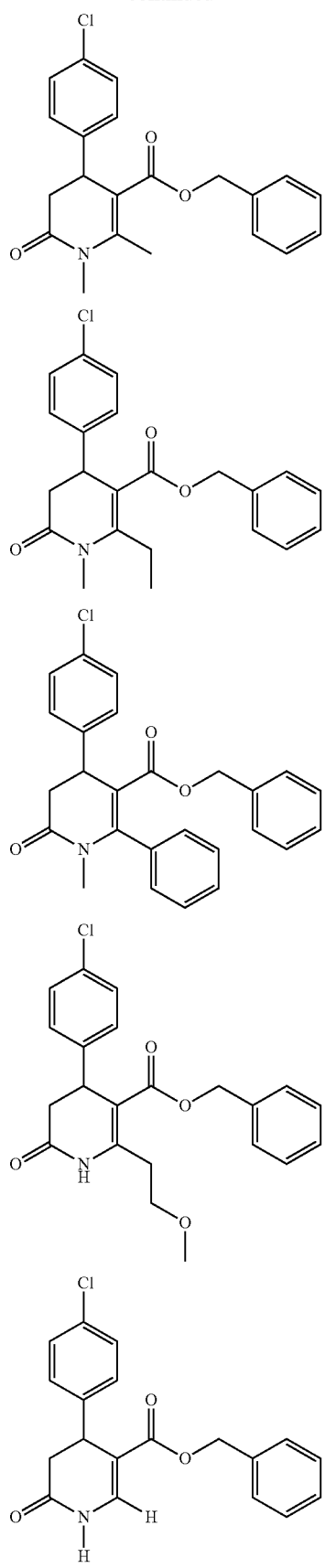

329
-continued
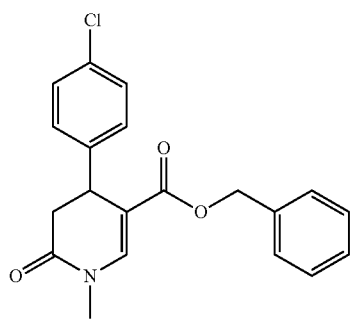 [SMILES: CN1C=C(C(=O)OCc2ccccc2)C(c2ccc(Cl)cc2)CC1=O]
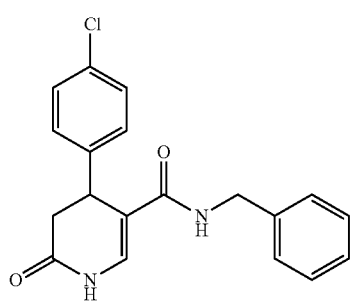
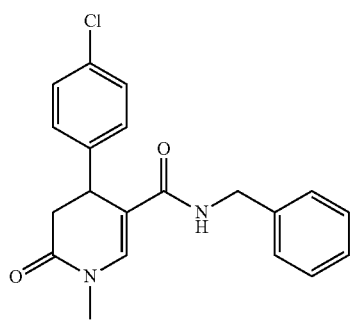
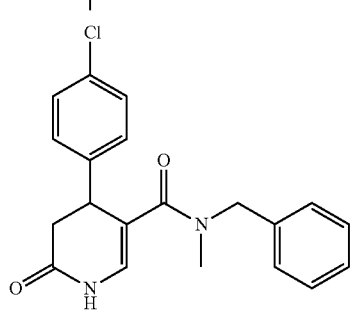
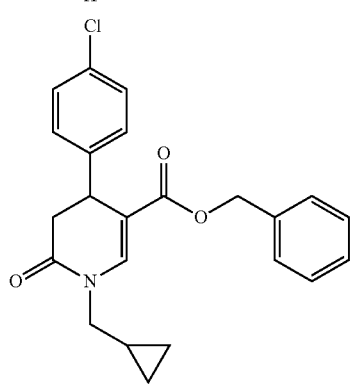
330
-continued
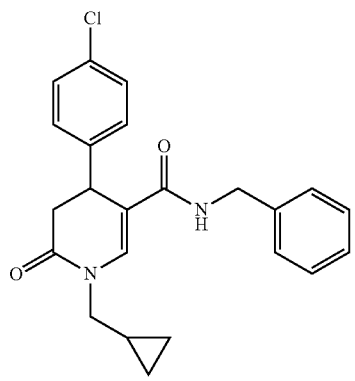
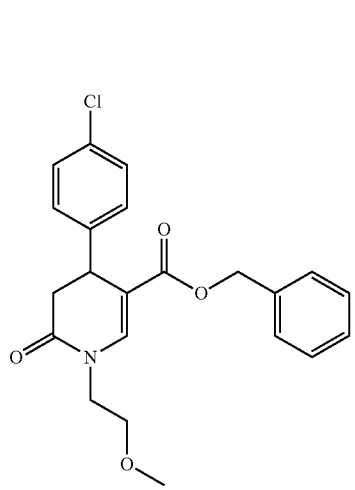
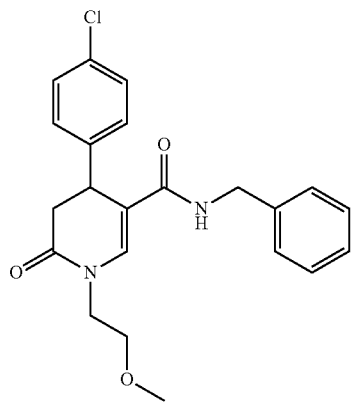
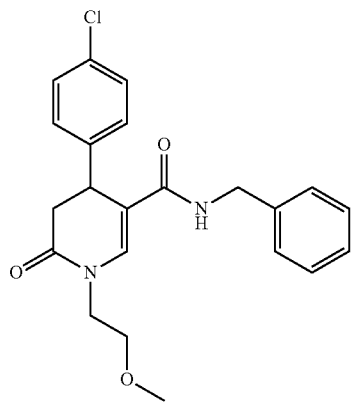

331
-continued
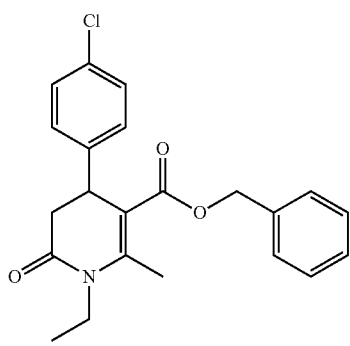
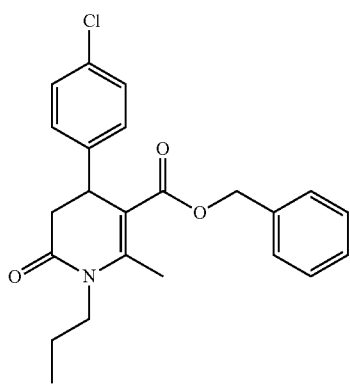
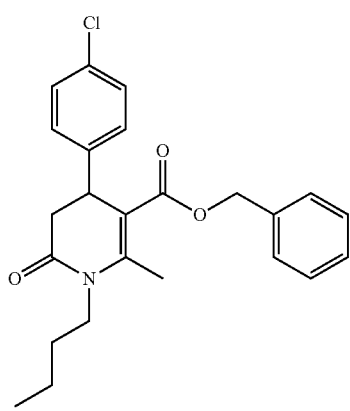
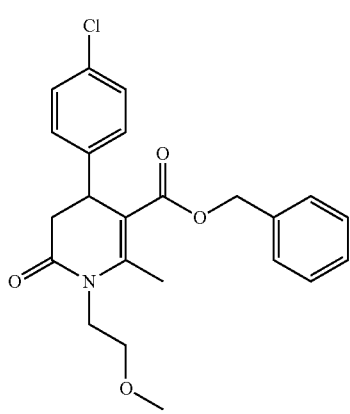
332
-continued
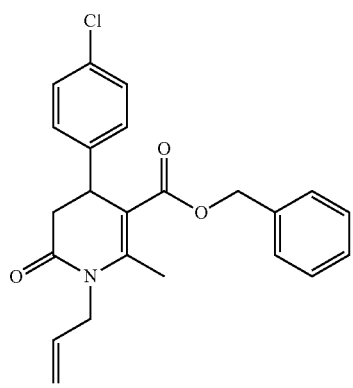
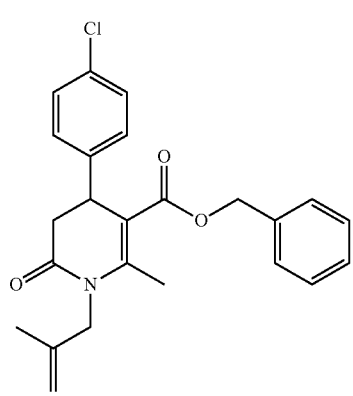
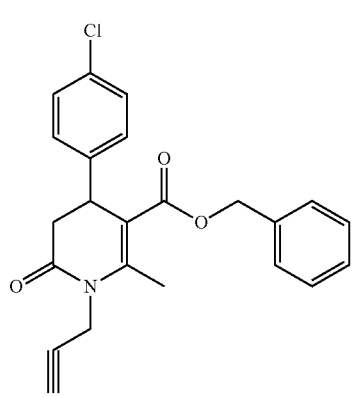
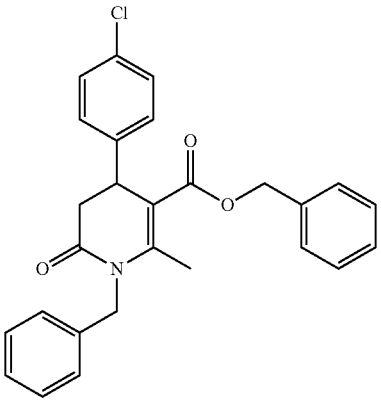

333
-continued
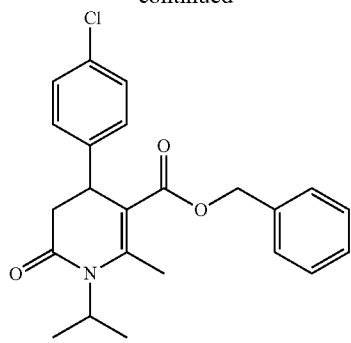
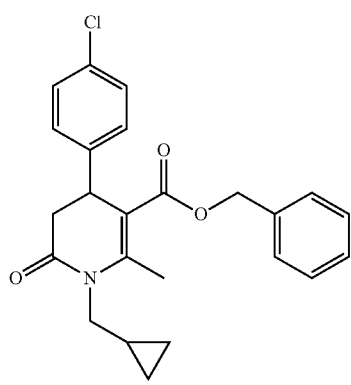
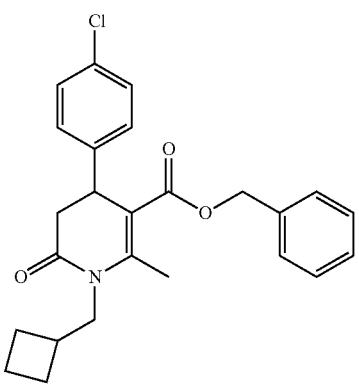
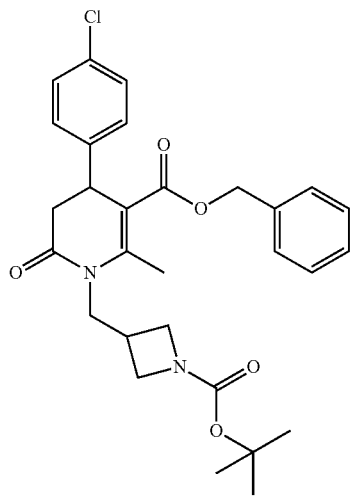
334
-continued
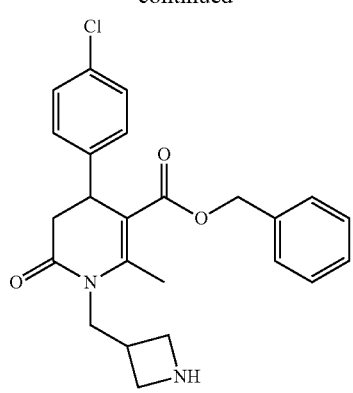
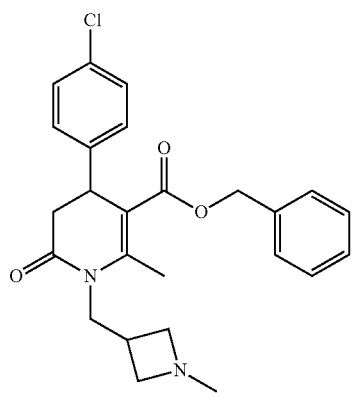
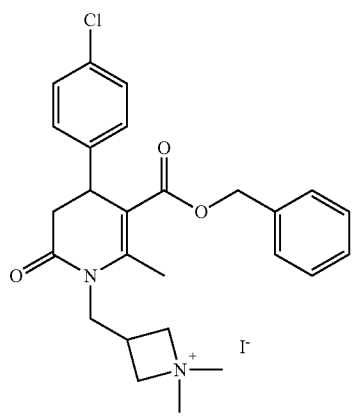
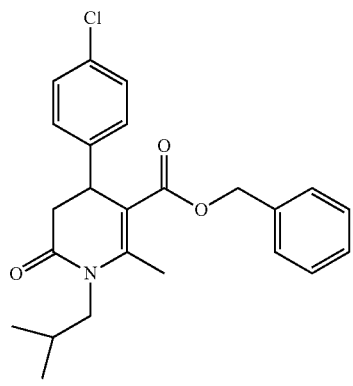

335
-continued
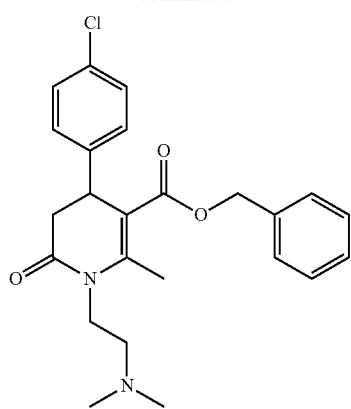
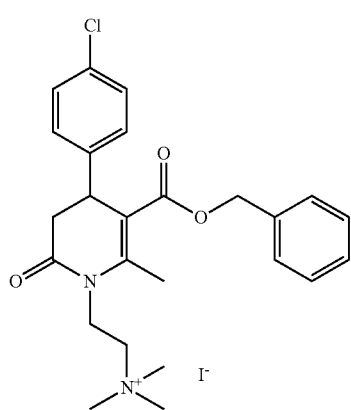
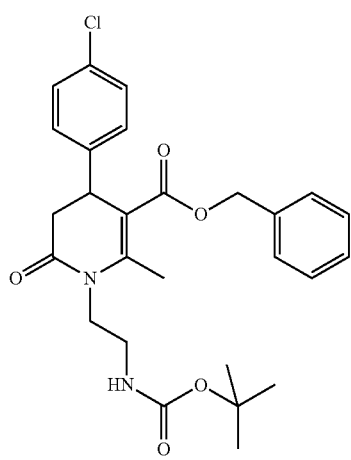
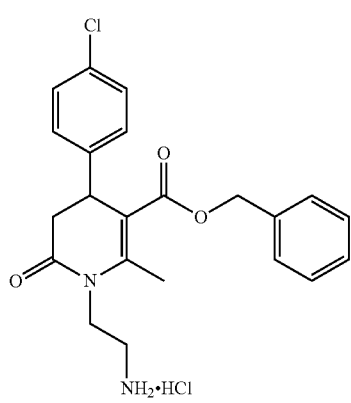
336
-continued
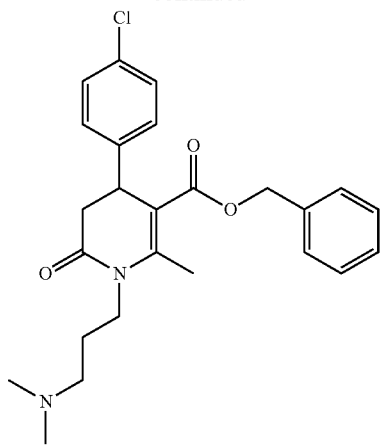
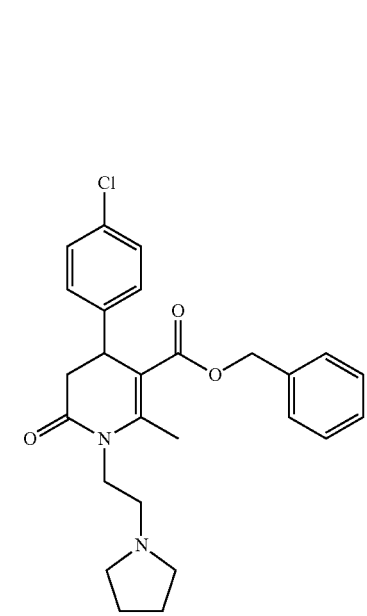
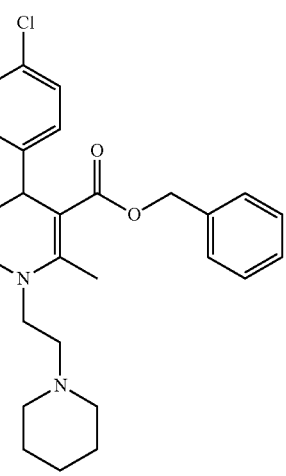

337
-continued
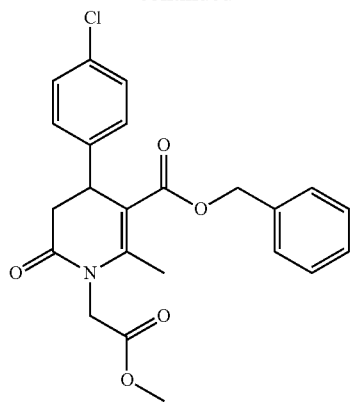
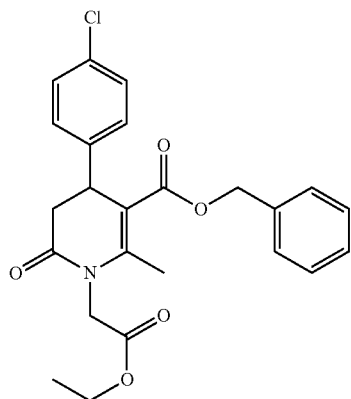
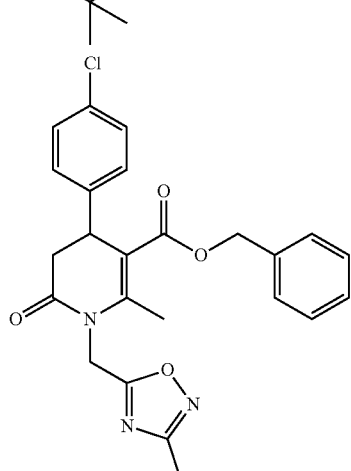
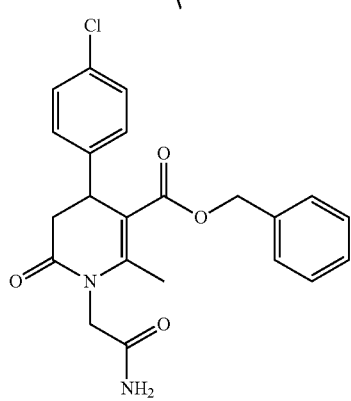
338
-continued
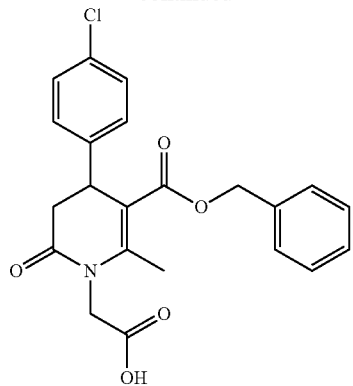
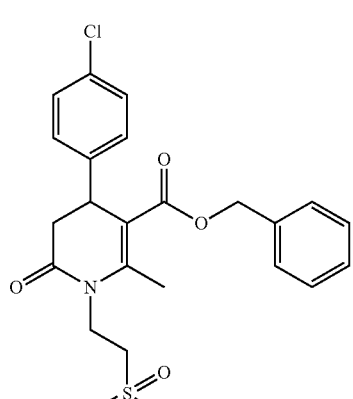
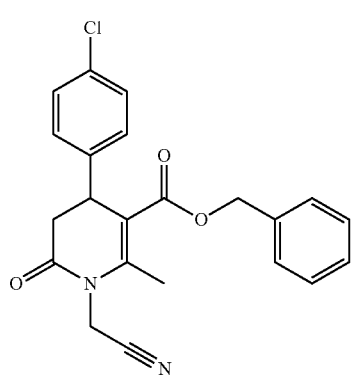
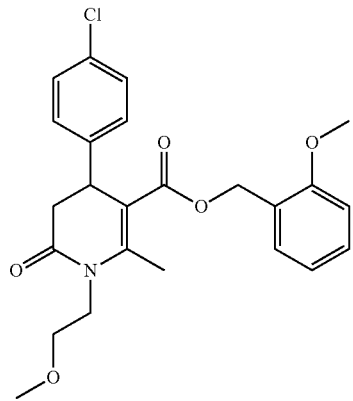

339
-continued
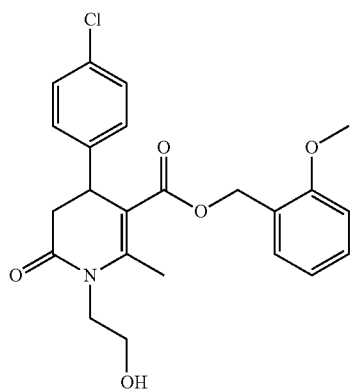
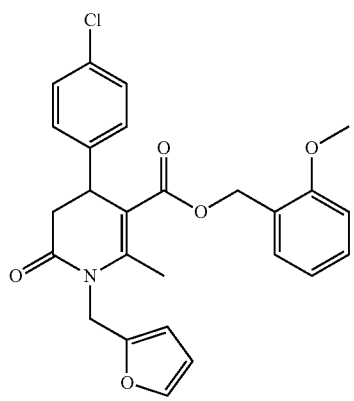
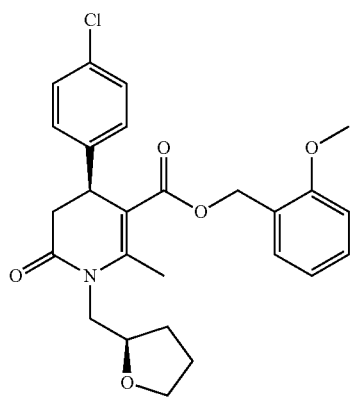
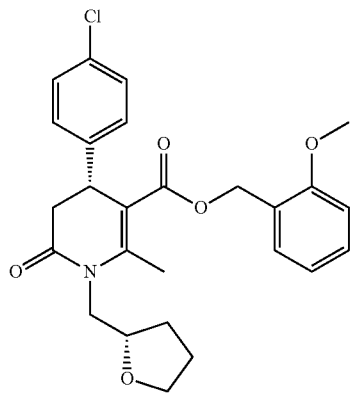
340
-continued
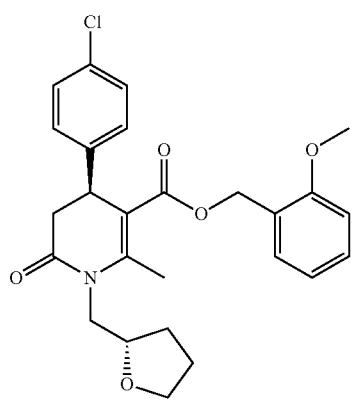
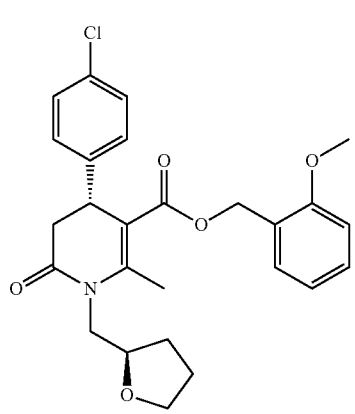
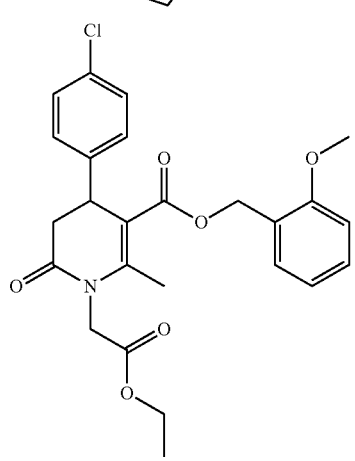
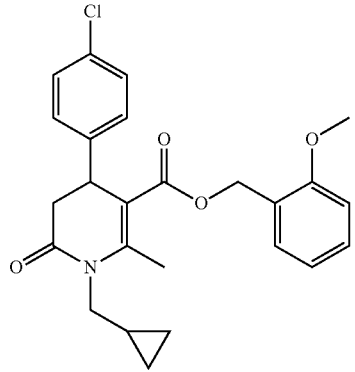

341
-continued
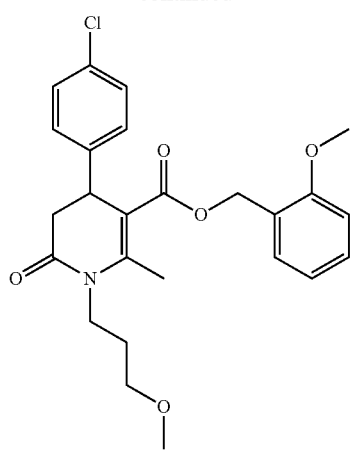
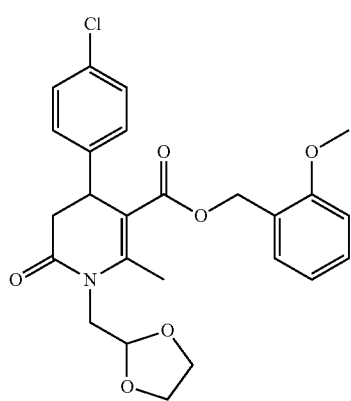
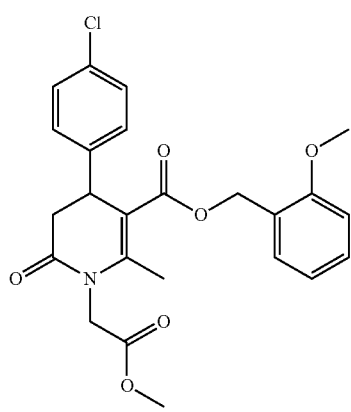
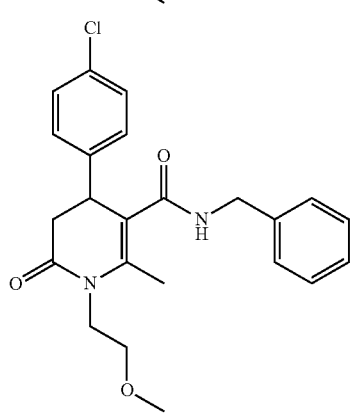
342
-continued
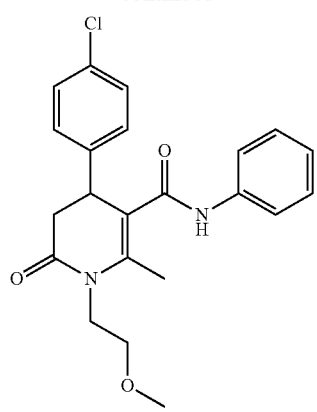
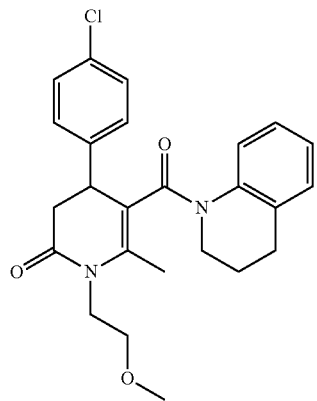
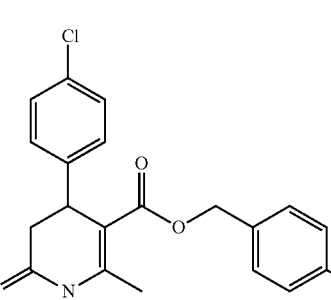
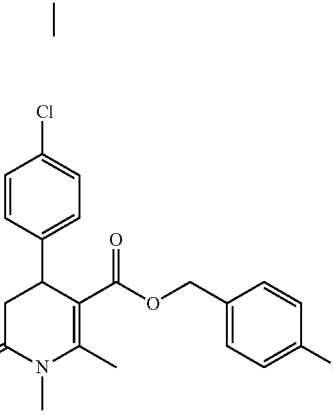

343
-continued
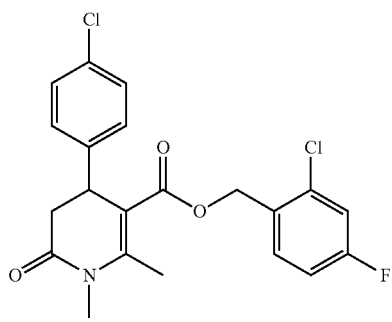
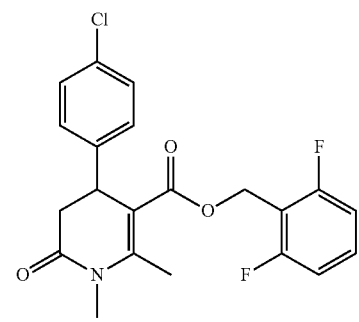
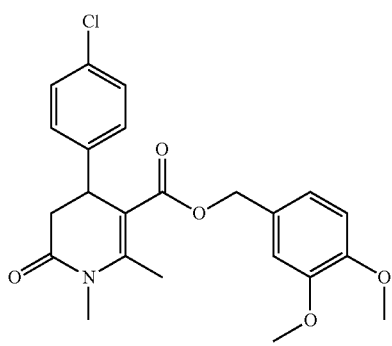
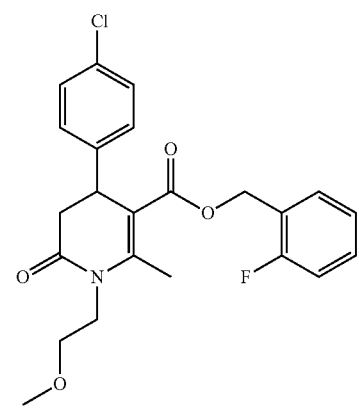
344
-continued
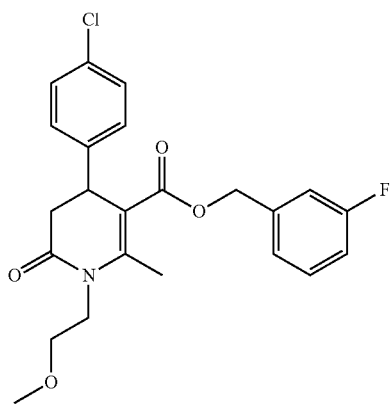
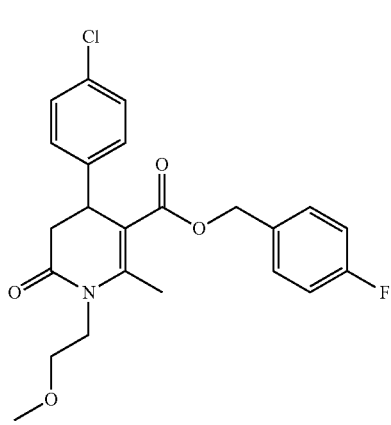
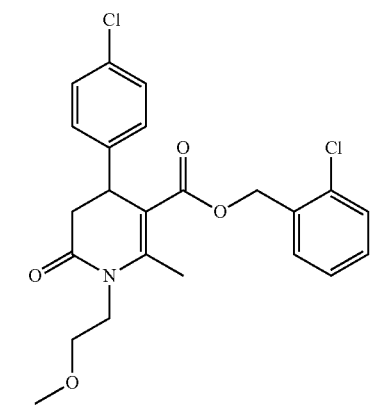
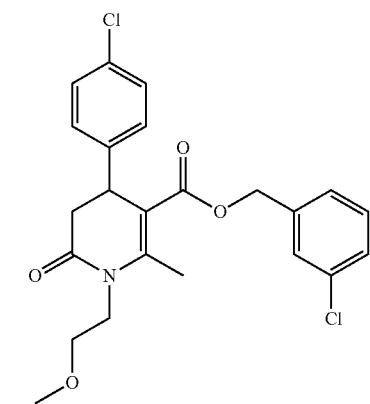

345
-continued
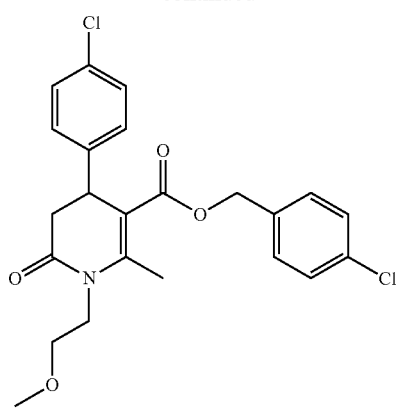
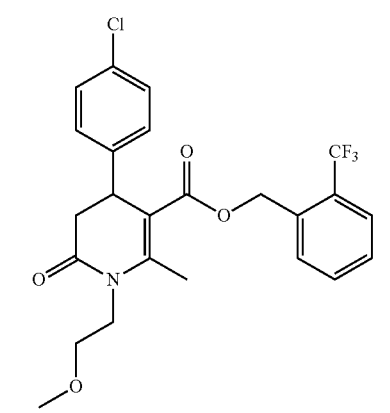
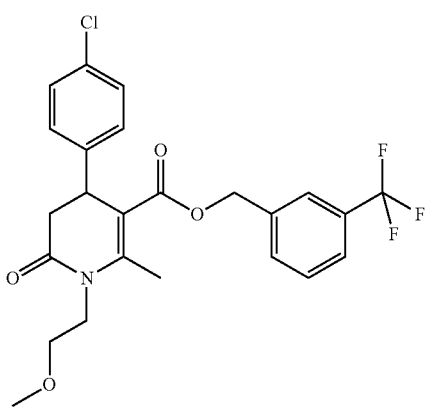
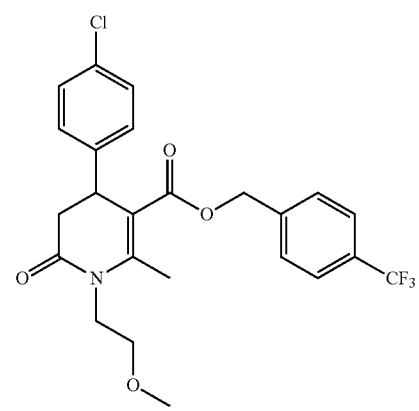
346
-continued
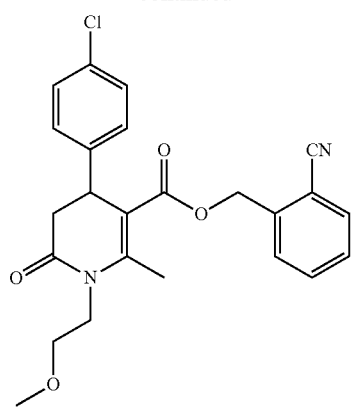
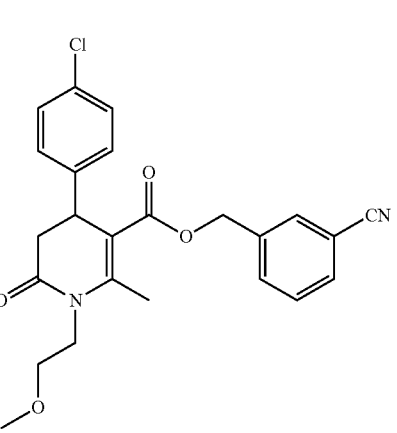
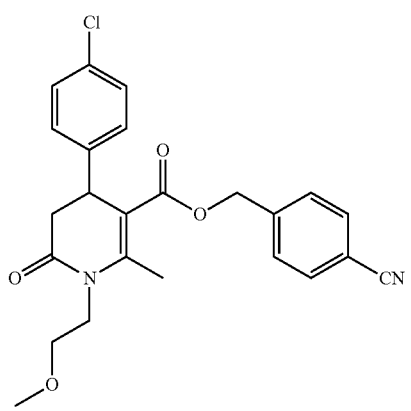
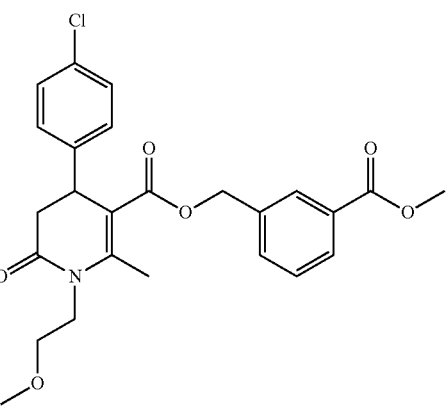

347
-continued
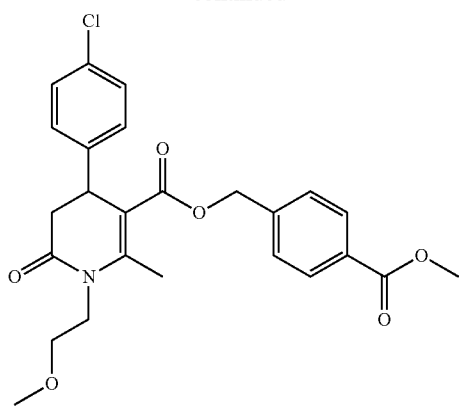
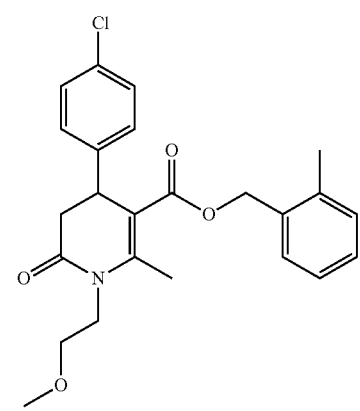
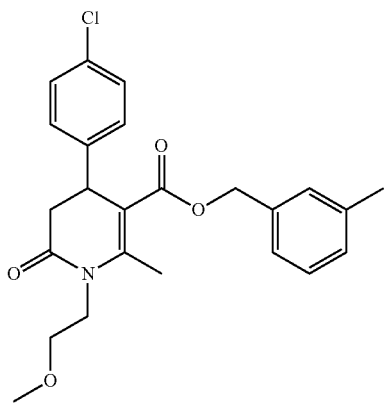
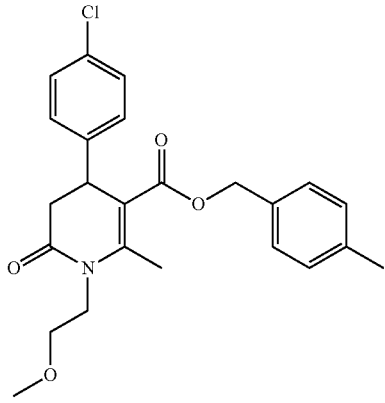
348
-continued
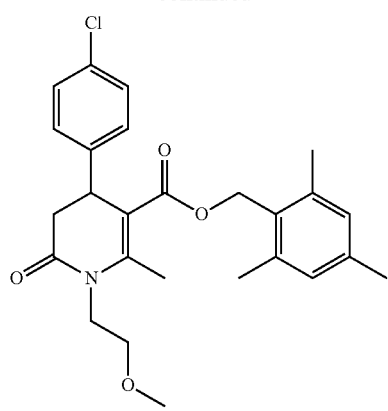
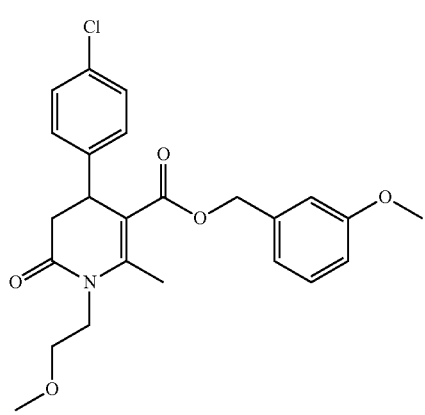
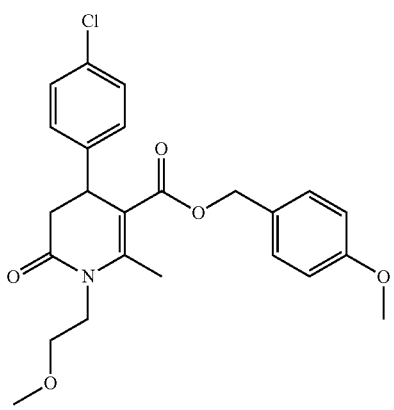
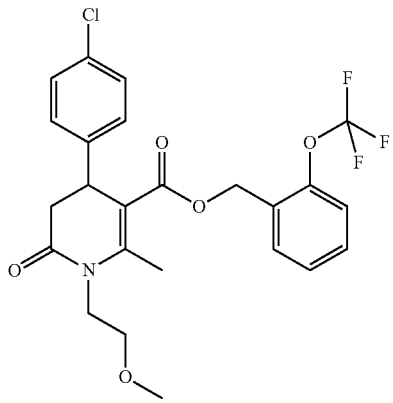

349
-continued
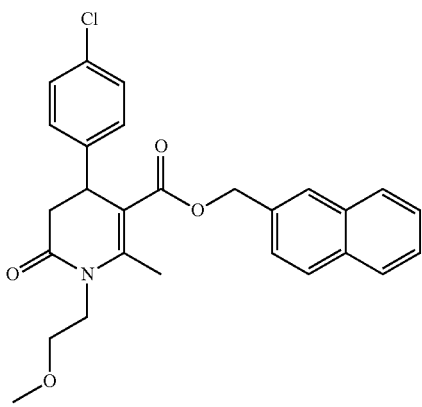
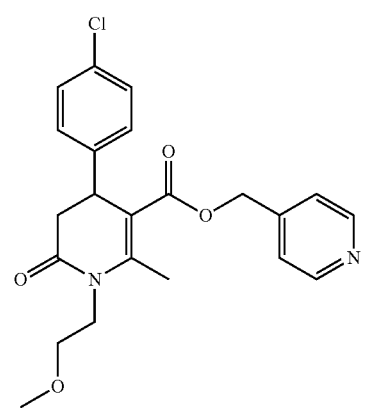
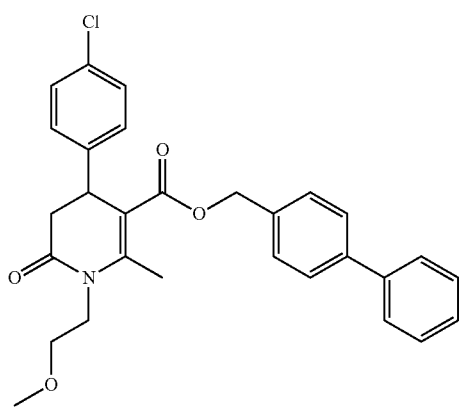
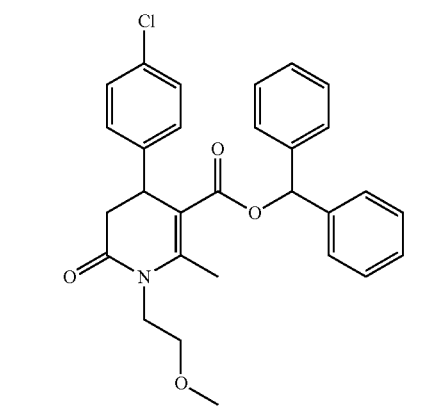
350
-continued
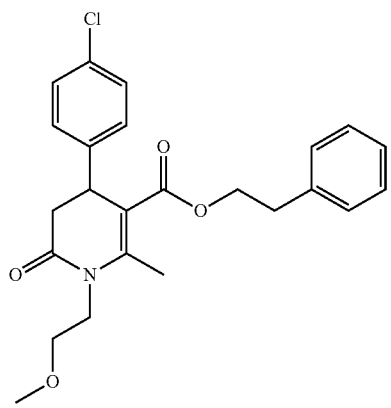
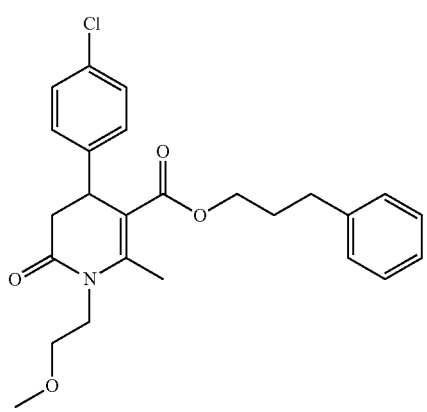
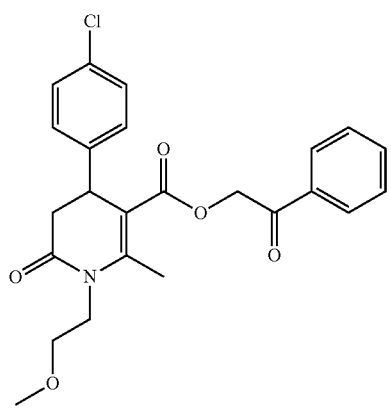
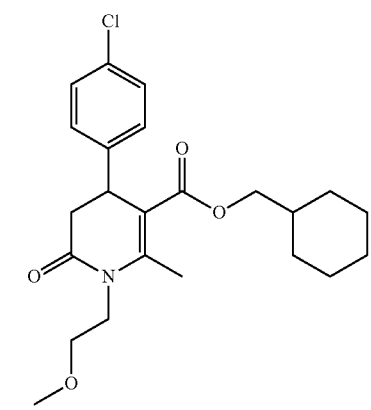

351
-continued
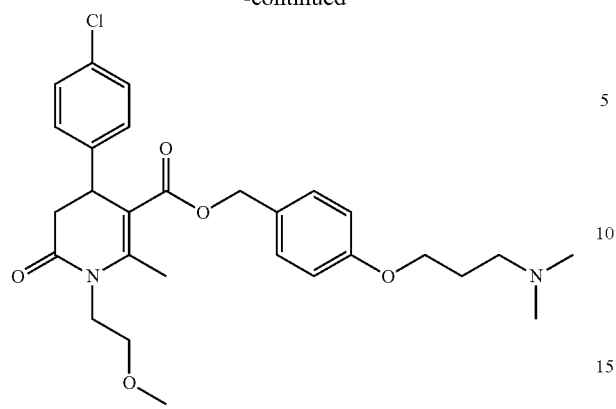
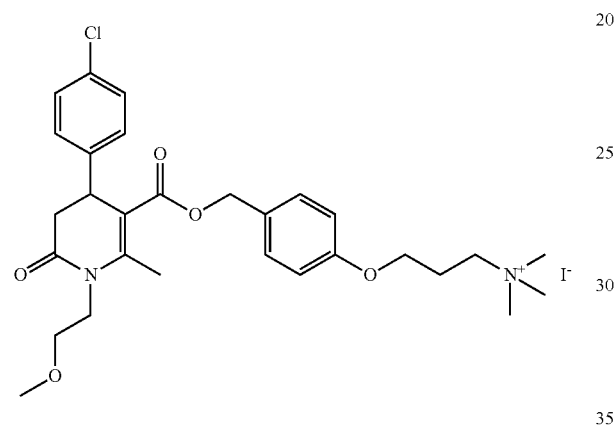
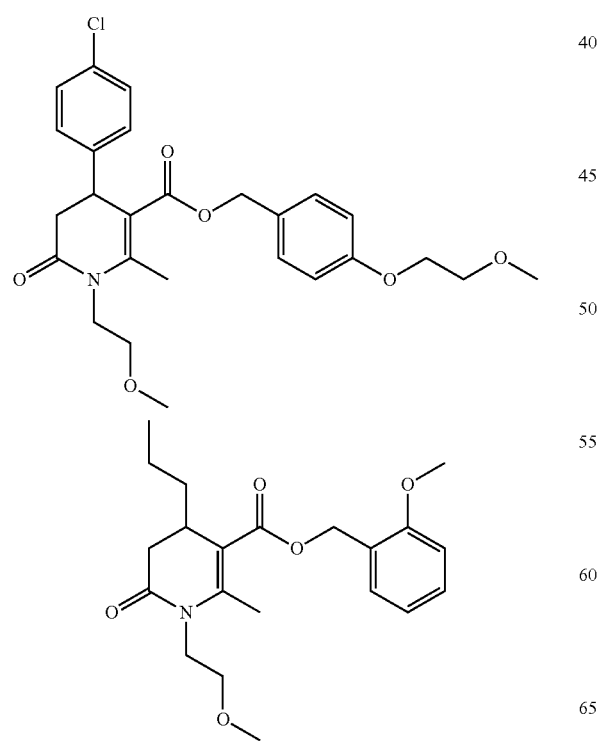
352
-continued
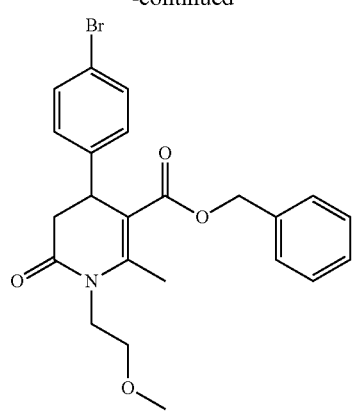
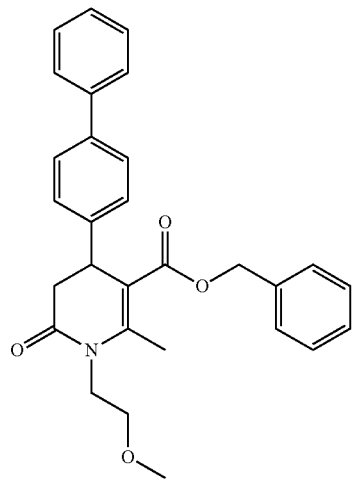
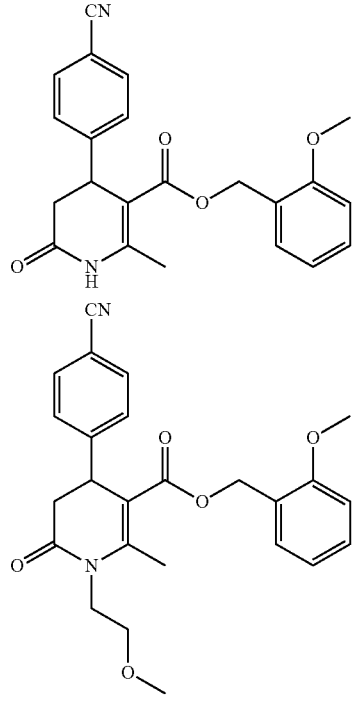

353
-continued
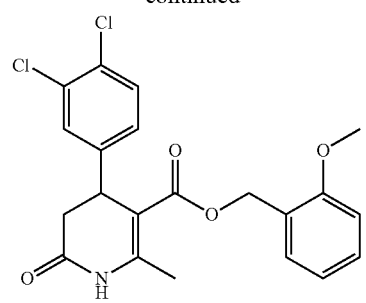
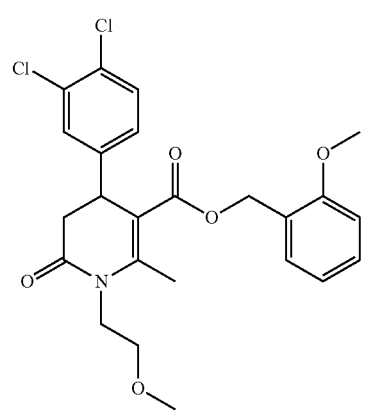
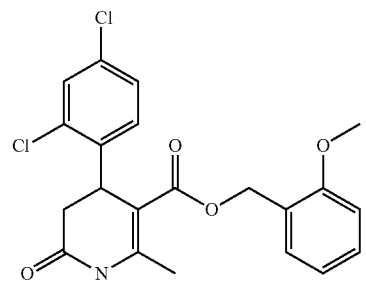
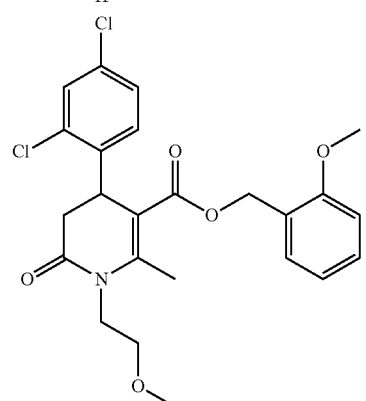
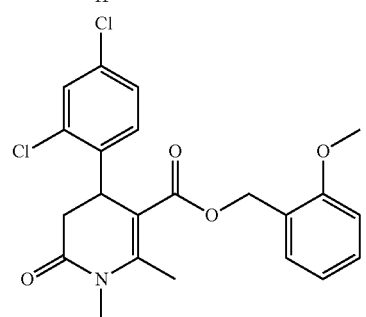
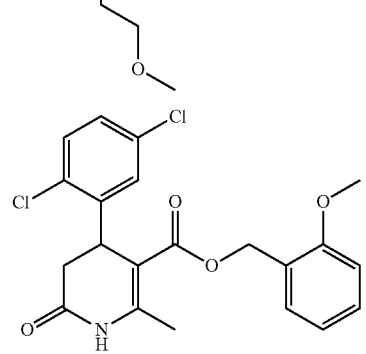
354
-continued
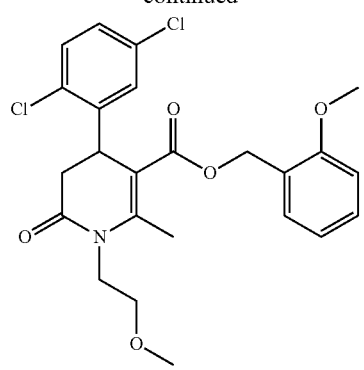
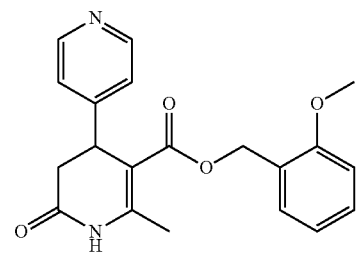
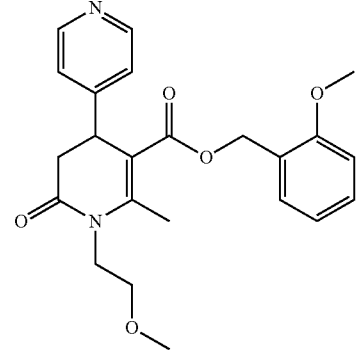
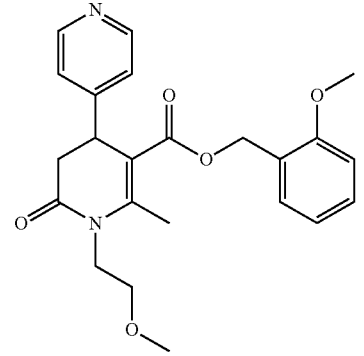
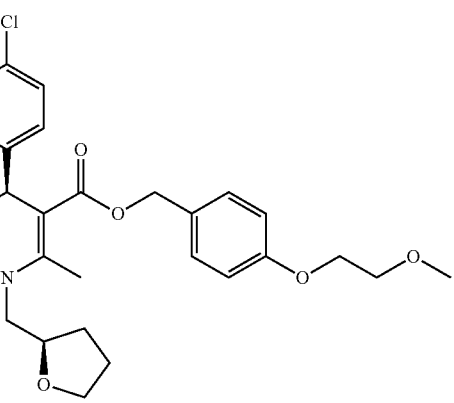

355
-continued
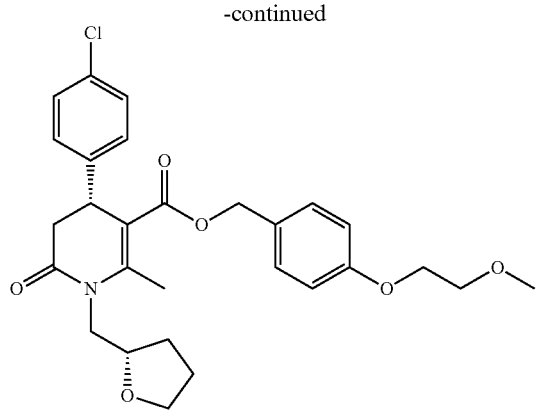
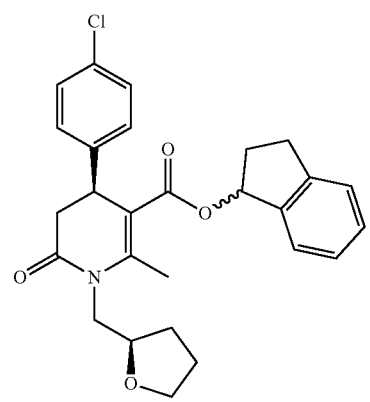
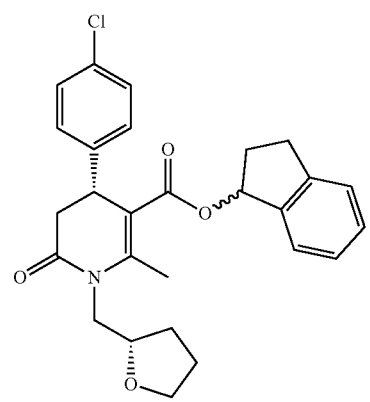
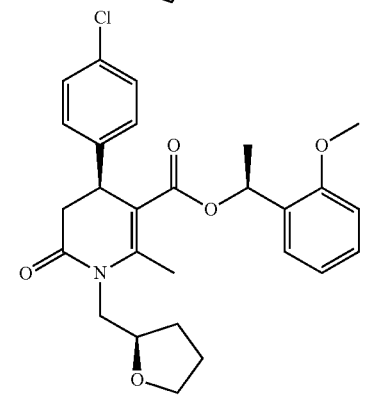
356
-continued
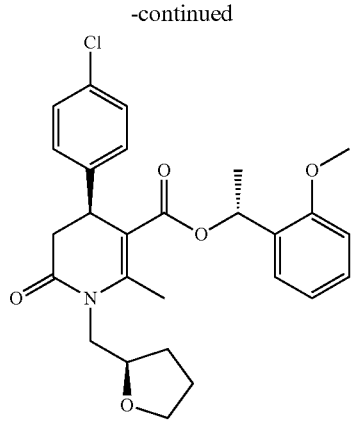
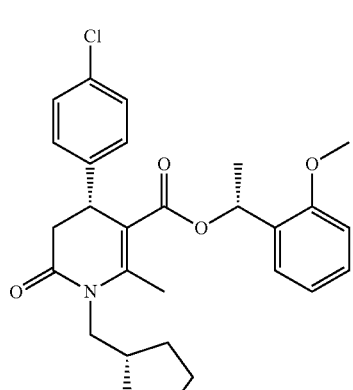
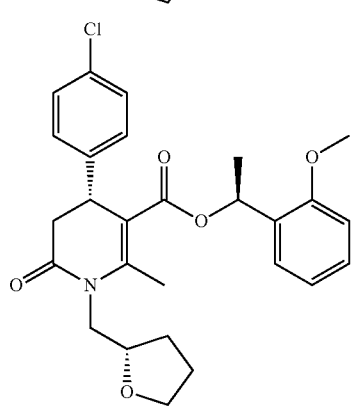
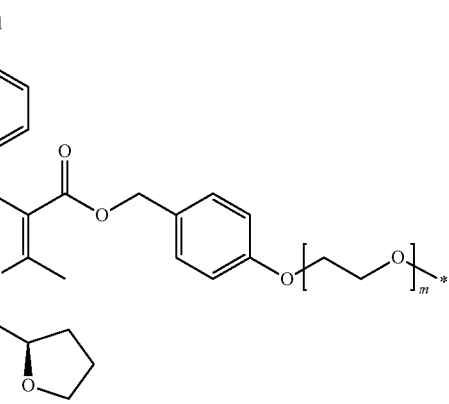
m = 8-13

357
-continued
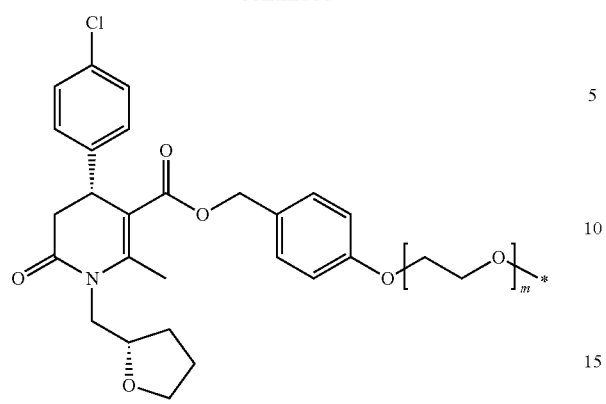
m = 8-13
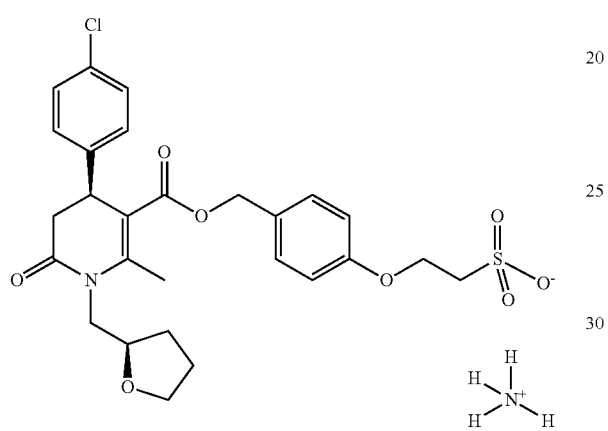
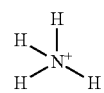
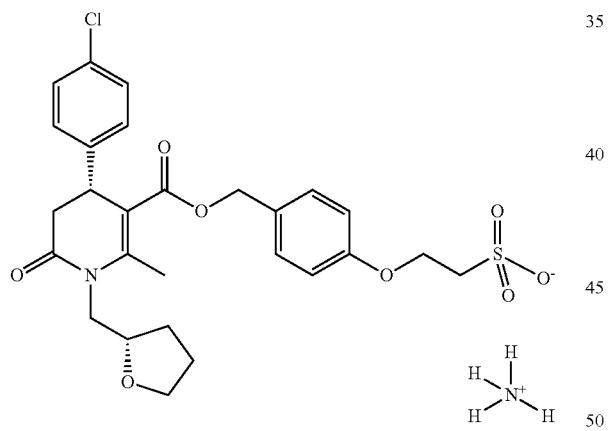
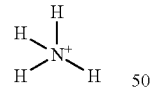
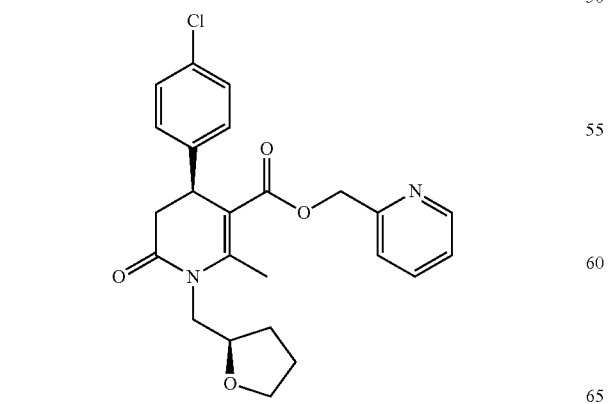
358
-continued
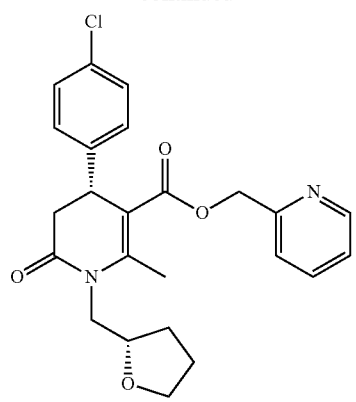
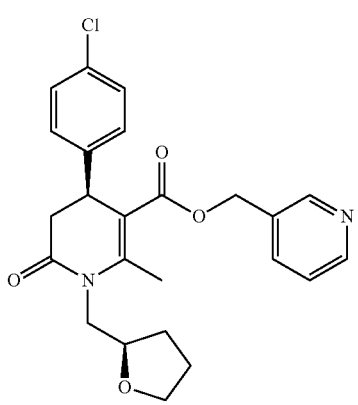
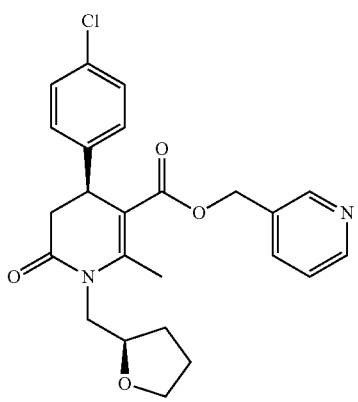
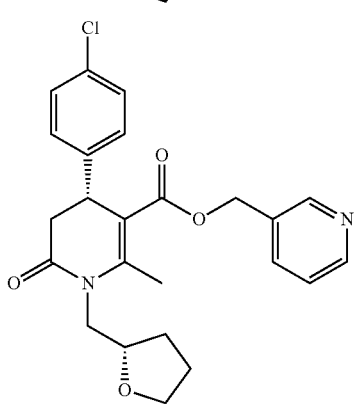

359
-continued
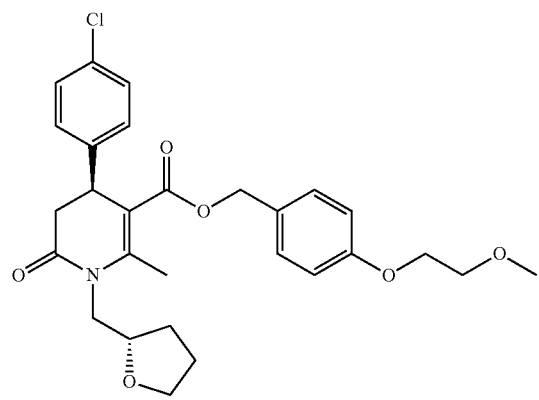
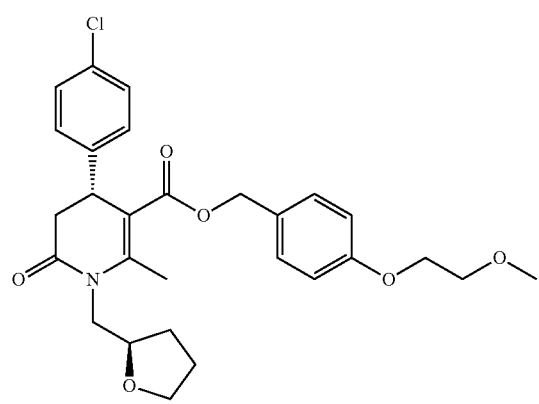
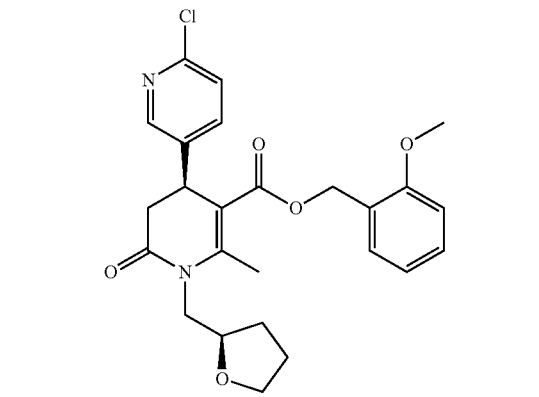
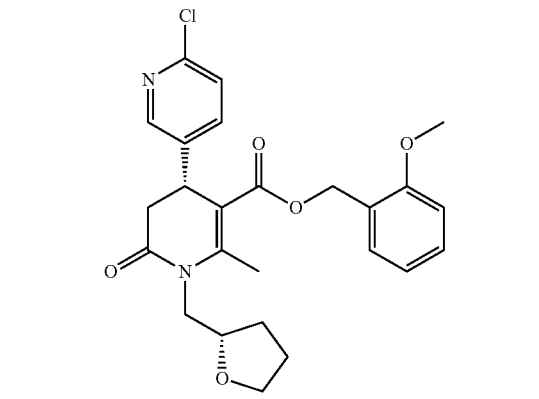
360
-continued
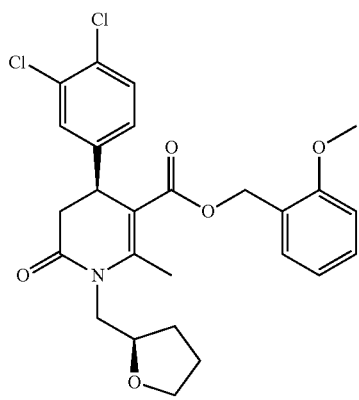
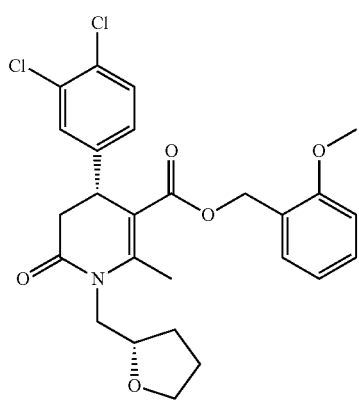
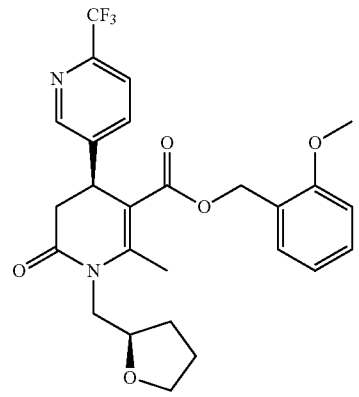
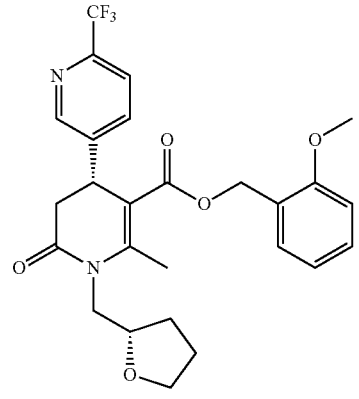

361
-continued
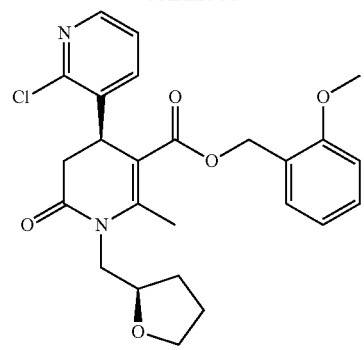
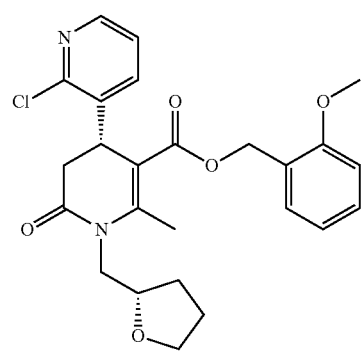
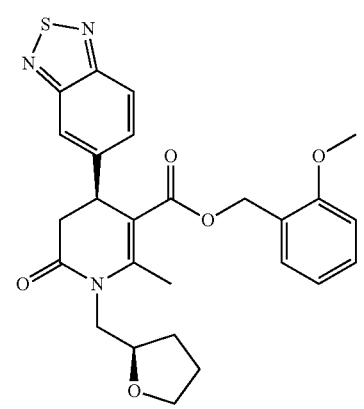
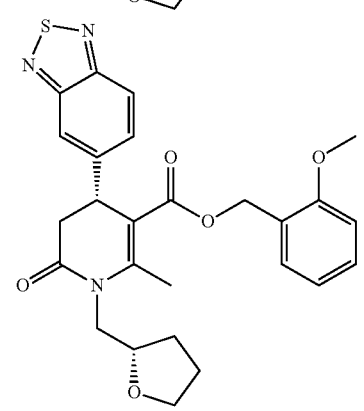
362
-continued
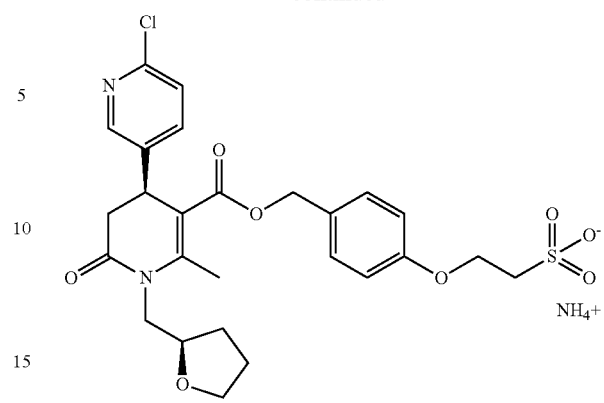
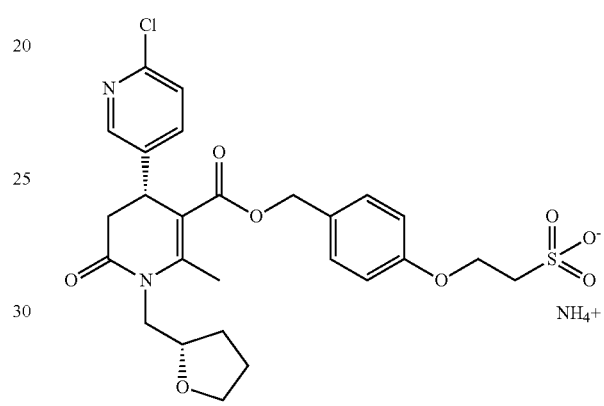
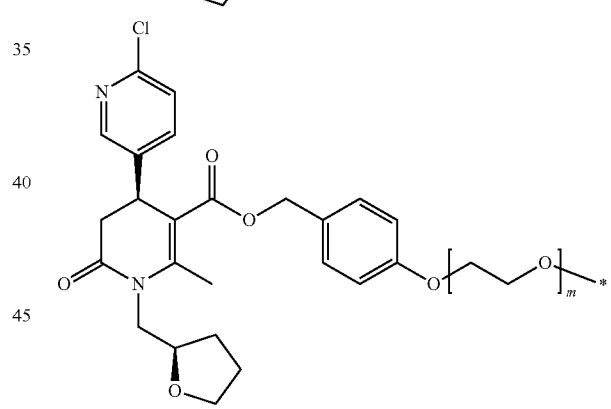
m = 7-10
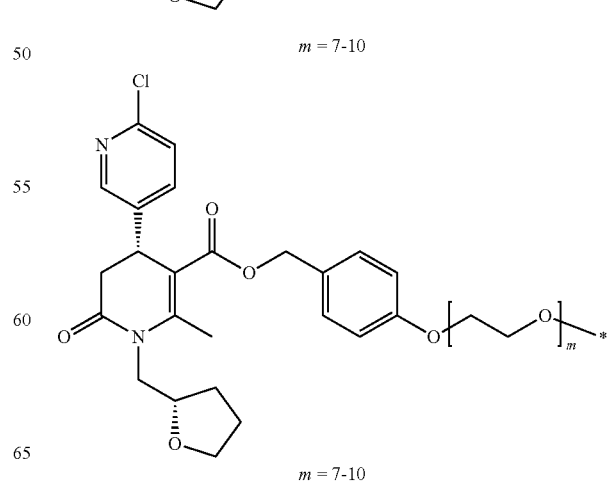
m = 7-10

363
-continued
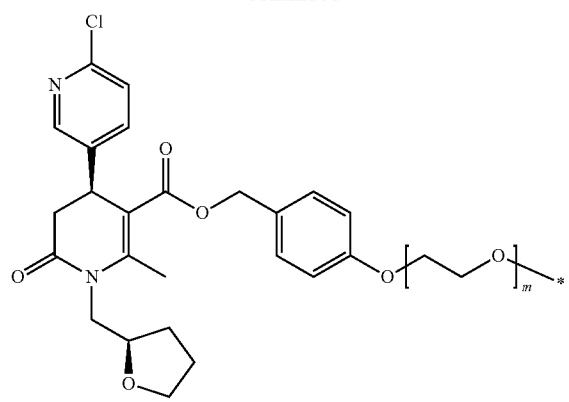
m = 18-23
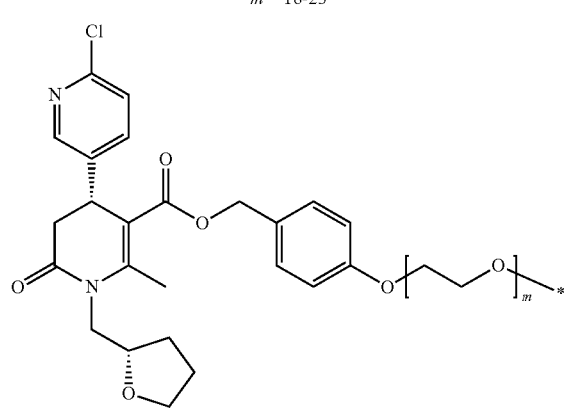
m = 18-23
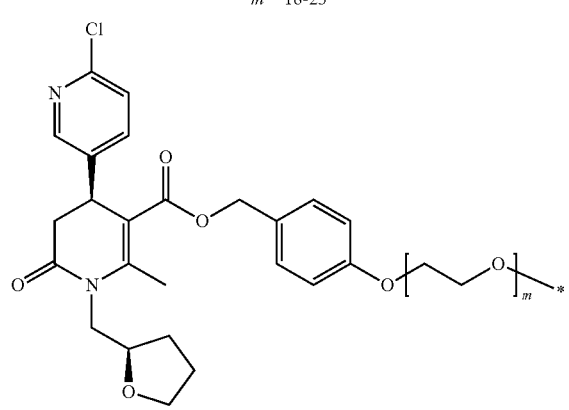
m = 35-44
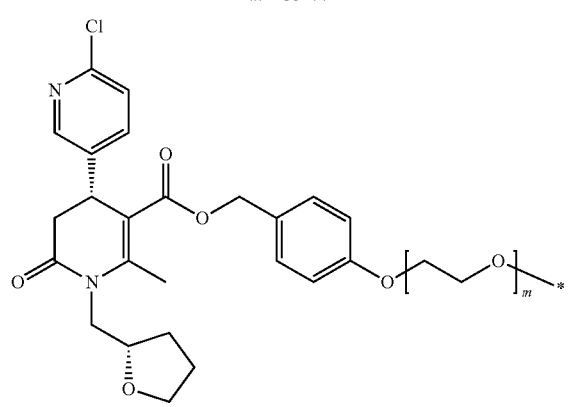
m = 35-44
364
-continued
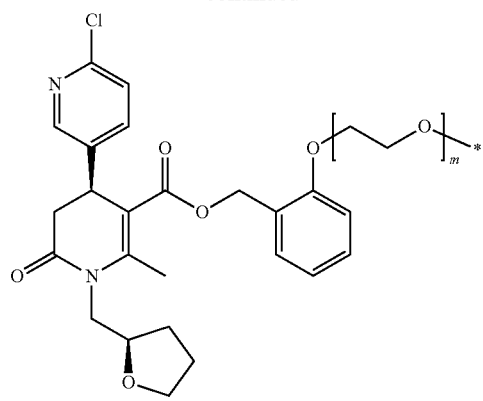
m = 10-14
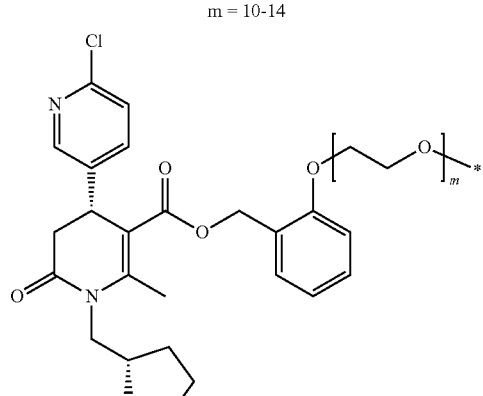
m = 10-14
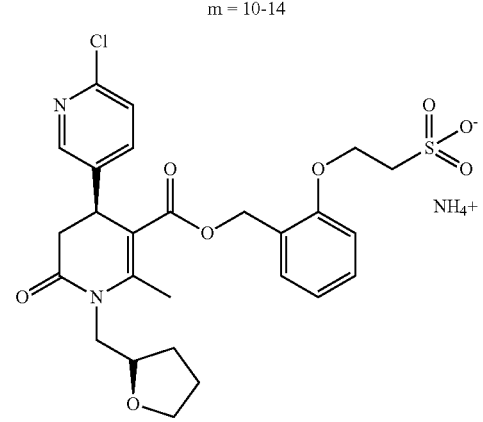
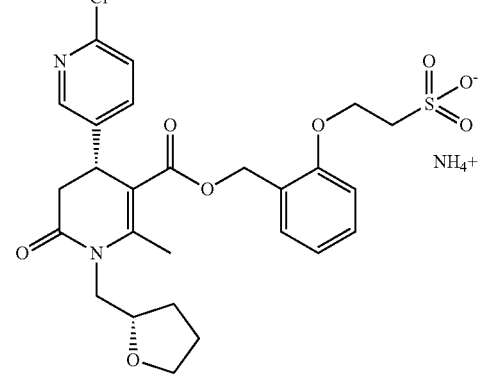

365
-continued
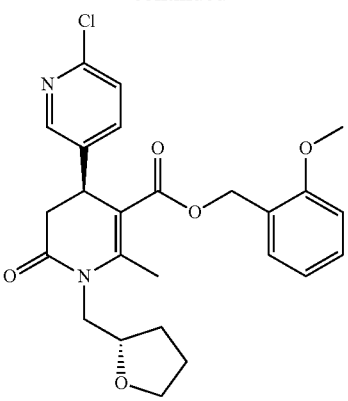
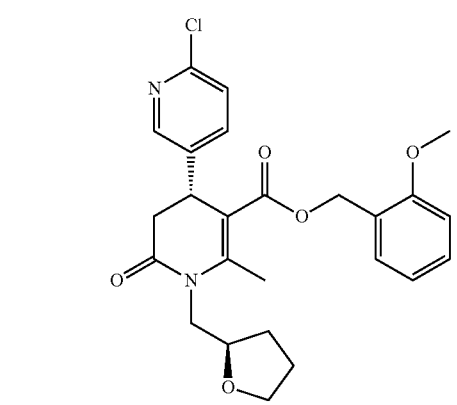
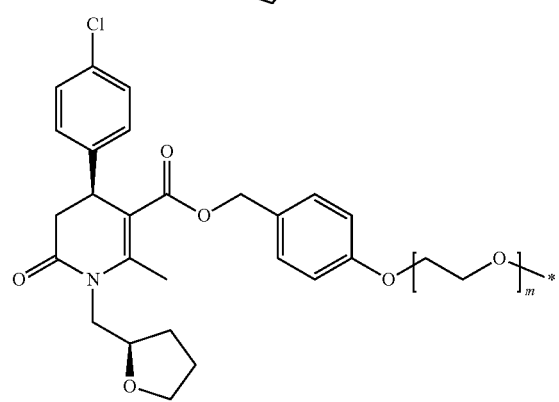
m = 11-18
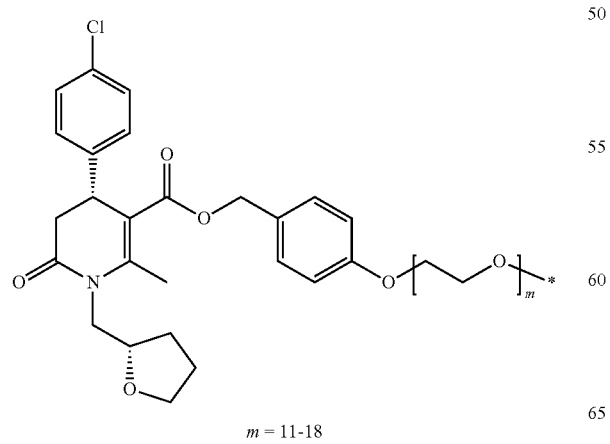
m = 11-18
366
-continued
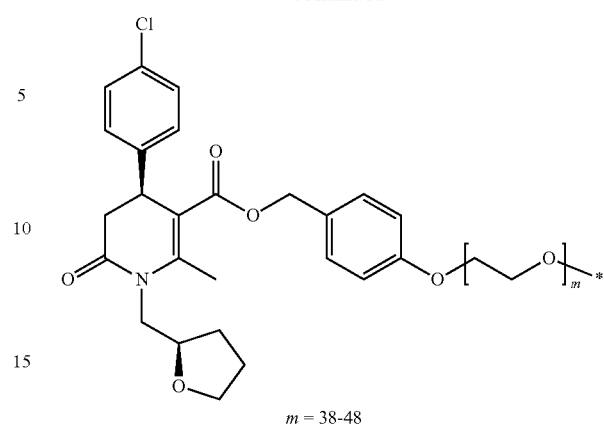
m = 38-48
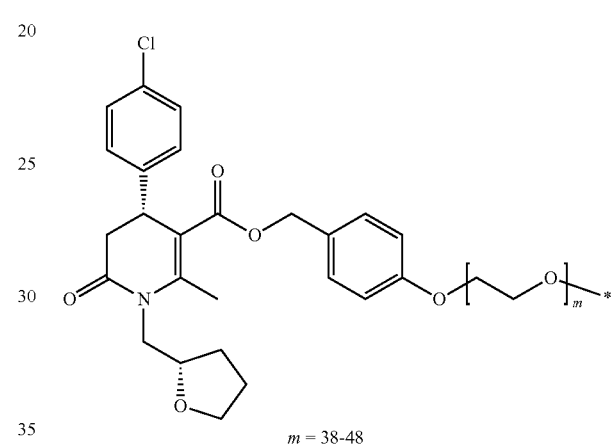
m = 38-48
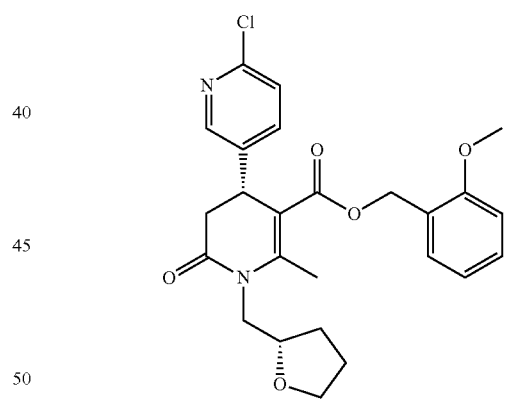
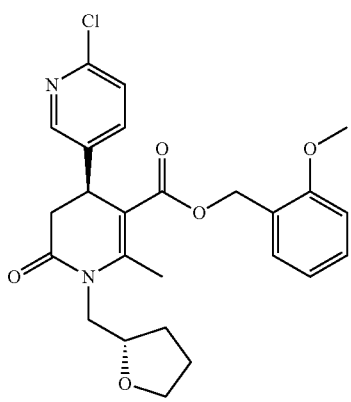

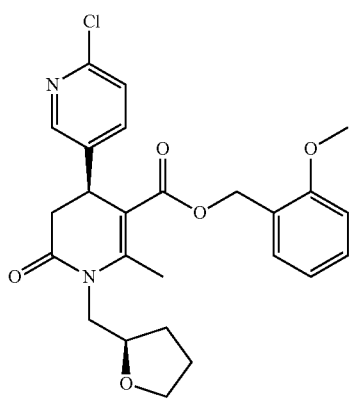

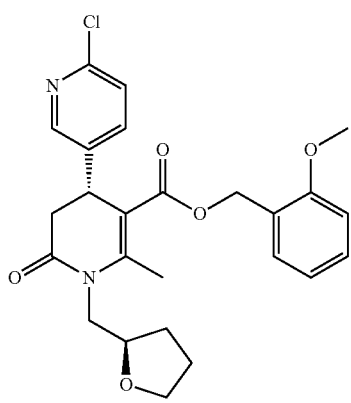

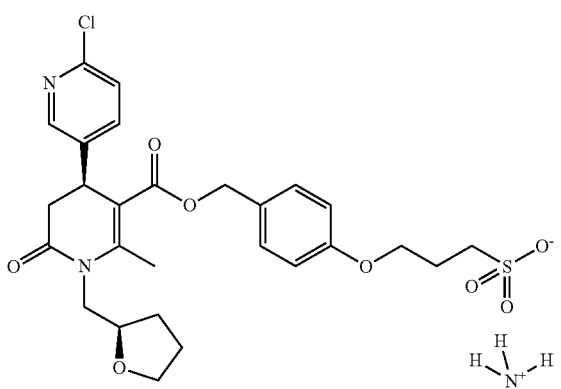

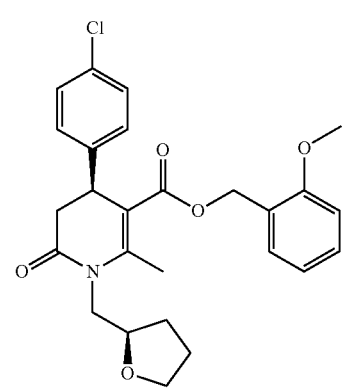

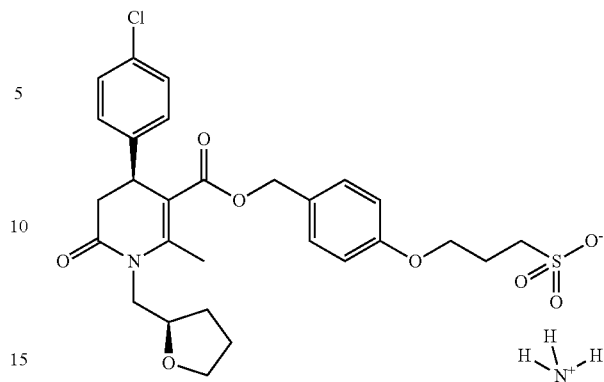

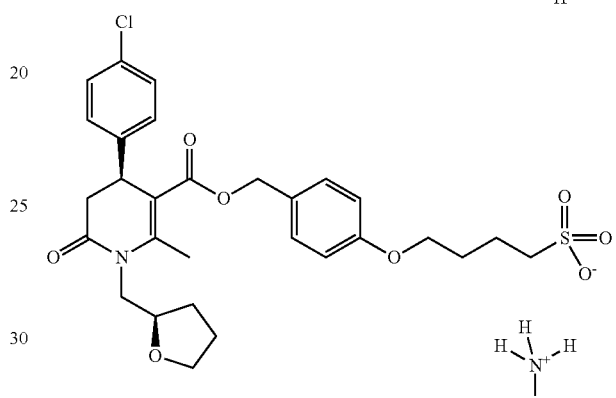

and pharmaceutically acceptable salts, and solvates thereof.

25. The method according to claim 14, wherein the TGR5 related disease is selected from metabolic and/or gastrointestinal diseases.

26. The method according to claim 14 wherein the disease is a metabolic disease selected from the group consisting of type II diabetes, obesity, dyslipidemia such as mixed or diabetic dyslipidemia, hypercholesterolemia, low HDL cholesterol, high LDL cholesterol, hyperlipidemia, hypertriglyceridemia, hypoglycemia, hyperglycemia, glucose intolerance, insulin resistance, hyperinsulinemia, hypertension, hyperlipoproteinemia, metabolic syndrome, syndrome X, thrombotic disorders, cardiovascular disease, atherosclerosis and its sequelae including angina, claudication, heart attack, stroke and others, kidney diseases, ketoacidosis, nephropathy, diabetic neuropathy, diabetic retinopathy, nonalcoholic fatty liver diseases such as steatosis or nonalcoholic steatohepatitis (NASH).

27. The method according to claim 14, wherein the disease is a gastrointestinal disease selected from the group consisting of Inflammatory Bowel Diseases (IBD), Irritable Bowel Syndrome (IBS), intestinal injury disorders, diseases involving intestinal barrier dysfunction, and gastrointestinal disorders characterized by hypermotilenemia or gastrointestinal hypermotility.

28. A method for modulating TGR5 receptor activity, in a patient, in need of such treatment, which comprises administering to said patient an effective amount of a compound of Formula I

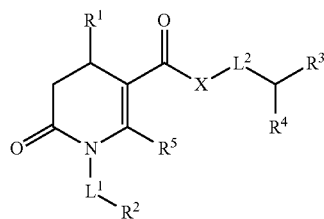

or pharmaceutically acceptable salts or solvates thereof, wherein

R¹ is C1-C6-alkyl, aryl or heteroaryl, wherein said aryl moiety is independently substituted by one or more groups selected from the group consisting of halo, cyano, C1-C2-alkyl, C1-C2-alkoxy, C1-C2-haloalkyl, and 5- or 6-membered aryl, and said heteroaryl moiety is optionally independently substituted by one or more groups selected from the group consisting of halo, cyano, C1-C2-alkyl, C1-C2-alkoxy, C1-C2-haloalkyl, and 5- or 6-membered aryl;

L¹ is a single bond or $(CH_2)_n$, wherein n is 1, 2 or 3;

R² is H, C1-C4 alkyl, alkenyl, alkynyl, alkoxy, hydroxy, hydroxycarbonyl, alkoxycarbonyl, carbamoyl, aminoalkyl, alkylaminoalkyl, dialkylaminoalkyl, alkoxycarbonylamino, cyano, alkylsulfonyl, aralkyl, cycloalkyl, heterocyclyl, or heteroaryl, wherein said heterocyclyl moiety is optionally substituted by one or more substituents independently selected from the group consisting of alkyl and alkoxycarbonyl, and said heteroaryl moiety is optionally substituted by one or more C1-C2-alkyl;

L² is a single bond or $(CH_2)_n$, wherein n is 1 or 2;

R³ is aryl, heteroaryl, cycloalkyl or arylcarbonyl wherein each of said moieties is optionally substituted by one or more substituents independently selected from the group consisting of halo, alkyl, haloalkyl, aryl, cyano, alkoxy, haloalkoxy, alkoxycarbonyl, aminoalkoxy, alkylaminoalkoxy, dialkylaminoalkoxy, HO₃S-alkoxy,

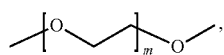

wherein m is 1 to 500, $[N(R^8)_3\text{-alkoxy}]^+ Q^-$, wherein $R^8$ is linear C1-C4-alkyl and $Q^-$ is a counter anion, and a cyclic moiety selected from the group consisting of

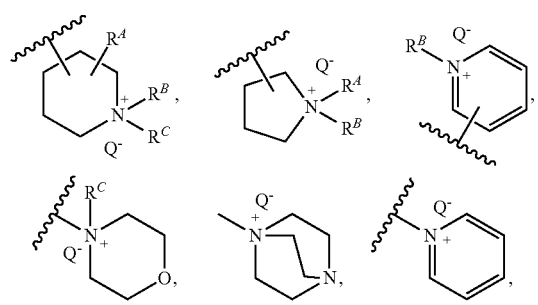

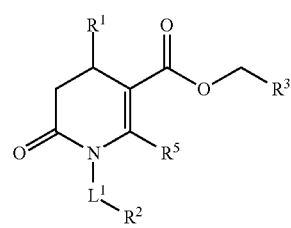

wherein $R^A$ is H, OH, C0-C4-alkyl-COOH or C1-C6-alkyl, $R^B$ is C1-C6-alkyl optionally substituted with —COOH, $R^C$ is C1-C6-alkyl, and $Q^-$ is a counter anion;

or wherein said cycloalkyl moiety is fused to 4 an aryl, preferably phenyl, moiety;

R⁴ is H, C1-C2-alkyl or 5- or 6-membered aryl;

R⁵ is H, C1-C4-alkyl, 5- or 6-membered aryl, or alkoxyalkyl; and

X is O or NR', wherein R' is H, C1-C2-alkyl or R' taken together with L² and R³ form a 5- or 6-membered heterocyclyl moiety which is optionally fused to an aryl moiety.

29. The method according to claim 28 wherein the compound has Formula II

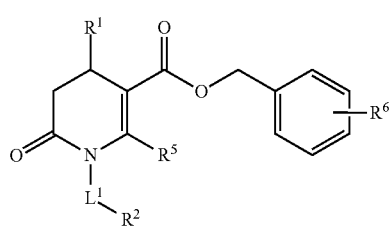

and pharmaceutically acceptable salts and solvates thereof.

30. The method according to claim 28 wherein the compound has Formula IIa

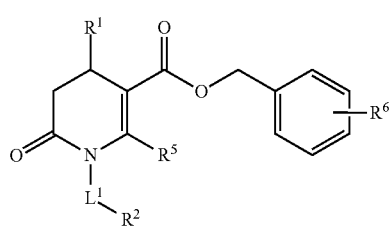

and pharmaceutically acceptable salts, and solvates thereof, wherein

R⁶ is halo, alkyl, haloalkyl, aryl, cyano, alkoxy, haloalkoxy, alkoxycarbonyl, aminoalkoxy, alkylaminoalkoxy, dialkylaminoalkoxy, HO₃S-alkoxy,

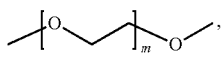

wherein m is 1 to 500,

[N(R⁸)₃-alkoxy]⁺ Q⁻, wherein R⁸ is linear C1-C4-alkyl and Q⁻ is a counter anion, or a cyclic moiety selected from the group consisting of

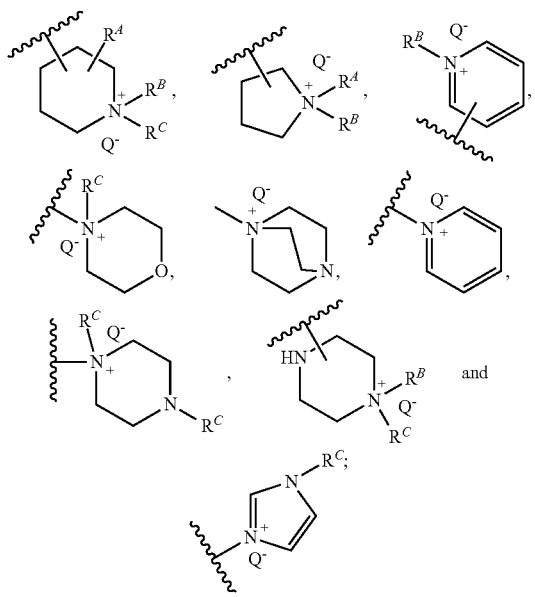

wherein $R^A$ is H, OH, C0-C4-alkyl-COOH or C1-C6-alkyl, $R^B$ is C1-C6-alkyl optionally substituted with —COOH, $R^C$ is C1-C6-alkyl, and Q⁻ is a counter anion.

31. The method according to claim 28 wherein the compound has Formula III

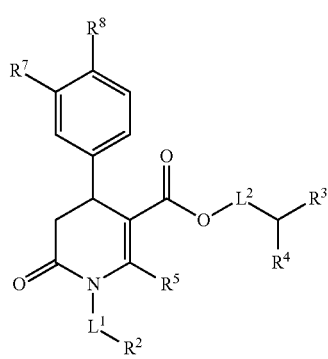

and pharmaceutically acceptable salts, and solvates thereof, wherein $R^7$ and $R^8$ are independently selected from the group consisting of H, halo, haloalkyl, and cyano, with the proviso that at least one of $R^7$ and $R^8$ is not H.

32. The method according to claim 28 wherein the compound has Formula IV

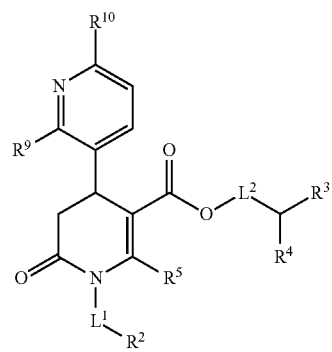

and pharmaceutically acceptable salts, and solvates thereof, wherein $R^9$ and $R^{10}$ are independently selected from the group consisting of H, halo, haloalkyl, and cyano, with the proviso that at least one of $R^9$ and $R^{10}$ is not H.

33. The method according to claim 28 wherein the compound has Formula V

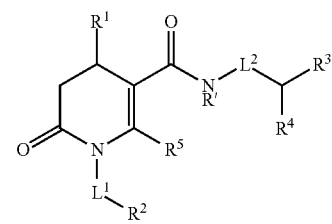

and pharmaceutically acceptable salts, and solvates thereof.

34. The method according to claim 28 wherein $R^5$ is methyl.

35. The method according to claim 28 wherein $L^1$ and $R^2$ are taken together to form a moiety selected from the group consisting of cycloalkylmethyl heterocyclylmethyl, heteroarylmethyl, 2-alkoxyeth-1-yl, 3-alkoxyprop-1-yl, and alkoxycarbonylmethyl, said heteroarylmethyl moiety being optionally substituted by one or more C1-C2 alkyl.

36. The method according to claim 28 wherein $R^2$ is tetrahydrofuranyl.

37. The method according to claim 28 wherein $L^1$ is CH₂.

38. The method according to claim 28, wherein the compound is selected from the group consisting of

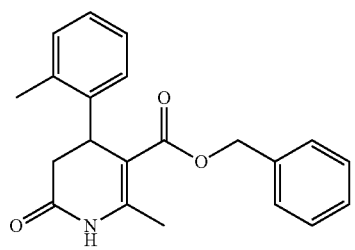

373
-continued
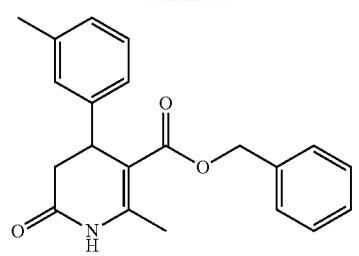
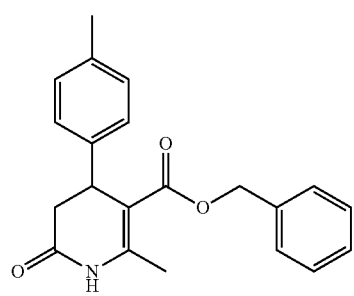
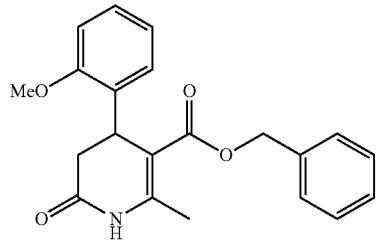
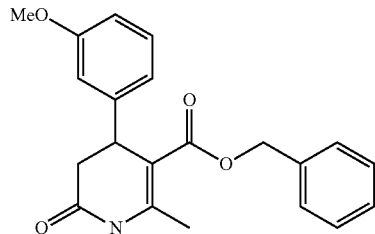
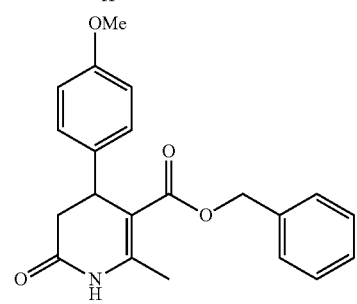
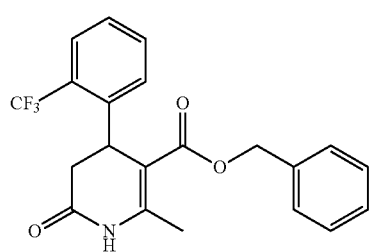
374
-continued
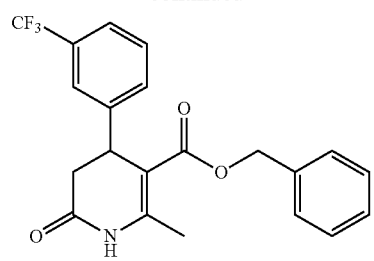
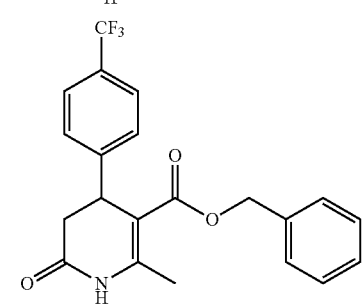
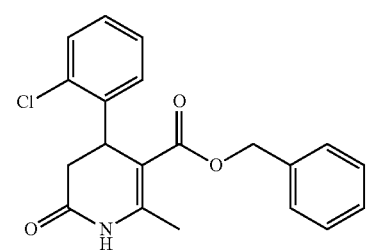
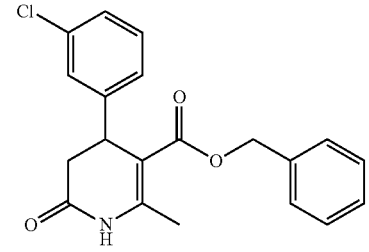
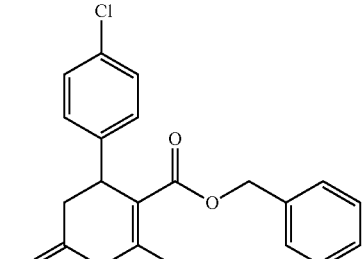
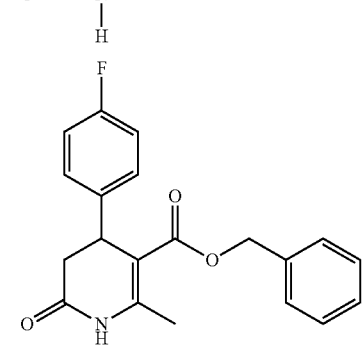

375
-continued
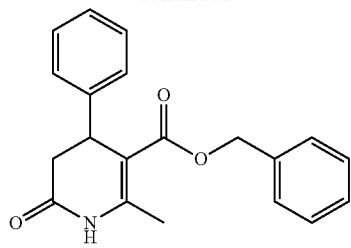
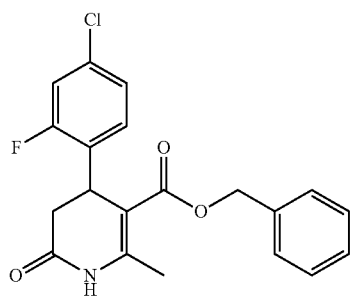
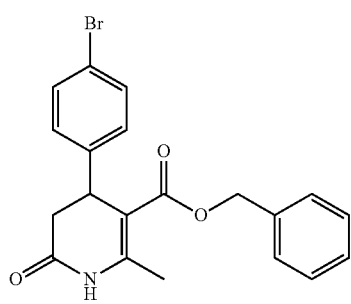
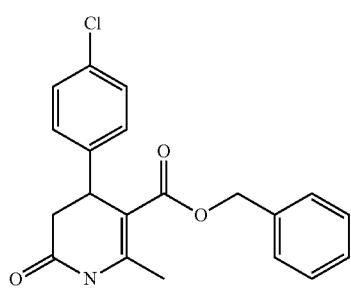
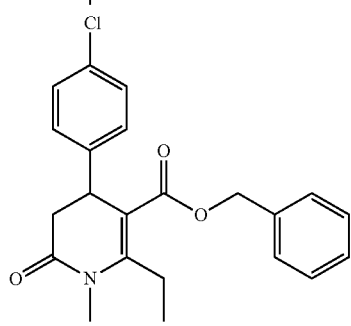
376
-continued
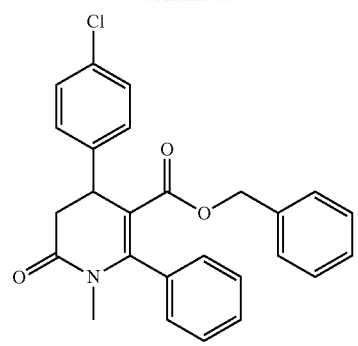
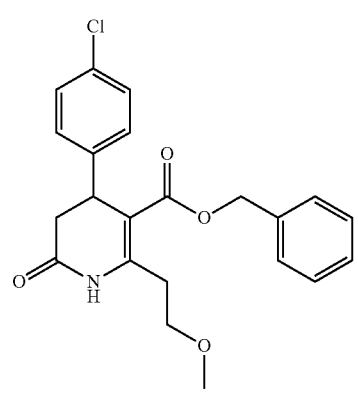
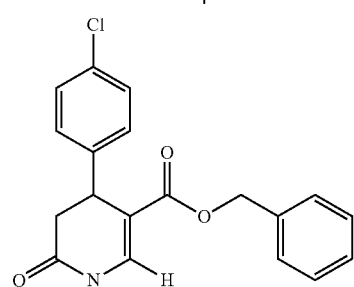
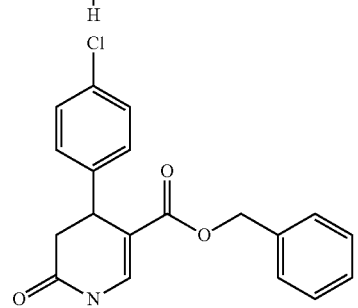
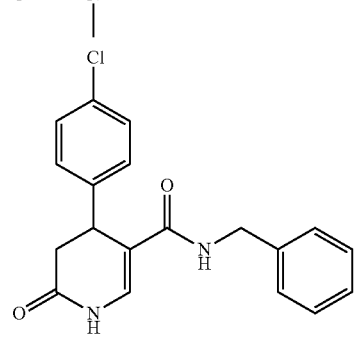

377
-continued
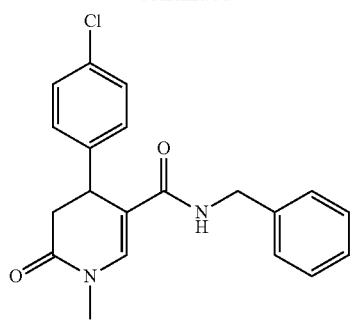
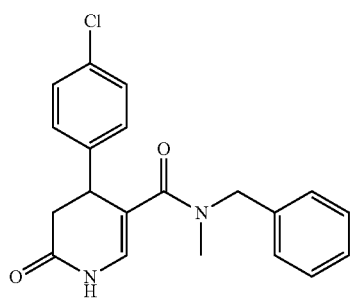
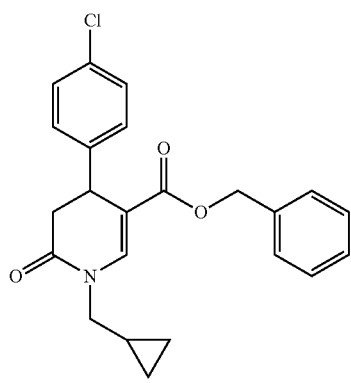
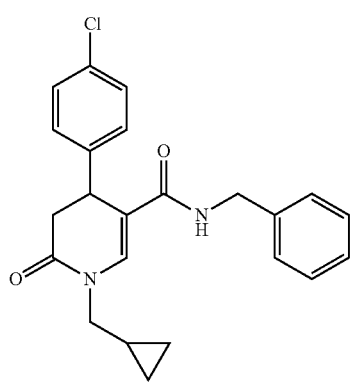
378
-continued
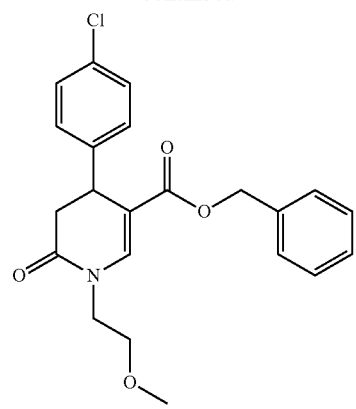
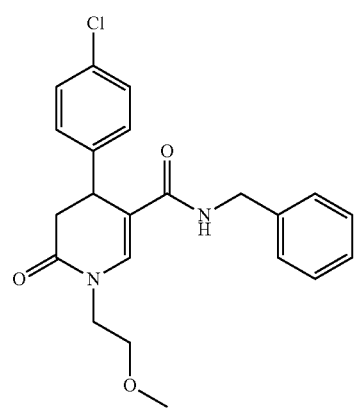
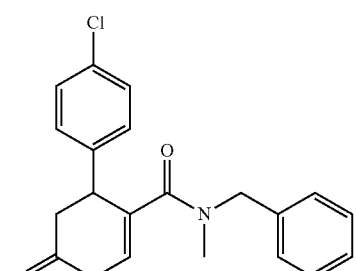
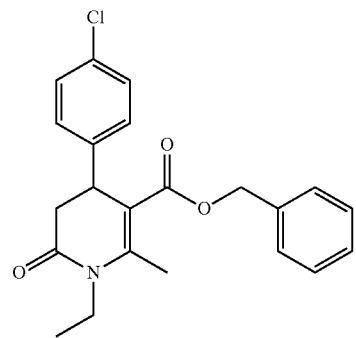

379
-continued
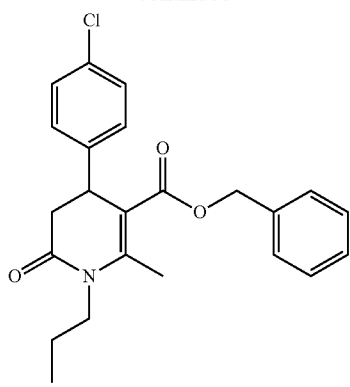
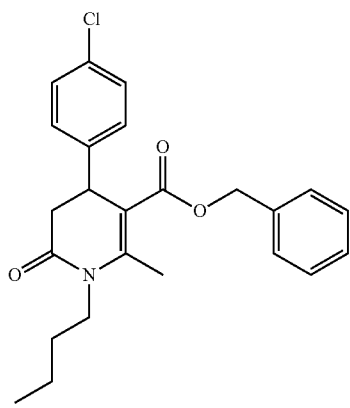
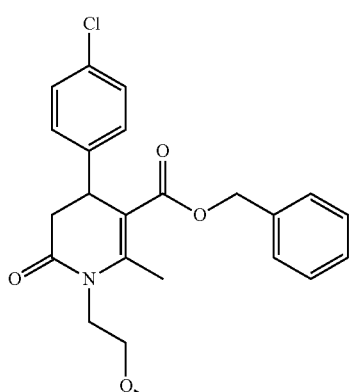
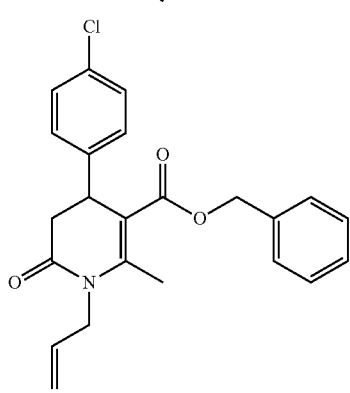
380
-continued
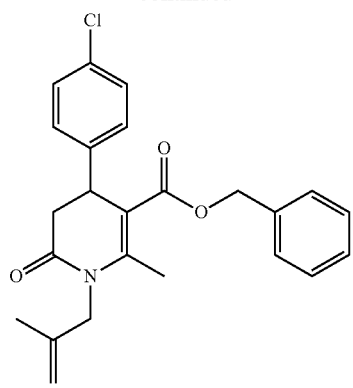
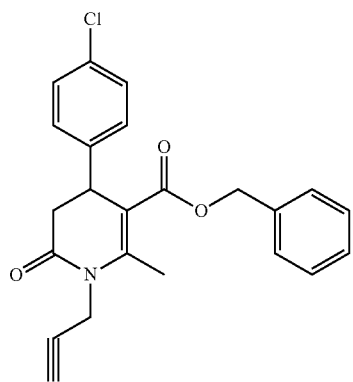
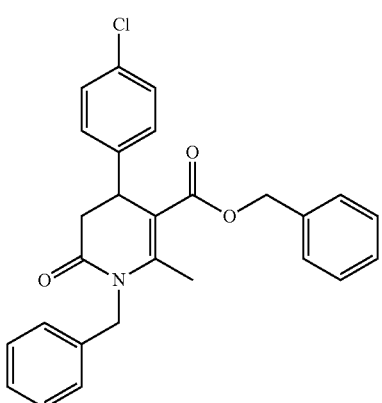
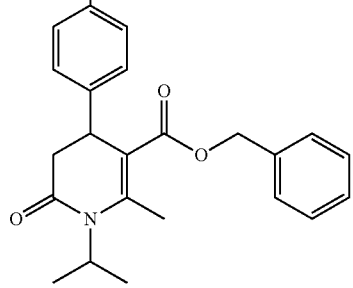

381
-continued
382
-continued
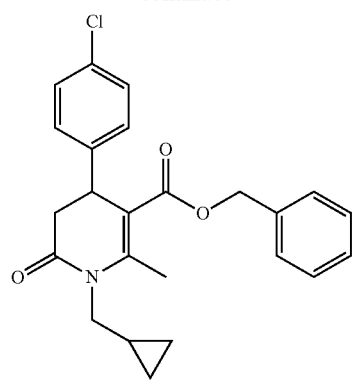
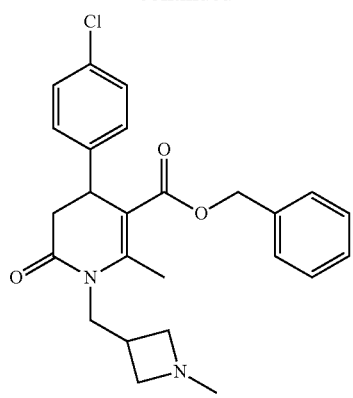

383
-continued
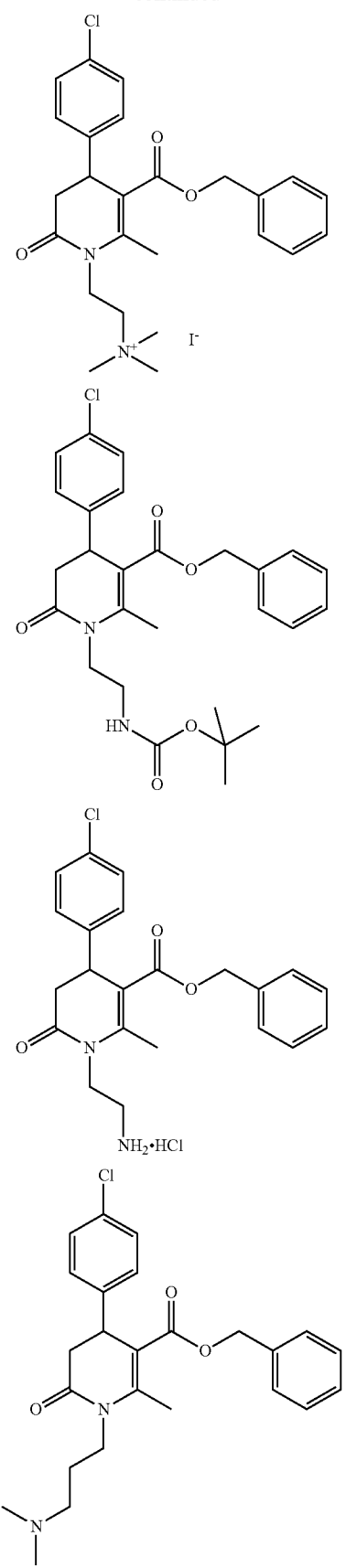
384
-continued
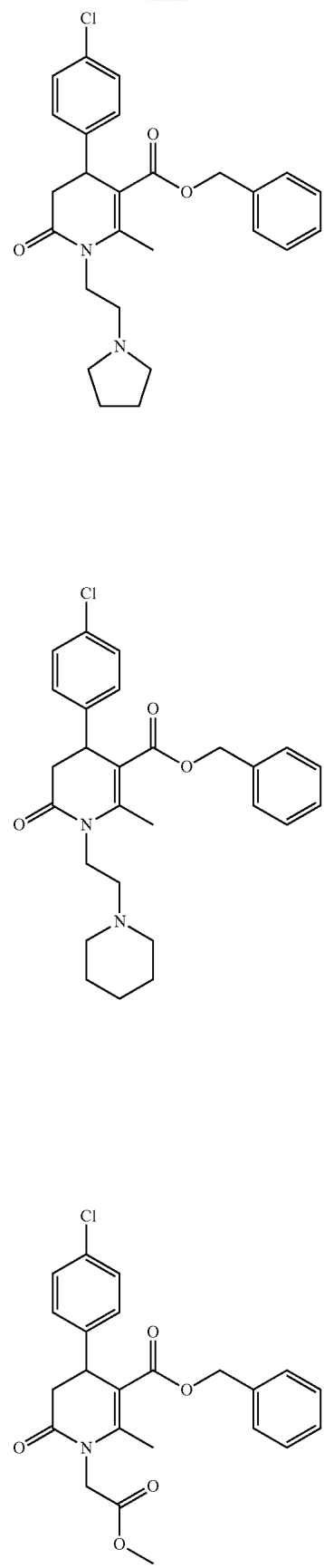

385
-continued
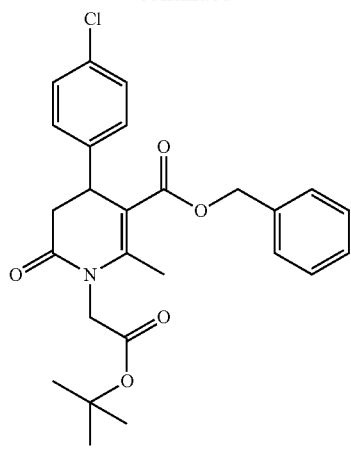
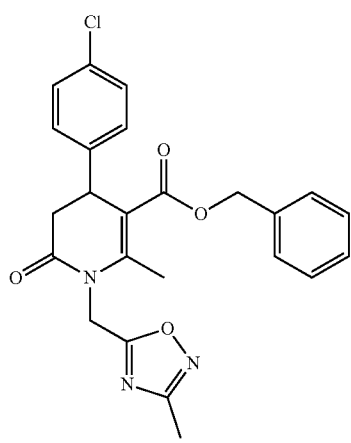
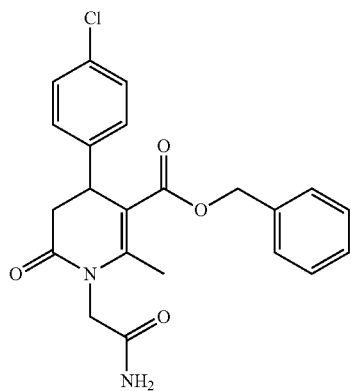
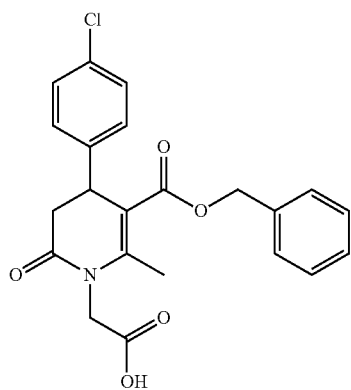
386
-continued
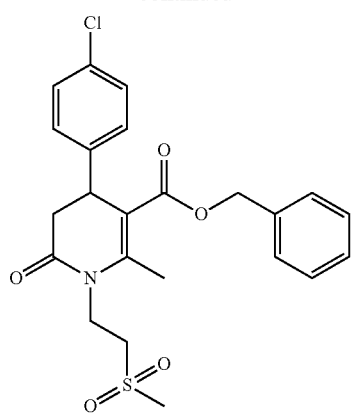
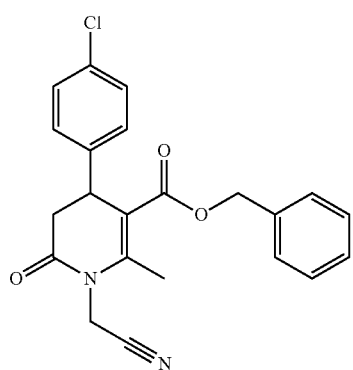
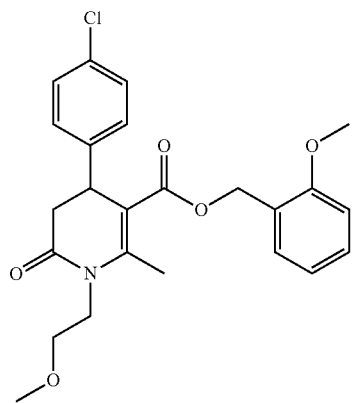
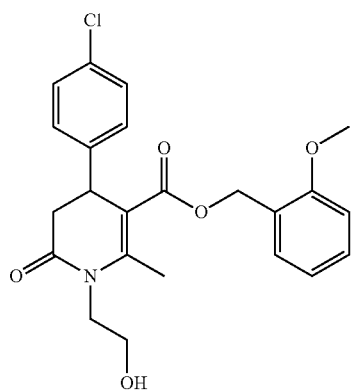

387
-continued
388
-continued
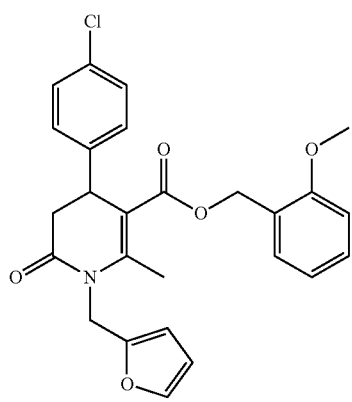
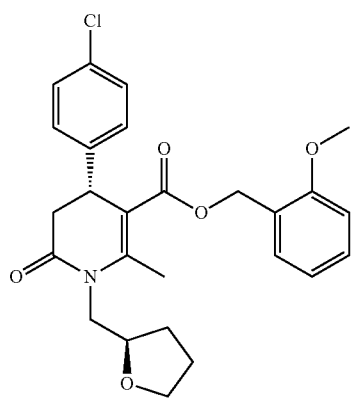

389
-continued
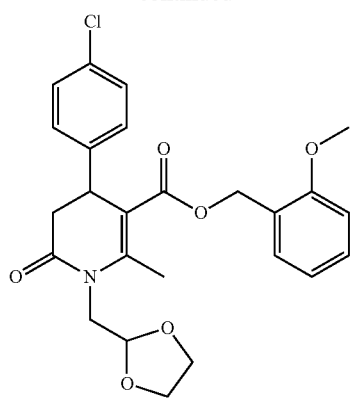
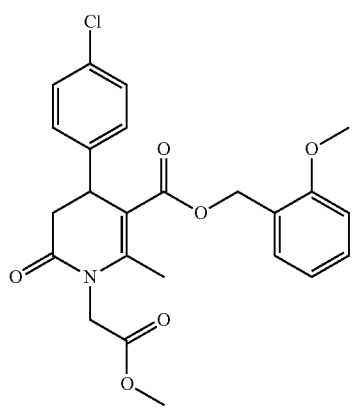
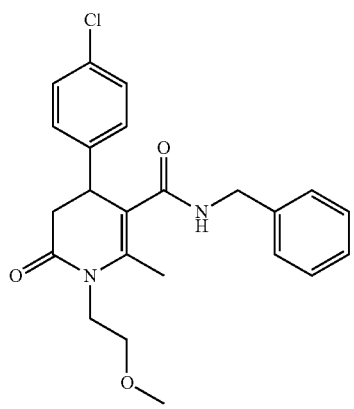
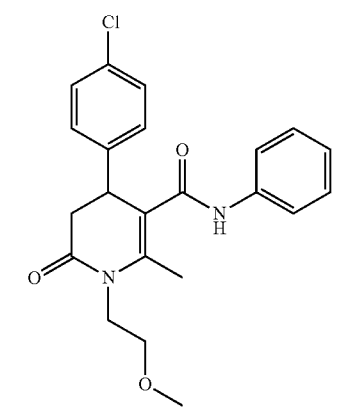
390
-continued
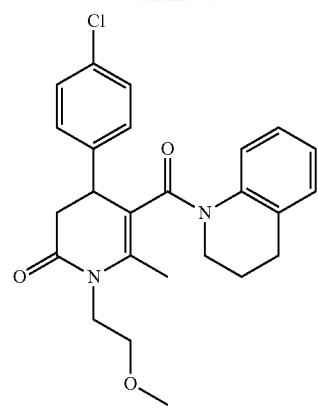
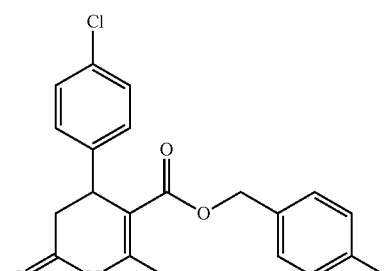
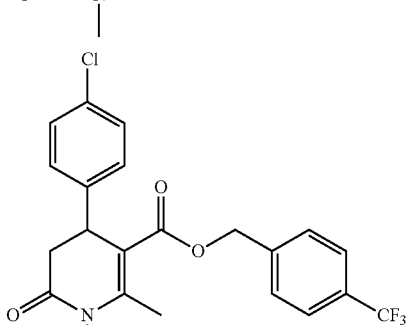
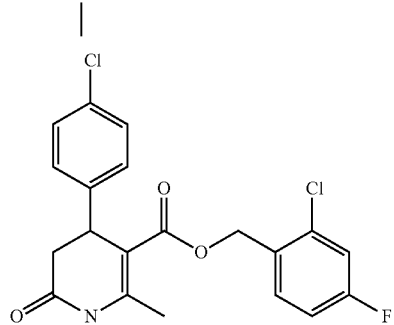
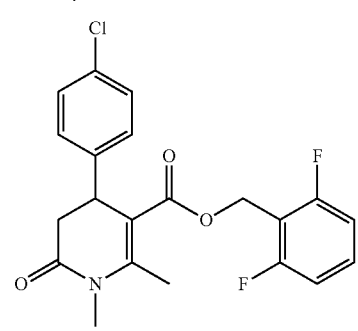

391
-continued
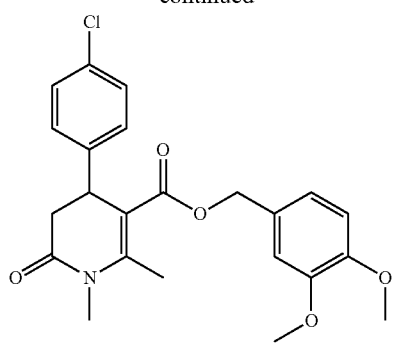
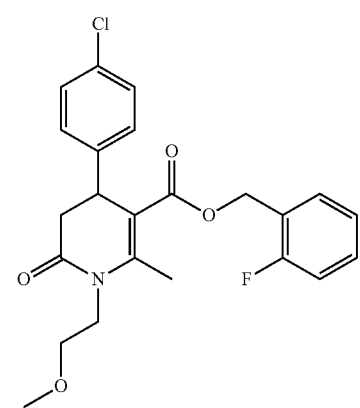
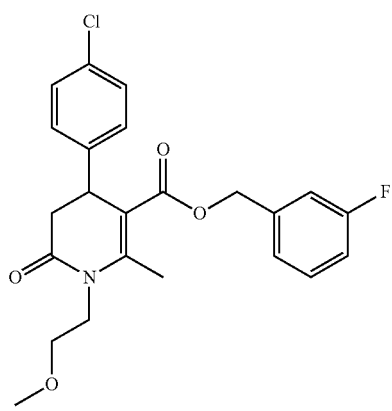
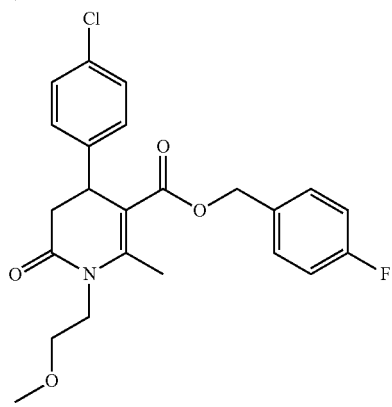
392
-continued
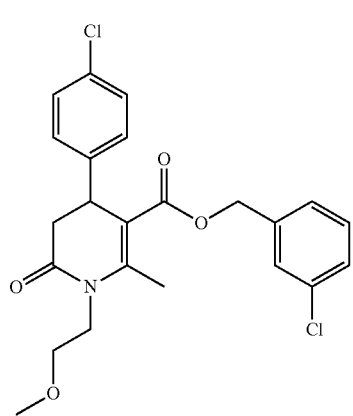
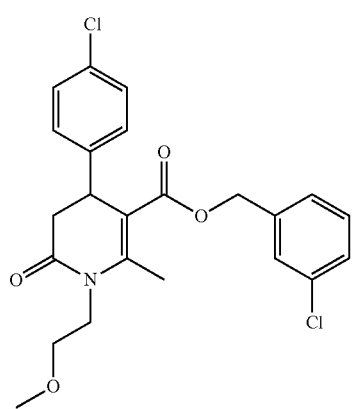
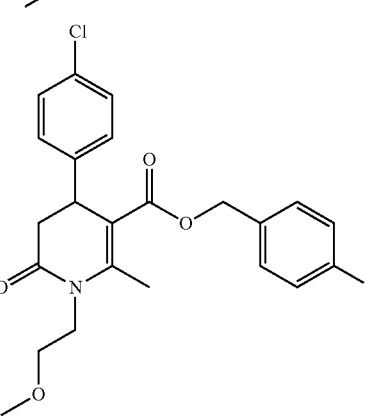
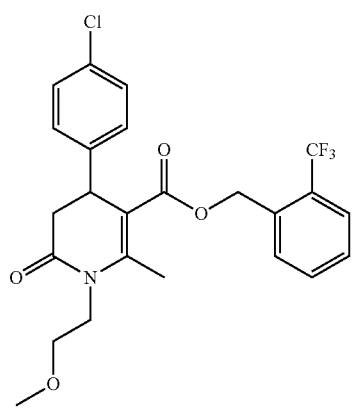

393
-continued
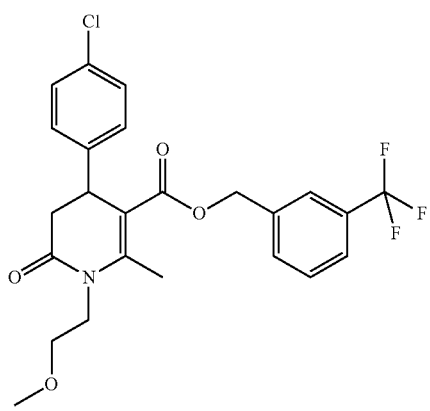
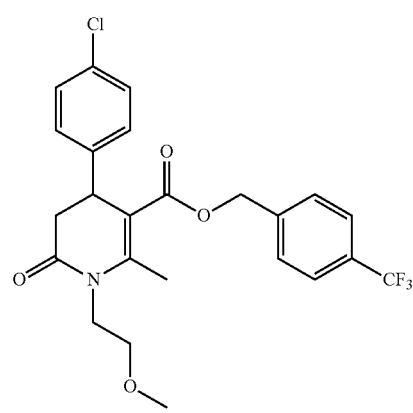
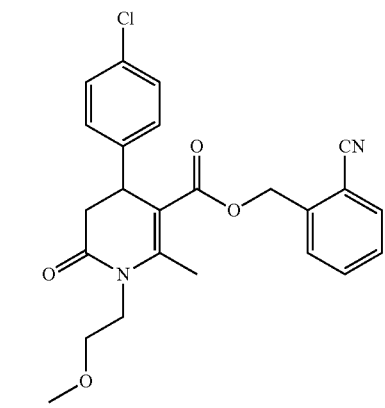
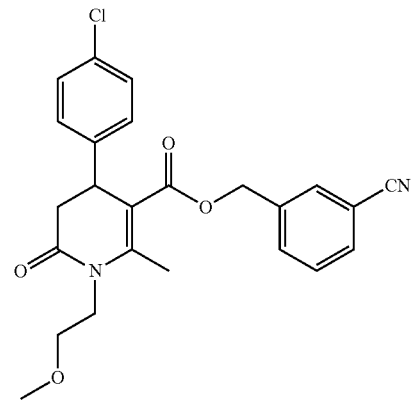
394
-continued
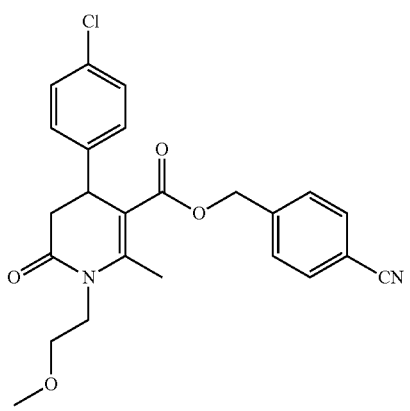
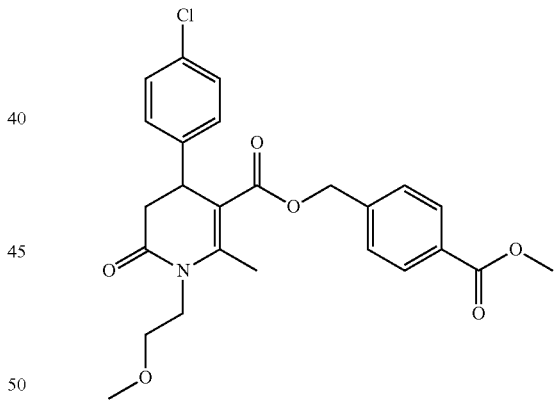
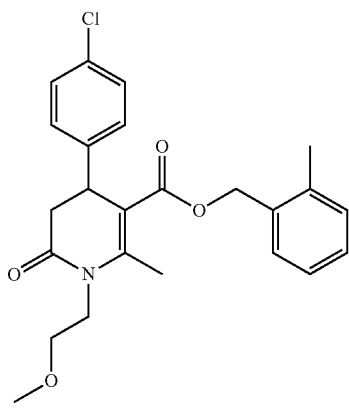

395
-continued
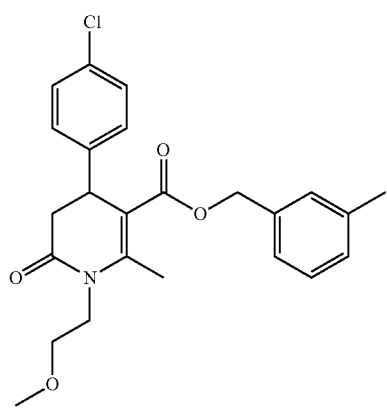
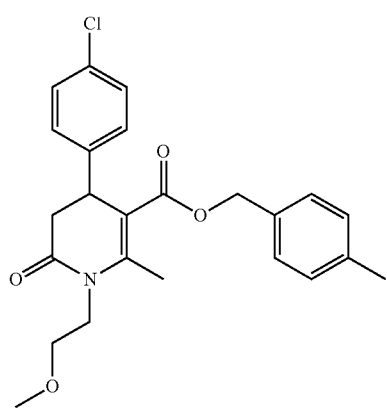
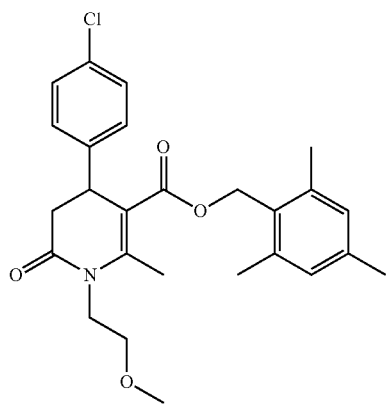
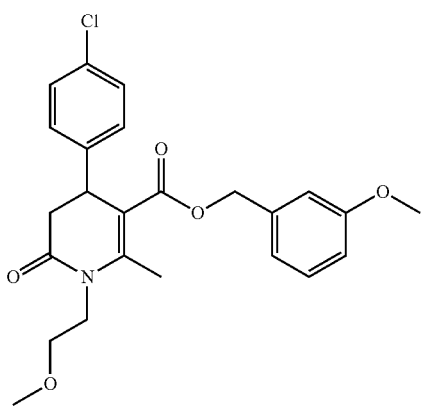
396
-continued
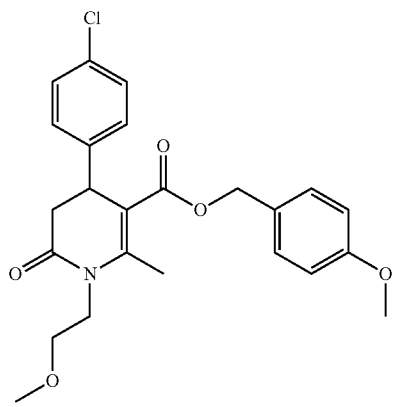
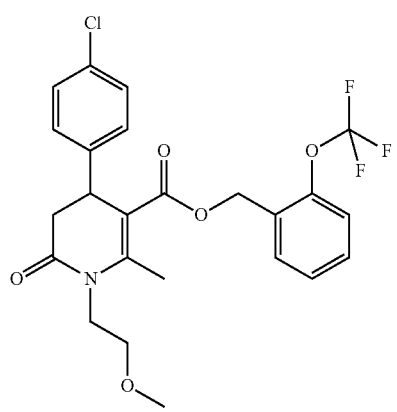
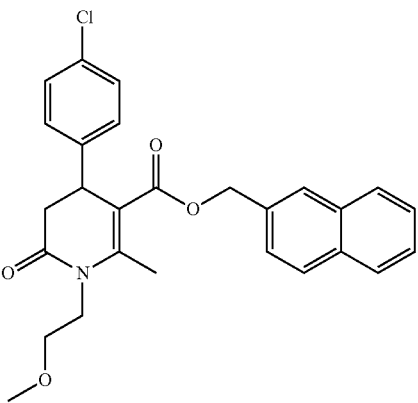
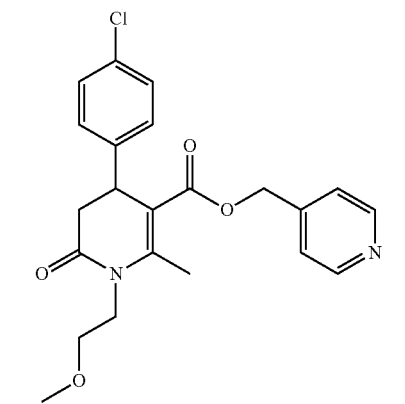

397
-continued
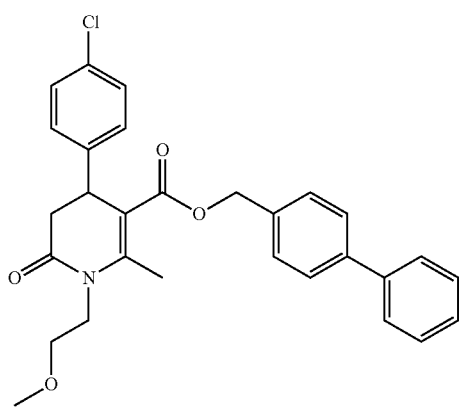
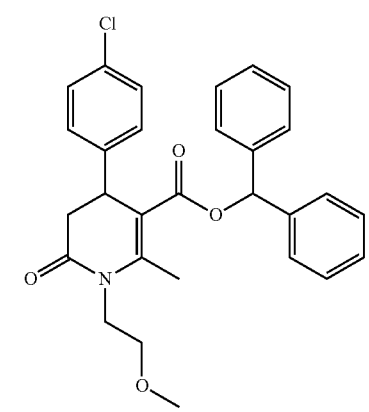
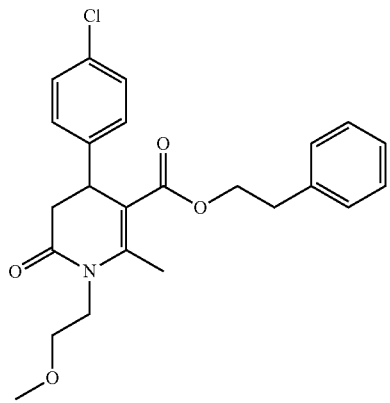
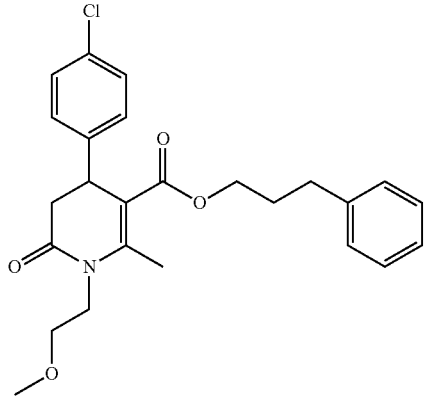
398
-continued
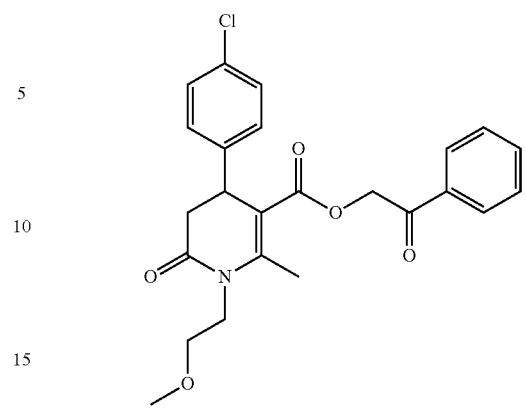
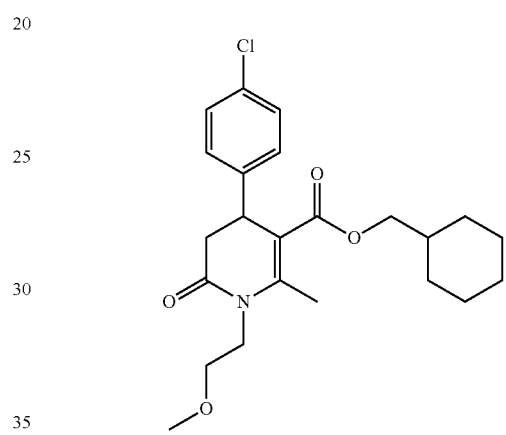
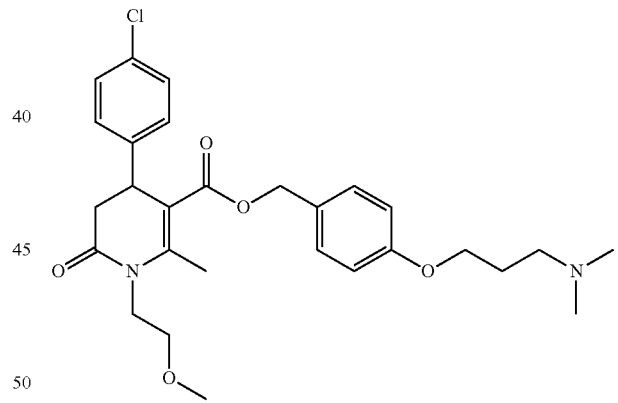
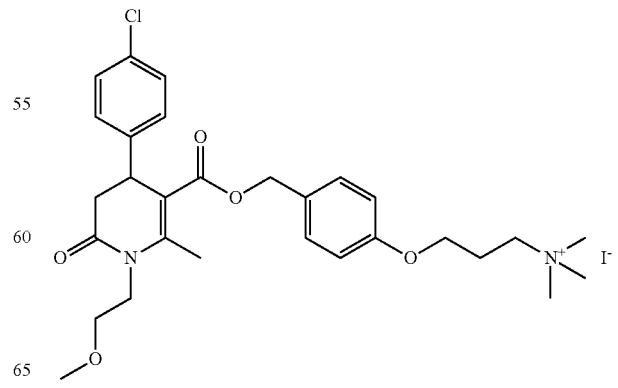

399
-continued
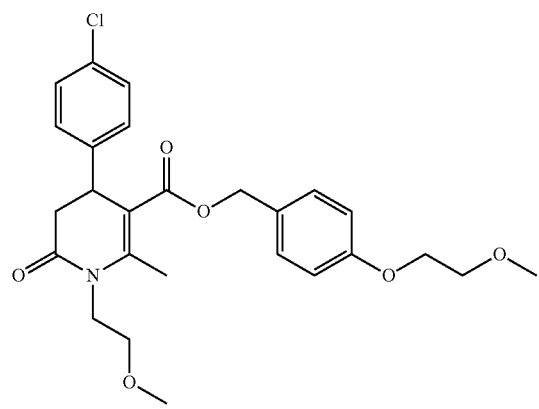
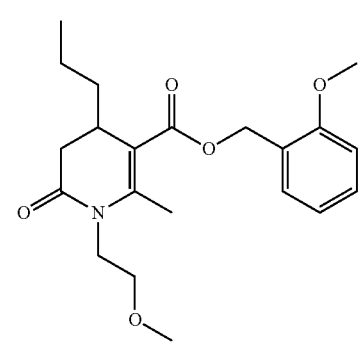
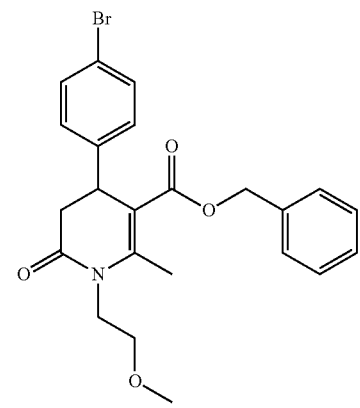
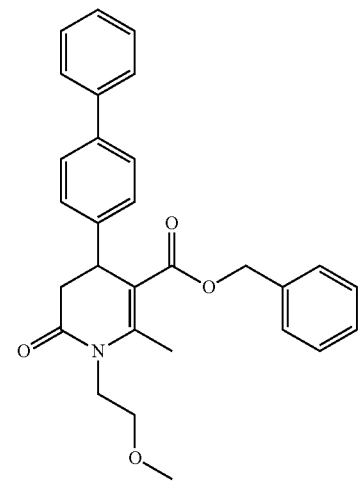
400
-continued
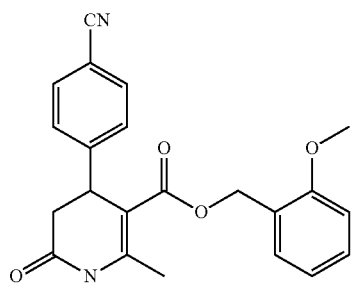
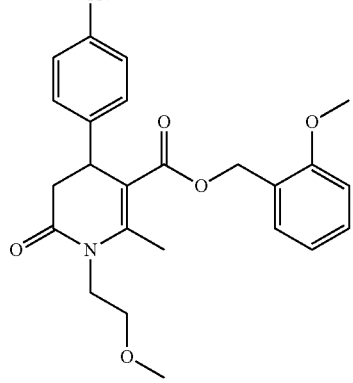
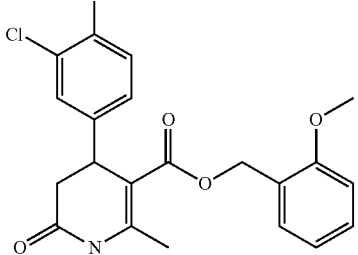
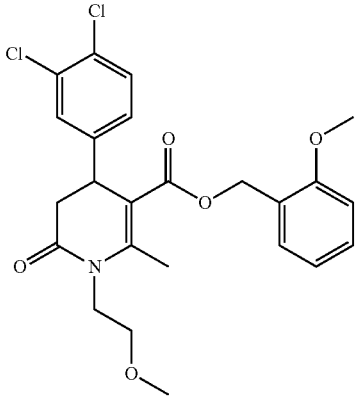
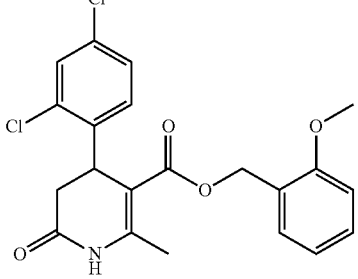

401
-continued
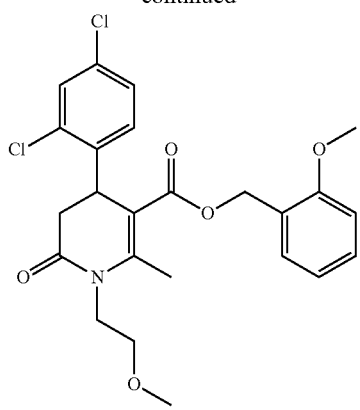
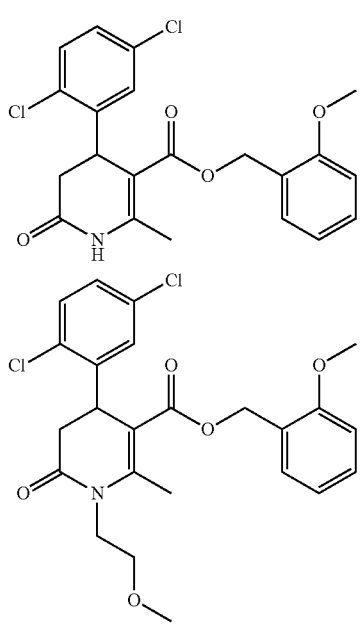
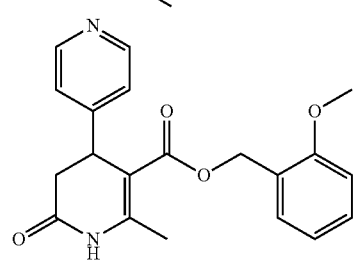
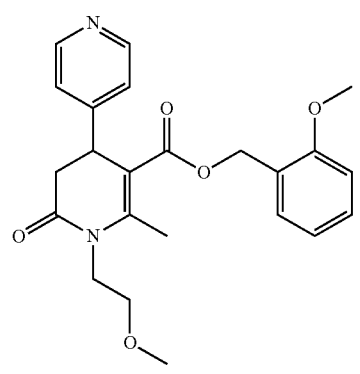
402
-continued
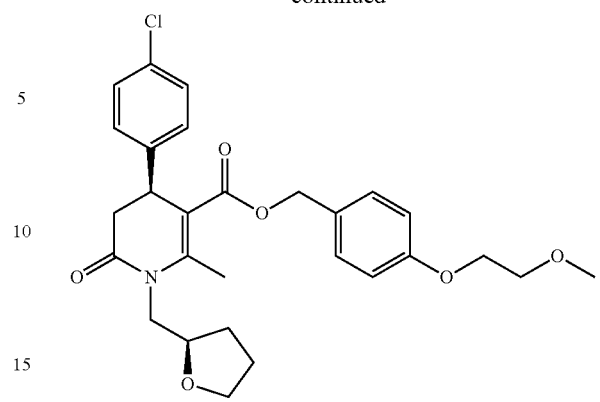
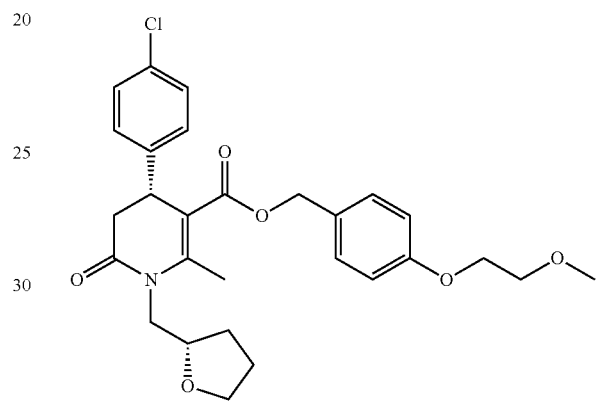
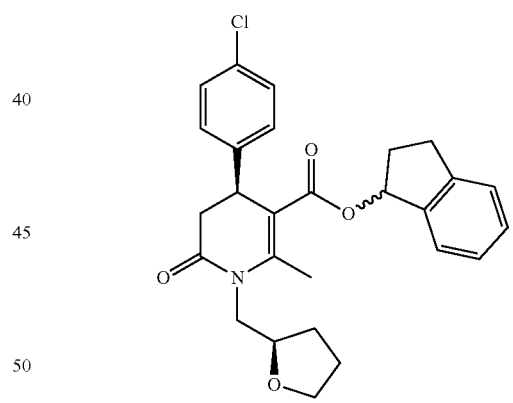
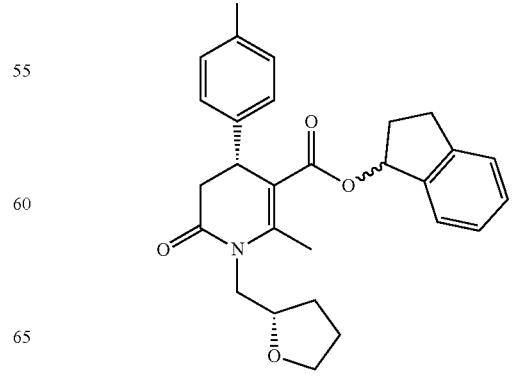

403
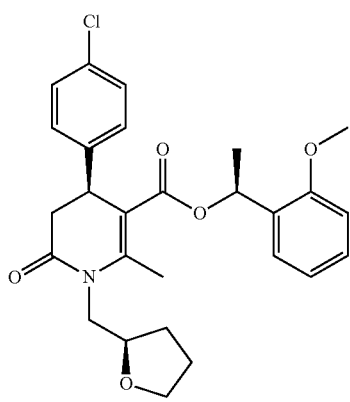
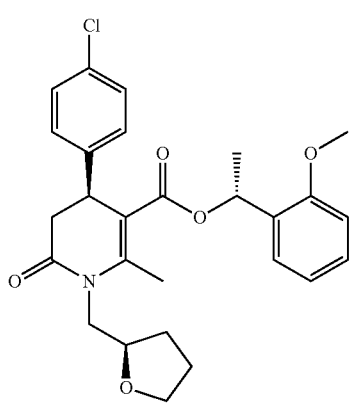
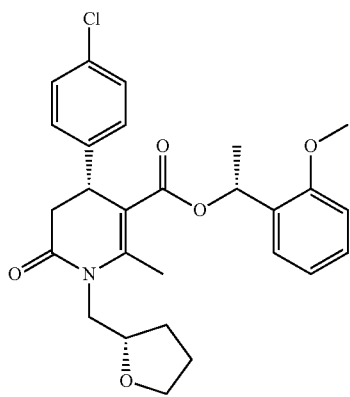
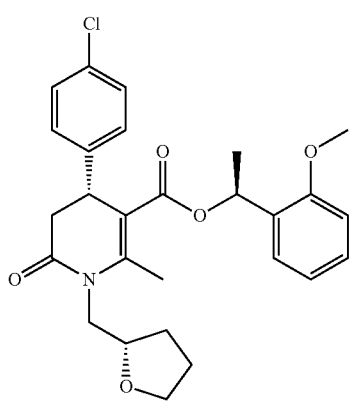
404
-continued
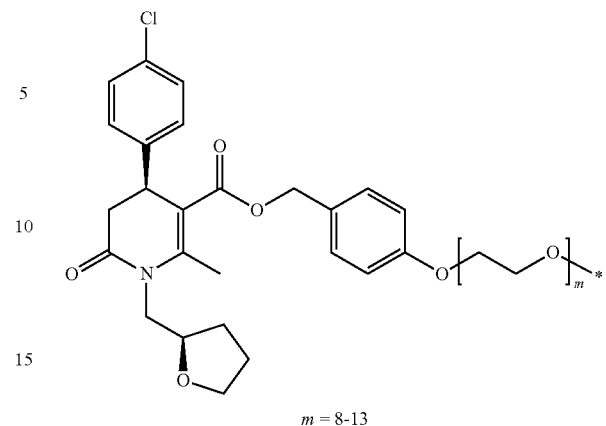
m = 8-13
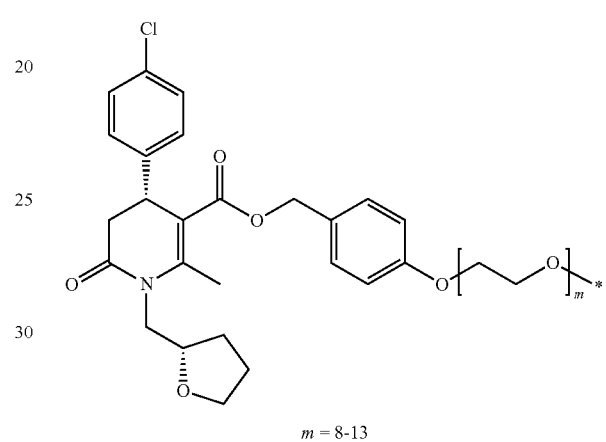
m = 8-13
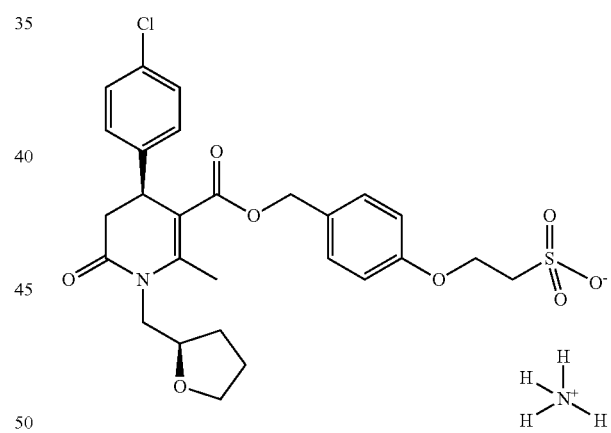
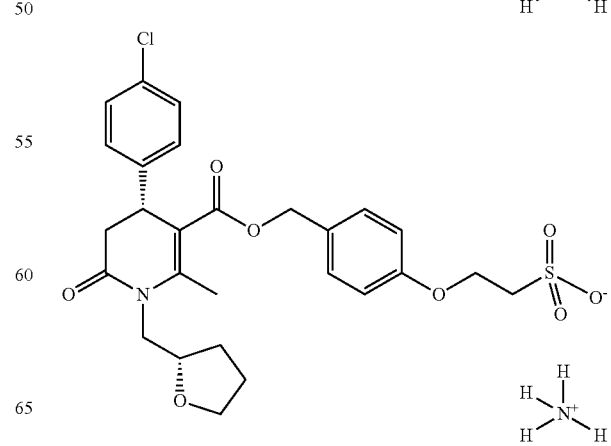

405
-continued
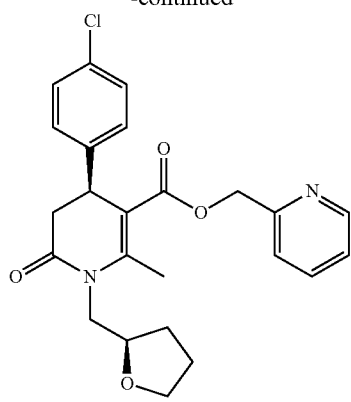
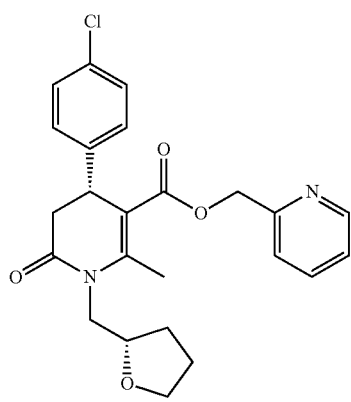
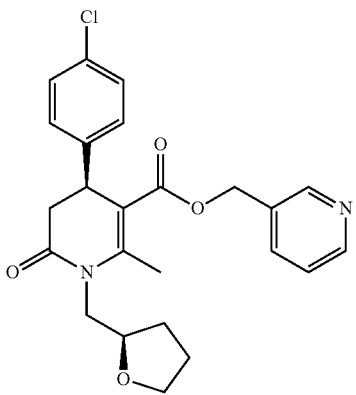
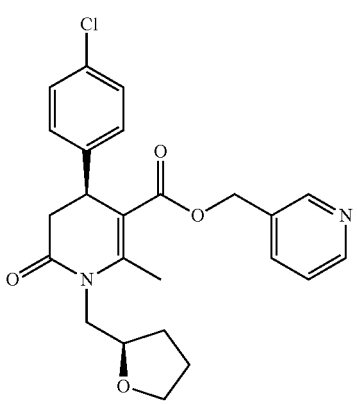
406
-continued
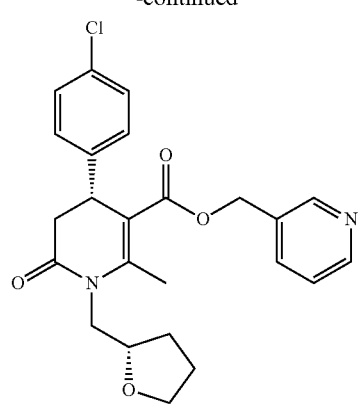
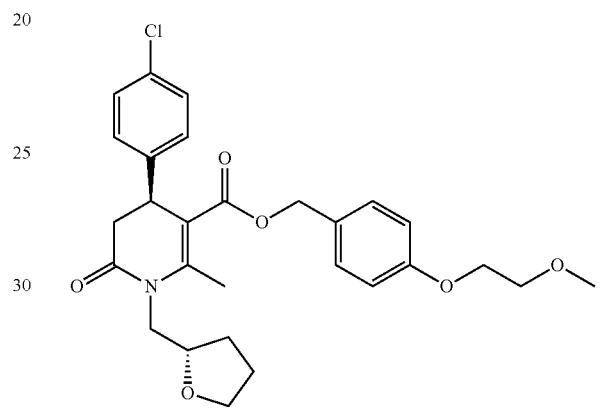
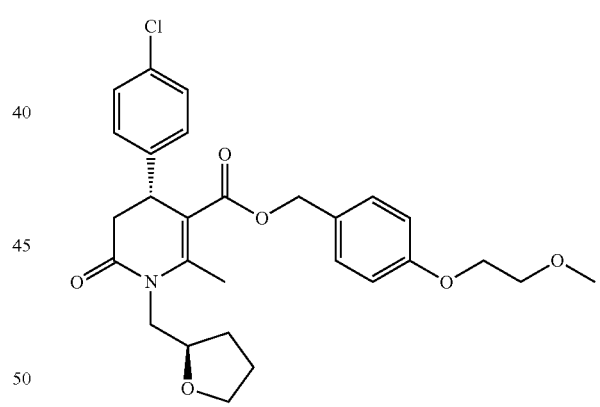
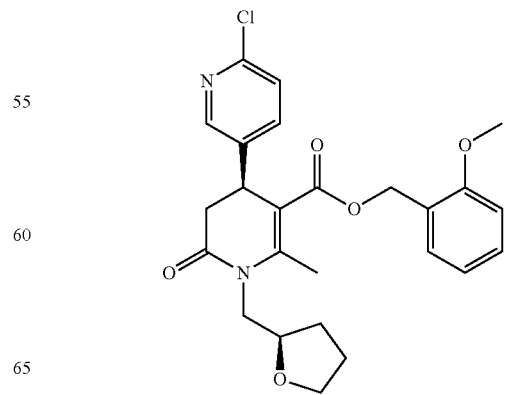

407
-continued
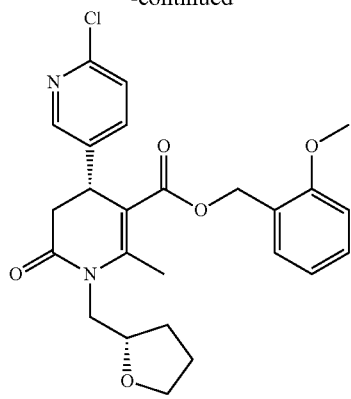
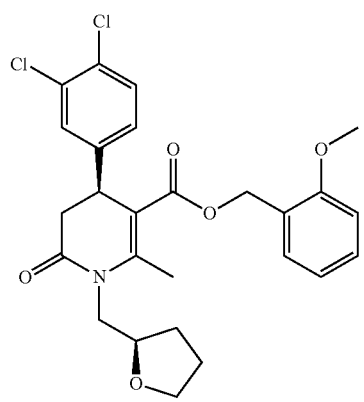
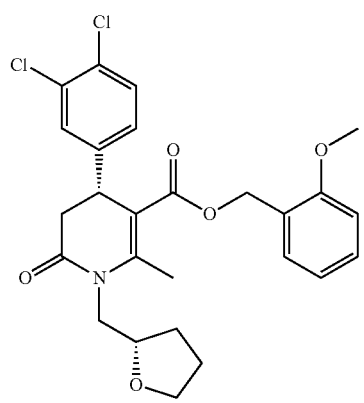
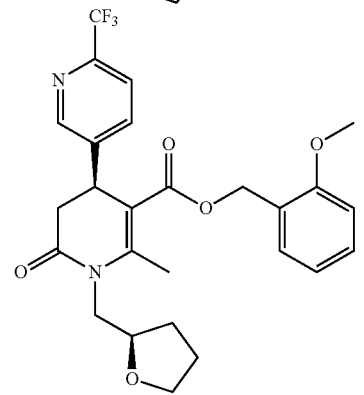
408
-continued
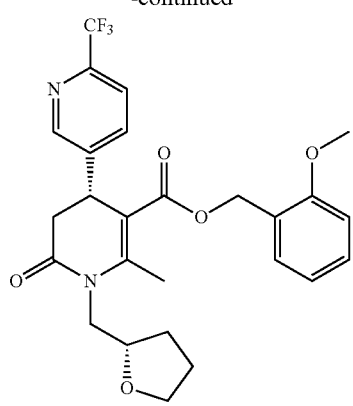
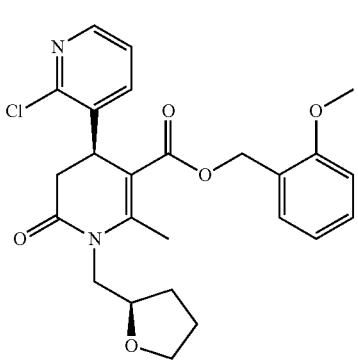
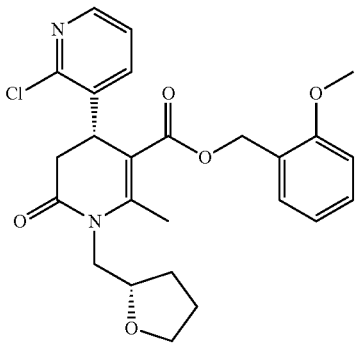
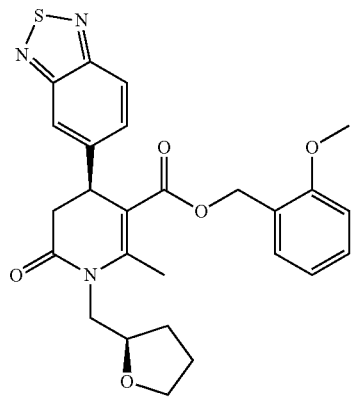

409
-continued
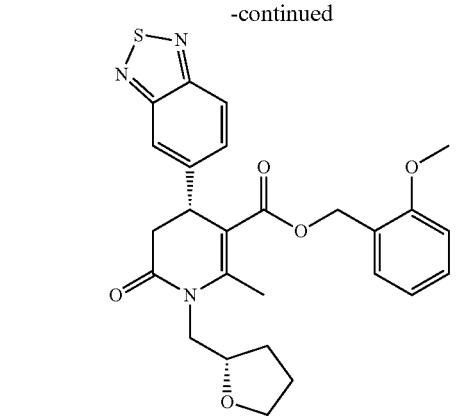
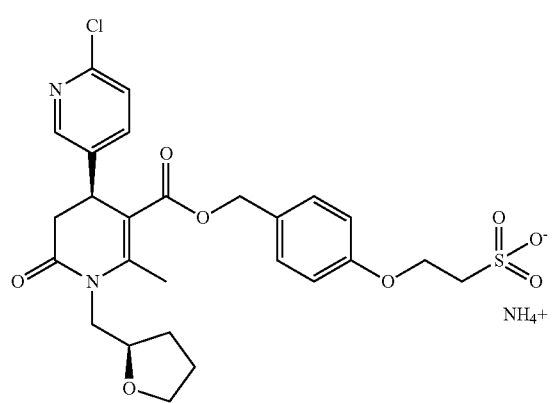
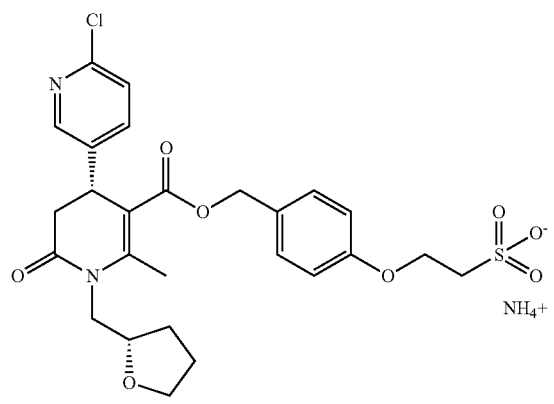
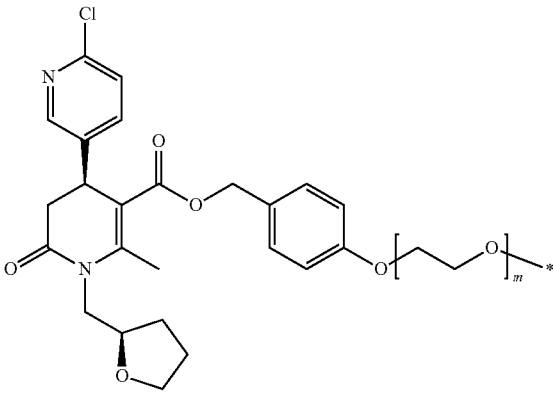
m = 7-10
410
-continued
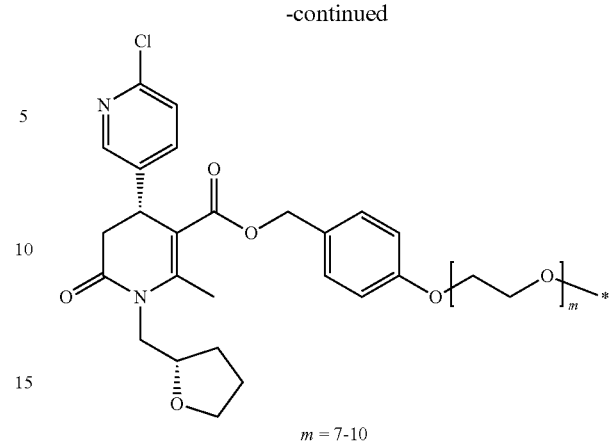
m = 7-10
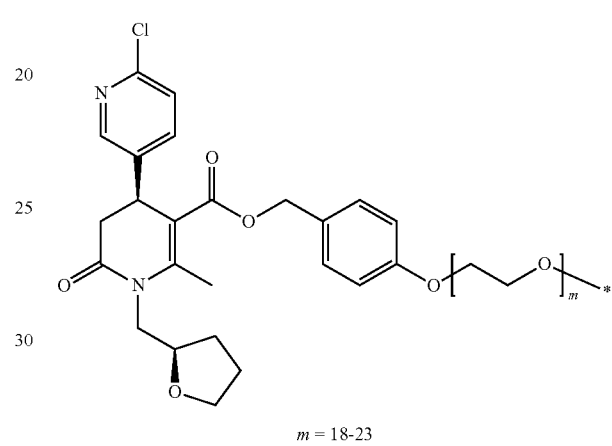
m = 18-23
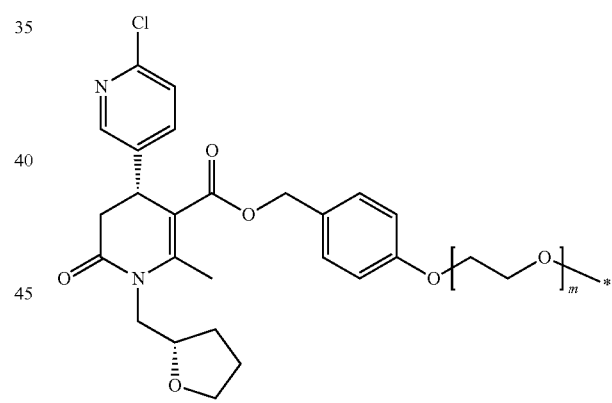
m = 18-23
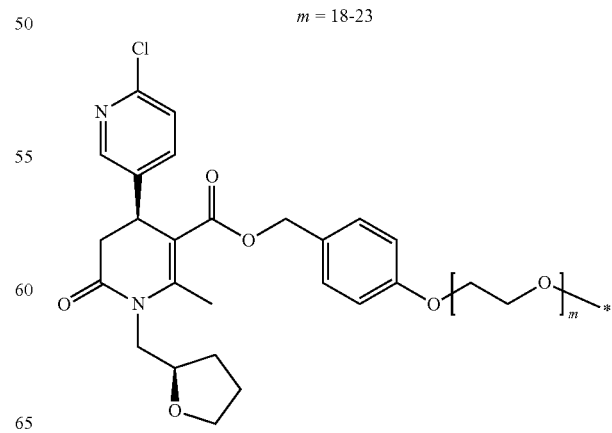
m = 35-44

411
-continued
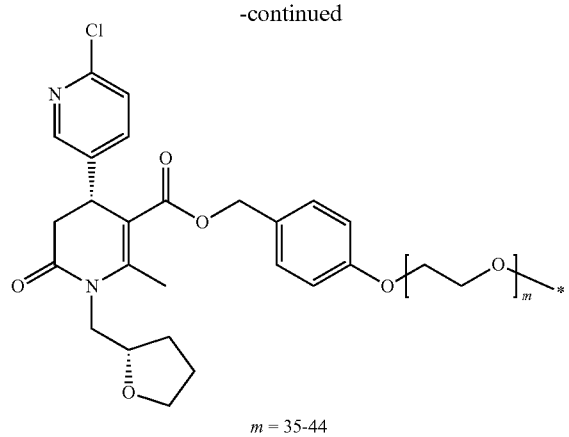
m = 35-44
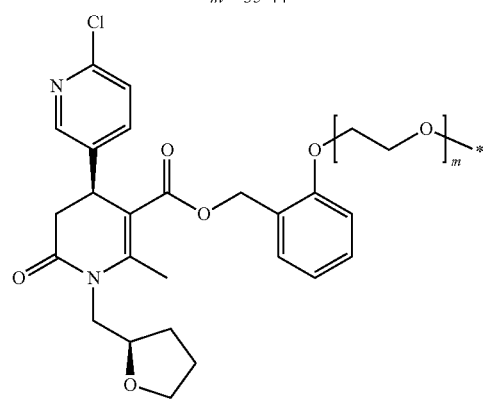
m = 10-14
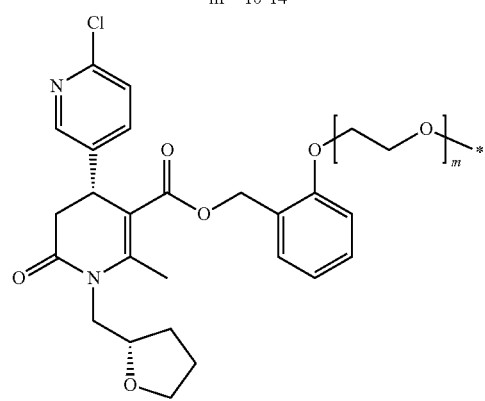
m = 10-14
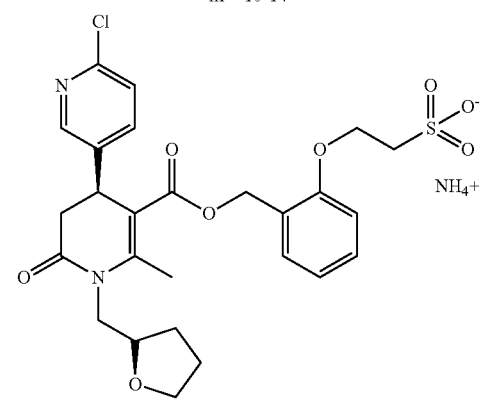
412
-continued
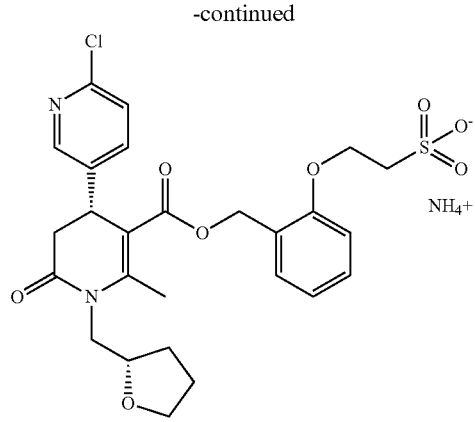
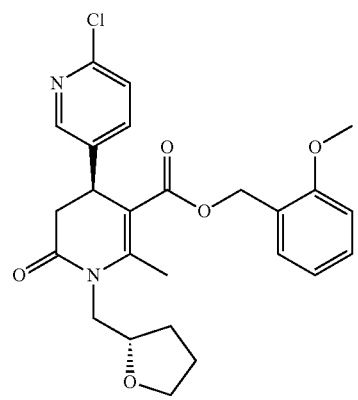
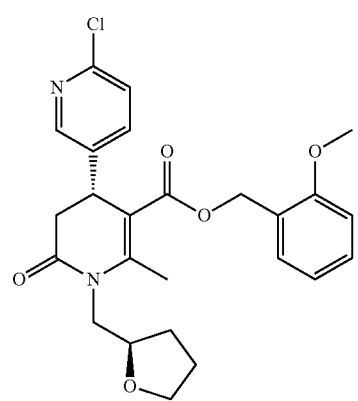
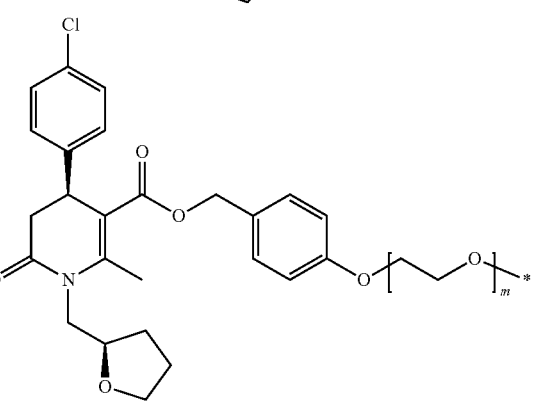
m = 11-18

413
-continued
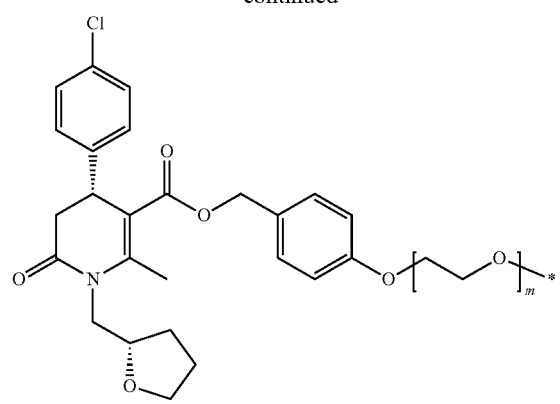
m = 11-18
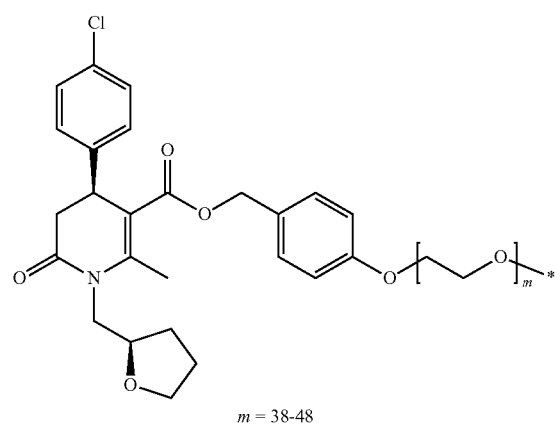
m = 38-48
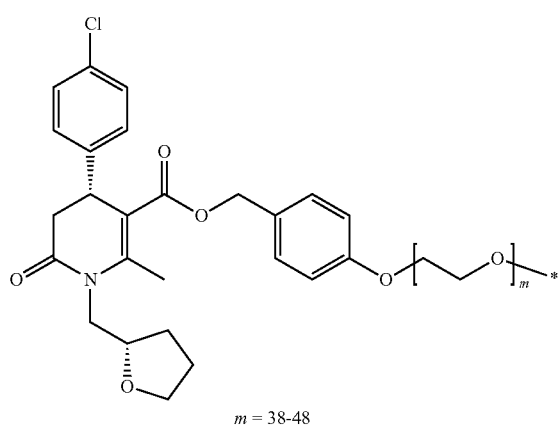
m = 38-48
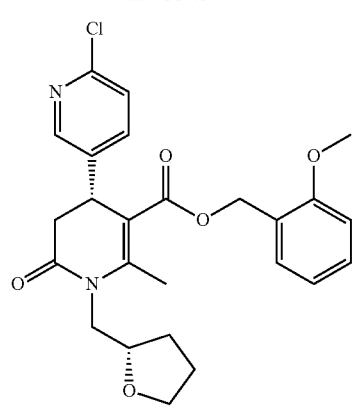
414
-continued
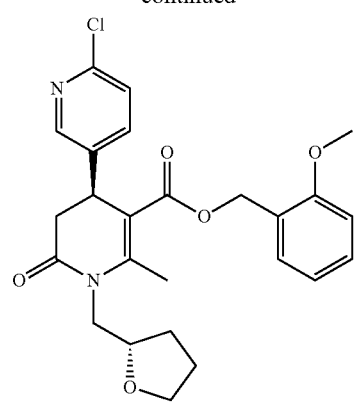
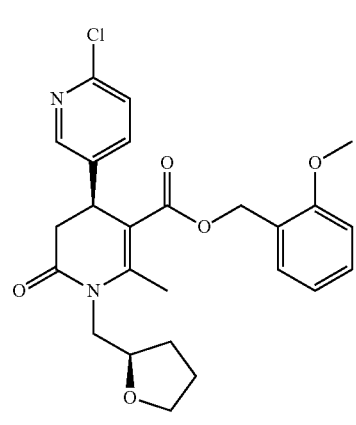
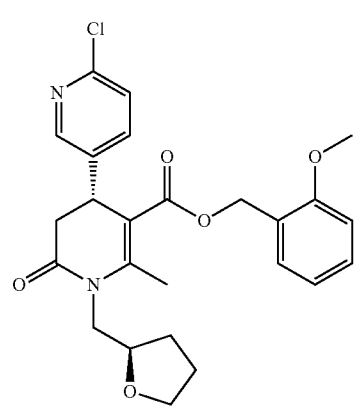
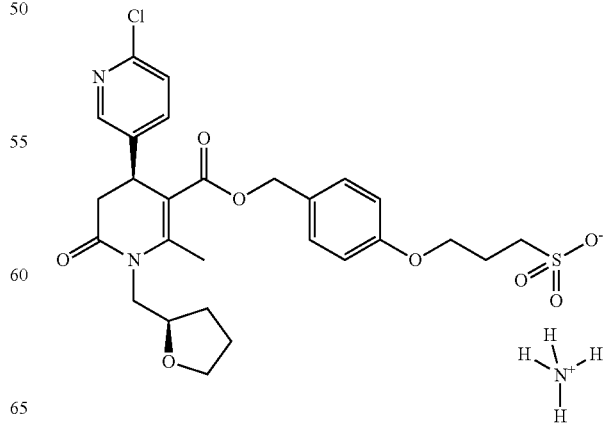

415
-continued
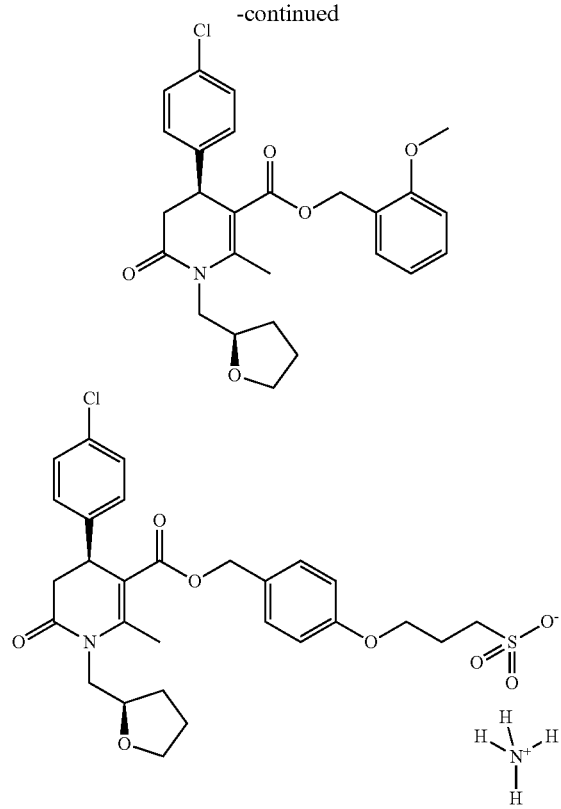
416
-continued
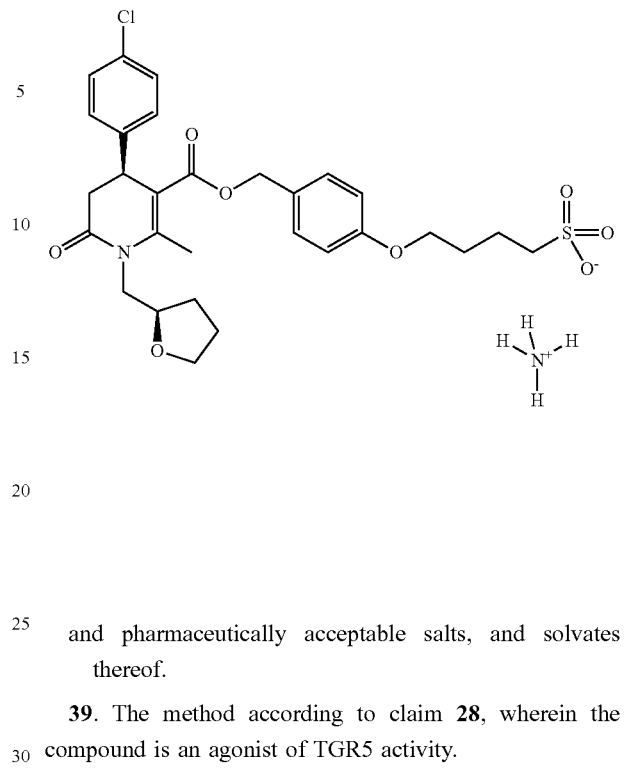
and pharmaceutically acceptable salts, and solvates thereof.
39. The method according to claim 28, wherein the compound is an agonist of TGR5 activity.
* * * * *